US007667100B2

(12) United States Patent
Shukla et al.

(10) Patent No.: US 7,667,100 B2
(45) Date of Patent: Feb. 23, 2010

(54) NUCLEIC ACID COMPOSITIONS CONFERRING HERBICIDE RESISTANCE

(75) Inventors: Vipula Kiran Shukla, Indianapolis, IN (US); Kelley Ann Smith, Lebanon, IN (US); Theodore Jack Letherer, Indianapolis, IN (US); James Patrick Connell, Indianapolis, IN (US); Ignacio Mario Larrinua, Indianapolis, IN (US); Kelley L. Ralph, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 346 days.

(21) Appl. No.: 10/487,804

(22) PCT Filed: Aug. 30, 2002

(86) PCT No.: PCT/US02/27881

§ 371 (c)(1),
(2), (4) Date: Aug. 16, 2004

(87) PCT Pub. No.: WO03/020956

PCT Pub. Date: Mar. 13, 2003

(65) Prior Publication Data

US 2005/0066392 A1 Mar. 24, 2005

(51) Int. Cl.
*C12N 15/29* (2006.01)
*C12N 15/82* (2006.01)

(52) U.S. Cl. .................. 800/300; 435/320.1; 536/23.1; 800/278; 800/298

(58) Field of Classification Search ....................... None
See application file for complete search history.

(56) References Cited

U.S. PATENT DOCUMENTS 6,211,439 B1 4/2001 Anderson et al. ........... 800/300
6,337,431 B1 1/2002 Tricoli et al. ................ 800/280
6,506,962 B1 1/2003 Bougri et al. ............... 212/348

*Primary Examiner*—David H Kruse
(74) *Attorney, Agent, or Firm*—Kenneth Ludwig

(57) ABSTRACT

The present invention relates to nucleic acid and amino acid sequences that confer herbicide resistance in plants, as well as herbicide resistance in plants, plant seeds, plant tissues and plant cells comprising such sequences. In a preferred embodiment, the sequences of the present invention confer a tolerant phenotype in plants in response to a chronic and/or acute inhibitin dose of auxinic herbicides. The present invention also provides homologous sequences with a high degree of functional similarity.

10 Claims, 86 Drawing Sheets

Figure 1

*This figure describes the sequences of contigs corresponding to genes ("hits") claimed in this patent. Contigs were assembled from multiple sequencing runs. Each entry header contains the contig identifier in the following format: contig name; source organism.*

> SEQ ID NO:1 129424 Poppy

GAATTCAATCAAATGGCTACTGCTAGAGTTTTGGCTGCTAGTATGTTGCA
TGAATGCAACAACACTCACAGTGCTTCATTTCTTTTGAGACAATCTTCTT
TCATCTTACCTATTAAACATCAAAGTATTAATTTCAGTAGAAGAGCATCT
TCTAGGAGAGCTTTTACTTGCAAATCTCTTTACAAACCTGAAATTCAAAT
CAAACAAGAAGGTGAACCTCAAACCCTAGATTACAGAGTCTTCTTTCATG
ATAAATCTGGCAAAAAGCTTTCACCTTGGCATGATGTACCATTGCAATTG
GGTGATGGAGTGTTCAATTTTATCGTGGAAATACCAAAAGAGACAAGTGC
AAAGATGGAAGTTGCAACTGATGAGCCATATACTCCCATTAAACAGGACA
CCAAGAAGGGAAAACTTAGATTCTACCCCTACAACATCAATTGGAACTAT
GGATTGCTCCCACAGACATGGGAAGACCCAACAGTAGCTAATTCTGAAGT
TGAAGGGGCATTCGGAGATAATGATCCAGTTGATGTTGTTGAAATTGGGG
AGAGGCAAGGAAAAATTGGCGAGATTCTTAAAGTCAAGCCTTTAGGTGCT
TTGGCTATGATTGACGAAGGAGAACTCGACTGGAAAATTGTTGCGATTTC
GTTGGATGACCCAAAAGCTTCACTCGTCAATGATGTTGGTGATGTTG

> SEQ ID NO:2 129426 Poppy

GAATTCAGAAGCAAATGTTTTGTGTTGTGCTGGGGAAGCAGCTCTATGTT
GGGCTTGTGATGTTAAAGTACATGCAGCTAATAAGCTTGCTAGTAAACAC
CAGAGGATTCCTTTGTCTACTTCTTCTTCTTCTCAGATTCCTAAATGTGA
TGTTTCTATACACACAGCAAATTCATATGTATCAAGCCACCAGAGGTTTC
TGCTTACAGGCGTGAAAGTAGGCCTAGAACCCACACAACCGATTGGGTTG
TCTACCAATGAAAAATGTGACTCTGCTGACAAAACTGTGGAAAGGGAGAC
TCAGACAATGTCCATGATAGATACTTCTGTATCATGGAATGGCAGAAATG
GTGAATTATTATCTCGACAGCCTGGTGGAGATGGCGGGCGACATGCAACT
AAGCTGTCAATGTCTGGGGGGACAACTGGTGGAAGTATGCCTGAGTGGCC
TCTGGATGAGTTCTTTGGACTAACTGATTTCACTCAGAATTTCGGATGTA
TGGATAATGGAACTTCCAAGGCTGATAGCGGCAAGACTGGGGAGTCTGGA
TTCTCTCCAACTTTGCAACTCACTGATGAGGACTTTGACATGGACGAGTG
TTTGGGTAAGGTCCCAGAGATCCCAAGGATGGTGCCCGAGGTCCCATCTC
CGCCCACTGCCTCTGGACTCTTCTGGCCAAAAAACTTCCGGAACTCATCA
GATCACGAGCTCTCA

> SEQ ID NO:3 129516 Poppy

TTCCTTTCAAATGAAACGGAGCTGCCATGCTCCGTTTACGGGGTCATTAT
TTTTACTTTGTTCCCGCGCAGTTATCAAAAGCAAAAGGAATAGGTAAAAA
TATTCTTCTCAAATTACAGTTAGTTATAAGGATTTCCTTAACTGCTTCTC
CTCACCATCATGTTATTTTCGCCACATCATAATCCTGGGCTTGCTGAAGA
ATAATTGAAATGATATTATTAATTCCACTGCCTTTGGTAGAGGAAAGTGC
TAAATAATAATCAATTGTTAAATTATTGTGCATTTCACTACTGGAACTGT
AATCAGAAAAGATAGACATGCTTAGCCAATCTCTATTTGATTGAATTGAA
AGATGTTTGTTAAGGCATGGATGCAAGCTATAGATTCTGATACGGTCAAT
AAAAGAGAATTGCTTAACAATTTTGCAAAATGTATTGGCGAGTAAGAACC
GCATTTGGTACTTTCCGGGCAACCGCCAGACGATTCTTTATTGGTAATGA
GAATAATTAACAATTAAAGAGCGTCGCGAAAGAATAATGTGTCTCGACAG
GGGAGACACAGTACGAATCGACATAAGGTGATCGTCTGAATCACCAGAAT
AAATAAAGTCTGTGGGTGATGCTGCCAAC

> SEQ ID NO:4 129702 Contig A Poppy

GAATTCAAAAAAATAACTATGTAACTAGTTGATGAGAGTTGTCATGCATC
TCACCGGCAACCTAATATATTTGATCCTATCAAATGATTTTGATCCGAAA
TCGTCAAGGCACCATGTGCTCTCCTTGTATAAACAACAACATTAGCAATC
GCATCTGGGACAACTGCGGTCTCCTTGTAGAAACAACAACATTAGCAATC

Figure 1 continued

GCATTTTAGACAACTGCGCGCGGTCTCCTCAACCAATATCTATAACTTC
TATAAAAATCTAGTAAAGAACACCAAATAATCTGACATATTTCGTAGTTA
AACATGCTTAGAGAACTAATACTTACGTTTTGCCGACTTTTTTTAAGATT
AGGAGCAGCATCAACAATGTTTTAACAACGTTATGCAATATTTCTCTCA
TTTCACATCTACCTAGCTAGCACAACATTTGTTCACACTAGAAGGGGCTA
GTGCCTGGTATTAATATGGAACAAGTGGGCTCAGTTGGCCCACGTTGGGA
GTTAGTGGGCTAGGGTTTAGTGACGCATAGTCCTACTCCTATATAAATCT
TTTTAGCTGAGGAAGCTCTTTTTTCACTACAACTACTCTTTTAGCTTGCA
GTCTTTCACTCACACTTAGATCTAGTCTTCTTCTT

> SEQ ID NO:5 129702 Contig B Poppy
TCAAAATGATTATAGAAATCATGGTTAATCCTCACATACAGAACAAAATCATCCTTCTTTAACCATGTCATGATG
ACTTATCCTCTCAAAAACATCATCTTTTTTGTCTTCAATGCTGTTGTTGAAGTGCTTTCTTCTTCGAAGTCAAGA
GGTTAGCAGAGACAAGAGTATTAACTTCGAGAAGAATAAGGGAAACCCAACCCACTCTGAAACTACCAACTTGAC
ATGTATCGGATCCTTGTTATGGAAGAAGGAGAAGGATTCTTCAGATAATGTAGTTGTTGTTGTAACTTTTTATGA
TAAATTTATTATGAAATGCAGATTCTTTTTTGAGCTGTCTTTGGTATTTTATTAGTTGATACATTGATAGTCACT
GTGAAATCTGTTCTTTTTTCTTTTTTAATTTGTTCTTGTAATTGAAATAGGCTTGTTAATCTGTTGTAACTCCTG
TTTAAATTAAGACAATGAAGTTCCCTTAGATTTGAAGATTTTTGGTATTGGTGCAAGGTCTGCATATATGCTCGC
TCAGGTGTTTTTTGGTGGTGGTTTTGTGTCATTAATTTCCATGGCTTATTTAGTGTGCCATTTTATGCAATTGTT
CCAACTGCGACAAAGCAACTTTCTAAATTGGAAATGTCAACAGACAAAAAAA > SEQ ID NO:6 129858 Poppy
CCGAATTCAATACGCGCTGGGTACTGAAAGTGATTGAGAAAGTCTGTAAT
GGAGAATCACCAATAGCAATGACTGTTTTCTTTGGTGCTAATGATGCTTC
TCTTCCTGATCGAACTAGTGCTTTCCAACATGTTCCTCTTCATGAATACA
AGCAGAACCTGCAATCAATAGTTTCCTTCATTAAGAAAAAATGGCCAACT
ACCCTTATTCTGCTTATAACTCCACCTCCAATTGATGAAGATGGACGTAT
TAGGCATCCTTTTGTAGATAATCCATCAGGTCTGCCGGAGAGGACGAATG
AGGCTGCCGGTGCTTATGCTAAGGCATGTGTGGAGGTTGCTGATGAATGT
GGAGTGATTGGAGTGGATTTATGGACTAAAATGCAACAATACCCTAATTG
GGAAAAATGTTGTCTCAGTGATGGCTTACACCTAACACCAACTGGGAACA
GAATTGTATATGAGGAAGTGATCAAAAAGCTTACAAAAGAAGGGGTAAAT
GTTGAAACTTTATCAGCAGATCTCCCTCTCCTATCTCAGATCGATCCTTG
TGATCCCTTGAAAGCATTCCAGAACTGAGAGATTCCTGAATTATCCGCAT
TACATATACCAGGGGACTCTTTTAGTTAGTTAGTTACACAAATTATCATT
TAAGAAGCAACACATATATGTGGTGGTAATTAATACAAAGTTTGCTGCTC
TCCCCATCTTTGTTGTTTTGATCATTGAAATGATGCTTTT > SEQ ID NO:7 129863 Poppy
GAATTCTATTTTGATTTTTTAAAAAATTCAGTGGGCCAGAATCGGGTTTT
GTTCGTCACAATGAAAACCGATTCCTTTAATAATCGGTTTTTGTTCATAT
ATATGAAGTCCGATGCTTCTGCAACTAATTGAGAATCGGGGTTTGTTCGT
AACAAACAAAACCGATTCTCGTTGACAATGTTTCTGTATACCAAGAATCG
GGTTTTTTGTGAATGTCGAGTAGACCGATTCCCGTAGCCAAAGTTTCTGT
GTAGTAGGAATCGGGTTTCATGTTCATGTAGAGTAATCCGATTACAACAG
CCAATGTCAATCTTTCTGTGTAGCAAGAATCGGGTTTTTTGTGCATGTCG
AGTACACCGATTATATAAACCAATATTTCTGTGTAGTAGGAATCGGATTT
CATGTTCATGTAGGGTAAACCGATTTCCAAAGCCAATGTTTCTGTATAGT
TGGAATCGGATTTCATGTGCATGTAGAGTAAACCGATTGTGTGCTTGAAT
CCTTGTTATGCAGGAAAAAACCAGCTGAAAAGAAATCTAGGGAGAGAAAA
CAACTTGATACTCCTGCTTCTTTGAAACCACGTCGAGTTGGAGGTAAAAA
TTTGAATGCTTCCAACCGAAGAGTTATAATCAAAGTCAA > SEQ ID NO:8 129866 Poppy
GAATTCAATAACTATATTGCAAAAAAGAGCTAGGGATTAATGATATAGGA
AAGGTACAAAAAGGTGGAAACGCAAAGGATTTACAAGAGCAATAATTGGC
AATAATTCGCAAGAAAAAGTTATTCTTTGGGAGAAACTCCACGATCCTCT
TTTTCCCCACTTTCCTTGACTTCATTATTTTACCATCTCCATCAATATT

Figure 1 continued

TTCTGGTTCCTTCCTTTCCTTCTCATTGTCATCCTCAACAAAATATGCTT
CAGAAAAATCATTCTCAAGATCAATATCTTCAGCATTGAGACTTGGAATA
TTTTCTTCAACTTCCTTTGAAGGTCTGGGAAATCAGATTCAGGAATCCC
ATAGGTTTTGCAAACCTGTTCATAAATCATGTTGCAATAACATTCCACCT
TTGTATTTATTCCCTTTTTCTATATTAAGCTCCTGCTTATATAGATCACA
TCTTCGAGTACGATGTGATAGCTTCTCCGCAAGCCGGTGATTATCAATCT
CTAATTCTTTAACCTTTTTCTCAGAAGCTGCAAGAAACGAAAAGATGAAA
TTGTGATTAAGAATGAAGAATTGAAGAAAATGAGAAACAAAGAAAAGACA
GATGGAAACCTTCTTTTTCATAAATTAAATCATTTATCAAA

> SEQ ID NO:9 129870 Poppy

GAATTCAGAGGCAGATAGAGAGAGAGACAATGGGAATGGCAACAAGTAGG
TTGATGGTGGTGCAACAAAAACAACCATCCTCATGTCTATTACCACCATC
ATCTCTTTCTGACTTCAATGGTATTAGACTGAAACACCCAATTCAGTACA
AAAGAAAGGAATGGCAGACAAGAGGAGCATTGCAGGTGAAAGCATCAGCT
GCAAAGAAAATCCTGATTATGGGAGGAACCAGATTTATTGGTATCTTTTT
GTCTAGGCTCCTTGTGAAGGAAGGTCATCAAGTAACTTTGTTCACAAGAG
GGAAAGCACCAATCAGCCAACCATTACCCGGGGAGTCGGAACAAGATTAC
CTAGATTTTTCTTCCAAGATTTCCCACTTGAAAGGAGACAGAAAGGACTA
TGATTTTGTTAAGACTAGCCTAGCAGCTGAAGGCTTTGACGTTGTCTATG
ATATCAATGGAAGAGAGGCAGAAGAAGTAGAACCCATATTGGACGCGCTT
CCAAAGCTTGAGCAGTACATATACTGTTCATCCGCTGGTGTGTATCTGAA
GTCTGATTTACTGCCTCATTTTGAGTCTGATGCAGTGGATCCCAAGAGCA
GGCACAAGGGAAAACTTGAAACAGAGAGTTTACTTGTATCA

> SEQ ID NO:10 129965 Poppy

TTAATTAAGTCGACGAATTCGAGAGAAACAGAAAAAGGAGATTCAGAATT
GGGTAATCACGGCTATATTTGGAGACGGAGGGTGGAATTTCCACCACAAC
CAAAGATTGATTCATTCATCATCATCTTGTAACCAAATCGAAAAAAGAAA
CCCTTCACCACACGGTGGTAGAGGAGCTTTGCCGTCAGAAGGTGGTTCTC
CTCCTGATCTTCTTTTCCTTGCCGGTGGTGGTGAATTTCTCATCAAATAC
CCAATCAACTGACCCCCTTATTCTTTTGATTTTTTCCTAGATTTACCAAT
TCATTTTCTTAACTTGAAAACCAAATCATATTCTAGTACATAATACATTA
CAATATACAATATGTTGACCATCAAAAGAGTTCCTACTGTTGTTTCTAAT
TACCAAGAAGATGGTTCTGCCGCTGCTGCTGAAACTGTTGGCTGTGGCCG
TAATTGCCTTGGAAAGTGCTGTTTACCTGTGTCCAAGCTTCCTTTGTATG
CATTCAAGGGAGATGGGATTGATTCAATCAAAGGAGGAGAGGAACCTGAG
GTGTCTTTCTTTGATACCTTAATTCTTGGGCAATGGGAGGATCGAATGAG
CCGTGGCCTTTTCCGATATGATGTAACACAGTGTGAGACTAAGGTTATTC
CCGGAGAGTATGGATTTGTTGCACAACTGAATGAAGGACGTCATCTTAAG
AAACGACCAACTGAGTTTCGTGTTGATCGAGTGCTACAACCCTTTGATGG
GAGCAAATTCAACTTCACAAAAGTTGGGCAGGAAGAGGTGCTTTTGCGCT
TTGAGCAGAGTTTGGATGAAAAGACCCATTACTTTGCTAGTTCAGCTGTT
GACTTGGATTCTATTTCTCCTAGTGTGGTCGCCATTAATGTGAGTCCAAT
TGAGTATGGGCATGTACTTCTGATTCCCCGCGTTCTTGAATGCTTGCCTC
AAAGGATTGACCATGAGAGCTTCTTGTTAGCTCTTCATATGGCGAAAGAA
GCAGCAAACCCCTTTTTCAGATTGGGTTTTAATAGTTTGGGTGCCTTTGC
AACAATCAATCATCTCCATTTCCAGGCGTATTACTTATCTGTGCCCTTCC
CTGTTGAGAAGGCTCCTACTCGGAAGATAACCATGGCAAATGGACTTCCA
GATAATGGGGTTACAATCTCCGAGCTGTTGAACTATCCGGTTAGAGCTCT
TGTTTTTGAGGGGGGCAACACATTAAAAGATCTCTCTGACGTTGTCTCTA
ATGCTTGCATTTTTCTTCAAGAGACCAACATTCCATACAATGTTCTCATC
TCTGATTGTGGAAAACGAATCTTCCTCTTCCCTCAGTGTTACGCTGAAAA
GCAAGCACTTGGAGAAGTGAGTCAGGAGCTTCTTGATACCCAAGTAAATC
CAGCTGTGTGGGAGATAAGTGGACATATAGTGTTGAAGAGGAAGAATGAC
TACGAGGACGCATCTGAAAATTATGCTTGGAGGCTCCTTGCAGAGGTGTC
TCTCTCCGAGGAAAGGTTTCAAGAAGTGAAAACCTATATATTTGAAGCTG
CAGGTGTTCAGGAAATGGTTTGTGTTGCAGAAAAAGAGGAAGGAGATGTC

Figure 1 continued

AAGGATGAGGATGAAGATTCTTTTTTCGGGGGCTCATCTCGCACCTCTGC
CACATATTACCCCCAAGGTTGTCTGGTTCAGCAGTGAAGAAGTACTATTA
GGGTTTCAAGAGGGTTGCAGTGTTGTCTCTTGTTCTTTCAACTTTTCTGTT
ACCTGCGTAACAAAGTAGGATAGTTTTAGTAGTTATTGCGTGTAGTTTGAT
TTTGATCATTCAATAATGATCTTAATGCATGTGTACTTTGCTCAGTGAAGT
GGTTGTGTACATCTCTCTCTCTACCTTATATGAAAAATGAAAATTTGTTAA
AAAAAAAAAAAAAAAAAAA

> SEQ ID NO:11 129965 Contig B Poppy
CTGACGTTGTCTCTAATGCTTGCATTTTTCTTCAAGAGACCAACATTCCATACAATGTTCTCATCTCTGATTGTG
GAAAACGAATCTTCCTCTTCCCTCAGTGTTACGCTGAAAAGCAAGCACTTGGAGAAGTGAGTCAGGAGCTTCTTG
ATACCCAAGTAAATCCAGCTGTGTGGGAGATAAGTGGACATATAGTGTTGAAGAGGAAGAATGACTACGAGGACG
CATCTGAAAATTATGCTTGGAGGCTCCTTGCAGAGGTGTCTCTCTCCGAGGAAAGGTTTCAAGAAGTGAAAACCT
ATATATTTGAAGCTGCAGGTGTTCAGGAAATGGTTTGTGTTGCAGAAAAAGAGGAAGGAGATGTCAAGGATGAGG
ATGAAGATTCTTTTTTCGGGGGCTCATCTCGCACCTCTGCCACATATTACCCCCAAGGTTGTCTGGTTCAGCAGT
GAAGAAGTACTATTAGGGTTTCAAGAGGGTTGCAGTGTTGTCTCTTGTTCTTTCAACTTTTCTGTTACCTGCGTA
ACAAAGTAGGATAGTTTTAGTAGTTATTGCGTGTAGTTTGATTTTGATCATTCAATAATGATCTTAATGCATGTG
TACTTTGCTCAGTGAAGTGGTTGTGTACATCTCTCTCTCTACCTTATATGAAAAATGAAAATTTGTTAAAAAAAA
AAAAAAAAAAAAACTCAAG > SEQ ID NO:12 130156 Poppy
GAATTCAAGAAGACCATCGGAGATTGTTCATCCGGCCGTTTCTCTACATT
TTCGGTCATTTCAAGGAGCAAGCAGTATTTTAAGGAGGCAAAATGAGTCA
GAAAAAAGGGGGTGGCAAGCTATCTGTTCCTGGTAGTAGTGGTTCACCTG
CAAAAGGGAAAGATGCAGGTGGACAAATCCCTGGAGTTTTAGGCTCTGGT
AACCAAAAGACTGGAGTTGTTCAGCTGGGTTCTAATATCGCAAACCTAAG
CCTTGATTCCAGTAAAGATTCTGAGTGGGAGGTAGTGTCTCGCAAGAATC
GAGGCGCGGCAAGTGCACCAAAACCATGGGGTCCCCAGAATTCCTCTTCT
CCATCCTTGGTTTCAGGAAGTTCCCAAAATTCCTCTTCTGCATCCTGGGT
TGCAGGAAAGGCTACAGGAGGTGCCCAAAATTCCTCTTCTCCATCCTTGG
TTTCAGGAAGTTCCCAAAATTCCTCTTCTGCATCCTGGGTTGCAGGAAAG
GCTACAGGAGGTGCCTGGCAGGATAATAAGTCAGGTGGAGGAGGAACTAC
GAAAAGCCAATCTCCCAATGCATGGGAGAAAAATTACATGGCACCACCAA
GTAAGATTGCTCCTCCTTTACAACATGGTTGGCAGTGGGGTGCAA > SEQ ID NO:13 130203 Poppy
GAATTCGGGAGCACAACAAGTAAATTAGAACCCGGTGGTCACAATTTCTG
CCTCTCTTCAATGGCTGCCTCTGCAAGTCCCCTCATCTAATCCTAGAAAA
CAAAGAAATCCACTTTCATTGCAGATAAGCTTTTCTTCACTCCATCAAAG
GAACAAAGTCGAGAGAGAGAGAGCACAACAAGTAAATTAGAACCCTCTGG
TCACAATTTCTGCCTCTCTTCAATGGCTGCCTCTGCAAGTCCTCTCTCTT
CATTCGCTTCCCTTTCTATCTCAACATCTAGAAAATTTCTCCCAAACCAC
ACTTCTTTCTCCTTCTCAAACATCAAAACCCATAAACTCATCACCCCAAT
TTCTTCCCTAAAATTCCCCCATTCAAAACCCCAAAAACCTAAACCCATAA
AAGCTACACCCTCTGATGCAGAAACCATTTTCATGGAAAATGAAATAAGC
CCAGATGAAGATTTCACATTTGAGCCACCACCAAGACCAGAAGGTTACAT
TGAACCACCTTCATTTGATGATCTTCCGCCAGAATCTGAAGATGAAATTG
CAGCAGCCTATGAAGAATTGTATGGTCCTGCTTATAGTGGTATGAGTGTG
CTAGGTAACGATGTATATGTTATGGATTCTAAGATGAAGAAAGCAACTGG
GTTTGGTACAAAGACTAAGAAAG > SEQ ID NO:14 130213 Poppy
TTAATTAAGTCGACGAATTCATATGAAGAAATGGTTGAATTTATGGAAAAAGTAACAACAAATGTTGAATCAGAG
GAACTTTCAGTTGAAGAGAGAAATTTATTGTCAGTTGCTTACAAAAATGTGATTGGTGCACGCAGAGCATCATGG
AGAATTATTTCATCAATTGAACAGAAAGAAGAAAGCCGTGGTAACGAAGAGAATGTATTGACCATTCGTGATTAT
AGATCTAAGATTGAAACTGAACTTTCAGGCATCTGTGATGGGATTTTGAAGTTGCTTGATACTAGATTGATTCCA
TCTGCATCTTCTGGTGATTCTAAAGTGTTTTATTTGAAAATGAAAGGTGATTATCATCGTTATTTGGCTGAGTTT
AAAACTGGTACCGAAAGGAAAGAAGCTGCTGAAAGTACCCTTTCTGCTTATAAATCTGCTCAGGATATCGCAACT

Figure 1 continued

GCTGAACTTGCACCCACTCACCCAATCAGGCTGGGACTTGCTCTTAACTTTCTCCGTCTTTTACTACGAGATCTT
GAATTCTCCTGCCGTGCTTGTAATCTCGCCAAACAGGCATTTGATGAGGCTATCGCGGAGCTGGATACCCTTGGT
GAAGAATCATACAAAGACAGCACTCTAATCATGCAGCTCCTTCGTGACAATCTTACTCTGTGGACCTCCGACATG
CAGGATGATGGTGCAGATGAAATTAAAGAAGCATCCAAGCCTGAAGATGAACATTAATGATAGTTTGTCTGCCAC
ATTTAGGATCTTACCTCCTCTCAGTTTGTTTTATTAAAAGGAGAAGGTGCTTTCTTGGTACACAACTCCTCCAAG
TCTACTATTAATTATTAAGGAGTTTAGGGTGGGTACTGTTAGTTTGTCATTCTTCTTATCCTTTGTGCTCGTCTT
TTCCTATCTTAATTCTTCTCTTAAAAGAGTTTGAAGTTATATGTTTATCTGAATCTGTGTGGGAACTCCGTTTTA
TCTAAATTATCTTTTAAGATGACGATAAAAAAAAAAAAAAAAAAA

> SEQ ID NO:15 130294 Contig A Poppy
TTAATTAAGTCGACGAATTCAAATTAGGTCTAAAGATGGCGTCTTTAGCT
CAACAATTCTCAGGATTAAGATGCCCACCACTTTCTTCTTCTCATCTAAC
AAAACCCTTTTCTTCAAAACCCCAGAAAACCACCTTTTCACCTATAGTTT
CAGCAGCTGTCATTTCTAATGCACAAACTAAAGAAAGAAGTAGACTTAAA
GAAATCTTCGAAGATGCTTATGAAAGATGTAGAACTACTCCAATGCAAGG
TGTTGGTTTTACTGTTGATGATTTTCATGCTGCTCTTGAAAAGTATGATT
ACAATTCTGAGATTGGTACCAGGGTTAAAGGAACTGTGTTCTGTACAGAC
AACAACGGAGCATTAGTTGACATCACGGCGAAATCTTCAGCCTATTTACC
AATCCAAGAGGCATGTATTCACAAAATAAAGCATGTAGAAGAAGCAGGAA
TAGTTGCAGGCCTACGTGAAGAGTTGTGATTATTGGAGAGAACCAAGCTG > SEQ ID NO:16 130294 contig B Poppy
CGGCATCTTAGGTCCCCTGACGCCAGACTTGCCTGCTGAAGGTCTAGATTTGAGCGACATTCCTNCAGCTGATGA
TGCATAGAAACCAATAAATATGAATTAAATCTGTCTTGACGTTTCTTCTCNTCACCATTTTTAGGCTATGTAAGA
TGGGTCTATAGGTTGTTCAAAGTGTNGACTTGTGTATTTATCTTGATAGTTCAAAGTGTACTTCTTTAAGCGATA
ATCATTGAAAAGAAAAAATGGAGAAGGTAAAAGATAAAAATATCCAAAAAAAAAAAAAAAAAAAAAAAA > SEQ ID NO:18 130964 Poppy
GAATTCAGGGAAACAGCCCGGATCACCAGCTAAGGGGCCTAAATGACCGC
TCAGTGATAAAGGAGGTAGGGGTGCAGAGACAGCCAGGAGGTTTGCCTAG
AAGCAGCCACCCTTGAAAGAGTGCGTAATAGCTCACTGATCGAGCGCTCT
TGCGCCGAAGATGAACGGGGCTAAGCGATCTGCCGAAGCTGTGGGATGTA
AAAATGCATCGGTAGGGGAGCGTTCCGCCTTCAACAAAAGGGTACCTGTA
CCCGAAACCGACACAGGTGGGTAGGTAGAGAATACCTAGGGAAGCGAGAA
TGTCGGCTTGAGTAACGCAAACATTGGTGAGAATCCAATGCCCCGAAAAC
CTAAGGGTTCCTCCGCAAGGTTCGTCCACGGAGGGTGAGTCAGGGCCTAA
GATCAGGCCGAAAGGCGTAGTCGATGGACAACAGGTGAATATTCCTGTAC
TACCCCTTGTTGGTCCCGAGGGACGGAGGAGGCTAGGTTAGCCGAAAGAT
GGTTATCGGTTCAAGGACGCAAGGTGACCTTAGGGTAAGAAGGGGTAGAG
AAAATGCCTCGAGCCAATGTCCGAGTACCAGGCGCTACGGGGCTGAAGTA
ACTCATGCCATACTCCCAGGAAAAGCTCGAACGACCATCAT > SEQ ID NO:19 130795 Poppy
TTAATTAAGTCGACGAATTCATGTCAATGGAGACTTGCTTATAATACTAA
ACGCATGGGTTATGTGTGATCGTTTTGATTATATATTCATTCTTTTTTTC
TTTGTGTTGTGATATAGTAATGGGGGAAAGAAATAATGAGAATTCGGCAG
ATATTGATAATGAATATCCAAAAGATTTGTTACAGAGATTTATGGCGGGA
AACCATTTCCCAACGGAATTTGCAGCGAAAACTGAGGAAACAGAAGAAG
ATGATGAAGATATTGAATTAAATTTATCATTAGGAGGTTGTTTTGGTGTT
AACCCAAGTGAGAAAAAGAGGTTGATGAGGTCATCGTCAATATCAGTATC
AGGATTAAGTAATCTGTTTAAAGATGAAGAAGAAGGGAATAATTCTTCAT
CAGCAGCATCTTTGATAAGAACATGTTCATTGCCTGTAGTAGTAGCAACA
GAAGAAGACAGAAGGAAAAGGAAAGAGTTACAATCTCTAAGAAGATTAGA
AGCCAAGAGAAAGACATCAGAAAAACAAAGGAATTGTACTAGGGTTAACA
ATAATAAAGATATTCAACAAGAGAAGATGCAACAGCAGCA > SEQ ID NO:20 130994 Poppy
TTAATTAAGTCGACGAATTCACATCTAAAGTCAACAACAAGAGCTTCTCK

Figure 1 continued

CTTCTCCTCGTCTCTGTTCTCCTCTCTTTTGCAATCCTCTCTCAATCTGC
TGATGATTGTGTATACACAGTATACACAAGAACAGGATCAATCATCAAAG
GAGGAACGGATTCAAAAATCTCACTAAGATTATACAGCAAATACGGTAAG
TACATCGAGATCCCAAATCTTGAATCATGGGGTGGATTAATGGGTCCTGG
TTACGATTATTTCGAAAGAGGTAATCTTGATATCTTCAGCGGAAGAGGTT
ATTGTCTGGGTTCACCGGTTTGTGCCATGAATCTGACTTCCGATGGTACT
GGKTCCSGTCACGGATGGTATGTGAATTATGTTGAARKTACTACTACCGG
TGCACATATTAATTGTGGTCAACARAATTTTGAAGTGGAAGAWTGGCTTG
CTCTTGATAGAWCTCCYTATARTCTTACCCGCTWTCAAGAAATAATTGTA
ATCAGAAATTATCTGATCATGATTCTCATTCTGCTGATCAGTCTATGTAA
AATTTGATCTCTTGTTTGATTCGGTGGTGGTCTAGTATGAGTGATCGGAC
GGTCGTCATTGTGTGTTGTAATGTTGAAATTATTTCTTGAATAAAATGA
TTGAGTGAGTAGTG

> SEQ ID NO:21 131002 Contig A Poppy
TTAATTAAGTCGACGAATTCAGCCGTTTGGGGGATCCGGAGGCGTAGAGG
KATAACTGTACCTTGTATCAGTGGGAGATTGATAGGGGTTCTTCTATAGA
TCAGTCCGAAGTTAGTTGGAGTAGGCTAGTATCTGTAGCGGCTTAATACA
GTGTATATCTAATCTGGACTAGGTCCCGGGGTTTTTCTGCATCTGCGGTT
TCCTCGTTAACAAAATCTCTGGTGTCTGTGTTATTTCTTTTCCGCATCTT
TTTAGATAGAAATAATACAGGTTGTGCGTTGGTAAGTTTAATCAGTTTAC
AGATCCAATCTTGTTATTGTTGATCTTGCTGATTAACACTTGGATATTGG
TTTTTGATACCGTCCAAGTCTTTATCTCCTTGGTTTGACCAGACTCGCAA
ACTTGTTTGTTTGAGTAGTTCTCAAATCAAGAGAGAGAGATATCAACTCC
TTGAGTCACTATATTCTTCAGATCCTGACTGTCTAGTCGTTTCTTTAGTA
GAGTGATTTGGAGGKTGTCCTTGATCAGAWTGCTAATCGAAAAGTTTGGG
TGTGTTGTTAGACCCCCGCTTTTTCAGCAAGTTATATTTCTGACATTGAA
CCTCACTGTAAGTTTTGTAATAGTAGTAATGAAACCATTGAGCATTTGCT
AATTGAATGTGATTATGCTATAGGAACATGAAACTGGAATATGGAACTCC
TTGCAGGTAGATATTCTTACTACTACTC > SEQ ID NO:22 131002 Contig B Poppy
TGCAAGAACTACTTCCACCACCCAGAATTCAAGTATAGAAGATTGGATACGACCAGAAGATGGATATCTGAAACT
GAACATTGATGCTTCTTATATTTCAGAACCAAGAAAAGGTAGATTTGGTCTAATATTACGTAATCATGCAGGTTA
GATAATAGGAGTCAAAGGAGCTAATCTGGAGGAGGAGGTGGATGCAGAAGTAGGAGCGGAACAATTTGAATGTAA
AGCTCTGATCTAGGCAGTATAATGGATGGAGGAAGGTGGTTACAATAAAGTCATTTTCGACTTGGACTGTGCTAA
TGTTGTGGAATCTGTCGACTGTGAAGAATCTAAAGTTCACTTGTTCAATCAACATCTAATATCTGCAGTCAGAAA
TAATTTTTTAAGGAATAAATTTTGGTTTTGCGAAGTAATTAATATGACAAGTAATAGTGTAGCTCATGAACTAGC
TAGAAAAGCTAGGCTTGAAGCTCTTTCTTACTTTTATGTTTCAAAATTTCCNCTGGATATCTCCAATTGGATAGA
AAAAAACAATGNACTTCAATCTATTCATTAATAAATCTCTTTTAGTATCGAAAAAAAAAAAAAAAAAAA > SEQ ID NO:23 131007 Contig A Poppy
TTAATTAAGTCGACGAATTCAGGCACATGCAAACAAAACCAAACAAAATS
SCTCGGTTTTGAAATCACAAGAAATTGAATGAACATGATTAAATGAAGTT
TTGTTTGTTGGTTGAAGAATCAAAGAGAAGAAGAAGAAGAAGAATTAGCA
TGGTTGGAATTGAAACTAGGTCAATTGCAAACATAACTAATAAGATTCGA
CGTCATGGATATGCTGAAACTACCAGATTCAATTTCAGCTGAAACATTGT
GTAGATTAGCAAATGGGAATACATTAGTTGCTGGTTTTTCCTTCGTTCTT
ATATCCTTCTCCTTGCTCTTCCAACTAATCCCGTCCCTTCTTTCGCCTTA
CAAAACAACCTCCAATCGTCCTTGAAATCATGGTAGGACTCTTTTTGGGG
AAACGTAGGGTTCATGGGTTCAGTATCTTAACTTGGTTTTCAAGTCACCA
CATTCGCAGCAATTGCAGAAATCGGAATGAGTTGTTATGCTTTAGTTTTA
GGGATAAATTTTGATGTAACTCTACTTGGACATACCCCACCTGAAGCCAT
AGTAGCTTACACTGTGATTTTATCAACTGTCCTCGTTACTGCTACTACAG
CTGTACCACTCATACATTTTGGATTTGATCATGATATTAAGGATACTGCG
AATTTCGGCTTCATATTTGCATTGTCATTAACCGTGGCAGGGACTTCTTC
TCCAGTGTTAACACAATTATTTACTGAAGAAAATTTCT

Figure 1 continued

> SEQ ID NO:24 131007 Contig B Poppy
CCGTCAAAGTTGTTCTTCCTTTAGGTAATTGTACTGAGGGGAAAATTTTAGGANCTAAATTTNTGGCATTATTCT
GGGATTTCATTGGCCNATCGCAGTCGCAATAGGATTGTTTTAAACGTCAAGGGTCCATTTCATATTTTCATTGC
CACGTTCGCGGTCGAGGTAACATANTACTGCCAAATNACCATTTTCTTGTAATAGGATTATCATTCCTAGTAATT
AATGNGTTTGTAAATATGAATGTGTAANGTGTTTGTAAATATGAATGTGTTTAAAANGAATTCATGGGCGNTGGC
AGCTTCCTNGTGTTCCTATTAAAAAAAAAAAAAAAAAAAAAAAA

> SEQ ID NO:25 131048 Contig A Poppy
TTAATTAAGTCGACGAATTCAGGACCAAGAGGAAAGTTGATCAGAAACTT
CAAGCATCTGAACTTAGATTTTCAGCTCATTAAGAATGCTGAAACTGGGA
AGAAACAGCTTAAAGTTGATGCCTGGTTTGGATCCAGAAAGACTTCTGCT
TCAATTAGAACTGCACTTTCTCATGTTAACAATCTTATTACTGGTGTTAC
CAAAGGGTACCGTTACAAGATGAGATTCGTGTATGCCCATTTTCCCATCA
ACGCTTCAATCACCAACGGAAACAAGGGTATTGAGATCCGTAACTTTCTT
GGAGAGAAAAAGGTGCGAAAGGTTGATATGCTTGATGGAGTGAGTATTGT
CAGGTCAGAGAAGGTCAAGGATGAGCTTGTGTTGGATGGTAATGATGTTG
AGCTCGTCTTCAGATCTTGTGCCTTGATCAACCAGAAATGCCATGTGAAG
AACAAGGATATCAGGAAGTTTTTGGATGGTATCTATGTGAGTGAAAAAGG
GCTGTTGAGGTCGAAAAATAAATTTGTGGTACGACGCTATTGGTTTTGTG
TTCAGAAGGTTTTCCTCCCCCCGTTNCGTCATAATTAGTTTGTTATTTCG
GTTTTGTGTTCAGAAGGTTTTCCTCCCTCCGTTACGTCATAATTAGTTTG
TTATTTCTTAAACTAGTATAAGTTGACATCCNTTTTAAANATTGTTATTT
CTTTTTGAGTTTAAAATTTTTGCGGTACTGATAGTTGTAGCTTAATGTTA
TGGTTGGGCAATTATCANAGAATTCCTTTGACTTAATTATATTTTGGATG
AGTAAATCAAAGCATTTTCTGGTTATGCTNAAAAAAAAAAAAAAAAAAAA
AAAA

> SEQ ID NO:26 131048 Contig B Poppy
GAATTCAAACTAGTAGCCATGGCTGTTGCTTCATCGGCTGCTACAGTGGT
TTTTGGGGTTTTATCTTCTTCTCCTAAAAACCTTAAATCTCTTTGCAAGT
TCAAACCTTTTCTCCTCCCTCTACACCCCAATTCACCTCTTACTCAATCC
ACACTTACTTTCTCCGCCCGTAGAAACAACCCCAACTCTGCAATTACTTC
GTCTTCTAAAAAGAAGAAGAACAACAGCAGCAACAGCAATAACAAGAGCA
AGAAGAAGAATTTGACTAAAAAGAGTGAAGTGGAGGTGGTAGATGATATA
GATGAAGATGCTATTGAGGCACTATTTAATCAGCTGGAAGAAGACCTTAA
AAGTGATGGATCCTTTGAAGATGGTGATGATGATTTAACTGAGGAAGACT
TAGCTAGGCTTGAAAAAGAGTTGAAGGAGGCTTTTGGTGAAGATGCTGAT
TTATTTGAAATGTTACAATATAGTGAAGAGGGCATTCAAAACAGTGATGA
TGCTGAAGATGGGGAAGAAGACGAAGAAGATGAAGAAGAAGAGGAAGAAA
TTGATGATGATGACGACGAAGAAGAAGAAGAAAGTCCAGTGCAGCTTAAA
AATTGGCAGCTGCGACAATTGGCTACAGCTTTGA

> SEQ ID NO:27 131133 Contig A Poppy
TTAATTAAGTCGACGAATTCGGTAACCTTTCAGTTTCATTTAGCTCTAAC
AAACTATCATATTAATGGCAACCATGGCTCTCTCTTCTCCATCATTTGCA
GGGAAAGCTGTATCTCTAAACTCACAATCAGAATTCCCAGTCAATGCTAG
ATCCACTAGCAATGGTAAGATCTCGATGAGGAAGACATCCGCAAAGAAGC
CTGCTGCTTCTTCTGGAAGTCCATGGTACGGTCCAGACCGTGTCAAGTAT
CTCGGTCCCTTCTCTGGTGAGTCTCCTTCTTACCTGACCGGTGAATTCGC
TGGTGACTATGGCTGGGACACTGCTGGACTATCARCTGACCCARAGACAT
TTGCCAAGAACCGCGAACTTGAGGTGATCCATTCAAGATGGGCGATGCTT
GGTGCTTTGGGCTGTGKCTTYCCCGAGCTCCTATCAAAGAAATGGAGTCC
AATTCGGCGAAGCAGTTTGGTTCAAAGCTGGATCTCAGATTTTCAGTGAA
GGAGGACTAGACTATTTGGGTAATTCCAGCTTGGTTCATGCACAGAGCAT
TTTAGCTATTTGGGCCACACAGGTCATCCTTATGGGAGCC

> SEQ ID NO:28 131133 Contig B Poppy

Figure 1 continued

TTCGTTCAGGCTATTGGNACTGGAAAAGGTCCCCTAAAAAACCTTNCANACCCCCTTGCCGACCCAGTGAACAAC
AATGCCTGGTCATATGCTACCAACTTCGCTCCCGGGAAGTGANAATATTTGTAACAGTGAACTAAAACGTTTGCT
NTCCCNTCAATGGAAAAATGGGGTTGGNTTCCTACTTTTTCATTAAGATCCTCTGNACATATTTACCGATCCGTT
TCCTCAGTAATANAATCCATTTTTTTTTTGNNAAAAAAAAAAAAAAAAAAAAAAAAAA

> SEQ ID NO:29 131216 Poppy
TTAATTAAGTCGACGAATTCATATGTAGCAAATGTGCAGCAGGCATTGC
AACGTTCAGCTGTGCAACCGAGGAAGACAAGGTCTGGCGCGTCGAGAATG
TCACAACCTGATACATTGAATGCAGAGACACCGCCATCAAAAAAGTTGA
AGAAAAACTGATGATTTTTGGTTAAATGCTCTTTAATTTATTATTTTTGC
GGACGCTTTGAAAGTTGTATTCATTTCTTGTTTCGTTTGCTAATTTTGTC
ATTTAGAAGAAGGTGATGTTTAAGAATGCTTTTACTACTTAGGTATTGGA
ATCATGAAATACTTTAGGTCCGATCTTATTATATCTTTGCCAATACTTTT
AACAAATTTAACAAAAAATCAAGATTGAACAAGTAAAGTGCTATTGAAA
GTAAAGTACTCCTGTACGAAGATGTTCATCATAATGATCTTTGCGTGGAT
TTGGATGAGAATGAGGAACCAGACCAATCTGACAAAGAACCTGACTCATT
TAACAATTTCATTAATTGATTTTTTTAAACAGGGTTTTTGATGTGTGAAC
TTCTAGTTTACGTATGTTTATACGTAAAGCATTAAGCATTACGTCTGACC
AGTTTGTTTTCACTGGTGGTTGTATTTATTTTCTAAGTACTGCACTAGAT
GCATGCTTTTTACGCTGATAGATTAGGTTGACTTTTATGTGATGAATGAT
TCACGCTAAGCTTTTATGTTTTCTGGAAATAATGAACATGAAAATGGATC
GGTTTAGAATTATACGTTTCCTACATAGGTGTCACTAATAATTCATAAGT
TTCCTCCCAAAACCAAGAATAATAATGGAGACAACCTAGTTTAAAAATAT
TAAGGAAAATATTATTCGAAATAGGAAAGTACTATGGCCACTTCACGAGT
TGGCTAGAGATGAAACTAAATTTCGGAAAATTTGGGAAACAATTTTATCA
TAACTGTCCACGATATATTCTCTCGTAAAATAAGGAAACTAACCATATTG
GTTACACATTAAAATTTTGGAAAAAAGAATAAAGAAAAACAATATATTTT
CTCGTAAAATAAGAAAACTAACCATATTGGTTACACATCAAAAATTTGGA
AAAAAAAAAAAAAAAAAAAA

> SEQ ID NO:30 131365 Poppy
GCGGCCGCTTGAGTTTTTCTTTTTTGGTATATGGATGAAAAACTTTCATT
AATTTTTTTTTGAATAAATTAATAAGTTAGACATCAAATGCGAATGCCTG
CATTGTTATGTCATGGGACATGAAACAGTGTTCAAGCATGATATGTCTTG
AGCCATTTCCCGTTGATGACTGCTTCCACCTTGCCTCCATCCACTTTAAT
GATTTTGTAGTACCCAGTGCTGTAAGACTTGGTAACCACATAGGGTCCTT
CCCACTTGGGAGAAAACTTTGGTGCAGACATGTCTTGTTGAATGTGTTTG
GCTGTCTTCAACACTAGATCCCCAACTTTAAAACTTCGTAGCCTTACGGA
CTTGTCATATGCCCTAGAGACTCTGTTTCTGTACACTTGAGCACGTTCTT
CCGCCTTGCTTCTCCTGTAGTCTAGAGTGTCAAGCTCAGCGATTCTGCAG
TTAGACGCCTCAACCTCGTTCCAGTGAACTCCACTTGCCGCTGCGATCCG
GGCTGATGGGATTTTGATTTCTGCTGGGAGAACGGCATCAGTTCCGTAAA
CGAGTGAGTATGGAGATACTCCAATGGAACTCCTGGGTGCCGTTCGGTAT
GCCCACAATGCCATCGGTAATTGTTCATGCCACTCTCTTGCATTGTCAT
GTACTGTCCGGCTAAGAATCCGAATTAACGTCTTGTTGGTGCTCTCAGCC
TGCCCGTTCCCCTGGGGGTAGTAGATGGTGGAGAAGACTTGTTTAATCCC
ATATTCTTCARGCARCTCCCGGACTTGCTTGTWGRCGAAAGGAGTACCGT
TATCTGTAATGATATGTYTAGGTACACCGAAACGAMAGATGATGTGTTCT
TTAATGAARGCTGMAATYGTCGCTCCTGTAGTKCCACGCAGAGGAATAGC
TTCTACCCATYYGGTGAAATATWCTGTYSCGGWTATGATGTATTCGTGCT
GCTTCGATGATGGCGGATTGATCTTTCCAATAATATCAAGTCCCCAGCTA
TAGAATGGCAGCGGACTACTTACTGAATGTAAGGGGTGTGGAARGAGCCG
TGGACAAWGTTTCCCGTGAATTTGACATTTGTGGCAGCTCTGGACGAA
AGCAGCCGCATCGTCCTCCATAGTTGGCCAATAATATTTCTCGTGTATC
TGGAGAAACRATTTTTTCTTTCCTTGATGWTCTCSTTCATGCATCTCTTT
CAAAATGGYTGAAATTTCCGCTCCAGCTAGGCACCGTAGGAGATCACCTC
CAAAACTTTTCCTGTACAGGATTCCTTCGTGGAATACAAAGCGTTTTGCT
CTCTGTTTCATTTTGACCACCTCCTTCGGGGTTACCAGGAACTGCGCCAT

Figure 1 continued

CGCGAAGATAGTTGATGTATGACTGCCTCCAGTCCCCAGTGTGGCTCAC
GTTGAGAATCTCTAGTTGGTGAGGTGGTGCCTGGCAGCTTGAGCAAGATT
GTTGAAGTGTTCGAGATTGTGCTTCCATCTCCGGCCAGTAGTATCCCAAA
CGTTGGAGGCGTCGATAGAGTGTTACCACCAACGTTTGTCCACAAATATC
ATTGTGGACACGATTAAGCTGTAATTGTGCCTCTTCCTCTCCAAGACATC
TCGACAGGGAGCTATCTGGATTCCGATGATAAAGCATGCCATGGAGTATG
AAAAAGTTCTGTAAGGCTTTAAGGCTAACCTTCCCTTGAGAGAGTGAACT
ACTGAGCTCTTGAACAATCGGAGTCCGCCAGTCACGGATTTCAGCGTCCT
TGTGTTGTGAAAGCCATGTCGACTCCACCGTTCTTCTTTTCACCGTCAGG
CTTTCCTCTGTGCCTTCAAACTGCAGCTTGGAAGCCAGCGTTGCTAGAC
AATCGGCGTGTCTATTGTTGTTGCGTCCAACATGAGTCACAGATGCGTCT
GCAAAATAATTCAGCAACCTTTGCGCTTCTGATCGGTATGGGGCTAAAGT
TACGAATTCGTCGACTTAATTAATGRCCAAGAACACGAACTGAGAATGGA
GWAGTGATACTGTAAGATCTATTTAAAACGAATCGGGTTTNTCCAAAGGG
NTTNAA

> SEQ ID NO:31 131371 Contig A Poppy
TTAATTAAGTCGACGAATTCAAAGAGACAGAGGAAACAGCAAAGTTCAAC
RGGACCCTGATGTCTACCCCAACCAGTAGAAGCTCTCTTTGTGACCAAGC
TACTCGTGATATTATCGCCCGCCGCGAAACTGACAAAGCTATTAAGCTAT
TAGACCTTTACAAGTTCTTCCGGAGGCTATTTCCGGCTCCAGCTTTCGGA
TATGGTTGCCGTGACGTAGCAATAGACGAGATGTACTTGCCATCTGTTGT
TTCACCGGAATCATCGACTGTGGAATTTGATACCAACGCCGATGGAAAGT
GTTACCGGAACAAGGAAGCTACCGGAGCAGCTTTTACAAATCATTCTTCT
GTTCACAGTTCTCTTCTAGGTGACGCAATGTCAGACAGGGTGAACTTGCC
AGTTTCTTCTCTATCACTGAAATCAGCCGACCAAGTTTATATCAAAATTG
ATGGAAAGTGTTCTCAGACCAAGGGATGCAGCATCTCTTGAAAATCATTC
CGGTCGCGGTGATTTTCATGTTTGTGATCATCCTAGATGTTCGGTAAAAT
GAAACTAAAGATAGGTTTC > SEQ ID NO:32 131371 Contig B Poppy
GTGCTCCTAATTCTCATACTACATTCTCGCCGAGAATGCCACCCATACAAGAAGGTTATCCTTGCCATCAGCAAT
TCGGCATCATTTCTTTTTATGCTACTTGGTTATGGCCTCGTGATAGGTTTCAATATCCAACGTGCTTGAGCATTT
CAATGTTGAGGTTTGGTTCTTTATCTGCTCATGAGGTTTCCTGCCTGTGTANTGCGNATTTTATTTCTTTGCTAT
GCAGTCTGAGTGATGNTTCCTCTCGGTTTTTTTCATCACTNTANANGCCGTTCCATCGTTATGTTTGTTTTATG
CCCCGTGCAGGCAAGGTCAGNGNTAGTTTGTGTGTCCTAAGTTCTTTGAACAAAAGACAAACTACTTGTATTTTA
ATGTTAGATTTGGTTGTCTAATCAACTATGATCCTTTTTACCTGAAAAAAAAAAAAAAAAAA > SEQ ID NO:33 167306 Contig A Poppy
GAAGATCCACCCGGTAATATTATGAAGAAATGCAATAAAAATAAAGGCTT
GGGAACTCGTTGCAACCACATTTTAGTTAACTAAAATTCTGCAACTTGAT
AAAATAAGAACATTAAATAATTAACACACAAGTCAAACAGAATACAGGTT
AGAAATGAGGATCAATCCATAAAATTGTTGGCTTGTGTCAATCCAAAATG
AAAATATCTTAACAAAGCTAAGGTATTAATCAGTAAGAAACACAAAGTTT
CCCCTGTGTCTACACTTCCTTTCAAGTAGTTCTAATGGACATCCTACTTA
TCAACTTATTAAGTCATGACTAATAATCGAACAATTAAGGTAGTCACACT
ACAACTTAAAGTAAGAAAAACATACAGCTTCCATGTCAACCGTACTAGCT
CAACACATCCATCCCCAATGACTAACTGCAAAATTCACGACTTCTGTTGA
TATGCATATATTAGTATTTCTTTAAACAAAAGGTAAGAAGCATGTATAAT
TAAAAACCACCGAAGGATTGAACTAGCACTACTTATTTAGTCAGTRCAAC
CAACAAGATGCTACGTTTTATGTTGTTAGCCCAACAGAATCCTCTAGAGT
AATTTTTAACACCGTACATACATTATAGATTAAACCAAAACCCTTTTGTG
TGCTTCCTTTACTGTGTTAATTTCCCAACATACCTCGGCACAATGTTTGG
CCACTTTCAAACATTACGCATACGGAGTCCAGGCTAACCCCATTTCCTTC
CTTTTCATTCTAACAAGATCTATAGCATACCGGTACCTGTCGATCGCCCA
TGAGAGAAATCTAGCACGTGTAATTCCAGTACATATAAACAAAAGAATAC
AATCGAAAATCACGATTGATGGCTTAATATAGATGGTTCCATACATAGTA
AACTACTTTCCACTATCTGCAAGAGTAGTGCCAACACTGCAACCTACCAG

Figure 1 continued

AACTAATTAAAATGTTAAGCCAACGTTAACGGATCACCTTGAAACTTTTA
CAGCATATTTACTACACAGGTTACAAAAACATATTCAATATTCAGCAATT
TACAACGGTGCATTAAAAAGATATACACCTTACATCTTGACTGCTTTCGT
TGTCGATTCGCAGAATTCAGTGATGATTTTTCCACATCTAGGGGTACCTA
AAGAAATCGGATCTTCCTGAAATTTTTACAGTAGATTATCTACAGGCCTA
TAAACAACATACAAAAATTTCAACTTGATCCGATAAACAGGTAATGAGAA
ATATCATAAATACTTAACTGTCCAGGGTCTGAATTCTGCACATTGCAGCC
ACAAATTACTCAATCTTCGAACTAGTAAACATGACCTGATTCTCCTGAGA
TTTTTATGGTACCTCTACCGTGTAATTAGTTATTAGATACTAAAATTTCA
TTAAAATCCAACCACCGGATCTTAAATTATCAGTATAATAAAACATGCAT
ACTAGGGTGAATTCGTCGACTTAATTAATGACAAGAAC

> SEQ ID NO:34 167306 Contig B Poppy
ACGACATAAGCGATTACTTTGTGTGGGATGAAGTGGTGGACTACAATCCCATGGTTTGTTCAATTTGCTGCTGGT
GGTGTTGCTACTCCTGCTGATGCTGCTCTGATGATCCAATTGGGTTGTGATGGTGTTTTCGTTGGTTCCGGTGTT
TTTAAGAGTGGTGATCCTGCTAAACGTGCTAGGGCGATTGTGCAAGCTGTGACTCATTATAGCGATCCTGACATT
CTTGCTGATGTTAGCTCTGGTTTGGGTGAAGCTATGGTTGGAATTAACCTTAATGCCCGTAAGGTTGAAAGGTTT
GCTGCTCGGTCTGAATGAATAATCAAAGGCTTTGATTCGACTGAATTGCATTGGAGGTGAGAATTAGACCTCATT
TCCTTGCACACTTTGGTTATTCATAGGAAAAAAAAAGAAAATTTCATATATGAGTGTTTCGTTTTTTATTTGTTC
CCATGTGTCTGGTAGATATAGATAGTCGTGGGGATCTTTTAAAATGTTAGGTGCTCTAGTTTCGTTTCTCTTCTG
TGTAACTGAAGAAGAAGGGTTGTTGTTTTTAAGAATCTTATGGAATGATGTTGGTTCAGATATATTCTATTGAAT
ATTTCCTAAT > SEQ ID NO:35 167361 Contig A Poppy
TTAATTAAGTCGACGAATTCAAAAGGATTCATAAAATCTTTCCCTCATTT
ATGTCTCACAAACCCTAGAAATTAACGATACCCCAAACCCTACCAGAGAA
AAATCAATCTCTTTATTTAAGAGGACAACACAAAGTTGAAATTGTTGCAA
AGAAAGAAGAAAAAAAAAAGTTCGATTGAATTGGAGGTAAAGATGTTTGTG
GAAAAGGAAGATTTAGGATTAAGTTTGAGTTTATGTTCATCAACATCAAC
AACAACAGCAGAGAATAGATATCCATTACAACTAAATCTAATGCCTCCTT
CTGCTGGTTCAGTCTCTAATAATCCTTCACCATTTTTGATTCATCATCAG
AAGACTAACAGTATTACCAATTGGAATGAAGCTTTCGGATCATCTGATCG
GATTACAGCAGAGATGTACAGAGGAGAAACMMGATCATTTTTAAGAGGAA
TTGATGTGAACAGAATGCCATCAACAACAGCAACAGTAGATTGTGAAGAA
GAAGTAGGAGTTTCATCACCAAATAGTACAGTTTCGAGTATAAGTGGGAA
TAAAAGAAGAAGTATCGAAAGAGATACCATAAATTGTTCTGGTGGTGATG
GGGAAGATAATGAAATCG > SEQ ID NO:36 167361 Contig B Poppy
GACACCACCAGCAACAAANAGCCTTGCCCACCAATCCTTGGGCCCAAACTCCTGTTGTCTTTAGAAAATGAATAG
TTTAGTTAGTTGTTGTTAGGATCTAGGAGATTAGTCTTAGTTTTACTTTTATCTCCTTTTTGGTTTTATTGGGTT
NTTTATTTAANCTTGNGACTCCTTTCGGTTTTCCATNTACTTTTTGGAGGAATTCCAAAGTTAGCTTGTGAAAGG
CAATAGATGAAAAAAAACCTCAACTCTTTTTTTGTCATATGGAAAATAGGTTTGGGATGTAAAGTTTTATCAAAC
TGAAATTCTGAAGTTTGAATTAATTTCTAATTCAATGAAAAGAAAAAAAGAAGTATGTTAATAGTAAGAAAAAAA
AAAAAAAAAAAAAAAAAA > SEQ ID NO:37 167373 Poppy
GTGTTCTTGTCATTAATTAAGTCGACGAATTCACACAATCACACAATTACTGGATTAGCAGTTGCACTGAAACAG
GCAACTACCCCAGAATACAAGGCTTATCAAGAACAAGTGCTCAAAAATTGCTCACAGTTTGCCAAAACCTTGAAC
GCATTGGGATATGACCTTGTTTCCGGTGGTACTGAAAACCATTTAGTCTTGGTCAATTTGAAAAACAAGGGTATT
GATGGCTCAAGAGTTGAGAAAGTAATGGAATTGGTTCATATCGCTGCTAACAAGAACACTGTTCCCGGGGATGTC
TCTGCCATGGTTCCTGGTGGCATTCGAATGGGAACACCTGCTCTCACTTCAAGGGGATTCCTTGAGGAAGATTTC
GCTAAAGTAGCAGAGTTCTTTGATGCTGCTGTGAATTTGGCCTTGAAAGCCAAAGCTGAATGCAAAAAAGGTGCA
AAATTGAAGGACTTTATGGCCGCGGTTGAAAACAGTGCTAGCATTCAGTCTGAAATTAAACAGCTCCGTCATGAC
GTTGAGGAATATGCAAAGCAATTCCCTACAATCGGGTTCTGCAAAACAACAATGAAATACAAGCAATAAACTCCA
CTATTATAAGTGGGCATATATGCTTCGGTAGTGCAGTGGAGTSTCTACAAAGGCGAATGAGATGGACACGGGAAG
GGAGCAAACTGCCTTTTAATGTAGGGAATATATGAATGCTTTCAATCAGTGAATGGGATATATTGTTGACACTAC

Figure 1 continued

AGGGTTCTAAGCATGAAGAGAGTACCATTTGGTTCAAATTTCATTCTTCATTCAAGAATTGAATTATATGTATAT
TATTAAACTTGATCAATTATAATGCAACAATATAAAGCTTGTCCCAAAAAAAAAAAAAAAAAAAAAAAAAAA

> SEQ ID NO:38 167516 Poppy
TTAATTAAGTCGACGAATTCACAACAACAACAACAAGAGAAGTAGATTAA
GCAGTTAAGGTAGAGAAACAAAGTTGAGGAGAACGGCCATGGCAACCTCT
TCTATGGCATCTGCAGCATCTGGTTTTGTGTTAACATCTAGTCTTTCCTC
CACCACCACCACAACCTCATCCAGGAGCAGCATATACTTCCAAATAAGAA
CTAACAATAACTCAAGGCTCGTTGTTCGTGCAGCAGATGAAGCCGCCACC
CCTGCCCCAGCTGCTGCTGCCGCTACTAAAGAAGCTGAAGCTCCAGCCGC
AGTCAAGAAACCTCCTCCAATTGGCCCCAAGAGAGGCACTAAGGTGAAGA
TTCTCAGGAAGGAATCCTATTGGTACAACGGCATTGGATCAGTCGTAGCT
GTTGATCAGGACCCAAAGACTCGCTACCCAGTCGTCGTCCGGTTCACCAA
GGTCAACTATGCTAATGTCTCTACAAACAACTACGCCTTGGATGAGATTA
CGGAAGTGAAGTGATGAGTAATCAGCAATCCAAAAATGTTGAATTTGTAG
CTAGCTAGCTTATCCTATCAAGTCTTTGTATTATACCTTGTTCCGTGTGA
TCTATTTTTCTGTATTCTTATTTATATTTTCAACAAATTCCAGTGAAGTC
GAACTGAAATGCATAATCACTCAAAAAAAAAAAAAAAAAAAAAAAAAAAA > SEQ ID NO:39 168165 Poppy
GAATTCAGGACTCTATAAGTCTTCAGGAAATGGCGTTACACATTGCGAAG
CTGAGGGTTTCAGGAAGATAACATATTACCAGGATCGCCCTGACGTGATG
GCTAAGTACACTTGCAGGGTTGAAGGCGACAAGGCGCTATATCCAGTATT
GCTGTCGAATGGAAATCTCATAGAACAAGGAGATCTCGAGGGTGGTAAGC
ATTATGCAGTTTGGGAGGATCCACACAAGAAACCATGCTACTTGTTTGCA
TTGGTTGCTGGACAGTTGCAGAGCAGGGATGACTCTTTCGTCACTCGGTC
GGGGAGGAATGTGTCGCTTAAGATTTGGACCACCGCACAGGATTTACCAA
AAACTGCTCATGCCATGAATTCACTCAAGGAAGCTATGAAGTGGGATGAG
GATGTTTTTGGTCTTGAGTATGACTTGGACCTTTTCAACATCGTAATGGT
TGCAGATCTTAA > SEQ ID NO:40 168550 Poppy
TTAATTAAGTCGACGAATTCATGTAAGAGGTCTTTCTGTTTAATATATTC
TATTATCTTTGTTTAAAAAAATAAAAAAAGAGTTCGTACGTCTTTTTGTC
CCAAACTAACGGCAGGAAAAAGGTGGATAACCACCGTTAGGCATTTTGGT
CAAAACTGGCCTACTTTTGTTATGCGAAAGCAAACAGGCCTAGAATTGTA
ACCCTCAAAAAAAACAGGCCTATATCTGTTTTTTACCCAACTTTTTATAC
AAAGATTTAAGAAAAGAAGCAGCCAGGATTGGTTTAGAAATGAACAGCGT
CCTTACTTACATCTTTGAAAAGAATTTTGCCAATATCAAAGTTCACTTCT
GGATTGACAGTGGCAAGCTTCATTGATAGGAACTACAAAAAGAAAAGAGA
TAATGAATAAATCAATTTGGTCTAACTCATCTTACTTCTTACTTGAATCA
AGTTCTAAATCAATTTACAAAATCTGGGGAAGAACAAGACGAACCCTAGT
TCTCAATTCCACCACCGRAAAAACAAGAAGTGAAGATGAATAGTTCTCAA
TTTCATCAAGTGATGGATGCTCAATATTTATGGTATTAAAAACCCGTCTT
GTAATACTATCTAACTCATCTTACTTCTTACTTGAATCAAGTTCTAAATC
AATTTACAAAATCTGGGGAAGAACAAGACGAACCCTAGTAAGAAGTAAGA
AGTAAGAACTTGCTTCACAGATTTAATTGAACCACAACCCAATCGTTATT
AATCATCTAACAATAACCCAAATAATCTCTCAATCCTGCACAAACCCTAA
CCAAAATCCCTAACTTCTGATTCTCTAATCTCCAATCTCACATCATGTTG
ATTCTGATTATGAAACATAATAATCTTTACCACCTGATACACCTCATGAA
TCAAACCCTTATTAATTCTTCTTTCAAACCCTCAGTTTGATTCCTCAAAC
TCTCAACAGACATAGAACATGAAARRAAAAAAAAAAAAA > SEQ ID NO:359 129870FL *Poppy*
TTAATTAAGTCGACGAATTCAGAGGCAGATAGAGAGAGAGACAATGGCAATGGCAACAAGTAGGTTGATGGTGGT
GCAACAAAAACAACCATCCTCATGTCTATTACCACCATCATCTCTTTCTGACTTCAATGGTATTAGACTGAAACA
CCCAATTCAGTACAAAAGAAAGGAATGGCAGACAAGAGGAGCATTGCAGGTGAAAGCATCAGCTGCAAAGAAAAT

Figure 1 continued

CCTGATTATGGGAGGAACCAGATTTATTGGTATCTTTTTGTCTAGGCTCCTTGTGAAGGAAGGTCATCAAGTAAC
TTTGTTCACAAGAGGGAAAGCACCAATCAGCCAACCATTACCCGGGGAGTCGGAACAAGATTACCTAGATTTTTC
TTCCAAGATTTCCCACTTGAAAGGAGACAGAAAGGACTATGATTTTGTTAAGACTAGCCTAGCAGCTGAAGGCTT
TGACGTTGTCTATGATATCAATGGAAGAGAGGCAGAAGAAGTAGAACCCATATTGGACGCGCTTCCAAAGCTTGA
GCAGTACATATACTGTTCATCCGCTGGTGTGTATCTGAAGTCTGATTTACTGCCTCATTTTGAGTCTGATGCAGT
GGATCCCAAGAGCAGGCACAAGGGAAAACTTGAAACAGAGAGTTTACTTGTATCAAAGGGCGTGAACTGGACTTC
GCTGAGACCAGTTTATATCTACGGTCCTTTGAATTACAACCCTGTTGAAGAATGGTTTTTCCACAGATTGAAGGC
CGGTAGACCAATCCCCATACCAAATTCTGGCAACCAGATAACACAATTGGGTCATGTTAAGGATTTGGCGACCGC
ATTTATTAACGTTCTTGGTAACGATAAAGCGAGCCAGCAAGTGTTTAACATATCTGGAGATAAATATGTGACATT
CGACGGATTGGCAAGGGCTTGTGCTAAGGCTGGTGGATTTCCTGAGCCAGAACTAGTTCACTACAATCCTAAAGA
ATTCGATTTTGGCAAAAAGAAGGCATTCCCCTTCAGAGACCAGCATTTCTTTGCATCAATTGAGAAAGCAAAGAG
TGAATTGGGGTGGAAACCAGAATATGATTTGGTGGAAGGTCTAACAGACTCCTACGATCTTGATTTCGGTAGGGG
AACTTTCAGGAAAGCGGCTGACTTCTCAACTGATGACATGATTCTTGAAAAATGTCTTGTTCCACAATAATTTAA
GCTTTCCATTGTATGAAATTCAAGTAGGCATTTATGATTGTTTGTGAGTCTACCGAAGGTTATAGCTATCATTCA
ACTTTTGAACATGGGAAAGGACAATCTTGTTTCCAGCGTATGTTTCTTGGCAGATAATAAAACACAGCTTTTTAA
ATAAAAAAAAAAAAAAAAAAAAAA

> SEQ ID NO:360 130294FL *Poppy*

TTAATTAAGTCGACGAATTCAAATTAGGTCTAAAGATGGCGTCTTTAGCTCAACAATTCTCAGGATTAAGATGCC
CACCACTTTCTTCTTCTCATCTAACAAAACCCTTTTCTTCAAAACCCCAGAAAACCACCTTTTCACCTATAGTTT
CAGCAGCTGTCATTTCTAATGCACAAACTAAAGAAAGAAGTAGACTTAAAGAAATCTTCGAAGATGCTTATGAAA
GATGTAGAACTACTCCAATGCAAGGTGTTGGTTTTACTGTTGATGATTTTCATGCTGCTCTTGAAAAGTATGATT
ACAATTCTGAGATTGGTACCAGGGTTAAAGGAACTGTGTTCTGTACAGACAACAACGGAGCATTAGTTGACATCA
CGGCGAAATCTTCAGCCTATTTACCAATCCAAGAGGCATGTATTCACAAAATAAAGCATGTAGAAGAAGCAGGAA
TAGTTGCAGGCCTACGTGAAGAGTTTGTGATTATTGGAGAGAACCAAGCTGATGATAGCTTGATCTTGAGTTTGC
GTTCAATCCAATTTGACCTCGCATGGGAACGGTGTAGACAACTTCAGGCAGAGGATGTCGTCCTCAAGGGTAAGG
TTGTTGGTGGAAACAAAGGCGGTGTGGTGGCAATTGTCGAAGGCCTTCGTGGTTTTATTCCATTCTCACAAATAT
CTTCAAAATCAACCGCGGAAGATCTCATTGATAAGGAGCTTCCTCTGAAATTTGTGGAAGTTGATGAGGAGCAGT
CTAGACTTGTCCTCAGTAATCGCAAGGCCATGGCAGACAGCCAGGCACAGCTTGGTATTGGATCAGTTGTCACTG
GAACAGTACAGAGTCTTAAGCCATATGGCGCTTTCATCGACATTGGTGGAATCAATGGTCTTCTTCATGTTAGTC
AAATTAGTCATGATCGTGTCTCGGATATTGCAACAGTTCTTCAACCCGGCGACACTCTAAAGGTGATGATATTGA
GCCACGACCGTGAGAGAGGCCGAGTCAGTCTATCCACCAAAAAGCTAGAGCCTACTCCAGGAGATATGATCCGTA
ACCCCAAGCTTGTTTTCGAGAAGGCTGAAGAAATGGCTCAGACATTCAGGCAGAGAATAGCTCAAGCAGAAGCTA
TGGCCCGTGCGGACATGCTGAGATTCCAACCCGAGAGTGGATTGACTCTAAGCTCAGACGGCATCTTAGGTCCCC
TGACGCCAGACTTGCCTGCTGAAGGTCTAGATTTGAGCGACATTCCTGCAGCTGATGATGCATAGAAACCAATAA
ATATGAATTAAATCTGTCTTGACGTTTCTTCTCATCACCATTTTTAGGCTATGTAAGATGGGTCTATAGGTTGTT
CAAAGTGTTGACTTGTGTATTTATCTTGATAGTTCAAAGTGTACTTCTTTAAGCGATAATCATTGAAAAGAAAAA
ATGGAGAAGGTAAAAGATAAAAATATCCAAAAAAAAAAAAAAAAAAAAAAAA

> SEQ ID NO:361 130994FL *Poppy*

TTAATTAAGTCGACGAATTCACATCTAAAGTCAACAACAAGAGCTTCTCTCTTCTCCTCGTCTCTGTTCTCCTCT
CTTTTGCAATCCTCTCTCAATCTGCTGATGATTGTGTATACACAGTATACACAAGAACAGGATCAATCATCAAAG
GAGGAACGGATTCAAAAATCTCACTAAGATTATACAGCAAATACGGTAAGTACATCGAGATCCCAAATCTTGAAT
CATGGGGTGGATTAATGGGTCCTGGTTACGATTATTTCGAAAGAGGTAATCTTGATATCTTCAGCGGAAGAGGTT
ATTGTCTGGGTTCACCGGTTTGTGCCATGAATCTGACTTCCGATGGTACTGGTTCCGGTCACGGATGGTATGTGA
ATTATGTTGAAGTTACTACTACCGGTGCACATATTAATTGTGGTCAACAGAATTTTGAAGTGGAAGATTGGCTTG
CTCTTGATAGATCTCCTTATAGTCTTACCGCTATCAAGAATAATTGTAATCAGAAATTATCTGATCATGATTCTC
ATTCTGCTGATCAGTCTATGTAAAATTTGATCTCTTGTTTGATTCGGTGGTGGTCTAGTATGAGTGATCGGACGG
TCGTCATTGTGTGTTGTAATGTTGAAATTATTTCTTGAATAAAATGATTGAGTGAGTAGTGTTTGATTTTGCTT
GGCCATCTTAGACATGATGGTGAGACTGTTTCTCGATTCGATGCAATTTTTTGGTTTTCTTGGTTGCAATCAATT
CACGTTTGGTGAAAAAAAAAAAAAAAAAAAAAAAAAAAAAAAAAAAAAAAAA

> SEQ ID NO:362 129424FL *Poppy*

GAATTCAATCAAATGGCTACTGCTAGAGTTTTAGCTGCTAGTATGTTGCATGAATGCAACAACACTCACAGTGCT
TCATTTCTTTTGAGACAATCTTCTTTCATCTTACCTATTAAACATCAAAGTATTAATTTCAGTAGAAGAGCATCT
TCTAGGAGAGCTTTTACTTGCAAATCTCTTTACAAACCTGAAATTCAAATCAAACAAGAAGGTGAACCTCAAACC
CTAGATTACAGAGTCTTCTTTCATGATAAATCTGGCAAAAAGCTTTCACCTTGGCATGATGTACCATTGCAATTG
GGTGATGGAGTGTTCAATTTTATCGTGGAAATACCAAAAGAGACAAGTGCAAAGATGGAAGTTGCAACTGATGAG

Figure 1 continued

CCATATACTCCCATTAAACAGGACACCAAGAAGGGAAAACTTAGATTCTACCCCTACAACATCAATTGGAACTAT
GGATTGCTCCCACAGACATGGGAAGACCCAACAGTAGCTAATTCTGAAGTTGAAGGGGCATTCGGAGATAATGAT
CCAGTTGATGTTGTTGAAATTGGGGAGAGGCAAGGAAAAATTGGCGAGATTCTTAAAGTCAAGCCTTTAGGTGCT
TTGGCTATGATTGACGAAGGAGAACTCGACTGGAAAATTGTTGCGATTTCGTTGGATGACCCAAAAGCTTCACTC
GTCAATGATGTTGGTGATGTTGAGAAACATTTCCCGGGCACTCTCACTGCTATAAGAGATTGGTTCAGAGACTAC
AAGATCCCAGATGGAAAGCCTGCCAATAAGTTTGGACTTGGGAACAAAGCAGCCAACAAGGATTATGCTCTGAAG
GTAATAACTGAAACCAACGAAGCTTGGGCTAAACTTGTCAAGAGAACTGTTCCTGCTGGGGAGCTCTCCCTTCTG
TAAATTTTGAATTTTTAAAAGTTGAAGATAAGAGGCACTTTGGCCCGCTCCTATCCCCCTCCTCTCTCTATTGTT
TTCTTTCATGCTGGATTCCAAACAAACTTCCTCCAATTTTTTGGACGAAGTATTGATAATTTCTAATCATTGAGC
TCCATTTTTCAAAAAAAAAAAA

> SEQ ID NO:363 232732FL *Saleginella lepidophylla*
TTAATTAACTCGACCCACGCGTCCGCACCACGAGAAAAAGCTCTCCCTTTGGGCTCTCCCAAACCCTAGGAAAGC
AAGGGCGGCAGCGCACGGCGAGGAACAGGGATGTCGAATCTTCGCGAGGAGAATGTCTACATGGCCAAGCTCGCG
GAGCAGGCCGAGCGCTACGACGAGATGGTGGAATTCATGGAGAAGGTGGTCAAGGCCGTGGACGTGGAGGAGCTG
ACGGTCGAGGAGCGGAATCTCCTGTCGGTGGCCTACAAGAACGTGATCGGCGCCCGCCGGGCATCGTGGAGGATA
ATCTCCTCCATCGAGCAAAAGGAGGAATCCAAGGGCAACGACGAGCACGTCTCGATGATCAAGGAGTACCGTGCC
AAGGTGGAGTCGGAGCTGAGCACCATTTGCGACAGCATCCTCAAGCTGCTGGACAGCCATCTCATCCCCTCATCG
TCCAGTGGCGAGTCCAAGGTCTTCTACTTGAAGATGAAGGGTGACTACCACCGATACTTGGCCGAGTTTAAGACC
GGGGCCGAGAGGAAAGAGGCCGCGGAGAACACTCTCCTCGCCTACAAGTCGGCCCAGGACATCGCTCTCACACAG
CTGCCGCCGACGCACCCCATCCGGCTGGGTCTCGCTCTCAATTTTTCGGTCTTCTACTACGAGATTTTGAATTCG
CCCGATCGAGCTTGTACGCTTGCCAAGCAGGCATTTGACGAGGCCATAGCCGAGCTGGACACTTTGGGAGAGGAA
TCTTACAAGGATAGTACTCTGATCATGCAGCTGCTGCGCGATAATCTAACGCTGTGGACCTCAGACATGCAGGAG
GAAGGTGCCGGCGAGGGGAAGGACGAGAAGCCGTGAGTAAAATAATACGTTCGAATTTCGTTTTCTATGCTACTA
GCTAGCTGTTTAGACGCCTTCTCTCTCAACACCTTGGTACTGTTGATTCTTTTGTTCCTGAATACATTATTTGGC
TTGCACTAAAAAAAAAAAAAAAAAAAAAAAAAAAAAAA > SEQ ID NO:364 238465FL *Saleginella lepidophylla*
CTCGACCCACGCGTCCGCGAAGAGTGAGTTGATCGAATAGATTTGATTCCTTTCTCTTGGTAGGGAGAGCTGGCG
ACGAAAGGGTTGGATCACGCAGAGTTTCCACCACGGCTTTGAATTCCAGGCGTCGCGATTCCCTGGTCGGTGTGG
ACGCTGCCAGGAGCTTGTGCGTGGTAGCGCGCCTTGCCAGCTTCCACGGTGGTCGCGGCGCAGCTCCGGCTGCCG
GAGGTCGCCCCTCGGATCTCTTGAACTTGGCCGGCGGCGGTGTTGCCCTCCCCTCTTGCTCTTGGTCGCTGCCAC
CTTTCCGGGGCATCGATCAGTGAGCTTGTAGAGAAGTGAAGTTTAGTCCTTTCCAGCCAAAAGTTGGATTTTTTT
TTTTCCCTTTTCCTCCGCCATGGACAAGGTTTTGAAGATTCGAAGGATTCCAACCATTGTGTCCAATTACCAGGA
GAGCCTCGACTTCCAGTCCGGATGTGGCAAGAATTGTCTCGGGTCGTGTTGCATTCCTGGAGCAAAATTGCCATT
GTATCTCTTTGGCAAACCGGATGTGGATGAGAGTGGAGAAGTCCCTACCAAGGAGCTGGGACAAAACTCTTTCCT
GGATTCAGCTATTCTCGGTCAGTGGGCTGATAGGCAAGCCAAGGGACTATTTCGCTACGACGTTACCGCGTGCGA
CACAAAGGTGCTGCCTGGAAAGTATGGTTTTATTGCGCAATTGAATGAAGGCCGACACCTGAAGAAACGTCCCAC
TGAATTCCGCGTTGATCAAGTCCTCCAGCCTTTCGATGCAAAGAAGTTTAACTTCACAAAGGTCGGTCAGGAGGA
GATGATCTTTTGCTTCGAGCAGAGCCACGAGGACAAGAGCTTCCACCACGAACAAGCTCAAGTGAAAGGAAGTCC
AAACGTTGTGGTGATCAACGTGAGCCCGATCGAGTATGGACATGTTTTGCTGGTTCCTCGAGTTCTCGATTGTAT
CCCGCAGCATCTGGAGACGGATACTTTCCTTTTGGCTCTTCATATGGCTGCAGAGGCATCCAGTCCATATTTCCG
CTTGGGATATAATAGTCTTGGAGCTTTCGCGACGATCAATCATCTCCATTTCCAGGCATATTATTTGGGAAACAT
CTTCCCCGTGGAGAAGGCTCCACAGAAATTAATATACAGTCACAGCAAAGGTTTCAGGATTTACGAACTGGAGGA
TTATCCAGTCAAGGGCCTTGTTTACGAGCTTGGAACAAGCAGCTTTGAAGAGCTTGCGTTTTACGTGGCTAAAGT
CTGCAAAGCTCTCCAAGGTCGAAACATCCCATATAACGTTCTCATTGCGAACAAAGGTTCACGAGTATTCTTATT
TCCTCAGTGCTTTGCGGAGAAACAAGCACTCGGCCAGGTTGACGTCGAGATACTGGAAACTCAAGTCAATCCCGC
GGTGTGGGAGATTAGCGGCCACATCGTGTTGAAGCGCAAGGAAGATTACGAGCGAGCTACAGAGGAATACGCATG
GAAGCTGCTGGCCGAAGTTTCTTTGACTGAGAAGGCATTTGGCGATATATCGAAGCTTTGCATCAACTCAGCCGA
GGACAAGTTTGACGACAGGACTCACGAAAAGAACGAAAAGAGCTCGTGTTCCACGGAGATCACGTATTATACAAC
TGGAGAAAACCATATTATTGTGGTATAAGATAAAAGCAAGAAAAAAAATAAATATATTAGTTAGGAAAATGCTCA
AAAAAAAAAAAAAAAAAAAAAAAAAA > SEQ ID NO:365 273716FL *Nicotiana benthamiana*
ACGCGTCCGTGCCAATTCCATTCCTCTACATCTTCTTCTTTTCCTTACCAATCCACCTCCAATCTCTTTGAAATC
AAGTTACAGAAATCTTTTGTTCGTGTAGGAAATTCGAGAAATCTTAGAAAAAAAATATATTATTGCTGTTTAGAA
AGGGTAAATCCCAGGTGAACAAGTTGTAGACATCACGGCTATACACAAAGCAAACCGCCGACCATTCTTACATGT
TCGTTCAGTACGACGTAAGGGTTGTGTAACTGCCACCAATCCTGCGCCGCACGGCGGACGTGGCGCTTTGCCCTC

Figure 1 continued

TGAAGGCGGTAGTCCTTCCGACCTCCTCTTCCTTGCCGGCGGTGGTTCTCTCCTTTCTTCTACCTGCTAGATTTA
CTTACTTATATACCTTACATAGTTAATTCCTTCTCCGTAAATTACTAATTGTTTTGCACATTAGCAATTATTAAG
GTTGTTCTTGTACCTAGTATTTTTACCTTGAAAAATCAAAGGAAAAAAAAGCAAACATGATGCTCAAGATTAAGA
GGGTTCCTACACTTGTTTCCAACTTCCAAAAGGAAGAGGCTGAAGAAGCTCTTGCTCGTGGTGCTGGCTGTGGCC
GCAATTGCCTCCGAAACTGCTGCCTTCCAGGGTCAAAGCTGCCACTGTATGCTTCCAAGAACTTGAGAAAGGGCA
AGTCTGTTGCCGATGAAACCAAGGAGCCTCCTGTTGACTTCTTGGAATCCCTCCTTCTTGGAGAATGGGAGGATC
GTCAGCAGAAAGGTCTCTTTCGCTATGATGTCACTGCTTGCGAAACCAAGGTTATTCCTGGAGAATATGGTTTCG
TTGCTCAGCTGAATGAGGGAAGGCACCTCAAGAAGAGGCCAACTGAGTTTCGCGTTGATAAGGTGCTGCAGCCTT
TTGATGGAAGCAAGTTCAACTTCACTAAGGTTGGTCAGGAAGAGTTGCTCTTCCAGTTTGAAGCAAGTGAGGACA
ACGAAGTTCAATTCTTTCCAAATGCACCCATTGATGCCGAGAAATCTCGAAGTGTTGTTGCCATCAATGTCAGTC
CCATTGAGTATGGACATGTGCTTTTGATCCCTAAGGTCCTTGAATGCCTTCCCCAGAGGATTGACAGGGACAGCC
TATTGCTTGCACTGCACATGGCTGCCGAAGCAGCTAACCCATACTTCCGATTGGGTTATAACAGCTTGGGTGCAT
TTGCTACCATCAACCATCTTCACTTTCAGGCCTATTACTTGGCTGTGCCATTCCCCATTGAGAAGGCCCCCACTC
GGAAGATTACCTTTGCTGATGCTGGAGTGAAGATATCTGAGATGCTGAATTATCCAGTTCGAGGACTTGTCTTTG
AGGGTGGAAATACTTTGGAGGATTTCGCCAATGTTGTCTCTGGTTCTTGCATTTGCCTGCAAGAGAATAACATTC
CCTACAATGTTCTAATCTCTGATTCGGCAAAAAGGGTATTCCTTCTCCCACAGTGCTACGCAGAGAAACAGGCTC
TAGGGGAGGTCAGCTCTGAACTGCTTGATACTCAAGTCAATCCTGCAGTATGGGAGATTAGTGGACACATGGTCT
TGAAGAGGAAGGAGGATTACGAGGGTGCAACCGAGGCAAATGCCTGGAGGCTTCTCGCTGAGGTCTCACTTTCTG
AAGCGAGGTTCCAAGAAGTGACTGCTCTCATCTTTGAAGCCATTGATTGCAGTGTTGAAGAGAATGAGAATGCCA
ATGAAGGTTCTCCTGAGAAGCCAGATGTTGCACCTCAGCCTATGGAGGAAATTGATGCTCTCAACACCCATGCTA
CCATGGTTCCCGTGTAGGGTTTTCATGGTCGAGCTGTGGTGTTTGTCCTGTTGTTACTATTTCAACTATATGAAC
ATTGAGGGAGTTTCTATCTATGGCTGCACTTGTGAAATATCCCTAAATAAGGCTAGCCATGTTCTATGTATTGAT
GAAGTTGTTTGGTTCCTATGTGAATTGAACCTTGTCTTTTATTGCTTCATATTAATGTGGAGTTGCTCAGTGTCC
TCTGGGAATTGACCTTGGATACTATGTTTGTTGTCTGTTATTTAAGACAATATATTTGGTAATGGAAGTTGGAGT
TTCCCTGAAAAAAAAAAAAAAAAAAAAAAAAAAAA

Figure 2

*This file describes the contig sequences of internal DAS clones that have homology to any given claimed hit contig with a Pz score ≤ 1 x e-20. Each entry header contains the contig identifier in the following format: hit contig name; homolog contig name.*

> SEQ ID NO:41 129424 210913
GAGAAAAGCAGCGACTCTTCGTCTTCGTCTCCAACCACCACAATGTCTGGCTACACCGTCCGCAAGGTTGCTGCC
CAGAACACTCTGGAGCACCGCGTCTACATCGAGAAGGATGGCGTCCCCGTGTCGCCCTTCCACGACATTCCTCTC
TTTGCCAACCAGGAGCAGACCATCCTGAACATGGTTGTCGAGATTCCTCGATGGACCAATGGCAAGCTCGAGATC
TCCAAGGAGGAGCTCCTTAACCCCATCAAGCAGGACGTCAAGAAGGGCAAGCTTCGCTTCGTCCGCAACTGCTTC
CCCCACAAGGGCTACCTCTGGAACTACGGTGCCTTCCCCCAGACCTGGGAAGACCCCAACACCGTCCACCCCGAG
ACCAAGGCCAAGGGTGACAACGACCCTCTCGATGTCTGCGAGATCGGTGAGCTTGTTGGCTACCCCGGCCAGATC
AAGCAGGTCAAGGTCCTCGGTGTCATGGCCCTTCTCGACGAAGAGGAGACTGACTGGAAGGTCATTGTCAttgaC
GTCAAcgaaccccttgatCCTAAGTTgAACGaCgTTGAGGACGTCGagcGCCACCTgactggCcTg

> SEQ ID NO:42 129424 224082
AATGTCTACCTACACTACCCGGTCCATTGGTGCCCCCAACACTCTCGACTACAAGGTCTACATTGAGAAGGACGG
CAAGCCCGTTTCCGCCTTCCACGACATTCCTCTGTACGCCAATGCTGAGAAGACCATTCTCAACATGATTGTCGA
GGTTCCTCGATGGACCAACGCCAAGATGGAGATCTCCAAGGACCTTGCTCTGAACCCCATCATCCAGGACACCAA
GAAGGGCAAGCTCCGATTCGTCCGAAACTGGTTCCCCCACCACGGATACATTCACAACTACGGTGCTTTCCCCCA
GACCTGGGAGGAACCCAACCACGTCCACCCCGAGACCAAGGCCAAGGGTGACAACGACCCGCTCGACGTCTGCGA
GATCGGTGAGACTGTTGGCTACACTGGGCAGGTCAAGCAGGTCAAGGTCCTCGGTGTCATGGCTCTCCTCGACGA
GGGTGAGACTGACTGGAAGATCATCGCCATCGATGTCAAGGACCCTCTTGCCTCCAAGGTCAATGACATTGAGGA
TGTTGAGCGACACCTGCCCGGTCTTCTGCGAGCCACCAACGAATGGTTCCGAATCTACAAGATCCCTGACGGAAA
GCCCGAGAAC

> SEQ ID NO:43 129424 243145
AAATCATTTATTGATTTAATCTCCTTTTTCCTTTATCATAATGCAAAGAATCCATTAAGAGAAGCACTTCAAACG
AGCGAGAGATCCCCCGCCGGGGCAGACCTTGTCACAAGCTTCACCCACGCTTGATGCGTCTCCTGGATCACCTTG
AGCGCGTACTCCTTGCCAGCAGCCTTGTTCCCCAGCCCAAACTTATTCTGCGGCTTCCCATCCGGCACCTTGTAG
TCGCGGAACCAGTCCCGGATCTCCATCAGCGTCCCGGGAAAGTACTTCTCCACATCACTCTCATCGTTGAAAAGC
CCAGCCCTGGGATCATCCACGGAGATGGCCACCACCTTCCAGTCCAGCTCCCCCTCATCGATCATCGCCAGCACC
GCCACCGGCTTCACTCGAAGAACTTCCCCACGCCCCGCCTTTCGCTCGCCGATCTCGACAACGTCGACCGGATCA
TTGTCACCAAGCGCTCCCTCCACATCCGGGTTGGCGTGGTTTGGATCTTCCCAAGTTTGCGGAAGAAGCCCGTAG
TTCCAGCGTATGTCGTATGGATAGAACCGTAGCTTGCCTTTCTTCACGTCCTGCTTGATCGGCGT

> SEQ ID NO:44 129424 227659
GTCGCTCCGCCGCCGCCGCCGCTGTTCACTCCGCACCAACTCCGACGATCCCCCGGCGAGCTCTCGACGATGGCG
ACGGCGGCGACGGCGTCGGCTACGGCGGCCACCCGCTTCACGCGGCTGGCGGGGGTCGGCTCCGGCGCACGGCC
CGCCTCCCCACGGCCGTGCGGTTCCAGCGCCGGGTGCTCGCCACCACCGCGCTCCTCAGGACCGCCGAGCTCCGG
CCCAAGGAGCAGGGCCTGCCCGAGACGCTCGACTACCGCGTGTTCCTCGTCGACGGCGGGGCCGCAAGGTTGTC
GCCGTGGCACGACGTGCCCCTGCGCGCAGGCGACGGGGTTGTTCCACTTCGTCGTGGAGAATCCCAAGGAGAGCA
GCGCCAAGATGGGAGGTCGCCACCGACGAGTCATTCACCCCCATCAAGCAGGACACCAAGAAGGGCAACCTCCGA
TACTACCCGTACAACATTAATTGGAATTATGGATTATTTCCCCAAACATGGGAGGACCCAACTCTTGCAAACACC
GATGTCGAAGGAGCATTTGGGGATAATGATCCTGTTGATGTTGTTGAGATTGGTGAAAGACGTGCTAACATTGGA
GATGTTCTTAAGGTAAAACCGTTGGCAGCTTTAGC

> SEQ ID NO:45 129426 190609
cccccccccgtttcactcatccgccgctgagctctatctatctACTAGTTAGTTTAGTCGTCTCGAGGGTAAATT
GAGCTTTGTGTGCGGTTTTGAGGGGAGTACATCGGCATGAGGATCCAGTGCGACGCGTGCGAGGCCGCGGCGGCC
ACGGTGGTGTGCTGCGCGGACGAGGCGGCGCTGTGCGCGCGCTGCGACGTCGAGATCCACGCCGCCAACAAGCTC
GCCAGCAAGCACCAGCGCCTCCCGCTCGACGCCGCGCTCCCCGCCGCCCTCCCGCGCTGCGACGTCTGCCAGGAG
AAGGCGGCGTTCATCTTCTGCGTGGAGGACAGGGCGCTCTTCTGCCGGGACTGCGACGAGCCCATCCACGTCCCG
GGGACGCTCTCCGGCAACCACCAGCGCTACCTCACCACCGGCATCCGCGTCGGGTTCAGCTCCGTCTGTAGCGCC
AACGCCGACCACCTCCCGCCGCCAGCGCCCAAGGGGAACTCCAAGCCGCCGGCAAGCGGCATCGCTGCTGCTGCT
GCTCCCAAGCCGGCCGTGTCCGCGGCGGCGCAGGAGGTGCCGTCGTCACCGTTCTTGCCGCCGTCGGGCTGGGCC
GTCGAGGATCTCCTGCAGCTCTCCGACTACGAGTCCAGCGACAAGAaggg CTCTCCTATTGgGTTCaagga

Figure 2 continued

> SEQ ID NO:46 129426 246320
TTCGCGAGAGAGCTGGGCGATCAATCCAGATTTTGGAGGCGCTCCACGGCCGGCGCCAGCGAAATCCAGGTACTC
TTGGTGATTTCCGGGGAGAGATCTCGATCGATTCCGTGGCGTGATTTTGGGGCGGAGAGATGAGGGTCCAATGCG
ACGTGTGTGAGAAGGCCGAGGCGGCGCTGGTTTGCTGCGCCGACGAAGCCGCGCTGTGTGCCGTGTGTGATGCCG
AGGTCCATGCCGCCAACAAGCTTGCCGGGAAGCACCAGCGATTGCCTTTGAGCGCCTCTGGAAATTCTCCTAGCT
GCGACGTCTGCCAGGAGAAAACTGGATGGTTTTTTGTGTGGAGGACCGTGCTTTGCTCTGCCGGGCTTGCGATG
TCTCCATACACTCGTCCAACGCACGGGCTTCCGGCCACAACAGGTTTCTGGTCACCGGTGTGAGAGTGGCGCTCA
ATGCGCTGTCTGCCCAAGACTTTCTCGAAGCACCAATGACCCCACGATGTCGGCAACCCGGGAACGCGAACTCCT
CGGCTTCTGGAGCCAGCTCGTCGGGAAATtCGCTTTCGGCCAATCGCACGCAGGAGGAGAGGTTtGACAGAGGAG
AGcccgagactgtcatggaAaaGAg

> SEQ ID NO:47 129858 125506
CTTGGTGGCTGGGGTGCTTCTCTTGTCAACCACTTCAACCGCACGGTGGATGTGGTGTTAAGAGGGTATAGCGGG
TATAACACAAGGTGGGCATTAAAGGTGATAGAGAAAGTTTTTGATGAGGGAACGGCGCCATTGGCAGTGACAGTG
TTCTTTGGAGCAAATGATGCTTGTCTCCCTGATAGATGCTCTTCCTTTCAACATGTTCCTATTGATGAGTACAAG
CTGAATCTTCATTCCATCGTCTCCTTTCTCAAGGGGCGATGGCCAACAACTCAAATTGTCCTCATCTCACCTCCT
CCAATTGATGAACCTACGCGGCTCCTATATCCTTTTATGGAGAACAAATTGGGCCTGTCAGAGAGGACCAATGAA
ACTGCTGGAAACTATGCTAAAGCAAGTCTAGCTGTAGCAGCTGAATGTGGGGTTTTGGCTGTGGATTTATGGACC
AGAATGCAGCAAATTCCTGGCTGGCAAACAGCTTGTTTAAGTGATGGTTTGCACCTGAGTAAAACTGGGAACGAG
ATTGTGTTTGAGGAGGTGGTGGCGGCTCTTAAGAAGAAAGGGTTGAGTGTGGAAGCTCTACCAGTTGATCTGCCA
GTGATTAATGAAAT

> SEQ ID NO:48 129858 129806
GAATTCACCATACGAATTTTATTGCCGGTGACTGATACATCATGAAAAGTCTACCTTCTCTCCTTAAATCCTGTT
ACCGGCGTAGAATGTTGTGCTCATGCATGTGATCGATCTAATGTCAAACAGTCTATACAGCTATATCAATAATAC
TACAAAACTGAAAATAAAAATAAATGTGTCTATATAATGTAAGCTATCCAACTATAATTGTGATAAAAATATCGT
CGCCTAACCATAAGGATGGACGCAGGTTATATCCTCATGTAGGTTATCCATCAGGTCTGCCGGAAAGGACGAATG
AGGCTGCCGGTGCTTATGCTAAGGCATGTGTGGAGGTTGCTGATGAATGTGGAGTGATTGGAGTGGATTTATGGA
CTAAAATGCAACAATACCCTAATTGGGAAAAAATGTTGTCTCAGTGATGGCTTACACCTAACACCAACTGGGAACA
GAATTGTATATGAGGAAGTGATCAAAAAGCTTACAAAAGAAGGGGTAAATGTTGAAACTTTATCAGCAGATCTCC
CTCTCCTATCTCAGATCGATCCTTGTG

> SEQ ID NO:49 129858 129806
AAAGGCATCATTTCAATGATCAAAACAACAAAGATGGGGAGAGCAGCAAACTTTGTATTAATTACCACCACATAT
ATGTGTTGCTTCTTAAATGATAATTTGTGTAACTAACTAACTAAAAGAGTCCCCTGGTATATGTAATGCGGATAA
TTCAGGAATCT

> SEQ ID NO:50 129870 131306
gcgcgccttaattaggatcgaaggaaggtcatcaagtaacttggTTCACAAGAGGGAAAGCACCAATCAGCCAAC
CATTACCCGGGGAGTCAGAACAAGATTACCTAGATTTCTCTTCCAAGATCTCGCACTTGAAAGGAGACAGAAAGG
ACTACGATTTTGTTAAGACTAGCCTAGCAGCTGAAGGCTTTGACGTTGTCTATGATATCAATGGAAGAGAGGCAG
ATAGAGAGAGAGACAATGGCAATGGCAACAAGTAGGTTGGTGGTGGTGCAACAAAAACAACCATCCTCATGTCTA
TTACCACCATCATCTCTTTCTGATTTCAATGGTATTAGACTGAAACACCCAATTCAGTACAAAAGAAAGGAATGG
CAGACAAGAGGAGCATTGCAGGTGAAAGCATCAGCTGCAAAGAAAATCCTGATAATGGGAGGAACCAGATTTATT
GGAATCTTTTTGTCTAGGCTCCTTGTGAAGGAAGGTCATCAAGTAACTTTGTTCACAAGAGGGAAAGCACCAATC
AGCCAACCATTACCCGGGGAGTCAGAACAAGATTACCTAGATTTCTCTTCCAAGATCTCGCACTTGAAAGGAGAC
AGAAAGGACTACGATTTTGTTAAGACTAGCCTAGCAGCTGAAGGCTTTGACGTTGTCTATGATATCAATGGTATT
GGAAGAGAGGCAGAAGAAGTAGAACCCATATTGGACGCGCTTCCAAAGCTTGAGCAGTACATATACTGTTCATCC
GCTGGTGTGTATCTGAAGTCTGATTTACTGCCTCATTTTGAGTCTGATGCAGTGGATCCCAAGAGCAGGCACAAG
GGAAAACTTGAAACAGAGAGTTTACTTGTATCAAAGGGCGTGAACTGGACTTCGCTGAGACCAGTTTATATCTAC
GGTCCTTTGAATTACAACCCTGTTGAAGAATGGTTTTTCCACAGATTGAAGGCCGGTAGACCAATCCCCATACCA
AATTCTGGCAACCAGATGACACAATTGGGTCATGCTAAGGATTTGGCGACCGCATTTATTAACGTTCTTGGTAAC
GATAAAGCGAGCCAGCAAGTGTTTAACATATCTGGAGATAAATATGTGACATTCGACGGATTGGCAAGGGCTTGT
GCTAaggcTGGTGGATTTCCTGAGCCAGAACTAGTTCACTACAATCCTAAAGAATTCGATTTTGGCAAAAAgaag
gcaTTCCCCTTCAgagacCagCATTTCTTTGCATCAATTGAGaAAGCaaAGAGTGAATt

> SEQ ID NO:51 129870 270847

Figure 2 continued

TTTTATATCATCAGCCAAATTTGCTGAAGAAGGCACCACCAAATGGCTAGTTTGGTTGCAGTTCAACACAAACAG
CCTTCTTTTGCTGTCCTCCCTTCTTCCCATTCTGACTTCAATGGTGCCAAATTGATCTCCTCTCTTCAGTTTAAG
AGGAAACCATGCCAGCCAAAAGGAGCATTGCATGTTACTGCATCAAGTGCCAAGAAAATCCTTATAATGGGAGGC
ACTCGATTTATTGGTGTCTTTCTATCCAGACTTCTTGTAAAAGAAGGCCATCAGGTTACTCTGTTCACAAGAGGA
AAAGCTCCCATCTCTCAACAATTACCAGGTGAATCAGACCAGGATTATGCTGATTTTTCCTCCAAGTTACTGCAC
TTGAAGGGTGACAGAATGGATTTTGATTTTGTGAAGACTAGTCTTTCTGCAGAGGGCTTTGATGTTGTGTACGAC
ATAAATGGACGAGAAGCAGTAGAAGTGGAACCAATATTGGATGCATTACCTAATTTAGAACAGTACACATACTGC
TCTTCAGCTGGTGTATACCTCAAAACTGATTATTTACCACATTTTGAGGCTGATGCAGTTGACCCAAAGAGCAGG
CATAAAGGAAAGCTTGAGACAGAGAGCTTGTTAGAATCACGAGATGTTAATTGGACTTCTGTAAGGCCTGTTTAT
ATTTATGGGCCACTTAACTACAAT

> SEQ ID NO:52 129870 135395
gtcgacgcacgcgtccgAAACAAGAAAAAAAAGAGAGAGAGATGGCAGCAACAGCCTCCCTGAAGAGCAGCCTCC
TGCTACCATCTCCTATCTCTGACTTCAGTAGTGCAGCACTCTCCATCTCAACCCAGGCTAGGAGGAGGTCATGGC
AGCCAAGGGGGGCAAGGATGCAGGTAGCAGCAGCTGCAGACTCCAAGAACATTCTTGTGATGGGGGGAACCAGGT
TCATTGGTGTCTTCTTGTCCAGGATCCTTGTCAAGGAGGGGCACCAGGTCACATTGTTCACTAGAGGAAAGGCCC
CCATTACCCAGCAGTTGCCAGGAGAGTCAGATGCAGAGTATGCAGAGTTCTCTTCAAAGGTGTTGCACTTGAAAG
GTGACAGGCAAGACTTTGATTTCGTTAAGaCAAGCCTTGCGGCAAAGGGCTTCGATGTTGTTTACGACATAAACG
GGAGAGAAGCTGTTGAGGTAGCCCCAATCCTAGACGCATTGCCAAACCTTGAACAGTACATCTACTGCTCATCAG
CAGGAGTGTACCTGAAATCAGACCTGCTCCCGCACTTCGAGACcGACGCCGTCGACCCGAAAAGCcGgCACAAgG
GGA

> SEQ ID NO:53 129870 17586
CCCACGCGTCCGGGCGAAGATGATGATGTTGCAACAGCATCAGCCTTCTTTCTCTCTCCTTACTTCTTCTCTGTC
TGACTTCAATGGCGCTAAGCTCCATTTACAAGTCCAGTACAAGAGGAAGGTTCATCAGCCAAAAGGAGCACTCTA
TGTTTCAGCGTCGAGCGAAAAGAAGATTCTGATAATGGGTGGTACTCGATTCATTGGTCTGTTCTTGTCCAGGAT
CCTTGTCAAAGAGGGACATCAGGTTACATTGTTCACAAGGGGTAAATCTCCTATTGCCAAACAATTGCCCGGTGA
ATCTGACCAAGACTTTGCTGATTTCTCTTCTAAGATTCTTCACTTGAAAGGAGACACAGAAAGGACTATGACTTTGT
GAAGTCAAGTCTTTCagcagaaggcttcGATGTTGttTATGATATCAACGGGAGGGAGGCCgaagaagTTGAGCC
CATACTAgaaGCACTACCCAAACTAGAGCAGTACATCTACTGTTCTTCAGCTGgtgTTTATCTGAAATCTGATAT
CTtgccacATTgtgAGGAGGATGCagtTGatccGAagagcAggCAcaagggGaagcTGGagaCtgagagcttACT
GCaatcaaaaggtgtaaacTGgACttctAtacGtcctgtcTacaTCTAc

> SEQ ID NO:54 129965 238465
GAAGAGTGAGTTGATCGAATAGATTTGATTCCTTTCTCTTGGTAGGGAGAGCTGGCGACGAAAGGGTTGGATCAC
GCAGAGTTTCCACCACGGCTTTGAATTCCAGGCGTCGCGATTCCCTGGTCGGTGTGGACGCTGCCAGGAGCTTGT
GCGTGGTAGCGCGCCTTGCCAGCTTCCACGGTGGTCGCGGCGCAGCTCCGGCTGCCGGAGGTCGCCCCTCGGATC
TCTTGAACTTGGCCGGCGGCGGTGTTGCCCTCCCCTCTTGCTCTTGGTCGCTGCCACCTTTCCGGGGCATCGATC
AGTGAGCTTGTAGAGAAGTGAAGTTTAGTCCTTTCCAGCCAAAAGTTGGATTTTTTTTTTCCCTTTTCCTCCGC
CATGGACAAGGTTTTGAAGATTCGAAGGATTCCAACCATTGTGTCCAATTACCAGGAGAGCCTCGACTTCCAGTC
CGGATGTGGCAAGAATTGTCTCGGGTCGTGTTGCATTCCTGGAGCAAAATTGCCATTGTATCTCTTTGGCAAACC
GGATGTGGATGAGAGTGGAGAAGTCCCTACCAAGGAGCTGGGACAAAACTCTTTCCTGGATTCAGCTATTCTCGG
TCAGTGGGCTGAT

> SEQ ID NO:55 129965 271909
CTCGTGGTGCTGGCTGTGGCCGCAACTGCCTCCGAAACTGCTGCCTTCCAGGGTCAAAGCTGCCACTGTATGCTT
GCAAGAGTTTGAGAAATGGCACGTCTGTTGCCGATGAAACCAAGGAACCTCCCGTTGACTTCTTGGAATCCCTCC
TTCTCGGGGAATGGGAGGATCGTCAGCAGAAAGGTCTCTTTCGCTATGATGTCACTGCTTGCGAAACCAAGGTTA
TTCCTGGAGAATATGGTTTCATTGCTCAACTGAATGAGGGAAGGCACCTCAAGAAGAGACCAACTGAGTTTCGCG
TTGATAAGGTGCTGCAGCCTTTTGATGGAAGCAAGTTCAACTTCACTAAGGTTGGTCAGGAGGAGTTGCTCTTTC
AGTTTGAAGCAAGTGAGGATAATCAAGTCCAATTCTTTCCAAATGCGCCCATTGATGCCGAAAAATCTCCAAGTG
TCG

> SEQ ID NO:56 129965 119239
AAGCAAGTTCAACTTCACTAAGGTTGGTCAGGAAGAGTTGCTCTTCCAGTTTGAAGCAAGTGAGGACAACGAAGT
TCAATTCTTTCCAAATGCACCCATTGATGCCGAGAAATCTCGAAGTGTTGTTGCCATCAATGTCAGTCCCATTGA
GTATGGACATGTGCTTTTGATCCCTAAGGTCCTTGAATGCCTTCCCCAGAGGATTGACAGGGACAGCCTATTGCT
TGCACTGCACATGGCTGCCGAAGCAGCTAACCCATACTTCCGATTGGGTTATAACAGCTTGGGTGCATTTGCTAC

Figure 2 continued

CATCAACCATCTTCACTTTCAGGCCTATTACTTGGCTGTGCCATTCCCCATTGAGAAGGCCCCCACTCGGAAGAT
TACCTTTGCTGATCCTGGAGTGAAGATATCTGAGATGCTGAATTATCCAGTTCGAGGACTTGTCTTTGAGGGTGG
AAATACTTTGGAGGATTTCGCCAATGTTGTCTCTGGTTCTTGCATTTGCCTGCAAGAGAATAACATTCCCTACAA
TGTTCTAATCTCTGATTCGGCAAAAAGGGTATTCCTTCTCCCACAGTGCTACGCAGAGAAACAGGCTCTAGGGGA
GGTCAGCTCTGAACTGCTTGATACTCAAGTCAATCCTG

> SEQ ID NO:57 129965 129806
ACCATACAACCTTGGGGGTAATATGTGGCAAAAGTGCGAGATGAGCCCCCGAAAAAAAAATCTTCATCCTCATCC
TTGA

> SEQ ID NO:58 130156 130156
GAATTCAAGAAGACCATCGGAGATTGTTCATCCGGCCGTTTCTCTACATTTTCGGTCATTTCAAGGAGCAAGCAG
TATTTTAAGGAGGCAAAATGAGTCAGAAAAAAGGGGGTGGCAAGCTATCTGTTCCTGGTAGTAGTGGTTCACCTG
CAAAAGGGAAAGATGCAGGTGGACAAATCCCTGGAGTTTTAGGCTCTGGTAACCAAAAGACTGGAGTTGTTCAGC
TGGGTTCTAATATCGCAAACCTAAGCCTTGATTCCAGTAAAGATTCTGAGTGGGAGGTAGTGTCTCGCAAGAATC
GAGGCGCGGCAAGTGCACCAAAACCATGGGGTCCCCAGAATTCCTCTTCTCCATCCTTGGTTTCAGGAAGTTCCC
AAAATTCCTCTTCTGCATCCTGGGTTGCAGGAAAGGCTACAGGAGGTGCCCAAAATTCCTCTTCTCCATCCTTGG
TTTCAGGAAGTTCCCAAAATTCCTCTTCTGCATCCTGGGTTGCAGGAAAGGCTACAGGAGGTGCCTGGCAGGATA
ATAAGTCAGGTGGAGGAGGAACTACGAAAAGCCAATCTCCCAATGCATGGGAGAAAAATTACATGGCACCACCAA
GTAAGATTGCTCCTCCTTTACAACATGGTTGGCAGTGGGGTGCAA

> SEQ ID NO:59 130203 167669
gaattcacaaagaaatccactttcattgcagataagcttttcttcactccatcaaaggaacaaagtcgagagaga
gagagCACAACAAGTAAATTAGAACTCTCTGGTCACAATTTCTGCCTCTGCAAGTCCTCTCTCTTCATTCGCTTC
CCTTTCTATCTCAACATCTAGAAAATTTCTCCCAAACCACACTTCTTTCTCCTTCTCAAACATCAAAACCCATAA
ACTCATCACCCCAATTTCTTCCCTAAAATTCCCCCATTCAAAACCCCCAAAACCTAAACCCATAAAAGCTACACC
CTCTGATGCAGAAACCATTTTCATGGAAAATGAAATAAGCCCAGATGAAGATTTCACATTTGAGCCACCACCAAG
ACCAGAAGGTTACATTGAACCACCTTCATTTGATGATCTTCCACCAGAATCTGAAGATGAAATTGCAGCAGCCTA
TGAAGAATTGTATGGTCCTGCTTATAGTGGTATGAGTGTGCTAGGTAACGATGTATATGTTATGGATTCTAAGAT
GAAGAAAGCAACTGGGTTTGGTACAAAGACTAAGAAAGAGAAAATTAGAGATGGTTTTGAAGAAAGAGTTGTTCA
AGTTAGAAGGGTTACCAAAGTTGTTAAAGGTGGGAAACAATTGCATTTTAAAGCTGTTGTTGTTGTTGGTGATAA
ACAAGGTCAAGTTGGagTTGGtgTTGGTAAAGCTAAAGAAGTTGTTTCtgcaGTtcaaaagtctGctggtaaTgc
tagaAGgaaTATTATTACTgTGCCCTTAACTAAGTaTTCAACTTtccCtcacagagCTGACGgagATTAc > SEQ ID NO:60 130213 114368
agcgacaatcagaaaccaccccgctgtaaccctaggtttttttcacaaacaacaaatatgactgagtcatcgcggga
agaaaATGTGTACATGGCCAAGCTTGCTGAGCAGGCCGAGCGATATGAGGAAATGATTGAGTTTATGGAGAAGGT
TGCAAAGACAGGTGATGTCGAGGAGCTGACTGTTGAGGAAAGGAATCTCCTTTCTGTGGCATACAAAAATGTGAT
TGGTGCAAGAAGGGCCTCGTGGAGAATAATCTCTTCAATTGAGCAGAAAGAGGAGAGCCGTGGAAATGAAGATCA
TGTCAAAACTATTAAAGAATACAGAGCCAAAATTGAGGCTGAACTCAGCAAGATCTGTGATGGGATTTTGGGTCT
CCTTGAGTCCCATTTAATACCATCAGCCTCCACAGCTGAGTCCAAAGTTTTTTACTTGAAGATGAAAGGTGATTA
CCACAGGTACTTGGCTGAGTTTAAGACAGGGGCagaAAGGAAAGAaGCCGCAGAGAACACTTTATTaccCTACAA
GTCTGCTCAGGATATTGCTTTGGATGAACTGGCTCCTACTCACCCAATCAGGCTGGGACTTGCCCTCAACTTTTC
agtgTTCTACTATGAAATTctcaacTcgtcggAtcgtgcTTGTAATCTTGCaaagcaagccTTTGATGatgccat
TGCCGagcTgGa > SEQ ID NO:61 130213 252933
TGGTTGTTATTGTTGTTGCTGTGTTTATCTTCTTCGCCTTCGTGTTCGTCGGTGGTGTTGGTAGTGGGAAGATGG
GTGTGGAGAAGGAGCGTGAGAGTGATGTGTACATGGCTAAGCTCGCTGAGCAGGCGGAACGTTATGATGAGATGG
TGGAATTCATGAAAAAGGTGGCAAACTTGGATGTGGAGCTATCTGTAGAGGAGAGGAATCTGATGTCAGTTGGGT
ACAAGAATGTGATTGGGGCACGGAGGGCCTCTTGGCGCATCCTCTCCTCCATCGAGCAGAAGGAGCGAGGGAAAA
GGCAATGAAGTGAATGCCAAGCGCATCAAAGAATACAAGCACAAGGTCGAGGAAGAGCTTTCAAACATCTGCAAC
GATGTCCTCTCCGTTATTGAGGATCATCTCATCCCTGCGTCTAGCACGGGGGAATCTTCTGTCTTCTATTACAAA
ATGAAAGGGGATTACTTCCGATATTCGGCAGAGTTTAAATCTGGAAATGAGAAGAAGGAAGCCGGAGAGCAGTCT
TTGAAAGCATACCAGGCTGCTATGGACATAGCGACATCTAGCCTTCCGACGACTCATCCGATCAGGCTTGGTCTT
GCTCTCAACTTCTC

> SEQ ID NO:62 130213 232468

Figure 2 continued tcgacccacgcgtccgggcggcagcgcacggcgaGGAACAGGTGAGTGCCCGTGGATGTGATCTAGATCTACCCT
CCAAGCCCCAAAATCTCAGTAGAAATCCTCCAAATCGCGCCGCCGGAAGAGAGATCCAATCCACCACTGTCCCCA
TTTCTCGGCTTGTTCCAGGGATGTCGAATCTTCGCGAGGAGAATGTCTACATGGCCAAGCTCGCGGAGCAGGCCG
AGCGCTACGACGAGATGGTGGAATTCATGGAGAAGGTGGTCAAGGCCGTGGACGTGGAGGAGCTGACGGTCGAGG
AGCGGAATCTCCTGTCGGTGGCCTACAAGAACGTGATCGGCGCCCGCCGGGCATCGTGGAGGATAATCTCCTCCA
TCGAGCAAAAGGAGGAATCCAAGGGCAACGACGACCACGTCTCGATGATCAAGGAGTACCGTGCCAAGGTGGAGT
CGGAGCTGAGCACCATCTGCGACAGCATCCTCAAGCTGCTGGACAGCCATCTCATCCCCTCATCGTCCAGTGGCG
AGTCCAAGGTCTTTTACTTGAAGATGAAGGGTGACTACCACCGATACTTGGCCGAGTTTAAGACCGGGGCCGAGA
GGAAAGAGGCCGCGGAGAACACTCTCCTCGCCTACAAGTCGGCCCAGGACATCGCTCTCACACAGCTGCCGCCGA
CGCATCCCATCCGGCTGGGTCTCGCTCTCAATTTTTCGGTCTTCTACTACGAGATTTTGAATTCGCCCGATCGAG
CTTGTACGCTTGcCAAGCAGGCatttgacGAggccatAGccgagctggacacTTTGGg > SEQ ID NO:63 130213 228143
gaatttgaactccacctgagcacaggagaagccgcagccagtgagatttgaccttctgtttctaccagaaaaaca
caaacAGTGAAGATGTCGCAGCCTGCTGAGCTTTCCCGTGAGGAGAATGTGTACATGGCTAAGCTTGCAGAGCAG
GCCGAGAGGTATGAGGAGATGGTTGAGTTCATGGAGAAGGTTGCTAAGACAGTTGACTCTGAGGAGCTCACTGTT
GAGGAGCGCAACCTTCTATCAGTTGCTTACAAGAATGTTATTGGTGCTCGCCGTGCGTCATGGCGCATCATATCA
TCCATTGAACAGAAGGAAGAGAGCCGTGGTAATGAGGATCGTTGCACGCTCATCAAGGAATACAGGGGAAAGATT
GAAACTGAGCTCTCCAAGATCTGTGATGGCATCCTCAAGCTTCTTGACTCCCACCTTGTGCCTTCATCCACTGCT
CCAGAGTCCAAGGTCTTCTACCTCAAGATGAAAGGCGACTACTACAGGTACCTCGCAGAGTTTAAGACTGGAGCT
GAGAGGAAGGATGCTGCtGAGAATACCATGGTGGCATACAAggctgcTCAGGACATTGCTTtggctgagctGCCT
CCTactcatCCAATTaggcttgggcttagctcttaACTTCTCAGTgttctaCTATgagatccTCAA > SEQ ID NO:64 130213 191394
ccccgcccccccgggcgaacaaaaagcattcgcatccacgagagcactcgaacccgacccgcctcgccgccgccgc
caccgAAGTAATCCCTTAATTGGTCAAAATGTCTCGGGAGGagaATGTCTACATGGCCAAGCTGGCCGagCAGGC
TGAAAGGTATGAggacaTGGTTGagTACATGGAGAAGGTTGCAAAGACTGTAGATGTGGAAGAGCTCACTGTTGA
GGAGCGCAACCTCTTGTCTGTTGCTTACAAGAATGTGATTGGTGCCCGCCGTGCCTCCTGGCGTATTGTCTCATC
CATTGAACAGAAGGAGGAGGGTCGTGGCAATGAGGAACATGTTACTCTGATCAAGGAGTACCGTGGCAAGATTGA
AGCTGAGCTGAGCAAGATTTGCGATGGTATCCTGAAGTTGCTTGACTCACACCTTGTGCCCTCATCTACTGCTGC
AGAATCTAAGGTGTTTTACCTCAAGATGAAGGGTGATTACCACAGGTACCTTGCGGAATTTAAGACTGGTGCCGA
GAGAAAGGAAGCTGCTGAGAGCACAATGGTGGCTTACAAGGCTGCTCAGGATATTGCTCTGGCGGATCTTGCTCC
CACCCATCCCATAAGGCTTGGACTGGCACTTAACTTCTCTGTGTTCTACTACGAGATTCTAAACTCTCCAGACAA
GGCTTGCAACCTTGCTAAGCAGGCGTTTGACGAAGCCATCTCCGAGTTGGATACCCTCGGGGAGGAGTCTTACAA
GGACAGCACTTTGATCATGCAGCTCCTGAGGGACAACTTGaCcCTCTggacctCTGaCctcacggaggacGGTGG
TGATgaggTGAAAGAagccTCCAaggGcgacgcCTGcgagggccagtaAAATGGGAagatcGaTCGATCGAtggC
tccgcatGTTATTGGAGaccatcgatttagatgcctcaTGCTGCTg > SEQ ID NO:65 130213 191021
CCCCCTGGAGGATCATCTCTTCTATGGAGCAGAAGGAGGAGAGCCGTGGGAATGAGGCATATGTTGCATCAATTA
AGGAGTACCGTAGCAGGATTGAAACTGAGCTCAGCAAGATCTGTGATGGTATCCTTAAGCTTCTGGATTCCCACC
TTGTCCCATCTGCCACTGCTGCAGAGTCCAAGGTGTTCTACCTGAAAATGAAGGGTGACTACCACAGGTACCTTG
CTGAGTTTAAGTCAGGAGCTGAGAGGAAGGAAGCAGCTGAGAACACTCTTGTGGCATACAAGTCTGCCCAGGATA
TTGCACTCGCTGACCTGCCTACAACTCACCCGATAAGGCTTGGACTTGCACTGAACTTCTCAGTGTTCTACTATG
AGATACTGAACTCACCAGACCGTGCTTGCAACCTTGCAAAGCAGGCGTTCGACGATGCTATTGCTGAACTGGACA
CTCTTGGCGAGGAGTCTTACAAGGACAGCACCTTGATCATGCAACTTCTTCGTGACAATCTGACTCTCTGGACCT
CTGACAATGCGGAGGATGGTGGTGA > SEQ ID NO:66 130213 179614
ttgcaagttccattccctgttcttctctctcaacgaagcatcaaccccccttttctCCCAGAACCGCGTCTCATC
GCACCTGCCATAAAACTCCAAAAAATCTCAAAAACCAACCGTCAAAATGGGTCACGAAGATGCTGTTTATCTGGC
CAAGCTCGCCGAGCAGGCCGAGCGATATGAGGAGATGGTCGAGAACATGAAGATCGTCGCCTCCGAGGACCGCGA
CCTGACCGTCGAGGAGCGCAACCTCCTCTCCGTCGCCTACAAGAACGTCATTGGTGCCCGCCGTGCCTCTTGGAG
AATAGTCACTTCCATCGAGCAGAAGGAGGAGTCTAAGGGCAACTCTTCCCAGGTTACCCTTATCAAGGAGTACCG
CCAGAAGATTGAGGCCGAGCTTGCCAAGATCTGCGATGACATTCTCGATGTTCTTGACAAGCACCTGATTCCTTC
TGCCAAGTCTGGAGAGTCCAAGGTCTTCTACCACAAGATGAAGGGTGACTACCACCGTTACCTTGCCGAGTTCGC
CATTGGCGACCGCCGCAAGGACTCCGCCGACAAGTCTCTCGAGGCTTACAAGGCTGCTACCGAGGTTGCCCAGAC

Figure 2 continued

CGAGCTGCCTCCTACCCACCCTATCCGCCTGGGTCTTGCGCTCAACTTCTcCGTCTTCTACTACGAGatCCTCAA
CGCCCCTGACCagGCttGCCACCtcGCt

> SEQ ID NO:67 130213 159293
acgcactctgtcgagaatcCATTCTATTTCGCCTAAACTTTCTCTCTCTACAACAACAACAATGGCGGCTCTGCT
CACAGACAATCTCAACCGCGAACAATACCTCTACTTAGCCAAACTCGCCGAACAAGCCGAACGCTATGAAGAAAT
GGTCCAGTACATGGACAAACTAGTACTCAGTTCCACTCCCGCCGCCGAACTCACCGTCGAGGAACGAAACCTCCT
TTCCGTCGCTTACAAAAACGTGATCGGCTCTCTTCGTGCCGCGTGGCGTATCGTATCCTCCATTGAGCAGAAAGA
GGAATCGCGTAAGAACGAAGAACACGTTTCGCTCGTTAAGGAGTACAGAGGTAAAGTTGAGAATGAGTTAACGGA
GGTTTGTGCTGGTATCCTCAAGTTGCTTGAGTCAAATCTCGAGCCGTCTGCTTCTACGGGTGAATCGAGGGTGTT
TTACCTCAAAATGAAAGGTGATTATTACCGGTATCTAGCGGAGTTTAAgGTTGGAGATGAGCGGAAGCAGGCTGC
TGAAGaCACTATGAATTCTTATAAGGCTGCtcaggAAATTGCACTagCAGATCTgcctccaaCAcatccTAtaag
gctgggTCtTGCACttaaTtTctcagtcttCTactttgagattCTGaAcTCATCtG

> SEQ ID NO:68 130213 158868
GTTATAAATCCTTATCTTTTTCAACACACAGATTAAAATCTTCAGAAAGAGAGAGAGAGATCCCAAAATGGGTGA
ACGTGAGAACTTCGTATACATAGCTAAGCTTGCCGAGCAAGCTGAACGCTATGATGAGATGGCTGATGCGATGAA
GAATCTTGCAAATATGGATGTTGAATTGACAGCGGAAGAGAGGAATTTGTTTTCTGTTGGTTATAAGAATGTGGT
TGGAGCTAGGAGAGCATCGTGGAGGATCTTGTCTTCCATCGAGCAGAACGAAGAGTCTAGAGGAAATGAGCAGAA
CGTGAAGCGGATTAAGGAGTACCAGCCAAAAGTGGAGTCAGAGCTCACCGACATTTGCAATAATATCAT

> SEQ ID NO:69 130213 6504
cccacgcgtccgtagAGGAAAGAAGAGAGCAAAGGGAACGAAGATCATGTTGCTATTATCAAGGATTACAGAGGA
AAGATTGAATCCGAGCTTAGCAAAATCTGTGATGGGATTTTGAATGTTCTTGAAGCTCATCTTATTCCTTCTGCT
TCACCAGCTGAATCTAAAGTGTTTTATCTTAAGATGAAGGGTGATTATCATAGGTATCTTGCTGAGTTTAAGGCT
ggtGCTGAAAGGAAAgaaGCTGCTGAAAGCACTTTGGTTGCTTACAagtCTGcttccgaCATTGCCACTGCTGAG
TTAGCTCCTACTCACCCGATAAGGCTTggtctTGCACTCAACTTCTCTgtgtttTactATGAAATCCtcaactcg
ccTGAtcgtgcttgc

> SEQ ID NO:70 130213 47368
CGGACGCGTGGGAAAAAAATCAAATCTCTCTCTTTCTCTCTCTAATGGCGGCGACATTAGGCAGAGACCAGTATG
TGTACATGGCGAAGCTCGCCGAGCAGGCGGAGCGTTACGAagaGATGGTTCAATTCATGGAACAGCTCGTTACAG
GCGCTACTCCAGCGGAAGAGCTCACCGTTGAAGAGAGGAATCTCCTCTCTGTTGCTTACAAAAACGTGATCGGAT
CTCTACGCGCCGCCTGGAGGATCGTGTCTTCGATTGAGCagAAGGAAGAGAGTAGGAAGAACGACGAGCACGTGT
CGCTTGtCAAgGATTACAGATCTAAAGttGAGTCTGAGCTTTCTTctgtttgctctGgaatcctTAagCTccTtG
ACTCGcaTCTGATccCAtctgctggAGC

> SEQ ID NO:71 130213 271878
aAAAGGGAGAGGAAAAGCGCAAAATCTCCCTTCGATTATCAGTACAAAACCTCTGATTTGAGAGATCGGAAATGG
CTTCCTCCAAAGAACGCGAGAACTTCGTCTACGTCGCTAAGCTTGCTGAGCAGGCCGAACGCTACAATGAAATGG
TTGATGCGATGAAGAGTGTAGCAAATATGGATGTTGAATTGACTGTTGAGGAAAGGAATCTGCTTTCTGTTGGTT
ATAAAAATGTGGTAGGTTCTAGGAGAGCATCTTGGAGGATCTTATCCTCTATTGAGCAGAAGGAAGAATCTAGAG
GAAATGAGCAAAATGTCAAGCGAATTAAGGAGTACCGACAAAAGGTGGAGACAGAGCTCACCAGCATTTGCAACG
ATATCATGGTGGTCATTGATCAGCATCTAATTCCTTCATGCACTGCAGGCGAATCAACTGTGTTTTACCACAAGA
TGAAGGGAGACTATTATCGTTATCTTGCAGAATTTAAATCTGGCAATGACAAGAAAGAGGTTGCAGAGCTTTCAT
TGAAAGCATATCAGTCAGCTACAACTGCTGCAGAGGCGGAATTACCACCCACTCATCCCATTCGGTTGGGATTGG
CTTTGAATTTCTCTGTTTTCTATTATGAGATCATGAATTCACCTGAAAGGGCATGCCATCTGGCAAAGCAGGCCT
TTGATGAAGCAATATCTGAGTTGGATAGCCTGAACGAGGATTCCTACAAAGACAGCACCTTGATTATGCAGCTTC
TAAGGGACAATCTCACCTTGTGGACTTCTGATCTTCCAGaGGATGCAGAAGATGCCCAAAAGGGAGATGCCACAA
ACAAAGCAAGTGGaggTGAAGATGCagagtAAATGGGCCTAATGGTTAGaaCTACCTTgtGCATTTGGAGCTGtg
aggacggTGATACACCAaagggATGTGTGTGTGTTAaGtc

> SEQ ID NO:72 130213 265563
TTTTTCTAGCACACAGACCATCAATGGCATCGCCGCGCGAGGAGAACGTGTACCTGGCGAAGCTGGCTGAGCAAG
CCGAGCGCTACGAGGAGATGGTAGAGTTCATGGAGAAAGTTGTCGGCGACGGCGACGACGAACTCACCGTCGAGG
AACGCAACCTCCTCTCCGTCGCGTACAAAAACGTGATCGGAGCGAGGAGAGCGTCGTGGCGCATAATCTCATCGA
TCGAGCAGAAAGAAGAGAGTCGCGGTAATGAAGATCATGTTGCCTCCATTAAAACCTACAGATCTAAGATCGAAT
CTGAATTGACTTCGATCTGTAACGGTATCCTTAAGTTGCTCGATTCAAAACTCATCGGCACCGCTGCTACCGGTG

Figure 2 continued

ACTCTAAGGTTTTTATTTGAAAATGAAGGGAGATTATTACAGGTACTTGGCTGAGTTCAAAACCGGAGCTGAGA
GAAAAGAAGCCGCCGAGAATACTCTTTCGGCTTACAAGTCGGCTCAGGATATTGCTAATGTCGAATTAGCCCCTA
CACATCcAATCCGATTGGGGCTAGCTCTCAATTTCTCAGTGTTTACTATGAGATATTGAATTCTCCTGACCGTG
CTTGTAATCTTGCCAAACAGGCATTTGATGAGGCAATTGCGGAGCTTGACACCCTTGGAGAggAGTCtTACAAGg
ATAGCACCTtGAttATGCAGCTTCTtCGtgataaccttacgtt

> SEQ ID NO:73 130213 257978
AGGAGCTTAGATCGATCGACGACGCCATCGCCGCCGGAGCTGCCATGGGAATGGAGAAGGAGAGGGAATGCTTCG
TCTACATGGCCAAGCTCGCGGAGCAAGCCGAGCGTTACGATGAAATGGTTGAATCGATGAAGAAAGTCGCGAAGC
TGGACGTGGAGCTGACCGTGGAGGAGAGGAATCTCCTGTCCGTGGGCTACAAGATCGTGATTGGGGCGCGGCGGG
CGTCGTGGCGGATCTTGTCCTCGATCGAGCAAAAGGAGGAGAGCAAAGGCAACGAGCAGAACGTCAAGAGGATTG
GAGAGTACCAGCAAAAGGTCGAGGACGAGCTCTCCAAGATTTGCAATGACATTCTCACGATCATTGACGAGCATC
TAGTGCCGGCTTCCAGCACTGGCGAATCCACGGTCTTTTACTACAAGATGAAAGGTGACTACTTTCGATACCTTG
CAGAGTTTAAGACCGGGAACGAAAGAAAAGAAGCTGCCGATCAATCGTTCAAGGCTTACCAGGCTGCGAGCGATA
CTGCTTCAAGCGATCTTCCCCCAACACATCCTATCCGGCTGGGACTGGCATTGAATTTCTCTGTTTTCTACTACG
AGATTCTAAACTCGCCAGACCGCGCTTGCCAGCTAGCGAAGCAAGCTTTTGACGATGCGATTGCGGAGCTGGACA
CGCTCAGCGAAGAATCCTACAAAGACAGCACCTTGATCATG

> SEQ ID NO:74 130213 256490
ttcgcatctCTCCATCGCCGCCGCCGCCGTTTCTGCCGCCGCATAGGCATCCGTCGCCAGGTAGCGCAGCCGCAG
CCGCAGCCGCCGCCGCAAAGCTAGGTTGTTTCTCGCCGAAATGCCGGAATCCAAGGAGGAGAATGTCTACATGGC
CAAGCTCGCGGAGCAGGCCGAGCGCTACGACGAGATGGTGGAGTACATGGAGAAGGTGGCCAAGGCCGTGGAGGC
GGAGGAGCTGAGCGTGGAGGAGAGGAATCTCCTGTCGGTGGCGTACAAGAATGTGATTGGGGCGCGGCGGGCTTC
GTGGCGGATCATCTCGTCGATCGAGCAGAAGGAGGAGTCCAAGGGCAACGAGGAGCATGTAGGCTTGATCAAGAA
CTACAGGTCCAAGGTGGAGACGGAGCTGAGCAACATCTGCCACGGGATCTTGGGGCTGCTGGATTCGCACCTCAT
CGGATCCTGCTCCACGGGCGAATCCAAGGTCTTCTACCTCAAGATGAAGGGCGACTACAATCGCTACCTTGCCGA
GTTTAAGACGGGGCAGGAGAGGCAGGAGGCAGCCGAGGCCACCTTGATGGCCTACAAGTCGGCACAGGACATTGC
GCTGGCGGAGCTTGCTCCAACTCACCCCATTCGACT

> SEQ ID NO:75 130213 256066
TTTCTCTCTCTCTCTCTCTCTCTCTCTCTCCCTCCGTCGACATGGGCATCGAGATGGAGCGAGAGAGCCTTGTCT
ACCTATCCAAGCTCTCCGAGCAGGCAGAACGCTATGAGAAATGGTGGAGTCGATGAAGAAAGTATTTAAGTTGGA
TGTAGAGCTTACGATTGAGGAGAGGAATTTGCTCTCAGTGGGGTATAAGTATTTTATCGGAGCGCGAAGGGCCTC
GTGGCGAATTCTCTCCTCCATTGAGCAGAAAGAAGAGAGCAAGGGCAATGAGACCAATGTAAAACGCATCAAGGA
GTACCGCAACAAAGTGGAGGAAGAGCTTTCCAAGATTTGCAGTGACATCCTAACTATCATCGATGAGCATCTTAT
CCCCTCATCTGGCACAGCAGAATCTACCGTTTTCTATTACAAAATGAAAGGGGATTATTATCGCTACCTTGCTGA
GTTCAAGACAGGACATGAGAGAAAGGAAGCTGCAGATCAATCTCTGAAAGCTTATCAGACTGCAAGTGACACGGN
CAACACGGCTCTGCCATCTACCCATCCGATCAGGCTTGGACTTGCACTCAACTTTTCAGTCTTTTACTATGAGAT
TTTGAGTTCGCCGGAGCGTGCGTGCCATCTTGCCAAGCAAGC

> SEQ ID NO:76 130213 253819
CACGCGTCGCGACAGTCGAAACGGGGTCCCGGGAGGAGAGTGTGTACATGGCCAAGCTCGCGGAGCAGGCCGAGC
GCTACGAGGAGATGGCCGAGTTCATGGACGCTGTCTCCAAGGGCGCCGGTGCTGAGGAGATGTCCGTTGAGGAGC
GTAACCTCCTCTCTGTCGCCTACAAGAATGTCATTGGTGCCCGTAGAGCCTCCTGGCGCATTGTCTCCTCCATCG
AGCAGAAGGAGGAGAGCAAGGGCAATGAAGACCACGTCGCCGCCATCCGCGGCTACCGCGTCAAAGTTGAGGCTG
AGCTCACCAAGATCTGCCAGCGCATTCTCGACCTCCTTGACAGCCACCTTGTCCCCTCTGCGCTCAACCCCGAGT
GCAAGGTCTTCTACCTGAAGATGAAAGGGGATTACCACCGTTACCTTGCCGAGTTCAAGACCGGTGCTGACCGCA
AGGAAGCGGCTGAGAGTACGCTCGTCGCTTACAAATCTGCCGAGGAAATTGCCCTGGCTGAGCTGCCTTCGACAC
ACCCCATTCGTTTAGGCCTTGCTCTGAATTTTTCAGTTTTTTACTATGAAATTTTGAACTCCCCAGACAGAGCTT
GCAATCTAGCTAAGCAGGCTTTTGATGAGGCCATTGCTGAACTGGACACTCTGGGGGAAGATTCCTATAAGGACA
GTACTTTGATAATGCAACTTC

> SEQ ID NO:77 130213 14133
CCCACGCGTCCGCTTCAGACAAAGCTTGTAACATGGCCAAACAGGCTTTTGAGGAGGCCATAGCTGAGCTTGACA
CTCTGGGAGAGGAATCCTACAAAGACAGCACTCTCATAATGCAGTTGCTGAGGGACAATTTAACCCTTTGGACCT
CCGATATGCAGGAGCAGATGGACGAGGCCTGAGGATCTAGATGAAGGGGGGGAGGGTTGTTACGCGATGTTTCTG
CCACCAAATCGATCTCAAAATCCCCATAACCTTTGCTCAAAAACTGTGAAAAAAGATTGAAGTGTTTATGATGAT
TATGATTGTGCACAGCTTGATGATTTATCTACTCTACT

Figure 2 continued

> SEQ ID NO:78 130213 142802
CAGCTCTCTCTCTCCCTTCAAACATCGATGGCGTCGTCGCGCGATGAGTTCGTGTACATGGCGAAGCTTGCGG
AGCAAGCTGAGCGGTACGAGGAGATGGTAGAGTTTATGGAGAAGGTCGTAACCGCCTCGGACGGCGGCGAGGAAC
TCACCATCGAAGAACGTAATCTTCTATCCGTAGCATACAAAAACGTGATCGGAGCACGACGAGCCTCGTGGCGAA
TCATTTCCTCAATCGAGCAAAAAGAAGAGAGCCGAGGCAATGAGGAGCACGTGACCTCTATTAAAACTTACAGAT
CTAAGATCGAGTCGGAGTTGACCTCGATCTGTGACGGTATCCTCAAGCTGCTCGATTCGAATCTCATTGGCGCTG
CGTCAATCGGAGATTCTAAGGTGTTTTATTTGAAAATGAAAGGAGATTATCACCGGTATTTGGCTGAGTTTAAGA
CCGGAGCTGAGAGAAAGGAAGCTGCTGAGAATACTCTTTCGTCTTATAAGTCCGCTCAGGATATTGCAAATGCGG
AACTGGCACCTACACATCCTATTCGATTGGGGCTAGTTCTCAATTTCTCTGTATTTTACTATGAGATATTGAATT
CACCTGATCGTGCTTGTAATCTG

> SEQ ID NO:79 130213 147350
agaaaatcgaaaaactcccacatccagatctccccccccccccccaAAAAAAAATACAGAGAACAAATCTTAAC
ATGGCGGTGGCACCGACGGCGCGTGAGGAGAACGTGTACATGGCAAAGCTTGCAGAGCAAGCTGAGAGGTACGAA
GAAATGGTTGAATTCATGGAAAAGGTCTCCAACTCTCTCGGCTCAGAAGAACTCACCGTGGAGGAACGAAACCTC
CTTTCCGTGGCGTACAAGAACGTGATCGGAGCGCGTAGGGCATCGTGGCGTATTATCTCATCGATTGAGCAAAAG
GAAGAGTCCAGAGGGAACGAGGAACACGTGAACTCTATCCGCGAGTACAGATCTAAGATTGAGAATGAGCTCTCT
AAGATCTGTGATGGTATTCTGAAATTGCTCGATGCAAAGCTTATCCCTTCTGCAGCATCTGGTGATTCTAAGGTG
TTTTACCTGAAAATGAAAGGAGATTACCACCGCTATTTGGCTGAGTTCAAGACCGGTGCTGAACGTAAGGAGGCT
GCTGAGAGTACACTCACTGCCTACAAAGCTGCTCAGGACATTGCAACTACTGAACTTGCCCCAACACATCCCATC
CGACTTGGACTGGCTCTTAACTTCTCTGTGTTTTACTATGAGATCTTGAACTCTCCTGACCGTGCTTGCAATCTT
GCTAAACAGGCCTTTGATGAAGCAATTGCTGAGCTGGATACATTGGGCGAGGAGTCTTACAAGGATAGCACTTTG
ATCATGCAACTTCTTCGTGACAATCTCACTCTCTGGACTTCTGATATGCAGGATGATGGGGCTGATGAAATCAAg
GAAGATCCCAAACCTGATGAAGCCAAAAATTGAAGGAAATGAAACTCTCTAATTTGCTTTTCACTTCTTCCTGGT
TGTTTTTATTGGAAGAAGCTGATTATCGTAATTTCCTTACTATTATGGTTCTCcACTAGGGGGTTGTCATCTTAT
TGGAAATGAACAACTTTTAATATTGATGTttcagagttccATCTTTGATttaaTgtggtttTCTGgtgattagtt
tTCttCT > SEQ ID NO:80 130213 156770
TACAAAACTCCCTCTCTCATTTCCTCTCTCATAGCAACATGAATGGCGTCGCCACGCGAGGAGAACGTGTACATG
GCAAAGCTTGCCGAGCAAGCCGAGCGTTACGAGGAGATGGTTGAGTTCATGGAGAAAGTCATCGCCGCCGCCGAC
GGCGCCGAGGAACTTACCGTCGAAGAACGGAACCTCCTCTCCGTCGCATACAAAAATGTTATCGGAGCACGGCGA
GCCTCGTGGCGTATCATCTCCTCCATTGAGCAAAAAGAGGAGAGCCGCGGCAACGAAGATCACGTTGCCTCCATC
AAGGAGTACAGATCTAAGATCGAGATCGAACTTACCTCGATCTGTAACGGCATTCTCAAGCTCCTCGATTCTAAG
CTCATTGGCGCCGCTGCTACCGGTGACTCTAAGGTGTTTTACTTGAAAATGAAAGGAGATTATCATCGCTATTTG
GCTGAGTTTAAAACCGGCGCGGAGCGAAAGGAAGCCGCCGAAAATACTCTCTCGGCTTACAAATCCGCTCAGGAT
ATTGCAAATACCGAGCTTGCTCCTACACATCCAATCCGATTGGGACTTGCTCTCAATTTCTCTGTATTTTACTAC
GAAATTTTGAATTCTCCTGATCGTGCTTGTAATCTCGCCAAACAGGCTTTTGACGAGGCAATTGCCGAGCTGGAC
ACATTGGGCGAAGAGTCATACAAGGATAGCACTCTGATCATGCAGCTTCTTCGCGATAACCTCACTTTATGGACT
TCAGATATGCAGGATGATGGAACTGATGagaTCAAAGAAGCAGCAAAACCAGATaATGagCAGCAGTAAACCGGT
GACATtTCTttaggattGAAAtTCATGttgTaacTTTTTATTTTTCAatT > SEQ ID NO:81 130213 155114
AAGCTGAGAGATATGATGAAATGGTGGAAGCAATGAAGACGGTTGCTAAGATGGATGTCGAACTGACTGTTGAGG
AGAGAAATTGGTGTCAGTCGGGTATAAGAATGTAATTGGAGCAAGAAGGGCTTCATGGCGGATATNGTCTTCGAT
TGAACAAAAGGAGGAGAGTAAGGGTCATGAGCAGAATGTTAAGAGAATAAAGACTTACAGACAGAGGGTTGAAGA
CGAGCTTACAAAAATATGCGTTGACATTTTGTCGGTGATCGATGAGCACCTTGTTCCTTCATCTACTGCTGGTGA
ATCTACTGTCTTCTACTATAAGATGAAGGGAGACTACTATCGCTATTTAGCAGAGTTCAAATCAGGGGATGATCG
TAAAGAGGCAGCTGATCAGTCACTTAATGCTTATGAGGCTGCTACTGCCACAGCTAGCGCAGATCTTGCTCCTAC
TCATCCAATTAGACTTGGACTTGCATTGAACTTCT > SEQ ID NO:82 130213 13783
CCCACGCGTCCGAGAAGAAGAAGAAGAAGAAGAAAAAACTATGGAGAATGAGAGGGAAAAGCAGGTTTACTTGGC
TAAGCTCTCCGAGCAAACCGAAAGATACGATGAAATGGTGGAGGCGATGAAGAAAGTTGCTCAGCTTGATGTGGA
GCTAACTGTGGAAGAGAGGAATCTTGTATCTGTAGGGTACAAGAATGTGATTGGTGCAAGGAGAGCATCATGGAG
AATACTATCTTCCATTGAGCAGAAGGAAGAGTCCAAGGGAAATGATGAAAATGTCAAGAGGCTTAAGAATTATCG
TAAGAGAGTTGAAGATGAGCTTGCTAAAGT

Figure 2 continued

> SEQ ID NO:83 130213 128752
ccccccgagatctcaaaaattcaacattggcACAACCAAAAAGAAAAGAGATCCCTAAATTGGAATTCATTATGG
CGCGTGAGGAGAACGTGTACATGGCGAAGCTTGCCGAGCAAGCCGAGAGATACGAGGAAATGGTGTCGTTCATGG
AGAAAGTCTCTACTTCCTTAGGGACGTCAGAGGAACTCACGGTAGAGGAGAGAAATCTCCTCTCGGTGGCGTACA
AAAATGTTATCGGGGCTCGTAGAGCCTCGTGGCGTATAATCTCCTCCATCGAACAGAAGGAGGAGTCGAGGGGAA
ACGAGGACCATGTGAAATGCATTCAGGAGTACAGATCTAAGATTGAATCTGAACTCTCTAGTATCTGTGATGGCA
TTCTCAAGCTCCTTGATTCTTGTCTTATTCCTTCTGCTTCAGCTGGTGATTCTAAGGTGTTTTACCTTAAAATGA
AGGGTGATTATCATCGTTATTTGGCTGAGTTTAAGACTGGTGCTGAACGTAAGGAAGCCGCTGAGAGTACTCTCT
CCGCCTACAAAGCCGCTCAGGATATTGCAAATGCTGAACTTGCCCCAACTCACCCAATCCGACTTGGACTGGCTC
TCAACTTCTCTGTGTTTTATTATGAGATTTTGAACTCTCCTGATCGTGCCTGCAATCTTGCTAAACAGGCCTTTG
ACGAAGCAATTGCTGAATTGGACACACTGGGAGAGGAGTCTTACAAGGATAGCACTTTGATCATGCAACTGCTTC
GTGACAATCTTACTCTCTGGACCTCTGATATGCAGGATGATGGCGCTGATGAAATCAAGGAAACCAAAGCTGACA
ATGAACAACAGTGAGGAAACTGCCCCTCATATTGTCTTTTGACTTCTTCCTGTTGGTTTTTATTGGGAGAAGCTG
TTTCCTTTTATTTCCTTTTTAATGTGGTTTCCCTTcagcgTTCTCTTATCCGTCGCAATAACAACTTTGACAATT
GATGTTCAATGATTTTATCTTTATTTT

> SEQ ID NO:84 130294 104619
cccacgcgtccggttgaaatgcccaccaatttcaacaacaggggttgaatccAAGAAGCTTAAGGTGAATCCCAT
TAATCATCAGAATAAGAAGGCTAACAAAGCAAGAGTAGTAGCACAAGCTGCAGCAGTGGTCACAAATGCACAAAC
AAGAGAAAGACAAAAGCTTAAGGAGATGTTCGAGGATGCCTATGAGCGATGCCGTACTGCACCTCTCGAAGGTGT
TGCCTTTACCGTTGATGATTTTCACTCTGCCCTTGAAAAATATGATTTTGACTCCGAAGTTGGTACCAAGGTCAA
AGGAACAGTTTTCTCTCTGGATGCAAATGGAGCTCTAGTTGACATCACTGCTAAATCATCTGCATACTTGCCTTT
ACGGGAGGCTTCACTTCACACCATCAAGCACGTAGAGGAAGCCGGAATATTTCCTGGTTTGCGTGAGGAGTTTGT
GGTGGTTGGCGAAAATGAAGCTGATGATAGTTTGATTTTGAGCTTGCAATCGATTCAATATGACCTTGCATGGGA
ACGATGTAGGCAGCTACAAGCGGAAGATGTTGTTGTCAAaggcAAggtcGTTGGTGCAAATAAAggTGGAGTggT
GGCTCTGgTggaggGCTtCGtggttTTg

> SEQ ID NO:85 130294 47044
AAAACTCTCTGTGTGAGTGAGTGAGACTCAACCATGGCGTCTTTGGCTCAGCAATTCTCGGGATTGAGATGTTCC
CCACTCTCTTCTTCTTCTAGGTTATCGAGGAGAGCTTCGAAGAACTTTCCCCAGAACAAATCTGCCTCTGTTTCT
CCGACTATTGTCGCCGCGGTTGCAATGTCTAGCGGTCAAACAAAGGAGCGTCTTGAGCTGAAGAAGATGTTCGAA
GATGCTTATGAACGATGTAGAACTTCTCCTATGGAAGGTGTTGCTTTCACCGTCGACGATTTCGCTGCTGCTATT
GAACAATACGACTTCAATTCCGAAATCGGCAC

> SEQ ID NO:86 130294 167654
gaattcagggaaaacagagtcgtttctggtacaaattaggtctaaagatggcgtctttAGCTCAACAATTCTCAG
GATTAAGATGCCCACCACTTTCTTCTTCTCATCTAACAAAACCCTTTTCTTCAAAACCCCAGAAAACCACCTTTT
CACCTATAGTTTCAGCAGCTGTCATTTCTAATGCACAAACTAAAGAAAGAAGTAGACTTAAAGAAAATCTTCGAAG
ATGCTTATGAAAGATGTAGAACTACTCCAATGCAAGGTGTTGGTTTTACTGTTGATGATTTTCATGCTGCTCTTG
AAAAGTATGATTACAATTCTGAGATTGGTACCAGGGTTAAAGGAACTGTGTTCTGTACAGACAACAACGGAGCAT
TAGTTGACATCACGGCGAAATCTTCAGCCTATTTACCAATCCAAGAGGCATGTATTCACAAAATAAAGCATGTAG
AAGAAGCAGGAATAGTTGCAGGCCTACGTGAAGAGTTTGTGATTATTGGAGAGAACCAAGCTGATGATAGCTTGA
TCTTGAGTTTGCGTTCAATCCAATTTGACCTCGCATGGGAACGGtgTaGaCAACTTCAGgCagaggATGTCGTCc
TcaagggTAaggttgtTGGTGGAAACAAa

> SEQ ID NO:87 130964 232178
cggacgcgtgggGCCAGGGCTCTGACCGCGTGCCTGTTGAAGAATGAGCCGGCGACTCATAGGCAGTGGCTTGGT
TAAGGGAACCCACCGGAGCCGTAGCGAAAGCGAGTCTTCATAGGGCAATTGTCACTGCTTATGGACCCGAACCTG
GGTGATCTATCCATGACCAGGATGAAGCTTGGGTGAAACTAAGTGGAGGTCCGAACCGACTGATGTTGAAGAATC
AGCGGATGAGTTGTGGTTAGGGGTGAAATGCCACTCGAACCCAGAGCTAGCTGGTTCTCCCCGAAATGCGTTGAG
GCGCAGCAGTTGACTGGACATCTAGGGGTAAAGCACTGTTTCGGTGCGGGCCGCGAGAGCGGTACCAAATCGAGG
CAAACTCTGAATACTAGATATGACCCCAAAATAACAGGGGTCAAGGTCGGCCAGTGAGACGATGGGGGATAAGCT
TCATCGTCGAGAGGGAAACAGCCCGGATCACCAGCTAAGGCCCCTAAATGACCGCTCAGTGATAAAGGAGGTAGG
GGTGCAGAGACAGCCAGGAGGTTTGCCTAGAAGCAGCCACCCTTGAAAGAGTGCGTAATAGCTCACTGATCGAGC
GCTCTTGCGCCGAAGATGAACGGGGCTAAGCGATCTGCCGAAGCTGTGGGATGTAAAAATGCATCGGTAGGGGAG
CGTTCCGCCTTAGAGGGAAGCACCCGCGCGAGCAGGTGTGGACGAAGCGGAAGCGAGAATGTCGGCTTGAGTAAC
GCAAACATTGGTGAGAATCCAATGCCCCGAAAACCTAAGGGTTCCTCCGCAAGGTTCGTCCACGGAGGGTGAGTC

Figure 2 continued

AGGGCCTAAGATCAGGCCGAAAGGCGTAGTCGATGGACAACAGGTGAATATTCCTGTACTACCCCTTGTTGGTCC
CGAGGGACGGAGGAGGCTAGGTTAGCCGAAAGATGGTTATCGGTTCAAGGACGCAAGGTGACCTTAGGGTAAGAA
GGGGTAGAGAAAATGCCTCGAGCCAATGTCCGAGTACCAGGCGCTACGGCGCTGAAGTAACTCATGCCATACTCC
CAGGAAAAGCTCGAACGACCTTCAACAAAAGGGTACCTGTACCCGAAACCGACACAGGTGGGTAGGTAGAGAATA
CCTAGGGGCGCGAGACAACTCTCTCTAAGGAACTCGGCAAAATAGCCCCGTAACTTCGGGAGAAGGGGTGCCTCC
TCACAAAGGGGGTCGCAGTGACCAGGCCCGGGCGACTgtttaccaAAAACACAGGTCTCCGCAAAGTCGTAagac
cATGTATGGGGGCTGACGccTgcccaGTGc > SEQ ID NO:88 130994 111720
CATTTCTGGTCCCTTCTCTTCATAGTCTTTTTCTCTTTCTCCATCTCCTCCATTTCCGGATCTGATGATGATTGC
GTGTACACAGCTTACGTCCGAACGAGTTCAATAATAAAGGGTGGAACAGATTCGATTATCAGTTTGACTCTCTAC
GATGCAAACGGGTATGGTCTTAGAATCAAGAACCTTGAGGCCTGGGGTGGGCTTATGGCTCTGGTTACAACTAT
TTCGAGAGGGGAAATTTGGACATTTTCAGCGGACGAGGCCCATGTTTGACTGGGCCTGTCTGCAAGATGAACCTC
ACTTCCGACGGAACTGGCCAAGGCCATGGATGGTACTGTAACTACGTGGAGGTCACCGTCACCGGAGTCCATAAA
GCATGCAACCAACAGAATTTCGAAGTGGAGCAGTGGCTCGCTACTGATGCGCCGCCTTATCAGCTTACGGCTGTT
AGAGACAACTGTAAGAAGACCAAGTCCGATGAGAAACTGTCCATTTCCGATGTCTACGGAACTCATTCCACTCCA
CCTGTTTCTGTGATTTAAATTTCTAGTTATTGGGTTTTAATGGGCCTGGACCCACATTTCCCTTTTACCCTTATT
ACTGTGATGTGAAATTTATCAGGGGTAAGAATGACATT > SEQ ID NO:89 130994 128356
TCATTTTCTAGAGAAAGAAACAACAAGACGTACAGAACGAGAGTTCAAGAATCTGCAATGGGAGTGGCTCGAGTT
AACCAATTCTGGTTGCATCTTGTCATCCTCTTCTCCATCTCCGTTGCTTCCATTTCTAGCACTGAACTGAATTGT
GTATACACAGCTTATGTTCGGACTGGGACATACTGGGGGTCTGGAACTGACTCAAAAATTTCCTTGTCTCTTTAC
GATGCCAATGGCCATGGTCTTAGAATCAATAACCTACAAGCCTGGGGTGGGCTTATGGCCCGGGTTATGACTAC
TTTGAAATGGACCAATTGGATATGTTTACGGGCCGTGGTCCATGTTTGACTGGACCAATCTGTAAAATGAACTTG
ACTTCTGATGGATCAGGTGAGCACCACGGATGGTACTGTAACTACGTGGAAGTCACGTCTACAGCAGAACACAAA
CGATGCAGCCAACAGGTGTTCACCGTGGAGACGTGGCTCAGTGCCGGTCAGTACCCagaTGGGTTGACCGCCATT
AGGAACAACTGTAAGCGTATTtccaaCGAACAACAACCAATTCATGATTCTGATcaaTCTTATCATGttgtgGAT
GTAATTTaattCGAgtttattggaCGttGTATGATTTACgaaggccATTtaggccaaggccTGATATGTACTCTc
acGagtgCTACATagttggAatggaaaagttTtCtttAccca > SEQ ID NO:90 130994 252626
GATGTCGACGGGGAAAGGCTTAGCTCTAATCCTGGCATTTGCTGCCATCGCCACCTGCATCACCTCTGCTACGAA
CCAATGCGTATACACTATTTATGTGAGGACGGGAAAGGTGATAAAAGGGGGGACAGATTCAAACATTTCGGCACG
ATTCTATGATGCCAACGGATACTATATCAATTTGGAAAATTTGGCAGAATGGGGTGGTTTGGGAGGTCCTGGCTA
CAACTACTTTGAGAGAGGCAATTTGGATGTGTTCACAGGCCTTGGGCAGTGCCTCACGGCCCCCATTTGCGCGCT
CAACCTGACCTCAGACGGCACTGGAGACCAACACGGGTGGTACTGCAACTATGTCGAGGTCACCTCCACCGGGCC
CCACATCCCTTGCAGCCAACACCAATTCACCATCGAGCAATGGCTTGCCACTGACACCTACCCTTTCGAGCTCAA
TGCCACCCGTGACGATTGCCTGGTCGAGGGCAAAACCAGCGCCTCCAAGGCAATTTCATCAGAGTCGAGCTAGAG
TTCCAGCTGGGCCTTTTTTGGCTTCCGTTTTTGATGAATAAGCAAGCTCCTTCT > SEQ ID NO:91 130994 47162
AAAAAAACAAAATGGCTCGTCGCGATGTTCTCCTCCCTTTCCTCCTCCTTCTCGCCACCGTCTCCGCCGTAGCTT
TCGCCGAAGATGATCCAGACTGTGTATACACATTCTACCTCAGAACCGGATCGATCTGGAAAGCCGGAACCGATT
CGATCATCAGCGCAAGAATCTACGATAAGGACGGTGACTACATCGGAATCAAAAACCTTCAAGCTTGGGCTGGAT
TAATGGGACCTGATTACAATTACTTCGAGAGGGGTAATCTCGACATTTTCAGTGGAAGAGCACCGTGTTTACCTA
GTCCGATCTGTGCCTTAAACCTAACCTCCGATGGCTCCGGCGATCACCATGGTTGGTACGTTAATTACGTTGAG > SEQ ID NO:92 130994 285363
acggaAAATCTTAAAAGAAAGAAAGAAATGATGACGAATCGCCACTTCCTCTTCGCTCTTCTTTTCACTTTCTTT
CTTTCAGCTGTTGCTGCAGATTCTTCTGAAGAGTGTGTATACACATTGTATGTTAAAACTGGATCAATCATAAAG
GGTGGAACAGACTCCAAAATCAGCGTTACACTTGGCGATGCTAAAGGAAAATCAGTATATATTCCAGATCTAGAG
AAATGGGGTTTAATGGGCCCAAATTATGATTACTACGAAAGGGGTAATGTGGATATCTTCACTGGTAGAGGCCAA
TGTTTAAGCCCACCAATTTGCAGGCTTAATGTTACTTCCGATGGATCAGGTGACCACCACGGTTGGTTTCTTGAT
TTTGTTGAGACTACTTTTACTGGGCCACACAAAACTTGTAGCCAATCCATATTCTATGTCGAACAATGGTTGGCT
TCTGATGCTCCTCCTTATGAGTTATCAGTTTCTCTTGATGGTTGTAAAAAGAAGACTGGGCTTCGACATGCTCGG
CGTTTTGTCGTGGGCCagCCCAATGGGTCTGCTTCAGAATAGTTTGGCCCGTTGAAGTTCTTTTTGTAATTTTGT
CGTTGAGATGATTTTGATGTGTAGaTTGccCTGTGTTTTCCCTTCTCTTTGGTTGAAATAAattTCTTGTTTGGG

Figure 2 continued

GCttcctttCTTGCttgtttagtCGtcaTATCTTTgacttAttGGCTCtTTGgCATTTGCATCTTTtatgtacT
ca

> SEQ ID NO:93 130994 171733
CCCCGATCTCCACCACCACTTTCCCGGGGACCGCGGCGGGAAAGGGCCTTCGAGACTTGGGAGGTTGGAGCGAGC
AAGCTCGGCCATGGCGAAGCTCTCCTGCCTTCTCATCGTCTCCTTCGCCGTCGTCGCGGCGTTGGCGGCCACGGA
CGACGACGCGGCGGCGGCGGCTGAGGGGATCACGGTGGCGGAGGCGTCGTCGGACCCGGAGAACAAGTGCGTGTA
CACGATATACGTGCGGACGGGGACGATCTGGAAGGGCGGGACGGACTCGGTGATCGGCGTGACGCTGCTGGGCGC
CGACGGCTCCGGGGTGCGGATCCGCGACCTGGAGCGGTGGGGCGGCCTCATGGGCGACGGCCACGACTACTACGA
GCGCGGCAACCTCGACATCTTCA

> SEQ ID NO:94 130994 158728
ATTTTTCTAGAGAAAGAGAGTTCAAGAAACCATGGGAGTAGCTCAAGTTAACCAAATATGGTTCCATTTCATGAT
AATCCTCTTCTTCATCTCCATATCTTCTAGTTCTGCATCAGAAGATGATTGTGTGTACACAGCTTACGTTCGAAC
TGGATCAATCATAAAGGCTGGAACTGACTCAAACATTATTTGACTCTCTACGATGCCGCTGGCTATGGGATAAG
AATCAAGAACTTAGAGGCATGGGGTGGGCTTATGGGCCCAGGTTACAACTATTTCGAAAGAGGAAACTTGGATAT
ATTCAGTGGACGTGGTCCATGTTTGACTGGGCCGATCTGCAAAATGAATCTGACTTCTGATGGATCAGGCCCACA
TGCCGGATGGTACTGTAACTACGTCGAAGTTACCGTTACTGGAGCCCACCAACAATGCAACCAGCAGCTTTTCAC
CGTGGAGCAGTGGCTCGGCACTGACGTTTCGCCGTATGAGCTGACGG

> SEQ ID NO:95 130994 130994
GAATTCACATCTAAAGTCAACAACAAGAGCTTCTCGCTTCTCCTCGTCTCTGTTCTCCTCTCTTTTGCAATCCTC
TCTCAATCTGCTGATGATTGTGTATACACAGTATACACAAGAACAGGATCAATCATCAAAGGAGGAACGGATTCA
AAAATCTCACTAAGATTATACAGCAAATACGGTAAGTACATCGAGATCCCAAATCTTGAATCATGGGGTGGATTA
ATGGGTCCTGGTTACGATTATTTCGAAAGAGGTAATCTTGATATCTTCAGCGGAAGAGGTTATTGTCTGGGTTCA
CCGGTTTGTGCCATGAATCTGACTTCCGATGGTACTGGTTCCGGTCACGGATGGTATGTGAATTATGTTGAAGTT
ACTACTACCGGTGCACATATTAATTGTGGTCAACAGAATTTTGAAGTGGAAGATTGGCTTGCTCTTGATAGATCT
CCTTATAGTCTTACCGCTATCAAGAATAATTGTAATCAGAAATTATCTGATCATGATTCTCATTCTGCTGATCAG
TCTATGTAAAATTTGATCTCTTGTTTGATTCGGTGGTGGTCTAGTATGAGTGATCGGACGGTCGTCATTGTGTGT
TGTAATGTTGAAATTATTTTCTTGAATAAAATGATTGAGTGAGTAGTG

> SEQ ID NO:96 131002 130593
GAATTCATGTTCTTTATTGTTTGTTTTTCTTAAGGCTTCCAACTCTCTACATCTCTTGCTCTCTCAATGATCAAA
AAAATTTGGGGAGAAGAGATTAAAAGAAAAAAAGAAAAGAAAAAGAAGGTTGGACAAGTTTCCGTTTTGGTTATG
AGAATTGGTTTTGAAAATGCCTGCTAAGAGTCCAACTTCCTGCTGGCTTTTATGATTTTGCGAGGTATCAAAAA
CCAATGTCCAAGTGTTAATCAATGAAATCAACAATCACAATATTGGATCTCTAATTGATTAAACTTAACAACGCA
CAACCAGTATTGTTTCAATTATATAAAATATAATTCGGAAAATAAATAACACAGACACCAGAATTTTGTTAACGA
GGAAACCGCAAATGCAGAAAAACCTCGGGACCTAGTCCAGATTACATACACACTGTATTAAGCCGCTATAGACAC
TAGCCTTTTCCAAACTAACTTCGGGCTGACCTATAGTTGAACCAGTACCAGTCTCCCACGGATACAAGGTACAAT
TGCACCTCTACGCCTCTGATCCCAGCAGGATGTTATGTACTTGATTCCCTTTGCAGATCTGACCAGCGTAGTACT
CACATGGAA

> SEQ ID NO:97 131002 181566
gaattcggagaggtgatcatcaatctaggctaccattgggcacataagaccggattgattgattaggttccttag
gtaccTTGGTATTTAATATCAAAAACGGAACAAAGAGTTTAGGGTTTTTCTGTGGGAGACAGATTGATCCTTTTG
ATAgaCTTATCTGTGTGATACAGATTTGTTTATTGTTAAGCCTGCGTTTGTGTGCGTancAACTCGTTGCAGTGG
GTGAGATCTGCATCGGGATTCAAGTACGTGGTGTCCAGCCGTTTGGGGGATCCGGAGGCGTagaGGTATAACTGT
ACCTTGTATCAGTGGGagATTGATAGGGGTTCTTCTATagaTCAGTCCGAAGTTAGTTGGAGTaggCTAGTATCT
GTAGCGGCTTAATACAGTGTATGTCTAATCTGGACTAGGTCCCGGGCTTTTTCTGCATCTGCGGTTTCCTCGTTA
ACAAAATCTCTGGTGTCTGTGTTATTTCTTTTCCGcatCTTTTTAgaTTGAAATAATACAGGTTGTGcgttggta
actttaATCAGTTTATagatccAATCTTGTTATTGTTGATCTTGCTGATTAACACTTGGATATTGGTTTTTGATA
CCGTCCAAGTCTATATCTCTTTGGTTTGACTAGACTCGCAAACTTGTTTGTTTGAGTAGTTCTCAAATCAAGAGA
TAGAGATATCAACTCCTTGAGTCACTATATTCTAGATTGATCCTGACTGTCTAGTCGTTTCTCTAGTAGCGTGAT
TCGGAGGTTGTCCTAATCAGATTGCTAATCGAAAAGTTTggTGGTGTTGTTAGAGCCCCGCTTTTTCAATCCTTA
GAAGAAGAAAGACATTACGCATGCGCAGAAGCAGCGAGAAgttcTaAAGGATTAGCAgGTTGTTGCGAAATCTCC
TttagttgaaTCGGAACTTCttGGGGAACttccACAaa

> SEQ ID NO:98 131048 12899

Figure 2 continued

CCCACGCGTCCGCAAGCCGTCGTCTCCAAAGTTCCCCCTCAGAGACGAAAAAATGAAGACCATTTTGTCCTCGGA
GACTATGGACATCCCCGACGGCGTCGCCATTAAGGTAAACGCCAAGGTGATTGAGGTCGAAGGTCCACGAGGTAA
ACTCACTCGTGACTTCAAGCATCTGAATCTCGATTTCCAGTTGATTAAAGACCAAGTCACTGGAAAACGTCAGCT
TAAGATTGATTCTTGGTTTGGTTCTCGTAAGACAAGTGCTTCGATTAGAACTGCTTTAAGCCATGTTGATAATCT
CATT

> SEQ ID NO:99 131048 195865
cccacgcgtccggccccgacaacCCCCAAGTCACAGCAGCCATGAGGTACATTCACTCTCAGGAGATCCTGGAAA
TTCCAGAGGGCGTCAAGGTCAACATCAAGACCCGTATCGTCACCGTTGAGGGTCCCCGAGGCAAGCTCACCAAGA
ACCTCGGTCACTTGGCTGTCAACTTCGGTCACCCCAAGAAGAACACCATCTCCATCGAGATCCACCACGGCAACC
GTAAGAATGTCGCCACTCTCCGTACCGTCCGCTCCATCATCGAGAACTTGATCACCGGTGTCACCAAGGGCTTCA
AGTACAAGATGCGATACGTCTACGCCCATTTTCCCATCAACGTCAACCTGGACAAGAACAAGGAGACCGGTCTGT
TCGAGGTGGAGATCCGAAACTTCATCGGCGAGAAGATCGTCCGACGGGTTACCATGCACGAGGGTGTCGATGTTG
AGATCTCCAAGGCCCAGAAGGATGAGCTCATCCTGACCGGCAACTCACTCGAGAACGTTTCCCAGAGCGCCGCAG
ATATCCAGCAGATCTgccGGGTGCGCAaCaaggATATccGAAAgttctTGGAcggtcTGTACG

> SEQ ID NO:100 131048 237440
gggTGCGAGGAGGAGGAGGCGGGCGCGATGAAGACGATCTTGTCGGCCCAGACGATGGACATCCCCGAGGGGGTG
AAGGTAGAGATCCGGGCGAAGCAGATCCGGGTGACGGGGCCGCGGGGGGTGCTGCACAGGAATTTCAAGCACCTC
AACCTCGACTTCCAGCTGCTGGAGAATGGGCGCAAGCTCAAGGTGGAGGCGTGGTTTGGGTCGCGCAAGACCATC
GCCGCCATCCGCACCGCCGTGAGCCACGTGAAGAACCTCATCACCGGCGTCACCAAGGGCTTCCAGTACAAGATG
AGGTTTGTCTACGCTCACTTCCCCATCAACGCCAACATCTCTGCCACCAAGCAAAACATCGAGATCCGGAACTTC
CTCGGCGAGAAGAGGGTGAGAACTGTCGACATGCTTCCGGGTGTGACTGTGACCAGGACGGAGAAGGTCAAGGAC
GAGCTTGTTCTCGAGGGGAATGACATCGAGCTTGTGTCGAGATCGGCCGCTCTCATCAACCAGAAATGCCATGTC
AAGAACAAGGATATCAGGAAGTTCTTGGATGGTATCTACGTGAGCGAGAAGGGAACGATCGCTGTGGAGGAGTAG
ACCTGttgcctGTTCTgAGTATaat

> SEQ ID NO:101 131048 136965
CCCCCCCCCGCTTCCTTCTTCTTCCACGCCGGGCATCGCCGCCGCCGCCGCCGCCGCCGGAGAGGGAGAGAGAGA
GAGAGAGATCGAGAGCAAGAGATGAAAACGATCTTGGCTTCGGAGACGATGGAGATCCCGTCGGGGGTGACGGTG
CACGTGGCGGCGAAGGTGGTGACGGTGGAGGGTCCCCGTGGGAAGCTGACGCGCAACTTCAAGCACCTGAACCTG
GACTTCCAGCTGCTGGAGGTGGAGGGGGTGAGGAAGCTGCAGGTGGACGCGTGGTTCGGCACCCGCCGCACCATG
GCCGCCATCCGCACCGCCATCTCCCACGTCCAGAACCTCATCACCGGCGTCACCAAGGGCTACCGCTACAAGATG
CGCTTCGTCTATGCCCATTTCCCCATCAACGCCTCCATCACCAACTCCAACACCGCCATCGAGATCAGGAACTTC
CTCGGCGAGAAGAAGGTGAGGAAAGTGGACATGCTTGAGGGTGTGACAATTTTGCGTTCTGAGAA

> SEQ ID NO:102 131048 258567
gcaatgaagtcatccagtccGACGTTCTGCTCGATATCCCCGAGGGTGTCACCGTTGACATCAAGGCCCGACGAA
TCACCGTCACCGGCCCCCGAGGTACCCTCAAGAAGAACCTGTCTCACATCAACGTTGCCTTCGAGAAGGTCTCCG
ATGACCAGATCAAGATCACCATCTTCGATGGTGACCGAAAGCACGTCGCTgctCTGCGAACCGTCAAGACCCTCA
TCAACAACATGATCACCGGTGTCACCCGAGGTTACAAGTACAAGATGCGATACGTCTACGCCCATTTCCCCATCA
ACGTCAACCTCATTAAGGACGGTTCCGTCGTTGAGATCCGAAACTTCCTCGGTGAGAAGCGAGTCCGAGAAGTCC
CCATCCACGAGGGCTGCAGCGCTGAGATCTCTACCAACCAGaAGgaTGAGATCTGCATCATCGGTAACTCCATCG
AGAACGTCTCTCAGACCTGTGCTGACATCCagcagatctggcgagTCcgacacaaggATATCCGaaagttcCtTG
ATGGTATCTacgtttccgagaat

> SEQ ID NO:103 131048 271912
GCTGCTAGGGTTTTAGCGATCGCCATTTTCACACACACAGAGGGAGAGCGATAGAGAGAAACTAAGACAAGATGA
AGACCATTCTGTCATCAGAAACCATGGATATCCCCGACGGCGTGAGCATCAAGGTGAAGGCAAAGCAAATCGAAG
TAGAGGGACCAAGGGGCAAACTTGTCCGAAACTTCAAGCATCTCAACCTCGATTTTCAGCTGATCAAGGATGAGG
AAACTGGCAAGAAGAAACTGAAGATCGACGCTTGGTTTGGTTCTCGTAAGACTACCGCTGCTATCCGTACTGCTC
TTAGCCATGTTGAGAATCTCATCACTGGTGTTACGAAAGGTTACCGCTACAAGATGCGTTTCGTGTATGCTCACT
TTCCCATCAATGCCTCCATCACCGGTGGTAACAAGTCCATTGAGATCCGTAACTTCCTTGGCGAGAAGAGAGTTA
GGAAAGTGGACATGCTTGATGGGGTTACAGTTGTTCGATCTGAGAAGGTGAAGGATGAGCTTGTATTGGATGGAA
ATGACATTGAGCTCGTTTCTCGCTCTGCTGCCCTCATCAATCAAAAATGCCATGTGAAGAACAAGGATATCCGAA
AGTTTCTTGATGGTATCTATGTCAGTGAGAAGGGCAGAATTGCAGAAGAAGAATGAGCAGCTGTTTTAGAAGTAG
GCATATCACTGATGATTCATAtccagaatGCCCTTTTTACTTttc

Figure 2 continued

> SEQ ID NO:104 131048 268876
GCCGGTAGGCAGTAGTGAGCGCAGAAGCAGGGAGAGACACAAAAAATGAAGACTATACTCTCATCAGAAACGATG
GATATCCCCGATGGGGTGAAAATCAAGGTAAAAGCAAAGCAAATAGAAGTGGAGGGACCAAGAGGAAAGCTAACC
CGCAACTTCAAGCACTTGAATCTTGATTTTCAGCTCATAAAAGATGAAGAAACTGGAAAGAAAAAGCTCAAGATT
GATGCTTGGTTTGGATCTCGTAAAACCACAGCTGCTATTCGCACTGCTCTTAGTCACGTTGATAATCTCATAACT
GGTGTCACAAAAGGGTACCGTTACAAGATGCGTTTTGTTTATGCCCATTTTCCTATCAATGCTTCTATCACTGGT
GGGAACAAGGCTATTGAGATCAGGAACTTTCTGGGCGAGAAAAGGGTGAGGAAAGTCGATATGCTTGATGGGGTT
ACTGTTGTGAGGTCTGAGAAAGTTAAGGATGAATTGGTATTGGATGGAAATGACATTGAGCTTGTTTCTCGGTCT
GCTGCCCTCATCAATCAGAAATGCCATGTGAAGAACAAAGATATCCGTAAGTTCCTGGATGGTATCTATGTGAGT
GAGAAGGGAAGAATAGTTGAAGAAGAGTGAGTTTTAGCAGACTTGTTGTGGGGTTGTTTGGGATCATGTGCTGAT
TTCGTACGAACTCATTTGAAGTTAATTCAACAATTTTGGTTCCATGGTTTTCTGGATGAATTATCTGTTAAAGTG
TAATATTATGTTTTATGTCTTGCTCATTGAGTAGAGATGGATGTTTTCGTTTGATGGTTTGCTTATTAAAAGATC
AATTTTTATGTCAGCTTTTCACCTTATAAAAAATGTCAGTTTTTTCCTTTTAACTGCTGTTGCcttatgcatttt
gagatgtatttaacttccttttctggggttaggtggatttgacttatatacagaatcgatgtgtctt

> SEQ ID NO:105 131133 103543
tggtatcaacgcagagtggccattacggccgggGATCACAACTAACTTTGACATCTCAAACTAGCAACCTCTCAC
TTTCCTCTTGATAAACCATGGCTGCTTCTACAATGGCTCTTTCTTCCCCTTCTTTTGCTGGACAGGCAGTGAAAC
TCTCCCCATCTGCCTCAGAAATCACTGGAAATGGAAGGGTCTCCATGAGAAAGACTGTCACCAAACCCGTCGCAT
CTAGCAGCCCATGGTACGGCCCAGACCGTGTTAAGTACTTGGGCCCATTCTCCGGTGAGGCCCCAAGCTACTTGA
CCGGTGAATTCCCAGGTGATTACGGGTGGGATACTGCTGGACTTTCAGCAGATCCAGAAACATTTGCCAAGAACC
GTGAACTCGAAGTGATCCACTGCAGATGGGCTATGCTTGGAGCTCTTGGATGTGTCTTCCCTGAGCTCTTGGCTC
GTAACGGTGTCAAGTTTGGTGAAGCTGTCTGGTTCAAGGCTGGATCCCAAATCTTTAGTGAGGGTGGACTTGACT
ACTTGGGCAACCCAAGCTTGGTCCATGCACAAAGCATCTTGGCCATCTGGGCTTGCCAAGTTATCTTGATGGGAG
CCGTTGAGGGTTACCGCGTTGCTGGTGGGCCTCTTGGTGAAGTTGTCGACCCACTCTACCCTGGTGGCAGCTTTG
ACCCATTAGGCCTTGCTGATGACCCAGAGGCATTTGCTGAGCTCAAAGTaaagGAGATCAAGAATGGTAGACTTG
CCATGTTCTCTATGTTCGGATTCtTTG

> SEQ ID NO:106 131133 103636
tttcttTATCACTTCAGCCATCAGAAAACTCTTCATTCTCCTTATTAAGCCATGGCTGCTTCTACAATGGCTCTT
TCCTCTTCTTTTGCCGGGAAGGCACTAAAACTCTCGCCATCTTCCTCTGAAATCACCGGAAATGGAAAGTTACC
ATGAGGAAGACTGCTAGCAAGCCCAAGCCTGTATCTTCTGGCAGCCCATGGTACGGTCCTGACCGTGTCAAGTAC
TTGGGTCCATTCTCTGGTGAGTCCCCAAGCTACTTGACTGGTGAGTTCCCTGGTGACTACGGGTGGGACACTGCT
GGACTTTCAGCTGATCCAGAAACTTTTGCCAAGAACCGTGAGTTGGAGGTGATCCACTGCAGATGGGCAATGCTT
GGAGCTCTTGGTTGTGTCTTCCCCGAGCTCTTGGCCCGTAACGGTGTCAAGTTTGGTGAGGCTGTATGGTTCAAG
GCTGGATCCCAAATTTTTAGCGAGGGTGGACTTGACTACTTGGGCAACCCAAGTTTGGTCCATGCTCAAAGCATC
TTGGCCATTTGGGCTTGTCAAGTTGTGTTGATGGGAGCCGTTGAGGGTTACCGTGTTGCTGGTGGGCCTCTTGGG
GAGGTTGTTGATCCACTCTACCCCGGTGGCAGCTTCGACCCATTGGGCCTCGCTGAAGACCCAGAAGCTTTTGCT
GAGCTCAAGGTAAAAGAGATCAAAAATGGTAGACTTGCCATGTTCTCCATGTTTGGATTCTTTGttcaggctAtC
GTaaCTGGaaagggcCCATtggagaaccttGccGATcAcctTGCagacccagttaataacaacGCttGGGcctAc
gcaaCaaacttTGtccc

> SEQ ID NO:107 131133 108311
CTGCATTCAAGAGTTTTTCATCTTCTTTCTATAATGGCAGCTTCTACAATGGCTCTCTCTTCCTCTTCATTTGCC
GGAAAGGCGGTAAAACTCTCATCATCTTCCTCTGAAATCATTGGAAATGGGAAAGTTATCATGAGGAAGGCGGTT
ACCAAGGCTAAGCCAGTCTCTTCAGGCAGCCCATGGTACGGTCCTGACCGTGTCAAGTACTTAGGACCATTCTCC
GGTGAGTCTCCGAGCTACTTGACTGGTGAATTTCCTGGTGACTATGGATGGGACACTGCTGGACTTTCAGCTGAT
CCAGAAACTTTTGCCAAGAACCGAGAGTTGGAGGTGATTCACTGTAGATGGGCTATGCTTGGAGCTCTTGGTTGC
GTCTTCCCTGAGCTCTTGGCACGTAATGGTGTCAAGTTCGGTGAAGCTGTATGGTTCAAGGCTGGATCCCAAATT
TTCAGCGAGGGTGGACTTGACTACTTGGGTAACCCAAGTTTGGTCCACGCACAAAGCATCTTagcCATCTGGGCT
TGCCAAGTTGTGTTGATGGGAGCCgttGaggGTTACCgtGTTGCTGgTGGACCTCTTG

> SEQ ID NO:108 131133 126123
ccccccGACAGCTAACTTCTCTATTACTTCAGCCATCAAAAAACACTTATTTTTCCTTATTAAACCATGGCTGCT
TCTACAATGGCTCTCTCTTCCACTTCTTTTGCCGGAAAGGCAGTAAAACTCTCACCATCTTCCTCTGAAATCACC
GGAAATGGGAAAGTTATCATGAGGAAGACTGCTAGCAAGCCCAAGCCTGTCTCTTCTGGCAGCCCATGGTACGGT
CCTGACCGTGTCAAATATTTGGGTCCATTCTCCGGTGAATCTCCAAGTTACTTAACTGGTGAGTTTCCTGGTGAC
TATGGATGGGATACCGCTGGACTTTCAGCTGATCCAGAAACTTTTGCCAAGAATCGTGAGTTGGAGGTAATCCAC

Figure 2 continued

TGCAGATGGGCTATGCTTGGAGCTCTTGGTTGTGTCTTCCCTGAGCTCTTGGCTCGTAACGGTGTCAAGTTCGGT
GAAGCTGTATGGTTCAAGGCTGGATCCCAGATTTTCAGCGAGGGTGGTCTTGACTACTTGGGCAACCCAAGTTTG
GTCCATGCTCAAAGCATCTTGGCTATTTGGGCTTGCCAAGTTATTTGATGGGAGCTGTTGAAGGTTACCGTGTT
GCCGGTGGACCTCTTGGCGAGGTTGTTGATCCACTTTACCCTGGTGGCAGTTTCGACCCGTTAGGCCTTGCTGAa
gacccagaagCTTTTGCTGAGCTaaagGTAAAGGaGaTcaaGaACGGCAgaCtTGCCATGTTTTCCATgTtTgga
ttctTTGt

> SEQ ID NO:109 131133 119058
ctgtgacagtgtgtgtagtgtgcttaatttttgtaaatagtgttagtgcttcttgatcttgcggatgtcgactcca
ttcagCCGCCTCAAGAGGGGTAACAAAGAAGATAAAAGAAAATTGTTCAAATGGCTACTTCTGCAATTCAACAAT
CTGCAATTGCTGGACAGACAGCTCTTAAGTCACAGAACGAGCTCATTAGGAAGATTGGTAGCTTTAATGGTGGAC
GTGCCACTATGCGACGTACGGTTAGAAGTGCCCCACAGAGCATTTGGTATGGAGAAGACAGACCAAAGTACTTGG
GACCATTCTCCGAGCAAACTCCTTCTTACTTGACTGGTGAGTTTCCAGGTGATTATGGGTGGGACACCGCTGGAC
TTTCAGCTGACCCTGAAACATTCGCCAGGAACCGTGAGCTTGAGGTGATCCATTGCCGTTGGGCCATGCTTGGTG
CTTTGGGTTGTGTCTTCCCTGAAATCCTTTCCAAGAATGGTGTTAAATTTGGTGAGGCAGTTTGGTTCAAGGCTG
GATCTCAAATCTTCTCAGAAGGCGGTCTTGACTACCTTGGTAACCCAAACCTTATTCATGCACAGAGCATTCTTG
CTATTTGGGCATCCCAAGTTGTGCTCATGGGTTTAATTGAAGGATACAGAGTTGGTGGAGGCCCACTTGGTGAAG
GTCTTGACAAGATCTATCCGGGAGGAGCTTTTGACCCACTAGGGCTCGCTGATGATCCCGAGGCATTTGCTGAAT
TGAAggTGAAggAAATAAAGAACGGCCGATtggctATGTTCTCAATGTTTGGATTTTTCgttcaAGCCAttgTCA
CAggaaagggaccaaTTGAAAACCttTTC

> SEQ ID NO:110 131133 182356
gaattcgCAGTCTtTAGTTTTCTCATCCATCCATATATCAGTTAGCCATGGCAGCTTCTACAATGGCTCTATCTT
CACCCGCATTGGCTGGTAAGGCACTTGTTCCTTCCAGCTCTGAAGTTTTCGGTGAAGGCAGAATCTCCATGAGAA
AAACCGTTGCAAAGCCAAAAAACCGTTTCATCTAGCCCATGGTACGGACCTGACCGTGTTAAGTACTTGGACCAT
TCTCTGGTGAATCTCCATCGTACTTAACCGGTGAGTTTGCCGGTGATTACGGTTGGGACACTGCCGGGCTTTCTG
CTGACCCAGAAACCTTCGCCAAGAACCGTGAGCTGGAGGTCATTCACTGCAGATGGGCTATGTTGGGAGCTCTTG
GATGTGTCTTCCCCGAATTGTTGTCTCGCAATGGTGTTAAATTTGGTGAAGCCGTTTGGTTCAAGGCTGGTTCAC
AAATTTTCAGTGAAGGTGGATTGGACTACTTGGGTAACTCAAGCTTGGTTCATGCTCAGAGCATCCTTGCCATTT
GGGCAACACAAGTTATCTTGATGGGTGCTGTTGAAGGTTACAGAGTTGGAGGAGGACCATTAggTGAGGTGGAGG
ACCCACTTTACCCTGGTGGAAGCTTCGACCCATtaggCTTAGCTGATGATCCAGaaGCTTTTGCTGAATTGAaGG
TGAAGGAAATtaagaACggcagaTTggctatgttctcCatGTTtggattctttgttcaaGcaatCgtgAccggga
aaggtccTttgGAaaatttggctGACCAC

> SEQ ID NO:111 131133 182017
GAATTCAATAGTCTTTCATTTCTAACAACAGAAACAGTTACTAATGGCAACCATGGCTCTTTCTTCTCCATCATT
TGCAGGGAAAGCCGTAACTCTGAACTCACAAACAGAATTTCCAGTCAATGTTAGATTCAGCAGCAATGGCAAGAT
CTCGATGAGGAAGACATCCGCAAAGAAGCCAGCTGCATCTTCAGGAAGTCCATGGTACGGTCCAGACCGTGTCAA
GTACCTCGGTCCATTTTCTGGTGAGTCTCCATCCTACTTAACTGGTGAATTCGCCGGTGACTATGGCTGGGATAC
TGCTGGACTATCAGCTGATCCGGAGACCTTTGCAAAGAACCGCGAACTTGAGGTGATCCATTCAAGGTGGGCTAT
GCTTGGCGCTTTGGGATGTGTCTTCCCTGAACTCCTCTCTAGAAATGGAGTCAAATTCGGCGAAGCAGTTTGGTT
CAAAGCTGGATCTCAGATCTTCAGTGAAGGAGGACTAGACTATTTGGGTAACTCTAGCTTGGTTCATGCACAAAG
CATCTTAGCTATTTGGGCCACACAGGTCATCCTTATGGGCGCTGTTGAGGGTTACAGAGTTGCCGGTGGTCCACT
TGgtgagGTc

> SEQ ID NO:112 131133 181296
gaattcaactacCATCTTCAGTTATCTTTCATTTTCAATACAAAAGATACATAAGAATGGCAACCATGGCTCTCT
CTTCTCCATCATTTGCAGGCAAAGCTGTGACTCTAAACCCTCAAACAGAATTCCCAACCAATGTAAGATCTGGCA
GCAACAGCAAGATCTCGATGAGGAAGACATCCGCAAAGAAGCCTGCAGCTTCTTCTGGAAGTCCATGGTATGGTC
CAGACCGAGTCAAGTACCTCGGTCCCTTCTCTGGTGAGTCTCCTTCTTACCTAACTGGTGAATTCGCTGGTGACT
ATGGCTGGGACACTGCTGGACTATCAGCTGATCCAGAGACCTTTGCCAAGAACCGTGAACTTGAGGTGATCCATT
CAAGGTGGGCGATGCTCGGCGCTTTGGGCTGTGTCTTCCCCGAACTCCTCTCTAGAAATGGAGTCAAATTCGGCG
AAGCAGTTTGGTTCAAAGCTGGATCTCAGATTTTCAGTGAAGGAGGACTAGACTATTTGGGAAATTCCAGCTTGG
TTCATGCACAGAGCATCTTAGCTATTTGGGCCACACAGGTCATCCTTATGGGAGCTGTTGAGGGCTACAGAGTTG
CCGGTGGTCCACTAGGTGAGATCGTCGATCCACTTTACCCAGGAGGCAGCTTCGATCCATTAGGCCTTGCAGAGG
ACCCAGAGGCATTTattgaggtaaaggtaAAGgtagttcaaaatgGtcgaCtcgctatgttctctagggttgGgt
tctttgTtcaGgctagtgtgAcAGgAAAAGGTcctttAGAGAACCTcggTgaccaCCTtgcgGACCCAGTgaaca
ACAatgcttgGTCaTatgataCCAacttcgctcccGGGaagtgAgaatagaCGTACCAAAGgaAAAaTgctCTtg

Figure 2 continued gGTTtttTACTTTTTccagtgatATcctctGTACATCCATTtAgATtgcaaAATTGTGTAGCAtgtctGAGTTTT
GTCTGAATAgcacttctgtATAAGGTGTACCTtgtAAaatgcatggtgacttggatataatcaatctaatagaat
ccatttttgcgaaatttaccgacaaagtccaaaaaaaaaa

> SEQ ID NO:113 131133 167852
gaattcactagaTCTTCAGCAGTCTTGTTATTTTCTCTTTAACAAAACATATAAATGGCATCCATGTCTCTCTCA
TCCCCATCATTTGCAGGCACAGCTGTAACTTTGAACGCACAATCGAAATTCCCAACCAATGTTAGATCCAGCAGC
AATGGAATGATTGTGATGAGGAAGACATCAGCAAAGAAGCCTGCTGCTTCTTCAGGAAGTCCATGGTACGGTCCG
GACCGTGTCAAGTACCTTGGACCCTTCTCTGGTGAGTCTCCATCATACCTAACTGGTGAATTCCCTGGTGACTAT
GGCTGGGATACTGCTGGACTATCTGCAGACCCAGAGACCTTTGCCAAGAACAGGGAATTGGAAGTGATTCATTCC
AGGTGGGCTATGCTTGGCGCTTTGGGATGTGTTTTCCCTGAACTTCTCTCTAGAAATGGAGTTAATTTTGGAGAA
GCAGTCTGGTTCAAAGCTGGTTCTCAGATTTTCAGTGAAGGCGGACTTGACTACTTGGGAAACTCCAGCCTGGTT
CATGCACAGAGCATCTTAGCTATTTGGGCCACTCAAGTTATCCTTATGGGAGCTGTTGAGGGATACAGAGTTGCT
GGTGGTCCACTAGGTGAGATCGTCGACCCACTTTACCCAGGTGGTAGCTTTGATCCCTTGGGACTTGCAGaGGAC
CCagaGGCATTTGCTGAGCTGAAGGTAAAGGAACTTAAGAACGGGAGACTTGCTATGTTCTCCATGTTCGGATTC
TTCGTTCaggCTATtgttACCGGCAaaggtccTcTagagaATCTTGCaGaTCACCTTTCTGaCCCTgt

> SEQ ID NO:114 131133 158561
cgtccgaaaattctttctgtgtgtAGTAGCTGCATTTTAAAGTATTTCTTTTTATTTCTACAATGGCAGCTGCTA
CAATGGCTCTCTCTTCCTCTACTTTTGTTGGAAAGGCAGTGAAACTCTCACCATTTTCCTCTGAAATCACTGGAA
ATGGGAAAGTTACCATGAGGAAGACGGCTAGCAAGGCCAAGCCAGTTTCTTCTGGTAGCCCATGGTACGGTCCTG
ACCGTGTCAAGTACTTGGGACCATTTTCTGGTGAGTCCCCAAGTTACTTGACTGGTGAATTTCCCGGTGATTATG
GGTGGGACACTGCCGGACTTTCAGCTGATCCAGAAACTTTTGCTAAGAACCGTGAGTTGGAGGTGATCCACTGTA
GATGGGCTATGCTTGGAGCTCTTGGTTGTGTCTTCCCTGAGCTCTTGGCCCGTAACGGTGTCAAATTCGGTGAAG
CTGTATGGTTTAAGGCTGGATCCCAAATTTTTAGTGAGGGTGGACTTGACTACTTGGGCAATCCAAGTTTGGTCC
ATGCACAAAGCATCTTGGCCATTTGGGCTTGTCAAGTCATGTTGATGGGAGCTGTTGAGGGTTACCGCATTGCTG
GTGGGCCTCTTGGTGAAGTTGTTGACCCACTTTACCCCGGTGGCAGCTTCGaccCATTaggtCTTGCTGAAGacc
CagaggcTTTTGCTGAGCTCaaggtAAAAGagaTCAAGaATGgCAGaCtTGCTATgttctCCATGTTTgGaTTCt
tcgttcaaGCTAt

> SEQ ID NO:115 131133 131323
gaattctagagtgctcaaagcaagcccaagctctggggacattagcatgggataacatcgtaggatttcggtcct
attgcGTTGGCCTTCGGGATCGGAGTAATGATTAACAGGGACAGTCGGGGGCATTCGTATTTCATAGTCAGAGGT
GAAATTCTTGGATTTATGAAAGACGAACAACTGCGAAAGCATTTGCCAAGGATGTTTTCATTAATCAAGAACGAA
AGTTGGGGGCTCGAAGACGATCAGATACCGTCCTAGTCTCAACCATAAACGATGCCGACCGTGTTAAGTACTTAG
GTCCATTTTCCGGCGAGTCTCCATCATACCTCACCGGTGAATTCCCTGGTGATTACGGTTGGGACACCGCAGGGC
TCTCAGCTGACCCTGAAACCTTCTCCAAAAACCGTGAGCTAGAAGTTATTCACTGCAGATGGGCAATGCTTGGAG
CTCTTGGTTGTGTCTTCCCTGAATTACTTTCCCGCAACGGTGTCAAATTCGGCGAAGCCGTATGGTTCAAAGCTG
GTTCTCAGATCTTCAGTGAGGGAGGATTGGACTACTTGGGTAACTCAAGTTTGGTTCATGCTCAGAGTAttcTAG
cAATCTGGGCTACACAGGTTATAtTGATGgGAGCAGTTgaggGttAccg

> SEQ ID NO:116 131133 130869
gaattcaaccttctcatacttcttcctactgcaacgcaaaacatttcgcaatggctgcttcAACTATGGCTCTCT
CTTCTCCCTCTCTTGCTGGAAGGCAGTGAAGCTTTCACCAGATGTCATTGGTGAAGGAAGGATCACTATGCTCT
TCCAAAAGAAGACAGCGCCAAAGACAGCAAAGCCAACCAAATCTGTATCCTCCGGCAGCCCATGGTACGGTGCCG
ACCGTGTTAAGTACTTGGGTCCATTCTCCGGTGAGTCTCCATCTTACCTCACTGGTGAATTCCCAGGTGATTACG
GTTGGGACACAGCTGGGCTTTCAGCTGACCCTGAAGCCTTCTCCAAGAACCGTGAGCTAGAAGTCATTCACTGCA
GATGGGCAATGCTTGGAGCTCTTGGTTGTGTCTTCCCTGAATTGCTTTCCCGTAACGGTGTTAAATTCGGCGAAG
CTGTATGGTTCAAAGTCGGTTCACAGATATTCAGCGAAGGTGGATTGGACTACTTGGGTAACTCAAGCTTGGTTC
ATGCTCAGAGTATTCTAGCTATCTGGGCTACACAAGTTATCTTGATGGGTGCAGTTGAAGGTTACCGTGTTGCTG
GTGGTCCActaggagaggttGTCGaCCCACTTTACCcaggtGGTAGCTTTGACccTCttggTCTTGCTGATGATc

> SEQ ID NO:117 131133 130767
gaattcaaaggcagtgaaagtgacaccatgcgtgggggaggGTGATGGAAGAATCACCATGCTCTTCCAGAAAAA
GACAGTGGCAAAGCCTACTAAATCTTCAAAACCCGCAGTTTCATCTAACAGCCCATGGTACGGTCCCGACAGAGT
TAAGTACTTGGGTCCCTTCAATGGCTGCTTCAACAATGGCTCTCTCATCTCCTTCTCTTGCTGGAAAGGCAGTGA
AAGTGACACCATGCGTTCAAGAGGGTGATGGAAGAATCACCATGCTCTTCCAGAAAAAGACAGTGGCAAAGCCTA
CTAAATCTTCAAAACCCGCAGTTTCATCTAACAGCCCATGGTACGGTCCCGACAGAGTTAAGTACTTGGGTCCCT

Figure 2 continued

TCTCAGGCGAGGCTCCATCGTATCTTAATGGTGAATTCCCAGGTGATTATGGCCGGGACACTGCCGGGTTTTCTG
CAGATCCAGAAACTTTCGCCAAAAACCGTGAACTTGAAGTGATTCATTGCAGATGGGCTATGCTTGGAGCTCTAG
GATGCATCTTCCCTGAATTGCTCTCACGCAATGGAGTTAAATTCGGTGAAGCCGTTTGGTTCAAAGCCGGAGCAC
AGATTTTCAGCGAGGGAGGATTGGACTACTTGGGTAACTCAAGCTTAGTACATGCTCAAAGCATTTTAGCTATTT
GGGCGACACAAGTTATCCTGATGGGTGCAGTGGaaggttACCGTGTCGCcGgTgGACCTCTTGGTGAGattgtcG
accCACTGtaCcCcggtggcaGcttcgaccCtCttggacttgCTGATGac

> SEQ ID NO:118 131133 130117
GAATTCATCTTCAATAAACTTTTATTTCTAACAAAAAAAACATATTAATGGCAACCATGGCTCTATCTTCTCCAT
CATTTGCAGGGAAAGCCGTGACTGTGAACCCACAAACAGAATTCCCAACTAATGTTAGATCCAGCAGAAATAACA
AGATCTCCATGAGGAAGACATCCGCAAAGAAGCCTGCTGCTTCTTCTGGAAGTCCATGGTACGGTCCAGACCGTG
TCAAGTACCTCGGTCCATTTTCTGGTGAGTCTCCTTCTTACTTAACCGGTGAATTTGCTGGCGACTATGGTTGGG
ACACGGCTGGACTATCAGCTGACCCAGAGACCTTTGCTAAGAACCGCGAACTTGAGGTGATCCATTCAAGGTGGG
CCATGCTCGGTGCTCTAGGCTGTGTTTTCCCCGAACTCCTCTCTAGAAACGGGGTCAAATTCGGTGAAGCAGTTT
GGTTCAAAGCCGGATCTCAGATTTTCAGTGAAGGAGGACTAGACTATTTGGGTAATTCCAGCTTGGTTCATGCAC
AGAGCATCCTAGCTATTTGGGCCACACAGGTCATCCTTATGGGAGCTGTTGAGGGATACAGAGTTGCTGGTGGTC
CACTTGGTGAGATCGTCCATCcactTTACCCA

> SEQ ID NO:119 131133 129760
gaattcaaccatttataattaattttagcattggtacttactcataatccagtacttagcaatggcagctgctgC
AATGGCTCTCTCTTCACCCACATTCGCCGGTAAGGCACTTGTTCCTTCCAGCTCTGAAGTTTTTGGTGAAGGAAG
AATCTCCATGAGAAAAACCGCCGCAAAGCCAAAAACCGTTTCAGCTAGTCCATGGTACGGTCCTGACCGTGTTAA
GTACTTGGGACCATTCTCTGGTGAGTCTCCATCATACTTAACCGGTGAATTCGCCGGTGATTACGGTTGGGACAC
CGCCGGGCTTTCTGCTGACCCAGAAACATTCGCAAAGAACCGTGAGCTCGAGGTCATTCACTGCAGATGGGCTAT
GTTGGGAGCTCTTGGATGTGTTTTCCCTGAACTGTTATCTCGCAACGGCGTTCAGTTTGGCGAAGCCGTTTGGTT
CAAGGCCGGTTCACAAATTTTCAGTGAAGGTGGATTGGACTACTTGGGTAACCCAAGTTTGGTTCATGCTCAGAG
CATCCTTGCCATTTGGGCAACACAAGTTATCTTGATGGGAGCAGTTGAAGGTTACAGAGTTGCAGGAGGACCACT
AGGTGAGATCGTCGACCCACTTTACCCCGgTGGAAGCTTCGACCCATTAGGCTTagCTGATGACCCAgaagctTT
CGCTGAATTgaaggtGAaagagaTcaagaacgggagattggCTATGTTCTCCATgtttggattCtttgttcaagc
aaTCGTca

> SEQ ID NO:120 131133 112407
catttatatacagttgatgcgggctcattaaactcAAGCCATAAATCAAATATTTTTTCTGTATAGTAGCTGCAT
TTTCAAGAGCATTTCACTTTATTTCTACAACAATGGCAGCTACTACAATGGTTCTTTCTTCCTCTTCTTTTGTGG
GAAAGGCGGTGAAACTCTCACCATCTTCCTCTGAGATCACCGGAAATGGAAAAGTTACCATGAGGAAGACAGTTA
CCAAGGCGAAGCCAGTCTCTTCTGGCAGCCCATGGTATGGTCCTGATCGTGTCAAGTATTTGGGCCCATTCTCCG
GTGAGTCCCCAAGTTACTTGACTGGTGAGTTCCCTGGTGATTATGGGTGGGACACTGCTGGACTTTCAGCTGATC
CCGAAACTTTTGCAAAGAATCGTGAGCTAGAGGTGATCCACTGCAGATGGGCCATGCTTGGAGCTCTTGGTTGTG
TCTTCCCTGAGCTCTTGGCCCGTAATGGTGTCAAATTCGGTGAGGCTGTATGGTTCAAGGCTGGATCTCAAATTT
TTAGCGAGGGTGGACTTGATTACTTGGGCAACCCAAGTTTGGTCCATGCACAAAGTATCTTGGCCATCTGGGCTT
GCCAAGTCGTGTTGATGGGAGCTGTTGAGGGTTATCGTGTTGCTGGTGGGCCTCTTGGTGAGGTTGTTGACCCAC
TCTACCCTGGTGGTAGCTTTGACCCATTAGGTCTTtGCTGATGATccagaggctTTtGCTGAGCTCaaggtgaagg
aGatcaagaacggTagacttgccATGtTCTCaaTgtttggattCttCg

> SEQ ID NO:121 131133 107135
aagagtttCTCATCTACTTTCTATAATGGCAGCTGCTACAATGGCTCTCTCTTCCTCTTCATTTGCCGGAAAGGC
GGTAAAACTCTCACCATCTTCCTCTAAAATCACTGGAAATGGAAAAGTTACCATGAGGAAGACGGTTACCAAGGC
CAAGCCTGTTTCTGCTGGTAGCCCGTGGTATGGTCCTGACCGTGTCAAGTACTTGGTACCATTCTCTGGTGAGTC
TCCCAGCTATTTGACTGGTGAGTTTCCTGGTGACTATGGATGGGACACTGCTGGACTTTCAGCCGATCCTGAAAC
TTTCGCCAAAAACCGTGAGCTAGAGGTTATCCACTGCAGATGGGCGATGCTTGGAGCTCTTGGTTGCGTCTTCCC
CGAGCTCTTGGCACGTAGCGGTGTCAAATTCGGTGAAGCTGTATGGTTCAAGGCTGGATCCCAAATTTTCAGCGA
GGGTGGACTTGACTACTTGGGCAACCCAAGTTTGGTTCACGCACAAAGCATCTTAGcCATATGGGCTTGCCAAGT
TGTGTTGATGGGAGCTGTtgagggttAtCGTGTtGCtGgtgGgccTc

> SEQ ID NO:122 131133 103660
tggtatcaacgcagagtggccattcggccggggAACAGAAAAGAAAAAAAGAAGCTTCTTTAGCTCACCAATTAA
AAAAATGGCTACTTCTGCAATTCAACAGTCTGCATTTGTTGGCCGGACAGTGGCTAAATCACAAAATGAGCTTGT
TAGGAAAATTGGCAGCTTTGGCGGAGGCCGTGCTACCATGAGACGTACTGTTAAAAGCGCTCCTCAAAGCATCTG

Figure 2 continued

GTATGGAGAAGACCGTCCAAAATATTTGGGCCCATTCTCTGAGCAAACTCCATCTTACCTTACTGGTGAATTTCC
CGGTGATTACGGGTGGGATACTGCTGGACTCTCAGCTGACCCAGAAACATTTGCCAAAAACCGTGAACTTGAGGT
GATCCATTGCCGTTGGGCCATGCTTGGTGCTTTGGGTTGTGTCTTCCCTGAAATTCTATCAAAGAACGGTGTTCA
ATTCGGTGAAGCAGTTTGGTTCAAGGCAGGAGCCCAAATCTTTTTAGAAGGTGGACTTGACTACCTTGGCAACCC
AAACCTCGTGCATGCCCAGAGCATCCTCGCCATTTGGGCTTGCCAAGTTGTCCTAATGGGCTTGATTGAAGGATA
CAGAGTTGGTGGAGGCCCACTTGGTGAAGGTCTTGACAAGATCTATCCAGGAGGTGCCTTCGACCCACTTGGCCT
AGCTGATGATCCCGAGGCTTTTGCTGAGTTGAAGGTTAAGGAAATCAAGAATGGACGATTGGCTATGTTTTCAAT
GTTCGGATTCTTTGTTCAGGCTATTGTTACAGGAAAAGGCCCAATCGAGAACCTTTACGACCACATTAATGACCC
AGTAGCCAACAATGCTTGGGCTTTTGCTACCAACTTTgtACCCGGAAAGTGAAATGTTTTGTCTgtGTTATATgt
AAAAATTTggGCTAATGAAGTTTtctgcttgt

> SEQ ID NO:123 131133 52310
TCGCGATCTAGAACTCTTATTAACTAAAGAGCCTTTTACTTGCGCCACACTCTCACCGCAATGGCCGCCTCGACA
ATGGCTCTCTCCTCTCCTGCTTTGACCGGAAAGGCCGTTAAGCTATCCCCGGCGGCCTCCGAAGTATTTGGAACC
GGCCGAATCACCATGCGCAAAGCCTCCAAGCCCACCGGTCCATCCGGCAGCCCATGGTACGGATCCGACCGAGTC
AAGTACTTGGGTCCATTCTCCGGTGAGCCTCCGAGCTACCTCACTGGAGAGTTCCCCGGTGATTACGGGTGGGAC
ACTGCCGGTCTATCCGCCGATCCCGAGACCTTCGCTAGGAACCGTGAGCTAGAAGTTATCCACAGCAGATGGGCC
ATGCTCGGAGCCCTAGGCTGCGTTTTCCCTGAGCTATTGGCTAGGAACGGAGTGAAGTTCGGAGAAGCGGTTTGG
TTCAAGGCTGGTTCACAGATCTTCAGCGACGGAGGATTGGACTACTTGGGCAACCCGAGCTTGGTCCACGCTCAG
AGCATCTTAGCCATTTGGGCTACTCAAGTTATCCTCATGGGAGCTGTTGAGGGCTACAGAGTCGCCGGAGATGGT
CCATTGGGAGAAGCAGAGGACTTGCTTTACCCAGGTGGGAGCTTCGACCCATTGGGCCTCGCTACTGACCCCGAG
GCTTTCGCGGAGTTG

> SEQ ID NO:124 131133 201276
GCACACACACCCCAGCAGCAGCAGCAGCAGCAGCTGAGCTTGAAGCAGCAGAGCGAGGTAGACATGGCCGCCGCC
ACCATGGCCCTCTCGTCCCCGGCGCTGGCCGGCAAGGCCGCCGCGAAGGTGTTCGGCGAGGGGCGCATCACCATG
CGCAAGTCGGCGGCGAAGCCCAAGCCCGCCGCGTCGGGGAGCCCGTGGTACGGCGCCGACCGCGTGCTCTACCTC
GGCCCGCTCTCCGGCGAGCCGCCGAGCTACCTGACCGGCGAGTTCCCCGGCGACTACGGGTGGGACACCGCGGGG
CTCTCCGCCGACCCGGAGACGTTCGCCAAGAACCGGGAGCTGGAGGTGATCCACTCCAGGTGGGCGATGCTCGGC
GCGCTGGGCTGCGTGTTCCCGGAGCTCCTCGCCCGCAACGGCGTCAAGTTCGGCGAGGCGGTGTGGTTCAAGGCG
GGGTCGCAGATCTTCAGCGAGGGCGGGCTCGACTACCTCGGCAACCCGAGCCTGATCCACGCGCAGAGCATCCTC
GCCATCTGGGCGGTCCAGGTGGTGCTCATGGGCGCCGTCGAGGGGTACCGCATCGCCGGCGGGCCGCTCGGCGAG
GTCGTCGACCCGCTCTACCCCGGCGGcAGCTTCGACCcgctCgggctcGCCGAcgacccgGAGGCC

> SEQ ID NO:125 131133 167637
GAATTCACCAACTTCGCTCCCGGGAAGTGAGAGTATTTGTAACAGTGAACTAAGACGTTTGCTCTCCCATCAATG
GAAAAATGGTGTTGGTTTCCTACTTTTTCATTAAGATCCTCTGTACATATTTACCGATCCGTTTCCTCAGTAATA
GAATCCATTTTTTTTTTG

> SEQ ID NO:126 131216 182074
GAATTCATAACTTGTTTTACGTAAATCAACCGTGTTTTTAGTTTGATTAAAGAATAAGTAAGAGATAGAAATATA
TTAACACCTAAATGGAACAGAATGCAAGTGTAAATTATAAAATTGATATTTGGTTACGGATTTTATTACGGGCGT
CTGTGAAAAATGGCGCGGCCATTAGTGAAGTTGGCTTTATTACATTGTTGGAAAAATGACTTTTGTCTCTCTTGT
TGAGAATTTACATGACAGACGAATTATCGTTGGATTTAGAATATATGTAATACATTGAATCTCTTGCCGCAGGAA
ACTCCACAGCATGGAAAACATCATGAGCAACCAGAACCGGTTTAGATTCTGAGAAGAAATTGGACAGTGCAAAA
CTGAATGAGGAGCTCCCAACAGCCAATCCACATTCGGGGAGTCATGCATCCTCTGAAAAGCTTTCTCAGAAGACT
AGTAAGACGCAGAAAAGGTTATACGTAGCAAATGTGCAGCAGGCATTGCAACTTTCAGCTGCGCAACCGAGGAAG
ACAAGGTCTGTCGCGTTGAGAATGTCACAATCTGATACATTGAATGCAGAGACACCGCCATCAAAAAAGTTGAAG
AAA

> SEQ ID NO:127 131365 129983
GAATTCAGCACCAAAGCATACTGAATTTCAGTCGTTCTAGTGCATGTGGAGGACATTTTTCAGGTAAGAAAACTG
CCCTGAAAGTTTTACAATGTGGTTTTTACTGGCCAACACTTTTCAAAGATGCATACTTGTTTTGCAAAGCATGTG
AAAGATGCCAAAAGGTAGGAAGAAATTCTCGACATGACATGATGCCATTGAATCCTATTTTGATTGTCGAAATTT
TTGATGTATGGGGCATAGACTTTATGGGCCCATTTCCTTCTTCTTTTGGTTATCAATACATATTGGTTGCTGTTG
ACTATGTTTCTAAATGGATTGAAGCTGTTGCTTGTAGGGATAATGATAGTAAGGTTGTTACTAAATTTCTGAAAG
AGAACATTTTGTCTCGCTTTGGCACCCCTAGAGCTATTATTAGTGATAGAGGTACTCATTTTTGTAACAAATCCT
TTGAAAAGCTAATGAAATCGTATGGCATAACTCACAAAGTAGCTACAGCATATCATCCTCAAACCAGTGGTCAAG

Figure 2 continued

TAGAAGTGTCCAACCGAGAGATAAAAGGTATATTGCATAAGACTGTAAATCCAGATCGCAAGGATTGGTCACTTC
GACTCAATGATGCATTGTGGGCTTATAGGACAGCTTTCAAAACTCCGTTAGGTATGTCTCCTTATAGGCTTGTAT
TTGGAAAACCATGTCATCTGCCTG

> SEQ ID NO:128 131365 130630
GAATTCAAGGGGTAGATTTTCCATATTTATTCTGAATGCACCAAGCAACATCTCTATGTTTTTCCTTCAAACT
GTTTCCCGTTATCTGATACCAATTGTGCTGGGATTCCAAATCTGCAAATTATATTTCAAAGATGAAAGTGAAAA
CATCCTTATCGCGGATGTGCTGAACAGCTTTCACTTCTGCCCATTTGGTGAAATGGTCTGTCGCAACTATCAAGT
ATCTCTTTTGTCTTGTACATGATAAGAAAGGTCCACAATATCTAGCCCCCACTTTCCAAAGGGCCAACAACTTGC
TGATGAGGTTAAGGACGCTCCTGGGGCATGTATTCTTTTGCCATGGCGTTGACAATCTTTACATCTTTGCGACAG
CTTTTTGGATCATCATGCATATATGGCCAAAAATACCCTTGCGTCTTAGCTCTGTGGGATAATGATCTCCCTGC
ACTGTGATTGCCGGCTTCTCCGCTATGCATCATCTGTAATATATTTTGTCTTTCTTCTTTTGATAAACATCTAAT
AGATGGTCCACTAAAGGTTTTTCGATATAATATTCCTTCTCTTAATTCTTAGTTAGTAGCTTTACCTCTTAACTT
ATGGGC

> SEQ ID NO:129 167373 111768
GGCAGATATGGCTCATATTAGTGGGTTAGTTGCAGCTGGAGTCATCCCATCACCATTTGATTATGCAGATGTTGT
GACTACCACAACCCACAAATCCCTTCGCGGGCCTCGTGGTGCCATGATTTTCTTCCGGAAGGGTGTGAAGGAGGT
TAACAAGCAAGGAAAGGAGGTGTTGTACGACTATGAAGATAAAATTAACCAGGCAGTCTTTCCTGGACTTCAAGG
TGGTCCTCACAATCATACAATTACTGGCTTGGCAGTTGCTTTGAAACAGGCAATGACTCCAGAATACAAAGCTTA
CCAAGAGCAATGCCTTAGCAACTGCTCAAAATTTGCCCAGGCGTTAGCGGGAATGGGTTATGAACTTGTTTCTGG
TGGAACAGAGAATCACTTGGTCTTGGTGAACTTGAAAAACAAGGGTATTGATGGTTCTAGGGTTGAAAAAGTTTT
GGAAGCGGTACATATTGCAGCCAATAAGAACACTGTTCCTGGAGATGTATCTGCCATGGTCCCTGGTGGCATCAG
AATGGGGACTCCTGCACTCACATCAAGGGGATTTATTGAGGAAGATTTTGTGAAAGTTGCTGAATTCTTTGATGC
TGCTGTGAAGATAGCAGTGAAAATAAAGGGTGAAGCTCAAGGAACAAAGTTGAAAGACTTTGTGACAACACTGCA
GTCTAGTGCTTCCATCCAGTCGGAGATTGCAAAACTCCGCCATGGTGTGGAGGAGTATGCAAAGCAGTTCCCTAC
AATTGGGTTTGAGAAGGAAACCATGAAGTACAAAAAATGAGAGCTCGACTGAGTGTATACACAAGGACCAATATC
CAACTTCTTGAAGGTGTATGGGATAGACTTTCAACTGCAGTTTGCTCTCAAGGATAGGATTCTCATCTTATAATA
ATATGTAAAATCCAGCAGTACTTGGTTCCAGACTTTGCACTTTGTATATTAACGAGTGTAAATCAACTGAGGTCC
TTGAAAGCAATAAACTCCTCTTATCTCAGTGa

> SEQ ID NO:130 167373 129507
TTTTTTTTTTTTATATTGTTGCATTATAATTGATCAAGTTTAATAATATACATATAATTCAATTCTTGAATGAAG
AATGAAATTTGAACCAAATGGTACTCTCTTCATGCTTAGAACCCTGTAGTGTCAACAATATATCCCATTCACTGA
TTGAAAGCATTCATATATTCCCTACATTAAAAGGCAGTTTGCTCCCTTCCCGTGTCCATCTCATTCGCCTTTGTA
GATACTCCACTGCACTACCGAAGCATATATGCCCACTTATAATAGTGGAGTTTATTGCTTGTATTTCATTGTTGT
TTTGCAGAACCCGATTGTAGGGAATTGCTTTGCATATTCCTCAACGTCATGACGGAGCTGTTTAATTTCAGACTG
AATGCTAGCACTGTTTTCAACCGCGGCCATAAAGTCCTTCAATTTTGCACCTTTTTTGCATTCAGCTTTGGCTTT
CAAGGCCAAATTCACAGCAGCATCAAAGAACTCTGCTACTTTAGCGAAATCTTCCTCAAGGAATCCCCTTGAAGT
GAGAGCAGGTGTTCCCATTCGAATGCCACCAGGAACCATGGCAGAGACATCCCCGGGAACAGTGTTCTTGTTAGC
AGCGATA

> SEQ ID NO:131 167373 167971
gaattcggagagagagacacacagtgagagaggtATGGCACTTGACCTTCCACATGGTGGGCATCTTTCTCATGG
GTATCAGACTGACACCAAAAAAATATCTGCTGTATCTATATTTTTTGAGACAATGCCATACCGATTGGATGAGAG
CACTGGTTACATTGATTACGACCAGTTGGAGAAGAGCGCTACACTCTTCAGGCCGAAACTGATTGTTGCTGGTGC
AAGTGCTTATTCACGATTCTACGATTATGCACGCATTCGCCAGGTGTGCGACAAGCAAAAAGCTATATTGTTGGC
AGATATGGCTCACATCAGTGGGCTTGTTGCTGCTGGTGTCATCCCATCTCCATTTGAGTATGCCGATGTGGTGAC
CACTACAACACATAAATCCCTTCGTGGACCACGTGGGGCGATGATATTTTACAGAAAGGGATTGAAGGAAGTCAA
CAAACAAGGCAAAGAGATCATGTATGACTACGAGGACAAAATTAATCAAGCCGTGTTTCCTGGGCTTCAAggAGG
TCCACATAATCACACAATTACTGGATTAGCAGTTGCACTGAAACAGGCAACTACCCCagaATACAAGGCTTATCA
AGaaCAAGTTCTCAAAAAttGCTCACAGttTgccaaaaccttGaACGCAtTgggaTATGACCttgt

> SEQ ID NO:132 167373 9601
CCCACGCGTCCGGTGGAGCCATGATTTTCTTCAGAAAGGGTGTTAAGGAAATTAACAAGCAAGGGAAAGAGGTTT
TGTATGATTTTGAAGACAAGATCAACCAAGCTGTCTTCCCTGGTCTTCAAGGTGGTCCACACAACCACACTATCA
CAGGACTAGCTGTTGCTTTGAAACAGGCAACTACTTCAGAGTACAAAGCATACCAAGAACAAGTCCTGAGTAACA

Figure 2 continued

GTGCAAAGTTTGCTCAGACTCTAATGGAGAGAGGATATGAACTTGTTTCTGGTGGAACTGACAACCATCTGGTTC
TAGTGAATCTAAAGCCCAAGGGAATTGATGGATCTAGAGTTGAGaaa > SEQ ID NO:133 167373 240415
AGCGGGCTCGTGGCTGCTGGTCAACTTGCTAATCCTTTCGAGTACTGTGATGTGGTTACAACCACTACTCACAAG
TCTTTAAGAGGTCCTCGTGGAGGAATGATATTTTTCCGGAAAGATCCAGTTCTGGGACTGGACTTGGAAACAGCT
ATAAACAATGCAGTATTCCCCGGTCTGCAGGGAGGACCTCACAATCACACAATTGCTGGACTGGCCGTGTGCCTG
AAGCACGCAGTAACCGAAGAATTCAAGCAGTATCAAAAGCAGGTGATTGCGAACTGTCAAGCGCTTGCAGACAAG
CTGGTGGAGTTGGGATTCACGCTGGTGTCTGGCGGAACCGAAAATCACCTGGTCCTTGTTGATCTGCGTCCTTTG
GGAATTGACGGTGCCAGAACTGAAAAGGTGCTGGATCGTGCTTCCATCACGCTCAACAAGAACTCAGTACCAGGT
GACAAGAGTGCGTTAGTTCCGGGAGGTGTACGCATCGGCACACCTGCATTGACAACGAGAGGACTCAAGGAAGAG
GACTTCGTCAAAGTAGCAGAGTTCATTCACGAAGGCGTCCAAATCGCCAGACAGCTCAAGGAAACAGTCCGGCAA
GGGAAAATGAAAGAGTACGTCCAGGCACTCGAATCTCCAGACTCTCCAGTCCAGACGAGCATCGCCGATCTACGG
AACAGAGTCGAAGC > SEQ ID NO:134 167373 175952
CCCCCCCCCCGCTGCTCCTCTGCGACATGGCGCACATCAGCGGCCTCGTCGCCGCGCAGGAAGCTGCAAATCCTT
TTGAGTACTGTGATGTGGTTACCACCACCACGCACAAGTCCCTCCGAGGACCAAGAGCTGGCATGATCTTCTACA
GGAAGGGCCCTAAGCCTCCCAAGAAGGGCCAGCCTGAGGGTGCTGTCTATGACTACGAGGACAAGATCAACTTCG
CAGTGTTCCCGTCACTGCAAGGTGGTCCTCACAACCACCAGATTGCAGCCCTTGCTGTTGCTCTGCAGCAAACCA
TGACACCTGGATTCAAGGCCTACGCAAAGCAGGTCAAGGCCAACGCTGTCGCCATTGGCAAGTATCTTATGAGCA
AGGGCTACAAAATGGTGACTGATGGAACTGAGAACCACCTTGTTCTCTGGGATCTTCGCCCTCTTGGCTTGACTG
GCAACAAGGTTGAGAAGATGTGTGACCTTTGCAGCATTACACTTAACAAGAATGCTGTCTTTGGTGACAGCAGTG
CATTGGCTCCTGGCGGTGTCCGCATTGGTACTCCTGCGATGACATCCAGGGGTCTTGTCGAGAAGGACTTTGAGC
AGATCGGCGAGTTCCTCCACC > SEQ ID NO:135 167373 159191
GATCTTCTACCGCAAGGGCCCTAAGCCACCAAAGAAGGGACAGCCTGAGGATGCGGTCTATGACTTTGAAGACAA
GATTAACTTTGCTGTTTTCCCCTCGCTCCAGGGTGGTCCTCACAACCACCAAATTGGTGCTCTTGCTGTTGCCCT
AAAACAGGCCGCAACTCCTGGTTTTAAGGCTTATGCTAAGCAAGTTAAGGCCAATGCAGTTGCTCTCGGCAACTA
CCTCATGAGCAAAGGATACAAACTCGTAACTGGTGGGACTGAGAACCATCTTGTCCTTTGGGATCTTAGACCTCT
TGGTTTGACTGGTAACAAGGTTGAGAAGCTTTGTGACCTTGCCAACATTACTGTTAACAAGAATGCTGTTTTTGG
TGACAGCAGTGCTTTGGCCCCAGGAGGTGTTCGTATTGGTACTCCTGCAATGACATCAAGGGGATTGGTTGAGAA
GGACTTCGAGCAGATTGCCGAGTTCCTCCACAGGGCTGTTACCATCACCTTGAACATCCAGAAGGAGTACGGAAA
GCTTTTGAAGGATTTCAACAAGGGGTCTTGTCAATAACAAGGAAATTGAAGAACTC > SEQ ID NO:136 167373 127290
CCCCCCCGCTTTATTGAGAAGAAATTGCAGACTGGTTACTGGAGGGACTGACAATCACATGATACTGTGGGATCT
GAGAAATCTTGGGTTAACAGGTAAGAATTTTGAAAAGGTTTGCGAGTTGTGTCACATCACTCTCAATAAAGTAAT
GGTCTTCGATGATAATGGAAGTATTACTCCTGGAGGTGTGAGGATAGGTACCCCTGCTATGACATCAAGAGGCTG
TATAGAGAATGATTTTGAGACGATAACAGATTTCCTCCTCAAGGCAGCACAGATTACAAATTCAGTACAGAGAGA
ACATGGAAAGCTCGCAAAGGCTTTTCTGAAAGGCCTTGAAAACAACAAAGATGTTATTGAGTTAAGAACACGCGT
TGAAAGTTTTGCATCACTGTTTGCAATGCCTGGATTTGAAGTATAATCTAGCTGGAAATCTCGTTCTGGTGGATG
AATTCTTTTTTTATTCGTTGACCAACCTTTTTTGTGGATTGGGAGAACAATGGTGCACCCAACTCTTGGTTAGTA
ATTGACTAGGCTTGATATGATTTTTAAGTGTCAATTGAGCTCAAAGCCTGGATTAACTTATGATTGCCACGTTGG
AGTATTTTGTGTCCTTATTGACTGTGAAGGTTGGCTGGAGGTGCCAAAATAAATC > SEQ ID NO:137 167516 108462
gtcaaagattgttttttcttgtttttcaacaacctcatatctagtaaaatttcAGACAAGTAAGACAATCAAGT
AAACTATGGCAAGTTGTAACATGGCTTCTGCTGCATCAAACTTTTTGGTAGCAACTCCTAATGTTGCCTCTAACA
CAAGTACTCCTCGTAGTACTATGTTGTTTTTCTCCTCCAAGAACAATGGCAGCACCGCCCCCGAGACTAATTGTAA
GGGCGGCGGAAGAGGCGGCGTCACCGGCTGCTGCCACTACAGCTGAACCGGCTGAAGCTCCGGTCAAAGCTGCCA
AGCCACCTCCAATTGGACCCAAGAGAGGAACCAAAGTGAGAATTCTAAGGAAGGAATCTTACTGGTACAAGGGCA
CAGGTTCAGTTGTAGCTTGTGACCAGGATCCAAATACTCGTTACCCAGTTGTTGTACGATTTAACAAAGTGAATT
ATGCTAATGTTTCAACCAACAACTATGCATTGGACGAAATTGAAGAAGTGAAATGAGAGTGTGCAGTTCATTATT
AGTATATTTGTAGAACGACAAGGCCTTTTGGTTTCCATGTTTATTCTCTAGTTATATACTGGCTTTGATTGTGAA
TGAATGTCTATTATAGTTTGTTCc

Figure 2 continued

> SEQ ID NO:138 167516 248733
GCACGCGCTCGGCTTTCTCGTTGCGAAGGTTTAAGGAGGAAGAGAGAAGAGGGATGGCGTCGGCAGCGGCATCCG
GATGTGTTGGATTGGTGTCCGGGGCAGCGGCGGCAACGACGAGCGCATCGTCGTGCAGATTGTTTGGTGGGCAAT
GCAGGGTCCCGTCGTGGAATCGAGGCTCGACTTGTTCTTCTTCTTCTTCGTCGAGATTGGTGGTGAGAGCTTCTGATG
CCGCTGCGGCTCCAGCTCCAGCAGCACCCGAGAAGAAGCCAGAGCCAATCGGTCCCAAGCGTGGATCTATGGTGA
AGATCTTGCGGCCTGAGTCGTATTGGTTCCTGAACACAGGCAAGGTCGTCACTGTGGATCAGACCCCTGGCGTGC
TCTACCCGGTTGTTGTTCGGTTCGAGAAGGTGAATTACGCTGGAAACACCACAAACAACTACGCGTTGGACGAGG
TCGAACAAGTATGAAGAAAGAGAAGAGAGGGTGTCGTTGTAAACCACATATATCCTCGCCTTATCTGTTGGAAAG
GATTTCTACACTTGTACTTAACGATTTAAAACAGA

> SEQ ID NO:139 167516 25687
AAAAGAAAACCAGAGATGGCGATGACGACAGCATCTACGGTATTTGTTCTACCGGCCAATGTCACCTCGGTCGCC
GGCGCTTCGTCGTCCAGGAGCTCCGTGTCTTTCTTGCCGATGAGAAACGCCGGTTCTAGGCTCGTAGTCAGGGCA
GCCGAAGATCCTGCTCCGGCTTCCTCTTCTTCAAAAGATTCTCCGGCAGCTGCCGCTGCTCCGGATGGAGCTACT
GCCACCAAACCCAAGCCACCACCGATTGGTCCTAAGAGAGGGTCTAAGGTCAAGATTCTAAGGAGAGAATCCTAT
TGGTTCAAGAACGTTGGATCAGTTGTTGCCGTTGATCAGGACCCTAAGACTCGATACCCGGTTGTGGTCCGGTTC
GCAAAAGTCAATTACGCCAACATATCGACCAACAACTATGCATTGGATGAGGTCGAAGAAGTTGCAGCTTAAATG
GGAGAATTCAAAAACTCTGTGTATTCTATACCGGTTTATCCGTTTGTAACTTGACCCAAACCGTATGTACCGCAA
AAGTTTACCAATTATTTCTCCTCA

> SEQ ID NO:140 167516 254995
AGAGAGGGGGTAGCAGCAGTGTTAGTGGTAGAGTCAGCAGTTTGTGCGAAGATAGCCATGGCGTGTGCTTCCTTG
ACCGCCACCACCACCGCCCTCGTAGCCGCCATGGCCTTGCCCTCGCTCGGCTCATCCTCCCCCTTGGCCTCCTCC
TTGGCCCTTCCCCAAACCCGGAGTGCTCGCATGGTCGCCCTCACCGTCGTCCGTGCCTCCGACGCCGCTTCCCCT
GTCCCCACCCCCTCTGAAAATCCTGCCGCCGCCCCCGCTGCCGAGAAGCCCAAGCCTATCGGCCCCAAGCGTGGT
ACCAAGGTAAAGATTTTACGCCCCGAGTCGTATTGGTTTAACGGAGTCGGAACAGTGGTCTCTGTGGATCAGAGC
CCCGATACGCGGTACCCAGCTGTGGTGAGGTTTGAAAAGGTGAACTACGCCGGCATCTCCACTAATAACTATGCT
TTGGATGAGATAGTGGAGGTTTAATAGTATCTTCATTGTTTCTTGTACACTCCTTTTCATTATCCATCCCTTATT
GGTAAATTTCCCACCTCATGAGTTGCC

> SEQ ID NO:141 167516 23991
TTTGGAAATCGATCTTGAGATTGTAAAAGATAAAAGATGAATTGTTGGTTAACTTTTTGGTACATACGGTTTTGT
TTAAGATTACAAACAGACGAACCGGTTTAGAGATAAACCATGTCTCTCATTTTACTTCTTCCACCTCGTCCAATG
CGTAGTTGTTGGTCGATATATTCGCGTAATTCACCTTGGCGAACCGGACCACAACCGGATATCGGGTCTTCGGGT
CCTGATCAACGGCCACAACTGATCCAACGTTCTTGTACCAGTATGATTCTTTCCTTAGAATCTTGACCTTGGATC
CTCTCTTTGGGCCAATTGGAGGAGGTTTAGCCTTAGCGGCCGGAACTTTCGCCGGAGCAGCAGCAGCGGTGGTGG
AAGAACTATCCGACGAGGCGGTTGCCGGAGGTGTATCTTCCGCCGCTCTGACTACTAGCCTTGAACCGAAGCTTC
TCATCGGCAAGAAAGACACAATGGTGGTGCTCTTTGAAGAACCACCGCCTATTGCCGCCGGGACGTTGGCCGTGA
GAATAAATCCGGTAGCTGCTGACGTCATCGCCATTTGTGTGTGATCGTTGGAAGTTGTGTGAGCGGACGCGTGGG

> SEQ ID NO:142 167516 227351
gcgtcGGCGAGCACCATTAACGTGGCGTCGGCCACCTCGAGGTTCCTGCTGGCCGGCGGGAACGGCGGCAGCGGC
GGCGGCGGGGCCAGCCGCGTGAGCTTCGCGGCGAACAGGGTCGGGAGGAGGATGGTGGTGGTCCGCGCCGAGGAG
GAGGCCGCGGCGCCGCCGCCGCCGCCGCCGCCCGCGGCGGAGGAGAAGCCGGCGGAGGCCGAGGCGGCCGTGGCG
ACCAAGGAGCCCGCCGCCGCCAAGCCGCCTCCCATTGGCCCCAAGAGAGGCACCAAGGTGAAGATCCTGAGGAGG
GAGTCCTACTGGTACAACGGCACTGGCTCCGTCGTCACCGTTGATCAGGATCCCAACACTCGCTACCCGGTGGTG
GTTCGGTTCGCCAAGGTGAACTACGCCGGCGTGTCGACCAACAACTACGCCCTGGACGAGATCCAGGAGGTCAAA
TGATTTTAATTCGGATGGATCGTCGTCGAGCTGGAGCTGCAAAGAATCATCTTAAATTGATCACGGAGTGAGGAG
AGGATGCATGTCGTACATGTGGAAGAAATTAATTAAGCTGCTTGATCGAGCTTTGTGTGTATTAGTGTAATGGTG
GTGGTTTCTTCTTTATAATCCGTATAATACTATGTAATTTGCCTGCCTCTgcttcttCCtcgtgGACTTGATAAT
CC

> SEQ ID NO:143 167516 184685
gcgcgccgggaccatcatttgaaggtgatagggcaggtgtatacgatttgggattatcagatgcagctggtgcag
atggtGATGGAGCAGGGGAATGTTTTGGCGAAgaTGGAGGTGGAGCATTAGTAGACGGTGGAGGAGCCGGAGGAC
TATTAGGTTCACTAGGTTAAGGTaGAGAAACAAAGTTGAGGAGAACGGCCATGGCAACCTCTTCTATGGCATCTG
CAGCATCTGGTTTTGTGTTAACATCTAGTCTTTCCTCCACCACCACCACAACCTCATCCAGGAGCAGCATATACT
TCCAAATAAGAACTAACAATAACTCAAGGCTCGTTGTTCGTGCAGCAGATGAAGCCGCCACCCCTgccCCAGCTG

Figure 2 continued

CTGCTGCCGCTACTAAAGAAGCTGAAGCTCCAGCCGCAGTCAAGAAACCTCCTCCAATTGGCCCCAAGAGAGGCA
CTAAGGTGAAGATTCTCAGGAAGGAATCCTATTGGTACAACGGCATTGGATCAGTCGTAGCTGTTGATCAGGAcC
CAAAGACTCGCTACCCAGTCGTCGTCCGGTTCACCAAGGTCAACTATGCTAATGTCTCTACAAACAACTACGCCT
TGGATGAGATTACGgAaGTGAAGTGATGAGTAATCAGCAATCCAAAAATGttgaaTTTgtagcTAGCTAGCTTAT
CCTATCAAGTCttt > SEQ ID NO:144 167516 120461
TTTCATCATTTCTTTGCAGCAGAGACAAATTAAGACATGGCAAGTAGCAGCATGGCTTCTGCTGCATCTGGTTTT
ATGGTGGCCACACCCAATATTGCCACCTCTAACACTGCTCCTCGCACCTCTATGTTATTCTTCTCCTCCTCCAAG
AACAACACCACCACCAACTTCTCTAGGCTCGTTGTTAGGGCCGCGGAAGAGGCTGCGCCACCAGCTGCTACTGCC
ACCGCTGAAGGTGAAGCTCCTCCTGTCAAAGCTGCCAAGCCACCTCCAATTGGACCCAAGAGAGGAACCAAAGTG
AGAGTTTTAAGGAAGGAGTCTTACTGGTACAAGGGGGGTTGGTTCAGTTGTAGCTGTTGATCAGGATCCCAACACA
CGCTACCCAGTTGTAGTAAGGTTCAACAAAGTGAACTATGCAAATGTATCTACCAACAACTACGCATTGGATGAA
GTCGAAGAAGTGAAATGAAAGAATGGAAGTAATTAATTAGTTCATGCTCTTCATATTTGTAATATGCCCGACCCT
GTGCTTTCCATGTTTAATCTCTAGTTCTATACTGGCTTTGAATGTGAATCTGTATCATAATTTCTTGCAAATTTC
TCCTTCCATTACTTATTAAGTTTGTTGGCAttG > SEQ ID NO:145 168165 143613
GCCGTAACGTCTCCCTGAGAATCTGGACCCCTGCACAATATCTGTCCAAGACAGCACATGCAATGTATTCGCTGA
AGGCAGCTATGGAGTGGGATGAAGATGTTTTCGGTCTGGAGTATGACCTGGATCTTTTAATATTGTTGCTGTTC
CTGATTTTAACATGGGAGCGATGGAAAACAAGAGCTTGAATATATTCAATTCCAAGCTTGTCCTGGCATCCCCAG
TAACTGCGACTGATGCTGATTATGCGGCAATATTGGGTGTGATTGGACATGAGTACTTCCACAACTGGACAGGCA
ACAGAGTTACCTGTCGTGACTGGTTCCAGCTCAGCTTAAAGGAAGGACTTACTGTTTTCCGTGATCAGGAGTTCT
CATCTGATATGGGAAGCCGTACCGTGAAAAGGATTGCTGATGTTTCAAAGCTTCGAATGTATCAGTACCCACAGG
ATTCTGGTCCAATGGCTCATCCTGTCCGGCCGCATTCTTATATAAAGATGGATAACTTCTACACAGTTACGGTTT
ATGAGAAGGGAGCTGAAGTGGTCAGGATGTACAAAACTTTGTTAGGGAGCCAAGGATTCAGAAAAGGCATGGATT
TATATTTCGAGAGGCACGATGGTCAAGCAGTAACATGTGATGA > SEQ ID NO:146 129424 1170936_302040_1b
AGAAAGAGAGAGACCAGAGAGAGAGAGAGAGAGAGAGACTGGTAACAATGGCAATGGCGTTGAGAGCAGCGTTCCAG
TGCACGCCAAGCGCATCATCCCTTTCGTCCTCCTCCTCCTCGGCATCGCCCCTCCTCCGTCGGGGTGCTGCTGCC
GCCCTGAGGTTTGCACGCTGCTCGACCCCCGGTAACGCGGGAAGCCCACTCTGCAGCCCTCCTCCCTTCAGAGCC
GCCGCTCGGTCCTGGCGCGCCCTCTCCCTCCCTGCCTCCCAGCTCACCGCCTCCCCTCCCACCCCCGCTTACACC
ATCAAGGAGGAGGGTAAGCCCGAGTCCCTCGACTTCCGCCTCTTCTACTTCAGCGATGATTCCGGCAAAAAGATC
TCACCATGGCACGACATACCTTTAGAAGCCAAGGATGGCATGTTCAACTGTATTATAGAGATTCCAAAGGAAACC
AGTGCGAAAATGGAAGTGGCCACCGACGAATTCTACACCCCTATCAAGCAAGATACTAAGAAGGGC > SEQ ID NO:147 129424 127868_300473_1b
CCCCCCGAGTTCCCCATTTCAGCAGCAAAGGCAACAATGGCGGCTGCAAGAGTAATGATATCAGCCAACAACACT
CTAACAACTTCTCTTTTATCCAAAATTCCTCTCCAAAAGCCCAATAGTTTCAACCTTTGTTTCCGCAATAGGTCT
GCTGCTGCACACAGGAGCCAACTTTTCACTTGCACTGCTATTTACAATCCCCAGATTCAAATCAAAGAACAAGGC
CAGCCCGAAACTTTAGATTACCGTGTCTTTTTCGTTGATGATTCCGGCAAAAAGGTGTCCCCTTGGCATGACATA
CCACTGCATTTAGGTGATGGTGTTTTCAATTTTATTGCTGAAATTCCTAAAGAATCGAGTGCAAAGATGGAAGTT
GCTACAGATGAGCTGTACACACCAATAAAGCAAGACACAAAGAAGGGGAAACTTAGATACTACCCATATAATATT
CATTGGAACTATGGATTGCTTCCTCAAACCTGGGAAGACCCCTCATTTGCAAATGCTGAAGTTGAGGGGGCATTC
GGAGATAATGACCCTGTTGATGTTGTCCAGATTGGGGAAAGTCGTGCTAAAATTGGCC > SEQ ID NO:148 129424 129116_300403_1b
CCCCCGAGTCTCCCGCCGCCGCCGCCGGGGGTCACTCCGCACCAACTCCGACGATCCCCCGGCGAGCTCTCGACG
ATGGCGACGGCGGCGACGGCGTCGGCTACGGCGGCCACCCGCTTCACGCGGCTGGCGGGGGTCGGGCTCCGGCGC
ACGGCCCGCCTCCCCACGGCCGTGCGGTTCCAGCGCCGCGTGCTCGCCACCACCGCGCTCCTCAGGACCGCCGAG
CTCCGGCCCAAGGAGCAGGGCCTGCCCGAGACGCTCGACTACCGCGTGTTCCTCGTCGACGGCGGGGCCGCAAG
GTGTCGCCGTGGCACGACGTGCCCCTGCGCGCAGGCGACGGGGTGTTCCACTTCGTCGTGGAGATCCCCAAGGAG
AGCAGCGCCAAGATGGAGGTCGCCACCGACGAGTCATTCACCCCCATCAAGCAGGACACCAAGAAGGGCAACCTC
CGATACTACCCGTACAACATTAATTGGAATTATGGATTATTTCCCCAAACATGGGAGGACCCAACTCTTGCAAAC
ACCGATGTCGAAGGAGCATTTGGGGATAATGATCCTGTTGATGTTGTTG > SEQ ID NO:149 129424 226311_300996_1b

Figure 2 continued

AGCAACATGTCTACCTACACTACCCGGTCCATTGGTGCCCCCAACACTCTCGACTACAAGGTCTACATTGAGAAG
GACGGCAAGCCCGTTTCCGCCTTCCACGACATTCCTCTGTACGCCAATGCTGAGAAGACCATTCTCAACATGATT
GTCGAGGTTCCTCGATGGACCAACGCCAAGATGGAGATCTCCAAGGACCTTGCTCTGAACCCCATCATCCAGGAC
ACCAAGAAGGGCAAGCTCCGATTCGTCCGAAACTGCTTCCCCCACCACGGATACATCCACAACTACGGTGCTTTC
CCCCAGACCTGGGAGGACCCCAACCACGTCCACCCCGAGACCAAGGCCAAGGGTGACAACGACCCGCTCGACGTC
TGCGAGATCGGTGAGACTGTTGGCTACACTGGCCAGGTCAAGCAGGTCAAGGTCCTCGGTGTCATGGCTCTCCTC
GACGAGGGTGAGACTGACTGGAAGATCATCGCCATCGATGTCAAGGACCCTCTTGCCTCCAAGGTCAATGACATT
GAGGATGTTGAGCGACACCTGCCCGGTCTTCTGCGAGCCACCAACGAATGGTTCCGAATCTACAAGATCCCTGAC
GGAAAGCCCGAGAAC

> SEQ ID NO:150 129424 216388_300868_1b
GCCCGTCACCTGGAGAAAAGCAGCGACTCTTCGTCTTCGTCTCCAACCACCACAATGTCTGGCTACACCGTCCGC
AAGGTTGCTGCCCAGAACACTCTGGAGCACCGCGTCTACATCGAGAAGGATGGCGTCCCCGTGTCGCCCTTCCAC
GACATTCCTCTCTTTGCCAACCAGGAGCAGACCATCCTGAACATGGTTGTCGAGATTCCTCGATGGACCAATGGC
AAGCTCGAGATCTCCAAGGAGGAGCTCCTTAACCCCATCAAGCAGGACGTCAAGAAGGGCAAGCTTCGCTTCGTC
CGCAACTGCTTCCCCCACAAGGGCTACCTCTGGAACTACGGTGCCTTCCCCCAGACCTGGGAAGACCCCAACACC
GTCCACCCCGAGACCAAGGCCAAGGGTGACAACGACCCTCTCGATGTCTGCGAGATCGGTGAGCTTGTTGGCTAC
CCCGGCCAGATCAAGCAGGTCAAGGTCCTCGGTGTCATGGCCCTTCTCGACGAAGAGGAGACTGACTGGAAGGTC
ATTGTCATTGACGTCAACGACCCCCTTGCTCCTAAGTTGAACGACGTTGAGGACGTCGAGCGCCACCTGCCTGGC
CTGCTCCGTGCCACCAACGAGTGGTTCCGTATCTACAAGATCCCCGAC

> SEQ ID NO:151 129426 1171292_302054_1b
CGACCAGCGTCGCTGTGTGAAGGTTCTTAGCTACATAATTCTCTCTCTCTCTCTCTCCATGTCTAGCAGATGC
AACATTCTAACCAGTACCGTTATGGGTTCTTAGCGAAAGGAGGATAGGCAGATACCTTGAAGGAAGCAATGAAGG
TGCAGTGCGATGCATGTGAGAAGGCTCCAGCATCACTCTTCTGCTGTGCAGACGAGGCGGCTCTCTGTGAGGAAT
GTGATGTGCGCATCCATGCTGCCAACAAGCTTGCTGGAAAACACCAACGTGTCCCTCTCATCCTTCAACCCCCTT
CCGATGCTCCCCGCTGCGATATTTGCCAGGAGAGGTCAGCTTACATTTTCTGCTTGGAGGACCGAGCACTTCTTT
GCAGGGAGTGTGATGTGCCTATCCATTCCTCCACCACCTTGGCGACGAAACACCAGAGGTTTCTAGTTGCGGGTA
TTCAAGTGGCATTAGGCACTATTGAGGGTGGTGCTATGAAATACTAATACTAATACTAATACTAATACCACTAAT
CAGCAGCCAGAAATAGCGAAAATGCAAGCCATGCCGCTAGTTTCTAGCTCTGGAACTGCCAAAAACACATATAAG
AAGGAACGGAATGTGGCGGTTTC

> SEQ ID NO:152 129426 135306_300413_1b
CCCACGCGTCCGTATCTATCGACTAGTTAGTTTAGTCGTCTCGAGGGTAAATTGAGCTTTGTGTGCGGTTTTGAG
GGGAGTACATCGGCATGAGGATCCAGTGCGACGCGTGCGAGGCCGCGGCGGCCACGGTGGTGTGCTGCGCGGACG
AGGCGGCGCTGTGCGCGCGCTGCGACGTCGAGATCCACGCCGCCAACAAGCTCGCCAGCAAGCACCAGCGCCTCC
CGCTCGACGCCGCGCTCTCCGCCGCCCTCCCGCGCTGCGACGTCTGCCAGGAGAAGGCGGCGTTCATCTTCTGCG
TGGAGGACAGGGCGCTCTTCTGCCGGGACTGCGACGAGCCCATCCACGTCCCGGGGACGCTCTCCGGCAACCACC
AGCGCTACCTCGCCACCGGCATCCGCGTCGGGTTCAGCTCCGTCTGTAGCGCCAACGCCGACCACCTCCCGCCGC
CAGCGCCCAAGGGGAACTCCAAGCCGCCGGCAAGCGGCATCGCTGCTGCTGCTGCTCCCAAGCCGGCCGTGTCCG
CGGCGGCGCAGGAGGTGCCGTCGTCACCGTTCTTGCCGCCGTCGGGCTGGGCCGTCGAGGATCTCCTGCAGCTCT
CCGACTACGAGTCCAGCGACAAGAAGGGCTCTCCTATTGGGTTCAAGGA

> SEQ ID NO:153 129426 190609_301609_1b
CCCCCCCAAATTGAGCTTTGTGTGCGGTTTTGAGGGGAGTACATCGGCATGAGGATCCAGTGCGACGCGTGCGAG
GCCGCGGCGGCCACGGTGGTGTGCTGCGCGGACGAGGCGGCGCTGTGCGCGCGCTGCGACGTCGAGATCCACGCC
GCCAACAAGCTCGCCAGCAAGCACCAGCGCCTCCCGCTCGACGCCGCGCTCTCCGCCGCCCTCCCGCGCTGCGAC
GTCTGCCAGGAGAAGGCGGCGTTCATCTTCTGCGTGGAGGACAGGGCGCTCTTCTGCCGGGACTGCGACGAGCCC
ATCCACGTCCCGGGGACGCTCTCCGGCAACCACCAGCGCTACCTCACCACCGGCATCCGCGTCGGGTTCAGCTCC
GTCTGTAGCGCCAACGCCGACCACCTCCCGCCGCCAGCGCCCAAGGGGAACTCCAAGCCGCCGGCAAGCGGCATC
GCTGCTGCTGCTGCTCCCAAGCCGGCCGTGTCCGCGGCGGCGCAGGAGGTGCCGTCGTCACCGTTCTTGCCGCCG
TCGGGCTGGGCCGTCGAGGATCTCCTGCA

> SEQ ID NO:154 129858 283732_200074_1b
AGACAACCTTTGATCATTCTTTGAGAAACAACAAAAGGAAGATGAGACCCAAGATTTATCTGTTTGGAGATTCCA
TCACTGAGATGTCCTTTGAGGATGGTGGCTGGGGTGCTTCTCTTGTCAACCACTTCAACCGCGCGGTGGATGTGG
TGTTAAGAGGGTATAGTGGGTATAACACAAGATGGGCATTGAAGGTGATAGAGAAAGTTTTCGACGAGGAAACTG
CAGTCACAGCGCCATTGGCAGTGACAGTGTTCTTTGGAGCAAATGATGCTTGTCTCCCTGATAGATGCTCTTCCT

Figure 2 continued

TTCAACATGTCCCTATTGATGAGTACAAGCTGAATCTTCATTCCATCGTCTCCTTTCTCAAGGGGCGATGGCCAA
CAACTCAAATTGTCCTCATCTCACCTCCTCCAATTGATGAACCTACGCGGCTCCTATATCCTTTTATGGAGAACA
AATTGGGCCTGTCAGAGAGGACCAATGAAACTGCTGGAAACTATGCTAAAGCAAGTCTAACTGTAGCAGCTGAAT
GTGGGGTTTTGGCTGTGGATTTATGGACCAGAATGCAGCAAATTCCTGGCTGGCAAACAGCTTGTTTAAGTGATG
GTTTGCACCTGAGTAAAACTGGGAACGAGATTGTGTTTGAGGAGGTGGTGGCGGCTCTTAAGAAGAAAGGGTTGA
GTGTGGAAGCTCTACCAGTTGATCTGCCAGTGATTAATGAAAT

> SEQ ID NO:155 129858 283094_200091_1b
GGGCGGACGCGTGGGCGGACGCGTGGGGGATTTCAGGAAATTTTGAACTTCTGATAATGAGGCCTCAAATAGTA
TTATTTGGGGACTCCATTACTGAACAATCTTTTAGATTCGGTGGTTGGGGTGCTGCTCTTGCTGATACTTATGTT
CGCAAGGCTGATATATTGAATCGTGGCTACGGTGGATACAACACCAAATGGGGATTGTTCTTGCTCCACCACCTA
TTTCCACTGGATGCTCCAACACCTCCTGTTGCTGCCACTATATTCTTTGGAGCCAATGATGCTGCTCTTTTGGGA
AGAACTAGTGAAAGGCAACATGTCCCACTCGAGGAATATAAGGAAAACCTAAGAAGAATTATACAACATTTGAAG
AAATGTTCCCCGTCAATCCTAGTAGTGCTGATAACTCCACCACCAGTTGATGAAGCAGGACGGTTTGAACAAGCA
AGGTCTATGTATGGAGACAAAGCAATGGAATTGCCAGAAAGGACAAATGAAGTGACAGGAGAGTACGCAAAACAG
TGCGTTCAATTGGCAAGGGAGCTAGGCCTCCCTTCCATCAATCTATGGTCTAAAATGCAGGAAACAGAGGGTTGG
CAAAAAAAATTCCTCAGTGATGGCTTACATCTCACAGCTGAAGGCAATGCCATTGTTCACCAAGAAGTTGTTAAA
GCGTTCAATGAA

> SEQ ID NO:156 129870 1171225_302053_1b
GGTCAAGATGGCGATGGCGATGCAGGCCACCTCTTCCTCTTCTCTCCGCAATACCTCCTTCCTTGCCTCTTTCCG
TGGGGAACAAATTCCCGGTGCACAGAAATCCGCAGTCGGCGGCTTTGCCTCCTCTCGTCAAGTGCAGAGTAATGT
TTCGACAGTTCTTATCTCTGTGAGGAATGAGAAGAAAAAGATGAGGGGAGTGAGTTGCAGAGCTTCTGCTGCAGA
TTCTCCAAAGCAAGTTGAAAGCAAAAAGGTTCTGATGATGGGAGGCACTCGCTTTATCGGCCTTTACTTGGCCCG
GTTGCTTGTACAGTCTGGCCACGAGGTCACCCTTTTTACCCGAGGAAAGGCGCCCATTACCCAACAATTAGCAGG
GGAGTCCGATGAGGAATACCAAGAATATGCCTCCAAAGTGAAGCACATGCAAGGTGATCGTCAGGATTTCGAAGG
CTTGAAGAGCAAGCTTTCCGAAGCATCTTTTGACATTGTGTATGATATAAATGGAAGAGAGGCTTTGGAGGTTGA
ACCCATTATTGAGGCCCTTCCTAATATGGAGCAGTATATCTACTGCTCGTCTGCGGGAGTGTACTTAAAATCAGA
TCT

> SEQ ID NO:157 129870 131306_300513_1b
GCGCGCCTTAATTAGGATCGAAGGAAGGTCATCAAGTAACTTGGTTCACAAGAGGGAAAGCACCAATCAGCCAAC
CATTACCCGGGGAGTCAGAACAAGATTACCTAGATTTCTCTTCCAAGATCTCGCACTTGAAAGGAGACAGAAAGG
ACTACGATTTTGTTAAGACTAGCCTAGCAGCTGAAGGCTTTGACGTTGTCTATGATATCAATGGAAGAGAGGCAG
ATAGAGAGAGAGACAATGGCAATGGCAACAAGTAGGTTGGTGGTGGTGCAACAAAAACAACCATCCTCATGTCTA
TTACCACCATCATCTCTTTCTGATTTCAATGGTATTAGACTGAAACACCCAATTCAGTACAAAAGAAAGGAATGG
CAGACAAGAGGAGCATTGCAGGTGAAAGCATCAGCTGCAAAGAAAATCCTGATAATGGGAGGAACCAGATTTATT
GGAATCTTTTTGTCTAGGCTCCTTGTGAAGGAAGGTCATCAAGTAACTTTGTTCACAAGAGGGAAAGCACCAATC
AGCCAACCATTACCCGGGGAGTCAGAACAAGATTACCTAGATTTCTCTTCCAAGATCTCGCACTTGAAAGGAGAC
AGAAAGGACTACGATTTTGTTAAGACTAGCCTAGCAGCTGAAGGCTTTGACGTTGTCTATGATATCAATGGTATT
GGAAGAGAGGCAGAAGAAGTAGAACCCATATTGGACGCGCTTCCAAAGCTTGAGCAGTACATATACTGTTCATCC
GCTGGTGTGTATCTGAAGTCTGATTTACTGCCTCATTTTGAGTCTGATGCAGTGGATCCCAAGAGCAGGCACAAG
GGAAAACTTGAAACAGAGAGTTTACTTGTATCAAAGGGCGTGAACTGGACTTCGCTGAGACCAGTTTATATCTAC
GGTCCTTTGAATTACAACCCTGTTGAAGAATGGTTTTTCCACAGATTGAAGGCCGGTAGACCAATCCCCATACCA
AATTCTGGCAACCAGATAACACAATTGGGTCATGTTAAGGATTTGGCGACCGCATTTATTAACGTTCTTGGTAAC
GATAAAGCGAGCCAGCAAGTGTTTAACATATCTGGAGATAAATATGTGACATTCGACGGATTGGCAAGGGCTTGT
GCTAAGGCTGGTGGATTTCCTGAGCCAGAACTAGTTCACTACAATCCTAAAGAATTCGATTTTGGCAAAAAGAAG
GCATTCCCCTTCAGAGACCAGCATTTCTTTGCATCAATTGAGAAAGCAAAGAGTGAATTGGGGTGGAAACCAGAA
TATGATTTGGTGGAAGGTCTAACAGACTCCTACGATC

> SEQ ID NO:158 129870 270847_200128_1b
TGAAGCAGGCACCACCTAATTACAACAATGGCTAGTTTGGTTGCAGTTCAACACAAACAGCCTTCTTTTGCTGTC
CTCCCTTCTTCCCATTCTGACTTCAATGGTGCCAAATTGATCTCCTCTCTTCAGTTTAAGAGGAAACCATGCCAG
CCAAAAGGAGCATTGCATGTTACAGCATCAAGTGCCAAGAAAATCCTTATAATGGGAGGCACTCGATTTATTGGT
GTCTTTCTATCCAGACTTCTTGTAAAAGAAGGCCATCAGGTTACTCTGTTCACAAGAGGAAAAGCTCCAATCTCT
CAACAATTACCAGGTGAATCAGACCAGGATTATGCTGATTTTTCCTCCAAGTTATTGCACTTGAAGGGTGACAGA
ATGGATTTTGATTTTGTGAAGAGCAGTCTTTCTGCAGAGGGCTTTGATGTTGTGTATGACATAAATGGACGTGAA
GCAGTAGAAGTGGAACCAATATTGGATGCATTACCTAATCTGGAACAGTACATATACTGCTCTTCAGCTGGTGTA

Figure 2 continued

TACCTCAAAACTGATTATTTACCACATTTTGAGGCTGACGCAGTTGACCCAAAGAGCAGGCATAAAGGAAAGCTT
GAGACAGAGAGCTTGTTAGAATCACGAGATGTTAATTGGACTTCTGTAAGGCCTGTTTATATTTATGGGCCACTT
AACTATAATCCAGTTGAAGAGTGGTTCTTCCACCGATTGAAAGCTGGTCGCCCAATTCCAATTCCTAACTCAGGG
CTGCAAATAACTCAACTTGGACATGTGAAGGATCTTGCAACGGCTTTTATTCAGGTTCTTGGAAATGAGAAAGCA
AGCAAGCAAGTATTTAACATATCTGGAGAGAAATATGTCACGTTCGATGGATTGGCTAAGGCTTGCGCCAAGGCT
GGCGGCTTCCCTGAACCCGAGATTGTTCACTACAACCCTAAGGAGTTTGACTTTGGCAAGAAGAAAGCTTTCCCA
TTCCGTGACCAGCATTTCTTTGCATCGGTCGAAAAGGCAAAGGCTGTGCTAGGTTGGAAGCCGGAATTCGAATTG
GTGGAAGGTTTGACAGACTCTTACAACCTAGATTTTGGTAGAGGAACTTACAGGAAAGAAGCTGATTTCTCTACA
GATGATCTCATTC

> SEQ ID NO:159 129870 256427_301672_1b
ATGGCTGCATCGTCTGCAATCAGAGGCTACGGTGCAGCAACTGCTGCTTCTCCTTACGATGTTTCAGTGCAGGAA
CGAAGATATGGAGCATCCATGTTGAAGAAGAATGTTTACTGCGGCAAAGTTGAGCTATGTCGAGCTTCGGACTTC
ACACAAAATGTCTTGCGCCAGGCCGCGAATCTAACGAGACTTCAAGCTCAAGCAGTCCGAAAGACGTCCGTCGTT
GCCATGGCCTCCTCATCGAAAAACATTTGATGATGGGAGGAACGCGGTTCATTGGAGTTTACCTGGCAAGGTTA
CTTGTGAAAGCCGGACACGAGGTGACGCTCTTCACTCGTGGAAAGTCGCCGATAACGCAAAAAATTGCCAGTGAA
ACTGATGAAGAGTATGCAGAGTATTCGTCGAAAGTACGTTTCACATCTGGTGGCTATTTATCTTTTCGTGTCTGC
CTTTCGCCAGATAAAACATATTCAAGGCGATCGCCAGGACTTCGAGGGGATGAAGAGCAAAATTGCCAATGCTGG
TTTCGAGATCGTGTATGATATCAACGGGAGGGAGGCTGTCGAAGTTGAACCCATCCTTGATGCACTTCCGGGCTT
GAAACAGTATGTATATTGTTCATCAGCAGGAGTATACTTGAAG

> SEQ ID NO:160 129870 21618_300070_1b
CCCACGCGTCCGGGCGAAGGGGATGATGTTGCAACAGCATCAGCCTTCTTTCTCTCTCCTTACTTCTTCTCTGTC
TGACTTCAATGGCGCTAAGCTCCATTTACAAGTCCAGTACAAGAGGAAGGTTCATCAGCCAAAAGGAGCACTCTA
TGTTTCAGCGTCGAGCGAAAAGAAGATTCTGATAATGGGTGGTACTCGATTCATTGGTCTGTTCTTGTCCAGGAT
CCTTGTCAAAGAGGGACATCAGGTTACATTGTTCACAAGGGGTAAATCTCCTATTGCCAAACAATTGCCCGGTGA
ATCTGACCAAGACTTTGCTGATTTCTCTTCTAAGATTCTTCACTTGAAAGGAGACAGAAAGGACTATGACTTTGT
GAAGTCAAGTCTTTCAGCAGAAGGCTTCGATGTTGTTTATGATATCAACGGGAGGGAGGCCGAAGAAGTTGAGCC
CATACTAGAAGCACTACCCAAACTAGAGCAGTACATCTACTGTTCTTCAGCTGGTGTTTATCTGAAATCTGATAT
CTTGCCACATTGTGAGGAGGATGCAGTTGATCCGAAGAGCAGGCACAAGGGGAAGCTGGAGACTGAGAGCTTACT
GCAATCAAAAGGTGTAAACTGGACTTCTATACGTCCTGTCTACATCTAC

> SEQ ID NO:161 129870 190530_300693_1b
CCCCCCCCGGAGGAGAGTAAACAAGAAAAAAAAAGAGAGAGAGATGGCAGCAACAGCCTCCCTGAAGAGCAGCCTC
CTGCTACCATCTCCTATCTCTGACTTCAGTAGTGCAGCACTCTCCATCTCAACCCAGGCTAGGAGGAGGTCATGG
CAGCCAAGGGGGGCAAGGATGCAGGTAGCAGCAGCTGCAGACTCCAAGAACATTCTTGTGATGGGGGGAACCAGG
TTCATTGGTGTCTTCTTGTCCAGGATCCTTGTCAAGGAGGGGCACCAGGTCACATTGTTCACTAGAGGAAAGGCC
CCCATTACCCAGCAGTTGCCAGGAGAGTCAGATGCAGAGTATGCAGAGTTCTCTTCAAAGGTGTTGCACTTGAAA
GGTGACAGGCAAGACTTTGATTTCGTTAAGACAAGCCTTGCGGCAAAGGGCTTCGATGTTGTTTACGACATAAAC
GGGAGAGAAGCTGTTGAGGTAGCCCCAATCCTAGACGCATTGCCAAACCTTGAACAGTACATCTACTGCTCATCA
GCAGGAGTGTACCTGAAATCAGACCTGCTCCCGCACTTCGAGACCGACGCCGTCGACCCGAAAAGCCGGCACAAG
GGGAAGCTGGAGACGGAGAGCCTGCTGGAGACCCGGGAC

> SEQ ID NO:162 129870 17586_300227_1b
CCCACGCGTCCGGGCGAAGATGATGATGTTGCAACAGCATCAGCCTTCTTTCTCTCTCCTTACTTCTTCTCTGTC
TGACTTCAATGGCGCTAAGCTCCATTTACAAGTCCAGTACAAGAGGAAGGTTCATCAGCCAAAAGGAGCACTCTA
TGTTTCAGCGTCGAGCGAAAAGAAGATTCTGATAATGGGTGGTACTCGATTCATTGGTCTGTTCTTGTCCAGGAT
CCTTGTCAAAGAGGGACATCAGGTTACATTGTTCACAAGGGGTAAATCTCCTATTGCCAAACAATTGCCCGGTGA
ATCTGACCAAGACTTTGCTGATTTCTCTTCTAAGATTCTTCACTTGAAAGGAGACAGAAAGGACTATGACTTT

> SEQ ID NO:163 129870 135395_300413_1b
CGGACGCGTGGGTGAGGAGAGGAAACATCAAACAAAAGAGAGAGAGAGATGGCAGGCGCAGCCTCCCTGAAGAGCAG
CCTCCTGCTACCATCTCCTATCTCTGACTTCAGTAGGGCAGCACTCTCCATCTCAACCCAGGCTAGGAGGAGGTC
ATGGCAGCCAAGGGGGGCAAGGATGCAGGTAGCAGCAGCTGCAGACTCCAAGAACATTCTTGTGATGGGGGGAAC
CAGGGTCATTGGCGTCTTCTTGTCCAGGCTCCTTGGCAAGGAGGGGCACCAAGTCACATTGTTCACTAGAGGAAA
GGCCCCCATTACCCAGCAGTTGCCAGGAGAGTCAGATGC

> SEQ ID NO:164 129965 119239_300024_1b

Figure 2 continued

AAGCAAGTTCAACTTCACTAAGGTTGGTCAGGAAGAGTTGCTCTTCCAGTTTGAAGCAAGTGAGGACAACGAAGT
TCAATTCTTTCCAAATGCACCCATTGATGCCGAGAAATCTCGAAGTGTTGTTGCCATCAATGTCAGTCCCATTGA
GTATGGACATGTGCTTTTGATCCCTAAGGTCCTTGAATGCCTTCCCCAGAGGATTGACAGGGACAGCCTATTGCT
TGCACTGCACATGGCTGCCGAAGCAGCTAACCCATACTTCCGATTGGGTTATAACAGCTTGGGTGCATTTGCTAC
CATCAACCATCTTCACTTTCAGGCCTATTACTTGGCTGTGCCATTCCCCATTGAGAAGGCCCCCACTCGGAAGAT
TACCTTTGCTGATGCTGGAGTGAAGATATCTGAGATGCTGAATTATCCAGTTCGAGGACTTGTCTTTGAGGGTGG
AAATACTTTGGAGGATTTCGCCAATGTTGTCTCTGGTTCTTGCATTTGCCTGCAAGAGAATAACATTCCCTACAA
TGTTCTAATCTCTGATTCGGCAAAAAGGGTATTCCTTCTCCCACAGTGCTACGCAGAGAAACAGGCTCTAGGGGA
GGTCAGCTCTGAACTGCTTGATACTCAAGTCAATCCTGCAGTATGGGAGATTAGTGGACACATGGTCTTGAAGAG
GAAGGAGGATTACGAGGGTGCAACCGAGGCAAATGCCTGGAGGCTTCTCGCTGAGGTCTCACTTTCTGAAGCGAG
GTTCCAAGAAGTGACTGCTCTCATCTTTGAAGCCATTGATTGCAGTGTTGAAGAGAATGAGAATGCCAATGAAGG
TTCTCCTGAGAAGCCAGATGTTGCACCTCAGCCTATGGAGGAAATTGATGCTCTCAACACCCATGCTACCATGGT
TCCCGTGTAGGGTTTTCATGGTCGAGCTGTGGTGTTTGTCCTGTTGTTACTATTTCAACTATATGAACATTGAGG
GAGTTTCTATCTATGGCTGCACTTGTGAAATATCCCTAAATAAGGCTAGCCATGTTCTATGTATTGATGAAGTTG
TTTGGTTCCTATGTGAATTGAACCTTGTCTTTTATTGCTTCATATTAATGTGGAGTTGCTCAGTGTCCTCTGGGA
ATCGACCTTGGATACTATGTTCGTTGTCTGTTATTTAAGACAATATATTTGGTAATGGAAGTTGGAGTTTCCCTG
T

> SEQ ID NO:165 129965 144926_301079_1b
GGAAATGCTGTTTGCCGGCGTCCAGGCTTCCTCTTTATGCATTCAAGAATGATGACAATGAGCCAATTGAAAACG
GTATTGATGCCTTGCCTGGGGAGGATTGTCAGATATCTTTTTTGAATGATCTGCTGTTGGGCCTATGGGAAGAGC
GGATGAGCCAGGGACTGTTTCGATATGATGTCACAACCTGTGAGACTAAAGTCATTCCTGGGAGATATGGTTTTA
TTGCACAGCTGAATGAGGGGCGCCACCTAAAAAAGCGCCCAACAGAGTTTCGCATCGATCAGGTTCTTCAGCCTT
TTGACGAGAACAAATTCAATTTTACCAAAGTGGGCCAGGACGAAGTGCTTTTCAGGTTTGAGCCAAGCACTGACT
GCAAGGCCCATTACTTTTCGGGTGTGGGAGTAGATGCTGGTGTTTCACCGAGTATTGTTGCTATCAATGTGAGCC
CAATCGAGTATGGCCATGTGCTTTTGATACCTCGAGTTCTTGATTACTTTCCTCAGAGAATTGATCGTGATAGTT
TCACGGTTGCTCTCCATTTCGCCAGAGAACTGGCTGATCCCTTCTTTAGGGTAGGTTATAACAGTCTGGGCGCCT
TCGCCACTATAAACC

> SEQ ID NO:166 129965 55977_300129_1b
TTATTGGTGGTAGTGATCTTCAAGGAAGAAGCTTTCTCTATCGGGAATTGCATTGCCAAATAGTAAGCCTGAAAG
TGAAGATGGTTAATGGTAGCGAAAGCGCCTAGACTGTTGTATCCAAGTCGGAAATACGTATTATCGGCTTCAGCC
GCCATTTGAAGAGCAAGCAAAAGGCTTTTGTGATCAATCCTTTGAGGTAAGCAATCAAGAACATTCCTTTCAACA
TTCTCATCTCTGACTCTGGCAAACGAATCTTCCTTCTCCCTCAGTGTTACGCAGAGAAACAGGCTTTAGGAGAAG
TTAGCTCAACGCTATTGGATACGCAAGTGAATCCAGCGGTTTGGGAGATGAGTGGACACATGGT

> SEQ ID NO:167 130213 1007385_301399_1b
GTCCATCTTTGTGTTGTGAAAGAAGCTTGCAGGCCATGGGGACGGAGAAAGAGCGCGAGAAAAATGTGTACATGG
CCAAGCTTGCTGAGCAGGCAGAGCGTTATCAAGAGATGGTTGAATACATGGAAACAGTGGCCAAGCTTGATCTTG
AGCTAACTGTGGAGGAGCGCAACCTTCTGTCTGTTGGCTACAAAAATGTTATTGGAGCCCACAGAGCCTCTTGGC
GTATCCTTTCTTCCATTGAACAGAAAGAAGAGAACAAGGGCAATGAGACTAATGTGAAGCGTACCAGGGATTATA
GGCATAAAGTTGAGACAGAACTTACCAAGATTAGCAGTGAAATTTTGACTATCCTTGATGAGCATCTCATCCCCT
CATCGGGAACTGGCGAATCATCTGTCTTCTACTATAAAATGAAGGGCGACTACTACCGTTACCTGGCAGAGTTTC
AGACAGGCGAGAAGAAAAAGGAATCTGCGGACGAGTCCTTCAAAGCATATCAGGCCGCATCAAGCACTGCAAACA
CAGATCTCCCGCCCACCCATCCAATCAGGCTGGGGCTTGCCCTGAACTTTTCTGTTTTCTACTATGAAATTATGA
ATTCCCCTGAACGGGCATGCGAGCTTGCTAAACAAGCATTTGATGAGGCGATTGCTGAGCTTGACACTCTGAGTG
AAGAGTCATACAAG

> SEQ ID NO:168 130213 1008583_301417_1b
GAGGAGCTCGTCTTCATGGCCAAGCTTGCTGAGCAGGCCGAGCGCTACGATGAGATGGCTGAGTTCATGGAGAAG
GTTGCCTCCATGTCCAGCTCTGGTGACGAGCTCGCTGTCGAGGAGCGTAACCTCCTCTCCGTCGCGTACAAGAAC
GTTGTCGGTGCCCGCCGCGCCTCCTGGCGTATTGTCTCCTCCATCGAGCAGAAGGAGGAGAACAAGGGCAACCAG
GATCACGTCTCCGCCATCCGCGGATACCGCACCAAGATCGAGAATGAGCTCGCCGGCATCTGTGAGGGCGTGTTG
AAGGTCCTCGCCTCTGCCCTCATCCCCGCCTGCGCCTCCAAGGAGTCCAAGGTCTTCTACCTCAAGATGAAAGGG
GATTACTACCGATACCTTGCTGAGTTCAAGACCGGCCCCGAGAGGAAAGACGCGGCTGAGTCCACACTTCTCTCA
TACAAGTCTGCTCAGGACATCGCACTCACTGAGATGCCTCCCACTCACCCGATTCGCCTTGGCCTCGCACTCAAC
TTCTCTGTATTCTACTACGAAATCCTAAACTCACCCGAACGGGCTTGCAGCCTTGCTAAGCAGGCATGTGATGAG
GCCATTTCTGAGCTGGACACACTTGGTGAGGAGTCCTACAAGGACAGCACCCTAATCATGCAGCTTCTCCGGGAT

Figure 2 continued

AACCTCACTTTGTGGACATCAGATC

> SEQ ID NO:169 130213 105222_300372_1b
AAAAATCTCATAAACGAAACACAAAAAAAAAACCCTCTCTCGAAAATTAAAAATAAAAAATACCCGGCGAATCTC
CGACGATGGCTTTGCCGGAAAATTTAACCAGAGAGCAGTGCCTATACTTAGCAAAGCTCGCCGAGCAAGCCGAGC
GTTACGAGGAGATGGTAAAATTCATGGACCGACTCGTAGCTGTCTCGGCTTCCTCTGAACTAACCGTAGAAGAGC
GAAACCTCCTCTCGGTAGCTTATAAGAACGTCATCGGTTCACTTCGAGCCGCGTGGAGGATAGTATCGTCAATTG
AGCAAAAGGAAGAAGGTAGGAAGAACGAGGAACACGTGGTTCTAGTGAAGGATTATAGATCTAAGGTTGAATCTG
AGCTTAGTGATGTATGTGCTGGAATTTTGAAGATTTTGGATCAGTATTTGATTCCTTCGGCTTCGGCTGGTGAAT
CGAAGGTGTTTTACTTGAAGATGAAGGGAGATTATTATCGTTATTTGGCTGAATTTAAAGTTAGTAATGAACGTA
AGGAGGCTGCTGAGGCCACTATGCTTGCCTACAAAGCTGCTCAGGACATTGCGCTTGCTGAGCTTGCCCCAACAC
ATCCTATACGACTTGGGCTAGCTCTCA

> SEQ ID NO:170 130213 1096679_301432_1b
GCTGTGTTTATCTTCTTCGCCTTCGTGTTCGTCGGTGGTGTTGGTAGTGGGAAGATGGGTGTGGAGAAGGAGCGT
GAGAGTGATGTGTACATGGCTAAGCTCGCTGAGCAGGCGGAACGTTATGATGAGATGGTGGAATTCATGAAAAAG
GTGGCAAACTTGGATGTGGAGCTATCTGTAGAGGAGAGGAATCTGATGTCAGTTGGGTACAAGAATGTGATTGGG
GCACGGAGGGCCTCTTGGCGCATCCTCTCCTCCATCGAGCAGAAGGAGGAGGGAAAAGGCAATGAAGTGAATGCC
AAGCGCATCAAAGAATACAAGCACAAGGTCGAGGAAGAGCTTTCAAACATCTGCAACGATGTCCTCTCCGTTATT
GAGGATCATCTCATCCCTGCGTCTAGCACGGGGGAATCTTCTGTCTTCTATTACAAAATGAAAGGGGATTACTTC
CGATATNTGGCAGAGTTTAAATCTGGAAATGAGAAGAAGGAAGCCGGAGAGCAGTCTTTGAAAGCATACCAGGCT
GCTATGGACATAGCGACATCT

> SEQ ID NO:171 130213 1100519_301461_1b
TCTTGTTTTTTGTTTGGTTGTTGACGGAAGAAGAGGAGGGAGAAGGCATGGGTGTGGAGAAGGATCGCGATGGC
CATATCTACATGGCCAAGCTCGCTGAGCAGGCCGAACGATACGATGAGATGGTCGATTTTATGAAAAAGGTGGCA
AACATGGATGTGGAGCTCACTGTGGAGGAGCGGAATCTTTTATCAGTAGGCTACAAAAATGTGATTGGGGCCCGC
AGGGCTTCGTGGCGTATTCTCTCCTCAATTGAGCAAAAGGAGGAAGCCAAAGGCAATGAGCAGAATGTGGGGCGT
ATCAAAGACTACAAGGAAAAGGTTGAGGAAGAGCTCTCAAAGATCTGCATTGACATCTTGTCGACTATCGATGAT
CATCTTATCCCTGCATCCAGCACTGACGAGTCTTCTGTGTTTTATTACCAAATGAAAGGGGATTACTTCCGCTAT
TTAGCAGAGTTCAAAGCCTCAAGCG

> SEQ ID NO:172 130213 1117183_301818_1b
TACAAATCCTCGACTGTGAAAGGAGCTTTCGCCATCTCTCTCCATGGGAATCGAGATGGACCGCGATGGGAATGT
CTACATGGCCAAGCTCGCTGAGCAAGCCGAACGCTATGATGAGATGGTGGAGTTCATGAAGAATGTGGCGAATAT
GGATACGGAACTGACTGTGGAGGAGCGCAACCTATTCTCCATAGGATATAAAAATGTGATCGGAGCTCGTCGGGC
TTCCTGGCGCATTCTCTCCTCCATTGAGCAGAGAGAGGAGAGCAAGGGCAACGAGGTGAATGCGAATCGCATCAA
GGAGTACCGTAACAGAGTCGACGAAGAGCTCTCCAAGATCTGCAAAGATGTCCTGAGCATCATCGATGATCATCT
CATCCCCTCTTCCACAACCAAAGAATCTGAGGTCTTCTATTACAAAATGAAGGGTGATTATTACCGCTATTTGGC
TGAGTTTAAGGCTGGTAGCGAGAGGAAGGATGCGGCAGATCACTCCCT

> SEQ ID NO:173 130213 6478_300322_1b
CCCACGCGTCCGTAAAGGAAAGAAGAGAGCAAAGGGAACGAAGATCATGTTGCTATTATCAAGGATTACAGAGGA
AAGATTGAATCCGAGCTTAGCAAAATCTGTGATGGATTTTGAATGTTCTTGAAGCTCATCTTATTCCTTCTGCT
TCACCAGCTGAATCTAAAGTGTTTTATCTTAAGATGAAGGGTGATTATCATAGGTATCTTGCTGAGTTTAAGGCT
GGTGCTGAAAGGAAAGAAGCTGCTGAAAGCACTTTGGTTGCTTACAAGTCTGCTTCCGACATTGCCACTGCTGAG
TTAGCTCCTACTCACCCGATAAGGCTTGGTCTTGCACTCAACTTCTCTGTGTTTTACTATGAAATCCTCAACTCG
CCTGATCGTGCTTGC

> SEQ ID NO:174 130213 157176_301735_1b
AGCCAAGTGAAAGCAAAAAGGGAGAGGAAAAGCGCAAAATCTCCCTTCGATTATCAGTACAAAACCTCTGATTTG
AGAGATCGGAAATGGCTTCCTCCAAAGAACGCGAGAACTTCGTCTACGTCGCTAAGCTTGCTGAGCAGGCCGAAC
GCTACAATGAAATGGTTGATGCGATGAAGAGTGTAGCAAATATGGATGTTGAATTGACTGTTGAGGAAAGGAATC
TGCTTTCTGTTGGTTATAAAAATGTGGTAGGTTCTAGGAGAGCATCTTGGAGGATCTTATCCTCTATTGAGCAGA
AGGAAGAATCTAGAGGAAATGAGCAAAATGTCAAGCGAATTAAGGAGTACCGACAAAAGGTGGAGACAGAGCTCA
CCAGCATTTGCAACGATATCATGGTGGTCATTGATCAGCATCTAATTCCTTCATGCACTGCAGGCGAATCAACTG
TGTTTTACCACAAGATGAAGGGAGACTATTATCGTTATCTTGCAGAATTTAAATCTGGCAATGACAAGAAAGAGG
TTGCAGAGCTTTCATTGAAAGCATATCAGTCAGCTACAACTGCTGCAGAGGCGGAATTACCACCCACTCATCCCA

Figure 2 continued

TTCGGTTGGGATTGGCTTTGAATTTCTCTGTGTTCTATTATGAGATCATGAATTCACCTGAAAGGGCATGCCATC
TGGCAAAGCAGGCCTTTGATGAAGCAATATCTGAGTTGGATAGCCTGAACGAGGATTCCTACAAAGACAGCACCT
TGATTATGCAGCTTCTAAGGGACAATCTCACCTTGTGGACTTCTGATCTTCCAGAGGATGCAGAAGATGCCCAAA
AGGGAGATGCCACAAACAAAGCAAGTGGAGGTGAAGATGCAGAGTGAATGGGCCTAATGGTTAGAACTACCTTGT
GCATTTGGAGCTGTGAGGACGGTGATACACCAAAGGGATGTGTGTGTGTTAAGTCCTAGTAGATTCTTATCTTAT
GGGCATGTCGTGTCAGTTTCTTTACATGTTAATTGGGTGTTGCAATTCAGCATGTGTGTGATTTGTATCCCTGTG
CTATTTCCTCTCCGTAAAGTGAGTTGTTTCAGTCTTTAGATGATTGGTCTGGTCCATAGGTGGTTTTATTTTTCA
GAGGACT

> SEQ ID NO:175 130213 156770_301369_1b
TACAAAACTCCCTCTCTCATTTCCTCTCTCATAGCAACATCAATGGCGTCGCCACGCGAGGAGAACGTGTACATG
GCAAAGCTTGCCGAGCAAGCCGAGCGTTACGAGGAGATGGTTGAGTTCATGGAGAAAGTCATCGCCGCCGCCGAC
GGCGCCGAGGAACTTACCGTCGAAGAACGGAACCTCCTCTCCGTCGCATACAAAAATGTTATCGGAGCACGGCGA
GCCTCGTGGCGTATCATCTCCTCCATTGAGCAAAAAGAGGAGAGCCGCGGCAACGAAGATCACGTTGCCTCCATC
AAGGAGTACAGATCTAAGATCGAGATCGAACTTACCTCGATCTGTAACGGCATTCTCAAGCTCCTCGATTCTAAG
CTCATTGGCGCCGCTGCTACCGGTGACTCTAAGGTGTTTTACTTGAAAATGAAAGGAGATTATCATCGCTATTTG
GCTGAGTTTAAAACCGGCGCGGAGCGAAAGGAAGCCGCCGAAAATACTCTCTCGGCTTACAAATCCGCTCAGGAT
ATTGCAAATACCGAGCTTGCTCCTACACATCCAATCCGATTGGGACTTGCTCTCAATTTCTCTGTATTTTACTAC
GAAATTTTGAATTCTCCTGATCGTGCTTGTAATCTCGCCAAACAGGCTTTTGACGAGGCAATTGCCGAGCTGGAC
ACATTGGGCGAAGAGTCCTACAAGGATAGCACTCTGATCATGCAGCTTCTTCGCGATAACCTCACTTTATGGACT
TCAGATATGCAGGATGATGGAACTGATGAGATCAAAGAAGCAGCAAAACCAGATAATGAGCAGCAGTAAACCGGT
GACATTTCTTTAGGATTGAAATTCATGTTGTAACTTTTTATTTTTCAATTGTCTGAGTTCAGCTCTTTTAGTTCT
AGATCTT

> SEQ ID NO:176 130213 14371_300244_1b
CCCACGCGTCCGGTAACGATGACCACGTCACGGCGATCCGTGAATATAGGTCTAAGATCGAGACGGAACTCTCCG
GAATCTGCGACGGAATCCTTAAGTTGCTTGACTCTAGACTCATCCCTGCCGCTGCTTCTGGTGATTCCAAGGTCT
TTTACCTTAAGATGAAGGGAGATTATCACAGGTACTTGGCTGAGTTTAAGACTGGTCAAGAGAGGAAAGACGCCG
CCGAACATACACTCGCCGCTTACAAATCTGCTCAGGATATTGCTAATGCAGAGCTTGCTCCAACACACCCAATTC
GTCTTGGTCTTGCATTGAACTTCTCTGTGTTCTATTACGAGATCCTCAATTCTCCTGATC

> SEQ ID NO:177 130213 139182_300407_1b
CGGCCGAACAAAAAGCATTCGCATCCACGAGACCACTCGAACCCGACCCGCCTCGCCGCCGCCGCCACCGAAGTA
ATCCCTTAATTGGTCAAAATGTCTCGGGAGGAGAATGTCTACATGGCCAAGCTGGCCGAGCAGGCTGAAAGGTAT
GAGGAGATGGTTGAGTACATGGAGAAGGTTGCAAAGACTGTAGATGTGGAAGAGCTCACTGTTGAGGAGCGCAAC
CTCTTGTCTGTTGCTTACAAGAATGTGATTGGTGCCCGCCGTGCCTCCTGGCGTATTGTCTCATCCATTGAACAG
AAGGAGGAGGGTCGTGGCAATGAGGAACATGTTACTCTGATCAAGGAGTACCGTGGCAAGATTGAAGCTGAGCTG
AGCAAGATTTGCGATGGTATCCTGAAGTTGCTTGACTCACACCTTGTGCCCTCATCTACTGCTGCAGAATCTAAG
GTGTTTTACCTCAAGATGAAGGGTGATTACCACAGGTACCTTGCGGAATTTAAGACTGGTGCCGAGAGAAAGGAA
GCTGCTGAGAGCACAATGGTGGCTTACAAGGCTGCTCAGGATATTGCTCTGGCGGATCTTGCTCCCACCCATCCC
ATAAGGCTTGGACTGGC

> SEQ ID NO:178 130213 134787_300418_1b
ACGAGATTCTAAACTCTCCAGACAAGGCTTGCAACCTTGCTAAGCAGGCGTTTGACGAAGCCATCTCTGAGTTGG
ATACCCTCGGGGAGGAGTCTTACAAGGACAGCACTTTGATCATGCAGCTCCTGAGGGACAACTTGACCCTCTGGA
CCTCTGACCTCACGGAGGACGGTGGTGATGAGGTGAAAGAAGCCTCCAAGGGCGACGCCGGCGAGGGCCAGTAAA
ATGGGAAGATCGATCGATCGATGGCTCCGCATGTTATTGGAGACCATTGATTTAGATGCCTCATGCTGCTGTCAC
CATGATGGATGGATTCTTCTTCTGTTCTACTAGAATGTTTTTCTTCCTGTCCCCCCTTCCTCTCTCTTCTCTGGT
TTTTACTAGGGTGGTAGCGGTCGAATTAGTTCTTCCCTTTGCTTTGCATTTGGTGCTAGTGGTCCGTCTGGGCTG
ATTGTTTTCCTCTGGATATGACTCTCGTGTGTGTTGTCTCCAGATAGTGTTTTATTGAGCAATATTTAAAGTTGT
CGTCC

> SEQ ID NO:179 130213 125521_300632_1b
CAAAAGTCCAAAATTTCCCCCACAAAAGCTCTCCTCTCTGAATTATTAAATCCCCATTCAGAAAATCGAAAAACT
CCCTCATTCAGATCTCCCAAAAAAAATACAGAGAAACAAATCTAAACATGGCGGTGGCACCGACGGCGCGTGAGGA
GAACGTGTACATGGCAAAGCTTGCAGAGCAAGCTGAGAGGTACGAAGAAATGGTTGAATTCATGGAAAAGGTCTC
CAACTCCCTCGGCTCAGAAGAACTCACCGTGGAGGAACGAAACCTCCTTTCCGTGGCGTACAAGAACGTGATCGG
AGCGCGTAGGGCATCGTGGCGTATTATCTCATCGATTGAGCAAAAGGAAGAGTCCAGAGGGAACGAGGAACACGT

Figure 2 continued

GAACTCTATCCGCGAGTACAGATCTAAGATTGAGAATGAGCTCTCTAAGATCTGTGATGGTATTCTGAAATTGCT
CGATGCAAAGCTTATCCCTTCTGCAGCATCTGGTGATTCTAAGGTGTTTTACCTGAAAATGAAAGGAGATTACCA
CCGCTATTTGGCTGAGTTCAAGACCGGTGCTGAACGTAAGGAGGCTGCTGAGAGTACACTCACTGCCTACAAAGC
TGCTCAGGACATTGCAACTACTGAACTTGCCCCAACACATCCCATCCGACTTGGACTGGCTCTTAACTTCTCTGT
GTTTTACTATGAGATCTTGAACTCTCCTGACCGTGCTTGCAATCTTGCTAAACAGGCCTTTGATGAAGCAATTGC
TGAGCTGGATACATTGGGCGAGGAGTCTTACAAGGATAGCACTTTGATCATGCAACTTCTTCGTGACAATCTCAC
TCTCTGGACTTCTGATATGCAGGATGATGGGGCTGATGAAATCAAGGAAGATCCCAAACCTGATGAAGCCAAAAA
TTGAAGGAAATGAAACTCTCTAATTTGCTTTTCACTTCTTCCTGGTTGTTTTTATTGGAAGAAGCTGATTATCGT
AATTTCCTTACTATTATGGTTCTCCACTAGGGGGTTGTCATCTTATTGGAAATGAACAACTTTTAATATTGATGT
TTCAGAGTTCCATCTTTGATTTAATGTGGTTTTCTGGTGATTAGTTTTCTTCT

> SEQ ID NO:180 130213 118303_300065_1b
CGGACGCGTGGGCCCAAAGAGAGAGAGCGAGAGAGAGAGCGGAGAAATGGAGAAGGAAAGAGAGAAACAGGTTTA
CTTGGCAAGGCTAGCTGAGCAAGCTGAGAGATATGATGAAATGGTAGAAGCAATGAAGACGGTTGCTAAGATGGA
TGTTGAACTGACTGTTGAGGAGAGGAATTTGGTGTCAGTTGGGTATAAGAATGTTATTGGAGCAAGAAGGGCTTC
ATGGCGGATATTGTCTTCAATTGAACAAAAGGAGGAGAGTAAGGGTCATGACCAGAATGTTACGAGAATAAAGAC
TTACCAACAGAGGGTCGAAGATGAGCTTACAAAAATATGCATTGACATTTTGTCGGTGATCGATGAGCACCTTGT
TCCTTCTTCCACTACCGGAGAATCTACTGTCTTCTACTATAAGATGAAGGGAGATTACTATCGCTATTTAGCAGA
GTTCAAATCAGGGGATGATCGTAAAGAGGCAGCTGATCAGTCACTTAAAGCTTATGAGGCTGCTACTTCCACAGC
TAGTGCAGATCTTGCTCCTACTCATCCAATTAGACTTGGACTTGCATTGAACTTCTCAGTCTTCTACTATGAG

> SEQ ID NO:181 130213 1171669_302055_1b
GAACAATGGGTGCCGAGAAGGAGAGGGAGGGTCATGTCTACCTGGCCAAGCTTGCAGAGCAGGCTGAGCGTTACG
ATGAGATGGTCGAGTTCATGAAGAAGGTAGCCAAGCTTGACATTGAGCTGACTGTGGAGGAGCGCAATCTTCTCT
CAGTGGCCTATAAGAATGTGATTGGAGCACGTAGGGCCTCTTGGCGTATTCTCTCCTCCATTGAGCAGAAGGAGG
AGAGCAAAGGGAATGAGGTTAACGTGAAGCGTATAAAGGATTACAGGCAAAAGGTCGATGAGGAACTCTCGAAGA
TCTGCCATGACATTTTGACTATCATAGATGAGCATCTCATCCCCTCTTCTGGGACTGGCGAATCGTCTGTCTTCT
ACTACAAAATGAAGGGAGATTACTACCGCTACCTCGCAGAGTTCAAAGCTGGTCCGCAGAAAAAGGAAGACGCAG
ATGAGTCCTTCAAAGCCTACCAAGCTGCGTCGAGCACCGCGAGTACTGATCTGCCACCTACCCATCCCATCAGGC
TTGGACTCGCCTTGAATTTCTCCGTTTTCTACTATGAAATTTTGAATTCGCCCGAGCAGGCATGCCAATTAGCAA
AACAAGCATTCGATGAGGCGATTGCAGAGCTCGATACTCTGAGCGAGGAGTCATACAAGGACAGCACCCTTATTA
TGCAGCTTCTAAGAGACAACCTGACCTTGTGGACTTCAGATCTGCAAGAAGATGGAGGTGATGAGCACTCCAAGG
GAGAGGATCTGAAAGTAGGAGATGCAGAGGAATCGTAGTGCCAGTTTGATTGTTCGAGCTGAGTTTTGAAGGAGT
CGAGCCGGATATGCATCCTTGGTACAAAATTTGACATGTGTTAGATTCTGTGTGGCATTTGTTTGAAGGAATATC
CTATGTAGATTGTTATGTTCTTGTTCTGCTCTATTGCTACAAGGGCTGTTGTTACAATTACAAGTTATACATTTT
CTATTTGAGGGAA

> SEQ ID NO:182 130213 114368_300007_1b
AGCGACAATCAGAAACCACCCGCTGTAACCCTAGGTTTTTTCACAAACAACAAATATGACTGAGTCATCGCGGGA
AGAAAATGTGTACATGGCCAAGCTTGCTGAGCAGGCCGAGCGATATGAGGAAATGATTGAGTTTATGGAGAAGGT
TGCAAAGACAGGTGATGTCGAGGAGCTGACTGTTGAGGAAAGGAATCTCCTTTCTGTGGCATACAAAAATGTGAT
TGGTGCAAGAAGGGCCTCGTGGAGAATAATCTCTTCAATTGAGCAGAAAGAGGAGAGCCGTGGAAATGAAGATCA
TGTCAAAACTATTAAAGAATACAGAGCCAAAATTGAGGCTGAACTCAGCAAGATCTGTGATGGGATTTTGGGTCT
CCTTGAGTCCCATTTAATACCATCAGCCTCCACAGCTGAGTCCAAAGTTTTTTACTTGAAGATGAAAGGTGATTA
CCACAGGTACTTGGCTGAGTTTAAGACAGGGGCAGAAAGGAAAGAAGCCGCAGAGAACACTTTATTACCCTACAA
GTCTGCTCAGGATATTGCTTTGGATGAACTGGCTCCTACTCACCCAATCAGGCTGGGACTTGCCCTCAACTTTTC
AGTGTTCTACTATGAAATTCTCAACTCGTCAGATCGTGCTTGTAACCTTGCAAAGCAGGCCTTTGATGATGCCAT
CGCCGAGCTGGATACATTGGGTGAGGAATCTTACAAGGACAGTACATTGATTATGCAGCTTCTCCGAGACAATCT
TACACTTTGGACTTCTGATACCACGGATGATGCCGGGGATGAGATCAAGGAAGCTTCAAAATGCGAATTAGGCGA
AGGAGAGCAGTAACGGCATAACATCATAGTCTTTTACTCTTTATTTTGTTTGATTTTAATATAGGACTACTGCGT
GAAAGCTAGACTGGATATGGATATAATTCGATGATTCCTCGTATTACTGCTGAAGTAGTTTGATATAAAAACATG
TTTTAGTACGATAAGAAATATAGTCATGCCGTTGATGTATTGGCTTGTATTTCTAGTTTCAATTGCATATGTTAT
TGACTGTTGAGCTTTGTATTTTCAAGTCATTCAATAATTCAATAGTTCCCAAAAA

> SEQ ID NO:183 130213 116870_300515_1b
CCCACGCGTCCGATGGTGGCGGCAAGGCTGCTCAGGACATTGCTTTGGCTGAGCTGCCTCCTACTCATCCAATTA
GGCTTGGGCTAGCTCTTAACTTCTCAGTGTTCTACTATGAGATCCTCAACTCGCCTGATCGTGCTTGCAACCTCG
CAAAGCAGGCTTTTGATGAGGCCATCTCGGAGCTGGACACCCTGAGCGAGGAGTCCTACAAGGACAGCACTTTGA

Figure 2 continued

TCATGCAACTCCTCCGTGATAACCTGACCCTGTGGACTTCAGACATCTCGGAGGACACCGCGGAAGAGATCAGGG
AAGCTCCGAAGCGCGACTCCAGCGAGGGGCAGTAAAGCCGGCTTTATGTGCCCTAGAAGCTTGTAGCTAGTGCTT
TGCTACTGTGTAATGACACCTATGTGGCTGTGATTGTTGTCGGGAAATCTGGGGCTCCCCCGTATGTGAGGTTGC
TAGCGATGGTTTTGCAGTCTCGCCTTTAAGCTACTCGTAGCAGAGCAGGTGGGGGTCTGTGGAGCCAGGCCTGGT
TGGGGGTGGGGGAGCCTCTTGAACTGCTTGGTGGCACTTCCTGTTTT

> SEQ ID NO:184 130213 1119703_301900_1b
AAAAAATCAGAGAAGTGAAGAGAAGAGATCAAGGGATCGATCCTTGAGAAGGCAATGGGAATCGAGAAGGAACGT
GAGACCCTCGTCTACCTCTCTAAGCTCGCTGAGCAAGCTGAGCGCTATGACGAAATGGTGGAGTCAATGAAGAAA
GTGGCTAAGTTGGACATTGAGTTGAGTGTGGAGGAAAGAAATCTGCTCTCCGTTGGATACAAGAATGTGATCGGA
GCACGCAGGGCCTCCTGGCGCATCCTCTCTTCCATTGAGCAGAAGGAAGAGAGCAAGGGCAATGAGACAAATGTG
AAGCGCATTAAGGACTATCGCTTCAAGGTGGAGGAAGAGCTCTCCAAGATATGCAGCGACATCCTAACCATCATC
GATGAGCACCTCATCCCCTCATCCAACACCGGTGAATCCACTGTTTTCTATTACAAAATGAAAGGGGATTATTAT
CGATACCTTGGGGAGTTCAAGTCTGGGCATTAAAAGAAAGAGGCTGGCGATCAATCTCTGAAAGCTTATCAAGCG
GGTAATAACACTGGGAACACGGATCTATCATCCACCCACCCAATCAG

> SEQ ID NO:185 130213 265563_200112_1b
TCCACATTCTCTCAACTTTCTCTTTCTAAAAACTCTTCCTATCTCTTTCTCTAGCACACAGACCATCAATGGCAT
CGCCGCGCGAGGAGAACGTGTACCTGGCGAAGCTGGCTGAGCAAGCCGAGCGCTACGAGGAGATGGTAGAGTTCA
TGGAGAAAGTCGTCGGCGCCGGCGACGACGAACTCACCGTCGAGGAACGCAACCTCCTCTCCGTCGCGTACAAAA
ACGTGATCGGAGCGAGGAGAGCGTCGTGGCGCATAATCTCATCGATCGAGCAGAAAGAAGAGAGTCGCGGTAATG
AAGATCATGTGGCCTCCATTAAAACCTACAGATCTAAGATCGAATCTGAATTGACTTCGATCTGTAACGGTATCC
TTAAGTTGCTCGATTCAAAACTCATCGGCACCGCTGCTACCGGTGACTCTAAGGTTTTTTATTTGAAAATGAAGG
GAGATTATTACAGGTACTTGGCTGAGTTCAAAACCGGAGCTGAGAGAAAAGAAGCCGCCGAGAATACTCTTTCGG
CTTACAAGTCGGCTCAGGATATTGCTAATGTCGAATTAGCCCCTACACATCCAATCCGATTGGGGCTAGCTCTCA
ATTTCTCAGTGTTTTACTATGAGATATTGAATTCTCCTGACCGTGCTTGTAATCTTGCCAAACAGGCATTTGATG
AGGCAATTGCGGAGCTTGACACCCTTGGAGAGGAGTCTTACAAGGATAGCACCTTGATTATGCAGCTTCTTCGTG
ATAACCTTACGTTGTGGACCTCGGATATGCAGGATGATGGGACTGATGAGATCGAAGTACCATCGAAAGCAGAGG
AGCAGCAGTAATGTGAGTGAAGCCTCCTTGTTTAGGATTGCAATCCTATGGACTGTGCTCATTGATCGGAATTTG
CTGTTTGTGTAGTTGTGAATTCCGTGAATTGTAATACGTAAAAGTGCTGTTTCTTGCCATTTGTTGTTTTCAGCA
AAGATTACTTTTTTGTGCAGTATGGTCCCTTGTATTTGGATGCTCCATTGGTGGAAATGAATTCTTGTTGTTAGG
GGAACAG

> SEQ ID NO:186 130213 258777_301699_1b
AAATCCTGAATTGCACCAACTAGTACAACGACAACAATGTCTTCTGAGAGAGAAACCAAGACCTTCCTTGCCCGG
CTCTGTGAGCAGGCTGACCGATACGACGAGATGGTCAACTACATGAAGGACGTCGCTAAGTCCGGTGAGGAGCTT
ACTGTCGACGAGCGAAATCTGGTTTCCGTCGCTTACAAGAACGTTATCGGCGCTCGACGAGCCAGCTGGAGAGTC
ATTTTCCCCATAGAGCAGAAGGAGGAGGCCAAGGGTGGCACCCACCATCTCGAGCTTCTCAAGACCTACAGAGCC
CAGATTGAGGGAGAGCTCGAAGACATCTGGAGCGATGTTCTTGATATTCTCAACAAACAACTCCTCCCCAAAGGC
GAGAACGCCGAGTCTAAGGTCTTCTACTACAAGATGAAGGGTGACTACCATCGATACCTTGCCGAGTTCACCTCC
GGCGAGAAGCGAAAAGAGGCTGCCACTGCCGCTCACGAGTCATACAAGAGCGCCACTGATGTTGCCCAGACTGAG
CTCAGCTCAACTCACCCCATCCGACTTGGTCTCGCTCTCAACTTCTCCGTCTTCTACTACGAGATTCTCAACTCG
CCAGACCGTGCTTGCCACCTTGCCAAGCAGGCTTTCGATGATGCCATCGCTGAGCTCGACACTCTCTCCGAGGAG
TCTTTCCGAGACTCTACCGTCATTATGCAGCTTCTGCGAGACAACCTGACCCTCTGGAAGAACGACCTCGAAGAG
TCTCTGCAAGCCCAGCAGTCTGAGGAGACCCCTGCCACCGATGCTGCCGCTGCTTCCACCGAGGCTGCTGCCCCC
AAGGAGGAGGCCAAGCCCGCTGCTGAGGAGCCCAAGGAGTAGAGTAGT

> SEQ ID NO:187 130213 232468_301215_1b
TCGACCCACGCGTCCGGGCGGCAGCGCACGGCGAGGAACAGGTGAGTGCCCGTGGATGTGATCTAGATCTACCCT
CCAAGCCCCAAAATCTCAGTAGAAATCCTCCAAATCGCGCCGCCGGAAGAGAGATCCAATCCACCACTGTCCCCA
TTTCTCGGCTTGTTCCAGGATGTCGAATCTTCGCGAGGAGAATGTCTACATGGCCAAGCTCGCGGAGCAGGCCG
AGCGCTACGACGAGATGGTGGAATTCATGGAGAAGGTGGTCAAGGCCGTGGACGTGGAGGAGCTGACGGTCGAGG
AGCGGAATCTCCTGTCGGTGGCCTACAAGAACGTGATCGGCGCCCGCCGGGCATCGTGGAGGATAATCTCCTCCA
TCGAGCAAAAGGAGGAATCCAAGGGCAACGACGACCACGTCTCGATGATCAAGGAGTACCGTGCCAAGGTGGAGT
CGGAGCTGAGCACCATTTGCGACAGCATCCTCAAGCTGCTGGACAGCCATCTCATCCCCTCATCGTCCAGTGGCG
AGTCCAAGGTCTTCTACTTGAAGATGAAGGGTGACTACCACCGATACTTGGCCGAGTTTAAGACCGGGGCCGAGA
GGAAAGAGGCCGCGGAGAACACTCTCCTCGCCTACAAGTCGGCCCAGGACATCGCTCTCACACAGCTGCCGCCGA
CGCATCCCATCCGGCTGGGTCTCGCTCTCAATTTTTCGGTCTTCTACTACGAGATTTTGAATTCGCCCGATCGAG

Figure 2 continued

CTTGTACGCTTGCCAAGCAGGCATTTGACGAGGCCATAGCCGAGCTGGACACTTTGGGAGAGGAATCTTACAAGG
ATAGTACTCTGATCATGCAGCTGCTGCGCGATAATCTAACGCTGTGGACCTCAGACATGCAGGAGGAAGGTGCCG
GCGAGGGGAAGGACGACAAGCCGTGAGTAAAATAATACGTTCGAATTTCGTTTCTATGCTACTAGCTAGCTGTT
TAGACGCCTTCTCTCTCAACACCTTGGTACTGTTGATTCTTTCGTTCCTGAATACATTATTTGGCTTG

> SEQ ID NO:188 130213 226749_301004_1b
TGCTGTCCGTGGCGTACAAGAACGTCATCGGCGCGCGCAGGGCGTCGTGGCGCATCGTGTCCTCCATCGAGCAGA
AGGAGGAAGGCCGCGGCGCCGCGGGCCACGCCGCCGCCGCGCGCTCCTACCGCGCCCGCGTCGAGGCCGAGCTCT
CCAACATCTGCGCGGGGATACTCCGCCTCCTCGACGAGCGCCTCGTCCCCGCCGCCGCCGCCGTCGACGCCAAGG
TCTTCTACCTCAAGATGAAGGGCGACTACCACCGCTACCTCGCCGAGTTCAAGACCGGAGCCGAGCGCAAGGACG
CCGCCGACGCCACCCTCGCCGGCTACCAGGCCGCGCAGGACATAGCCATGAAGGAGCTGTCGCCGACGCACCCCA
TCAGACTGGGCCTTGCGCTCAACTTCTCCGTGTTCTACTACGAGATCCTCAACTCGCCCGACCGCGCGTGCACGC
TCGCCAAG

> SEQ ID NO:189 130213 202218_300731_1b
CCAAAATTTCCGACGCCAGAGCGCGAGGAGACGCACACAGAGACTTGGCATTTGTAGAGTTTTTAGATTTATAGA
TAGCAAAGATGTCGGCACAGGCGGAGCTTTCCCGTGAGGAGAATGTGTACATGGCCAAGCTCGCTGAGCAAGCCG
AGAGGTACGAGGAGATGGTCGAATTCATGGAGAAGGTGGCCAAGACGGTTGACTCTGAGGAGCTCACCGTGGAGG
AGCGCAACCTCCTGTCTGTTGCATACAAGAATGTGATTGGAGCCCGCCGTGCGTCATGGCGCATTATCTCCTCCA
TTGAGCAGAAGGAGGAAAGCCGTGGTAACGAGGACCGTGTCACACTCATCAAGGACTACCGTGGCAAGATCGAGA
CTGAGCTCACCAAGATTTGCGACGGCATTCTCAAGCTGCTTGAATCCCACCTTGTCCCCTCTTCCACTGCCCCTG
AGTCCAAGGTCTTCTACCTCAAAATGAAGGGTGACTACTACAGGTACCTT

> SEQ ID NO:190 130213 2003_300335_1b
AATTCGGCACCAGAATCCATCCTCTTTCGCTTAAACTTTCTCTCTCTACAACAACAATGTCGGCTCTGCTCACAG
AAAATCTCAGCCACGAACAATACCTCTACTTAGCCAAGCTCGCCGAACAAGCCGAACGCTATGAAGAAATGGTCC
AGTACATGGACAAACTAGTCCTCAGTTCCACTCCGGCCGCCGAACTCACCGTCGAGGAACGAAACCTCCTTTCCG
TCGCTTACAAAAACGTGATCGGCTCTCTTCGTGCCGCGTGGCGTATCGTATCCTCCATTGAGCAGAAAGAGGAAT
CGCGCAAGAACGAAGAACACGTGTCGCTCGTTAAGGAGTACAGAGGTAAAGTCGAGAATGAGTTAACGGAG

> SEQ ID NO:191 130213 191394_300740_1b
GTACGAGACCACTCGAACCCGACCCGCCTCGCCGCCGCCGCCACCGAAGTAATCCCTTAATTGGTCAAAATGTCT
CGGGAGGAGAATGTCTACATGGCCAAGCTGGCCGAGCAGGCTGAAAGGTATGAGGAGATGGTTGAGTACATGGAG
AAGGTTGCAAAGACTGTAGATGTGGAAGAGCTCACTGTTGAGGAGCGCAACCTCTTGTCTGTTGCTTACAAGAAT
GTGATTGGTGCCCGCCGTGCCTCCTGGCGTATTGTCTCATCCATTGAACAGAAGGAGGAGGGTCGTGGCAATGAG
GAACATGTTACTCTGATCAAGGAGTACCGTGGCAAGATTGAAGCTGAGCTGAGCAAGATTTGCGATGGTATCCTG
AAGTTGCTTGACTCACACCTTGTGCCCTCATCTACTGCTGCAGAATCTAAGGTGTTTTACCTCAAGATGAAGGGT
GATTACCACAGGTACCTTGCGGAATTTAAGACTGGTGCCGAGAGAAAGGAAGCTGCTGAGAGCACAATGGTGGCT
TACAAGGCTGCTCAGGATATTGCTCTGGCGGATCTTGCTCCCACCCATCCCATAAGGCTTGGACTGGCACTTAAC
TTCTCTGTGTTCTACTACGAGATTCTAAACTCTCCAGACAAGGCTTGCAACCTTGCTAAGCAGGCGTTTGACGAA
GCCATCTCCGAGTTGGATACCCTCGGGGAGGAGTCTTACAAGGACAGCACTTTGATCATGCAGCTCCTGAGGGAC
AACTTGACCCTCTGGACCTCTGACCTCACGGAGGACGGTGGTGATGAGGTGAAAGAAGCCTCCAAGGGCGACGCC
TGCGAGGGCCAGTAAAATGGGAAGATCGATCGATCGATGGCTCCGCATGTTATTGGAGACCATCGATTTAGATGC
CTCATGCTGCTGTCACCATGATGGATGGATTCTTCTCCTGTTCTACTAGAATGTTTTTCTTCCTGTCCCCCCTTC
CTCTCTCTTCTCTGGTTTTTACTAGGGTGGTAGCGGTCGAATTAGTTCTTCCCATTGCTTTGCATTTGGTGCTAG
TGGTCCGTCTGGGCTGATTGTTTTCCTCTGGATATGACTCTCGTGTGTGTTGTCTCCAGATAGTGTTTTATTGAG
CAATATTTAAAGTTGTCGTCCACCTCCTCGATGTT

> SEQ ID NO:192 130213 190737_300779_1b
GAATTTGAACTCCACCTGAGCACAGGAGAAGCCGCAGCCACTGAGATTTGACCTTCTGTTTCTACCAGAAAAACA
CAAACAGTGAAGATGTCGCAGCCTGCTGAGCTTTCCCGTGAGGAGAATGTGTACATGGCTAAGCTTGCAGAGCAG
GCCGAGAGGTATGAGGAGATGGTTGAGTTCATGGAGAAGGTTGCTAAGACAGTTGACTCTGAGGAGCTCACTGTT
GAGGAGCGCAACCTTCTATCAGTTGCTTACAAGAATGTTATTGGTGCTCGCCGTGCGTCATGGCGCATCATATCA
TCCATTGAACAGAAGGAAGAGAGCCGTGGTAATGAGGATCGTTGCACGCTCATCAAGGAATACAGGGGAAAGATT
GAAACTGAGCTCTCCAAGATCTGTGATGGCATCCTCAAGCTTCTTGACTCCCACCTTGTGCCTTCATCCACTGCT
CCAGAGTCCAAGGTCTTCTACCTCAAGATGAAAGGCGACTACTACAGGTACCTCGCAGAGTTTAAGACTGGAGCT
GAGAGGAAGGATGCTGCTGAGAACACCATGGTGGCATACAAAGCCGCTCAGGATATTGCCCTGGCAGAGTTGCCC
CCAACTCATCCTATCAGACTTGGGCTGGCCCTCAACTTCTCGGTGTTTATTACGAGATCCTCAACTCTCCTGAC

Figure 2 continued

CGTGCTTGCAATCTTGCAAAGCAGGCTTTCGATGAGGCTATCTCAGAGCTGGACACTCTGAGTGAGGAATCCTAC
AAGGACAGCACTTTGATCATGCAGCTTCTGCGTGATAACCTGACGCTGTGGACTTCCGATATCTCGGAGGATGCT
GCTGAGGAAATCAAGGAGGCCCCCAAGGGCGAATCAGGAGATGGACAGTGAACATGATCGAATGCGTGCGCCCAC
AAACTAGAATAGTGACGCTGCAAATGTGCTGTGGGTTATCGTTTCATTTTATA

> SEQ ID NO:193 130213 187967_300682_1b
CCCACGCGTCCGCTCCACCTGAGCACAGGAGAAGCCGCAGCCACTGAGAAAAACACAAACAGTGAAGATGTCGCA
GCCTGCTGAGCTTTCCCGTGAGGAGAATGTGTACATGGCTAAGCTTGCAGAGCAGGCCGAGAGGTATGAGGAGAT
GGTTGAGTTCATGGAGAAGGTTGCTAAGACAGTTGACTCTGAGGAGCTCACTGTTGAGGAGCGCAACCTTCTATC
GGTTGCTTACAAGAATGTTATTGGTGCTCGCCGTGCGTCATGGCGCATCATATCATCCATTGAACAGAAGGAAGA
GAGCCGTGGTAATGAGGATCGTTGCACGCTCATCAAGGAATACAGGGGAAAGATTGAAACTGAGCTCTCCAAGAT
CTGTGATGGCATCCTCAAGCTTCTTGACTCCCACCTTGTGCCTTCATCCACTGCTCCAGAGTCCAAGGTCTTCTA
CCTCAAGATGAAAGGCGACTACTACAGGTACCTCGCAGAGTTTAAGACTGGAGCTGAAAGGAAGGATGCTGCTGA
GAACACCATGGTGGCATACAAAGCCGCTC

> SEQ ID NO:194 130213 255750_301643_1b
ACGCGTCGCCCTAACTAACCCTAACCGCCAAATATTGGGGGATTTATCATTTGGGTTTGGATCGAGTCAGTGCAG
TCTACGGTCTGCAAGCATGTCCGGGCACGATGAGCACGTGTTCATGGCTAAGCTCGCCGAACAGGCCGAGCGCTA
TGAGGAGATGGCCGAGTTCATGGAGAAGGTTGCTGGCCATGGGGACGACCTCACTGCCGAAGAGCGCAACCTCCT
CTCTGTCGCCTACAAGAACGTGGTGGGTGCTAGACGTGCCTCCTGGCGCATCATCTCCTCCATTGAGCAGAAGGA
GGAGGGCAAGGGCAACCAGGACCATGTCAGTGCCATCCGTGACTACCGGGCCAAGATCGAGGCCGAGCTTTGCAC
TATATGTGGGGGTGTCCTCAAGATCCTGGACACGCACCTCATCCCGGCCGGAGAAGCTGCTGAGTCGAAGGTCTT
CTACCTCAAGATGAAGGGTGATTACCATCGTTACGTGGCTGAATTCAAGACTGGTTCTGAAAGGAAGGAGTCTGC
TGAGAACACCATGTCTGCCTATAAGTCTGCCCAGGATATTGCCCTTGCAGAGCTTGCTTCAACTCATCCTATTCG
CCTGGGACTTGCGCTCAATTTCTCGGTAT

> SEQ ID NO:195 130213 182045_300628_1b
GAATTCAAGATCATGTTTCTATTATTAAAGAATATAGGGGAAAGATTGAATCTGAACTTCATAAGATTTGTCAAG
GGATTTTAGGGCTTTTGGATTCCCATCTTATTCCTTCATCAACTGCTGCTGAATCTAAGGTGTTTTACCTTAAGA
TGAAGGGTGATTACCACAGGTATTTGGCTAAGTTAGCTGAACAAGCTGAACGATATGAAGAGATGGTTGAATTTA
TGGAGAACGTTGCAAAAACTGTTGATTCTGATGAATTATCAGTTGAGGAACGAAACCTGTTGTCTGTTGCTTATA
AGAATGTGATTGGAGCTAGGAGAGCTTCATGGAGGATTATTTCAAGTATTGAACAAAAGGAAGAAAGCCGTGGGA
ATGAAGATCATGTTTCTATTATTAAAGAATATAGGGGAAAGATTGAATCTGAACTTCATAAGATTTGTCAAGGGA
TTTTAGGGCTTTTGGATTCCCATCTTATTCCTTCATCAACTGCTGCTGAATCTAAGGTGTTTTACCTTAAGATGA
AGGGTGATTACCACAGGTATTTGGCTGAGTTTAAATCTGGTAGTGACAGGAAAGAAGCTGCTGAGAGTACATTG

> SEQ ID NO:196 130213 179614_300562_1b
TTGCAAGTTCCATTCCCTGTTCTTCTCTCTCAACGAAGCATCAACCCCCCTTTTCTCCCAGAACCGCGTCTCATC
GCACCTGCCATAAAACTCCAAAAAATCTCAAAAACCAACCGTCAAAATGGGTCACGAAGATGCTGTTTATCTGGC
CAAGCTCGCCGAGCAGGCCGAGCGATATGAGGAGATGGTCGAGAACATGAAGATCGTCGCCTCCGAGGACCGCGA
CCTGACCGTCGAGGAGCGCAACCTCCTCTCCGTCGCCTACAAGAACGTCATTGGTGCCCGCCGTGCCTCTTGGAG
AATAGTCACTTCCATCGAGCAGAAGGAGGAGTCTAAGGGCAACTCTTCCCAGGTTACCCTTATCAAGGAGTACCG
CCAGAAGATTGAGGCCGAGCTTGCCAAGATCTGCGATGACATTCTCGATGTTCTTGACAAGCACCTGATTCCTTC
TGCCAAGTCTGGAGAGTCCAAGGTCTTCTACCACAAGATGAAGGGTGACTACCACCGTTACCTTGCCGAGTTCGC
CATTGGCGACCGCCGCAAGGACTCCGCCGACAAGTCTCTCGAGGCTTACAAGGCTGCTACCGAGGTTGCCCAGAC
CGAGCTGCCTCCTACCCACCCTATCCGCCTGGGTCTTGCGCTCAACTTCTCCGTCTTCTACTACGAGATCCTCAA
CGCCCCTGACCAGGCTTGCCACCTCGCTAAGCAGGCATTTGACGATGCTATT

> SEQ ID NO:197 130213 175041_300529_1b
GTCAGGAGCTGAGAGGAAGGAAGCAGCTGAGAACACTCTTGTGGCATACAAGTCTGCCCAGGATATTGCACTCGC
TGACCTGCCTACAACTCACCCAATAAGGCTTGGACTTGCACTGAACTTCTCAGTGTTCTACTATGAGATCCTGAA
CTCACCAGACCGTGCTTGCAACCTTGCAAAGCAGGCGTTCGACGATGCTATTGCTGAACTGGACACTCTTGGCGA
GGAGTCTTACAAGGACAGCACCTTGATCATGCAACTTCTTCGTGACAATCTGACTCTCTGGACCTCTGACAATGC
GGAGGATGGTGGTGACGAGATCAAGGAAGCAGCGAAGCCTGAAGGAGAGGGCCACTAATCTGTCCTGAAGTCTAT
TTCTGAGTCCATTTACTCAGCTACCTGCTGTATTACTGGATCATAAGATGTACTAGGATCAATTGCTATGTGGAA
TCATAAGATTAGGGCTGCGTATGTCAAAATGTGTCGAGCTGAAGTACCCAGTGGACACAGTTTATGTGCACTACA
TTGCTTCCGTGACTTATTTACTAGTTAATTAGCAACTTTCAACCACTTCCTGTATTTGCAGCACATTATTAGTAT
CGCTGTATTAGCGTTTTCCATGGGCTGGTTATGATTGAGAATACAGGCCAGGCATTGCATGTCC

Figure 2 continued

> SEQ ID NO:198 130213 159293_200022_1b
ACGCACTCTGTCGAGAATCCATTCTATTTCGCCTAAACTTTCTCTCTCTACAACAACAACAATGGCGGCTCTGCT
CACAGACAATCTCAACCGCGAACAATACCTCTACTTAGCCAAACTCGCCGAACAAGCCGAACGCTATGAAGAAAT
GGTCCAGTACATGGACAAACTAGTACTCAGTTCCACTCCCGCCGCCGAACTCACCGTCGAGGAACGAAACCTCCT
TTCCGTCGCTTACAAAAACGTGATCGGCTCTCTTCGTGCCGCGTGGCGTATCGTATCCTCCATTGAGCAGAAAGA
GGAATCGCGTAAGAACGAAGAACACGTTTCGCTCGTTAAGGAGTACAGAGGTAAAGTTGAGAATGAGTTAACGGA
GGTTTGTGCTGGTATCCTCAAGTTGCTTGAGTCAAATCTCGAGCCGTCTGCTTCTACGGGTGAATCGAGGGTGTT
TTACCTCAAAATGAAAGGTGATTATTACCGGTATCTAGCGGAGTTTAAGGTTGGAGATGAGCGGAAGCAGGCTGC
TGAAGACACTATGAATTCTTATAAGGCTGCTCAGGAAATTGCACTAGCAGATCTGCCTCCAACACATCCTATAAG
GCTGGGTCTTGCACTTAATTTCTCAGTCTTCTACTTTGAGATTCTGAACTCATCTGACAAAGCTTGTAGTATGGC
AAAACAGGGCTTTTGAGGAAGCCATAGCTGAGC

> SEQ ID NO:199 130213 158868_200020_1b
GTTATAAATCCTTATCTTTTTCAACACACAGATTAAAATCTTCAGAAAGAGAGAGAGAGATCCCAAAATGGGTGA
ACGTGAGAACTTCGTATACATAGCTAAGCTTGCCGAGCAAGCTGAACGCTATGATGAGATGGCTGATGCGATGAA
GAATCTTGCAAATATGGATGTTGAATTGACAGCGGAAGAGAGGAATTTGTTTTCTGTTGGTTATAAGAATGTGGT
TGGAGCTAGGAGAGCATCGTGGAGGATCTTGTCTTCCATCGAGCAGAAGGAAGAGTCTAGAGGAAATGAGCAGAA
CGTGAAGCGGATTAAGGAGTACCAGCAAAAAGTGGAGTCAGAGCTCACCGACATTTGCAATAATATCATGACCGC
GAT

> SEQ ID NO:200 130213 1110178_301527_1b
GGGTTTGGATCGAGTCAGTGCAGTCTACGGTCTGCAAGCATGTCCGGGCACGATGAGCACGTGTTCATGGCTAAG
CTCGCCGAACAGGCCGAGCGCTATGAGGAGATGGCCGAGTTCATGGAGAAGGTTGCTGGCCATGGGGACGACCTC
ACTGCCGAAGAGCGCAACCTCCTCTCTGTCGCCTACAAGAACGTGGTGGGTGCTAGACGTGCCTCCTGGCGCATC
ATCTCCTCCATTGAGCAGAAGGAGGAGGGCAAGGGCAACCAGGACCATGTCAGTGCCATCCGTGACTACCGGGCC
AAGATCGAGGCCGAGCTTTGCACTATATGTGGGGGTGTCCTCAAGATCCTGGACACGCACCTCATCCCGGCCGGA
GAAGCTGCTGAGTCGAAGGTCTTCTACCTCAAGATGAAGGGTGATTACCATCGTTACGTGGCTGAATTCAAGACT
GGTTCTGAAAGGAAGGAGTCTGCTGAGAACACCATGTCTGCCTATAAGTCTGCCCAGGATATTGCCCTTGCAGAG
CTTGCTTCAACTCATCCTATTCGCCTGGGACTTGCGCTCA

> SEQ ID NO:201 130213 1097704_301447_1b
TTGCAGATAACCCGTCTTGTTCATCTCTCTCTCTCATCTTCTCTAGCTCTCTCTCTGTCTGTCCCCTGTTTCCCT
GTCTTAGACCATGACTCCGTCGATGGAGGGGGGCAAGCGGGAGGAGAATGTGTACATGGCGAAGCTTGCGGAGCA
GGCCGAGCGGTACGAGGAGATGGCGGAGTTCATGGATGCCGTCGTCAAGGACGGTGCTGACGAGATGTCGGTGGA
GGAGCGGAACCTCCTCTCCGTCGCGTACAAGAACGTGATTGGCGCGCGTCGCGCCTCCTGGCGCATCGTCTCCTC
CATTGAGCAGCGCGAGGAGAGCAAGGGCAACCAGGAGCACGTCTCTGCCATCCGCGACTACCGTGCCTCCGTCGA
AACCGAGCTCACCAAGATCTGCAAAAGCATCCTTAGCCTCCTCGAGATGCACCTTGTCCCTTCCGCCACCACCCC
CGAATCCAAAGTCTTCTACCTCAAAATGAAGGGCGACTACCACCGCTACCTTGCGGAGTTCAAAATCGGGGCGGA
CCGCAAAAAACTGGCGATAAATACTCTCACCGCCTACAAATCTGCTCAGGAAATAGCCTTGGCTGAGCTGCCTTC
AACACACCCCATTCGTTTGGGGCTTGCTCTAAAT

> SEQ ID NO:202 130213 1096683_301432_1b
GTATGCTCACAGCTCACCTCACTCCTCTTTATTTTTAGGGTTCATTGGAAGGAAGAGAGAGAGAGAGAGAGAGAG
AGAGAGAGTCTTGCTGCACCAACCCAACCCAAGGAGCTCTTCTTTGTGTTCTACTCCCATGGGTATTGAGAAGGA
GAGAGAGAGCCATGTCTACATGGCCAAGCTTGCTGAGCAGGCAGAGAGATATGATGAAATGGTGGATTCCATGAA
AAAGATTGCCAAGTTGGACGTCGAGCTGACCATTGAGGAGAGAAATCTGCTTTCCGTGGGCTATAAAAATGTGAT
TGGGGCTCGGAGGGCCTCGTGGCGAATCCTCTCCTCAATTGAGCAGAAAGAGGAGAGCAAGGGCAATGAAACAAA
TGCCAAGCGCATTGAGAGTTACCGACATAAGGTTGAGGAAGAACTCTCTGGAATCTGCAAGGACATCCTGACTAC
CATCGATGAGTATCTCATCCCCTCGTCTGGCACGGCGGAATCCACCGTT

> SEQ ID NO:203 130213 1008629_301417_1b
GACATGGGCATCGAGAAGGAGCGAGAGAGCCTTGTCTACCTATCCAAGCTCTCCGAGCAGGCAGAACGCTATGAC
GAAATGGTGGAGTCGATGAAGAAAGTAGCTAAGTTGGATGTAGAGCTTACGATTGAGGAGAGGAATTTGCTCTCA
GTGGGGTATAAGAATGTGATCGGAGCGCGAAGGGCCTCGTGGCGAATTCTCTCCTCCATTGAGCAGAAAGAAGAG
AGCAAGGGCAATGAGACCAATGTAAAACGCATCAAGGAGTACCGCAACAAAGTGGAGGAAGAGCTTTCCAAGATT
TGCAGTGACATCCTAACTATCATCGATGAGCATCTTATCCCCTCATCTGGCACAGCAGAATCTACCGTTTTCTAT
TACAAAATGAAAGGGGATTATTATCGCTACCTTGCTGAGTTCAAGACAGGACATGAGAGAAAGGAAGCTGCAGAT

Figure 2 continued

CAATCTCTGAAAGCTTATCAGACTGCAAGTGACACG

> SEQ ID NO:204 130294 130511_300488_1b
GAATTCAGAGATGATGATAAATCAAACATAATAGGGATGTTAACTACACCCCACACATCGTCATCAGCATCCTCT
TCATCTTCTTCGAATCCTAGTCAACAAGAAAAAATTTCTGTCGTATCCATAGTGGGCATGGGTGGGTTAGGAAAA
ACTACACTTGCTCAATTGGTCTACAAAGATGACTCGATAATGAGACATTTTAAGACCAGAGCATGGGTTTGTGTT
TCTGATGTTTTTGATATCAAAAAAATCAAAACTAACATAATCGAGTCGGTTACAAAAAACAAGTGTGTTGATTTT
TCAAATGATGATGTCTTAACTAATAAACTTCAAGAAGAGTTGGGTAACAAGTTTTTTTTACTAGTACTAGATGAT
GTTTGGAGTGACAATCCAGAAGATTGGGATAACCTTAGAGGTTTGCTAAGTGTGGGTGCTTGTGGAAGTAAAGTC
TTAGTCACAACACGTAGCCACAAAGTTGCTTCTGCTTCCGGAGGTGTTGTTCCTCCATACAAACTAGAAGACCTA
CCTCATAGTGTTTGTTGGTCTATCATCAAGACCAAAGCTTTTTCTCCGGGTGGGGCAATAGTCAGTACAAAAAATG
ACATGTATAGGACAGGAGATTGCAAGAAA

> SEQ ID NO:205 130294 131277_300512_1b
GAATTCCAGAGATGAATTGGTACGTAAACAGTTTGGGCTAACAATGTGGGTCTACGTATCTGAGCATTTTGACGT
GATAAAGCTTTTGACAAAAATTATGGAATCCTCAACTAATGATAAGTTTGATACTTTGTCGAACTATGATGTACT
AGTCAGTAAAGTTCAGGAACAGCTAAATGGGAAAAGATATTTGCTAGTGCTCGACGATTTATGGAATGAGAATGC
TGATCAATGGGATAGACTCTGCAGCGCGTTGCTTGTTGGGGCTCAAGGGAGTAAAATATTAATCACTACTCGCAA
AAGTCAAGTTGCAGATATGGTTAGGGGGAGTATTCTTCCTTACAAATTGGGAAAGGAATAGCAAAGAAATGTAGT
GGCGTACCTCTTGCAGCAAAGTTCCTGGGAAGTCTAATGCGCTCAAAAAATAAAGAAGCTGATTGGTTGTCGATT
CAACAACTTGATGTTTTGAATACAAGCGAAATCATGCCGATACTAAAGTTGAGCTATGATAACTTGTCGTCTGAG
TTGAAACAATGTTTCTCCTACTGCTCTATATTTCCCAAAGATTGGGAGATAAATAGAGTAACTCTGATTCAGTTG
TGGATAGCAGAAGGGTTTCTCGACACTTGTAACCTAGGAAACAGAAGATCAATTGAAGACATCGCGGATGAATA

> SEQ ID NO:206 130294 160262_200051_1b
ATCAATTTCCTCGCTTCCGCCAAAATGGCTTCTTTGACACAACAATTCGGAGGGCTGAAATGCCCACCAATTTCA
ACAGCAAGGGTTGAATCTAAGAAGCTTAAGGTGAATCCCATTAATCATCAGAATAAGAAGGCTAACAAAGCAAGA
GTAGTAGCACAAGCTGCAGCAGTGGTCACAAATGCACAAACAAGAGAAAGACAAAAGCTTAAGGAGATGTTCGAG
GATGCCTATGAACGATGCCGTACTGCACCTTTGGAAGGTGTTGCCTTTACTGTTGAAGATTTTCACTCTGCCCTT
GAAAAATATGATTTTGACTCCGAAGTTGGTACCAAGGTCAAAGGAACAGTTTTCTCTGTGGATGCAAATGGAGCT
CTAGTTGACATCACTGCTAAATCATCTGCATACTTGCCTTTACGGGAGGCTTCACTTCACACCATCAAGCACGTA
GAGGAAGCTGGAATATTTCCTGGTTTGCGTGAGGAGTTTGTGGTGGTTGGCGAAAATGAAGCTGATGATAGTTTG
GTTTTGAGCTTGCGTTCGATTCAATATGACCTTGCATGGGAACGATGTAGGCAGCTACAAGCTGAAGATGTTGTT
GTCAAAGGCAAGGTCGTTGGTGCAAATAAAGGTGGAGTGGTGGCTCTGGTGGAGGGGCTTCGTGGTTTTG

> SEQ ID NO:207 130964 130825_300491_1b
GAATTCAAGCAGTGGGAGGAGCCTGGGCTCTGACGGGGTGCCTGTTGAAGAATGAGCCGGCGACTCATAGGCAGT
GGCTTGGTTAAGGGAACCCACCGGAGCCGTAGCGAAAGCGAGTCTTCATAGGGCAATTGTCACTGCTTATGGACC
CGAACCTGGGTGATCTATCCATGACCAGGATGAAGCTTGGGTGAAACTAAGTGGAGGTCCGAACCGACTGATGTT
GAAGAATCAGCGGATGAGTTGTGGTTAGGGGTGAAATGCCACTCGAACCCAGAGCTAGCTGGTTCTCCCCGAAAT
GCGTTGAGGCGCAGCAGTCGACTAGACATCTAGGGGTAAAGCACTGTTTCGGTGCGGGCCGCGAGAGCGGTACCA
AATCGAGGCAAACTCTGAATACTAGATATGACCCCAAAATATGGGGTCAAGGTCGGCCAGTGAGACGATGGGGGA
TAAGCTTCATCGTCGAGAGGGAAACAGCCCGGATCACCAGCTAAGGCCCCTAAATGACCGCTCAGTGATAAAGGA
GGTAGGGGTGCAGAGACAGCCAGGAGGTTTGCCTAGAAGCAGCCACCCTTGAAAGAGTGCGTAATAGCTCACTGA
TCGAGCGCTCTTGCGCCGAAGATGAACGGGGCTAAGCGATCTGCCGAAGCTGTGGGATGTAAAAATGCATCGGTA
GGGGAGCGTTCCGCCTTAGAGGGAAGCACCCGCGCGAGCAGGTGTGGACGAAGCGGAAGCGAGAATGTCGGCTTG
AGTAACGCAAACATTGGTGAGAATCCAATGCCCCGAAAACCTAAGGGTTCCTCCGCAAGGTTCGTCCACGGAGGG
TGAGTCAGGGCCTAAGATCAGGCCGAAAGGCGTAGTCGATGGACAACAGGTGAATATTCCTGTACTACCCCTTGT
TGGTCCCGAGGGACGGAGGAGGCTAGGTTAGCCGAAAGATGGTTATCGGTTCAAGGACGCAAGGTGACCTTAGGG
TAAGAAGGGGTAGAGAAAATGCCTCGAGCCAATGTCCGAGTACCAGGCGCTACGGCGCTGAAGTAACTCATGCCA
TACTCCCAGGAAAAGCTCGAACGACCTTCAACAAAAGGGTACCTGTACCCGAAACCGACACAGGTGGGTAGGTAG
AGAATACCTAGGGGCGCGAGACAACTCTCTCTAAGGAACTCGGCAAAATAGCCCCGTAACTTCGGGAGAAGGGGT
GCCTCCTCACAAAGGGGGTCGCAGTGACCAGGCCCGGGCGACTGTTTACCAAAAACACAGGTCTCCGCAAAGTCG
TAAGACCATGTATGGGGGCTGACGCCTGCCCAGTGCCGGAAGGTCAAGGAAGTTGGTGACCTGATGACAGGGAAG
CCGGCGACCGAAGCCCCGGTGAACGGCGGCCGTAACTATAACGGTCCTAAGGTAGCGAAATTCCTTGTCGGGTAA
GTTCCGACCCGCACGAAAGGCGTAACGATCTGGGCACTGTCTCGGAGAGAGGCTCGGTGAAATAGACATGTCTGT
GAAGATGCGGACTACCTGCACCT

Figure 2 continued

> SEQ ID NO:208 130964 232178_301237_1b

CGCGTCCGGGATAATTGGAGATCTGACCGCGTGCTGTTGAAGAATGAGCCGGCGACTTATAGGCGGCGGCCTGGT
TAAGGAAACCCACCGGAGCCGTAGCGAAAGCGAGTCTTCCCAGGGGCAACTGTCGCTGCTTATGGACCCGAACCC
GGGTGATCTATCCATGACCAGGATGAAGCTTGGATGAAACTAGGTGGAGGTCCGATATTGACTGATGTTGAAAAA
TCAGCGGATGAGTCGTGGTTAGGGGTGAAATGCCACTCGAACCCGGAGCTAGCTGGTTCTCCCCGAAATGCGTTG
AGGCGCAGCGGTTGACGAGGCTACCTGGGGTAAAGCACTGTTACGGTGCGGGCTGCGAGATCGGTACCAAACCG
AGGCAAACTCTGAATACTAGGTATGAGCCCCGAGTAACACGGGGGCTGAGGGTCAGCCAGTGAGACGGTGGGGA
TAAGCTTCACCGTCGAGAGGGGAACAGCCCGGATCACCAGCTAAGGCCCCTAAATGACCGCTCAGTGGTAAAGGA
GGTAGGAGTGCAAAGACAGCCGGGAGGTTTGCCCAGAAGCAGCCACCCTTGAAAGAGTGCGTAATAGCTCACTGA
TCAAGCGCTCCTGCGCCGAGGATGAACGGGACTAAGCGGTCTGCCGAAGCTGTGGGA

> SEQ ID NO:209 130964 8025_300286_1b

AATTCGGCACGAGACCCTTGAAAGAGTGCGTAATAGCTCACTGATCGAGCGCTCTTGCGCCGAAGATGAACGGGG
CTAAGCGATCTGCCGAAGCTGTGGGATGTCAAAATGCATCGGTAGGGGAGCGTTCCGCCTTAGGGGGAAGCAACC
GCGCGAGCGGCGGTGGACGAAGCGGAAGCGAGAATGTCGGCTTGAGTAACGCAAACATTGGTGAGAATCCAATGC
CCCGAAAACCCAAGGGTTCCTCCGCAAGGTTCGTCCACGGAGGGTGAGTCAGGGCCTA

> SEQ ID NO:210 130964 283754_200074_1b

CGGACGCGTGGGGCCAGGGCTCTGACCGCGTGCCTGTTGAAGAATGAGCCGGCGACTCATAGGCAGTGGCTTGGT
TAAGGGAACCCACCGGAGCCGTAGCGAAAGCGAGTCTTCATAGGGCAATTGTCACTGCTTATGGACCCGAACCTG
GGTGATCTATCCATGACCAGGATGAAGCTTGGGTGAAACTAAGTGGAGGTCCGAACCGACTGATGTTGAAGAATC
AGCGGATGAGTTGTGGTTAGGGGTGAAATGCCACTCGAACCCAGAGCTAGCTGGTTCTCCCCGAAATGCGTTGAG
GCGCAGCAGTTGACTGGACATCTAGGGGTAAAGCACTGTTTCGGTGCGGGCCGCGAGAGCGGTACCAAATCGAGG
CAAACTCTGAATACTAGATATGACCTCAAAATAACAGGGGTCAAGGTCGGCTAGTGAGACGATGGGGGATAAGCT
TCATCGTCGAGAGGGAAACAGCCCGGATCACCAGCTAAGGCCCCTAAATGATCGCTCAGTGATAAAGGAGGTAGG
GGTGCAGAGACAGCCAGGAGGTTTGCCTAGAAGCAGCCACCCTTGAAAGAGTGCGTAATAGCTCACTGATCGACC
GCTCTTGCGCCGAAGATGAACGGGGCTAAGCGATCTGCCGAAGCTGTGGGATGTAAAAATACATCGGTAGGGGAG
CGTTCCGCCTTAGAGAGAAGCCTCCGCGCGAGCGGTGGTGGACGAAGCGGAAGCGAGAATGTCGGCTTGAGTAAC
GCAAACATTGGTGAGAATCCAATGCCCCGAAAACCTAAGGGTTCCTCCGCAAGGTTCGTCCACGGAGGGTGAGTC
AGGGCCTAAGATCAGGCCGAAAGGCGTAGTCGATGGACAACAGGTGAATATTCCTGTACTGCCCCTTGTTGGTCC
CGAGGGACGGAGGAGGCTAGGTTAGCCGAAAGATGGTTATCGGTTCAAGAACGTGAGGTGTCCCTGCTTTGTCAG
GGTAAGAAGGGGTAGAGAAAATGCCTCGAGCCAATGTTCGAATACCAGGCGCTACGGCGCTGAAGTAACCCATGC
CATACTCCCAGGAAAAGCTCGAACGACTTTGAGCAAGAGGGTACCTGTACCCGAAACCGACACAGGTGGGTAGGT
AGAGAATACCTAGGGGCGCGAGACAACTCTCTCTAAGGAACTCGGCAAAATAGCCCCGTAACTTCGGGAGAAGGG
GTGCCTCCTCACAAAGGGGGTCGCAGTGACCAGGCCCGGCCGTAATGGCC

> SEQ ID NO:211 130964 174840_300527_1b

CCCACGCGTCCGCCCACGGGTCCGGAGGTCCGAACCGACTGATGTTGAAGAATCAGCGGATGAGTTGTGGTTAGG
GGTGAAATGCCACTCGAACCCAGAGCTAGCTGGTTCTCCCCGAAATGCGTTGAGGCGCAGCAGTTGACTGGACAT
CTAGGGGTAAAGCACTGTTTCGGTGCGGGCTGCGCGAGCGGTACCAAATCGAGGCAAACTCTGAATACTAGATAT
GACCCAAAAATAACAGGGGTCAAGGTCGGCCAGTGAGACGATGGGGGATAAGCTTCATCGTCGAGAGGGAAACAG
CCCGGATCACCAGCTAAGGCCCCTAAATGACCGCTCAGTGATAAAGGAGGTGGGGGTGCAAAGACAGCCAGGAGG
TTTGCCTAGAAGCAGCCACCCTTTAAAGAGTGCGTAATAGCTCACTGATCGAGCGCCCCTTGCGCTGAAGATGAAC
GGGGCTAAGCGATCTGCCGAAGCTGTGGGATGTCAAAATGCATCGGTAGGGGAGCGTTCCGCCTTAGAGGGAAGC
AACCGCGAAAGCGGGGGTCGACGAAGCGGAAGCGAGAATGTCGGCTTGAGTAACGAAA

> SEQ ID NO:212 130994 103518_300363_1b

TGTATGGCGCAGAGTGGCCATTCGGCCGGGGGAAGCCAAGTTTGGGAAAATCTTAAAAGAAAGAAAGAAATGATG
ACGAATCGCCACTTCCTCTTCGCTCTTCTTTTCACTTTCTTTCTTTCAGCTGTTGCTGCAGATTCTTCTGAAGAG
TGTGTATACACATTGTATGTTAAAACTGGATCAATCATAAAGGGTGGAACAGACTCCAAAATCAGCGTTACACTT
GGCGATGCTAAAGGAAAATCAGTATATATTCCAGATCTAGAGAAATGGGGTTTAATGGGCCCAAATTATGATTAC
TACGAAAGGGGTAATGTGGATATCTTCACTGGTAGAGGCCAATGTTTAAGCCCACCAATTTGCAGGCTTAATGTT
ACTTCCGATGGATCAGGTGACCACCACGGTTGGTTTCTTGATTTTGTTGAGACTACTTTTACTGGGCCACACAAA
ACTTGTAGCCAATCCATATTCTATGTCGAACAATGGTTGGCTTCTGATGCTCCTCCTTATGAGTTATCAGTTTCT
CTTGATGGTTGTAAAAAGAAGACTGGGCTTCGACATGCTCGGCGTTTTGTCGTGGGCCAGCCCAATGGGTCTGCT
TCAGAATAGTTTGGCCCGTTGAAGTTCTTTTTGTAATTTTGTCGTTGAGATGATTTTGATGTGTAGATTGCCCTG
TGTTTTCCCTTCTCTTTGGTTGAAATAAATTTCTTGTTTGGGGCTTCCTTTCTTGCTTGTTTAGTCGTCATATCT
TTGACTTATTGGCTCTTTTGGCAATTTGCAATCTTTTATGTACTCAATAAG

Figure 2 continued

> SEQ ID NO:213 130994 279714_200064_1b
GAGAGGAAGAAAAAGCTCAAGAGAAGACATGGGAATAGCAGCTCACTCCAACCATTTCTGGTCCCTTCTCTTCAT
AGTCTTTTTCTCTTTCTCCATCTCCTCCATTTCCGGATCTGATGATGATTGCGTGTACACAGCTTACGTCCGAAC
GAGTTCAATAATAAAGGGTGGAACAGATTCGATTATCAGTTTGACTCTCTACGATGCAAACGGGTATGGTCTTAG
AATCAAGAACCTTGAGGCCTGGGGTGGGCTTATGGGTCCTGGTTACAACTATTTCGAGAGGGGAAATTTGGACAT
TTTCAGCGGACGAGGCCCATGTTTGACTGGGCCTGTCTGCAAGATGAACCTCACTTCCGACGGAACAGGCAAAGG
CCATGGATGGTACTGTAACTACGTGGAGGTCACCGTCACCGGAGTCCATAAAGCATGCAACCAACAGAATTTCGA
AGTGGAGCAGTGGCTCGCTACTGATGCGCCGCCTTATGAGCTTACGGCTGTTAGAGACAACTGTAAGAAGTCCAA
GTCCGATGAGAAACTGTCCATTTCCGATGTCTACGGAACTCATCCCACTCCACATGTTTCTGTGATTTAAGTTTC
TAGTTATTGGGCTTTAATGGGCCTGGGCCAACATTTCCCTGTTTTACAATGACATTTGGTGTGTGCCAATGTTGC
TTTCATGTTTATAGTAT

> SEQ ID NO:214 130994 171733_300536_1b
CCCCGATCTCCACCACCACTTTCCCGGGGACCGCGGCGGGAAAGGGCCTTCGAGACTTGGGAGGTTGGAGCGAGC
AAGCTCGGCCATGGCGAAGCTCTCCTGCCTTCTCATCGTCTCCTTCGCCGTCGTCGCGGCGTTGGCGGCCACGGA
CGACGACGCGGCGGCGGCGGCTGAGGGGATCACGGTGGCGGAGGCGTCGTCGGACCCGGAGAACAAGTGCGTGTA
CACGATATACGTGCGGACGGGGACGATCTGGAAGGGCGGGACGGACTCGGTGATCGGCGTGACGCTGCTGGGCGC
CGACGGCTCCGGGGTGCGGATCCGCGACCTGGAGCGGTGGGGCGGCCTCATGGGCGACGGCCACGACTACTACGA
GCGCGGCAACCTCGACATCTTCAGCGGCCTCGGCCCCTGCATGCGCCAGGCGCCGTGCCGGATGAACCTCACCTC
CGACGGCACCGGCCCGCACCACGGCTGGTACTGCAACTACCTCGAGGCCACCGTCACGGGTCCCCACCTCGGCTG
CGCGCAGCAGCTCTTCACCGTCGAGCAGTGGCTCGCCACCGACGCATCGCCCTACCGCCTCTACGCCGTCGTCGA
CAACTGCAACAAGGCCAAGGACGCCGCCG

> SEQ ID NO:215 130994 157312_301737_1b
TTTGCCTTTATTCGTTCTCATTTTTCTAGAGAAAGAGAGTTCAAGAAACCATGGGAGTAGCTCAAGTTAACCAAA
TATGGTTCCATTTCATGATAATCCTCTTCTTCATCTCCATATCTTCTAGTTCTGCATCAGAAGATGATTGTGTGT
ACACAGCTTACGTTCGAACTGGATCAATCATAAAGGCTGGAACTGACTCAAACATTAGTTTGACTCTCTACGATG
CCGCTGGCTATGGGATAAGAATCAAGAACTTAGAGGCATGGGGTGGGCTTATGGGCCCAGGTTACAACTATTTCG
AAAGAGGAAACTTGGATATATTCAGTGGACGTGGTCCATGTTTGACTGGGCCGATCTGCAAAATGAATCTGACTT
CTGATGGATCAGGCCCACATGCCGGATGGTACTGTAACTACGTCGAAGTTACCGTTACTGGAGCCCACCAACAAT
GCAACCAGCAGCTTTTCACCGTGGAGCAGTGGCTCGGCACTGACGTTTCGCCGTATGAGCTGACGGCCGTCAGGA
ACAACTGTAAGAAGCCAAAGTTTGAGAAACAACAGGCCTTTTATGATTCTGAATCTTATCCAGTTGTTGATGTAA
TTTAATGGGGGTAG

> SEQ ID NO:216 130994 147510_301253_1b
AGAGAGTTCAAGAAACCATGGGAGTAGCTCAAGTTAACCAAATATGGTTCCATTTCATGATCATCCTCTTTTTCA
TATCTTCTATTTCGGCATCTGAAGATGATTGTGTGTACACAGCTTACGTTCGAACTGGATCAATCATAAAGGCTG
GAACTGACTCAAACATTAGTTTGACTCTCTACGATGCCGATGGCTATGGGATAAGAATCAAGAACTTAGAGGCAT
GGGGTGGGCTTATGGGCCCAGGTTACAACTATTTTGAAAGAGGAAACTTGGATATATTCAGTGGACGTGGTCCAT
GTTTGAATGGGCCGATCTGCAAAATGAATCTGACATCTGATGGATCGGGCCCACATGCCGGATGGTACTGTAACT
ACGTCGAAGTTACAGTTACTGGAGCCCACCAACAATGCAACCAGCAGCTTTTCACCGTGGAGCAGTGGCTCGGCA
CTAACGTTTCGCCATATGAGCTGACGGCCGTCAGGAACAACTGTAAGAAGTCCAAGTCCACAGTTTATGATTCTG
AATCTTATCCAGTTGTTGATGTAATTTAATGGGGGCAGCCCCACATATTGTCTCTGTGGTTTTTTCTTTAGAGTG
AGAAGAATTAACGTGATGC

> SEQ ID NO:217 130994 128348_300475_1b
CGACCATCTCAAAATCACTTGCTTTTTTCGTCTCATTTTCTAGAGAAAGAAACAACAAGACGTACAGAACGAGAG
TTCAAGAATCTGCAATGGGAGTGGCTCGAGTTAACCAATTCTGGTTGCATCTTCTCATCCTCTTCTCCATCTCCG
TTTCTTCCATTTCTGGCACTGAACTGAATTGTGTATACACAGCTTATGTTCGGACTGGGACATACTGGGGATCTG
GAACTGACTCAAAAATTTCCTTGTCTCTTTATGATGCCACTGGCCATGGACTTAGAATCAATAACCTACAAGCCT
GGGGCGGGCTTATGGGCCCGGGTTATGACTACTTTGAAATGGACCAATTGGATATGTTTACGGGCCGTGGTCCAT
GTTTGACTGGGCCAATCTGTAAAATGAACTTGACTTCTGATGGATCAGGTGAGCACCACGGATGGTACTGTAACT
ACGGGGAAATCACGTCTACAGCAGAACACAAACGATGCAGCCAACAGGCGTTCACCGTGGAGGCGTGGCTCAGTG
CCGGTCAGTACCCAGATGGGTTGACCGCCATTAAGGAACAACTGTAAGCGTATTTCCAACGAACAACAACCAATT
CATGATTCTGATCAATCTTATCATGTTGTGGATGTAATTTAATTCGAGTTTATTGGACGTTGTATGATTTACGAA
GGCCATTTAGGCCAAGGCCTGATATGTACTCTCACGAGTGCTACATAGTTGGAATGGAAAAGTTTTCTTTACCCA

Figure 2 continued

> SEQ ID NO:218 130994 11941_300283_1b

TGGTATCAACGCAAAGTGGCCTTACGGCCGGGGAAAGATAAAGAGAGTAACAGAGAAAGCTCAAGAGAAGACATG
GGAATAGCAGCTCACTTCAACCATTTCTGGTTCCTTCTCTTCATCCTCTTCTTCTCTTTCTCCATCTCCTTCATT
TCCGCATCCGATGATGATTGCGTGTACACAGCTTATGTCCGAACGAGTTCAATAATAAAGGGTGGAACAGATTCG
ATTATCAGTTTGAGTCTCTACGATGCAAACGGGTATGGTATTAGAATCAAGAACCTTGAGGCCTGGGGTGGGCTT
ATGGGTCCTGGTTACAACTATTTCGAGAGGGGAAATTTGGACATTTTCAGTGGACGAGGCCCATGTTTGACTGAG
CCAGTCTGCAAAATGAATTTGACTTCCGACGGAACAGGCAAA

> SEQ ID NO:219 130994 1108676_301519_1b

GTCATCACACAAGTGAAGAAGCAGTAGCAGTAGAAGGAGATAGAAGGGAACCTCTCTCTCTCTCTCTCTCTCTTT
GCTGATGATGAAGACGACTATGGCTGTTTTCGCCCTTCTCTCTCTCTTCCTTCTTCTCCTCCCCCCTTTTCCTTC
ATCAGCTGATGATCCTTGTGTATACTCAATCTATGTACGAACGGGGTCAATATTCAAGGGGGGAACGGATTCGAA
GATGAGTGTGGAGCTCTACGATGCGAATGGGTACTACATTACGATCAACAATTTGGAGGAGTGGGGGGGTTAAT
GGGTCCAGACCACGACTACTATGAGAGGGGCAATCTTGACATCTTTAGTGGTTTGGGGGACTGCCTGACCGGACC
CATCTGCGCTCTCAACCTCACCTCGGACGGCACGGGGGCCCACCATGGGTGGTATTGCAACTACCTGGAAGTTAC
TGCCACGGGTGCCCACATCCCTTGCTCCCAACAGCTCTTTACCATAGAGCAATGGCTTGCCACTGATACCTCTCC
TTACTCCCTCACTGCCCTTCGATATAATTGCCCTGATGCTTTGTCCTCGCCTCGCTTCCCTCGCATGCCTTCCAA
TTCGCAACCGAAGAATGGTCAACTAATGTCCCATTAGTACTCTATCACCCTGCTTCGTAATAAAAAGATAGCCCC
TTCTTGTGTACTATGGAGGGAGGGGGGTATCTCTCTCA

> SEQ ID NO:220 131002 130222_300486_1b

GAATTCCAAGACTTCATTGGGATTGTGAAGCCAGATCGATACTACTTTTTATTGTAGTTGGGTTATCTGATCCTA
CATCTTCTATCGTTAGGAGTACAATTGTTTCTGATCGGCTCGAGAACCTGATTCTCCGATAGGTAGGATAAACGT
GTTCACGGACATCTTCGTCTCACTGTTCGTGAATCCTTGATATTCTCTTTGTGTATTCAAAGATCGAGTATTGAG
AGGTGATTGATTAATCTAGACTGCTCTTCGGGAATATAAGACCGGATTAATCAATTGGTTTCTTGAATATACCTT
GATAGATTTTATCAAAAAACAGAAAAAAAGTTAGGGTTTATCTGTGGGAGACAGATTAATCCTTTGATAGACTTG
TCTGTGTGAGACAAATTTGTTTATTGGCAAAGCCTGCGATTTTGGGTCGTAGCAACTCTTTGTTGTGGGTCAGAT
CAGCAAAGAGAATCAAGTGCGTAGTATCCTGCTGGGATCAGAGGCGTAGGGGTGCAATTGTACCTTGTATCAGTG
GGAGACTGGTAGGGGTTCAATTATAGATCAGTCCGAAGTTAGTTTAGAGTAGGCTAGTGTCTGTAGCGGCTTAAT
ACAGTGTGTATCTAACATGGACTATGTC

> SEQ ID NO:221 131002 168111_300553_1b

GAATTCGTTCTCAAATAGAGAGATAGAGATGTGAACTCCTTGAGTCACTATATTCTAGATTTATCTAGTAGAGTG
ATTCGGAGGTTGTCCTTATCATATTGCTAATCGAAAAGTTTGGTGGTGTTGTTAGACCCCCGCTTTTTCAATTGG
TATCAGAGCAGGCAAACACTTAAAGACCTAATCAGTCTGTGTTTGTTGCAATCTGATTGTATGGACTGTGCTATC
TCCAAGAACGCCATACCAGTTAAAGGTCATTCGATGGAGGGAAATCATCCATGGAGAATAACTCCAACACATGT
TCTTCGCCCGTGTCTTCACATGACTGGGATAAATCACTTGATGAGCAGCTTGATGAACTCTCAGATGACAGTGAT
TCAGAAGAAGGACCAAATGTTGATGAGGAAGTCTCAGAATATATTTTGATGATTAATCGTGACCTAAAAGAAACA
AGGTCCTCCTCATGCATACGGAAGCATTTGGGACCACTTTGTCGAGAAAACAGAAAGTTGAGAAAACTCTTTAAT
GGGTATGACAGTGGTTATAAATTATTGCAAGCCACTGTTAAAGATCACAAAGAAGATGTTCTTCTAAAAGGAACC
GAGTGTGATAATCTTCTTC

> SEQ ID NO:222 131048 1110411_301789_1b

AAGACTCCTAAACTACAATACTATTAAATGATGGCAAACAGACATTCAATGATAAAGTAAGGATCAAAAATCTTA
AATCAAGACTACACTGAAAAATCCTGGTTTTACTATTCTATATGTCCAAAACTTTCAAAGAAAAATGAACACGTC
CCGTGGCTTCTTCAGCCTACTGCTGCTCATCGCCCTCAATGACTCCTCTCTCACTCACGTAGATGCCATCCAAAA
ACTTTCTGATATCCTTCTTTTTGACAAGGCATTTCTGGTTTATAAGAGCACATGAACGAGAGACGAGTTCGATGT
CATTCCCCTCCAGGACCAGCTCATCCTTTACTTTCTCAGACCGGGTAATTGTCACACCAGGAAGCATTTCTACTT
TCCGTACCCGCTTTTCTCCGAGAAAGTTTCGGATTTCGATGCAATCATTGCCTCCGGAGATGCTAGCATTGATGG
GGAAATGGGCA

> SEQ ID NO:223 131048 1112794_301793_1b

GAGAGAGAGAGGGGAGAGGGTAGGAGAGAGAGGTAGCAGGGTTAGGGGGGGCCAGCAGCAGGCAGAGGAGGATAG
AGAGAGAGAGAGGCAAGCAGCGATGAAGACGATCTTGGCCTCGCAGACGTTCGAGGTGCCGGAGGGTGTTTCCCT
CGAGATCAAGGCGAAGCAGATCCGGGTCAAGGGGCCCCGCGGTACCCTCACCCGTGACTTCAAGCACCTTAACCT
TGACTTCCAGCTCCAGGAGGGTGGCCGTAAGGTCAAGGTCGACGCCTGGTTCGGCTCGCGTAAGACCATGGCCGC
CATCCGCACCGCTATCTCCCACATTGGTAACCTCATCGGTGGTGTCACCAAGGGCTACCGTTACAAGATGCGGCT
TGTCTACGCTCATTTCCCCATCAATGCCAGCATCTCCGGAGTCAACGATTGCATTGAAATCCGAAACTTTCTCGG

Figure 2 continued

AGAAAAGCGGGTTCGGAAAGTAGAGATGCTTCCAGGTGTGACAATAACCCGGTCTGAGAAAGTCAAGGATGAGCT
AGTCCTTGAGGGAAACGATATTGAGCTTGTCTCTCGTTCGTGTGCTCTCATTAACCAGAAATGTCATGTTAAGAA
GAAGGACATCAGGAAGTTTCTGGATGGTATTTATGTGAGCGAGCGAGGTGTCATTGAGGGTGATGACCAGCAGTA
GTCTTGATTCAAGTTTTTTGATCCTTATTTTCTCATTTGCAATGTCTGTTTGCAATCATTTAGTAGTTAGTAGTT
TAGGAGTATTAAAACTAAAAGGGGTTCCTTGCCATAGTTGTTGTTACTATTCATTCAAAGGTGTCACAATGAGGA
AGTTTTAATGAT

> SEQ ID NO:224 131048 48461_300376_1b
GCTGCTAGGGTTTTAGCGATCGCCATTTTCACACACACAGAAGGAGAGCGGAAGAGAGAAACTAAGACAAGATGA
AGACCATTCTGTCATCAGAAACCATGGATATCCCCGACGGCGTGAGCATCAAGGTGAAGGCAAAGCAAATCGAAG
TAGAGGGACCAAGGGGCAAACTTGTCCGAAACTTCAAGCATCTCAACCTCGATTTTCAGCTGATCAAGGATGAGG
AAACTGGCAAGAAGAAACTGAAGATCGACGCTTGGTTTGGTTCTCGTAAGACTACCGCTGCTATCCGTACTGCTC
TTAGCCATGTTGAGAATCTCATCACTGGTGTTACGAAAGGTTACCGCTACAAGATGCGTTTCGTGTATGCTCACT
TTCCCATCAATGCCTCCATCACCGGTGGTAACAAGTCCATTGAGATCCGTAACTTCCTTGGCGAGAAGAGAGTTA
GGAAAGTGGACATGCTTGATGGGGTTACAGTTGTTCGATCTGAGAAGGTGAAGGATGAGCTTGTATTGGATGGAA
ATGACATTGAGCTCGTTTCTCGCTCTGCTGCCCTCATCAATCAAAAAATGCCATGTGAAGAACAAGGATATCCGAA
AGTTTCTTGATGGTATCTATGTCAGTGAGAAGGGCAGAATTGCAGAAGAAGAATGAGCAGCTGTTTTAGAAGTAG
GCATATCACTGATGATTCATATCCAGAATGCCCTTTTTACTTTTC

> SEQ ID NO:225 131048 47179_300174_1b
GGAGAGCAAAACAAAGATCGGAGAAGATGAAGACGATTCTTTCTTCCGAAACGATGGACATCCCCGACAGTGTTA
CCATCAAGGTTCACGCTAAAGTGATCGAAGTCGAAGGACCTCGCGGGAAGCTTGTTCGCGATTTCAAGCATCTCA
ACCTCGATTTCCAGCTGATCAAGGATCCAGAGACTGGAAAGAAGAAGCTTAAGATCGATTCGTGGTTTGGAACAC
GCAAAACCAGCGCCTCCATCAGAACCGCTCTTAGCCACGTCGATAACTTGATCTCCGGTGTTACCAGAGGTTTCC
GTTACAAGATGAGGTTCGTGTACGCCCATTTTCCCATCAACGCCTCCATCGGCGGTGACGGAAAGTCTATCGAGA
TCCGTAAC

> SEQ ID NO:226 131048 237440_301287_1b
GGGTGCGAGGAGGAGGAGGCGGGCGCGATGAAGACGATCTTGTCGGCCCAGACGATGGACATCCCCGAGGGGGTG
AAGGTAGAGATCCGGGCGAAGCAGATCCGGGTGACGGGGCCGCGGGGGGTGCTGCACAGGAATTTCAAGCACCTC
AACCTCGACTTCCAGCTGCTGGAGAATGGGCGCAAGCTCAAGGTGGAGGCGTGGTTTGGGTCGCGCAAGACCATC
GCCGCCATCCGCACCGCCGTGAGCCACGTGAAGAACCTCATCACCGGCGTCACCAAGGGCTTCCAGTACAAGATG
AGGTTTGTCTACGCTCACTTCCCCATCAACGCCAACATCTCTGCCACCAAGCAAAACATCGAGATCCGGAACTTC
CTCGGCGAGAAGAGGGTGAGAACTGTCGACATGCTTCCGGGTGTGACTGTGACCAGGACGGAGAAGGTCAAGGAC
GAGCTTGTTCTCGAGGGGAATGACATCGAGCTTGTGTCGAGATCGGCCGCTCTGATCAACCAGGTGAGCTCATCA
GAGTGGAAGATTCATGTGTCTAATATGTGTCTGTTTCTCTTGTGTGTGTAGAAATGCCATGTCAAGAACAAGGAT
ATCAGGAAGTTCTTGGATGGTATCTACGTGAGCGAGAAGGGAACGATCGCTGTGGAGGAGTAGACCTTTTGCCTG
TTCTGAGTATAATTTTGTGCTTTGCTTGTCTGAAATCAATCAAACACCAACTCTTTTGGAAATTTT

> SEQ ID NO:227 131048 195865_300638_1b
CCCACGCGTCCGGCCCCGACAACCCCCAAGTCACAGCAGCCATGAGGTACATTCACTCTCAGGAGATCCTGGAAA
TTCCAGAGGGCGTCAAGGTCAACATCAAGACCCGTATCGTCACCGTTGAGGGTCCCCGAGGCAAGCTCACCAAGA
ACCTCGGTCACTTGGCTGTCAACTTCGGTCACCCCAAGAAGAACACCATCTCCATCGAGATCCACCACGGCAACC
GTAAGAATGTCGCCACTCTCCGTACCGTCCGCTCCATCATCGAGAACTTGATCACCGGTGTCACCAAGGGCTTCA
AGTACAAGATGCGATACGTCTACGCCCATTTTCCCATCAACGTCAACCTGGACAAGAACAAGGAGACCGGTCTGT
TCGAGGTGGAGATCCGAAACTTCATCGGCGAGAAGATCGTCCGACGGGTTACCATGCACGAGGGTGTCGATGTTG
AGATCTCCAAGGCCCAGAAGGATGAGCTCATCCTGACCGGCAACTCACTCGAGAACGTTTCCCAGAGCGCCGCAG
ATATCCAGCAGATCTGCCGGGTGCGCAACAAGGATATCCGAAAGTTCTTGGACGGTCTGTACGTTTCCGAGAAGG
GCAACGTTGTTGAGGAGGCTTAAATGTACCGGACAAGGATCTCTGTTTCTTTTGCG

> SEQ ID NO:228 131133 103534_300363_1b
TGGTATGAACGCAGAGTGGCCATTACGGCCGGGGACAGCTATTTTCTCTATTACTTCAGCCATCAAAAAACACTT
ATTTCTCCTTATTAAACCATGGCTGCTTCTACAATGGCTCTCTCTTCCTCTTCTTTTGCCGGAAAGGCAGTAAAA
CTATTACCGTCTTCCTCTGAAATCACCGGAAATGGGAAAGTTACCATGAGGAAGACTGCTAGCAAGCCCAAGCCT
GTCTCTTCTGGCAGTCCATGGTATGGCCCTGACCGTGTCAAGTACTTGGGCCCATTCTCTGGTGAGTCCCCAAGC
TACTTGACTGGTGAGTTCCCTGGTGACTACGGGTGGGACACTGCTGGACTTTCAGCTGATCCAGAAACTTTTGCC
AAGAACCGTGAGTTGGAGGTGATCCACTGCAGATGGGCAATGCTTGGAGCTCTTGGTTGTGTCTTCCCCGAGCTC
TTGGCCCGTAACGGTGTCAAGTTTGGTGAGGCTGTATGGTTCAAGGCTGGATCCCAAATTTTTAGCGAGGGTGGA

Figure 2 continued

CTTGACTACTTGGGCAACCCAAGTTTGGTCCATGCTCAAAGCATCTTGGCCATTTGGGCTTGTCAAGTTGTGTTG
ATGGGAGCCGTTGAGGGTTACCGTGTTGCTGGTGGGCCTCTTGGGGAGGTTGTTGATCCACTCTACCCCGGTGGC
AGCTTCGACCCATTGGGCCTCGCTGAAGACCCAGAAGCTTTTGCTGAGCTCAAGGTAAAAGAGATCAAAAATGGT
AGACTTGCCATGTTCTCCATGTTTGGATTCTTTGTTCAGGCTATCGTAACTGGAAAGGGCCCATTGGAGAACCTT
GCCGATCACCTTGCAGACCCAGTTAATAACAACGCTTGGGCCTACGCAACAAACTTTGTCCC

> SEQ ID NO:229 131133 103543_300363_1b
TGGTATCAACGCAGAGTGGCCATTACGGCCGGGGATCACAACTAACTTTGACATCTCAAACTAGCAACCTCTCAC
TTTCCTCTTGATAAACCATGGCTGCTTCTACAATGGCTCTTTCTTCCCCTTCTTTCGCTGGACAGGCAGTGAAAC
TCTCCCCATCTGCCTCAGAAATCACTGGAAATGGAAGGGTCTCCATGAGAAAGACTGTCGCCAAACCCGTCGCAT
CTAGCAGCCCATGGTACGGTCCAGACCGTGTTAAGTACTTGGGCCCATTCTCCGGTGAGGCCCCAAGCTACTTGA
CCGGTGAATTCCCAGGTGATTACGGGTGGGATACTGCTGGACTTTCAGCAGATCCAGAAACATTTGCCAAGAACC
GTGAACTCGAGGTGATCCACTGCAGGTGGGCTATGCTTGGAGCTCTTGGATGTGTCTTCCCTGAGCTCTTGGCTC
GTAACGGTGTCAAGTTTGGTGAAGCTGTCTGGTTCAAAGCTGGATCACAAATCTTTAGTGAGGGTGGACTTGACT
ACTTGGGCAACCCAAGCTTGGTCCATGCACAAAGCATCTTGGCAATCTGGGCTTGCCAAGTTATCTTGATGGGAG
CTGTTGAGGGTTACCGTGTTGCTGGTGGGCCCCTTGGTGAGGTTGTCGACCCACTCTACCCTGGTGGCAGCTTTG
ACCCATTAGGCCTTGCTGATGACCCAGAGGCATTTGCTGAGCTCAAGGTAAAGGAGATCAAGAATGGGAGACTTG
CCATGTTTTCTATGTTCGGATTCTTTGTTCAGGCCATTGTTACCGGAAAAGGTCCATTGGAGAACCTTGCTGACC
ATCTTGCTGACCCAGTTAACAACAACGCCTGGTCCTACGCCACAAACTTTGTCCCCGGAAAATGAATATTGTAAA
AAAATC

> SEQ ID NO:230 131133 11655_300291_1b
TGGTATCAACGCTTAGTGGCCATTACGGCCGGGGACCATTGTCTGAGCAAACTCCATCATACCTCACTGGTGAGT
TTCCGGGTGATTACGGGTGGGACACTGCTGGACTCTCAGCTGACCCAGAAACATTCGCAAGAAACCGTGAACTTG
AAGTGATCCATTGTCGTTGGGCCATGCTTGGTGCTTTGGGTTGTGTCTTCCCTGAAATCCTTTCAAAGAACGGTG
TTCAATTCGGTGAAGCAGTTTGGTTCAAGGCAGGAGCCCAAATCTTTTCAGAAGGTGGACTCGACTACCTTGGCA
ACCCAAACCTCGTGCATGCCCAGAGCATCCTCGCCATTTGGGCTTGCCAAGTTGTCCTAATGGGCTTGATTGAAG
GATACAGAGTTGGTGGAGGCCCACTTGGT

> SEQ ID NO:231 131133 112407_300002_1b
AGGACTTTGGTCCTACCTAGTTATTTATATACAGTTGCTGCAAGGCCATTAAACTCAAGCCATAAATCAAATATT
CTTTCTGTGTAGTAGCTGCATTTTCAAGAGCATTTCACTTTATTTCTGCAACAATGGCAGCTTCTACAATGGCTC
TCTCTTCCTCTTCTTTTGCCGGAAAGGCGCTGAAACTCTCACCATCTTCCTCTGAGATCACCGGAAATGGAAAAG
TCACCATGAGGAAGACAGTTACCAAGGCGAAGCCAGTCTCTTCTGGCAGCCCATGGTATGGTCCTGATCGCGTCA
AGTATTTGGGCCCATTCTCTGGTGAGTCTCCAAGCTACTTGACTGGTGAGTTCCCTGGTGACTACGGATGGGATA
CTGCTGGACTTTCAGCTGATCCAGAAACTTTTGCTAAGAACCGTGAGCTAGAGGTGATCCACTGTAGATGGGCCA
TGCTTGGAGCTCTTGGTTGTGTCTTCCCCGAGCTCTTGGCCCGTAATGGTGTCAAATTCGGTGAGGCTGTATGGT
TCAAGGCTGGATCCCAGATTTTTAGCGATGGTGGACTTGACTACTTGGGCAACCCAAGTTTGGTCCATGCACAAA
GTATCTTGGCCATTTGGGCTTGCCAAGTCGTGTTGATGGGAGCTGTTGAGGGTTACCGTGTTGCTGGTGGGCCTC
TTGGTGAGGTTGTCGACCCACTCTATCCTGGTGGTAGCTTTGACCCATTAGGTCTTGCTGATGATCCAGAGGCTT
TTGCTGAGCTCAAGGTGAAGGAGATCAAGAACGGTAGACTTGCCATGTTCTCAATGTTTGGATTCTTCG

> SEQ ID NO:232 131133 130767_300490_1b
GAATTCAGGGGCAGTGAAAGTGACACCATGCGTTCAAGAGGGTGATGGAAGAATCACCATGCTCTTCCAGAAAAA
GACAGTGGCAAAGCCTACTAAATCTTCAAAACCCGCAGTTTCATCTAACAGCCCATGGTACGGTCCCGACAGAGT
TAAGTACTTGGGTCCCTTCAATGGCTGCTTCAACAATGGCTCTCTCATCTCCTTCTCTTGCTGGAAAGGCAGTGA
AAGTGACACCATGCGTTCAAGAGGGTGATGGAAGAATCACCATGCTCTTCCAGAAAAAGACAGTGGCAAAGCCTA
CTAAATCTTCAAAACCCGCAGTTTCATCTAACAGCCCATGGTACGGTCCCGACAGAGTTAAGTACTTGGGTCCCT
TCTCAGGCGAGGCTCCATCGTATCTTAATGGTGAATTCCCAGGTGATTATGGCCGGGACACTGCCGGGTTTTCTG
CAGATCCAGAAACTTTCGCCAAAAACCGTGAACTTGAAGTGATTCATTGCAGATGGGCTATGCTTGGAGCTCTAG
GATGCATCTTCCCTGAATTGCTCTCACGCAATGGAGTTAAATTCGGTGAAGCCGTTTGGTTCAAAGCCGGAGCAC
AGATTTTCAGCGAGGGTGGATTGGACTACTTGGGTAACTCAAGCTTAGTACATGCTCAAAGCATTTTAGCTATTT
GGGCGACACAAGTTATCTTGATGGGTGCAGTTGAAGGTTACCGTGTTGCCGGTGGACCTCTTGGTGAG

> SEQ ID NO:233 131133 130252_300486_1b
GAATTCAATGGCTGCTTCAACAATGGCTCTCTCTTCTCCTTCTCTTGCTGGAAAGGCAGTGAAGCTAACTCCATC
CATTCCAGAAGGCGAAGGAAGAATTACCATGCTCTTCCAGAAAAAGACACCGGCAAAAGCAGCTAAATCATCCAA
ACCCGCAGTTTCATCTAACAGCCCATGGTATGGTCCTGACAGAGTTAAGTACTTGGGACCTTTCTCCGGTGAGGC

Figure 2 continued

ACCATCATATCTCAATGGTGAATTTCCTGGTGACTATGGTTGGGATACCGCTGGGTTATCTGCTGATCCTGAAAC
TTTCGCCAAGAACCGTGAGCTTGAAGTGATCCATTGCAGATGGGCTATGCTCGGAGCTCTAGGATGCATCTTCCC
TGAATTGCTCTCGCGCAATGGAGTTAAATTCGGTGAAGCCGTTTGGTTCAAAGCCGGAGCACAGATTTTCAGCGA
GGGAGGATTGGACTACTTAGGTAACTCAAGCTTAGTACATGCTCAAAGCATTTTAGCTATTTGGGCGACACAAGT
TATCCTGATGGGTGCAGTGGAAGGTTACCGTGTCGCCGGTGGACCTCTTGGTGAGATTGTCGACCCACTGTACCC
CGGTGGCAGCTTCGACCCTCTTGGACTTGCTGATGACCC

> SEQ ID NO:234 131133 129795_300481_1b
GAATTCACTGCCGGGCTTTCTGCAGATCCAGGGACTTTCGCCAAAAACCATGAACTTGAAGTGATTCATTGCAGA
TGGGCTATGCTTGGAGCTCTAGGATGCATCTTCCCTTCAATGGCTGCTTCAACAATGGCTCTCTCATCTCCTTCT
CTTGCTGGAAAGGCAGTGAAAGTGATGGAAGAATCACCATGCTCTTCCAGAAAAAGACAGTGGCAAAGCCTACTA
AATCTTCAAAACCCGCAGTTTCATCTAACAGCCCATGGTACGGTCCCGACAGAGTTAAGTACTTGGGTCCCTTCT
CAGGCGAGGCTCCATCGTATCTTAATGGTGAATTCCCAGGTGATTATGGCCGGGACACTGCCGGGCTTTCTGCAG
ATCCAGAAACTTTCGCCAAAAACCGTGAACTTGAAGTGATTCATTGCAGATGGGCTATGCTTGGAGCTCTAGGAT
GCATCTTCCCTGAATTGCTCTCACGCAATGGAGTTAAATTCGGTGAAGCCGTTTGGTTCAAAGCCGGAGCACAGA
TTTTCAGCGAGGGAGGATTGGACTACTTGGGTAACTCAAGCTTAGTACATGCTCAAAGCATTTTAGCTATTTGGG
CGACACAAGTTATCTTGATGGGTGCAGTTG

> SEQ ID NO:235 131133 129760_300481_1b
GAATTCAACACAGTCTTTAGTTTTCTCATCCATCCATATATCAGTTAGCCATGGCAGCTTCTACAATGGCTCTAT
CTTCACCCGCATTGGCTGGTAAGGCACTTGTTCCTTCCAGCTCTGAAGTTTTCGGTGAAGGCAGAATCTCCATGA
GAAAAACCGTTGCAAAGCCAAAAACCGTTTCATCTAGCCCATGGTACGGACCTGACCGTGTTAAGTACTTGGGAC
CATTCTCTGGTGAATCTCCATCGTACTTAACCGGTGAGTTTGCCGGTGATTACGGTTGGGACACTGCCGGGCTTT
CTGCTGACCCAGAAACCTTCGCCAAGAACCGTGAGCTGGAGGTCATTCACTGCAGATGGGCTATGTTGGGAGCTC
TTGGATGTGTCTTCCCCGAATTGTTGTCTCGCAATGGTGTTAAATTTGGTGAAGCCGTTTGGTTCAAGGCTGGTT
CACAAATTTTCAGTGAAGGTGGATTGGACTACTTGGGTAACTCAAGCTTGGTTCATGCTCAGAGCATCCTTGCCA
TTTGGGCAACACAAGTTATCTTGATGGGAGCAGTTGAAGGTTACAGAGTTGCTGGAGGACCATTGGGTGAGGTGG
AGGACCCACTTTACCCTGGTGGAAGCTTCGACCCATTAGGCTTAGCTGATGATCCAGAAGCTTTTGCTGAATTAA
AGGTGAAGGAAATTAAGAACGGGAGATTGGCTATGTTCTCCATGTTTGGATTCTTTGTTCAAGCAATCGTGACCG
GGAAAGGTCCTTTGGAAAATTTGGCTGACCAC

> SEQ ID NO:236 131133 2044_300349_1b
AATTCGGCACGAGCTTCAATCTCCTTATTAAACAATGGCTGCTTCTACAATGGCTCTCTCCTCTTCTTTTGCCGG
AAAGGCAGTAAAACTCTCACCATCTTCCCCTGAAATCACCGGAAATGGAAAAGTTACCATGAGGAAGACTGCTAG
CAAGGCCAAGCCTGCCTCTTCTGGTAGCCCATGGTACGGTCCTGACCGCGTCAAGTACTTGGGCCCTTTCTCTGG
TGAGTCTCCAAGCTACTTGACTGGTGAGTTTCCTGGTGACTACGGATGGGACACTGCCGGACTTTCAGCTGATCC
AGAAACTTTTGCCAAGAACCGTGAGTTGGAGGTGATCCACTGCAGATGGGCCATGCTTGGAGCTCTTGGATGTGT
CT

> SEQ ID NO:237 131133 181296_300695_1b
GAATTCAACTACCATCTTCAGTTATCTTTCATTTTCAATACAAAAGATACATAAGAATGGCAACCATGGCTCTCT
CTTCTCCATCATTTGCAGGCAAAGCTGTGACTCTAAACCCTCAAACAGAATTCCCAACCAATGTAAGATCTGGCA
GCAACAGCAAGATCTCGATGAGGAAGACATCCGCAAAGAAGCCTGCAGCTTCTTCTGGAAGTCCATGGTATGGTC
CAGACCGAGTCAAGTACCTCGGTCCCTTCTCTGGTGAGTCTCCTTCTTACCTAACTGGTGAATTCGCTGGTGACT
ATGGCTGGGACACTGCTGGACTATCAGCTGATCCAGAGACCTTTGCCAAGAACCGCGAACTTGAGGTGATCCATT
CAAGGTGGGCGATGCTTGGCGCTTTGGGCTGTGTCTTCCCTGAACTCCTCTCGAGAAATGGAGTCAAATTCGGCG
AAGCAGTTTGGTTCAAAGCCGGCTCTCAGATATTCAGTGAAGGAGGACTTGACTATTTGGGAAATTCCAGCTTGG
TTCATGCACAGAGCATCCTGGCTATATGGGCCACTCAAGTCATCCTTATGGGCGCCGTCGAAGGCTACAGAGTTG
CTGGCGGTCCACTAGGTGAGGTTGTTGATCCCCTTTACCCAGGTGGAAGCTTCGATCCATTAGGCCTTGCAGAGG
ACCCAGAGGCATTTGCCGAGCTAAAGGTAAAAGAACTAAAGAACGGGCGACTTGCTATGTTCTCCATGTTTGGGT
TCTTCGTTCAGGCTATTGTGACGGGCAAAGGTCCTCTAGAGAACCTGGCAGACCACCTTGCCGACCCAGTGAACA
ACAATGCCTGGTCATATGCTACGAACTTCGCTCCCGGGAAGTGAGCATAAGCATAGCAAAGGCAAAATGGAGTTT
GATTTCCTACTTTTTTTCTGTAATATCCTCTGTACATTCATTTAGCTTGTAAAATTGTGTAGAATGTAGCTGCGG
TTGGTCT

> SEQ ID NO:238 131133 175615_300543_1b
CCCGAGCACGCACACACACCCCAGCAGCAGCAGCAGCAGCAGCTGAGCTTGAAGCAGCAGAGCGAGGTAGACATG
GCCGCCGCCACCATGGCCCTCTCGTCCCCGGCGCTGGCCGGCAAGGCCGCCGCGAAGGTGTTCGGCGAGGGGCGC

Figure 2 continued

ATCACCATGCGCAAGTCGGCGGCGAAGCCCAAGCCCGCCGCGTCGGGGAGCCCGTGGTACGGCGCCGACCGCGTG
CTCTACCTCGGCCCGCTCTCCGGCGAGCCGCCGAGCTACCTGACCGGCGAGTTCCCCGGCGACTACGGGTGGGAC
ACCGCGGGGCTCTCCGCCGACCCGGAGACGTTCGCCAAGAACCGGGAGCTGGAGGTGATCCACTCCAGGTGGGCG
ATGCTCGGCGCGCTGGGCTGCGTGTTCCCGGAGCTCCTCGCCCGCAACGGCGTCAAGTTCGGCGAGGCGGTGTGG
TTCAAGGCGGGGTCGCAGATCTTCAGCGAGGGCGGGCTCGACTACCTCGGCAACCCGAGCCTGATCCACGCGCAG
AGCATCCTCGCCATCTGGGCGGTCCAGGTGGTGCTCATGGGCGCCGTCGAGGGGTACCGCATCGCCGGCGGGCCG
CTCGGCGAGGTCGTCGACCCGCTCTACCCCGGCGGCAGCTTCGACCCGCTCGGGCTCGCCGACGACCCGGAGGCC

> SEQ ID NO:239 131133 174842_300527_1b
CCCAGCACGCACACACACCCCAGCAGCAGCAGCTGAGCTTGAAGCAGCAGAGCGAGGTAGACATGGCCGCCGCCA
CCATGGCCCTCTCGTCCCCGGCGCTGGCCGGCAAGGCCGCCGCGAAGGTGTTCGGCGAGGGGCGCATCACCATGC
GCAAGTCGGCGGCGAAGCCCAAGCCCGCCGCGTCGGGGAGCCCGTGGTACGGCGCCGACCGCGTGCTCTACCTCG
GCCCGCTCTCCGGCGAGCCGCCGAGCTACCTGACCGGCGAGTTCCCCGGCGACTACGGGTGGGACACCGCGGGGC
TCTCCGCCGACCCGGAGACGTTCGCCAAGAACCGGGAGCTGGAGGTGATCCACTCCAGGTGGGCGATGCTCGGCG
CGCTGGGCTGCGTGTTCCCGGAGCTCCTCGCCCGCAACGGCGTCAAGTTCGGCGAGGCGGTGTGGTTCAAGGCGG
GGTCGCAGATCTTCAGCGAGGGCGGGCTCGACTACCTCGGCAACCCGAGCCTGATCCACGCGCAGAGCATCCTCG
CCATCTGGGCGGTCCAGGTGGTGCTCATGGGCGCCGTCGAGGGGTACCGCATCGCCGGCGGGCCGCTCGGCGAGG
TCGTCGACCCGCTCTACCCC

> SEQ ID NO:240 131133 167852_300551_1b
GAATTCACTAGATCTTCAGCAGTCTTGTTATTTTCTCTTTAACAAAACATATAAATGGCATCCATGTCTCTCTCA
TCCCCATCATTTGCAGGCACAGCTGTAACTTTGAACGCACAATCGAAATTCCCAACCAATGTTAGATCCAGCAGC
AATGGAATGATTGTGATGAGGAAGACATCAGCAAAGAAGCCTGCTGCTTCTTCAGGAAGTCCATGGTACGGTCCG
GACCGTGTCAAGTACCTTGGACCCTTCTCTGGTGAGTCTCCATCATACCTAACTGGTGAGTTCCCTGGTGACTAT
GGCTGGGATACTGCTGGACTATCTGCAGACCCAGAGACCTTTGCCAAGAACAGGGAATTGGAAGTGATTCATTCC
AGGTGGGCTATGCTTGGCGCTTTGGGATGTGTTTTCCCTGAACTTCTCTCTAGAAATGGAGTTAATTTTGGAGAA
GCAGTCTGGTTCAAAGCTGGTTCCCAGATTTTCAGTGAAGGTGGACTTGACTACTTGGGAAACTCCAGCCTGGTT
CATGCACAGAGCATCTTAGCTATTTGGGCAACCCAAGTTATCCTTATGGGAGCTGTTGAGGGATACAGAGTTGCC
GGTGGTCCACTAGGTGAGATCGTCGACCCACTTTACCCAGGTGGTAGCTTTGACCCCTTAGGACTTGCAGAGGAC
CCAGAGGCATTTGCTGAGCTGAAGGTAAAGGAACTTAAGAACGGGAGACTTGCTATGTTCTCCATGTTCGGATTC
TTCGTTCAGGCTATTGTTACCGGCAAAGGTCCTTTAGAGAATCTGGCAGATCACCTGTCTGACCCTGTGAACAAC
AATGCTTGGTCATATGCTACCAATTTTGCTCCAGGAAAGTGAGAATGTACATGATAGTCAACTAAGATGATTTCA
TTTCCTTCAAAAGGCGAAGGAGATGGCTTTTCTTATCTTTCAACTTTTGTACATACATCCATTTAGCTTGTAAAA
CAATCTGGCATTCGGATTAATTTGTACTTAA

> SEQ ID NO:241 131133 52310_300086_1b
TCGCGATCTAGAACTCTTATTAACTAAAGAGCCTTTTACTTGCGCCACACTCTCACCGCAATGGCCGCCTCGACA
ATGGCTCTCTCCTCTCCTGCTTTGACCGGAAAGGCCGTTAAGCTATCCCCGGCGGCCTCCGAAGTATTTGGAACC
GGCCGAATCACCATGCGCAAAGCCTCCAAGCCCACCGGTCCATCCGGCAGCCCATGGTACGGATCCGACCGAGTC
AAGTACTTGGGTCCATTCTCCGGTGAGCCTCCGAGCTACCTCACTGGAGAGTTCCCCGGTGATTACGGGTGGGAC
ACTGCCGGTCTATCCGCCGATCCCGAGACCTTCGCTAGGAACCGTGAGCTAGAAGTTATCCACAGCAGATGGGCC
ATGCTCGGAGCCCTAGGCTGCGTTTTCCCTGAGCTATTGGCTAGGAACGGAGTGAAGTTCGGAGAAGCGGTTTGG
TTCAAGGCTGGTTCACAGATCTTCAGCGACGGAGGATTGGACTACTTGGGCAACCCGAGCTTGGTCCACGCTCAG
AGCATCTTAGCCATTTGGGCTACTCAAGTTATCCTCATGGGAGCTGTTGAGGGCTACAGAGTCGCCGGAGATGGT
CCATTGGGAGAAGCAGAGGACTTGCTTTACCCAGGTGGGAGCTTCGACCCATTGGGCCTCGCTACTGACCCCGAG
GCTTTCGCGGAGTTGA

> SEQ ID NO:242 131133 271915_200039_1b
TGCAGTCAAGAATACTTTCTTATCTCTTCCTTCTACAATGGCAACTGCTACAATGTCTCTCTCTTCCCCTTCTTT
TGCCGGAAAGGCAATAAAACTCTCACCATCTTCCTCTGAAATTACTGGAAATGGAAAAGTCACCATGAGGAAGAC
TGTTACCAAGGCTAAGCCTGTCTCCTCTGGCAGCCCATGGTACGGTCCTGATCGTGTCAAGTATTTGGGCCCATT
TTCTGGTGAGTCCCCAAGTTATTTGACTGGTGAATTTCCTGGTGATTACGGTTGGGATACTGCTGGACTTTCAGC
TGATCCGGAAACCTTTGCCAAAAACCGTGAGCTAGAGGTTATTCACTGCAGATGGGCTATGCTTGGAGCTCTTGG
TTGCGTCTTTCCTGAGCTCTTGGCCCGTAACGGTGTCAAGTTCGGCGAAGCTGTATGGTTCAAAGCTGGATCGCA
GATTTTCAGTGAGGGTGGACTTGACTACTTGGGCAACCCAAGCTTGGTCCACGCGCAAAGCATCTTGGCTATTTG
GGCTTGCCAAGTTGTGTTGATGGGAGCCGTCGAGGGTTATCGTATTGCTGGTGGACCTCTTGGTGAGGTTGTTGA
CCCACTTTATCCTGGTGGTAGTTTTGACCCATTGGGTCTTGCAGATGACCCGGAAGCTTTTGCTGAGCTTAAAGT

Figure 2 continued

> SEQ ID NO:243 131133 108295_300261_1b
CATTTATATACAGTTGATGCGGGCTCATTAAACTCAAGCCATAAATCAAATATTTTTTCTGTATAGTAGCTGCAT
TTTCAAGAGCATTTCACTTTATTTCTACAACAATGGCAGCTACTACAATGGTTCTTTCTTCCTCTTCTTTTGTGG
GAAAGGCGGTGAAACTCTCACCATCTTCCTCTGAGATCACCGGAAATGGAAAAGTTACCATGAGGAAGACTGTTA
CCAAGGCGAAGCCAGTCTCTTCTGGCAGCCCATGGTATGGTCCTGATCGTGTCAAGTACTTGGGCCCATTCTCCG
GTGAGTCCCCAAGTTACTTGACTGGTGAGTTCCCTGGTGATTATGGGTGGGACACTGCTGGACTTTCAGCTGATC
CCGAAACTTTTGCAAAGAATCGTGAGCTAGAGGTGATCCACTGCAGATGGGCCATGCTTGGAGCTCTTGGTTGTG
TCTTCCCTGAGCTCTTGGCCCGTAATGGTGTCAAATTCGGTGAGGCTGTATGGTTCAAGGCTGGATCTCAAATTT
TCAGCGAGGGTGGACTTGATTACTTGGGCAACCCAAGTTTGGTCCATGCACAAAGTATCTTGGCCATCTGGGCTT
GCCAAGTCGTGTTGATGGGAGCCGTTGAGGGTTATCGTGTTGCTGGTGGACCTCTTGGTGAGGTTGTTGACCCAC
TCTACCCTGGTGGTAGCTTTGACCCATTAGGCCTTGCTGATGACCCCGAGGCTTTTGCCGAGCTCAAGGTGAAGG
AG

> SEQ ID NO:244 131365 130538_300488_1b
GAATTCCGTAGGAACATGATGCCCTTGAACCCGGGTTTAATTGTTGAGGTCTTTCATGTGTGGGGTATTGACTTT
ATGGGTCCGTTTCCTAATTCTTTTGGTAACTTATACATCCTTGTCGCCGTAGACTATGTCTCCAAGTGGATTGAG
GCGGTTGCGTGTAAAACCAATGACCATAGGGTTGTGATTGAGTTCTTGAAAAAATAATATACTTACACGTTTTGGT
ACACCGCGAGCTATAATTAGTGATGGAGGGTCGCATTTTTGTAATGGTCCTTTTAGGCTTTTGATGAAGAAATAT
GGTATCACACATAAGGTAGCCACCCCGTATCATCCACAGACTAGTGGTCAGGTAGAGGTTTCCAATAAGGAGATA
AAACGTATATTAGAGAAAACAGTCAATCCTAATCGGAAAGACTGGTCGTCTAGGCTCACTGATGCCTTATGGGAT
TACCGTACTGCGTTTAAAACCCCAATTGGAATGTCGCCTTATCGACTTGTGTATGGCAAGGCATGTCATTTACCT
GTTGAGTTAGAACATAGAGCTTATTGGGCTGTCAAGCAGCTAAATTTTTCACTCGACAAGGCAGCAGCCCATAGG
AAACTCCAGCTCAATGAGTTGGATGAAA

> SEQ ID NO:245 167373 111768_300059_1b
GGCAGATATGGCTCATATTAGTGGGTTAGTTGCAGCTGGAGTCATCCCATCACCATTTGATTATGCAGATGTTGT
GACTACCACAACCCACAAATCCCTTCGCGGGCCTCGTGGTGCCATGATTTTCTTCCGGAAGGGTGTGAAGGAGGT
TAACAAGCAAGGAAAGGAGGTGTTGTACGACTATGAAGATAAAATTAACCAGGCAGTCTTTCCTGGACTTCAAGG
TGGTCCTCACAATCATACAATTACTGGCTTGGCAGTTGCTTTGAAACAGGCAATGACTCCAGAATACAAAGCTTA
CCAAGAGCAATGCCTTAGCAACTGCTCAAAATTTGCCCAGGCGTTAGCGGGAATGGGTTATGAACTTGTTTCTGG
TGGAACAGAGAATCACTTGGTCTTGGTGAACTTGAAAAACAAGGGTATTGATGGTTCTAGGGTTGAAAAAGTTTT
GGAAGCGGTACATATTGCAGCCAATAAGAACACTGTTCCTGGAGATGTATCTGCCATGGTCCCTGGTGGCATCAG
AATGGGGACTCCTGCACTCACATCAAGGGGATTTATTGAGGAAGATTTTGTGAAAGTTGCTGAATTCTTTGATGC
TGCTGTGAAGATAGCAGTGAAAATAAAGGGTGAGGCTCAAGGAACAAAGTTGAAAGACTTTGTGACAACACTACA
GTCTAGTGCTTCCATCCAGTCGGAGATTGCAAAACTCCGCCATGGTGTGGAGGAGTATGCAAAGCAGTTCCCTAC
AATTGGGTTTGAGAAGGAAACCATGAAGTACAAAAACTGAGAGCTCGACTGAGTATATACACAAGGACCAATATC
CAATTTCTTGAAGGTGTATGGGATGCACATTCAAACTGCAGTTTGCTCTCAAGGATAGGATTTTCATCTTATAAT
ATTATGTAAAATCCAGCAGTACTTGGTTCCCAACTTTGCACTTTGTATATTAACGATTGTAAATCATCTCAGGTC
CTTGAAAGCAATAAACTCCTCTTATCTCAGTAAAAAAGAAAGAAGAAAAACATTGNCCTGTATTGCTTAATATTT
TCCTTTTATTAATGAGAGTACCATGTGTTGTGTTGGAAAAAAAATG

> SEQ ID NO:246 167373 9601_300299_1b
CCCACGCGTCCGGTGGAGCCATGATTTTCTTCAGAAAGGGTGTTAAGGAAATTAACAAGCAAGGGAAAGAGGTTT
TGTATGATTTTGAAGACAAGATCAACCAAGCTGTCTTCCCTGGTCTTCAAGGTGGTCCACACAACCACACTATCA
CAGGACTAGCTGTTGCTTTGAAACAGGCAACTACTTCAGAGTACAAAGCATACCAAGAACAAGTCCTGAGTAACA
GTGCAAAGTTTGCTCAGACTCTAATGGAGAGAGGATATGAACTTGTTTCTGGTGGAACTGACAACCATCTGGTTC
TAGTGAATCTAAAGCCCAAGGGAATTGATGGATCTAGAGTTGAGAAAGTGTTGGAAGCTGTTCACATTGCATCCA
ACAAAAACACT

> SEQ ID NO:247 167373 55604_300134_1b
CACCCCTCGACCCACGCTCCGAAAGGGTGTTAAGGAAATCAACAAGCATTGGAAAGAGGTTTTTATGATTTTGA
AGACAAGATCAACCAAGCTGTCTTCCCTGGTCTTCAAGGTGGTCCACACAACCACACTATCACAGGACTAGCTGT
TGCTTTGAAACAGGCAACTACTTCAGAGTACAAAGCATACCAAGAACAAGTCCTGAGTAACAGTGCAAAGTTCGC
TCAGACTCTAATGGAGAGAGGATATGAACTTGTTTCTGGTGGAACTGACAACCATCTGGTTCTAGTGAATCTAAA
GCCCAAGGGAATTGATGGATCTACAATTGATAAAGTGTTGGAAGCTGTTTACATTGCATCCAACAAAAACAC

> SEQ ID NO:248 167373 48608_300033_1b
GCCATTACGGCCGGGGCATATTGCAGCCAATAAAAACACTGTGCCTGGTGATGTATCCGCCATGGTGCCTGGTGG

Figure 2 continued

CATTCGCATGGGAACCCCAGCTCTGACTTCTAGGGGATTTATTGAGGAGGATTTTGTGAAAGTGGCTGAATTTTT
TGATGCTGCTGTGAAGTTGGCCCTTAAGGTCAAGGCTGAGACCCAAGGAACAAAGTTGAAGGACTTTGTGGAAAC
TTTGAGTTCAGACTCCAAAATTCAATCTGAGATTGCCAGGCTAAGGCAGGACGTTGAGGACTATGCAAAACAATT
TCCTACTGTTGGTTTCGAGAAAGAAACAATGAAATACAAGGATTGAGCTGGGATCTAGTATTCAGATGGAATCGG
AAGGCATTTTTCTCCAATGAAGTTAGAACTTGTCTTTAGAAGTCTTCTGGAAGTCACTTGCAGGCGAGGAAAACA
GTTGCACGGATCACATTTGTATAATTTTCTAAATCAAAGTCATGATCAGATGTAATTTTCAAGCTGTAAAACAAC
TGTTCCAAAATTCAATTTGTCTCACTCTTGGTTTAGAGAAGGACGAGAAAGCCAACAATGGTTTACGGAAAGTCC
TTTGTGGAATACTCGCAAAGG

> SEQ ID NO:249 167373 240420_301314_1b
GAGCGGGCTCGTGGCTGCTGGTCAACTTGCTAATCCTTTCGAGTACTGTGATGTGGTTACAACCACTACTCACAA
GTCTTTAAGAGGTCCTCGTGGAGGAATGATATTTTTCCGGAAAGATCCAGTTCTGGGACTGGACTTGGAAACAGC
TATAAACAATGCAGTATTCCCCGGTCTGCAGGGAGGACCTCACAATCACACAATTGCTGGACTGGCCGTGTGCCT
GAAGCACGCAGTAACCGAAGAATTCAAGCAGTATCAAAAGCAGGTGATTGCGAACTGTCAAGCGCTTGCAGACAA
GCTGGTGGAGTTGGGATTCACGCTGGTGTCTGGCGGAACCGAAAATCACCTGGTCCTTGTTGATCTGCGTCCTTT
GGGAATTGACGGTGCCAGAACTGAAAAGGTGCTGGATCGTGCTTCCATCACGCTCAACAAGAACTCAGTACCAGG
TGACAAGAGTGCGTTAGTTCCGGGAGGTGTACGCATCGGCACACCTGCATTGACAACGAGAGGACTCAAGGAAGA
GGACTTCGTCAAAGTAGCAGAGTTCATTCACGAAGGCGTCCAAATCGCCAGACAGCTCAAGGAAACAGTCCGGCA
AGGGAAAATGAAAGAGTACGTCCAGGCACTCGAATCTCCAGACTCTCCAGTCCAGACGAGCATCGCCGATCTACG
GAACAGAGTCGAAGC

> SEQ ID NO:250 167373 11989_300283_1b
TGGTATCAACGCAGAGTGGCCTTACGGCCGGGGACTCCAGAATACAAAGCTTACCAAGAGCAATGCCTTAGCAAC
TGCTCAAAATTTGCCCAGGCGTTAGCGGGAATGGGTTATGAACTTGTTTCTGGTGGAACAGAGAATCACTTGGTC
TTGGTGAACTTGAAAAACAAGGGTATTGATGGCTCTAGGGTTGAAGAAGTTTTGGAAGCGGTACATATTGCAGCC
AATAAGAACACTGTTCCTGGAGATGTATCTGCCATGGTCCCTGGTGGCATCAGAATGGGGACTCCTGCACTCACA
TCAAGGGGATTTATTGAGGAAGATTTTGTGAAAGTTGCTGAATTCTTTGATGCTGCTGTGAAGATAGCAGTGAAA
ATAAAGGGTGAAGCTCAAGGAAC

> SEQ ID NO:251 167373 119088_300066_1b
TGTTTCTGGTGGAACAGAGAATCACTTGGTCTTGGTGAACTTGAAAAACAAGGGTATTGATGGCTCTAGGGTTGA
AAAAGTTTTGGAAGCGGTACATATTGCAGCCAATAAGAACACTGTTCCTGGAGATGTATCTGCCATGGTCCCTGG
TGGCATCAGAATGGGGACTCCTGCACTCACATCAAGGGGATTTATTGAGGAAGATTTTGTGAAAGTTGCTGAATT
CTTTGATGCTGCTGTGAAGATAGCAGTGAAAATAAAGGGTGAAGCTCAAGGAACAAAGTTGAAAGACTTTGTGAC
AACACTGCAGTCTAGTGCTTCCATCCAGTCGGAGATTGCAAAACTCCGCCATGGTGTGGAGGAGTATGCAAAGCA
GTTCCCTACAATTGGGTTTGAGAAGGAAACCATGAAGTACAAAAAATGAGAGCTCGACTGAGTGTATACACAAGG
ACCAATATCCAACTTCTTGAAGGTGTATGGGATAGACTTTCAACTGCAGTTTGCTCTCAAGGATAGGATTCTCAT
CTTATAATAATATGTAAAATCCAGCAGTACTTGGTTCCAGACTTTGCACTTTGTATATTAACGAGTGTAAATCAA
CTGAGGTCCTTGAAAGCAATAAACTCCTCTTATCTCAGTGA

> SEQ ID NO:252 167516 111269_300053_1b
CTCAAATCCTACTTGTGTTTTTGCCTCAATCCATTAATTTTTGTGTTTCATCATTTCTTTGCAGCAGAGACAAAT
TAAGACATGGCAAGTAGCAGCATGGCTTCTGCTGCATCTGGTTTTATGGTGGCCACACCCAATATTGCCACCTCT
AACACTGCTCCTCGCACCTCTATGTTATTCTTCTCCTCCTCCAAGAACAACACCACCACCAACTTCCCGAGGCTC
GTTGTTAGGGCCGCGGAAGAGGCTGCGCCGCCAGCTGCTACCGCCACCGCTGAAGGTGAAGCTCCTCCTGCCAAA
GCTACCAAGCCACCTCCAATTGGACCCAAGAGAGGAACCAAAGTGAGAGTTTTAAGGAAGGAGTCTTACTGGTAC
AAGGGGGTTGGTTCAGTTGTAGCTGTTGATCAGGATCCAAACACACGCTACCCAGTTGTAGTAAGGTTCAACAAA
GTGAACTATGCAAATGTATCTACCAACAACTACGCATTGGATGAAGTCGAAGAAGTGAAATGAAAGAATGGAAGT
AATTAATTAGTTCATGCTCTTCATATTTGTAATATGCCCGACCCTGTGCTTTCCATGTTTAATCTCTAGTTACAT
ACTGGCTTTGAATGTGAATCTGTATCATAATTTCTTGCAAATTTCTCCTTCCATTACTTATTAAGTTTGTTGGCA
TTG

> SEQ ID NO:253 167516 255233_301647_1b
GAGAAGCAAAGCACAGCAGGGATGGTTACCATGGCTTCTTCCAGCACATTGGGCGCCCTCGCTCCTTGTTCCTCC
TCCTCGATTTCGAGCACCAGCAGTCAGGCTCGCTTCCTTCATTTCGCCCCTTCCCCTTTCCGCTTGCGCAGGAAT
GGCTCGCCTGCATTGAGCGTGCGTGCTGCCGATGCCGCTGCCCCCGCTGAGTCTGCCCCTGTTGTGGAAAAGCCC
AAGCCCATTGGACCCAAGAGGGGTACTAAGGTGAAGATCTTGAGGCCTGAATCATACTGGTTCAACGGTGTTGGA
ACAGTGGTTTCTGTTGATCAGTCTCCTGGTACAAGGTACCCTGTTGTGGTCAGATTTGAGAAGGTCAACTATGCC

Figure 2 continued

GGCATCTCCACCAACAATTATGCTTTGGATGAAATATCAGAAGTGTAGGCGACATTATCTACTTATCAAATGCTA
GAAGGTCTCCGAAGAATTGAATCAGTGTATCTTGGCCTTTTGGAAGGCTTGTAAATGTATGTTAAAAGCTTTTCC
TGCAATGTTAAGAGATTCTGATTTTATTGGCTTGAATATGAGTTAGTCCATGATAAATGCATGCACTTGTATAGG

> SEQ ID NO:254 167516 254995_301640_1b
AGCAGTGTTAGTGGTAGAGTCAGCAGTTTGTGCGAAGATAGCCATGGCGTGTGCTTCCTTGACCGCCGCCACCAC
CGCCCTCGTAGCCGCCATGGCCTTGCCCTCGCTCGGCTCATCCTCCCCCTTGGCCTCCTCCTTGGCCCTTCCCCA
AACCCGGAGTGCTCGCATGGTCGCCCTCACCGTCGTCCGTGCCTCCGACGCCGCTTCCCCTGTCCCCACCCCCTC
TGAAAATCCTGCCGCCGCCCCCGCTGCCGAGAAGCCCAAGCCTATCGGCCCCAAGCGTGGTACCAAGGTAAAGAT
TTTACGCCCCGAGTCGTATTGGTTTAACGGAGTCGGAACAGTGGTCTCTGTGGATCAGAGCCCCGATACGCGGTA
CCCAGCTGTGGTGAGGTTTGAAAAGGTGAACTACGCCGGCATCTCCACTAATAACTATGCTTTGGATGAGATAGT
GGAGGTTTAATAGTATCTTCATTGTTTCTTGTACACTCCTTTTCATTATCCATCCCTTATTGGTAAATTTCCCAC
CTCATGAGTTGCC

> SEQ ID NO:255 167516 241067_301319_1b
GCACGCGCTCGGCTTTCTCGTTGCGAAGGTTTAAGGAGGAAGAGAGAAGAGGGATGGCGTCGGCGGCGGCATCCG
GATGTGTTGGATTGGTGTCCGGGGCAGCGGCGGCGGCGACGACGAGCGCATCGTCGTGCAGATTGTTTGGCGGGC
AATGCAGGGTCCCGTCGTGGAATCGAGGCTCGACTTGTTCTTCTTCTTCGTCGAGATTGGTGGTGAGAGCTTCTG
ATGCCGCTGCGGCTCCAGCTCCAGCAGCACCCGAGAAGAAGCCAGAGCCAATCGGTCCCAAGCGTGGATCTATGG
TGAAGATCTTGCGGCCTGAGTCGTATTGGTTCCTGAACACAGGCAAGGTCGTCACTGTGGATCAGACCCCTGGCG
TGCTCTACCCGGTTGTTGTTCGGTTCGAGAAGGTGAATTACGCTGGAAACACCACAAACAACTACGCATTGGACG
AGGTCGAAGAAGTATGAAGAAAGAGAAGAGAGGGTCTCGCTGTAAACCACATATATCCTCGCCTTATCTGTTGGA
AAGGATTTCTACACTTGTACTTAGCGATTTAAAACAGATAAAAGCACAACACCTGCTCCCGTGGCCTAATGGATA
AGGCATTTGACTTCTAATCAAA

> SEQ ID NO:256 167516 1117323_301820_1b
GAGTTGGAAGAGAAGCAAAGCACAGCAGGGATGGTTACCATGGCTTCTTCCAGCACATTGGGCGCCCTCGCTCCT
TGTTCCTCCTCCTCGATTTCGAGCACCAGCAGTCAGGCTCGCTTCTTTCATTTCGCCCCTTCCCCTTTCCGCTTG
CGCAGGAATAGCTCGCCTGCATTGAGCGTGCGTGCTGCCGATGCCGCTGCCCCCGCTGAGTCTGCCCCTGTTGTG
GAAAAGCCCAAGCCCATTGGACCCAAGAGGGGTACTAAGGTGAAGATCTTGAGGCCTGAATCATACTGGTTCAAC
GGTGTTGGAACAGTGGTTTCTGTTGATCAGTCTCCTGGTACAAGGTACCCTGTTGTGGTCAGATTTGAGAAGGTC
AACTATGCCGGCATCTCCACCAACAATTATGCTTTGGATGAAATATCAGAAGTGTAGGCGACATTATCTACTTAT
CAAATGCTAGAAGGTCTCCGAAGAATTGAATCAGTGTATCTTGGCCTTTTGGAAGGCTTGTAAATGTATGTTAAA
AGCTTTTCCTGCAATGTTAAGAGATTCTGATTTTATTGGCTTGAATATGAGTTAGTCCATGATAAATGCATGCAC
TTGTATAGGCAACTAGGCTTAATGTGCTTATTTCCTTGAGTTTCATGGAATCCCTTCTAGTTTTGC

> SEQ ID NO:257 167516 135259_300412_1b
CTGCACCTCCACCTCCACCACGCTGCTCCCACTTCACTTGGAATTCGAAATCCACACGAGCGCCGCCGCCGCCCG
CGGCGGAGGAGAAGCCGGCGGAGGCCGAGGCGGCCGTGGCGACCAAGGAGCCCGCCGCCGCCAAGCCGCCTCCCA
TTGGCCCCAAGAGAGGCACCAAGGTGAAGATCCTGAGGAGGGAGTCCTACTGGTACAACGGCACTGGCTCCGTCG
TCACCGTTGATCAGGATCCCAACACTCGCTACCCGGTGGTGGTTCGGTTCGCCAAGGTGAACTACGCCGGCGTGT
CGACCAACAACTACGCCCTGGACGAGATCCAGGAGGTCAAATGATTTAATTCGGATGGATCGTCGTCGAGCTGG
AGCTGCAAAGAATCATCTTTAATTGATCACGGAGTGAGGAGAGGATGCATGTCGTACATGTGGAAGAAATTAATT
AAGCTGCTTGATCGAGCTTTGTGTGTATTAGTGTAATGGTGGTGGTTTCTTCTTTATAATCCGTATAATACTATG
TAATTTGCCTGCCTCTGCTTCTTCCT

> SEQ ID NO:258 167516 227351_301027_1b
GCGTCGGCGAGCACCATTAACGTGGCGTCGGCCACCTCGAGGTTCCTGCTGGCCGGCGGGAACGGCGGCAGCGGC
GGCGGCGGGGCCAGCCGCGTGAGCTTCGCGGCGAACAGGGTCGGGAGGAGGATGGTGGTGGTCCGCGCCGAGGAG
GAGGCCGCGGCGCCGCCGCCGCCGCCGCCGCCCGCGGCGGAGGAGAAGCCGGCGGAGGCCGAGGCGGCCGTGGCG
ACCAAGGAGCCCGCCGCCGCCAAGCCGCCTCCCATTGGCCCCAAGAGAGGCACCAAGGTGAAGATCCTGAGGAGG
GAGTCCTACTGGTACAACGGCACTGGCTCCGTCGTCACCGTTGATCAGGATCCCAACACTCGCTACCCGGTGGTG
GTTCGGTTCGCCAAGGTGAACTACGCCGGCGTGTCGACCAACAACTACGCCCTGGACGAGATCCAGGAGGTCAAA
TGATTTTAATTCGGATGGATCGTCGTCGAGCTGGAGCTGCAAAGAATCATCTTAAATTGATCACGGAGTGAGGAG
AGGATGCATGTCGTACATGTGGAAGAAATTAATTAAGCTGCTTGATCGAGCTTTGTGTGTATTAGTGTAATGGTG
GTGGTTTCTTCTTTATAATCCGTATAATACTATGTAATTTGCCTGCCTCTGCTTCTTCCTCGTGGACTTGATAAT
CCCTTGCTTATAACCATTGTATTCTTTCTTCTACGGCCAAATTGTACATGCACATAAATTTCCATCATTCTAAG

Figure 2 continued

> SEQ ID NO:259 167516 22131_300070_1b

TAGAAAGAGACTTTTAACTGAATTTTCCAAACACATTCTGTGAAAGAATAAGAAAACCGGCTCGAGATTCAGATG
AGGAGAAATAATTGGTAAACTTTTGCGGTACATACGGTTTGGGTCAAGTTACAAACGGATAAACCGGTATAGAAT
ACACAGAGTTTTTGAATTCTCCCATTTAAGCTGCAACTTCTTCGACCTCATCCAATGCATAGTTGTTGGTCGATA
TGTTGGCGTAATTGACTTTTGCGAACCGGACCACAACCGGGTATCGAGTCTTAGGGTCCTGATCAACGGCAACAA
CTGATCCAACGTTCTTGAACCAATAGGATTCTCTCCTTAGAATCTTGACCTTAGACCCTCTCTTAGGACCAATCG
GTGGTGGCTTGGGTTTGGTGGCAGTAGCTCCATCCGGAGCAGCGGCAGCTGCCGGAGAATCTTTTGAAGAAGAGG
AAGCCGGAGCAGGATCTTCGGCTGCCCTGACTACGAGCCTAGAACCGGCGTTTCTCATCGGCAAGAAAGACACGG
AGCTCCTGGACGACGAAGCGCCGGCGACCGAGGTGACATTGGCCGGTAGAACAAATACCGTAGATGCTGTCGTCA
TCGCCATCTCTGGTTTTCTTTTCGGACGCGTGGG

> SEQ ID NO:260 167516 1117412_301891_1b

GGTAGCAGCAGTGTTAGTGGTAGAGTCAGCAGTTTGTGCGAAGATAGCCATGGCGTGTGCTTCCTTGACCGCCGC
CACCACCGCCCTCGTAGCCGCCATGGCCTTGCCCTCGCTCGGCTCATCCTCCCCCTTGGCCTCCTCCTTGGCCCT
TCCCCAAACCCGGAGTGCTCGCATGGTCGCCCTCACCGTCGTCCGTGCCTCCGACGCCGCTTCCCCTGTCCCCAC
CCCCTCTGAAAATCCTGCCGCCGCCCCCGCTGCCGAGAAGCCCAAGCCTATCGGCCCCAAGCGTGGTACCAAGGT
AAAGATTTTACGCCCCGAGTCGTATTGGTTTAACGGAGTCGGAACAGTGGTCTCTGTGGATCAGGTGAAGTAGTA
GAACACAGTTTAGTTTGGGCTGTCTTTCTAATGATAATAGAACTCAGTAAAAAGTGTAGGATCTTCCAATGTGGG
TTTTAATTACCTTTTTTTAATGCATTTTTTCAGAGCCCCGATACGCGGTACCCAGCTGTGGTGAGGTTTGAAAAG
GTGAACTACGCCGGCATCTCCACTAATAACTATGCTTTGGATGAGATAGTGGAGGTTTAATAGTATTTTCATTGT
TTCTTGTACA

> SEQ ID NO:261 168165 143613_200045_1b

GCCGTAACGTCTCCCTGAGAATCTGGACCCCTGCACAATATCTGTCCAAGACAGCACATGCAATGTATTCGCTGA
AGGCAGCTATGGAGTGGGATGAAGATGTTTTCGGTCTGGAGTATGACCTGGATCTTTTTAATATTGTTGCTGTTC
CTGATTTTAACATGGGAGCGATGGAAAACAAGAGCTTGAATATATTCAATTCCAAGCTTGTCCTGGCATCCCCAG
TAACTGCGACTGATGCTGATTATGCGGCAATATTGGGTGTGATTGGACATGAGTACTTCCACAACTGGACAGGCA
ACAGAGTTACCTGTCGTGACTGGTTCCAGCTCAGCTTAAAGGAAGGACTTACTGTTTTCCGTGATCAGGAGTTCT
CATCTGATATGGGAAGCCGTACCGTGAAAAGGATTGCTGATGTTTCAAAGCTTCGAATGTATCAGTACCCACAGG
ATTCTGGTCCAATGGCTCATCCTGTCCGGCCGCATTCTTATATAAAGATGGATAACTTCTACACAGTTACGGTTT
ATGAGAAGGGAGCTGAAGTGGTCAGGATGTACAAAACTTTGTTAGGGAGCCAAGGATTCAGAAAAGGCATGGATT
TATATTTCGAGAGGCACGATGGTCAAGCAGTAACATGTGATGA

> SEQ ID NO:262 129965 273716

ACGCGTCCGTGCCAATTCCATTCCTCTACATCTTCTTCTTTTCCTTACCAATCCACCTCCAATCTCTTTGAAATC
AAGTTACAGAAATCTTTTGTTCGTGTAGGAAATTCGAGAAATCTTAGAAAAAAAATATATTATTGCTGTTTAGAA
AGGGTAAATCCCAGGTGAACAAGTTGTAGACATCACGGCTATACACAAAGCAAACCGCCGACCATTCTTACATGT
TCGTTCAGTACGACGTAAGGGTTGTGTAACTGCCACCAATCCTGCGCCGCACGGCGGACGTGGCGCTTTGCCCTC
TGAAGGCGGTAGTCCTTCCGACCTCCTCTTCCTTGCCGGCGGTGGTTCTCTCCTTTCTTCTACCTGCTAGATTTA
CTTACTTATATACCTTACATAGTTAATTCCTTCTCCGTAAATTACTAATTGTTTTGCACATTAGCAATTATTAAG
GTTGTTCTTGTACCTAGTATTTTTACCTTGAAAAATCAAAGGAAAAAAAAGCAAACATGATGCTCAAGATTAAGA
GGGTTCCTACACTTGTTTCCAACTTCCAAAAGGAAGAGGCTGAAGAAGCTCTTGCTCGTGGTGCTGGCTGTGGCC
GCAATTGCCTCCGAAACTGCTGCCTTCCAGGGTCAAAGCTGCCACTGTATGCTTCCAAGAACTTGAGAAAGGGCA
AGTCTGTTGCCGATGAAACCAAGGAGCCTCCTGTTGACTTCTTGGAATCCCTCCTTCTTGGAGAATGGGAGGATC
GTCAGCAGAAAGGTCTCTTTCGCTATGATGTCACTGCTTGCGAAACCAAGGTTATTCCTGGAGAATATGGTTTCG
TTGCTCAGCTGAATGAGGGAAGGCACCTCAAGAAGAGGCCAACTGAGTTTCGCGTTGATAAGGTGCTGCAGCCTT
TTGATGGAAGCAAGTTCAACTTCACTAAGGTTGGTCAGGAAGAGTTGCTCTTCCAGTTTGAAGCAAGTGAGGACA
ACGAAGTTCAATTCTTTCCAAATGCACCCATTGATGCCGAGAAATCTCGAAGTGTTGTTGCCATCAATGTCAGTC
CCATTGAGTATGGACATGTGCTTTTGATCCCTAAGGTCCTTGAATGCCTTCCCCAGAGGATTGACAGGGACAGCC
TATTGCTTGCACTGCACATGGCTGCCGAAGCAGCTAACCCATACTTCCGATTGGGTTATAACAGCTTGGGTGCAT
TTGCTACCATCAACCATCTTCACTTTCAGGCCTATTACTTGGCTGTGCCATTCCCCATTGAGAAGGCCCCCACTC
GGAAGATTACCTTTGCTGATGCTGGAGTGAAGATATCTGAGATGCTGAATTATCCAGTTCGAGGACTTGTCTTTG
AGGGTGGAAATACTTTGGAGGATTTCGCCAATGTTGTCTCTGGTTCTTGCATTTGCCTGCAAGAGAATAACATTC
CCTACAATGTTCTAATCTCTGATTCGGCAAAAAGGGTATTCCTTCTCCCACAGTGCTACGCAGAGAAACAGGCTC
TAGGGGAGGTCAGCTCTGAACTGCTTGATACTCAAGTCAATCCTGCAGTATGGGAGATTAGTGGACACATGGTCT
TGAAGAGGAAGGAGGATTACGAGGGTGCAACCGAGGCAAATGCCTGGAGGCTTCTCGCTGAGGTCTCACTTTCTG
AAGCGAGGTTCCAAGAAGTGACTGCTCTCATCTTTGAAGCCATTGATTGCAGTGTTGAAGAGAATGAGAATGCCA
ATGAAGGTTCTCCTGAGAAGCCAGATGTTGCACCTCAGCCTATGGAGGAAATTGATGCTCTCAACACCCATGCTA

Figure 2 continued

CCATGGTTCCCGTGTAGGGTTTTCATGGTCGAGCTGTGGTGTTTGTCCTGTTGTTACTATTTCAACTATATGAAC
ATTGAGGGAGTTTCTATCTATGGCTGCACTTGTGAAATATCCCTAAATAAGGCTAGCCATGTTCTATGTATTGAT
GAAGTTGTTTGGTTCCTATGTGAATTGAACCTTGTCTTTATTGCTTCATATTAATGTGGAGTTGCTCAGTGTCC
TCTGGGAATTGACCTTGGATACTATGTTTGTTGTCTGTTATTTAAGACAATATATTTGGTAATGGAAGTTGGAGT
TTCCCTGAAAAAAAAAAAAAAAAAAAAAAAAAAAAAA

> SEQ ID NO:263 129424FL 1170936_302040_1d
AGAAAGAGAGAGACCAGAGAGAGAGAGAGAGAGAGACTGGTAACAATGGCAATGGCGTTGAGAGCAGCGTTCCAG
TGCACGCCAAGCGCATCATCCCTTTCGTCCTCCTCCTCCTCGGCATCGCCCCTCCTCCGTCGGGGTGCTGCTGCC
GCCCTGAGGTTTGCACGCTGCTCGACCCCCGGTAACGCGGGAAGCCCACTCTGCAGCCCTCCTCCCTTCAGAGCC
GCCGCTCGGTCCTGGCGCGCCCTCTCCCTCCCTGCCTCCCAGCTCACCGCCTCCCCTCCCACCCCCGCTTACACC
ATCAAGGAGGAGGGTAAGCCCGAGTCCCTCGACTTCCGCCTCTTCTACTTCAGCGATGATTCCGGCAAAAAGATC
TCACCATGGCACGACATACCTTTAGAAGCCAAGGATGGCATGTTCAACTGTATTATAGAGATTCCAAAGGAAACC
AGTGCGAAAATGGAAGTGGCCACCGACGAATTCTACACCCCTATCAAGCAAGATACTAAGAAGGGC

> SEQ ID NO:264 129424FL 227659_301030_1d
GTCGCTCCGCCGCCGCCGCCGCTGTTCACTCCGCACCAACTCCGACGATCCCCCGGCGAGCTCTCGACGATGGCG
ACGGCGGCGACGGCGTCGGCTACGGCGGCCACCCGCTTCACGCGGCTGGCGGGGGTCGGGCTCCGGCGCACGGCC
CGCCTCCCCACGGCCGTGCGGTTCCAGCGCCGGGTGCTCGCCACCACCGCGCTCCTCAGGACCGCCGAGCTCCGG
CCCAAGGAGCAGGGCCTGCCCGAGACGCTCGACTACCGCGTGTTCCTCGTCGACGGCGGGGGCCGCAAGGTTGTC
GCCGTGGCACGACGTGCCCCTGCGCGCAGGCGACGGGGTTGTTCCACTTCGTCGTGGAGAATCCCAAGGAGAGCA
GCGCCAAGATGGGAGGTCGCCACCGACGAGTCATTCACCCCCATCAAGCAGGACACCAAGAAGGGCAACCTCCGA
TACTACCCGTACAACATTAATTGGAATTATGGATTATTTCCCCAAACATGGGAGGACCCAACTCTTGCAAACACC
GATGTCGAAGGAGCATTTGGGGATAATGATCCTGTTGATGTTGTTGAGATTGGTGAAAGACGTGCTAACATTGGA
GATGTTCTTAAGGTAAAACCGTTGGCAGCTTTAGC

> SEQ ID NO:265 129424FL 243145_301336_1d
AAATCATTTATTGATTTAATCTCCTTTTTCCTTTATCATAATGCAAAGAATCCATTAAGAGAAGCACTTCAAACG
AGCGAGAGATCCCCCGCCGGGGCAGACCTTGTCACAAGCTTCACCCACGCTTGATGCGTCTCCTGGATCACCTTG
AGCGCGTACTCCTTGCCAGCAGCCTTGTTCCCCAGCCCAAACTTATTCTGCGGCTTCCCATCCGGCACCTTGTAG
TCGCGGAACCAGTCCCGGATCTCCATCAGCGTCCCGGGAAAGTACTTCTCCACATCACTCTCATCGTTGAAAAGC
CCAGCCCTGGGATCATCCACGGAGATGGCCACCACCTTCCAGTCCAGCTCCCCCTCATCGATCATCGCCAGCACC
GCCACCGGCTTCACTCGAAGAACTTCCCCACGCCCCGCCTTTCGCTCGCCGATCTCGACAACGTCGACCGGATCA
TTGTCACCAAGCGCTCCCTCCACATCCGGGTTGGCGTGGTTTGGATCTTCCCAAGTTTGCGGAAGAAGCCCGTAG
TTCCAGCGTATGTCGTATGGATAGAACCGTAGCTTGCCTTTCTTCACGTCCTGCTTGATCGGCGT

> SEQ ID NO:266 129424FL 49512_300159_1d
GCCATTACGGCCGGGGACTGGAAAATAGTTGCTATTTCACTAGACGATCCAAGAGCTTCACTTGTTAATGATGTT
GATGATGTAGAGAAACATTTTCCGGGCACTCTCACCGCAATCAGGGACTGGTTTAGAGACTATAAGATACCTGAT
GGAAAACCTGCCAATAGGTTTGCTCTTGGCAACAAGCCAGCAAACAAGGATTACGCTCTTAAGGTGATTACGGAA
ACCAATGAATCTTGGGCAAAGCTTGTCAAAAGATCTATCCCCGCTGGTGAGCTTTCACTTGTATAGATGCCAATT
GATAGAGCTTGAGCCAGCTAGTTTTCATGCTCGTAACCTAAACTGGACGCGGAAAATGGCCCCAGGATTATGCTC
TTCGCTTTTGAGGTGGAAGTCCATTCATATTCTTAAGACAGTTTTTTGTTAAAAATGTTACTGTTTTTCTATTTC
ATCATCCATAATTTTGTTCATGCAGTAGTGTTTTCAAATTTTATTTAGGGTGAAAACAGGTGTACTGACTACTGA
TAATTGAATTGATCGTCATTCCTC

> SEQ ID NO:267 129424FL 127868_300473_1d
CCCCCCGAGTTCCCCATTTCAGCAGCAAAGGCAACAATGGCGGCTGCAAGAGTAATGATATCAGCCAACAACACT
CTAACAACTTCTCTTTTATCCAAAATTCCTCTCCAAAAGCCCAATAGTTTCAACCTTTGTTTCCGCAATAGGTCT
GCTGCTGCACACAGGAGCCAACTTTTCACTTGCACTGCTATTTACAATCCCCAGATTCAAATCAAAGAACAAGGC
CAGCCCGAAACTTTAGATTACCGTGTCTTTTTCGTTGATGATTCCGGCAAAAAGGTGTCCCCTTGGCATGACATA
CCACTGCATTTAGGTGATGGTGTTTTCAATTTTATTGCTGAAATTCCTAAAGAATCGAGTGCAAAGATGGAAGTT
GCTACAGATGAGCTGTACACACCAATAAAGCAAGACACAAAGAAGGGGAAACTTAGATACTACCCATATAATATT
CATTGGAACTATGGATTGCTTCCTCAAACCTGGGAAGACCCCTCATTTGCAAATGCTGAAGTTGAGGGGGCATTC
GGAGATAATGACCCTGTTGATGTTGTCCAGATTGGGGAAAGTCGTGCTAAAATTGGCC

> SEQ ID NO:268 129424FL 129116_300403_1d
CCCCCGAGTCTCCCGCCGCCGCCGCCGGGGGTCACTCCGCACCAACTCCGACGATCCCCCGGCGAGCTCTCGACG

Figure 2 continued

ATGGCGACGGCGGCGACGGCGTCGGCTACGGCGGCCACCCGCTTCACGCGGCTGGCGGGGGTCGGGCTCCGGCGC
ACGGCCCGCCTCCCCACGGCCGTGCGGTTCCAGCGCCGCGTGCTCGCCACCACCGCGCTCCTCAGGACCGCCGAG
CTCCGGCCCAAGGAGCAGGGCCTGCCCGAGACGCTCGACTACCGCGTGTTCCTCGTCGACGGCGGGGGCCGCAAG
GTGTCGCCGTGGCACGACGTGCCCCTGCGCGCAGGCGACGGGGTGTTCCACTTCGTCGTGGAGATCCCCAAGGAG
AGCAGCGCCAAGATGGAGGTCGCCACCGACGAGTCATTCACCCCCATCAAGCAGGACACCAAGAAGGGCAACCTC
CGATACTACCCGTACAACATTAATTGGAATTATGGATTATTTCCCCAAACATGGGAGGACCCAACTCTTGCAAAC
ACCGATGTCGAAGGAGCATTTGGGGATAATGATCCTGTTGATGTTGTTG

> SEQ ID NO:269 129870FL 1187453_302172_1e
gtctgatTTGGTCTGTATACGGTTGATACATATGACGAAGTGATTGAAGCTTGGAGTGAGTGGATTTTCATCAAG
CTTATCGGATTTGTTGAGCTGGTGAAGGTCAAGATGGCGATGGCGATGCAGGCCACCTCTTCCTCTTCTCTCCGC
AATACCTCCTTCCTTGCCTCTTTCCGTGGGGAACAAATTCCCGGTGCACAGAAATCCGCAGTCGGTGGCTTTGCC
TCCTCTCGTCAAGTGCAGAGTAACGTTTCGACAGTTCTTATCTCTGTGAGGAATGAGAAGAAAAAGATGAGGGGA
GTGAGTTGCAGAGCTTCTGCTGCAGATTCTCCAAAGCAAGTTGAAAGCAAAAAGGTTCTGATGATGGGAGGCACT
CGCTTTATCGGCCTTTACTTGGCCCGGTTGCTTGTACAGTCTGGCCACGAGGTCACCCTTTTTACCCGAGGAAAG
GCGCCCATTACCCAACAATTAGCAGGGGAGTCCGATGAGGAATACCAAGAATATGCCTCCAAAGTGAAGCACATG
CAAGGTGATCGTCAGGATTTCGAAGGCTTGAAGAGCAAGCTTTCCGAAGCATCTTTTGACATTGTGTATGATATA
AATGGAAGAGAGGCt > SEQ ID NO:270 129870FL 121946_300014_1e
cccccccctcaggccggtgtacatctacggcccgctcaactacaaccccgtggaggagtggttcttccaccggct
caaggCTGGCCGCCCCATCCCTGTCCCCGGTGCCGGCAACCAAATCACCCAGCTCGGCCATGTCAAGGACTTGGC
GACGGCGTTCGTGCTGGCGCTCGGCAACCCGAAGGCGAGCAAGCAGGTGTTCAACATCTCCGGCGCCAAGTACGT
CACCTTCGACGGTCTAGCACGGGCGTGCGCCAAGGCTGGAGGATTCCCCGAGCCGGAGATCGTCCACTACAACCC
CAAGGACTTCGATTTCGGGAAGAAGAAGGCCTTCCCCTTCAGAGACCAGCATTTCTTCGCGTCAATCGAGAAGGC
GACCTTGGAGCTCGGGTGGAAGCCGGAGTACGACCTGGTGGAGGGCCTCACCGACTCGTACAACCTCGACTTCGG
CCGCGGCACGTTCAGGAAGGCGGCCGACTTCACCACCGACGACATGATCCTCGGCAAGAAGCTCGTCAGCGTCTG
AGCTCGCCGCCGTCCTTTCCGGACAGCGGACGGATTGCTTGCTGCGCGAcgCGAGCGGCtGACCGGCCGGGCCGC
CATGGCCGGTGGGCAgGagcAAGCGGagacgGTTTCAGTTTTGTTATCAACGCTGgttTGgTacaATATGGATAg
ttgGATAcacgcGTACAGGcgTAAG > SEQ ID NO:271 129870FL 135395_300413_1e
CGGACGCGTGGGTGAGGAGAGGAAACATCAAACAAAAGAGAGAGAGATGGCAGGCGCAGCCTCCCTGAAGAGCAG
CCTCCTGCTACCATCTCCTATCTCTGACTTCAGTAGGGCAGCACTCTCCATCTCAACCCAGGCTAGGAGGAGGTC
ATGGCAGCCAAGGGGGGCAAGGATGCAGGTAGCAGCAGCTGCAGACTCCAAGAACATTCTTGTGATGGGGGGAAC
CAGGGTCATTGGCGTCTTCTTGTCCAGGCTCCTTGGCAAGGAGGGGCACCAAGTCACATTGTTCACTAGAGGAAA
GGCCCCCATTACCCAGCAGTTGCCAGGAGAGTCAGATGC > SEQ ID NO:272 129870FL 171849_300624_1e
cggacgcgtgggcggcccgctcaactacaagcccgtggaggagtggttcttccaccggctcaaggctggccgccc
catcccCTGTCCCCGGTGCCGGCAACCAAATCACCCAGCTCGGCCATGTCAAGGACTTGGCGACGGCGTTCGTGCT
GGCGCTCGGCAACCCGAAGGCGAGCAAGCAGGTGTTCAACATCTCCGGCGCCAAGTACGTCACCTTCGACGGTCT
AGCACGGGCGTGCGCCAAGGCTGGAGGATTCCCCGAGCCGGAGATCGTCCACTACAACCCCAAGGACTTCGATTT
CGGGAAGAAGAaggccTTCCCCTTCAGAGACCAGCATTTCTTCGCGTCAATCGAGAAGgcgaccTTGGAGCTCGG
GtggaaGCCGGAGTACGACcTgGtggAgggcctCAccGacTCGTACAaccTCGACTtcgg > SEQ ID NO:273 129870FL 21618_300070_1e
CCCACGCGTCCGGGCGAAGGGGATGATGTTGCAACAGCATCAGCCTTCTTTCTCTCTCCTTACTTCTTCTCTGTC
TGACTTCAATGGCGCTAAGCTCCATTTACAAGTCCAGTACAAGAGGAAGGTTCATCAGCCAAAAGGAGCACTCTA
TGTTTCAGCGTCGAGCGAAAAGAAGATTCTGATAATGGGTGGTACTCGATTCATTGGTCTGTTCTTGTCCAGGAT
CCTTGTCAAAGAGGGACATCAGGTTACATTGTTCACAAGGGGTAAATCTCCTATTGCCAAACAATTGCCCGGTGA
ATCTGACCAAGACTTTGCTGATTTCTCTTCTAAGATTCTTCACTTGAAAGGAGACAGAAAGGACTATGACTTTGT
GAAGTCAAGTCTTTCAGCAGAAGGCTTCGATGTTGTTTATGATATCAACGGGAGGGAGGCCGAAGAAGTTGAGCC
CATACTAGAAGCACTACCCAAACTAGAGCAGTACATCTACTGTTCTTCAGCTGGTGTTTATCTGAAATCTGATAT
CTTGCCACATTGTGAGGAGGATGCAGTTGATCCGAAGAGCAGGCACAAGGGGAAGCTGGAGACTGAGAGCTTACT
GCAATCAAAAGGTGTAAACTGGACTTCTATACGTCCTGTCTACATCTAC > SEQ ID NO:274 129870FL 270847_200128_1e

Figure 2 continued

TGAAGCAGGCACCACCTAATTACAACAATGGCTAGTTTGGTTGCAGTTCAACACAAACAGCCTTCTTTTGCTGTC
CTCCCTTCTTCCCATTCTGACTTCAATGGTGCCAAATTGATCTCCTCTCTTCAGTTTAAGAGGAAACCATGCCAG
CCAAAAGGAGCATTGCATGTTACAGCATCAAGTGCCAAGAAAATCCTTATAATGGGAGGCACTCGATTTATTGGT
GTCTTTCTATCCAGACTTCTTGTAAAAGAAGGCCATCAGGTTACTCTGTTCACAAGAGGAAAAGCTCCAATCTCT
CAACAATTACCAGGTGAATCAGACCAGGATTATGCTGATTTTTCCTCCAAGTTATTGCACTTGAAGGGTGACAGA
ATGGATTTTGATTTTGTGAAGAGCAGTCTTTCTGCAGAGGGCTTTGATGTTGTGTATGACATAAATGGACGTGAA
GCAGTAGAAGTGGAACCAATATTGGATGCATTACCTAATCTGGAACAGTACATATACTGCTCTTCAGCTGGTGTA
TACCTCAAAACTGATTATTTACCACATTTTGAGGCTGACGCAGTTGACCCAAAGAGCAGGCATAAAGGAAAGCTT
GAGACAGAGAGCTTGTTAGAATCACGAGATGTTAATTGGACTTCTGTAAGGCCTGTTTATATTTATGGGCCACTT
AACTATAATCCAGTTGAAGAGTGGTTCTTCCACCGATTGAAAGCTGGTCGCCCAATTCCAATTCCTAACTCAGGG
CTGCAAATAACTCAACTTGGACATGTGAAGGATCTTGCAACGGCTTTTATTCAGGTTCTTGGAAATGAGAAAGCA
AGCAAGCAAGTATTTAACATATCTGGAGAGAAATATGTCACGTTCGATGGATTGGCTAAGGCTTGCGCCAAGGCT
GGCGGCTTCCCTGAACCCGAGATTGTTCACTACAACCCTAAggAGTTTGACTTTGGCAAGAAGAAAGCTTTCCCA
TTCCGTGACCAGCATTTCTTTGCATCGGTCGAAAAGGCAAAGGCTGTGCTAGGTTGGAAGCCGGAATTCGAATTG
GTGGAAGGTTTGACAGACTCTTACAACCTAGATTTTGGTAGGGGAACTTACAGGAAAGAAGCTGATTTCTCTACA
GATGATCTTATTCTAGGAAAGAATTAGTTCTCCACACCTACGCTTTCTGCTTTCAATTTTTTCAAATTTTGGCTT
CTTGCTTTTGTGAAATTGGGAATATAACATTCATACACATCTGCGTATGATATATTTTTCATTGTTTTGAG

> SEQ ID NO:275 129870FL 256427_301672_1e
ATGGCTGCATCGTCTGCAATCAGAGGCTACGGTGCAGCAACTGCTGCTTCTCCTTACGATGTTTCAGTGCAGGAA
CGAAGATATGGAGCATCCATGTTGAAGAAGAATGTTTACTGCGGCAAAGTTGAGCTATGTCGAGCTTCGGACTTC
ACACAAAATGTCTTGCGCCAGGCCGCGAATCTAACGAGACTTCAAGCTCAAGCAGTCCGAAAGACGTCCGTCGTT
GCCATGGCCTCCTCATCGAAAAACATTTTGATGATGGGAGGAACGCGGTTCATTGGAGTTTACCTGGCAAGGTTA
CTTGTGAAAGCCGGACACGAGGTGACGCTCTTCACTCGTGGAAAGTCGCCGATAACGCAAAAAATTGCCAGTGAA
ACTGATGAAGAGTATGCAGAGTATTCGTCGAAAGTACGTTTCACATCTGGTGGCTATTTATCTTTTCGTGTCTGC
CTTTCGCCAGATAAAACATATTCAAGGCGATCGCCAGGACTTCGAGGGGATGAAGAGCAAAATTGCCAATGCTGG
TTTCGAGATCGTGTATGATATCAACGGGAGGGAGGCTGTCGAAGTTGAACCCATCCTTGATGCACTTCCGGGCTT
GAAACAGTATGTATATTGTTCATCAGCAGGAGTATACTTGAAG

> SEQ ID NO:276 129870FL 202041_300722_1e
GTTTTTGCAGGGATTGTGAGGGGGAGGCCGGTGCCGATCCCGGGGTCGGGGATGCAGGTGACGAACATATCGCAC
GTGCGCGACCTGGCGAGCATGGTGGCGCTCGCCGTGGAGAGCCCCGGCGCGGCGGCGGGGAGGATCTTCAACTGC
GTCTCCGACCGCGCCGTCACCTTCAACGGCCTCGTCAAGATGTGCGCCGCCGCCGCCGGCGCCCAGCCGGAGATC
CTCCACTACGACCCCGCCGCCGTCGGCGTCGACGCCAAGAAGGCCTTCCCCTTCCGCAACATGCACTTCTACGCG
GAGCCGAGGGCGGCGAAGGAGGTGCTTGGATGGAGGAGCTCGACGAACCTGCCGGAGGACCTCAAGGAGAGGTTC
GCGGAGTACGCCAGCAGCGGCAGAGGGCACAAGGAGATGAGCTTCGACCTCGACGACAAGATCATCGCCGCCGCC
TAACAACACCCATCTCATCTCACCTCGTCATGGTCAAATACAAATACAAAGTGGTCGGGGATCTCTTCTTCTCGT
GATTGATTTTCTTCTCCCTCT

> SEQ ID NO:277 129870FL 190530_300693_1e
ccccccccGGAGGAGAGTAAACAAGAAAAAAAAGAGAGAGAGATGGCAGCAACAGCCTCCCTGAAGAGCAGCCTC
CTGCTACCATCTCCTATCTCTGACTTCAGTAGTGCAGCACTCTCCATCTCAACCCAGGCTAGGAGGAGGTCATGG
CAGCCAAGGGGGGCAAGGATGCAGGTAGCAGCAGCTGCAGACTCCAAGAACATTCTTGTGATGGGGGGAACCAGG
TTCATTGGTGTCTTCTTGTCCAGGATCCTTGTCAAGGAGGGGCACCAGGTCACATTGTTCACTAGAGGAAAGGCC
CCCATTACCCAGCAGTTGCCAGGAGAGTCAGATGCAGAGTATGCAGAGTTCTCTTCAAAGGTGTTGCACTTGAAA
GGTGACAGGCAAGACTTTGATTTCGTTAAGACAAGCCTTGCGGCAAAGGGCTTCGATGTTGTTTACGACATAAAC
GGGAGAGAAGCTGTTGAGGTAGCCCCAATCCTAGACGCATTGCCAAACCTTGAACAGTACATCTACTGCTCATCA
GCAGGAGTGTACCTGAAATCAGACCTGCTCCCGCACTTCGAGACCGACGCCGTCGACCCGAAAAGCCGGCACAAG
GGGAagctGgAgaCgGAgagccTGCTggagaccCGGGAc

> SEQ ID NO:278 129870FL 131306_300513_1e
gcgcgccttaattaggatcgaaggaaggtcatcaagtaacttggTTCACAAGAGGGAAAGCACCAATCAGCCAAC
CATTACCCGGGGAGTCAGAACAAGATTACCTAGATTTCTCTTCCAAGATCTCGCACTTGAAAGGAGACAGAAAGG
ACTACGATTTTGTTAAGACTAGCCTAGCAGCTGAAGGCTTTGACGTTGTCTATGATATCAATGGAAGAGAGGCAG
ATAGAGAGAGAGACAATGGCAATGGCAACAAGTAGGTTGGTGGTGGTGCAACAAAAACAACCATCCTCATGTCTA
TTACCACCATCATCTCTTTCTGATTTCAATGGTATTAGACTGAAACACCCAATTCAGTACAAAAGAAAGGAATGG
CAGACAAGAGGAGCATTGCAGGTGAAAGCATCAGCTGCAAAGAAAATCCTGATAATGGGAGGAACCAGATTTATT
GGAATCTTTTTGTCTAGGCTCCTTGTGAAGGAAGGTCATCAAGTAACTTTGTTCACAAGAGGGAAAGCACCAATC

Figure 2 continued

AGCCAACCATTACCCGGGGAGTCAGAACAAGATTACCTAGATTTCTCTTCCAAGATCTCGCACTTGAAAGGAGAC
AGAAAGGACTACGATTTTGTTAAGACTAGCCTAGCAGCTGAAGGCTTTGACGTTGTCTATGATATCAATGGTATT
GGAAGAGAGGCAGAAGAAGTAGAACCCATATTGGACGCGCTTCCAAAGCTTGAGCAGTACATATACTGTTCATCC
GCTGGTGTGTATCTGAAGTCTGATTTACTGCCTCATTTTGAGTCTGATGCAGTGGATCCCAAGAGCAGGCACAAG
GGAAAACTTGAAACAGAGAGTTTACTTGTATCAAAGGGCGTGAACTGGACTTCGCTGAGACCAGTTTATATCTAC
GGTCCTTTGAATTACAACCCTGTTGAAGAATGGTTTTTCCACAGATTGAAGGCCGGTAGACCAATCCCCATACCA
AATTCTGGCAACCAGATAACACAATTGGGTCATGTTAAGGATTTGGCGACCGCATTTATTAACGTTCTTGGTAAC
GATAAAGCGAGCCAGCAAGTGTTTAACATATCTGGAGATAAATATGTGACATTCGACGGATTGGCAAGGGCTTGT
GCTAAGGCTGGTGGATTTCCTGAGCCAGAACTAGTTCACTACAATCCTAAAGAATTCGATTTTGGCAAAAAGAAG
GCATTCCCCTTCAGagaCCAGCATTTCTTTGCATCAATTGAGAAAGCAAAGAGTGAATTGGGGTGGAAACCagaa
tATGATTTGGTggaaggtcTAACAGaCtccTACGATC > SEQ ID NO:279 130294FL 1191066_302180_1e
gATTTCCTtaTGCTTATTATTATTATTCCTTGAAGCCACTCGCTCTCATTTCTACTTCCCGTCAGGTGCAAGCGT
TTACCTTCAGGGGCTGTACCCTAGCTATGGCCGCTTCCATGACCCTAGGGCACCAAGTCACAGTGGGAGGAGGTG
TAGGTGGGGGTGCGAATGCGCCTCCCCCGCCTTTCTTGCGCAACGGATTTGCCAAAGGGCTGGGACTGGGTATAG
GGGGAGGAGTAGGGGCTTTGACCAAAGGTCGGCGAGAAGGGGGCGCTCGGTGCTCGGTGGCCACTCTGGCCATCC
CTAAGCCCAACCGTGATCTCCTCTCGGAGTTCGAGAAGCGATGGCAAAGGGCTGTGGACAACCCCTTGGAAGGCG
TCCCCTTCACCTACGAAGACTTCCGAGGTGCCCTCTCCAAGTACGACTTCAACTTCGAGATTGGTGATACCGTGA
AAGGTACCGTGTTCATGACGGAATCCAATGGTGCTCTTGTTGATATTGGTGCCAAGGCACCAGCCTTTCTACCTA
CTGTTGAAGCTTCATTGCACAAGGTCAAACATGTTCTGGAAGTAGGGATATCTTCAGGTATTGTTGAAGAATTTC
AGATTATCCGAGAGGACGATAACAATGGAAGAATGATTTTAAGCCTtaggaAAGCACAATATGACAtggcttggg
AACGATGcaaacagttgaTGGAggagGATGtt > SEQ ID NO:280 130294FL 56419_300139_1e
caaagcttgtcctcagcaaccgtaaagctgtagcagatagCCAAGCTCAGCTTGGAATTGGATCTGTGGTCCTCG
GAGTTGTTCAGAGCTTGAAACCTTATGGTGCCTTCATTGACATTGGTGGAATCAATGGGCTTCTTCATGTCAGTC
AGATAAGTCATGACCGTGTCTCAGATATCGCAACTGTTCTTCAGCCTGGtgACACTTTGAAGGTTATGATATTGA
GTCACGACCGTGACAGAGGAAGAGTAAGTCTctccaCAAAGAAGCTGGAGCCAACACCTggTGATATGATTCGta
aCCCAAAACTTGTGTtcgaGaaggCtgaggagATGgctcagacAttcagaCAGAGAatt > SEQ ID NO:281 130294FL 47044_300177_1e
AAAACTCTCTGTGTGAGTGAGTGAGACTCAACCATGGCGTCTTTGGCTCAGCAATTCTCGGGATTGAGATGTTCC
CCACTCTCTTCTTCTTCTAGGTTATCGAGGAGAGCTTCGAAGAACTTTCCCCAGAACAAATCTGCCTCTGTTTCT
CCGACTATTGTCGCCGCGGTTGCAATGTCTAGCGGTCAAACAAAGGAGCGTCTTGAGCTGAAGAAGATGTTCGAA
GATGCTTATGAACGATGTAGAACTTCTCCTATGGAAGGTGTTGCTTTCACCGTCGACGATTTCGCTGCTGCTATT
GAACAATACGACTTCAATTCCGAAATCGGCAC > SEQ ID NO:282 130294FL 225627_300989_1e
GGCGATCCATCGATCGAGCGGCGATGGCGGCGGCAGTGGCGGCGGCGACGGCAGCACAGGTAAACCTAGTAGGAT
TCAGCAGCAGCAGCGGCTTCGGCGGCAGGCCAGGGTTCCTCGGCAGCAATCGGCGGACCGGCATCGTCGCCAGGA
ATCCCGCCCGGATCCACTGCGTGGTCGCATTCGCCGACCCGCGGTCCCGGAACCTGGACGTCAAGGAAGAGATCG
AGCGGCGGTGGGAAGCTCTCCAGGAGAATCCACTAGAGGGCGTTCCATTCACGGTGGAAGAATTCGAGGAAGCTC
TAACCAAGTATGATTTCGATCACAGCGTTGGAGACGTTGTCAAGGGGACCGTCTTCGTCACCGACAAGCTTGGAG
CTCTCGTCGACATCGGTGGCAAGTCCATGGCCTTTCTTCCAATGGACCTGGCGTCGGTCTTCAAGCTCAAGGATC
TCCGGGTGATGGGACTCTTCTCCGGCGTCCGGGAAGAGTTCGAGGTGGTGAGAGAAGACGAGGAGAACAGCCGGT
TCATACTCTCTCTCCGGGAGATGCACGTAAAGATGTCGTGGGAGAGGCTGCGGCAGATCCAGGCCGAGGACGCTG
TTT > SEQ ID NO:283 130294FL 160262_200051_1e
atcaatttcCTCGCTTCCGCCAAAATGGCTTCTTTGACACAACAATTCGGAGGGTTGAAATGCCCACCAATTTCA
ACAGCAAGGGTTGAATCTAAGAAGCTTAAGGTGAATCCCATTAATCATCAGAATAAGAAGGCTAACAAAGCAAGA
GTAGTAGCACAAGCTGCAGCAGTGGTCACAAATGCACAAACAAGAGAAAGACAAAAGCTTAAGGAGATGTTCGAG
GATGCCTATGAACGATGCCGTACTGCACCTTTGGAAGGTGTTGCCTTTACTGTTGAAGATTTTCACTCTGCCCTT
GAAAAATATGATTTTGACTCCGAAGTTGGTACCAAGGTCAAAGGAACAGTTTTCTCTGTGGATGCAAATGGAGCT
CTAGTTGACATCACTGCAAAATCATCTGCATACTTGCCTTTACGGGAGGCTTCACTTCACACCATCAAGCACGTA
GAGGAAGCTGGAATATTTCCTGGTTTGCGTGAGGAGTTTGTGGTGGTTGGCGAAAATGAAGCTGATGATAGTTTG
GTTTTGAGCTTGCGTTCGATTCAATATGACCTTGCATGGGAACGATGTAGGCAGCTACAAGCTGAAGATGTTGTT

Figure 2 continued

GTCAAAGGCAAGGTCGTTGGTGCAAACAAAGGTGGAGTGGTGGCTCTGGTGGAGGGGCTTCGTGGTTTTGTTCCG
TTCTCGCAGATATCAACGAAATCAACTGCAGAGGAACTTTTGGAAAAGGAGCTTCCTCTGAAGTTTGTTGAGGTT
GATGAAGAGCAATCCAGACTTGTGCTCAGCAATCGTAAGGCCATGGCTGATAGTCAGGCACAATTGGGAATAGGC
TCAGTCGTTCTTGGAACAGTTCAGAGCTTGAAACCATATGGTGCCTTCATTGACATTGGTGGGATCAATGGCCTT
CTTCATGTGAGTCAGATTAGTCATGATCGTGTCTCTGATATTGCAACAGTCCTCCAGCCTGGTGACACTCTCAAG
GTCATGATATTGAGCCATGATCGTGAGAGAGGTCGAGTGAGCCTTTCAACAAAGAAGCTAGAGCCTACACCCGGA
GACATGATTCGCAATCCAAAGCTTGTCTTTGAGAAAGCCGAGGAGATGGCCCAAACATTCAGGCAGAGAATTGCC
CAAGCGGAAGCCATGGCCCGTGCAGATATGCTGAGGTTCCAacCTgagaGTGGATTGACCCTGAACTCTGACGGG
ATAttatgCcCgCTGACCTCTGAACTACCTGAAGATGGACTGGATTTGAgtgagattcCgtcagCTGAAGAttaa
tgaTTCTAAATGGAGatccCgcttctTTTTGACCTTttTgttgCagaaattggatAAATGCTCTTTGTaggctTa
GGAACCATTcatGATAAACGTattCCgtccGCAAtcaTTCtattgcaTTattaccatgattctaaACAAtttgGC
TTGCactactTgctaacaaTGAATCATTGTTAAATAGca > SEQ ID NO:284 130294FL 167654_300549_1e
gaattcagggaaaacagagtcgtttctggtacaaattaggtctaaagatggcgtctttAGCTCAACAATTCTCAG
GATTAAGATGCCCACCACTTTCTTCTTCTCATCTAACAAAACCCTTTTCTTCAAAACCCCAGAAAACCACCTTTT
CACCTATAGTTTCAGCAGCTGTCATTTCTAATGCACAAACTAAAGAAAGAAGTAGACTTAAAGAAATCTTCGAAG
ATGCTTATGAAAGATGTAGAACTACTCCAATGCAAGGTGTTGGTTTTACTGTTGATGATTTTCATGCTGCTCTTG
AAAAGTATGATTACAATTCTGAGATTGGTACCAGGGTTAAAGGAACTGTGTTCTGTACAGACAACAACGGAGCAT
TAGTTGACATCACGGCGAAATCTTCAGCCTATTTACCAATCCAAGAGGCATGTATTCACAAAATAAAGCATGTAG
AAGAAGCAGGAATAGTTGCAGGCCTACGTGAAGAGTTTGTGATTATTGGAGAGAACCAAGCTGATGATAGCTTGA
TCTTGAGTTTGCGTTCAATCCAATTTGACCTCGCATGGGAACGgtgTaGaCAACTTCAGgCagaggATGTCGTCc
TcaagggTAaggttgtTGGTGGAAACAAa > SEQ ID NO:285 130994FL 103518_300363_1e
tgtatggcgcagagtggccattcggccggggGAAGCCAAGTTTGGGAAAAATCTTAAAAGAAAGAAAGAAATGATG
ACGAATCGCCACTTCCTCTTCGCTCTTCTTTTCACTTTCTTTCTTTCAGCTGTTGCTGCAGATTCTTCTGAAGAG
TGTGTATACACATTGTATGTTAAAACTGGATCAATCATAAAGGGTGGAACAGACTCCAAAATCAGCGTTACACTT
GGCGATGCTAAAGGAAAATCAGTATATATTCCAGATCTAGAGAAATGGGGTTTAATGGGCCCAAATTATGATTAC
TACGAAAGGGGTAATGTGGATATCTTCACTGGTAGAGGCCAATGTTTAAGCCCACCAATTTGCAGGCTTAATGTT
ACTTCCGATGGATCAGGTGACCACCACGGTTGGTTTCTTGATTTTGTTGAGACTACTTTTACTGGGCCACACAAA
ACTTGTAGCCAATCCATATTCTATGTCGAACAATGGTTGGCTTCTGATGCTCCTCCTTATGAGTTATCAGTTTCT
CTTGATGGTTGTAAAAAGAAGACTGGGCTTCGACATGCTCGGCGTTTTGTCGTGGGCCAGCCCAATGGGTCTGCT
TCAGAATAGTTTGGCCCGTTGAAGTTCTTTTTGTAATTTTGTCGTTGAGATGATTTTGATGTGTAGATTGCCCTG
TGTTTTCCCTTCTCTTTGGTTGAAATAAATTTCTTGTTTGGGGCTTCCTTTCTTGCTTGTTTAGTCGTCATATCT
TTGACTTATTGGCTCTTTTGGCAATTTGCAATCTTTTATGTACTCAataag > SEQ ID NO:286 130994FL 252626_301603_1e
GATGTCGACGGGGAAAGGCTTAGCTCTAATCCTGGCATTTGCTGCCATCGCCACCTGCATCACCTCTGCTACGAA
CCAATGCGTATACACTATTTATGTGAGGACGGGAAAGGTGATAAAAGGGGGGACAGATTCAAACATTTCGGCACG
ATTCTATGATGCCAACGGATACTATATCAATTTGGAAAATTTGGCAGAATGGGGTGGTTTGGGAGGTCCTGGCTA
CAACTACTTTGAGAGAGGCAATTTGGATGTGTTCACAGGCCTTGGGCAGTGCCTCACGGCCCCCATTTGCGCGCT
CAACCTGACCTCAGACGGCACTGGAGACCAACACGGGTGGTACTGCAACTATGTCGAGGTCACCTCCACCGGGCC
CCACATCCCTTGCAGCCAACACCAATTCACCATCGAGCAATGGCTTGCCACTGACACCTACCCTTTCGAGCTCAA
TGCCACCCGTGACGATTGCCTGGTCGAGGGCAAAACCAGCGCCTCCAAGGCAATTTCATCAGAGTCGAGCTAGAG
TTCCAGCTGGGCCTTTTTTGGCTTCCGTTTTTGATGAATAAGCAAGCTCCTTCT > SEQ ID NO:287 130994FL 279714_200064_1e
gagaggaaGAAAAAGCTCAAGAGAAGACATGGGAATAGCAGCTCACTCCAACCATTTCTGGTCCCTTCTCTTCAT
AGTCTTTTTCTCTTTCTCCATCTCCTCCATTTCCGGATCTGATGATGATTGCGTGTACACAGCTTATGTCCGAAC
GAGTTCAATAATAAAGGGTGGAACAGATTCGATTATCAGTTTGAGTCTCTACGATGCAAACGGGTATGGTCTTAG
AATCAAGAACCTTGAGGCCTGGGGTGGGCTTATGGGCTCTGGTTACAACTATTTCGAGAGGGGAAATTTGGACAT
TTTCAGCGGACGAGGCCCATGTTTGACTGGGCCTGTCTGCAAAATGAATTTGACTTCCGACGGAACAGGCAAAGG
CCATGGATGGTACTGTAACTACGTGGAGGTCACCGTCACCGGAGTCCATAAAGCATGCAACCAACAGAATTTCGA
AGTGGAGCAGTGGCTAGCTACTGATGCTTCGCCGTATGAGCTTACGGCTGTTAGAGACAACTGTAAGAAGTCCAA
GTCCGATGAGAAACTGTCCATTTCCGATGTCTACGGAACTCATTCCACTCCACCTGTTTCTGTGATTTAAATTTC
TAGTTATTGGGTTTTAATGGGCCTGGACCCACATTTCCCTTTTACCCTTATTACTgtgATGTGAAATTTATCAGG
GGTAAGAATGACATttCATgTgTgTcaatgttgcTttCATGTTATAGTATGAGatagaggAgtaGT

Figure 2 continued

> SEQ ID NO:288 130994FL 47162_300174_1e
AAAAAAACAAAATGGCTCGTCGCGATGTTCTCCTCCCTTTCCTCCTCCTTCTCGCCACCGTCTCCGCCGTAGCTT
TCGCCGAAGATGATCCAGACTGTGTATACACATTCTACCTCAGAACCGGATCGATCTGGAAAGCCGGAACCGATT
CGATCATCAGCGCAAGAATCTACGATAAGGACGGTGACTACATCGGAATCAAAAACCTTCAAGCTTGGGCTGGAT
TAATGGGACCTGATTACAATTACTTCGAGAGGGGTAATCTCGACATTTTCAGTGGAAGAGCACCGTGTTTACCTA
GTCCGATCTGTGCCTTAAACCTAACCTCCGATGGCTCCGGCGATCACCATGGTTGGTACGTTAATTACGTTGAG

> SEQ ID NO:289 130994FL 292168_200194_1e
ttttccTCTCATTTTCTAGAGAAAGAAACAACAAGACGTACAGAACGAGAGTTCAAGAATCTGCAATGGGAGTGG
CTCGAGTTAACCAATTCTGGTTGCATCTTGTCATCCTCTTCTCCATCTCCGTTGCTTCCATTTCTAGCACTGTAA
GTCACCCTTCTCTACTTCTACTACGTTGACAGATTTAGAGTAGATGCACTGGATTACGTCGAACTCACCGCGTTA
AAAAGCTGCCCGGTGCAATAAGCTCCCGTAGTGGACGGGTCCGGAGAAGGGTCGAACTCACTGCTTTACTTCTTA
ATTACCTTATATGTAAGAAAAGAAACAAATATATATGAGTAAGAATACAACACATTGATTCTAAATTATAAATTT
GTCACTGTGTACCATAATATTTTTCATTTTGCAATTGCTGAATTGATGGGAAAATGCAGGAACTGAATTGTGTAT
ACACAGCTTATGTTCGGACTGGGACATACTGGGGATCTGGAACTGACTCAAAAATTTCCTTGTCTCTTTATGATG
CCACTGGCCATGGACTTAGAATCAATAACCTACAAGCCTGGGGCGGGCTTATGGGCCCGGGTTATGACTACTTTG
AAATGGACCAATTGGATATGTTTACGGGCCGTGGTCCATGTTTGACTGGGCCAATCTGTAAAATGAACTTGACTT
CTGATGGATCAGGTGAGCACCACGGATGGTACTGTAACTACGGGGAAATCACGTCTACAGCAGAACACAAACGAT
GCAGCCAACAGGCGTTCACCGTGGAGGCGTGGCTCAGTGCCGGTCAGTACCCAGATGGGTTGACCGCCATTAAGG
AACAACTGTAAGCGTATTTCCAACGAACAACAACCAATTCATGATTCTGATCAATCTTATCATGTTGTGGATGTA
ATTTAATTCGAGTTTATTGGACGTTGTATGATTTACGAAGGCCATTTAGGCCAAGGCCTGATATGTACTCTCACG
AGTGCTACATAGTTGGAATGAAAAGTTTTCTTTACCCATATCTTT > SEQ ID NO:290 130994FL 274067_200147_1e
GGGCGGACGCGTGGGCGGACGCGTGGGCGGACGCGTGGGGCCTTTTATCCTCTCATTTCTAGAGAAAGAAAAAAT
TTCTCTTGCACAACTAGCTGCCATGGGAGTAGCTCATCAAGTTAACCAATTCTGGTTCCCTCTCATTATCATCCT
CTTCTCCATCACCATTTCTTCTACTTCTGGAACTGAATCAAATTGTGTGTACACAGCTTACATTCGGACTGGGCC
ATTCATGGAGGATGCAACTGACTCAAAAATAAGCTTGACTCTCTACGATGCGAGTGGCTATGGAATTAGAATCAA
GAACCTAGTGGCTTGGGGTGGGCTTATGGGATCAGGGTACAACTACTTTGAAACGGACCACTCGGATATGTTCAG
TGGCCATGGACCATGTTTGACTGGGCCGATCTGCAAAATGGTCTTGACTTCTGATGGTACAGGCCGACACTCAGC
ATGGTACTGTAACTACGTGGAAGTCACCTCAACAGGAGACCACAAACAATGCAGTCAACAGCTGTTCAAAGTGGA
TCAGTGGCTTAGCACAGATCGTTCGCCGTATCAGTTGACTGCCACAAGAAACAACTGTAGGCGTATATCCGGTGA
CCAACAACCCATTGTTGTTGATGTAATTTAATTCGAGTTCATCATATTGGGCTACTTACAAACTAC > SEQ ID NO:291 130994FL 147510_301253_1e
AGAGAGTTCAAGAAACCATGGGAGTAGCTCAAGTTAACCAAATATGGTTCCATTTCATGATCATCCTCTTTTTCA
TATCTTCTATTTCGGCATCTGAAGATGATTGTGTGTACACAGCTTACGTTCGAACTGGATCAATCATAAAGGCTG
GAACTGACTCAAACATTAGTTTGACTCTCTACGATGCCGATGGCTATGGGATAAGAATCAAGAACTTAGAGGCAT
GGGGTGGGCTTATGGGCCCAGGTTACAACTATTTTGAAAGAGGAAACTTGGATATATTCAGTGGACGTGGTCCAT
GTTTGAATGGGCCGATCTGCAAAATGAATCTGACATCTGATGGATCGGGCCCACATGCCGGATGGTACTGTAACT
ACGTCGAAGTTACAGTTACTGGAGCCCACCAACAATGCAACCAGCAGCTTTTCACCGTGGAGCAGTGGCTCGGCA
CTAACGTTTCGCCATATGAGCTGACGGCCGTCAGGAACAACTGtAAGAAGTCCAAGTCCACAGTTTATGATTCTG
AATCTTATCCAGTTGTTGATGTAATTTAATGGGGGcagcccCCACATAttGTCTCTGTGGtttttttctttagaGtG
agaaGAattaacgTGAtgc > SEQ ID NO:292 130994FL 175132_300530_1e
AGGGCCTTCGAGACTTGGGAGGTTGGAGCGAGCAAGCTCGGCCATGGCGAAGCTCTCCTGCCTTCTCATCGTCTC
CTTCGCCGTCGTCGCGGCGTTGGCGGCCACGGACGACGACGCGGCGGCGGCGGCTGAGGGGATCACGGTGGCGGA
GGCGTCGTCGGACCCGGAGAACAAGTGCGTGTACACGATATACGTGCGGACGGGGACGATCTGGAAGGGCGGGAC
GGACTCGGTGATCGGCGTGACGCTGCTGGGCGCCGACGGCTCCGGGGTGCGGATCCGCGACCTGGAGCGGTGGGG
CGGCCTCATGGGCGACGGCCACGACTACTACGAGCGCGGCAACCTCGACATCTTCAGCGGCCTCGGCCCCCTGCAT
GCGCCAGGCGCCGTGCCGGATGAACCTCACCTCCGACGGCACCGGCCCGCACCACGGCTGGTACTGCAACTACCT
CGAGGCCACCGTCACGGGTCCCCACCTCGGCTGCGCGCAGCAGCTCTTCACCGTCGAGCAGTGGCTCGCCACCGA
CGCATCGCCCTACCGCCTCTACGCCGTCGTCGACAACTGCAACAAGGCCAAGGACGCCGCCG > SEQ ID NO:293 130994FL 1108676_301519_1e
GTCATCACACAAGTGAAGAAGCAGTAGCAGTAGAAGGAGATAGAAGGGAACCTCTCTCTCTCTCTCTCTCTCTTT

Figure 2 continued

GCTGATGATGAAGACGACTATGGCTGTTTTCGCCCTTCTCTCTCTCTTCCTTCTTCTCCTCCCCCCTTTTCCTTC
ATCAGCTGATGATCCTTGTGTATACTCAATCTATGTACGAACGGGGTCAATATTCAAGGGGGGAACGGATTCGAA
GATGAGTGTGGAGCTCTACGATGCGAATGGGTACTACATTACGATCAACAATTTGGAGGAGTGGGGGGGTTAAT
GGGTCCAGACCACGACTACTATGAGAGGGGCAATCTTGACATCTTTAGTGGTTTGGGGGACTGCCTGACCGGACC
CATCTGCGCTCTCAACCTCACCTCGGACGGCACGGGGGCCCACCATGGGTGTATTGCAACTACCTGGAAGTTAC
TGCCACGGGTGCCCACATCCCTTGCTCCCAACAGCTCTTTACCATAGAGCAATGGCTTGCCACTGATACCTCTCC
TTACTCCCTCACTGCCCTTCGATATAATTGCCCTGATGCTTTGTCCTCGCCTCGCTTCCCTCGCATGCCTTCCAA
TTCGCAACCGAAGAATGGTCAACTAATGTCCCATTAGTACTCTATCACCCTGCTTCGTAATAAAAAGATAGCCCC
TTCTTGTGTACTATGGAGGGAGGGGGGTATCTCTCTCAAGGtaccttatttgttGATGtttctcgaggcacctcg
caTTAAtgtatgTGttgtttactaTcttgtacGCttgtgtGATAAATct > SEQ ID NO:294 130994FL 157312_301737_1e
tttgcctttattcgttctcATTTTTCTAGAGAAAGAGAGTTCAAGAAACCATGGGAGTAGCTCAAGTTAACCAAA
TATGGTTCCATTTCATGATAATCCTCTTCTTCATCTCCATATCTTCTAGTTCTGCATCAGAAGATGATTGTGTGT
ACACAGCTTACGTTCGAACTGGATCAATCATAAAGGCTGGAACTGACTCAAACATTAGTTTGACTCTCTACGATG
CCGCTGGCTATGGGATAAGAATCAAGAACTTAGAGGCATGGGGTGGGCTTATGGGCCCAGGTTACAACTATTTCG
AAAGAGGAAACTTGGATATATTCAGTGGACGTGGTCCATGTTTGACTGGGCCGATCTGCAAAATGAATCTGACTT
CTGATGGATCAGGCCCACATGCCGGATGGTACTGTAACTACGTCGAAGTTACCGTTACTGGAGCCCACCAACAAT
GCAACCAGCAGCTTTTCACCGTGGAGCAGTGGCTCGGCACTGACGTTTCGCCGTATGAGCTGACGgccGTCAGGA
ACAACTGTAAGAAGCCAAAGTTTGAgaaACAACAGGCCTTTTATGATTCTGAATCTTATCCAgttgttGATGTaa
TttaatgggggTAg > SEQ ID NO:295 232732FL 105222_300372_1e
aaaaatctcataaacgaaacacaaaaaaaaaaaccctctctcgAAAATTAAAAATAAAAAATACCCGGCGAATCTC
CGACGATGGCTTTGCCGGAAAATTTAACCAGAGAGCAGTGCCTATACTTAGCAAAGCTCGCCGAGCAAGCCGAGC
GTTACGAGGAGATGGTAAAATTCATGGACCGACTCGTAGCTGTCTCGGCTTCCTCTGAACTAACCGTAGAAGAGC
GAAACCTCCTCTCGGTAGCTTATAAGAACGTCATCGGTTCACTTCGAGCCGCGTGGAGGATAGTATCGTCAATTG
AGCAAAAGGAAGAAGGTAGGAAGAACGAGGAACACGTGGTTCTAGTGAAGGATTATAGATCTAAGGTTGAATCTG
AGCTTAGTGATGTATGTGCTGGAATTTTGAAGATTTTGGATCAGTATTTGATTCCTTCGGCTTCGGCTGGTGAAT
CGAAGGTGTTTTACTTGAAGATGAAGGGAGATTATTATCGTTATTTGGCTGAATTTAAAGTTAGTAATGAACGTA
AGGAGGCTGCTGAGGCCACTATGCTTGCCTACAAAGCTGCTCAGGACATTGCGCTTGCTGAGCTTGCCCCAACAC
ATCCTATACGACTTGGGCTAGCTCTCAaCTattcAGTATTCTACTAtGAGattCTGAATGCATCagaaaaaGCAT
GCaGCATGgccaaaCAggccTTTg > SEQ ID NO:296 232732FL 1096679_301432_1e
GCTGTGTTTATCTTCTTCGCCTTCGTGTTCGTCGGTGGTGTTGGTAGTGGGAAGATGGGTGTGGAGAAGGAGCGT
GAGAGTGATGTGTACATGGCTAAGCTCGCTGAGCAGGCGGAACGTTATGATGAGATGGTGGAATTCATGAAAAAG
GTGGCAAACTTGGATGTGGAGCTATCTGTAGAGGAGAGGAATCTGATGTCAGTTGGGTACAAGAATGTGATTGGG
GCACGGAGGGCCTCTTGGCGCATCCTCTCCTCCATCGAGCAGAAGGAGGAGGGAAAAGGCAATGAAGTGAATGCC
AAGCGCATCAAAGAATACAAGCACAAGGTCGAGGAAGAGCTTTCAAACATCTGCAACGATGTCCTCTCCGTTATT
GAGGATCATCTCATCCCTGCGTCTAGCACGGGGGAATCTTCTGTCTTCTATTACAAAATGAAAGGGGATTACTTC
CGATATttgGCAGAGTTTAAATCTGGAAATGAGAAGAAGGAAGCCGGAGAGCAGTCTTTGAAAGCATACCAGGCT
GCTATGGACATAGCGACATCTAGCCTTCCGACGACTCATCCGATCAGGCttggTcttgctCTCAACTTCTCCGTT
TTCTACTATGAAATTATCAACTCCCCCGAGAAgGcatgccagctggCAAAACAAGCTTTTgatgatg > SEQ ID NO:297 232732FL 1098550_301485_1e
acctctaagccttgcagataacccgtcttgttcatctctctttctctcTCTCTCTCTCTCATCTTCTCTAGCTCT
CTCTCTGTGTGTCCCCTGTTTCCCTGTCTTAGACCATGACTCCGTCGATGGAGGGGGGCAAGCGGGAGGAGAATG
TGTACATGGCGAAGCTTGCGGAGCAGGCCGAGCGGTACGAGGAGATGGCGGAGTTCATGGATGCCGTCGTCAAGG
ACGGTGCTGACGAGATGTCGGTGGAGGAGCGGAACCTCCTCTCCGTCGCGTACAAGAACGTGATTGGCGCGCGTC
GCGCCTCCTGGCGCATCGTCTCCTCCATTGAGCAGCGCGAGGAGAGCAAGGGCAACCAGGAGCACGTCTCTGCCA
TCCGCGACTACCGTGCCTCCGTCGAAACCGAGCTCACCAAGATCTGCAAAAGCATCCTTAGCCTCCTCGAGATGC
ACCTTGTCCCTTCCGCCACCACCCCCGAATCCAAAGTCTTCTACCTCAAAATGAAGGGCGACTACCACCGCTACC
TTGCGGAGTTCAAAATCGGGGCGGACcCGCAaaaaaCtggcgataaaTACTCTCAccgcctACAAATCTgctCaGG
AAATAgccTtggctGagCtgccTTCAACACACCCCATTCGTTTGGGGCttgctCTAAAt > SEQ ID NO:298 232732FL 1117183_301818_1e
TACAAATCCTCGACTGTGAAAGGAGCTTTCGCCATCTCTCTCCATGGGAATCGAGATGGACCGCGATGGGAATGT

Figure 2 continued

CTACATGGCCAAGCTCGCTGAGCAAGCCGAACGCTATGATGAGATGGTGGAGTTCATGAAGAATGTGGCGAATAT
GGATACGGAACTGACTGTGGAGGAGCGCAACCTATTCTCCATAGGATATAAAAATGTGATCGGAGCTCGTCGGGC
TTCCTGGCGCATTCTCTCCTCCATTGAGCAGAGAGAGGAGAGCAAGGGCAACGAGGTGAATGCGAATCGCATCAA
GGAGTACCGTAACAGAGTCGACGAAGAGCTCTCCAAGATCTGCAAAGATGTCCTGAGCATCATCGATGATCATCT
CATCCCCTCTTCCACAACCAAAGAATCTGAGGTCTTCTATTACAAAATGAAGGGTGATTATTACCGCTATTTGGC
TGAGTTTAAGGCTGGTAGCGAGAGGAAGGATGCGGCAGATCACTCCCT

> SEQ ID NO:299 232732FL 114368_300007_1e
agcgacaatcagaaaccacccgctgtaaccctaggtttttcacaaacaacaaatatgactgagtcatcgcggga
agaaaATGTGTACATGGCCAAGCTTGCTGAGCAGGCCGAGCGATATGAGGAAATGATTGAGTTTATGGAGAAGGT
TGCAAAGACAGGTGATGTCGAGGAGCTGACTGTTGAGGAAAGGAATCTCCTTTCTGTGGCATACAAAAATGTGAT
TGGTGCAAGAAGGGCCTCGTGGAGAATAATCTCTTCAATTGAGCAGAAAGAGGAGAGCCGTGGAAATGAAGATCA
TGTCAAAACTATTAAAGAATACAGAGCCAAAATTGAGGCTGAACTCAGCAAGATCTGTGATGGGATTTTGGGTCT
CCTTGAGTCCCATTTAATACCATCAGCCTCCACAGCTGAGTCCAAAGTTTTTTACTTGAAGATGAAAGGTGATTA
CCACAGGTACTTGGCTGAGTTTAAGACAGGGGCAGAAAGGAAAGAAGCCGCAGAGAACACTTTATTAGCCTACAA
GTCTGCTCAGGATATTGCTTTGGATGAACTGGCTCCTACTCACCCAATCAGGCTGGGACTTGCCCTCAACTTTTC
AGTGTTCTACTATGAAATTCTCAACTCGTCGGATCGTGCTTGTAATCTTGCAAAGCAGGCCTTTGATGATGCCAT
TGCCGAGCTGGATACATTGGGTGAGGAATCTTACAAGGACAGTACATTGATTATGCAGCTTCTCCGAGACAATCT
TACACTTTGGACTTCTGATACCACGGATGATGCCGGGGATGAGATCAAGGAAGCTTCAAAATGCGAATTAGGCGA
AGGAGAGCAGTAACGGCATAACATCATAGTCTTTTACTCTTTATTTTGTTTGATTTTAATATAGGACTACTGCGT
GAAAGCTAGACTGGATATGGATATAATTCGATGATTCCTCGTATTACTGCTGAAGTAGTTTGATATAAAAACATG
TTTTAGTACGATAAGAAATATAGTCATGCCGTTGATGTATTGGCTTGTATTTCTAGTTTcAATTGCATATGTTAT
TGACTGTTGAGCTTTGTATTTTCAAGTCATTCAATAATtcaatAGTTCCcAAAAA

> SEQ ID NO:300 232732FL 1170775_302039_1e
gtggtttggattgggcaaagtttgaaagagaagagaagaagattcccctcactccctcctcccccactatttggg
tttttCTCTCTCTCTTTCTTTCTCCtagttAGTCTTCACTTTTAGATCTATATGCTCACAGCTCACCTCACTCCT
CTTTATTTTTAGGGTTCATTGGAAGGAAGAGAGAGAGAGAGAGAGAGAGAGAGGTCTTGCTGCACCAACCCAACCCA
AGGAGCTCTTCTTTGTGTTCTACTCCCATGGGTATTGAGAAGGAGAGAGAGAGAGCCATGTCTACATGGCCAAGCTT
GCTGAGCAGGCAGAGAGATATGATGAAATGGTGGATTCCATGAAAAAGATTGCCAAGTTGGACGTCGAGCTGACC
ATTGAGGAGAGAAATCTGCTTTCCGTGGGCTATAAAAATGTGATTGGGGCTCGGAGGGCCTCGTGGCGAATCCTC
TCCTCAATTGAGCAGAAAGAGGAGAGCAAGGGCAATGAAACAAATGCCAAGCGCATTGAGAGTTACCGACATAAG
GTTGAGGAAGAACTCTCTGGAATCTGCAAGGACATCCTGACTACCATCGATGAGTAtCtcaTCCCcTCGTCTGGC
ACGGCGGAATCCACCGTTttctat

> SEQ ID NO:301 232732FL 118303_300065_1e
cggacgcgtgggcccaaagagagagagcgagagagagagcggagaaatggagaaggaaagagagaaacaggttta
cttggCAAGGCTAGCTGAGCAAGCTGAGAGATATGATGAAATGGTAGAAGCAATGAAGACGGTTGCTAAGATGGA
TGTTGAACTGACTGTTGAGGAGAGGAATTTGGTGTCAGTTGGGTATAAGAATGTTATTGGAGCAAGAAGGGCTTC
ATGGCGGATATTGTCTTCAATTGAACAAAAGGAGGAGAGTAAGGGTCATGACCAGAATGTTACGAGAATAAAGAC
TTACCAACAGAGGGTCGAAGATGAGCTTACAAAAATATGCATTGACATTTTGTCGGTGATCGATGAGCACCTTGT
TCCTTCTTCCACTACCGGAGAATCTACTGTCTTCTACTATAAGATGAAGGGAGATTACTATCGCTATTTAGCAGA
GTTCAAATCAGGGGATGATCGTAAAGAGGCAGCTGATCAGTCACTTAAAGCTTATGAGGCTGCTACTTccACAGC
TAGTGCAGATCTTGCTCCTACTCATCCAATTAGACTTGGACTTGCATTGAACTTCTCAGTCttctACTATGAG

> SEQ ID NO:302 232732FL 1177052_302114_1e
GGGTTTGGATCGAGTCAGTGCAGTCTACGGTCTGCAAGCATGTCCGGGCACGATGAGCACGTGTTCATGGCTAAG
CTCGCCGAACAGGCCGAGCGCTATGAGGAGATGGCCGAGTTCATGGAGAAGGTTGCTGGCCATGGGGACGACCTC
ACTGCCGAAGAGCGCAACCTCCTCTCTGTCGCCTACAAGAACGTGGTGGGTGCTAGACGTGCCTCCTGGCGCATC
ATCTCCTCCATTGAGCAGAAGGAGGAGGGCAAGGGCAACCAGGACCATGTCAGTGCCATCCGTGACTACCGGGCC
AAGATCGAGGCCGAGCTTTGCACTATATGTGGGGGTGTCCTCAAGATCCTGGACACGCACCTCATCCCGGCCGGA
GAAGCTGCTGAGTCGAAGGTCTTCTACCTCAAGATGAAGGGTGATTACCATCGTTACGTGGCTGAATTCAAGACT
GGTTCTGAAAGGAAGGAGTCTGCTGAGAACACCATGTCTGCCTATAAGTCTGCCCAGGATATTGCCCTTGCAGAG
CTTGCTTCAACTCATCCTATTCGCCTGGGACTTGCGCTCAATTTCTCGGTATTTTACTACGAGATTTTGAATTCT
CCCGACAGAGCCTGTTCTCTTGCCAAGCAGGCTTTTGATGAGGCTATTTCTGAAttggaCACCcttggaGAGGAG
TCCTACAAGGATAGCAcAtngatCATGCAGCTTTTAAGGGATAACTTAACACTGTGGACATCAGATTTGCAGGAA
GATGGAGGTGATGAAGGTATCAAACTGAAGGATGTAGATGGTCACTAGCCTCTTTGAGGCATAtattggtAAGCG
TTGTAATGGTTTAATGCTTTCACAGGACCAGTCATGATACGGCGATTGGTTATATAGAACAGTACtg

Figure 2 continued

> SEQ ID NO:303 232732FL 241051_301319_1e
AAAGACTTGGTCTTTTCATCAACTTTCGATTTAACCAAATTCAAAACTATCTTCAAGGATGAAAGAAAAGATCTT
GTGTTTATGGCGCGCACCGCAGAAACTGCGGAACGCTATGAAGATATGTGCCGCGTCATGAGAGAATTAGTGAAG
TTTACCAACGGTAAAAAAGTCGATTTGACTGTCGAAGAGCGCAATTTGCTCTCTGTTGCATACAAGAATGTTATT
GGTGCTCGCAGAGCATCTTGGAGAACTCTCAATGTTGACGAACATAAAGACGATGCTTTGATCGTTGAATACAAG
AAGCAAGTCGAAAATGAACTTCAGACTATCTGCAAGGATGTTCTTGATTTATTAGAGAAATTCCTTATTCAACCT
CATGGAGCGGAAGACGAGTCTCAAGTCTTCTATCTTAAAATGACCGGTGATTATTACCGCTATCTTGCTGAGTTT
GTTGGCGATCAAGGCTATGCTCCAAAAGCCGCTGAATTCTACGACAAAGCGAGAACT

> SEQ ID NO:304 232732FL 237521_301288_1e
ttcgcatctCTCCATCGCCGCCGCCGCCGTTTCTGCCGCCGCATAGGCATCCGTCGCCAGGTAGCGCAGCCGCAG
CCGCAGCCGCCGCCGCAAAGCTAGGTTGTTTCTCGCCGAAATGCCGGAATCCAAGGAGGAGAATGTCTACATGGC
CAAGCTCGCGGAGCAGGCCGAGCGCTACGACGAGATGGTGGAGTACATGGAGAAGGTGGCCAAGGCCGTGGAGGC
GGAGGAGCTGAGCGTGGAGGAGAGGAATCTCCTGTCGGTGGCGTACAAGAATGTGATTGGGGCGCGGCGGGCTTC
GTGGCGGATCATCTCGTCGATCGAGCAGAAGGAGGAGTCCAAGGGCAACGAGGAGCATGTAGGCTTGATCAAGAA
CTACAGGTCCAAGGTGGAGACGGAGCTGAGCAACATCTGCCACGGGATCTTGGGGCTGCTGGATTCGCACCTCAT
CGGATCCTGCTCCACGGGCGAATCCAAGGTCTTCTACCTCAAGATGAAGGGCGACTACAATCGCTACCTTGCCGA
GTTTAAGACGGGGGCAGGAGAGGCAGGAGGCAGCCGAGGCCACCTTGATGGCCTACAAGTCGGCACAGGACATTGC
GCTGGCGGAGCTTGCTCCAACTCACCCCATTCGACT

> SEQ ID NO:305 232732FL 232468_301215_1e
tcgacccacgcgtccgggcggcagcgcacggcgaGGAACAGGTGAGTGCCCGTGGATGTGATCTAGATCTACCCT
CCAAGCCCCAAAATCTCAGTAGAAATCCTCCAAATCGCGCCGCCGGAAGAGAGATCCAATCCACCACTGTCCCCA
TTTCTCGGCTTGTTCCAGGGATGTCGAATCTTCGCGAGGAGAATGTCTACATGGCCAAGCTCGCGGAGCAGGCCG
AGCGCTACGACGAGATGGTGGAATTCATGGAGAAGGTGGTCAAGGCCGTGGACGTGGAGGAGCTGACGGTCGAGG
AGCGGAATCTCCTGTCGGTGGCCTACAAGAACGTGATCGGCGCCCGCCGGGCATCGTGGAGGATAATCTCCTCCA
TCGAGCAAAAGGAGGAATCCAAGGGCAACGACGACCACGTCTCGATGATCAAGGAGTACCGTGCCAAGGTGGAGT
CGGAGCTGAGCACCATTTGCGACAGCATCCTCAAGCTGCTGGACAGCCATCTCATCCCCTCATCGTCCAGTGGCG
AGTCCAAGGTCTTCTACTTGAAGATGAAGGGTGACTACCACCGATACTTGGCCGAGTTTAAGACCGGGGCCGAGA
GGAAAGAGGCCGCGGAGAACACTCTCCTCGCCTACAAGTCGGCCCAGGACATCGCTCTCACACAGCTGCCGCCGA
CGCATCCCATCCGGCTGGGTCTCGCTCTCAATTTTTCGGTCTTCTACTACGAGATTTTGAATTCGCCCGATCGAG
CTTGTACGCTTGCCAAGCAGGCATTTGACGAGGCCATAGCCGAGCTGGACACTTTGGGAGAGGAATCTTACAAGG
ATAGTACTCTGATCATGCAGCTGCTGCGCGATAATCTAACGCTGTGGACCTCAGACATGCAGGAGGAAGGTGCCG
GCGAGGGGAAGGACGacaagcCGTGAGTAAAATAATACGTTCGAATTTCGTTTTCTATGCTACTAGCTAgctGtt
TAGACGCCTTCTCTCTCAACACCTTGGTACTgttgAtTCTTtcgttcCTGAAtAcattATttggcTtg

> SEQ ID NO:306 232732FL 230624_301070_1e
ATCGACCCACGCGTCCGGCTACTAGCTAGCAGTTTAGACGCCTTCTCTCTCCACACCTGGTACTGTTGATTCTTT
GTTCCTGAATACATTATTTGGCTTGCACT

> SEQ ID NO:307 232732FL 226749_301004_1e
TGCTGTCCGTGGCGTACAAGAACGTCATCGGCGCGCGCAGGGCGTCGTGGCGCATCGTGTCCTCCATCGAGCAGA
AGGAGGAAGGCCGCGGCGCCGCGGGCCACGCCGCCGCCGCGCGCTCCTACCGCGCCCGCGTCGAGGCCGAGCTCT
CCAACATCTGCGCGGGGATACTCCGCCTCCTCGACGAGCGCCTCGTCCCCGCCGCCGCCGCCGTCGACGCCAAGG
TCTTCTACCTCAAGATGAAGGGCGACTACCACCGCTACCTCGCCGAGTTCAAGACCGGAGCCGAGCGCAAGGACG
CCGCCGACGCCACCCTCGCCGGCTACCAGGCCGCGCAGGACATAGCCATGAAGGAGCTGTCGCCGACGCACCCCA
TCAGACTGGGCCTTGCGCTCAACTTCTCCGTGTTCTACTACGAGATCCTCAACTCGCCCGACCGCGCGTGCACGC
TCGCCAAG

> SEQ ID NO:308 232732FL 191021_300738_1e
CCCCCTGGAGGATCATCTCTTCTATGGAGCAGAAGGAGGAGAGCCGTGGGAATGAGGCATATGTTGCATCAATTA
AGGAGTACCGTAGCAGGATTGAAACTGAGCTCAGCAAGATCTGTGATGGTATCCTTAAGCTTCTGGATTCCCACC
TTGTCCCATCTGCCACTGCTGCAGAGTCCAAGGTGTTCTACCTGAAAATGAAGGGTGACTACCACAGGTACCTTG
CTGAGTTTAAGTCAGGAGCTGAGAGGAAGGAAGCAGCTGAGAACACTCTTGTGGCATACAAGTCTGCCCAGGATA
TTGCACTCGCTGACCTGCCTACAACTCACCCGATAAGGCTTGGACTTGCACTGAACTTCTCAGTGTTCTACTATG
AGATACTGAACTCACCAGACCGTGCTTGCAACCTTGCAAAGCAGGCGTTCGACGATGCTATTGCTGAACTGGACA
CTCTTGGCGAGGAGTCTTACAAGGACAGCACCTTGATCATGCAACTTCTTCGTGACAATCTGACTCTCTGGACCT

Figure 2 continued

CTGACAATGCGGAGGATGGTGGTGA

> SEQ ID NO:309 232732FL 190737_300779_1e
GAATTTGAACTCCACCTGAGCACAGGAGAAGCCGCAGCCACTGAGATTTGACCTTCTGTTTCTACCAGAAAAACA
CAAACAGTGAAGATGTCGCAGCCTGCTGAGCTTTCCCGTGAGGAGAATGTGTACATGGCTAAGCTTGCAGAGCAG
GCCGAGAGGTATGAGGAGATGGTTGAGTTCATGGAGAAGGTTGCTAAGACAGTTGACTCTGAGGAGCTCACTGTT
GAGGAGCGCAACCTTCTATCAGTTGCTTACAAGAATGTTATTGGTGCTCGCCGTGCGTCATGGCGCATCATATCA
TCCATTGAACAGAAGGAAGAGAGCCGTGGTAATGAGGATCGTTGCACGCTCATCAAGGAATACAGGGGAAAGATT
GAAACTGAGCTCTCCAAGATCTGTGATGGCATCCTCAAGCTTCTTGACTCCCACCTTGTGCCTTCATCCACTGCT
CCAGAGTCCAAGGTCTTCTACCTCAAGATGAAAGGCGACTACTACAGGTACCTCGCAGAGTTTAAGACTGGAGCT
GAGAGGAAGGATGCTGCTGAGAACACCATGGTGGCATACAAAGCCGCTCAGGATATTGCCCTGGCAGAGTTGCCC
CCAACTCATCCTATCAGACTTGGCTGGCCCTCAACTTCTCGGTGTTTTATTACGAGATCCTCAACTCTCCTGAC
CGTGCTTGCAATCTTGCAAAGCAGGCTTTCGATGAGGCTATCTCAGAGCTGGACACTCTGAGTGAGGAATCCTAC
AAGGACAGCACTTTGATCATGCAGCTTCTGCgTGATAACCTGACGCTGTGGACTTCCGATATCTCGGAGGATGCT
GCTGAGGAAATCAAGGAGGCCCCCAAggGCGAATCAGGAGATGGACAgtgAACATGATCGAATgcgTGCGCCCAC
AAACTagaatAGTgAcgcTGCAAATgtgCTgtgggTTAtcgttTCATtTTATa > SEQ ID NO:310 232732FL 187967_300682_1e
CCCACGCGTCCGCTCCACCTGAGCACAGGAGAAGCCGCAGCCACTGAGAAAAACACAAACAGTGAAGATGTCGCA
GCCTGCTGAGCTTTCCCGTGAGGAGAATGTGTACATGGCTAAGCTTGCAGAGCAGGCCGAGAGGTATGAGGAGAT
GGTTGAGTTCATGGAGAAGGTTGCTAAGACAGTTGACTCTGAGGAGCTCACTGTTGAGGAGCGCAACCTTCTATC
GGTTGCTTACAAGAATGTTATTGGTGCTCGCCGTGCGTCATGGCGCATCATATCATCCATTGAACAGAAGGAAGA
GAGCCGTGGTAATGAGGATCGTTGCACGCTCATCAAGGAATACAGGGGAAAGATTGAAACTGAGCTCTCCAAGAT
CTGTGATGGCATCCTCAAGCTTCTTGACTCCCACCTTGTGCCTTCATCCACTGCTCCAGAGTCCAAGGTCTTCTA
CCTCAAGATGAAAGGCGACTACTACAGGTACCTCGCAGAGTTTAAGACTGGAGCTGAAAGGAAGGATGCTGCTGA
GAACACCATGGTGGCATACAAAGCCGCTC > SEQ ID NO:311 232732FL 182045_300628_1e
GAATTCAAGATCATGTTTCTATTATTAAAGAATATAGGGGAAAGATTGAATCTGAACTTCATAAGATTTGTCAAG
GGATTTTAGGGCTTTTGGATTCCCATCTTATTCCTTCATCAACTGCTGCTGAATCTAAGGTGTTTTACCTTAAGA
TGAAGGGTGATTACCACAGGTATTTGGCTAAGTTAGCTGAACAAGCTGAACGATATGAAGAGATGGTTGAATTTA
TGGAGAACGTTGCAAAAACTGTTGATTCTGATGAATTATCAGTTGAGGAACGAAACCTGTTGTCTGTTGCTTATA
AGAATGTGATTGGAGCTAGGAGAGCTTCATGGAGGATTATTTCAAGTATTGAACAAAAGGAAGAAAGCCGTGGGA
ATGAAGATCATGTTTCTATTATTAAAGAATATAGGGGAAAGATTGAATCTGAACTTCATAAGATTTGTCAAGGGA
TTTTAGGGCTTTTGGATTCCCATCTTATTCCTTCATCAACTGCTGCTGAATCTAAGGTGTTTTACCTTAAGATGA
AGGGTGATTACCACAGGTATTTGGCTGAGTTTAAATCTGGTAgTGACAGGAAAGaaGCTGCTgagagTACATtG > SEQ ID NO:312 232732FL 179614_300562_1e
ttgcaagttccattccctgttcttctctctcaacgaagcatcaaccccccttttctCCCAGAACCGCGTCTCATC
GCACCTGCCATAAAACTCCAAAAAATCTCAAAAACCAACCGTCAAAATGGGTCACGAAGATGCTGTTTATCTGGC
CAAGCTCGCCGAGCAGGCCGAGCGATATGAGGAGATGGTCGAGAACATGAAGATCGTCGCCTCCGAGGACCGCGA
CCTGACCGTCGAGGAGCGCAACCTCCTCTCCGTCGCCTACAAGAACGTCATTGGTGCCCGCCGTGCCTCTTGGAG
AATAGTCACTTCCATCGAGCAGAAGGAGGAGTCTAAGGGCAACTCTTCCCAGGTTACCCTTATCAAGGAGTACCG
CCAGAAGATTGAGGCCGAGCTTGCCAAGATCTGCGATGACATTCTCGATGTTCTTGACAAGCACCTGATTCCTTC
TGCCAAGTCTGGAGAGTCCAAGGTCTTCTACCACAAGATGAAGGGTGACTACCACCGTTACCTTGCCGAGTTCGC
CATTGGCGACCGCCGCAAGGACTCCGCCGACAAGTCTCTCGAGGCTTACAAGGCTGCTACCGAGGTTGCCCAGAC
CGAGCTGCCTCCTACCCACCCTATCCGCCTGGGTCTTGCGCTCAACTTCTCCGTCTTCTACTACGAGATCCTCAA
CGCCCCTGACCAGGCTTGCCACCTCGCtaagcaggCatTTGACGATGCTAtt > SEQ ID NO:313 232732FL 175041_300529_1e
gtcaggagctgagaggaaggaagcagctgagaacactcttgtggcatacaagtctgcccaggatattgcactcgc
tgaccTGCCTACAACTCACCCAATAAGGCTTGGACTTGCACTGAACTTCTCAGTGTTCTACTATGAGATCCTGAA
CTCACCAGACCGTGCTTGCAACCTTGCAAAGCAGGCGTTCGACGATGCTATTGCTGAACTGGACACTCTTGGCGA
GGAGTCTTACAAGGACAGCACCTTGATCATGCAACTTCTTCGTGACAATCTGACTCTCTGGACCTCTGACAATGC
GGAGGATGGTGGTGACGAGATCAAGGAAGCAGCGAAGCCTGAAGGAGAGGGCCACTAATCTGTCCTGAAGTCTAT
TTCTGAGTCCATTTACTCAGCTACCTGCTGTATTACTGGATCATAAGATGTACTAGGATCAATTGCTATGTGGAA
TCATAAGATTAGGGCTGCGTATGTCAAAATGTGTCGAGCTGAAGTACCCAGTGGACACAGTTTATGTGCACTACA
TTGCTTCCGTGACTTATTTACTAGTTAATTAGCAACTTTCAACCACTTCCTGTATTTGCAGCACATTATTAGTAT

Figure 2 continued

CGCTGTATTAGCGTTTTCCATGGGCTggttATGATTGAGaaTACAGgCCAggCATTGCATGTCC

> SEQ ID NO:314 232732FL 159293_200022_1e
acgcactctgtcGAGAATCCATTCTATTTCGCCTAAACTTTCTCTCTCTACAACAACAACAATGGCGGCTCTGCT
CACAGACAATCTCAACCGCGAACAATACCTCTACTTAGCCAAACTCGCCGAACAAGCCGAACGCTATGAAGAAAT
GGTCCAGTACATGGACAAACTAGTACTCAGTTCCACTCCCGCCGCCGAACTCACCGTCGAGGAACGAAACCTCCT
TTCCGTCGCTTACAAAAACGTGATCGGCTCTCTTCGTGCCGCGTGGCGTATCGTATCCTCCATTGAGCAGAAAGA
GGAATCGCGTAAGAACGAAGAACACGTTTCGCTCGTTAAGGAGTACAGAGGTAAAGTTGAGAATGAGTTAACGGA
GGTTTGTGCTGGTATCCTCAAGTTGCTTGAGTCAAATCTCGAGCCGTCTGCTTCTACGGGTGAATCGAGGGTGTT
TTACCTCAAAATGAAAGGTGATTATTACCGGTATCTAGCGGAGTTTAAGGTTGGAGATGAGCGGAAGCAGGCTGC
TGAAGACACTATGAATTCTTATAAGGCTGCTCAGGAAATTGCACTAGCAGATCTGccTccAACACATCCTATAAG
GCTGGGTCTTGCACTTAATTTCTcAgtCTTCTActttgAGATtCTGAACTCATCTGacaaagcttgtaGTATGgc
aaaacagggctTTtGAggaagccatagCTGAGc

> SEQ ID NO:315 232732FL 158868_200020_1e
gttataaatccttatctttttcaacacacagattaaaatcttcagaaagagagagagagatcccaaaatgggtga
acgtgAGAACTtcgTaTACAtagcTAAGCTtgCCGAGCAAGCTGAACGCTATGATGAGATGgctgatGcGatGAA
GAATCTTGCAAATATGGATGTTGAATTGACAGcGGAAGAGAGGAATTTGTTTTCTGTTGGTTATAAGAATGTGGT
TGGAGCTAGGAGAGCATCGTGGAGGATCTTGTCTTCCATCGAGCAgaaggAAGAGTCTAGAGGAAATGAGCAGAA
CGTGAAGCGGATTAAGGAGTACCAgcaaAAAgTGGAGTCAGAGCTCACCGACATTTGCAATAATATCatGACCgc
gat

> SEQ ID NO:316 232732FL 50015_300166_1e
CGGACGCGTGGGAAAAAAATCAAATCTCTCTCTTTCTCTCTCTAATGGCGGCGACATTAGGCAGAGACCAGTATG
TGTACATGGCGAAGCTCGCCGAGCAGGCGGAGCGTTACGAAGAGATGGTTCAATTCATGGAACAGCTCGTTACAG
GCGCTACTCCAGCGGAAGAGCTCACCGTTGAAGAGAGGAATCTCCTCTCTGTTGCTTACAAAAACGTGATCGGAT
CTCTACGCGCCGCCTGGAGGATCGTGTCTTCGATTGAGCAGAAGGAAGAGAGTAGGAAGAACGACGAGCACGTGT
CGCTTGTCAAGGATTACAGATCTAAAGTTGAGTCTGAGCTTTCTtctgtttgctctGgaatcctTAagCTccTtG
ACTCGcaTCTGATccCAtctgctggAGC

> SEQ ID NO:317 232732FL 285977_200243_1e
TACAAAACTCCCTCTCTCATTTCCTCTCTCATAGCAACATCAATGGCGTCGCCACGCGAGGAGAACGTGTACATG
GCAAAGCTTGCCGAGCAAGCCGAGCGTTACGAGGAGATGGTTGAGTTCATGGAGAAAGTCATCGCCGCCGCCGAC
GGCGCCGAGGAACTTACCGTCGAAGAACGGAACCTCCTCTCCGTCGCATACAAAAATGTTATCGGAGCACGGCGA
GCCTCGTGGCGTATCATCTCCTCCATTGAGCAAAAAGAGGAGAGCCGCGGCAACGAAGATCACGTTGCCTCCATC
AAGGAGTACAGATCTAAGATCGAGATCGAACTTACCTCGATCTGTAACGGCATTCTCAAGCTCCTCGATTCTAAG
CTCATTGGCGCCGCTGCTACCGGTGACTCTAAGGTGTTTTACTTGAAAATGAAAGGAGATTATCATCGCTATTTG
GCTGAGTTTAAAACCGGCGCGGAGCGAAAGGAAGCCGCCGAAAATACTCTCTCGGCTTACAAATCCGCTCAGGAT
ATTGCAAATACCGAGCTTGCTCCTACACATCCAATCCGATTGGGACTTGCTCTCAATTTCTCTGTATTTTACTAC
GAAATTTTGAATTCTCCTGATCGTGCTTGTAATCTCGCCAAACAGGCTTTTGACGAGGCAATTGCCGAGCTGGAC
ACATTGGGCGAAGAGTCATACAAGGATAGCACTCTGATCATGCAGCTTCTTCGCGATAACCTCACTTTATGGACT
TCAGATATGCAGGATGATGGAACTGATGagaTCAAAGAAGCAGCAAAACCAGATaATGagCAGCAGTAAACCGGT
GACATtTCTttaggattGAAAtTCATGttgTaacTTTTTATTTTTCAatT

> SEQ ID NO:318 232732FL 282658_200236_1e
gggcagagaaccaaaaagaaaggggaaactgaaaagtGAAGAATCTCCTTTGGCTCACAGAAATCGGACATGGCT
TCCTCCAAAGAACGCGAGAACTT

> SEQ ID NO:319 232732FL 271221_200032_1e
CAGCTCTCTCTCTCTCCCTTCAAACATCGATGGCGTCGTCGCGCGATGAGTTCGTGTACATGGCGAAGCTTGCGG
AGCAAGCTGAGCGGTACGAGGAGATGGTAGAGTTTATGGAGAAGGTCGTAACCGCCTCGGACGGCGGCGAGGAAC
TCACCATCGAAGAACGTAATCTTCTATCCGTAGCATACAAAAACGTGATCGGAGCACGACGAGCCTCGTGGCGAA
TCATTTCCTCAATCGAGCAAAAAGAAGAGAGCCGAGGCAATGAGGAGCACGTGACCTCTATTAAAACTTACAGAT
CTAAGATCGAGTCGGAGTTGACCTCGATCTGTGACGGTATCCTCAAGCTGCTCGATTCGAATCTCATTGGCGCTG
CGTCAATCGGAGATTCTAAGGTGTTTTATTTGAAAATGAAAGGAGATTATCACCGGTATTTGGCTGAGTTTAAGA
CCGGAGCTGAGAGAAAGGAAGCTGCTGAGAATACTCTTTCGTCTTATAAGTCCGCTCaggATATTGCAAATGCGG
AACTGGCACCTACACATCCTATTCGATTGGGGCtAgTTCTCAATTTCTCTgtaTTTACTATGAGATATTGaaTT
CACCTGATCGTGCTTGTaaTCTg

Figure 2 continued

> SEQ ID NO:320 232732FL 258777_301699_1e
aaatcctgaattgcaccaactagtacaacgacaacaatgtcttctgagagagaaaccaagaccttccttgcccgg
ctctgTGAGCAGGCTGACCGATACGACGAGATGGTcAACTACAtGaAGgacgtcgCTAAGtCCGGTGaggagCTT
ActgtcgacgagcGaAATCTggtTTCCgtcGCTTAcaagaACGTTATcggcgctCGacgagcCagctGgagagtC
ATTTTCCCCATagagcagaaggaggaggccaaggGtggcacccCaccATcTcgagcTTCTCAaGaccTacaGagcc
cagaTTgagggagagctcgaagacatctggagcgatGTTCTTgatAttctcaacAAAcaaCTcCTCCCCAaagGc
gagaacGCCGAGTCTAAGGTCTTCTACTACAAGATGAAGGGTGACTACCATCGATACCTTGCCGAGTTCACCTCC
GGCGAGAAGCGAAAAGAGGCTGCCACTGCCGCTCACGAGTCATACAAGAGCGCCACTGATGTTGCCCAGACTGAG
CTCAGCTCAACTCACCCCATCCGACTTGGTCTCGCTCTCAACTTCTCCGTCTTCTACTACGAGATTCTCAACTCG
CCAGACCGTGCTTGCCACCTTGCCAAGCAGGCTTTCGATGATGCCATCGCTGAGCTCGACACTCTCTCCGAGGAG
TCTTTCCGAGACTCTACCGTCATTATGCAGCTTCTGCGAGACAACCTGACCCTCTGGAaGaACGAccTcgaAGaG
TCTCTGCAAGCCCAGCAGTCTGAGGAGAccCCTGCCAcCGATGCTgccgCTGCTTCCACCGAGGCTGCtgccCCC
aaggaggaggccaaGcCcGCTGCTGaggagCCCAAggAGTaGaGTAGT

> SEQ ID NO:321 232732FL 258531_301697_1e
AACCATGACGCGACAAGACAACATCTACCTGGCTCGTCTTTCCGAGCAGGCCGACCGTTACGAATACATGGTGGA
CTACATGAAGGAGATTGCCACCGGCGACCAGGAGCTGTCTGTGGAGGAGCGAAACCTGCTCTCCGTGGCATACAA
GAACGTGATTGGCGCTCACCGAGCATGGTGGCGACTGGTCAGCAGCTGCGATCAGAAGGAGGAGCAAAAGGGCAA
GGAGACCAAGATCATCCACGACTTCCGTCAGAAGATTGATGCCGGTCTGCACGACATTTGCCATGACATTCTCAA
CGTGCTTGACAAGCACCTGATCCCCAAGCTCGAGAAGCCCTCGGCCGAGGCCACTGACGCTGCTGCCAAGGATGG
CGCCGACCCC

> SEQ ID NO:322 232732FL 257978_301687_1e
AGGAGCTTAGATCGATCGACGACGCCATCGCCGCCGGAGCTGCCATGGGAATGGAGAAGGAGAGGGAATGCTTCG
TCTACATGGCCAAGCTCGCGGAGCAAGCCGAGCGTTACGATGAAATGGTTGAATCGATGAAGAAAGTCGCGAAGC
TGGACGTGGAGCTGACCGTGGAGGAGAGGAATCTCCTGTCCGTGGGCTACAAGATCGTGATTGGGGCGCGGCGGG
CGTCGTGGCGGATCTTGTCCTCGATCGAGCAAAAGGAGGAGAGCAAAGGCAACGAGCAGAACGTCAAGAGGATTG
GAGAGTACCAGCAAAAGGTCGAGGACGAGCTCTCCAAGATTTGCAATGACATTCTCACGATCATTGACGAGCATC
TAGTGCCGGCTTCCAGCACTGGCGAATCCACGGTCTTTTACTACAAGATGAAAGGTGACTACTTTCGATACCTTG
CAGAGTTTAAGACCGGGAACGAAAGAAAAGAAGCTGCCGATCAATCGTTCAAGGCTTACCAGGCTGCGAGCGATA
CTGCTTCAAGCGATCTTCCCCCAACACATCCTATCCGGCTGGGACTGGCATTGAATTTCTCTGTTTTCTACTACG
AGATTCTAAACTCGCCAGACCGCGCTTGCCAGCTAGCGAAGCAAGCTTTTGACGATGCGATTGCGGAGCTGGACA
CGCTCAGCGAAGAATCCTACAAAGACAGCACCTTGATCATG

> SEQ ID NO:323 232732FL 256066_301646_1e
TTTCTCTCTCTCTCTCTCTCTCTCTCTCCCTCCGTCGACATGGGCATCGAGATGGAGCGAGAGAGCCTTGTCT
ACCTATCCAAGCTCTCCGAGCAGGCAGAACGCTATGAGAAATGGTGGAGTCGATGAAGAAAGTATTTAAGTTGGA
TGTAGAGCTTACGATTGAGGAGAGGAATTTGCTCTCAGTGGGGTATAAGTATTTTATCGGAGCGCGAAGGGCCTC
GTGGCGAATTCTCTCCTCCATTGAGCAGAAAGAAGAGAGCAAGGGCAATGAGACCAATGTAAAACGCATCAAGGA
GTACCGCAACAAAGTGGAGGAAGAGCTTTCCAAGATTTGCAGTGACATCCTAACTATCATCGATGAGCATCTTAT
CCCCTCATCTGGCACAGCAGAATCTACCGTTTTCTATTACAAAATGAAAGGGGATTATTATCGCTACCTTGCTGA
GTTCAAGACAGGACATGAGAGAAAGGAAGCTGCAGATCAATCTCTGAAAGCTTATCAGACTGCAAGTGACACGGN
CAACACGGCTCTGCCATCTACCCATCCGATCAGGCTTGGACTTGCACTCAACTTTTCAGTCTTTTACTATGAGAT
TTTGAGTTCGCCGGAGCGTGCGTGCCATCTTGCCAAGCAAGC

> SEQ ID NO:324 232732FL 255750_301643_1e
ACGCGTCGCCCTAACTAACCCTAACCGCCAAATATTGGGGATTTATCATTTGGGTTTGGATCGAGTCAGTGCAG
TCTACGGTCTGCAAGCATGTCCGGGCACGATGAGCACGTGTTCATGGCTAAGCTCGCCGAACAGGCCGAGCGCTA
TGAGGAGATGGCCGAGTTCATGGAGAAGGTTGCTGGCCATGGGGACGACCTCACTGCCGAAGAGCGCAACCTCCT
CTCTGTCGCCTACAAGAACGTGGTGGGTGCTAGACGTGCCTCCTGGCGCATCATCTCCTCCATTGAGCAGAAGGA
GGAGGGCAAGGGCAACCAGGACCATGTCAGTGCCATCCGTGACTACCGGGCCAAGATCGAGGCCGAGCTTTGCAC
TATATGTGGGGGTGTCCTCAAGATCCTGGACACGCACCTCATCCCGGCCGGAGAAGCTGCTGAGTCGAAGGTCTT
CTACCTCAAGATGAAGGGTGATTACCATCGTTACGTGGCTGAATTCAAGACTGGTTCTGAAAGGAAGGAGTCTGC
TGAGAACACCATGTCTGCCTATAAGTCTGCCCAGGATATTGCCCTTGCAGAGCTTGCTTCAACTCATCCTATTCG
CCTGGGACTTGCGCTCAATTTCTCGGTAT

> SEQ ID NO:325 232732FL 253819_301630_1e

Figure 2 continued

CACGCGTCGCGACAGTCGAAACGGGGTCCCGGGAGGAGAGTGTGTACATGGCCAAGCTCGCGGAGCAGGCCGAGC
GCTACGAGGAGATGGCCGAGTTCATGGACGCTGTCTCCAAGGGCGCCGGTGCTGAGGAGATGTCCGTTGAGGAGC
GTAACCTCCTCTCTGTCGCCTACAAGAATGTCATTGGTGCCCGTAGAGCCTCCTGGCGCATTGTCTCCTCCATCG
AGCAGAAGGAGGAGAGCAAGGGCAATGAAGACCACGTCGCCGCCATCCGCGGCTACCGCGTCAAAGTTGAGGCTG
AGCTCACCAAGATCTGCCAGCGCATTCTCGACCTCCTTGACAGCCACCTTGTCCCCTCTGCGCTCAACCCCGAGT
GCAAGGTCTTCTACCTGAAGATGAAAGGGGATTACCACCGTTACCTTGCCGAGTTCAAGACCGGTGCTGACCGCA
AGGAAGCGGCTGAGAGTACGCTCGTCGCTTACAAATCTGCCGAGGAAATTGCCCTGGCTGAGCTGCCTTCGACAC
ACCCCATTCGTTTAGGCCTTGCTCTGAATTTTTCAGTTTTTTACTATGAAATTTTGAACTCCCCAGACAGAGCTT
GCAATCTAGCTAAGCAGGCTTTTGATGAGGCCATTGCTGAACTGGACACTCTGGGGGAAGATTCCTATAAGGACA
GTACTTTGATAATGCAACTTC

> SEQ ID NO:326 232732FL 252933_301610_1e
TGGTTGTTATTGTTGTTGCTGTGTTTATCTTCTTCGCCTTCGTGTTCGTCGGTGGTGTTGGTAGTGGGAAGATGG
GTGTGGAGAAGGAGCGTGAGAGTGATGTGTACATGGCTAAGCTCGCTGAGCAGGCGGAACGTTATGATGAGATGG
TGGAATTCATGAAAAAGGTGGCAAACTTGGATGTGGAGCTATCTGTAGAGGAGAGGAATCTGATGTCAGTTGGGT
ACAAGAATGTGATTGGGGCACGGAGGGCCTCTTGGCGCATCCTCTCCTCCATCGAGCAGAAGGAGCGAGGGAAAA
GGCAATGAAGTGAATGCCAAGCGCATCAAAGAATACAAGCACAAGGTCGAGGAAGAGCTTTCAAACATCTGCAAC
GATGTCCTCTCCGTTATTGAGGATCATCTCATCCCTGCGTCTAGCACGGGGGAATCTTCTGTCTTCTATTACAAA
ATGAAAGGGGATTACTTCCGATATTCGGCAGAGTTTAAATCTGGAAATGAGAAGAAGGAAGCCGGAGAGCAGTCT
TTGAAAGCATACCAGGCTGCTATGGACATAGCGACATCTAGCCTTCCGACGACTCATCCGATCAGGCTTGGTCTT
GCTCTCAACTTCTC

> SEQ ID NO:327 232732FL 202218_300782_1e
cCAAAATTTCCGACGCCAGAGCGCGAGGAGACGCACACAGAGACTTGGCATTTGTAGAGTTTTTAGATTTATAGA
TAGCAAAGATGTCGGCACAGGCGGAGCTTTCCCGTGAGGAGAATGTGTACATGGCCAAGCTCGCTGAGCAAGCCG
AGAGGTACGAGGAGATGGTCGAATTCATGGAGAAGGTGGCCAAGACGGTTGACTCTGAGGAGCTCACCGTGGAGG
AGCGCAACCTCCTGTCTGTTGCATACAAGAATGTGATTGGAGCCCGCCGTGCGTCATGGCGCATTATCTCCTCCA
TTGAGCAGAAGGAGGAAAGCCGTGGTAACGAGGACCGTGTCACACTCATCAAGGACTACCGTGGCAAGATCGAGA
CTGAGCTCACCAAGATTTGCGACGGCATTCTCAAGCTGCTTGAATCCCACCTTGTCCCCTCTTCCACTGCCCCTG
AGTCCAAGGTCTTCTACCTCAAAATGAAGGGTGACTACTACAGGTACCTT

> SEQ ID NO:328 232732FL 191394_300740_1e
gtacgagacCACTCGAACCCGACCCGCCTCGCCGCCGCCGCCACCGAAGTAATCCCTTAATTGGTCAAAATGTCT
CGGGAGGAGAATGTCTACATGGCCAAGCTGGCCGAGCAGGCTGAAAGGTATGAGGAGATGGTTGAGTACATGGAG
AAGGTTGCAAAGACTGTAGATGTGGAAGAGCTCACTGTTGAGGAGCGCAACCTCTTGTCTGTTGCTTACAAGAAT
GTGATTGGTGCCCGCCGTGCCTCCTGGCGTATTGTCTCATCCATTGAACAGAAGGAGGAGGGTCGTGGCAATGAG
GAACATGTTACTCTGATCAAGGAGTACCGTGGCAAGATTGAAGCTGAGCTGAGCAAGATTTGCGATGGTATCCTG
AAGTTGCTTGACTCACACCTTGTGCCCTCATCTACTGCTGCAGAATCTAAGGTGTTTTACCTCAAGATGAAGGGT
GATTACCACAGGTACCTTGCGGAATTTAAGACTGGTGCCGAGAGAAAGGAAGCTGCTGAGAGCACAATGGTGGCT
TACAAGGCTGCTCAGGATATTGCTCTGGCGGATCTTGCTCCCACCCATCCCATAAGGCTTGGACTGGCACTTAAC
TTCTCTGTGTTCTACTACGAGATTCTAAACTCTCCAGACAAGGCTTGCAACCTTGCTAAGCAGGCGTTTGACGAA
GCCATCTCCGAGTTGGATACCCTCGGGGAGGAGTCTTACAAGGACAGCACTTTGATCATGCAGCTCCTGAGGGAC
AACTTGACCCTCTGGACCTCTGACCTCACGGAGGACGGTGGTGATGAGGTGAAAGAAGCCTCCAAGGGCGACGCC
TGCGAGGGCCAGTAAAATGGGAAGATCGATCGATCGATGGCTCCGCATGTTATTGGAGACCATCGATTTAGATGC
CTCATGCTGCTGTCACCATGATGGATGGATTCTTCTCCTGTTCTACTAGAATGTTTTTCTTCCTGTCCCCCCTTC
CTCTCTCTTCTCTGGTTTTTACTAGGGTGGTAGCGGTCGAATTAGTTCTTCCCATTGCTTTGCATTTGGTGCTAG
TGGTCCGTCTGGGCTGATTGTTTTCCTCTGGATATGACTCTCGTGTGTGTTGTCTCCAGATAGTGTTTTATTGAG
CAATATTTAAAGTTGTCgtccacctcctcgatgtt > SEQ ID NO:329 232732FL 128752_300477_1e
ccccccgagatctcaaaaattcaacattggcACAACCAAAAAGAAAAGAGATCCCTAAATTGGAATTCATTATGG
CGCGTGAGGAGAACGTGTACATGGCGAAGCTTGCCGAGCAAGCCGAGAGATACGAGGAAATGGTGTCGTTCATGG
AGAAAGTCTCTACTTCCTTAGGGACGTCAGAGGAACTCACGGTAGAGGAGAGAAATCTCCTCTCGGTGGCGTACA
AAAATGTTATCGGGGCTCGTAGAGCCTCGTGGCGTATAATCTCCTCCATCGAACAGAAGGAGGAGTCGAGGGGAA
ACGAGGACCATGTGAAATGCATTCAGGAGTACAGATCTAAGATTGAATCTGAACTCTCTAGTATCTGTGATGGCA
TTCTCAAGCTCCTTGATTCTTGTCTTATTCCTTCTGCTTCAGCTGGTGATTCTAAGGTGTTTTACCTTAAAATGA
AGGGTGATTATCATCGTTATTTGGCTGAGTTTAAGACTGGTGCTGAACGTAAGGAAGCCGCTGAGAGTACTCTCT
CCGCCTACAAAGCCGCTCAGGATATTGCAAATGCTGAACTTGCCCCAACTCACCCAATCCGACTTGGACTGGCTC

Figure 2 continued

TCAACTTCTCTGTGTTTTATTATGAGATTTTGAACTCTCCTGATCGTGCCTGCAATCTTGCTAAACAGGCCTTTG
ACGAAGCAATTGCTGAATTGGACACACTGGGAGAGGAGTCTTACAAGGATAGCACTTTGATCATGCAACTGCTTC
GTGACAATCTTACTCTCTGGACCTCTGATATGCAGGATGATGGCGCTGATGAAATCAAGGAAACCAAAGCTGACA
ATGAACAACAGTGAGGAAACTGCCCCTCATATTGTCTTTTGACTTCTTCCTGTTGGTTTTTATTGGGAGAAGCTG
TTTCCTTTTATTTCCTTTTTAATGTGGTTTCCCTTcagcgTTCTCTTATCCGTCGCAATAACAACTTTGACAATT
GATGTTCAATGATTTTATCTTTATTTT

> SEQ ID NO:330 232732FL 127750_302395_1e

TCCACATTCTCTCAACTTTCTCTTTCTAAAAACTCTTCCTATCTCTTTCTCTAGCACACAGACCATCAATGGCAT
CGCCGCGCGAGGAGAACGTGTACCTGGCGAAGCTGGCTGAGCAAGCCGAGCGCTACGAGGAGATGGTAGAGTTCA
TGGAGAAAGTCGTCGGCGCCGGCGACGACGAACTCACCGTCGAGGAACGCAACCTCCTCTCCGTCGCGTACAAAA
ACGTGATCGGAGCGAGGAGAGCGTCGTGGCGCATAATCTCATCGATCGAGCAGAAAGAAGAGAGTCGCGGTAATG
AAGATCATGTTGCCTCCATTAAAACCTACAGATCTAAGATCGAATCTGAATTGACTTCGATCTGTAACGGTATCC
TTAAGTTGCTCGATTCAAAACTCATCGGCACCGCTGCTACCGGTGACTCTAAGGTTTTTTATTTGAAAATGAAGG
GAGATTATTACAGGTACTTGGCTGAGTTCAAAACCGGAGCTGAGAGAAAAGAAGCCGCCGAGAATACTCTTTCGG
CTTACAAGTCGGCTCAGGATATTGCTAATGTCGAATTAGCCCCTACACATCCAATCCGATTGGGGCTAGCTCTCA
ATTTCTCAGTGTTTTACTATGAGATATTGAATTCTCCTGACCGTGCTTGTAATCTTGCCAAACAGGCATTTGATG
AGGCAATTGCGGAGCTTGACACCCTTGGAGAGGAGTCTTACAAGGATAGCACCTTGATTATGCAGCTTCTTCGTG
ATAACCTTACGTTGTGGACCTCGGATATGCAGGATGATGGactGATGAGATcgaagtacCAtcgaaAGCAGAGG
AGCAGCAGTAATGTGAGTGaaGcctccttgtttAGGAttgcaatcCTATGGACtgtgctcattGAtCgGAATTTG
CTGTTtgtgTAGTTGTgaatTCCgtgaATTGtaaTACGTAAAAGtgctgtTtCTTgccATTTGTTGTTTTcAgCA
AAgattactttttttgtgcagtatggtcccttgtatttggatgctccattggtggaaatgaattcttgttgttagg
ggaacag

> SEQ ID NO:331 232732FL 125521_300632_1e ccacaaAAAAGCTCTCCTCTCTCAATTATTAAATCCCCATTCAGAAAATCGAAAAACTCCCTCATTCAGATCTCC
CAAAAAAATACAGAGAAACAAATCTAAACATGGCGGTGGCACCGACGGCGCGTGAGGAGAACGTGTACATGGCAA
AGCTTGCAGAGCAAGCTGAGAGGTACGAAGAAATGGTTGAATTCATGGAAAAGGTCTCCAACTCCCTCGGCTCAG
AAGAACTCACCGTGGAGGAACGAAACCTCCTTTCCGTGGCGTACAAGAACGTGATCGGAGCGCGTAGGGCATCGT
GGCGTATTATCTCATCGATTGAGCAAAAGGAAGAGTCCAGAGGGAACGAGGAACACGTGAACTCTATCCGCGAGT
ACAGATCTAAGATTGAGAATGAGCTCTCTAAGATCTGTGATGGTATTCTGAAATTGCTCGATGCAAAGCTTATCC
CTTCTGCAGCATCTGGTGATTCTAAGGTGTTTTACCTGAAAATGAAAGGAGATTACCACCGCTATTTGGCTGAGT
TCAAGACCGGTGCTGAACGTAAGGAGGCTGCTGAGAGTACACTCACTGCCTACAAAGCTGCTCAGGACATTGCAA
CTACTGAACTTGCCCCAACACATCCCATCCGACTTGGACTGGCTCTTAACTTCTCTGTGTTTTACTATGAGATCT
TGAACTCTCCTGACCGTGCTTGCAATCTTGCTAAACAGGCCTTTGATGAAGCAATTGCTGAGCTGGATACATTGG
GCGAGGAGTCTTACAAGGATAGCACTTTGATCATGCAACTTCTTCGTGACAATCTCACTCTCTGGACTTCTGATA
TGCAGGATGATGGGGCTGATGAAATCAAgGAAGATCCCAAACCTGATGAAGCCAAAAATTGAAGGAAATGAAACT
CTCTAATTTGCTTTTCACTTCTTCCTGGTTGTTTTTATTGGAAGAAGCTGATTATCGTAATTTCCTTACTATTAT
GGTTCTCcACTAGGGGGTTGTCATCTTATTGGAAATGAACAACTTTTAATATTGATGTttcagagttccATCTTT
GATttaaTgtggtttTCTGgtgattagtttTCttCT

> SEQ ID NO:332 232732FL 120294_300383_1e

CATCATGGCTAAACAGGCCTTTGAGGAAGCTATTGCCGAACTGGACACTTTGGGGGAGGAATCCTATAAGGATAG
CACCCTTATCATGCAGTTATTGAGGGACAATCTCACTCTCTGGACTTCCGATATGCAGGAGCAGATGGACGAGGC
TTGACATTAAACTGCTCCTCCGGGGGGTGGGCTCAAATTTCACACAGCAACTCTGTAATCTACGCATGCAACTGA
TAGCTTTTGTAATTTTATTTCTCATCCCTCCTTTGATAATTATCTTATTCAAACTCTGGTTTGAAACTTAATGTT
TTTGATTTTATTTCTCGAGCTTCCCTTTTTAAG

> SEQ ID NO:333 232732FL 1188189_302137_1e tcttttctagtgcaaaggtgggaatctaaggaggaggaggaggaggaggaggaggggagtagtagattcttccat
tgctgATTCCGATCTGCCTCTAGCTATGGCCCCCAGAGAGGAGCTCGTTTTCATGGCCAAGCTTGCTGAGCAGGC
CGAGCGCTACGATGAGATGGCTGAGTTCATGGAGAAGGTTGCCTCCATGTCCAGCTCTGGTGACGAGCTCGCTGT
CGAGGAGCGTAACCTCCTCTCCGTCGCGTACAAGAACGTTGTCGGTGCCcgccgcGCCTCCTGGCGTATTGTCTC
CTCCATCGAGCAGAAGGAGGAGAACAAGGGCAACCAGGATCACGTCTCCGCCATCCGCGGATACCGCACCAAGAT
CGAGAATGAGCTCGCCGGCATCTGTGAGGGCGTGTTGAAGGTCCTCGCCTCTGCCCTCATCCCCGCCTGCGCCTC
CAAGGAGTCCAAGGTCTTCTACCTCAAGATGAAAGGGGATTACTACCGATACCTTGCTGAGTTCAAGACCGGCCC
CGAGAGGAAAGACGCGGCTGAGTCCACACTTCTCTCATACAAGTCTGCTCAGGACATCGCACTCACTGAGATGCC
TCCCACTCACCCGAttcGCCTtggcctCGCACTCAaCTTCTCTGTATTCTACTACGAAAtcctacaCTCACCCGa

Figure 2 continued aCGggCttGCAGCCTTGCTAAGCAGGCatgtgATGAGGccatttcTGAGCtggacACACTTgGTGaggagTcCTA
CaaggACAGCAcCCTAATCATGCagcttctcCGGGAtaacctcaCTttgTggACATCAGATC

> SEQ ID NO:334 232732FL 116870_300515_1e
CCCACGCGTCCGATGGTGGCGGCAAGGCTGCTCAGGACATTGCTTTGGCTGAGCTGCCTCCTACTCATCCAATTA
GGCTTGGGCTAGCTCTTAACTTCTCAGTGTTCTACTATGAGATCCTCAACTCGCCTGATCGTGCTTGCAACCTCG
CAAAGCAGGCTTTTGATGAGGCCATCTCGGAGCTGGACACCCTGAGCGAGGAGTCCTACAAGGACAGCACTTTGA
TCATGCAACTCCTCCGTGATAACCTGACCCTGTGGACTTCAGACATCTCGGAGGACACCGCGGAAGAGATCAGGG
AAGCTCCGAAGCGCGACTCCAGCGAGGGGCAGTAAAGCCGGCTTTATGTGCCCTAGAAGCTTGTAGCTAGTGCTT
TGCTACTGTGTAATGACACCTATGTGGCTGTGATTGTTGTCGGGAAATCTGGGGCTCCCCCGTATGTGAGGTTGC
TAGCGATGGTTTTGCAGTCTCGCCTTTAAGCTACTCGTAGCAGAGCAGGTGGGGGTCTGTGGAGCCAGGCCTGGT
TGGGGGTGGGGGAGCCTCTTGAACTGCTTGGTGGCACTTCCTGTTTT

> SEQ ID NO:335 232732FL 1098561_301485_1e
AAAAAATCAGAGAAGTGAAGAGAAGAGATCAAGGGATCGATCCTTGAGAAGGCAATGGGAATCGAGAAGGAACGT
GAGACCCTCGTCTACCTCTCTAAGCTCGCTGAGCAAGCTGAGCGCTATGACGAAATGGTGGAGTCAATGAAGAAA
GTGGCTAAGTTGGACATTGAGTTGAGTGTGGAGGAAAGAAATCTGCTCTCCGTTGGATACAAGAATGTGATCGGA
GCACGCAGGGCCTCCTGGCGCATCCTCTCTTCCATTGAGCAGAAGGAAGAGAGCAAGGGCAATGAGACAAATGTG
AAGCGCATTAAGGACTATCGCTTCAAGGTGGAGGAAGAGCTCTCCAAGATATGCAGCGACATCCTAACCATCATC
GATGAGCACCTCATCCCCTCATCCAACACCGCTGAATCCACTGTTTTCTATTACAAAATGAAAGGGGATTATTAT
CGATACCTTGCGGAGTTCAAGTCTGGGCATGAGAGGAAGGAGGCTGCCGATCAATCTCTGAAAGCTTATCAGGCG
GCTAGTAACACTGCGAACACGGATCTACCATCCACCCACCCAATCAGGCTtgGGCTCGCACTTAACTTCTCAGTC
TTCTACTATGAGATTTTgaattCTCCtg

> SEQ ID NO:336 232732FL 1099978_301489_1e
TCTTGTTTTTTGTTTTGGTTGTTGACGGAAGAAGAGGAGGGAGAAGGCATGGGTGTGGAGAAGGATCGCGATGGC
CATATCTACATGGCCAAGCTCGCTGAGCAGGCCGAACGATACGATGAGATGGTCGATTTTATGAAAAAGGTGGCA
AACATGGATGTGGAGCTCACTGTGGAGGAGCGGAATCTTTTATCAGTAGGCTACAAAAATGTGATTGGGGCCCGC
AGGGCTTCGTGGCGTATTCTCTCCTCAATTGAGCAAAAGGAGGAAGCCAAAGGCAATGAGCAGAATGTGGGGCGT
ATCAAAGACTACAAGGAAAAGGTTGAGGAAGAGCTCTCAAAGATCTGCATTGACATCTTGTCGACTATCGATGAT
CATCTTATCCCTGCATCCAGCACTGACGAGTCTTCTGTGTTTTATTACAAAATGAAAGGGGATTACTTCCGCTAT
TTAGCAGAGTTCAAAGCCTCAAGCGAGAAAAAAGATGCTGCAGAGCAGTCTCTGAAAGCATACCAGGTTGCAGCA
GATAAAGCAGCCAAGAGTCTTCCAACAACTAATCCGATCAGGCTTGGGCTTGCTTTgAACTTTTCAGTTTTCTAC
TATGAAaTCATGaactcCCCTGAAAA

> SEQ ID NO:337 232732FL 157176_301735_1e
agccaagtgaaagcaAAAAGGGAGAGGAAAAGCGCAAAATCTCCCTTCGATTATCAGTACAAAACCTCTGATTTG
AGAGATCGGAAATGGCTTCCTCCAAAGAACGCGAGAACTTCGTCTACGTCGCTAAGCTTGCTGAGCAGGCCGAAC
GCTACAATGAAATGGTTGATGCAATGAAGAGTGTAGCAAATATGGATGTTGAATTGACTGTTGAGGAAAGGAATC
TGCTTTCTGTTGGTTATAAAAATGTGGTAGGTTCTAGGAGAGCATCTTGGAGGATCTTATCCTCTATTGAGCAGA
AGGAAGAATCTAGAGGAAATGAGCAAAATGTCAAGCGAATTAAGGAGTACCGACAAAAGGTGGAGACAGAGCTCA
CCAGCATTTGCAACGATATCATGGTGGTCATTGATCAGCATCTAATTCCTTCATGCACTGCAGGCGAATCAACTG
TGTTTTACCACAAGATGAAGGGAGACTATTATCGTTATCTTGCAGAATTTAAATCTGGCAATGACAAGAAAGAGG
TTGCAGAGCTTTCATTGAAAGCATATCAGTCAGCTACAACTGCTGCAGAGGCGGAATTACCACCCACTCATCCCA
TTCGGTTGGGATTGGCTTTGAATTTCTCTGTGTTCTATTATGAGATCATGAATTCACCTGAAAGGGCATGCCATC
TGGCAAAGCAGGCCTTTGATGAAGCAATATCTGAGTTGGATAGCCTGAACGAGGATTCCTACAAAGACAGCACCT
TGATTATGCAGCTTCTAAGGGACAATCTCACCTTGTGGACTTCTGATCTTCCAGAGGATGCAGAAGATGCCCAAA
AGGGAGATGCCACAAACAAAGCAAGTGGAGGTGAAGATGCAGAGTGAATGGGCCTAATGGTTAGAACTACCTTGT
GCATTTGGAGCTGTGAGGACGGTGATACACCAAAGGGATGTGTGTGTGTTAAGTCCTagtagaTTCTTATCTTAT
GGGCATGTCGTGTcAGTTTCTTTACATGttaATTGGGTGttgCAATTCAGCATGTGTGTGATTTGTaTCCCTGTG
CTATTTCCTCTCCGTAAAGTGagTTGttTCAGTCTTtagatGATTGGTCTggtccataggtGGTTTTATTTTTca
gaGgact

> SEQ ID NO:338 232732FL 139182_300407_1e
CGGCCGAACAAAAAGCATTCGCATCCACGAGACCACTCGAACCCGACCCGCCTCGCCGCCGCCGCCACCGAAGTA
ATCCCTTAATTGGTCAAAATGTCTCGGGAGGAGAATGTCTACATGGCCAAGCTGGCCGAGCAGGCTGAAAGGTAT
GAGGAGATGGTTGAGTACATGGAGAAGGTTGCAAAGACTGTAGATGTGGAAGAGCTCACTGTTGAGGAGCGCAAC
CTCTTGTCTGTTGCTTACAAGAATGTGATTGGTGCCCGCCGTGCCTCCTGGCGTATTGTCTCATCCATTGAACAG

Figure 2 continued

AAGGAGGAGGGTCGTGGCAATGAGGAACATGTTACTCTGATCAAGGAGTACCGTGGCAAGATTGAAGCTGAGCTG
AGCAAGATTTGCGATGGTATCCTGAAGTTGCTTGACTCACACCTTGTGCCCTCATCTACTGCTGCAGAATCTAAG
GTGTTTTACCTCAAGATGAAGGGTGATTACCACAGGTACCTTGCGGAATTTAAGACTGGTGCCGAGAGAAAGGAA
GCTGCTGAGAGCACAATGGTGGCTTACAAGGCTGCTCAGGATATTGCTCTGGCGGATCTTGCTCCCACCCATCCC
ATAAGGCTTGGACTGGC

> SEQ ID NO:339 232732FL 134787_300418_1e
ACGAGATTCTAAACTCTCCAGACAAGGCTTGCAACCTTGCTAAGCAGGCGTTTGACGAAGCCATCTCTGAGTTGG
ATACCCTCGGGGAGGAGTCTTACAAGGACAGCACTTTGATCATGCAGCTCCTGAGGGACAACTTGACCCTCTGGA
CCTCTGACCTCACGGAGGACGGTGGTGATGAGGTGAAAGAAGCCTCCAAGGGCGACGCCGGCGAGGGCCAGTAAA
ATGGGAAGATCGATCGATCGATGGCTCCGCATGTTATTGGAGACCATTGATTTAGATGCCTCATGCTGCTGTCAC
CATGATGGATGGATTCTTCTTCTGTTCTACTAGAATGTTTTTCTTCCTGTCCCCCCTTCCTCTCTCTTCTCTGGT
TTTTACTAGGGTGGTAGCGGTCGAATTAGTTCTTCCCTTTGCTTTGCATTTGGTGCTAGTGGTCCGTCTGGGCTG
ATTGTTTTCCTCTGGATATGACTCTCGTGTGTGTTGTCTCCAGATAGTGTTTTATTGAGCAATATTTAAAGTTGT
CGTCC

> SEQ ID NO:340 232732FL 130213_300486_1e
GAATTCATATGAAGAAATGGTTGAATTTATGGGGGGAGTAACAACAAATGTTGAATCAGAGGAACTTTCAGTTGA
AGAGAGAAATTTATTGTCAGTTGCTTACAAAAATGTGATTGGTGCACGCAGAGCATCATGGAGAATTATTTCATC
AATTGAACAGAAAGAAGAAAGCCGTGGTAACGAAGAGAATGTATTGACCATTCGTGATTATAGATCTAAGATTGA
AACTGAACTTTCAGGCATCTGTGATGGGATTTTGAAGTTGCTTGATACTAGATTGATTCCATCTGCATCTTCTGG
TGATTCTAAAGTGTTTTATTTGAAAATGAAAGGTGATTATCATCGTTATTTGGCTGAGTTTAAAACTGGTACCGA
AAGGAAAGAAGCTGCTGAAAGTACCCTTTCTGCTTATAAATCTGCTCAGGATATCGCAACTGCTGAACTTGCACC
CACTCACCCAATCAGGCTGGGACTTGCTCTTAACTTCTCCGTCTTTTACTACGAGATCTTGAATTCTCCTGACCG
TGCTTGTAATCTCGCCAAACAGGCATTTGATGAGGCTATCGCGGAGCTGGATACCCTTGGTGAAGAATCATACAA
AGACAGCACTCTAATCATGCAGCTCCTTCGTGACAATCTTACTCTGTGGACCTCCGACATGCAGGATGATGGTGC
AGATGAAATTAAAGAAGCA

> SEQ ID NO:341 232732FL 1101416_301476_1e
gtccatcTTTGTGTTGTGAAAGAAGCTTGCAGGCCATGGGGACGGAGAAAGAGCGCGAGAAAAATGTGTACATGG
CCAAGCTTGCTGAGCAGGCAGAGCGTTATCAAGAGATGGTTGAATACATGGAAACAGTGGCCAAGCTTGATCTTG
AGCTAACTGTGGAGGAGCGCAACCTTCTGTCTGTTGGCTACAAAAATGTTATTGGAGCCCACAGAGCCTCTTGGC
GTATCCTTTCTTCCATTGAACAGAAAGAAGAGAACAAGGGCAATGAGACTAATGTGAAGCGTACCAGGGATTATA
GGCATAAAGTTGAGACAGAACTTACCAAGATTAGCAGTGAAATTTTGACTATCCTTGATGAGCATCTCATCCCCT
CATCGGGAACTGGCGAATCATCTGTCTTCTACTATAAAATGAAGGGCGACTACTACCGTTACCTGGCAGAGTTTC
AGACAGGCGAGAAGAAAAAGGAATCTGCGGACGAGTCCTTCAAAGCATATCAGGCCGCATCAAGCACTGCAAACA
CAGATCTCCCGCCCACCCATCCAATCAGGCTGGGGCTTGCCCTGAACTTTTCTGTTTCTACTATGAaAttaTGA
ATTCCCCTGAACGGGCATGcGAGcTTGCTAAACAAGCATTTGATGAGGCGATTgCTGAGCTTGACACTCTGAGTG
AAGAGTCATACAagGACagcacTCTCATTATGCAGCTACTGAGagaca

> SEQ ID NO:342 232732FL 1101740_301492_1e
ttttcttccttcatcaagctgtctctctctctctctctctctcttcctcTTTGTGAACAATGGGTGCCGAG
AAGGAGAGGGAGGGTCATGTCTACCTGGCCAAGCTTGCAGAGCAGGCTGAGCGTTACGATGAGATGGTCGAGTTC
ATGAAGAAGGTAGCCAAGCTTGACATTGAGCTGACTGTGGAGGAGCGCAATCTTCTCTCAGTGGCCTATAAGAAT
GTGATTGGAGCACGTAGGGCCTCTTGGCGTATTCTCTCCTCCATTGAGCAGAAGGAGGAGAGCAAAGGGAATGAG
GTTAACGTGAAGCGTATAAAGGATTACAGGCAAAAGGTCGATGAGGAACTCTCGAAGATCTGCCATGACATTTTG
ACTATCATAGATGAGCATCTCATCCCCTCTTCTGGGACTGGCGAATCGTCTGTCTTCTACTACAAAATGAAGGGA
GATTACTACCGCTACCTCGCAGAGTTCAAAGCTGGTCCGCAGAAAAAGGAAGACGCAGATGAGTCCTTCAAAGCC
TACCAAGCTGCGTCGAGCACCGCGAGTACTGATCTGCCACCTACCCATCCCATCAGGCTTGGACTCGCCTTGAAT
TTCTCTGTTTTCTACTATGAAATTTTGAATTCGCCCGAGCAGGCATGCCAATTAGCAAAACAAGCATTCGATGAG
GCGATTGCAGAGCTCGATACTCTGAGCGAGGAGTCATACAAGGACAGCACCCTTATTATGCAGCTTCTAAGAGAC
AACCTGACCTTGTGGACTTCAGATCTGCAAGAAGATGGAGGTGATGAGCACTCCAAGGGAGAGGATCTGAAAGTA
GGAGATGCAGAGGAATCGTAGTGCCAGTTTGATTGTTCGAGCTGAGTTTgAAGGAGTCGAGCCGGATATGCATC
CTTGGTACAAAATTTgACATGTGTTAGATTCTgTGTGGCATTTgttTGAAGGAATATCCTATGTAGAttgttATG
ttCTTgttCtgctCTATTgctAcaagGGCTgttgtTACAATTACAAGTTATACAtTTTCTATTTGAGGGaa

> SEQ ID NO:343 238465FL 129965_301240_1e
gaattcgagagaaacagaaaaaggagattcagaattgggtaatcacggctatatttggagacggagggtggaatt

Figure 2 continued tccacCACAACCAAAGATTGATTCATTCATCATCATCTTGTAACCAAATCGAAAAAAGAAACCCTTCACCACACG
GTGGTAGAGGAGCTTTGCCGTCAGAAGGTGGTTCTCCTCCTGATCTTCTTTTCCTTGCCGGTGGTGGTGAATTTC
TCATCAAATACCCAATCAACTGACCCCCTTATTCTTTTGATTTTTTCCTAGATTTACCAATTCATTTTCTTAACT
TGAAAACCAAATCATATTCTAGTACATAATACATTACAATATACAATATGTTGACCATCAAAAGAGTTCCTACTG
TTGTTTCTAATTACCAAGAAGATGGTTCTGCCGCTGCTGCTGAAACTGTTGGCTGTGGCCGTAATTGCCTTGGAA
AGTGCTGTTTACCTGTGTCCAAGCTTCCTTTGTATGCATTCAAGGGAGATGGGATTGATTCAATCAAAGGAGGAG
AGGAACCTGAGGTGTCTTTCTTTGATACCTTAATTCTTGGGCAATGGGAGGATCGaatgagccGTGgccttttcc
gATATGATGTAACACAGtGTGagaCTaaggttATTcccggagAGTATGGATTTG > SEQ ID NO:344 238465FL 245696_301570_1e
acgcgtcggactccagtccggatgcggcaagaatgtctcgggtcgtgtgcattcctggagcaaagttgccattgt
atctcTTTGGCAAACCGGATGTGGATGAGAGTGGAGAAGTCCCTACCAAGGAGCTGGGACAAAACTCTTTCCTGG
ATTCAGCTATTCTCGGTCAGTGGGCTGATAGGCAAGCCAAGGGACTATTTCGCTACGACGTTACCGCGTGCGACA
CAAAGGTGCTGCCTGGGAAGTATGGTTTTATTGCGCAATTGAATGAAGGCCGACACCTGAAGAAACGTCCCACTG
AATTCCGCGTTGATCAAGTCCTCCAGCCTTTCGATGCAAAGAAGTTTAACTTCACAAAGGTCGGTCAGGAGGGGA
TGATCTTTTGCTTCGAGCAGAGCCACGAGGACAAGAGCTTCCACCACGAACAAGCTCAAGTGAAAGGAAGTCCAA
ACGTTGTGGTGATCAACGTGAGCCCGATCGAGTATGGACATGTTTTGCTGGTTCCTCGAGTTCTCGATTGTATCC
CGCAGCATCTGGAAACGGATACTTTCCTTTTGGCTCTTCATATGGCTGCAGAGGCATCCAGTCCATATTTCCGCT
TGGGATATAATAGTCTTGGAGCTTTCGCGACGATCAATCATCTCCATTTCCAGGCATATTATTTGGGAAACATAT
TCCCCGTGGAGAaggctccacAgAAAttaaTATACAg > SEQ ID NO:345 238465FL 56392_300123_1e
catcaatgttagtccgatagagtatggccatgtgctgctgattcctcgtgttcttgactgcttgcctcaaaggat
cgatcACAAAAGCCTTTTGCTTGCAGTTCACATGGCTGCTGAGGCTGCTAATCCATACTTCAGACTCGGTTACAA
CAGCTTGGGTGCTTTTGCCACTATCAATCATCTCCACTTTCAGGCTTATTACTTGGCCATGCCTTTCCCACTGGA
GAAAGCTCCTACCAAGAAGATAACTACCACTGTTAGTGGTGTCAAAATCTCAGAGCTTCTAAGTTACCCTGTGAG
AAGTCTTCTCTTTGAAGGTGGAAGCTCTATGCAAGAACTATCTGATACTgttTCagactgctGTGTTTgccttCA
AAAc > SEQ ID NO:346 238465FL 55977_300129_1e
ttattggtggtagtgatcttcaaggaagaagctttctctatcgggaattgcattgccaaatagtaagcctgaaag
tgaagATGGTTAATGGTAGCGAAAGCGCCTAGaCTGTTGTATCCAAGTCGGAAATACGTATTATCGGCTTCAGCC
GCCATTTGAAGAGCAAGCAAAAGGCTTTTGTGATCAATCCTTTGAGGTAAGCAATCAagaacATTCCTTTCAACA
TTCTCATCTCTGACtCTGGCAAACGAATCTtccTtctccCTCAgtgttACGCagAGAAACAggCtttaggAGAAG
TTAGCTCaaCGCTATTGGATAcgcaaGTGaatccagCGGtttGGGAGATGAGTggACACATGgt > SEQ ID NO:347 238465FL 285026_200241_1e
accggatcccttcccctcacggcggtaggggtgcctctccttctgaaggcggttgcccctccgatctcctcttcc
tcgccGGCGGCGGTCCCCTTTTTCCTCTCTCCTAATTTTTCTTATTTGTAAAGCGCACATACGGATTTGGATACT
GGTGTATATTACGTATAGCATACGCAGAAAATATTTATATTTTTGATCATCCATCCAAGAATAATAGGAAGGGAT
GCTGACTATTAAAAGGGTGCCGACCCTAGTTTCCAACTACCAAGAGGATGTGCCTGAAAGCAACAACGTAGTTGG
TTGTGGCCGCAATTGCCTTGGAAAATGCTGTTTGCCGGCGTCCAGGCTTCCTCTTTATGCATTCAAGAATGATGA
CAATGAGCCAATTGAAAACGGTATTGATGCCTTGCCTGGGGAGGATTGTCAGATATCTTTTTTGAATGATCTGCT
GTTGGGCCTATGGGAAGAGCGGATGAGCCAGGGACTGTTTCGATATGATGTCACAACCTGTGAGACTAAAGTCAT
TCCTGGGAGATATGGTTTTAtTGCACAGCTGAATGAGGGGCGCCACCTAAAAAAGCGCCCAACAGAGTTTCGCAT
CGATCAGGTTCTTCAGCCTTTTGACGAGAACAAATTCAATTTTACCAAAGTGGGCCAGGACGAAGTGCTTTTCAG
GTTTGAGCCAAGCACTGACTGCAAGGCCCATTACTTTTCGGGTGTGGGAGTAGATGCTGGTGTTTCACCGAGtat
TGTTGCTATCAATGTGAGCCCAATCGAGTATGGCCATGTGCTTTTGATACCTCGAGtTCTTGATTACTTTCCTCA
GAGAATTGATCGTGATAGTTTCACGGTTGCTCTCCATTTCGCCAGAGAACTGGCtGATCCCTTCTttagggTAGG
TTATAACAGTCTGGGCGCCTTCgccactATAAAcc > SEQ ID NO:348 238465FL 129965_301607_1e
TTTTTTTTTAACAAATTTTCATTTTTCATATAAGGTAGAGAGAGAGATGTACACAACCACTTCACTGAGCAAAGT
ACACATGCATTAAGATCATTATTGAATGATCAAAATCAAACTACACGCAATAACTACTAAAACTATCCTACTTTG
TTACGCAGGTAACAGAAAAGTTGAAAGAACAAGAGACAACACTGCAACCCTCTTGAAACCCTAATAGTACTTCTT
CACTGCTGAACCAGACAACCTTGGGGGTAATATGTGGCAGAGGTGCGAGATGAGCCCCCGAAAAAAGAATCTTCA
TCCTCATCCTTGACATCTCCTTCCTCTTTTTCTGCAACACAAACCATTTCCTGAACACCTGCAGCTTCAAATATA
TAGGTTTTCACTTCTTGAAACCTTTCCTCGGAGAGAGACACCTCTGCAAGGAGCCTCCAAGCATAATTTTCAGAT

Figure 2 continued

GCGTCCTCGTAGTCATTCTTCCTCTTCAACACTATATGTCCACTTATCTCCCACACAGCTGGATTTACTTGGGTA
TCAAGAAGCTCCTGACTCACTTCTCCAAGTGCTTGCTTTTCAGCGTAACACTGAGGGAAGAGGAAGATTCGTTTT
CCACAATCAGAGATGAGAACATTGTATGGAATGTTGGTCTCTTgAagaaAAATgcaaGCAttagaGACAaCGTcA
g > SEQ ID NO:349 238465FL 240678_301316_1e
gcattcgtgcatgcagaagtgtttgcactgaccggcctagactggggctggtccgtgccgcatgttccgcaacca
cggctCTGATTAATCTCCCCGGGCGCCCCAGCCTCGCCTATGCGCGCACTGGTTTCCCCACTTGCAACACTCTGC
TGAGCTCGCCATCTTTCCACGGCGGTCGAGGGGCCAGCCCCTCGGAAGGAGGGCATCCCTCCGACCTCACCTTCC
TCGCCGGTGGTGGTGGTGCCGCCGCCGCCGCCGCTTCTTGCAGCCaggggaAAGTTCGCGTTTTTTTATACAACT
TAACTTCCGAAGATGCTGACTATTAAGCGAGTTCCAACGCTCCTGTCCGTGAACCAGGACGAGTGCTTGGCAAGC
TGCTGCATTACAGAGATGGACCTTCCTTTGTTTAAGTATACAAAGAAGAGTGTTAGGCGTCCTTCCGATGAGGAG
TTGCCACCAGCCATTGAAACATCCTTCCTCGGGACGTTGCTGCTGTCTCAGTGGGAAGAACGCGCATGCCAAGGA
TTGTTTCGATACGATGTCACTGCTTGTGAATCGCAGGTGCTTCCGGGGAAACATGGATTTattgcaCAGCTCAAC
GAAGGACGgcaCctgaaGAAGCGgccGACTGAGTTTCGAGTTgATcaagtccttcaaGAGTTTGATCCc > SEQ ID NO:350 273716FL 114938_300010_1e
aattaccaattccaTTCCTCCACAGCTTCTTCTTTTCCTTAGTAACCCGCCACTAATCTCTTTGAAATCCAAGTT
ACAAAATCTTTTGTTCGTGTAGGAAATTCGAGAAATCTTAGGAAAAGAGTATTATTGTTGTTTAGAGAGGGTAAA
TCCCAGGTAAACAAGTTGTAGACATCACGGCTATACACAAAGCAAACCGTCGATCATTCTTACATGTTCGTTCAG
TACGACGTAAGGGTTGTGTAACTGCCACCAATCCTGCGCCGCACGGCGGACGTGGCGCTTTGCCCTCTGAAGGCG
GTAGTCCTTCCGACCTCCTCTTCCTTGCCGGCGGTGGTTCTCTCCTTTCTTCTACCTGCTAGATTTAGTTACTTA
TCCTTACATAGTTACTTCCTTCTCCGTAAATTATTTTAATTGTTTTGCACATTAGCAATTATTAAGGTTGTTCT
TGTACCTAGTATTTTTCCCTTGAAAAATCAAAGCAAAAAAAACCAAACATGATGCTCAAGATTAAGAGGGTTCCT
ACGCTTGTTTCCAACTTCCAAAAGGAAGAGGCTGAAGAAACTCTTGCTCGTGGTGCTGGCTGTGGCCGCAACTGC
CTCCGAAACTGCTGCCTTCCAGGGTCAAAGCTGCCACTGTATGCTTGCAAGAGTTTGAGAAATGGCACGTCTGTT
GCCGATGAAACCAAGGAACCTCCCGTTGACTTCTTGGAATCCCTCCTTCTCGGGGAATGGAGGATCGTCAGCAG
AAAGGTCTCTTTCGCTATGATGTCACTGCTTGCGAAACCAAGGTTATTCCTGGAGAATATGGTTTCGTTGCTCAA
CTGAATGAGGGAAGGCACCTCAAGAAGAGGCCAACTGAGTTTCGCGTTGATAAGGTGCTGCAGCCTTTTGATGGA
AGCAAGTTCAACTTCACTAAGGTTGGTCAGGAGGAGTTGCTCTTCCAGTTTGAAGCAAGTGAGGATAATGAAGTC
CAATTCTTTCCAAATGCGCCCATTGATGCCGAAAAATCTCCAAGTGTCGTTGCCATCAATGTCAGTCCCATTGAG
TACGGACACGTGCTTTTGATACCTAAGGTTCTTGAATGCCTTCCCCAGAGGATCGACAGGGACAGCTTATTGCTT
GCACTGCAAATGGCTGCCGAAGCAGCAAACCCATACTTCCGTTTGGGTTATAACAGCTTGGGTGCATTTGCGACT
ATCAACCATCTTCACTTTCAGGCTTATTACTTGGCTGTGCCATTCCCCATGGAGAAGGCCCCCACGCGGAAGATA
ATCTTTGCTGATGCTGGCGTGATGATATCTGAGATGCTGAATTATCCAGTTCGAGGACTTGTCTTTGAGGGTGGA
AATACTTTGGAGGATTTCGCCAATGTTGTCTCTGGTTCTTGCATTTGCCTGCAAGAGAATAACATTCCCTACAAT
GTTCTAATCTCTGATTCGGCAAAAAGGGTATTCCTTCTCCCACAGTGCTACGCAGAGAAACAGGCTCTAGGGGAG
GTCAGCTCTGAACTGCTTGATACTCAAGTCAATCCTGCAGTATGGGAGATTAGTGGACACATGGTCTTGAAGAGG
AAGGAGGATTACGAGGGTGCAACCGAGGCAAATGCCTGGAGGCTTCTCGCTGAGGTCTCACTTTCTGAAGCGAGG
TTCCAAGAAGTGACTGCTCTCATCTTTGAAGCCATTGATTGCAGTGTTGAAGAGAATGAGAATGCCAATGAAGGT
TCTCCTGAGAAGCCAGATGTTGCACCTCAGCCTATGGAGGAAATTGATGCTCTCAACACCCATGCTACCATGGTT
CCCGTGTAGGGTTTTCATGGTCGAGCTGTGGTGTTTGTCCTGTTGTTACTATTTCAACTATATGAACATTGAGGG
AGTTTCTATCTATGGCTGCACTTGTGAAATATCCCTAAATAAGGCTAGCCATGTTCTATGTATTGATGAAGTTGT
TTGGTTCCTATGTGAATTGAACCTTGTCTTTTATTGCTTCATATTAATGTGGAGTTGCTCAGTGTCCTCTGGGAA
TTGACCTTGGATACTATGTTTGTTGTCTGTTATTTAAGACAATATATTTGGTAATGGAAGTTGGAGTTTCCCTGT > SEQ ID NO:351 273716FL 245696_301570_1e
acgcgtcggactccagtccggatgcggcaagaatgtctcgggtcgtgtgcattcctggagcaaagttgccattgt
atctcTTTGGCAAACCGGATGTGGATGAGAGTGGAGAAGTCCCTACCAAGGAGCTGGGACAAAACTCTTTCCTGG
ATTCAGCTATTCTCGGTCAGTGGGCTGATAGGCAAGCCAAGGGACTATTTCGCTACGACGTTACCGCGTGCGACA
CAAAGGTGCTGCCTGGGAAGTATGGTTTTATTGCGCAATTGAATGAAGGCCGACACCTGAAGAAACGTCCCACTG
AATTCCGCGTTGATCAAGTCCTCCAGCCTTTCGATGCAAAGAAGTTTAACTTCACAAAGGTCGGTCAGGAGGGGA
TGATCTTTTGCTTCGAGCAGAGCCACGAGGACAAGAGCTTCCACCACGAACAAGCTCAAGTGAAAGGAAGTCCAA
ACGTTGTGGTGATCAACGTGAGCCCGATCGAGTATGGACATGTTTTGCTGGTTCCTCGAGTTCTCGATTGTATCC
CGCAGCATCTGGAAACGGATACTTTCCTTTTGGCTCTTCATATGGCTGCAGAGGCATCCAGTCCATATTTCCGCT
TGGGATATAATAGTCTTGGAGCTTTCGCGACGATCAATCATCTCCATTTCCAGGCATATTATTTGGGAAACATAT
TCCCCGTGGAGAaggctccacAgAAAttaaTATACAg

Figure 2 continued

> SEQ ID NO:352 273716FL 57229_300132_1e
TGCAATTGCcAATTCCATTCCTCTACATCTTCTTCTTTTCCTTACCAATCCACCTCCAATCTCTTTGAAATCAAG
TTACAGAAATCTTTTGTTCGTGTAGGAAATTCGAGAAATCTTAGAAAAAAAATATATTATTGCTGTTTAGAAAGG
GTAAATCCCAGGTGAACAAGTTGTAGACATCACGGCTATACACAAAGCAAACCGCCGACCATTCTTACATGTTCG
TTCAGTACGACGTAAGGGTTGTGTAACTGCCACCAATCCTGCGCCGCACGGCGGACGTGGCGCTTTGCCCTCTGA
AGGCGGTAGTCCTTCCGACCTCCTCTTCCTTGCCGGCGGTGGTTCTCTCCTTTCTTCTACCTGCTAGATTTACTT
ACTTATATACCTTACATAGTTAATTCCTTCTCCGTAAATTACTAATTGTTTTGCACATTAGCAATTATTAAGGTT
GTTCTTGTACCTAGTATTTTTACCTTGAAAAATCAAAGGAAAAAAAAGCAAACATGATGCTCAAGATTAAGAGGG
TTCCTACACTTGTTTCCAACTTCCAAAAGGAAGAGGCTGAAGAAGCTCTTGCTCGTGGTGCTGGCTGTGGCCGCA
ATTGCCTCCGAAACTGCTGCCTTCCAGGGTCAAAGCTGCCACTGTATGCTTCCAaGaACTTGAGaAagGGCAAGT
CTGTTGCCGATGAAaccaaggAGcctccTGttgacttCttg > SEQ ID NO:353 273716FL 56392_300123_1e
catcaatgttagtccgatagagtatggccatgtgctgctgattcctcgtgttcttgactgcttgcctcaaaggat
cgatcACAAAAGCCTTTTGCTTGCAGTTCACATGGCTGCTGAGGCTGCTAATCCATACTTCAGACTCGGTTACAA
CAGCTTGGGTGCTTTTGCCACTATCAATCATCTCCACTTTCAGGCTTATTACTTGGCCATGCCTTTCCCACTGGA
GAAAGCTCCTACCAAGAAGATAACTACCACTGTTAGTGGTGTCAAAATCTCAGAGCTTCTAAGTTACCCTGTGAG
AAGTCTTCTCTTTGAAGGTGGAAGCTCTATGCAAGAACTATCTGATACTgttTCagactgctGTGTTTgccttCA
AAAc > SEQ ID NO:354 273716FL 55977_300129_1e
ttattggtggtagtgatcttcaaggaagaagctttctctatcgggaattgcattgccaaatagtaagcctgaaag
tgaagATGGTTAATGGTAGCGAAAGCGCCTAGaCTGTTGTATCCAAGTCGGAAATACGTATTATCGGCTTCAGCC
GCCATTTGAAGAGCAAGCAAAAGGCTTTTGTGATCAATCCTTTGAGGTAAGCAATCAagaacATTCCTTTCAACA
TTCTCATCTCTGACtCTGGCAAACGAATCTTtccTtctccCTCAgtgttACGCagAGAAACAggCtttaggAGAAG
TTAGCTCaaCGCTATTGGATAcgcaaGTGaatccagCGGtttGGGAGATGAGTggACACATGgt > SEQ ID NO:355 273716FL 285026_200241_1e
accggatcccttcccctcacggcggtaggggtgcctctccttctgaaggcggttgcccctccgatctcctcttcc
tcgccGGCGGCGGTCCCCTTTTTCCTCTCTCCTAATTTTCTTATTTGTAAAGCGCACATACGGATTTGGATACT
GGTGTATATTACGTATAGCATACGCAGAAAATATTTATATTTTTGATCATCCATCCAAGAATAATAGGAAGGGAT
GCTGACTATTAAAAGGGTGCCGACCCTAGTTTCCAACTACCAAGAGGATGTGCCTGAAAGCAACAACGTAGTTGG
TTGTGGCCGCAATTGCCTTGGAAAATGCTGTTTGCCGGCGTCCAGGCTTCCTCTTTATGCATTCAAGAATGATGA
CAATGAGCCAATTGAAAACGGTATTGATGCCTTGCCTGGGGAGGATTGTCAGATATCTTTTTTGAATGATCTGCT
GTTGGGCCTATGGGAAGAGCGGATGAGCCAGGGACTGTTTCGATATGATGTCACAACCTGTGAGACTAAAGTCAT
TCCTGGGAGATATGGTTTTAtTGCACAGCTGAATGAGGGGCGCCACCTAAAAAAGCGCCCAACAGAGTTTCGCAT
CGATCAGGTTCTTCAGCCTTTTGACGAGAACAAATTCAATTTTACCAAAGTGGGCCAGGACGAAGTGCTTTTCAG
GTTTGAGCCAAGCACTGACTGCAAGGCCCATTACTTTTCGGGTGTGGGAGTAGATGCTGGTGTTTCACCGAGtat
TGTTGCTATCAATGTGAGCCCAATCGAGTATGGCCATGTGCTTTTGATACCTCGAGtTCTTGATTACTTTCCTCA
GAGAATTGATCGTGATAGTTTCACGGTTGCTCTCCATTTCGCCAGAGAACTGGCtGATCCCTTCTTtagggTAGG
TTATAACAGTCTGGGCGCCTTCgccactATAAAcc > SEQ ID NO:356 273716FL 240678_301316_1e
gcattcgtgcatgcagaagtgtttgcactgaccggcctagactggggctggtccgtgccgcatgttccgcaacca
cggctCTGATTAATCTCCCCGGGCGCCCCAGCCTCGCCTATGCGCGCACTGGTTTCCCCACTTGCAACACTCTGC
TGAGCTCGCCATCTTTCCACGGCGGTCGAGGGGCCAGCCCCTCGGAAGGAGGGCATCCCTCCGACCTCACCTTCC
TCGCCGGTGGTGGTGGTGCCGCCGCCGCCGCCGCTTCTTGCAGCCaggggaAAGTTCGCGTTTTTTTATACAACT
TAACTTCCGAAGATGCTGACTATTAAGCGAGTTCCAACGCTCCTGTCCGTGAACCAGGACGAGTGCTTGGCAAGC
TGCTGCATTACAGAGATGGACCTTCCTTTGTTTAAGTATACAAAGAAGAGTGTTAGGCGTCCTTCCGATGAGGAG
TTGCCACCAGCCATTGAAACATCCTTCCTCGGGACGTTGCTGCTGTCTCAGTGGGAAGAACGCGCATGCCAAGGA
TTGTTTCGATACGATGTCACTGCTTGTGAATCGCAGGTGCTTCCGGGGAAACATGGATTTattgcaCAGCTCAAC
GAAGGACGgcaCctgaaGAAGCGgccGACTGAGTTTCGAGTTgATcaagtccttcaaGAGTTTGATCCc > SEQ ID NO:357 273716FL 129965_301240_1e
gaattcgagagaaacagaaaaggagattcagaattgggtaatcacggctatatttggagacggagggtggaatt
tccacCACAACCAAAGATTGATTCATTCATCATCATCTTGTAACCAAATCGAAAAAAGAAACCCTTCACCACACG
GTGGTAGAGGAGCTTTGCCGTCAGAAGGTGGTTCTCCTCCTGATCTTCTTTTCCTTGCCGGTGGTGGTGAATTTC
TCATCAAATACCCAATCAACTGACCCCCTTATTCTTTTGATTTTTTCCTAGATTTACCAATTCATTTTCTTAACT

Figure 2 continued

TGAAAACCAAATCATATTCTAGTACATAATACATTACAATATACAATATGTTGACCATCAAAAGAGTTCCTACTG
TTGTTTCTAATTACCAAGAAGATGGTTCTGCCGCTGCTGCTGAAACTGTTGGCTGTGGCCGTAATTGCCTTGGAA
AGTGCTGTTTACCTGTGTCCAAGCTTCCTTTGTATGCATTCAAGGGAGATGGGATTGATTCAATCAAAGGAGGAG
AGGAACCTGAGGTGTCTTTCTTTGATACCTTAATTCTTGGGCAATGGGAGGATCGaatgagccGTGgcctttcc
gATATGATGTAACACAGtGTGagaCTaaggttATTcccggagAGTATGGATTTG > SEQ ID NO:358 273716FL 129965_301607_1e
TTTTTTTTTAACAAATTTTCATTTTTCATATAAGGTAGAGAGAGAGATGTACACAACCACTTCACTGAGCAAAGT
ACACATGCATTAAGATCATTATTGAATGATCAAAATCAAACTACACGCAATAACTACTAAAACTATCCTACTTTG
TTACGCAGGTAACAGAAAAGTTGAAAGAACAAGAGACAACACTGCAACCCTCTTGAAACCCTAATAGTACTTCTT
CACTGCTGAACCAGACAACCTTGGGGGTAATATGTGGCAGAGGTGCGAGATGAGCCCCCGAAAAAAGAATCTTCA
TCCTCATCCTTGACATCTCCTTCCTCTTTTTCTGCAACACAAACCATTTCCTGAACACCTGCAGCTTCAAATATA
TAGGTTTTCACTTCTTGAAACCTTTCCTCGGAGAGAGACACCTCTGCAAGGAGCCTCCAAGCATAATTTTCAGAT
GCGTCCTCGTAGTCATTCTTCCTCTTCAACACTATATGTCCACTTATCTCCCACACAGCTGGATTTACTTGGGTA
TCAAGAAGCTCCTGACTCACTTCTCCAAGTGCTTGCTTTTCAGCGTAACACTGAGGGAAGAGGAAGATTCGTTTT
CCACAATCAGAGATGAGAACATTGTATGGAATGTTGGTCTCTTgAagaaAAATgcaaGCAttagaGACAaCGTcA
g

Figure 3

This figure contains results of BLASTX queries against the non-redundant protein database at Genbank using assembled hit contigs as query sequences. Only results with Pz values < 1 x e-4 were considered, and only the result with highest homology is shown.

| SEQ ID NO | Hit Contig | Length (bp) | Pz Score | Annotation |
|---|---|---|---|---|
| 1 | 129424 | 697 | 9.00E-86 | >pir\|\|T49933 inorganic pyrophosphatase-like protein - Arabidopsis thaliana emb\|CAB89365.1\| (AL353994) inorganic pyrophosphatase-like protein [Arabidopsis thaliana] dbj\|BAB09520.1\| (AB020752) inorganic pyrophosphatase-like protein [Arabidopsis thaliana] emb\|CAC19853.1\| (AJ252210) inorganic pyrophosphatase [Arabidopsis thaliana] |
| 2 | 129426 | 715 | 1.00E-41 | >gb\|AAD30576.1\|AC007260_7 (AC007260) Highly similar to rice zinc finger protein [Arabidopsis thaliana] |
| 9 | 129870 | 641 | 5.00E-81 | >gb\|AAD18098.1\| (AC006416) Identical to gb\|Y10557 g5bf gene from Arabidopsis thaliana. ESTs gb\|R30578, gb\|R90475, gb\|T22384, gb\|T22425, gb\|N64934 and gb\|T46767 come from this gene. gb\|AAG40395.1\|AF325043_1 (AF325043) At1g09340 [Arabidopsis thaliana] |
| 10 | 129965 | 1929 | e-160 | >pir\|\|T04808 hypothetical protein F10M23.190 Arabidopsis thaliana emb\|CAB36531.1\| (AL035440) putative protein [Arabidopsis thaliana] emb\|CAB79540.1\| (AL161565) putative protein [Arabidopsis thaliana] |
| 11 | 129965 Contig B | 694 | 5.00E-41 | >dbj\|BAB08581.1\| (AB010071) gene_id:MCO15.7~pir\|\|T04808~strong similarity to unknown protein [Arabidopsis thaliana] |
| 13 | 130203 | 673 | 5.00E-11 | >gb\|AAC69132.1\| (U78721) 30S ribosomal protein S5 [Arabidopsis thaliana] |
| 14 | 130213 | 1033 | e-105 | >emb\|CAB42546.2\| (AJ238681) 14-3-3-like protein [Pisum sativum] |
| 15 | 130294 Contig A | 500 | 2.00E-56 | >sp\|P29344\|RR1_SPIOL 30S RIBOSOMAL PROTEIN S1, CHLOROPLAST PRECURSOR (CS1) pir\|\|S26494 ribosomal protein S1, chloroplast - spinach pir\|\|A44121 ribosomal protein S1 precursor, chloroplast - spinach emb\|CAA46927.1\| (X66135) ribosomal protein S1 [Spinacia oleracea] gb\|AAA34045.1\| (M82923) chloroplast ribosomal protein S1 [Spinacia oleracea] |
| 17 | 130294 Contig C | 654 | 6.00E-42 | >pir\|\|T02213 NBS-LRR type resistance protein - rice (fragment) gb\|AAB96985.1\| (AF032688) NBS-LRR type resistance protein [Oryza sativa] |
| 18 | 130964 | 641 | 3.00E-26 | >pir\|\|D75542 hypothetical protein - Deinococcus radiodurans (strain R1) gb\|AAF09840.1\|AE001886_6 (AE001886) hypothetical protein [Deinococcus radiodurans] |
| 19 | 130795 | 589 | 6.00E-13 | >dbj\|BAB01982.1\| (AP002457) contains similarity to unknown protein~gb\|AAF27062.1~gene_id:MWE13.5 [Arabidopsis thaliana] |
| 20 | 130994 | 664 | 4.00E-49 | >gb\|AAK01359.1\|AF314810_1 (AF314810) dehydration stress-induced protein [Brassica napus] |

Figure 3 continued

| SEQ ID NO | Hit Contig | Length (bp) | Pz Score | Annotation |
|---|---|---|---|---|
| 22 | 131002 Contig B | 600 | 4.00E-08 | >gb\|AAK39575.1\|AC025296_10 (AC025296) putative reverse transcriptase [Oryza sativa] |
| 25 | 131048 | 860 | 1.00E-75 | >gb\|AAF97345.1\|AC021045_2 (AC021045) Putative 60S ribosomal protein L9 [Arabidopsis thaliana] gb\|AAF97348.1\|AC021045_5 (AC021045) Putative 60S ribosomal protein L9 [Arabidopsis thaliana] gb\|AAG40039.1\|AF324688_1 (AF324688) At1g33120 [Arabidopsis thaliana] gb\|AAG41455.1\|AF326873_1 (AF326873) putative 60S ribosomal protein L9 [Arabidopsis thaliana] gb\|AAK00376.1\|AF339694_1 (AF339694) putative 60S ribosomal protein [Arabidopsis thaliana] gb\|AAK53003.1\|AF375419_1 (AF375419) At1g33140/T9L6_10 [Arabidopsis thaliana] |
| 27 | 131133 Contig A | 590 | 4.00E-71 | >sp\|P27495\|CB24_TOBAC CHLOROPHYLL A-B BINDING PROTEIN 40 PRECURSOR (LHCII TYPE I CAB-40) (LHCP) pir\|\|CDNT40 chlorophyll a/b-binding protein precursor (cab-40) - common tobacco emb\|CAA36958.1\| (X52744) Cab40 protein precursor [Nicotiana tabacum] |
| 28 | 131133 Contig B | 300 | 1.00E-12 | >gb\|AAB87573.1\| (AF034631) chlorophyll a/b binding protein of LHCII type I precursor [Panax ginseng] |
| 30 | 131365 | 2050 | 2.00E-80 | >dbj\|BAA96774.2\| (AP002521) Similar to Arabidopsis thaliana chromosome II BAC F26H6; putative retroelement pol polyprotein (AC006920) [Oryza sativa] dbj\|BAB08213.2\| (AP002539) Similar to Arabidopsis thaliana chromosome II BAC F26H6; putative retroelement pol polyprotein (AC006920) [Oryza sativa] |
| 34 | 167306 Contig B | 610 | 6.00E-22 | >sp\|Q39963\|ER1_HEVBR ETHYLENE-INDUCIBLE PROTEIN HEVER pir\|\|S60047 ethylene-responsive protein 1 - Para rubber tree gb\|AAA91063.1\| (M88254) ethylene-inducible protein [Hevea brasiliensis] |
| 35 | 167361 Contig A | 618 | 4.00E-08 | >emb\|CAA64221.1\| (X94449) homeobox-leucine zipper protein [Pimpinella brachycarpa] |
| 37 | 167373 | 910 | 1.00E-82 | >sp\|P34899\|GLYM_PEA SERINE HYDROXYMETHYLTRANSFERASE, MITOCHONDRIAL PRECURSOR (SERINE METHYLASE) (GLYCINE HYDROXYMETHYLTRANSFERASE) (SHMT) pir\|\|A42906 glycine hydroxymethyltransferase (EC 2.1.2.1) - garden pea gb\|AAA33687.1\| (M87649) serine hydroxymethyltransferase [Pisum sativum] |
| 38 | 167516 | 713 | 3.00E-27 | >sp\|Q41229\|PSE2_NICSY PHOTOSYSTEM I REACTION CENTRE SUBUNIT IV B PRECURSOR (PSI-E B) pir\|\|T16963 photosystem I chain PSI-E, isoform b - wood tobacco gb\|AAB31705.1\| (S72358) photosystem I subunit PSI-E [Nicotiana sylvestris, leaves, Peptide Chloroplast, 143 aa] |
| 39 | 168165 | 462 | 1.00E-73 | >gb\|AAG52451.1\|AC010852_8 (AC010852) putative aminopeptidase, 3' partial; 76469-79469 [Arabidopsis thaliana] |

Figure 3 continued

| SEQ ID NO | Hit Contig | Length (bp) | Pz Score | Annotation |
|---|---|---|---|---|
| | 129870 FL | 1374 | 0.0 | >ref\|NP_172405.1\| (NM_100804) putative RNA-binding protein [Arabidopsis thaliana] gb\|AAD18098.1\| (AC006416) Identical to gb\|Y10557 g5bf gene from Arabidopsis thaliana. ESTs gb\|R30578, gb\|R90475, gb\|T22384, gb\|T22425, gb\|N64934 and gb\|T46767 come from this gene gb\|AAG40395.1\|AF325043_1 (AF325043) At1g09340 [Arabidopsis thaliana] gb\|AAK59555.1\| (AY035050) putative RNA-binding protein [Arabidopsis thaliana] gb\|AAL16114.1\|AF428282_1 (AF428282) At1g09340/T31J12_6 [Arabidopsis thaliana] gb\|AAL47493.1\| (AY070022) putative RNA-binding protein [Arabidopsis thaliana] |
| | 130294 FL | 1477 | 0.0 | >sp\|P29344\|RR1_SPIOL 30S ribosomal protein S1, chloroplast precursor (CS1) pir\|\|S26494 ribosomal protein S1, chloroplast - spinach pir\|\|A44121 ribosomal protein S1 precursor, chloroplast - spinach emb\|CAA46927.1\| (X66135) ribosomal protein S1 [Spinacia oleracea] gb\|AAA34045.1\| (M82923) chloroplast ribosomal protein S1 [Spinacia oleracea] |
| | 130994 FL | 805 | 2e-54 | 2e-54 >gb\|AAK01359.1\|AF314810_1 (AF314810) dehydration stress-induced protein [Brassica napus] |
| | 129424 FL | 1072 | e-121 | >ref\|NP_196527.1\| (NM_121002) inorganic pyrophosphatase - like protein [Arabidopsis thaliana] pir\|\|T49933 inorganic pyrophosphatase-like protein - Arabidopsis thaliana emb\|CAB89365.1\| (AL353994) inorganic pyrophosphatase-like protein [Arabidopsis thaliana] dbj\|BAB09520.1\| (AB020752) inorganic pyrophosphatase-like protein [Arabidopsis thaliana] emb\|CAC19853.1\| (AJ252210) inorganic pyrophosphatase [Arabidopsis thaliana] gb\|AAK76619.1\| (AY045945) putative inorganic pyrophosphatase [Arabidopsis thaliana] gb\|AAL85086.1\| (AY079355) putative inorganic pyrophosphatase [Arabidopsis thaliana] |
| | 232732 FL | 1012 | e-119 | >dbj\|BAB47119.1\| (AB042299) 14-3-3 protein [Vigna angularis] |
| | 238465 FL | 1752 | e-136 | >gb\|AAL07213.1\| (AY056134) unknown protein [Arabidopsis thaliana] |
| | 273716 FL | 2137 | e-170 | >gb\|AAL07213.1\| (AY056134) unknown protein [Arabidopsis thaliana] |

Figure 4

This file describes the results of querying the Derwent AA database (7/01) with hit contigs using tBLASTX. Only results with Pz values < 1 x e-4 were considered, and only the result with highest homology is shown.

| SEQ ID NO | Hit Contig | Pz Score | Result |
|---|---|---|---|
| 1 | 129424 | 2.00E-86 | >gnl\|Derwent\|AAG49336 300 AA.Arabidopsis thaliana protein fragment SEQ ID NO: 62404.EP1033405-A2. |
| 2 | 129426 | 9.00E-47 | >gnl\|Derwent\|AAG50676 299 AA.Arabidopsis thaliana protein fragment SEQ ID NO: 64245.EP1033405-A2. |
| 6 | 129858 | 9.00E-65 | >gnl\|Derwent\|AAG37821 262 AA.Arabidopsis thaliana protein fragment SEQ ID NO: 46568.EP1033405-A2. |
| 9 | 129870 | 7.00E-82 | >gnl\|Derwent\|AAG44048 407 AA.Arabidopsis thaliana protein fragment SEQ ID NO: 55127.EP1033405-A2. |
| 10 | 129965 | e-160 | >gnl\|Derwent\|AAG43794 431 AA.Arabidopsis thaliana protein fragment SEQ ID NO: 54780.EP1033405-A2. |
| 12 | 130156 | 5.00E-04 | >gnl\|Derwent\|AAB31798 625 AA.Amino acid sequence of the Arabidopsis SGS3 polypeptide.WO200105951-A2. |
| 13 | 130203 | 1.00E-11 | >gnl\|Derwent\|AAG36872 379 AA.Arabidopsis thaliana protein fragment SEQ ID NO: 45248.EP1033405-A2. |
| 14 | 130213 | e-102 | >gnl\|Derwent\|AAG44531 259 AA.Arabidopsis thaliana protein fragment SEQ ID NO: 55793.EP1033405-A2. |
| 15 | 130294 Contig A | 1.00E-50 | >gnl\|Derwent\|AAG17577 416 AA.Arabidopsis thaliana protein fragment SEQ ID NO: 18650.EP1033405-A2. |
| 17 | 130294 Contig C | 7.00E-38 | >gnl\|Derwent\|AAY58842 172 AA.Maize resistance gene homologue clone M5-1-encoded polypeptide.WO200004155-A2. |
| 19 | 130795 | 4.00E-09 | >gnl\|Derwent\|AAG44096 344 AA.Arabidopsis thaliana protein fragment SEQ ID NO: 55192.EP1033405-A2. |
| 20 | 130994 | 2.00E-49 | >gnl\|Derwent\|AAG10813 182 AA.Arabidopsis thaliana protein fragment SEQ ID NO: 9285.EP1033405-A2. |
| 25; 26 | 131048 | 7.00E-76 | >gnl\|Derwent\|AAG44594 185 AA.Arabidopsis thaliana protein fragment SEQ ID NO: 55878.EP1033405-A2. |
| 27 | 131133 Contig A | 2.00E-68 | >gnl\|Derwent\|AAY56860 269 AA.Pea type I LhcIIb Cab protein.US6011198-A. |
| 28 | 131133 Contig B | 2.00E-12 | >gnl\|Derwent\|AAY56860 269 AA.Pea type I LhcIIb Cab protein.US6011198-A. |
| 30 | 131365 | 6.00E-49 | >gnl\|Derwent\|AAY32434 1801 AA.Plant generic retroelement.WO9960842-A2. |
| 34 | 167306 Contig B | 2.00E-21 | >gnl\|Derwent\|AAG44329 269 AA.Arabidopsis thaliana protein fragment SEQ ID NO: 55515.EP1033405-A2. |
| 35 | 167361 Contig A | 3.00E-05 | >gnl\|Derwent\|AAG32364 282 AA.Arabidopsis thaliana protein fragment SEQ ID NO: 39028.EP1033405-A2. |
| 37 | 167373 | 2.00E-81 | >gnl\|Derwent\|AAG34074 538 AA.Zea mays protein fragment SEQ ID NO: 41406.EP1033405-A2. |
| 38 | 167516 | 1.00E-27 | >gnl\|Derwent\|AAG08646 143 AA.Arabidopsis thaliana protein fragment SEQ ID NO: 6266.EP1033405-A2. |
| 39 | 168165 | 2.00E-48 | >gnl\|Derwent\|AAY75347 867 AA.Neisseria meningitidis ORF 665 protein sequence SEQ ID NO:2168.WO9957280-A2. |

Figure 5

This figure describes the results of querying the Derwent NUC database with hit contigs using BLASTN. Only results with Pz values < 1 x e-4 were considered, and only the result with highest homology is shown.

| SEQ ID NO | Hit Contig | Pz Score | Results |
|---|---|---|---|
| 1 | 129424 | 7.00E-41 | >gnl\|Derwent\|AAC49778 1136 BP.Arabidopsis thaliana DNA fragment SEQ ID NO: 62402.EP1033405-A2. |
| 6 | 129858 | 2.00E-07 | >gnl\|Derwent\|AAC46952 964 BP.Arabidopsis thaliana DNA fragment SEQ ID NO: 52012.EP1033405-A2. |
| 9 | 129870 | 2.00E-35 | >gnl\|Derwent\|AAC47789 1337 BP.Arabidopsis thaliana DNA fragment SEQ ID NO: 55126.EP1033405-A2. |
| 10 | 129965 | 2.00E-15 | >gnl\|Derwent\|AAC47696 1456 BP.Arabidopsis thaliana DNA fragment SEQ ID NO: 54779.EP1033405-A2. |
| 14 | 130213 | 3.00E-38 | >gnl\|Derwent\|AAC47972 1283 BP.Arabidopsis thaliana DNA fragment SEQ ID NO: 55791.EP1033405-A2. |
| 15 | 130294 Contig A | 1.00E-10 | >gnl\|Derwent\|AAC37783 1488 BP.Arabidopsis thaliana DNA fragment SEQ ID NO: 18649.EP1033405-A2. |
| 17 | 130294 Contig C | 2.00E-04 | >gnl\|Derwent\|AAZ58277 515 BP.Rice resistance gene homologue clone R5-1.WO200004155-A2. |
| 18 | 130964 | e-124 | >gnl\|Derwent\|AAQ04525 134525 BP.Total base sequence of rice plant chloroplast DNA.JP02100682-A. |
| 20 | 130994 | 3.00E-05 | >gnl\|Derwent\|AAC53356 670 BP.Arabidopsis thaliana DNA fragment SEQ ID NO: 74240.EP1033405-A2. |
| 25; 26 | 131048 | 1.00E-27 | >gnl\|Derwent\|AAA78471 797 BP.Plant SDF polynucleotide sequence SEQ List 1 NO:130.WO200040695-A2. |
| 27 | 131133 Contig A | 1.00E-31 | >gnl\|Derwent\|AAZ46858 1166 BP.Pea type I LhcIIb Cab protein encoding DNA.US6011198-A. |
| 28 | 131133 Contig B | 5.00E-09 | >gnl\|Derwent\|AAZ46858 1166 BP.Pea type I LhcIIb Cab protein encoding DNA.US6011198-A. |
| 34 | 167306 Contig B | 1.00E-14 | >gnl\|Derwent\|AAA14856 897 BP.DNA encoding snooze (SNZ) 2/3 protein.WO200022169-A1. |
| 37 | 167373 | 1.00E-36 | >gnl\|Derwent\|AAC48307 1602 BP.Arabidopsis thaliana DNA fragment SEQ ID NO: 57005.EP1033405-A2. |
| 38 | 167516 | 4.00E-21 | >gnl\|Derwent\|AAF77826 2991 BP.SfUCPa derived exothermicity relating gene coding sequence #2.JP2000354489-A. |

Figure 6

This figure summarizes results from the seedling and greenhouse screening for each of the "hit" sequence IDs. Sequences were determined to be a "hit" if reproducibility was demonstrated from primary to secondary screen (seedlings), from primary screen in seedlings to greenhouse testing in more mature plants, or within the primary screen if more than one seedling demonstrated tolerance. Reproducibility in the greenhouse was tested with some sequences to exemplify claims.

| | | Seedlings | | Greenhouse Plants | | | |
|---|---|---|---|---|---|---|---|
| | | (# Tolerant Plants/ # Tested) | | (% 0-25 Injury Rating for 13 g ae/ha) | | | |
| SEQ ID NO | Sequence ID | Primary Screen | Secondary Screen | Trial # | 2 dat | 7 dat | 14 dat |
| 10; 11 | 129965 | 1/3 | 5/25 | 1 | 67 | 50 | 58 |
| | | | | 2 | 33 | 58 | 75 |
| 14 | 130213 | 2/5 | 0/25 | 1 | 0 | 45 | 91 |
| | | | | 2 | 0 | 42 | 50 |
| 15; 16; 17 | 130294 | 1/5 | 0/25 | 1 | 10 | 20 | 60 |
| | | | | 2 | 17 | 50 | 58 |
| 20 | 130994 | 1/1 | 1/20 | 1 | 0 | 67 | 67 |
| | | | | 2 | 0 | 42 | 42 |
| 1 | 129424 | 1/5 | 0/25 | 1 | 30 | 60 | 30 |
| 2 | 129426 | 1/5 | 0/25 | 1 | 0 | 70 | 40 |
| 3 | 129516 | 2/5 | 0/25 | 1 | 20 | 20 | 50 |
| 9 | 129870 | 1/5 | 0/23 | 1 | 0 | 0 | 42 |
| | | | | 2 | 0 | 42 | 33 |
| 38 | 167516 | 1/5 | 2/25 | 1 | 23 | 40 | 40 |
| 35; 36 | 167361 | 1/5 | 3/25 | 1 | 17 | 42 | 33 |
| 40 | 168550 | 1/6 | 0/22 | 1 | 0 | 33 | 33 |
| 4; 5 | 129702 | 2/5 | 4/25 | 1 | 31 | 54 | no data |
| 6 | 129858 | 2/5 | 0/25 | 1 | 11 | 6 | 33 |
| 12 | 130156 | 1/5 | 0/25 | 1 | 31 | 5 | 30 |
| 33; 34 | 167306 | 1/5 | 4/25 | 1 | 43 | 0 | 0 |
| 29 | 131216 | 2/5 | 2/25 | 1 | 17 | 0 | 8 |
| 8 | 129866 | 1/5 | 0/24 | 1 | 0 | 17 | 25 |
| 37 | 167373 | 2/5 | 4/25 | 1 | 0 | 0 | 8 |
| 39 | 168165 | 2/5 | 3/25 | 1 | 0 | 0 | 0 |
| 21; 22 | 131002 | 1/5 | 3/25 | 1 | 0 | 0 | 0 |
| 25; 26 | 131048 | 1/5 | 3/25 | 1 | 8 | 0 | 8 |
| 30 | 131365 | 1/5 | 4/23 | 1 | 0 | 0 | 0 |
| 18 | 130964 | 2/5 | 0/25 | 1 | 0 | 0 | 25 |
| 27; 28 | 131133 | 1/5 | 0/25 | 1 | 8 | 17 | 8 |
| 31; 32 | 131371 | 1/5 | 0/25 | 1 | 0 | 25 | 17 |
| 7 | 129863 | 1/5 | 0/25 | 1 | 33 | 8 | 8 |
| 23; 24 | 131007 | 2/5 | 0/25 | 1 | 0 | 0 | 0 |
| 13 | 130203 | 2/5 | 0/25 | 1 | 0 | 0 | 0 |
| 19 | 130795 | 2/5 | 0/25 | 1 | 0 | 0 | 0 |

Figure 7

Summary of tolerance observed from cross-resistance testing of 5 hit sequences. Six compounds were used, representing 5 classes of auxins, as defined in Example 13. The shaded squares indicate the lowest threshold (25% or 35% injury) at which 30% or more of the test population demonstrated a tolerant phenotype.(nt=not tested)

| | | | Trial #1 | | Trial #2 | |
|---|---|---|---|---|---|---|
| | | | % of population "tolerant" | | % of population "tolerant" | |
| Sequence ID | Herbicide | Dose (g ae/ha) | 0-25% injury | 0-35% injury | 0-25% injury | 0-35% injury |
| 129965 | 6 | 5 | 45 | 55 | 70 | 90 |
| | 5 | 5 | 65 | 65 | 65 | 65 |
| | 3 | 32 | 78 | 89 | 80 | 100 |
| | 4 | 200 | 30 | 50 | 0* | 70 |
| | 1 | 200 | nt | nt | 50 | 90 |
| | 2 | 42 | 22 | 44 | 0 | 30 |
| 130213 | 6 | 5 | 60 | 80 | 65 | 75 |
| | 5 | 10 | 11 | 55 | 20 | 90 |
| | 3 | 32 | 45 | 81 | 60 | 100 |
| | 1 | 100 | 65 | 75 | 25 | 65 |
| 130294 | 6 | 5 | 71 | 85 | 45 | 45 |
| | 5 | 10 | 20 | 65 | 30 | 70 |
| | 3 | 32 | 11 | 55 | 30 | 70 |
| | 1 | 100 | 40 | 60 | 35 | 55 |
| 130994 | 6 | 5 | nt | nt | 70 | 80 |
| | 5 | 10 | 10 | 30 | 10 | 30 |
| | 3 | 32 | 20 | 40 | 11 | 33 |
| | 1 | 100 | 25 | 35 | 60 | 90 |
| 129870 | 6 | 5 | 50 | 60 | 60 | 90 |
| | 5 | 10 | 20 | 70 | 0 | 50 |
| | 3 | 32 | 20 | 90 | 0 | 70 |
| | 1 | 100 | 30 | 90 | 20 | 50 |

*250 g dose

Figure 8

This figure summarizes results from testing homologs to sequences 129965 and 130213 using the greenhouse evaluation method as described in Example 9. Percent of plants tolerant is reported at 14 days after treatment (dat).

| Clone | # plants tolerant/tested at 14 dat (%)<br>*1st trial* | *2nd trial* |
|---|---|---|
| 238465 | 1/4 (25%) | 7/22 (32%) |
| 129965 control | 8/11 (73%) | 1/2 (50%) |
| RTH-1 | 12/12 (100%) | |
| RTH-5 | 12/12 (100%) | |
| RTH-10 | 10/12 (83%) | |
| 129965 control | 6/11 (55%) | |
| 232732 | 5/12 (42%) | |
| 130213 control | 2/12 (17%) | |

SEQUENCE LISTING

<160> NUMBER OF SEQ ID NOS: 378

<210> SEQ ID NO 1
<211> LENGTH: 697
<212> TYPE: DNA
<213> ORGANISM: Poppy

<400> SEQUENCE: 1
gaattcaatc aaatggctac tgctagagtt ttggctgcta gtatgttgca tgaatgcaac 60
aacactcaca gtgcttcatt tcttttgaga caatcttctt tcatcttacc tattaaacat 120
caaagtatta atttcagtag aagagcatct tctaggagag cttttacttg caaatctctt 180
tacaaacctg aaattcaaat caaacaagaa ggtgaacctc aaaccctaga ttacagagtc 240
ttctttcatg ataaatctgg caaaaagctt tcaccttggc atgatgtacc attgcaattg 300
ggtgatggag tgttcaattt tatcgtggaa ataccaaaag agacaagtgc aaagatggaa 360
gttgcaactg atgagccata tactcccatt aaacaggaca ccaagaaggg aaaacttaga 420
ttctacccct acaacatcaa ttggaactat ggattgctcc cacagacatg ggaagaccca 480
acagtagcta attctgaagt tgaaggggca ttcggagata atgatccagt tgatgttgtt 540
gaaattgggg agaggcaagg aaaaattggc gagattctta aagtcaagcc tttaggtgct 600
ttggctatga ttgacgaagg agaactcgac tggaaaattg ttgcgatttc gttggatgac 660
ccaaaagctt cactcgtcaa tgatgttggt gatgttg 697

<210> SEQ ID NO 2
<211> LENGTH: 715
<212> TYPE: DNA
<213> ORGANISM: Poppy

<400> SEQUENCE: 2
gaattcagaa gcaaatgttt tgtgttgtgc tggggaagca gctctatgtt gggcttgtga 60
tgttaaagta catgcagcta ataagcttgc tagtaaacac cagaggattc ctttgtctac 120
ttcttcttct tctcagattc ctaaatgtga tgtttctata cacacagcaa attcatatgt 180
atcaagccac cagaggtttc tgcttacagg cgtgaaagta ggcctagaac ccacacaacc 240
gattgggttg tctaccaatg aaaaatgtga ctctgctgac aaaactgtgg aaagggagac 300

```
tcagacaatg tccatgatag atacttctgt atcatggaat ggcagaaatg gtgaattatt    360

atctcgacag cctggtggag atggcgggcg acatgcaact aagctgtcaa tgtctggggg    420

gacaactggt ggaagtatgc ctgagtggcc tctggatgag ttctttggac taactgattt    480

cactcagaat ttcggatgta tggataatgg aacttccaag gctgatagcg gcaagactgg    540

ggagtctgga ttctctccaa ctttgcaact cactgatgag gactttgaca tggacgagtg    600

tttgggtaag gtcccagaga tcccaaggat ggtgcccgag gtcccatctc cgcccactgc    660

ctctggactc ttctggccaa aaaacttccg gaactcatca gatcacgagc tctca         715
```

<210> SEQ ID NO 3
<211> LENGTH: 629
<212> TYPE: DNA
<213> ORGANISM: Poppy

<400> SEQUENCE: 3

```
ttcctttcaa atgaaacgga gctgccatgc tccgtttacg ggtcattat ttttactttg      60

ttcccgcgca gttatcaaaa gcaaaaggaa taggtaaaaa tattcttctc aaattacagt    120

tagttataag gatttcctta actgcttctc ctcaccatca tgttattttc gccacatcat    180

aatcctgggc ttgctgaaga ataattgaaa tgatattatt aattccactg cctttggtag    240

aggaaagtgc taaataataa tcaattgtta aattattgtg catttcacta ctggaactgt    300

aatcagaaaa gatagacatg cttagccaat ctctatttga ttgaattgaa agatgtttgt    360

taaggcatgg atgcaagcta tagattctga tacggtcaat aaaagagaat tgcttaacaa    420

ttttgcaaaa tgtattggcg agtaagaacc gcatttggta ctttccgggc aaccgccaga    480

cgattcttta ttggtaatga gaataattaa caattaaaga gcgtcgcgaa agaataatgt    540

gtctcgacag gggagacaca gtacgaatcg acataaggtg atcgtctgaa tcaccagaat    600

aaataaagtc tgtgggtgat gctgccaac                                      629
```

<210> SEQ ID NO 4
<211> LENGTH: 634
<212> TYPE: DNA
<213> ORGANISM: Poppy

<400> SEQUENCE: 4

```
gaattcaaaa aaataactat gtaactagtt gatgagagtt gtcatgcatc tcaccggcaa     60

cctaatatat ttgatcctat caaatgattt tgatccgaaa tcgtcaaggc accatgtgct    120

ctccttgtat aaacaacaac attagcaatc gcatctggga caactgcggt ctccttgtag    180

aaacaacaac attagcaatc gcattttaga caactgcgcg cggtctcctc aaccaatatc    240

tataacttct ataaaaatct agtaaagaac accaaataat ctgacatatt tcgtagttaa    300

acatgcttag agaactaata cttacgtttt gccgactttt tttaagatta ggagcagcat    360

caacaatgtt tttaacaacg ttatgcaata tttctctcat ttcacatcta cctagctagc    420

acaacatttg ttcacactag aaggggctag tgcctggtat taatatggaa caagtgggct    480

cagttggccc acgttgggag ttagtgggct agggtttagt gacgcatagt cctactccta    540

tataaatctt tttagctgag gaagctcttt tttcactaca actactcttt tagcttgcag    600

tctttcactc acacttagat ctagtcttct tctt                                634
```

<210> SEQ ID NO 5
<211> LENGTH: 652
<212> TYPE: DNA

<213> ORGANISM: Poppy

<400> SEQUENCE: 5

```
tcaaaatgat tatagaaatc atggttaatc ctcacataca gaacaaaatc atccttcttt     60
aaccatgtca tgatgactta tcctctcaaa aacatcatct tttttgtctt caatgctgtt    120
gttgaagtgc tttcttcttc gaagtcaaga ggttagcaga gacaagagta ttaacttcga    180
gaagaataag ggaaacccaa cccactctga aactaccaac ttgacatgta tcggatcctt    240
gttatggaag aaggagaagg attcttcaga taatgtagtt gttgttgtaa ctttttatga    300
taaatttatt atgaaatgca gattcttttt tgagctgtct ttggtatttt attagttgat    360
acattgatag tcactgtgaa atctgttctt ttttcttttt taatttgttc ttgtaattga    420
aataggcttg ttaatctgtt gtaactcctg tttaaattaa gacaatgaag ttcccttaga    480
tttgaagatt tttggtattg gtgcaaggtc tgcatatatg ctcgctcagg tgtttttttgg    540
tggtggtttt gtgtcattaa tttccatggc ttatttagtg tgccatttta tgcaattgtt    600
ccaactgcga caaagcaact ttctaaattg gaaatgtcaa cagacaaaaa aa            652
```

<210> SEQ ID NO 6
<211> LENGTH: 740
<212> TYPE: DNA
<213> ORGANISM: Poppy

<400> SEQUENCE: 6

```
ccgaattcaa tacgcgctgg gtactgaaag tgattgagaa agtctgtaat ggagaatcac     60
caatagcaat gactgttttc tttggtgcta atgatgcttc tcttcctgat cgaactagtg    120
ctttccaaca tgttcctctt catgaataca agcagaacct gcaatcaata gtttccttca    180
ttaagaaaaa atggccaact acccttattc tgcttataac tccacctcca attgatgaag    240
atggacgtat taggcatcct tttgtagata atccatcagg tctgccggag aggacgaatg    300
aggctgccgg tgcttatgct aaggcatgtg tggaggttgc tgatgaatgt ggagtgattg    360
gagtggattt atggactaaa atgcaacaat accctaattg ggaaaaatgt tgtctcagtg    420
atggcttaca cctaacacca actgggaaca gaattgtata tgaggaagtg atcaaaaagc    480
ttacaaaaga aggggtaaat gttgaaactt tatcagcaga tctccctctc ctatctcaga    540
tcgatccttg tgatcccttg aaagcattcc agaactgaga gattcctgaa ttatccgcat    600
tacatatacc aggggactct tttagttagt tagttacaca aattatcatt taagaagcaa    660
cacatatatg tggtggtaat taatacaaag tttgctgctc tccccatctt tgttgttttg    720
atcattgaaa tgatgctttt                                                740
```

<210> SEQ ID NO 7
<211> LENGTH: 639
<212> TYPE: DNA
<213> ORGANISM: Poppy

<400> SEQUENCE: 7

```
gaattctatt ttgatttttt aaaaaattca gtgggccaga atcgggtttt gttcgtcaca     60
atgaaaaccg attcctttaa taatcggttt ttgttcatat atatgaagtc cgatgcttct    120
gcaactaatt gagaatcggg gtttgttcgt aacaaacaaa accgattctc gttgacaatg    180
tttctgtata ccaagaatcg ggttttttgt gaatgtcgag tagaccgatt cccgtagcca    240
aagtttctgt gtagtaggaa tcgggtttca tgttcatgta gagtaatccg attacaacag    300
ccaatgtcaa tctttctgtg tagcaagaat cgggtttttt gtgcatgtcg agtacaccga    360
```

```
ttatataaac caatatttct gtgtagtagg aatcggattt catgttcatg tagggtaaac    420

cgatttccaa agccaatgtt tctgtatagt tggaatcgga tttcatgtgc atgtagagta    480

aaccgattgt gtgcttgaat ccttgttatg caggaaaaaa ccagctgaaa agaaatctag    540

ggagagaaaa caacttgata ctcctgcttc tttgaaacca cgtcgagttg gaggtaaaaa    600

tttgaatgct tccaaccgaa gagttataat caaagtcaa                           639


<210> SEQ ID NO 8
<211> LENGTH: 641
<212> TYPE: DNA
<213> ORGANISM: Poppy

<400> SEQUENCE: 8

gaattcaata actatattgc aaaaaagagc tagggattaa tgatatagga aaggtacaaa     60

aaggtggaaa cgcaaaggat ttacaagagc aataattggc aataattcgc aagaaaaagt    120

tattctttgg gagaaactcc acgatcctct ttttccccac tttccttgac ttcattattt    180

ttaccatctc catcaatatt ttctggttcc ttcctttcct tctcattgtc atcctcaaca    240

aaatatgctt cagaaaaatc attctcaaga tcaatatctt cagcattgag acttggaata    300

ttttcttcaa cttccttttg aaggtctggg aaatcagatt caggaatccc ataggttttg    360

caaacctgtt cataaatcat gttgcaataa cattccacct ttgtatttat tccctttttc    420

tatattaagc tcctgcttat atagatcaca tcttcgagta cgatgtgata gcttctccgc    480

aagccggtga ttatcaatct ctaattcttt aacctttttc tcagaagctg caagaaacga    540

aaagatgaaa ttgtgattaa gaatgaagaa ttgaagaaaa tgagaaacaa agaaaagaca    600

gatggaaacc ttctttttca taaattaaat catttatcaa a                        641


<210> SEQ ID NO 9
<211> LENGTH: 641
<212> TYPE: DNA
<213> ORGANISM: Poppy

<400> SEQUENCE: 9

gaattcagag gcagatagag agagagacaa tgggaatggc aacaagtagg ttgatggtgg     60

tgcaacaaaa acaaccatcc tcatgtctat taccaccatc atctctttct gacttcaatg    120

gtattagact gaaacaccca attcagtaca aaagaaagga atggcagaca agaggagcat    180

tgcaggtgaa agcatcagct gcaaagaaaa tcctgattat gggaggaacc agatttattg    240

gtatcttttt gtctaggctc cttgtgaagg aaggtcatca agtaactttg ttcacaagag    300

ggaaagcacc aatcagccaa ccattacccg gggagtcgga acaagattac ctagattttt    360

cttccaagat ttcccacttg aaaggagaca gaaaggacta tgattttgtt aagactagcc    420

tagcagctga aggctttgac gttgtctatg atatcaatgg aagagaggca gaagaagtag    480

aacccatatt ggacgcgctt ccaaagcttg agcagtacat atactgttca tccgctggtg    540

tgtatctgaa gtctgattta ctgcctcatt ttgagtctga tgcagtggat cccaagagca    600

ggcacaaggg aaaacttgaa acagagagtt tacttgtatc a                        641


<210> SEQ ID NO 10
<211> LENGTH: 1923
<212> TYPE: DNA
<213> ORGANISM: Poppy

<400> SEQUENCE: 10
```

-continued

```
ttaattaagt cgacgaattc gagagaaaca gaaaaaggag attcagaatt gggtaatcac     60
ggctatattt ggagacggag ggtggaattt ccaccacaac caaagattga ttcattcatc    120
atcatcttgt aaccaaatcg aaaaaagaaa cccttcacca cacggtggta gaggagcttt    180
gccgtcagaa ggtggttctc ctcctgatct tcttttcctt gccggtggtg gtgaatttct    240
catcaaatac ccaatcaact gacccccctta ttcttttgat tttttcctag atttaccaat   300
tcattttctt aacttgaaaa ccaaatcata ttctagtaca taatacatta caatatacaa    360
tatgttgacc atcaaaagag ttcctactgt tgtttctaat taccaagaag atggttctgc    420
cgctgctgct gaaactgttg gctgtggccg taattgcctt ggaaagtgct gtttacctgt    480
gtccaagctt cctttgtatg cattcaaggg agatgggatt gattcaatca aaggaggaga    540
ggaacctgag gtgtctttct ttgatacctt aattcttggg caatgggagg atcgaatgag    600
ccgtggcctt ttccgatatg atgtaacaca gtgtgagact aaggttattc ccggagagta    660
tggatttgtt gcacaactga atgaaggacg tcatcttaag aaacgaccaa ctgagtttcg    720
tgttgatcga gtgctacaac cctttgatgg gagcaaattc aacttcacaa aagttgggca    780
ggaagaggtg cttttgcgct ttgagcagag tttggatgaa aagacccatt actttgctag    840
ttcagctgtt gacttggatt ctatttctcc tagtgtggtc gccattaatg tgagtccaat    900
tgagtatggg catgtacttc tgattccccg cgttcttgaa tgcttgcctc aaaggattga    960
ccatgagagc ttcttgttag ctcttcatat ggcgaaagaa gcagcaaacc cctttttcag   1020
attgggtttt aatagtttgg gtgcctttgc aacaatcaat catctccatt tccaggcgta   1080
ttacttatct gtgcccttcc ctgttgagaa ggctcctact cggaagataa ccatggcaaa   1140
tggacttcca gataatgggg ttacaatctc cgagctgttg aactatccgg ttagagctct   1200
tgtttttgag gggggcaaca cattaaaaga tctctctgac gttgtctcta atgcttgcat   1260
ttttcttcaa gagaccaaca ttccatacaa tgttctcatc tctgattgtg gaaaacgaat   1320
cttcctcttc cctcagtgtt acgctgaaaa gcaagcactt ggagaagtga gtcaggagct   1380
tcttgatacc caagtaaatc cagctgtgtg ggagataagt ggacatatag tgttgaagag   1440
gaagaatgac tacgaggacg catctgaaaa ttatgcttgg aggctccttg cagaggtgtc   1500
tctctccgag gaaaggtttc aagaagtgaa aacctatata tttgaagctg caggtgttca   1560
ggaaatggtt tgtgttgcag aaaaagagga aggagatgtc aaggatgagg atgaagattc   1620
ttttttcggg ggctcatctc gcacctctgc cacatattac ccccaaggtt gtctggttca   1680
gcagtgaaga agtactatta gggtttcaag agggttgcag tgttgtctct tgttctttca   1740
acttttctgt tacctgcgta acaaagtagg atagttttag tagttattgc gtgtagtttg   1800
attttgatca ttcaataatg atcttaatgc atgtgtactt tgctcagtga agtggttgtg   1860
tacatctctc tctctacctt atatgaaaaa tgaaaatttg ttaaaaaaaa aaaaaaaaaa   1920
aaa                                                                 1923
```

<210> SEQ ID NO 11
<211> LENGTH: 694
<212> TYPE: DNA
<213> ORGANISM: Poppy

<400> SEQUENCE: 11

```
ctgacgttgt ctctaatgct tgcatttttc ttcaagagac caacattcca tacaatgttc     60
tcatctctga ttgtggaaaa cgaatcttcc tcttccctca gtgttacgct gaaaagcaag    120
cacttggaga agtgagtcag gagcttcttg atacccaagt aaatccagct gtgtgggaga    180
```

```
taagtggaca tatagtgttg aagaggaaga atgactacga ggacgcatct gaaaattatg    240
cttggaggct ccttgcagag gtgtctctct ccgaggaaag gtttcaagaa gtgaaaacct    300
atatatttga agctgcaggt gttcaggaaa tggtttgtgt tgcagaaaaa gaggaaggag    360
atgtcaagga tgaggatgaa gattcttttt tcgggggctc atctcgcacc tctgccacat    420
attacccccca aggttgtctg gttcagcagt gaagaagtac tattagggtt tcaagagggt    480
tgcagtgttg tctcttgttc tttcaacttt tctgttacct gcgtaacaaa gtaggatagt    540
tttagtagtt attgcgtgta gtttgatttt gatcattcaa taatgatctt aatgcatgtg    600
tactttgctc agtgaagtgg ttgtgtacat ctctctctct accttatatg aaaaatgaaa    660
atttgttaaa aaaaaaaaaa aaaaaaaact caag                                 694
```

<210> SEQ ID NO 12
<211> LENGTH: 645
<212> TYPE: DNA
<213> ORGANISM: Poppy

<400> SEQUENCE: 12

```
gaattcaaga agaccatcgg agattgttca tccggccgtt tctctacatt ttcggtcatt     60
tcaaggagca agcagtattt taaggaggca aaatgagtca gaaaaaaggg ggtggcaagc    120
tatctgttcc tggtagtagt ggttcacctg caaaagggaa agatgcaggt ggacaaatcc    180
ctggagtttt aggctctggt aaccaaaaga ctggagttgt tcagctgggt tctaatatcg    240
caaacctaag ccttgattcc agtaaagatt ctgagtggga ggtagtgtct cgcaagaatc    300
gaggcgcggc aagtgcacca aaaccatggg gtccccagaa ttcctcttct ccatccttgg    360
tttcaggaag ttcccaaaat tcctcttctg catcctgggt tgcaggaaag gctacaggag    420
gtgcccaaaa ttcctcttct ccatccttgg tttcaggaag ttcccaaaat tcctcttctg    480
catcctgggt tgcaggaaag gctacaggag gtgcctggca ggataataag tcaggtggag    540
gaggaactac gaaaagccaa tctcccaatg catgggagaa aaattacatg gcaccaccaa    600
gtaagattgc tcctccttta caacatggtt ggcagtgggg tgcaa                     645
```

<210> SEQ ID NO 13
<211> LENGTH: 673
<212> TYPE: DNA
<213> ORGANISM: Poppy

<400> SEQUENCE: 13

```
gaattcggga gcacaacaag taaattagaa cccggtggtc acaatttctg cctctcttca     60
atggctgcct ctgcaagtcc cctcatctaa tcctagaaaa caaagaaatc cactttcatt    120
gcagataagc ttttcttcac tccatcaaag gaacaaagtc gagagagaga gagcacaaca    180
agtaaattag aaccctctgg tcacaatttc tgcctctctt caatggctgc ctctgcaagt    240
cctctctctt cattcgcttc cctttctatc tcaacatcta gaaaatttct cccaaaccac    300
acttctttct ccttctcaaa catcaaaacc cataaactca tcaccccaat ttcttcccta    360
aaattccccc attcaaaacc ccaaaaacct aaacccataa aagctacacc ctctgatgca    420
gaaaccattt tcatggaaaa tgaaataagc ccagatgaag atttcacatt tgagccacca    480
ccaagaccag aaggttacat tgaaccacct tcatttgatg atcttccgcc agaatctgaa    540
gatgaaattg cagcagccta tgaagaattg tatggtcctg cttatagtgg tatgagtgtg    600
ctaggtaacg atgtatatgt tatggattct aagatgaaga aagcaactgg gtttggtaca    660
```

```
aagactaaga aag                                                      673

<210> SEQ ID NO 14
<211> LENGTH: 1020
<212> TYPE: DNA
<213> ORGANISM: Poppy

<400> SEQUENCE: 14

ttaattaagt cgacgaattc atatgaagaa atggttgaat ttatggaaaa agtaacaaca     60

aatgttgaat cagaggaact ttcagttgaa gagagaaatt tattgtcagt tgcttacaaa    120

aatgtgattg gtgcacgcag agcatcatgg agaattattt catcaattga acagaaagaa    180

gaaagccgtg gtaacgaaga gaatgtattg accattcgtg attatagatc taagattgaa    240

actgaacttt caggcatctg tgatgggatt ttgaagttgc ttgatactag attgattcca    300

tctgcatctt ctggtgattc taaagtgttt tatttgaaaa tgaaaggtga ttatcatcgt    360

tatttggctg agtttaaaac tggtaccgaa aggaaagaag ctgctgaaag taccctttct    420

gcttataaat ctgctcagga tatcgcaact gctgaacttg cacccactca cccaatcagg    480

ctgggacttg ctcttaactt tctccgtctt ttactacgag atcttgaatt ctcctgccgt    540

gcttgtaatc tcgccaaaca ggcatttgat gaggctatcg cggagctgga tacccttggt    600

gaagaatcat acaaagacag cactctaatc atgcagctcc ttcgtgacaa tcttactctg    660

tggacctccg acatgcagga tgatggtgca gatgaaatta aagaagcatc caagcctgaa    720

gatgaacatt aatgatagtt tgtctgccac atttaggatc ttacctcctc tcagtttgtt    780

ttattaaaag gagaaggtgc tttcttggta cacaactcct ccaagtctac tattaattat    840

taaggagttt agggtgggta ctgttagttt gtcattcttc ttatcctttg tgctcgtctt    900

ttcctatctt aattcttctc ttaaaagagt ttgaagttat atgtttatct gaatctgtgt    960

gggaactccg ttttatctaa attatctttt aagatgacga taaaaaaaaa aaaaaaaaaa   1020

<210> SEQ ID NO 15
<211> LENGTH: 500
<212> TYPE: DNA
<213> ORGANISM: Poppy

<400> SEQUENCE: 15

ttaattaagt cgacgaattc aaattaggtc taaagatggc gtctttagct caacaattct     60

caggattaag atgcccacca ctttcttctt ctcatctaac aaaacccttt tcttcaaaac    120

cccagaaaac cacctttca cctatagttt cagcagctgt catttctaat gcacaaacta    180

aagaaagaag tagacttaaa gaaatcttcg aagatgctta tgaaagatgt agaactactc    240

caatgcaagg tgttggtttt actgttgatg attttcatgc tgctcttgaa aagtatgatt    300

acaattctga gattggtacc agggttaaag gaactgtgtt ctgtacagac aacaacggag    360

cattagttga catcacggcg aaatcttcag cctatttacc aatccaagag gcatgtattc    420

acaaaataaa gcatgtagaa gaagcaggaa tagttgcagg cctacgtgaa gagttgtgat    480

tattggagag aaccaagctg                                                500

<210> SEQ ID NO 16
<211> LENGTH: 294
<212> TYPE: DNA
<213> ORGANISM: contig B Poppy
<220> FEATURE:
<221> NAME/KEY: misc_feature
<222> LOCATION: (65)..(65)
<223> OTHER INFORMATION: The residue at this position can be any
```

nucleotide.
<220> FEATURE:
<221> NAME/KEY: misc_feature
<222> LOCATION: (126)..(126)
<223> OTHER INFORMATION: The residue at this position can be any nucleotide.
<220> FEATURE:
<221> NAME/KEY: misc_feature
<222> LOCATION: (176)..(176)
<223> OTHER INFORMATION: The residue at this position can be any nucleotide.

<400> SEQUENCE: 16

```
cggcatctta ggtcccctga cgccagactt gcctgctgaa ggtctagatt tgagcgacat     60
tcctncagct gatgatgcat agaaaccaat aaatatgaat taaatctgtc ttgacgtttc    120
ttctcntcac catttttagg ctatgtaaga tgggtctata ggttgttcaa agtgtngact    180
tgtgtattta tcttgatagt tcaaagtgta cttctttaag cgataatcat tgaaaagaaa    240
aaatggagaa ggtaaaagat aaaaatatcc aaaaaaaaaa aaaaaaaaaa aaaa          294
```

<210> SEQ ID NO 17
<211> LENGTH: 641
<212> TYPE: DNA
<213> ORGANISM: Poppy

<400> SEQUENCE: 17

```
gaattcaggg aaacagcccg gatcaccagc taaggggcct aaatgaccgc tcagtgataa     60
aggaggtagg ggtgcagaga cagccaggag gtttgcctag aagcagccac ccttgaaaga    120
gtgcgtaata gctcactgat cgagcgctct tgcgccgaag atgaacgggg ctaagcgatc    180
tgccgaagct gtgggatgta aaaatgcatc ggtaggggag cgttccgcct tcaacaaaag    240
ggtacctgta cccgaaaccg acacaggtgg gtaggtagag aatacctagg gaagcgagaa    300
tgtcggcttg agtaacgcaa acattggtga gaatccaatg ccccgaaaac ctaagggttc    360
ctccgcaagg ttcgtccacg gagggtgagt cagggcctaa gatcaggccg aaaggcgtag    420
tcgatggaca acaggtgaat attcctgtac taccccttgt tggtcccgag ggacggagga    480
ggctaggtta gccgaaagat ggttatcggt tcaaggacgc aaggtgacct tagggtaaga    540
aggggtagag aaaatgcctc gagccaatgt ccgagtacca ggcgctacgg ggctgaagta    600
actcatgcca tactcccagg aaaagctcga acgaccatca t                        641
```

<210> SEQ ID NO 18
<211> LENGTH: 589
<212> TYPE: DNA
<213> ORGANISM: Poppy

<400> SEQUENCE: 18

```
ttaattaagt cgacgaattc atgtcaatgg agacttgctt ataatactaa acgcatgggt     60
tatgtgtgat cgttttgatt atatattcat tcttttttc tttgtgttgt gatatagtaa    120
tgggggaaag aaataatgag aattcggcag atattgataa tgaatatcca aaagatttgt    180
tacagagatt tatggcggga aaccatttcc caacggaatt tgcagcgaaa actgaggaaa    240
cagaagaaga tgatgaagat attgaattaa atttatcatt aggaggttgt tttggtgtta    300
acccaagtga gaaaaagagg ttgatgaggt catcgtcaat atcagtatca ggattaagta    360
atctgtttaa agatgaagaa gaagggaata attcttcatc agcagcatct ttgataagaa    420
catgttcatt gcctgtagta gtagcaacag aagaagacag aaggaaaagg aaagagttac    480
aatctctaag aagattagaa gccaagagaa agacatcaga aaaacaaagg aattgtacta    540
```

gggttaacaa taataaagat attcaacaag agaagatgca acagcagca 589

<210> SEQ ID NO 19
<211> LENGTH: 664
<212> TYPE: DNA
<213> ORGANISM: Poppy

<400> SEQUENCE: 19
ttaattaagt cgacgaattc acatctaaag tcaacaacaa gagcttctck cttctcctcg 60
tctctgttct cctctctttt gcaatcctct ctcaatctgc tgatgattgt gtatacacag 120
tatacacaag aacaggatca atcatcaaag gaggaacgga ttcaaaaatc tcactaagat 180
tatacagcaa atacggtaag tacatcgaga tcccaaatct tgaatcatgg ggtggattaa 240
tgggtcctgg ttacgattat ttcgaaagag gtaatcttga tatcttcagc ggaagaggtt 300
attgtctggg ttcaccggtt tgtgccatga atctgacttc cgatggtact ggktccsgtc 360
acggatggta tgtgaattat gttgaarkta ctactaccgg tgcacatatt aattgtggtc 420
aacaraattt tgaagtggaa gawtggcttg ctcttgatag awctccytat artcttaccc 480
gctwtcaaga aataattgta atcagaaatt atctgatcat gattctcatt ctgctgatca 540
gtctatgtaa aatttgatct cttgtttgat tcggtggtgg tctagtatga gtgatcggac 600
ggtcgtcatt gtgtgttgta atgttgaaat tattttcttg aataaaatga ttgagtgagt 660
agtg 664

<210> SEQ ID NO 20
<211> LENGTH: 728
<212> TYPE: DNA
<213> ORGANISM: Poppy

<400> SEQUENCE: 20
ttaattaagt cgacgaattc agccgtttgg gggatccgga ggcgtagagg kataactgta 60
ccttgtatca gtgggagatt gatagggggtt cttctataga tcagtccgaa gttagttgga 120
gtaggctagt atctgtagcg gcttaataca gtgtatatct aatctggact aggtcccggg 180
gtttttctgc atctgcggtt tcctcgttaa caaaatctct ggtgtctgtg ttatttcttt 240
tccgcatctt tttagataga aataatacag gttgtgcgtt ggtaagttta atcagtttac 300
agatccaatc ttgttattgt tgatcttgct gattaacact tggatattgg tttttgatac 360
cgtccaagtc tttatctcct tggtttgacc agactcgcaa acttgtttgt ttgagtagtt 420
ctcaaatcaa gagagagaga tatcaactcc ttgagtcact atattcttca gatcctgact 480
gtctagtcgt ttctttagta gagtgatttg gaggktgtcc ttgatcagaw tgctaatcga 540
aaagtttggg tgtgttgtta gacccccgct ttttcagcaa gttatatttc tgacattgaa 600
cctcactgta agttttgtaa tagtagtaat gaaaccattg agcatttgct aattgaatgt 660
gattatgcta taggaacatg aaactggaat atggaactcc ttgcaggtag atattcttac 720
tactactc 728

<210> SEQ ID NO 21
<211> LENGTH: 594
<212> TYPE: DNA
<213> ORGANISM: Poppy
<220> FEATURE:
<221> NAME/KEY: misc_feature
<222> LOCATION: (502)..(502)
<223> OTHER INFORMATION: The residue at this position can be any nucleotide.

```
<220> FEATURE:
<221> NAME/KEY: misc_feature
<222> LOCATION: (537)..(537)
<223> OTHER INFORMATION: The residue at this position can be any
      nucleotide.

<400> SEQUENCE: 21

tgcaagaact acttccacca cccagaattc aagtatagaa gattggatac gaccagaaga     60

tggatatctg aaactgaaca ttgatgcttc ttatatttca gaaccaagaa aaggtagatt    120

tggtctaata ttacgtaatc atgcaggtta gataatagga gtcaaaggag ctaatctgga    180

ggaggaggtg gatgcagaag taggagcgga acaatttgaa tgtaaagctc tgatctaggc    240

agtataatgg atggaggaag gtggttacaa taaagtcatt ttcgacttgg actgtgctaa    300

tgttgtggaa tctgtcgact gtgaagaatc taaagttcac ttgttcaatc aacatctaat    360

atctgcagtc agaaataatt ttttaaggaa taaattttgg ttttgcgaag taattaatat    420

gacaagtaat agtgtagctc atgaactagc tagaaaagct aggcttgaag ctctttctta    480

cttttatgtt tcaaaatttc cnctggatat ctccaattgg atagaaaaaa acaatgnact    540

tcaatctatt cattaataaa tctcttttag tatcgaaaaa aaaaaaaaaa aaaa          594


<210> SEQ ID NO 22
<211> LENGTH: 738
<212> TYPE: DNA
<213> ORGANISM: Poppy

<400> SEQUENCE: 22

ttaattaagt cgacgaattc aggcacatgc aaacaaaacc aaacaaaats sctcggtttt     60

gaaatcacaa gaaattgaat gaacatgatt aaatgaagtt ttgtttgttg gttgaagaat    120

caaagagaag aagaagaaga agaattagca tggttggaat tgaaactagg tcaattgcaa    180

acataactaa taagattcga cgtcatggat atgctgaaac taccagattc aatttcagct    240

gaaacattgt gtagattagc aaatgggaat acattagttg ctggtttttc cttcgttctt    300

atatccttct ccttgctctt ccaactaatc ccgtcccttc tttcgcctta caaaacaacc    360

tccaatcgtc cttgaaatca tggtaggact ctttttgggg aaacgtaggg ttcatgggtt    420

cagtatctta acttggtttt caagtcacca cattcgcagc aattgcagaa atcggaatga    480

gttgttatgc tttagtttta gggataaatt ttgatgtaac tctacttgga catacccccac   540

ctgaagccat agtagcttac actgtgattt tatcaactgt cctcgttact gctactacag    600

ctgtaccact catacatttt ggatttgatc atgatattaa ggatactgcg aatttcggct    660

tcatatttgc attgtcatta accgtggcag ggacttcttc tccagtgtta acacaattat    720

ttactgaaga aaatttct                                                  738


<210> SEQ ID NO 23
<211> LENGTH: 344
<212> TYPE: DNA
<213> ORGANISM: Poppy
<220> FEATURE:
<221> NAME/KEY: misc_feature
<222> LOCATION: (54)..(54)
<223> OTHER INFORMATION: The residue at this position can be any
      nucleotide.
<220> FEATURE:
<221> NAME/KEY: misc_feature
<222> LOCATION: (63)..(63)
<223> OTHER INFORMATION: The residue at this position can be any
      nucleotide.
<220> FEATURE:
<221> NAME/KEY: misc_feature
```

-continued

<222> LOCATION: (91)..(91)
<223> OTHER INFORMATION: The residue at this position can be any nucleotide.
<220> FEATURE:
<221> NAME/KEY: misc_feature
<222> LOCATION: (175)..(175)
<223> OTHER INFORMATION: The residue at this position can be any nucleotide.
<220> FEATURE:
<221> NAME/KEY: misc_feature
<222> LOCATION: (187)..(187)
<223> OTHER INFORMATION: The residue at this position can be any nucleotide.
<220> FEATURE:
<221> NAME/KEY: misc_feature
<222> LOCATION: (230)..(230)
<223> OTHER INFORMATION: The residue at this position can be any nucleotide.
<220> FEATURE:
<221> NAME/KEY: misc_feature
<222> LOCATION: (253)..(253)
<223> OTHER INFORMATION: The residue at this position can be any nucleotide.
<220> FEATURE:
<221> NAME/KEY: misc_feature
<222> LOCATION: (282)..(282)
<223> OTHER INFORMATION: The residue at this position can be any nucleotide.
<220> FEATURE:
<221> NAME/KEY: misc_feature
<222> LOCATION: (296)..(296)
<223> OTHER INFORMATION: The residue at this position can be any nucleotide.
<220> FEATURE:
<221> NAME/KEY: misc_feature
<222> LOCATION: (309)..(309)
<223> OTHER INFORMATION: The residue at this position can be any nucleotide.

<400> SEQUENCE: 23
ccgtcaaagt tgttcttcct ttaggtaatt gtactgaggg gaaaatttta gganctaaat 60
ttntggcatt attctgggat ttcattggcc natcgcagtc gcaataggat tgtttttaaa 120
cgtcaagggt ccatttcata ttttcattgc cacgttcgcg gtcgaggtaa catantactg 180
ccaaatnacc attttcttgt aataggatta tcattcctag taattaatgn gtttgtaaat 240
atgaatgtgt aangtgtttg taaatatgaa tgtgtttaaa angaattcat gggcgntggc 300
agcttcctng tgttcctatt aaaaaaaaaa aaaaaaaaaa aaaa 344

<210> SEQ ID NO 24
<211> LENGTH: 854
<212> TYPE: DNA
<213> ORGANISM: Poppy
<220> FEATURE:
<221> NAME/KEY: misc_feature
<222> LOCATION: (576)..(576)
<223> OTHER INFORMATION: The residue at this position can be any nucleotide.
<220> FEATURE:
<221> NAME/KEY: misc_feature
<222> LOCATION: (682)..(682)
<223> OTHER INFORMATION: The residue at this position can be any nucleotide.
<220> FEATURE:
<221> NAME/KEY: misc_feature
<222> LOCATION: (690)..(690)
<223> OTHER INFORMATION: The residue at this position can be any nucleotide.
<220> FEATURE:
<221> NAME/KEY: misc_feature
<222> LOCATION: (768)..(768)
<223> OTHER INFORMATION: The residue at this position can be any nucleotide.
<220> FEATURE:

-continued

<221> NAME/KEY: misc_feature
<222> LOCATION: (830)..(830)
<223> OTHER INFORMATION: The residue at this position can be any
      nucleotide.

<400> SEQUENCE: 24

```
ttaattaagt cgacgaattc aggaccaaga ggaaagttga tcagaaactt caagcatctg     60
aacttagatt ttcagctcat taagaatgct gaaactggga agaaacagct taaagttgat    120
gcctggtttg gatccagaaa gacttctgct tcaattagaa ctgcactttc tcatgttaac    180
aatcttatta ctggtgttac caaagggtac cgttacaaga tgagattcgt gtatgcccat    240
tttcccatca acgcttcaat caccaacgga aacaagggta ttgagatccg taactttctt    300
ggagagaaaa aggtgcgaaa ggttgatatg cttgatggag tgagtattgt caggtcagag    360
aaggtcaagg atgagcttgt gttggatggt aatgatgttg agctcgtctt cagatcttgt    420
gccttgatca accagaaatg ccatgtgaag aacaaggata tcaggaagtt tttggatggt    480
atctatgtga gtgaaaaagg gctgttgagg tcgaaaaata aatttgtggt acgacgctat    540
tggttttgtg ttcagaaggt tttcctcccc ccgttncgtc ataattagtt tgttatttcg    600
gttttgtgtt cagaaggttt tcctccctcc gttacgtcat aattagtttg ttatttctta    660
aactagtata agttgacatc cnttttaaan attgttattt ctttttgagt ttaaaatttt    720
tgcggtactg atagttgtag cttaatgtta tggttgggca attatcanag aattcctttg    780
acttaattat attttggatg agtaaatcaa agcattttct ggttatgctn aaaaaaaaaa    840
aaaaaaaaaa aaaa                                                      854
```

<210> SEQ ID NO 25
<211> LENGTH: 634
<212> TYPE: DNA
<213> ORGANISM: Poppy

<400> SEQUENCE: 25

```
gaattcaaac tagtagccat ggctgttgct tcatcggctg ctacagtggt ttttggggtt     60
ttatcttctt ctcctaaaaa ccttaaatct ctttgcaagt tcaaaccttt tctcctccct    120
ctacacccca attcacctct tactcaatcc acacttactt tctccgcccg tagaaacaac    180
cccaactctg caattacttc gtcttctaaa aagaagaaga acaacagcag caacagcaat    240
aacaagagca agaagaagaa tttgactaaa aagagtgaag tggaggtggt agatgatata    300
gatgaagatg ctattgaggc actatttaat cagctggaag aagaccttaa aagtgatgga    360
tcctttgaag atggtgatga tgatttaact gaggaagact tagctaggct tgaaaaagag    420
ttgaaggagg cttttggtga agatgctgat ttatttgaaa tgttacaata tagtgaagag    480
ggcattcaaa acagtgatga tgctgaagat ggggaagaag acgaagaaga tgaagaagaa    540
gaggaagaaa ttgatgatga tgacgacgaa gaagaagaag aaagtccagt gcagcttaaa    600
aattggcagc tgcgacaatt ggctacagct ttga                                634
```

<210> SEQ ID NO 26
<211> LENGTH: 590
<212> TYPE: DNA
<213> ORGANISM: Poppy

<400> SEQUENCE: 26

```
ttaattaagt cgacgaattc ggtaaccttt cagtttcatt tagctctaac aaactatcat     60
attaatggca accatggctc tctcttctcc atcatttgca gggaaagctg tatctctaaa    120
```

-continued

```
ctcacaatca gaattcccag tcaatgctag atccactagc aatggtaaga tctcgatgag    180

gaagacatcc gcaaagaagc ctgctgcttc ttctggaagt ccatggtacg gtccagaccg    240

tgtcaagtat ctcggtccct tctctggtga gtctccttct tacctgaccg gtgaattcgc    300

tggtgactat ggctgggaca ctgctggact atcarctgac ccaragacat ttgccaagaa    360

ccgcgaactt gaggtgatcc attcaagatg ggcgatgctt ggtgctttgg gctgtgkctt    420

ycccgagctc ctatcaaaga aatggagtcc aattcggcga agcagtttgg ttcaaagctg    480

gatctcagat tttcagtgaa ggaggactag actatttggg taattccagc ttggttcatg    540

cacagagcat tttagctatt tggccacac aggtcatcct tatgggagcc              590
```

<210> SEQ ID NO 27
<211> LENGTH: 282
<212> TYPE: DNA
<213> ORGANISM: Poppy
<220> FEATURE:
<221> NAME/KEY: misc_feature
<222> LOCATION: (18)..(18)
<223> OTHER INFORMATION: The residue at this position can be any nucleotide.
<220> FEATURE:
<221> NAME/KEY: misc_feature
<222> LOCATION: (46)..(46)
<223> OTHER INFORMATION: The residue at this position can be any nucleotide.
<220> FEATURE:
<221> NAME/KEY: misc_feature
<222> LOCATION: (49)..(49)
<223> OTHER INFORMATION: The residue at this position can be any nucleotide.
<220> FEATURE:
<221> NAME/KEY: misc_feature
<222> LOCATION: (118)..(118)
<223> OTHER INFORMATION: The residue at this position can be any nucleotide.
<220> FEATURE:
<221> NAME/KEY: misc_feature
<222> LOCATION: (151)..(151)
<223> OTHER INFORMATION: The residue at this position can be any nucleotide.
<220> FEATURE:
<221> NAME/KEY: misc_feature
<222> LOCATION: (156)..(156)
<223> OTHER INFORMATION: The residue at this position can be any nucleotide.
<220> FEATURE:
<221> NAME/KEY: misc_feature
<222> LOCATION: (178)..(178)
<223> OTHER INFORMATION: The residue at this position can be any nucleotide.
<220> FEATURE:
<221> NAME/KEY: misc_feature
<222> LOCATION: (206)..(206)
<223> OTHER INFORMATION: The residue at this position can be any nucleotide.
<220> FEATURE:
<221> NAME/KEY: misc_feature
<222> LOCATION: (238)..(238)
<223> OTHER INFORMATION: The residue at this position can be any nucleotide.
<220> FEATURE:
<221> NAME/KEY: misc_feature
<222> LOCATION: (256)..(256)
<223> OTHER INFORMATION: The residue at this position can be any nucleotide.
<220> FEATURE:
<221> NAME/KEY: misc_feature
<222> LOCATION: (257)..(257)
<223> OTHER INFORMATION: The residue at this position can be any nucleotide.

<400> SEQUENCE: 27

-continued

```
ttcgttcagg ctattggnac tggaaaaggt cccctaaaaa accttncana ccccccttgcc      60

gacccagtga acaacaatgc ctggtcatat gctaccaact tcgctcccgg gaagtganaa     120

tatttgtaac agtgaactaa aacgtttgct ntcccntcaa tggaaaaatg gggttggntt     180

cctacttttt cattaagatc ctctgnacat atttaccgat ccgtttcctc agtaatanaa     240

tccatttttt ttttgnnaaa aaaaaaaaaa aaaaaaaaaa aa                        282
```

<210> SEQ ID NO 28
<211> LENGTH: 1117
<212> TYPE: DNA
<213> ORGANISM: Poppy

<400> SEQUENCE: 28

```
ttaattaagt cgacgaattc atatgtagca aatgtgcagc aggcattgca acgttcagct      60

gtgcaaccga ggaagacaag gtctggcgcg tcgagaatgt cacaacctga tacattgaat     120

gcagagacac cgccatcaaa aaagttgaag aaaaactgat gatttttggt taaatgctct     180

ttaatttatt atttttgcgg acgctttgaa agttgtattc atttcttgtt tcgtttgcta     240

attttgtcat ttagaagaag gtgatgttta agaatgcttt tactacttag gtattggaat     300

catgaaatac tttaggtccg atcttattat atctttgcca atactttttaa caaatttaac    360

aaaaaatcaa gattgaacaa gtaaagtgct attgaaagta aagtactcct gtacgaagat     420

gttcatcata atgatctttg cgtggatttg gatgagaatg aggaaccaga ccaatctgac     480

aaagaacctg actcatttaa caatttcatt aattgatttt tttaaacagg gtttttgatg     540

tgtgaacttc tagtttacgt atgtttatac gtaaagcatt aagcattacg tctgaccagt     600

ttgttttcac tggtggttgt atttattttc taagtactgc actagatgca tgctttttac     660

gctgatagat taggttgact tttatgtgat gaatgattca cgctaagctt ttatgttttc     720

tggaaataat gaacatgaaa atggatcggt ttagaattat acgtttccta cataggtgtc     780

actaataatt cataagtttc ctcccaaaac caagaataat aatggagaca acctagttta     840

aaaatattaa ggaaaatatt attcgaaata ggaaagtact atggccactt cacgagttgg     900

ctagagatga aactaaattt cggaaaattt gggaaacaat tttatcataa ctgtccacga     960

tatattctct cgtaaaataa ggaaactaac catattggtt acacattaaa attttggaaa    1020

aaagaataaa gaaaaacaat atattttctc gtaaaataag aaaactaacc atattggtta    1080

cacatcaaaa atttggaaaa aaaaaaaaaa aaaaaaa                             1117
```

<210> SEQ ID NO 29
<211> LENGTH: 2050
<212> TYPE: DNA
<213> ORGANISM: Poppy
<220> FEATURE:
<221> NAME/KEY: misc_feature
<222> LOCATION: (2035)..(2035)
<223> OTHER INFORMATION: The residue at this position can be any nucleotide.
<220> FEATURE:
<221> NAME/KEY: misc_feature
<222> LOCATION: (2045)..(2045)
<223> OTHER INFORMATION: The residue at this position can be any nucleotide.
<220> FEATURE:
<221> NAME/KEY: misc_feature
<222> LOCATION: (2048)..(2048)
<223> OTHER INFORMATION: The residue at this position can be any nucleotide.

<400> SEQUENCE: 29

-continued

```
gcggccgctt gagtttttct tttttggtat atggatgaaa aactttcatt aatttttttt     60
tgaataaatt aataagttag acatcaaatg cgaatgcctg cattgttatg tcatgggaca    120
tgaaacagtg ttcaagcatg atatgtcttg agccatttcc cgttgatgac tgcttccacc    180
ttgcctccat ccactttaat gattttgtag tacccagtgc tgtaagactt ggtaaccaca    240
tagggtcctt cccacttggg agaaaacttt ggtgcagaca tgtcttgttg aatgtgtttg    300
gctgtcttca acactagatc cccaacttta aaacttcgta gccttacgga cttgtcatat    360
gccctagaga ctctgtttct gtacacttga gcacgttctt ccgccttgct tctcctgtag    420
tctagagtgt caagctcagc gattctgcag ttagacgcct caacctcgtt ccagtgaact    480
ccacttgccg ctgcgatccg ggctgatggg attttgattt ctgctgggag aacggcatca    540
gttccgtaaa cgagtgagta tggagatact ccaatggaac tcctgggtgc cgttcggtat    600
gcccacaatg ccatcggtaa ttgttcatgc cactctcttg cattgtcatg tactgtccgg    660
ctaagaatcc gaattaacgt cttgttggtg ctctcagcct gcccgttccc ctgggggtag    720
tagatggtgg agaagacttg tttaatccca tattcttcar gcarctcccg gacttgcttg    780
twgrcgaaag gagtaccgtt atctgtaatg atatgtytag gtacaccgaa acgamagatg    840
atgtgttctt taatgaargc tgmaatygtc gctcctgtag tkccacgcag aggaatagct    900
tctacccaty yggtgaaata twctgtyscg gwtatgatgt attcgtgctg cttcgatgat    960
ggcggattga tctttccaat aatatcaagt ccccagctat agaatggcag cggactactt   1020
actgaatgta aggggtgtgg aargagccgt ggacaawgtt tcccgtgaat ttgacatttg   1080
tggcagctct ggacgaaagc agccgcatcg tcctccatag ttggccaata atatttctcg   1140
tgtatctgga gaaacrattt tttctttcct tgatgwtctc sttcatgcat ctctttcaaa   1200
atggytgaaa tttccgctcc agctaggcac cgtaggagat cacctccaaa acttttcctg   1260
tacaggattc cttcgtggaa tacaaagcgt tttgctctct gtttcatttt gaccacctcc   1320
ttcggggtta ccaggaactg cgccatcgcg aagatagttg atgtatgact gcctccagtc   1380
cccagtgtgg ctcacgttga gaatctctag ttggtgaggt ggtgcctggc agcttgagca   1440
agattgttga agtgttcgag attgtgcttc catctccggc cagtagtatc ccaaacgttg   1500
gaggcgtcga tagagtgtta ccaccaacgt ttgtccacaa atatcattgt ggacacgatt   1560
aagctgtaat tgtgcctctt cctctccaag acatctcgac agggagctat ctggattccg   1620
atgataaagc atgccatgga gtatgaaaaa gttctgtaag gctttaaggc taaccttccc   1680
ttgagagagt gaactactga gctcttgaac aatcggagtc cgccagtcac ggatttcagc   1740
gtccttgtgt tgtgaaagcc atgtcgactc caccgttctt cttttcaccg tcaggctttc   1800
ctctgtgcct tcaaactgca gcttggaagc cagcgttgct agacaatcgg cgtgtctatt   1860
gttgttgcgt ccaacatgag tcacagatgc gtctgcaaaa taattcagca acctttgcgc   1920
ttctgatcgg tatggggcta aagttacgaa ttcgtcgact taattaatgr ccaagaacac   1980
gaactgagaa tggagwagtg atactgtaag atctatttaa aacgaatcgg gtttntccaa   2040
agggnttnaa                                                          2050
```

<210> SEQ ID NO 30
<211> LENGTH: 569
<212> TYPE: DNA
<213> ORGANISM: Poppy

<400> SEQUENCE: 30

```
ttaattaagt cgacgaattc aaagagacag aggaaacagc aaagttcaac rggaccctga     60
```

```
tgtctacccc aaccagtaga agctctcttt gtgaccaagc tactcgtgat attatcgccc    120

gccgcgaaac tgacaaagct attaagctat tagaccttta caagttcttc cggaggctat    180

ttccggctcc agctttcgga tatggttgcc gtgacgtagc aatagacgag atgtacttgc    240

catctgttgt ttcaccggaa tcatcgactg tggaatttga taccaacgcc gatggaaagt    300

gttaccggaa caaggaagct accggagcag cttttacaaa tcattcttct gttcacagtt    360

ctcttctagg tgacgcaatg tcagacaggg tgaacttgcc agtttcttct ctatcactga    420

aatcagccga ccaagtttat atcaaaattg atggaaagtg ttctcagacc aagggatgca    480

gcatctcttg aaaatcattc cggtcgcggt gattttcatg tttgtgatca tcctagatgt    540

tcggtaaaat gaaactaaag ataggtttc                                      569
```

<210> SEQ ID NO 31
<211> LENGTH: 438
<212> TYPE: DNA
<213> ORGANISM: Poppy
<220> FEATURE:
<221> NAME/KEY: misc_feature
<222> LOCATION: (202)..(202)
<223> OTHER INFORMATION: The residue at this position can be any nucleotide.
<220> FEATURE:
<221> NAME/KEY: misc_feature
<222> LOCATION: (207)..(207)
<223> OTHER INFORMATION: The residue at this position can be any nucleotide.
<220> FEATURE:
<221> NAME/KEY: misc_feature
<222> LOCATION: (241)..(241)
<223> OTHER INFORMATION: The residue at this position can be any nucleotide.
<220> FEATURE:
<221> NAME/KEY: misc_feature
<222> LOCATION: (267)..(267)
<223> OTHER INFORMATION: The residue at this position can be any nucleotide.
<220> FEATURE:
<221> NAME/KEY: misc_feature
<222> LOCATION: (270)..(270)
<223> OTHER INFORMATION: The residue at this position can be any nucleotide.
<220> FEATURE:
<221> NAME/KEY: misc_feature
<222> LOCATION: (272)..(272)
<223> OTHER INFORMATION: The residue at this position can be any nucleotide.
<220> FEATURE:
<221> NAME/KEY: misc_feature
<222> LOCATION: (321)..(321)
<223> OTHER INFORMATION: The residue at this position can be any nucleotide.
<220> FEATURE:
<221> NAME/KEY: misc_feature
<222> LOCATION: (323)..(323)
<223> OTHER INFORMATION: The residue at this position can be any nucleotide.

<400> SEQUENCE: 31

```
gtgctcctaa ttctcatact acattctcgc cgagaatgcc acccatacaa gaaggttatc     60

cttgccatca gcaattcggc atcatttctt tttatgctac ttggttatgg cctcgtgata    120

ggtttcaata tccaacgtgc ttgagcattt caatgttgag gtttggttct ttatctgctc    180

atgaggtttc ctgcctgtgt antgcgnatt ttatttcttt gctatgcagt ctgagtgatg    240

nttcctctcg gtttttttc atcactntan angccgttcc atcgttatgt ttgttttatg    300

ccccgtgcag gcaaggtcag ngntagtttg tgtgtcctaa gttctttgaa caaaagacaa    360
```

-continued

```
actacttgta ttttaatgtt agatttggtt gtctaatcaa ctatgatcct ttttacctga    420

aaaaaaaaaa aaaaaaaa                                                  438
```

<210> SEQ ID NO 32
<211> LENGTH: 1488
<212> TYPE: DNA
<213> ORGANISM: Poppy

<400> SEQUENCE: 32

```
gaagatccac ccggtaatat tatgaagaaa tgcaataaaa ataaaggctt gggaactcgt     60

tgcaaccaca ttttagttaa ctaaaattct gcaacttgat aaaataagaa cattaaataa    120

ttaacacaca agtcaaacag aatacaggtt agaaatgagg atcaatccat aaaattgttg    180

gcttgtgtca atccaaaatg aaaatatctt aacaaagcta aggtattaat cagtaagaaa    240

cacaaagttt cccctgtgtc tacacttcct ttcaagtagt tctaatggac atcctactta    300

tcaacttatt aagtcatgac taataatcga acaattaagg tagtcacact acaacttaaa    360

gtaagaaaaa catacagctt ccatgtcaac cgtactagct caacacatcc atccccaatg    420

actaactgca aaattcacga cttctgttga tatgcatata ttagtatttc tttaaacaaa    480

aggtaagaag catgtataat taaaaaccac cgaaggattg aactagcact acttatttag    540

tcagtrcaac caacaagatg ctacgtttta tgttgttagc ccaacagaat cctctagagt    600

aatttttaac accgtacata cattatagat taaaccaaaa ccctttttgtg tgcttccttt    660

actgtgttaa tttcccaaca tacctcggca caatgtttgg ccactttcaa acattacgca    720

tacggagtcc aggctaaccc catttccttc cttttcattc taacaagatc tatagcatac    780

cggtacctgt cgatcgccca tgagagaaat ctagcacgtg taattccagt acatataaac    840

aaaagaatac aatcgaaaat cacgattgat ggcttaatat agatggttcc atacatagta    900

aactactttc cactatctgc aagagtagtg ccaacactgc aacctaccag aactaattaa    960

aatgttaagc caacgttaac ggatcacctt gaaactttta cagcatattt actacacagg   1020

ttacaaaaac atattcaata ttcagcaatt tacaacggtg cattaaaaag atatacacct   1080

tacatcttga ctgctttcgt tgtcgattcg cagaattcag tgatgatttt tccacatcta   1140

ggggtaccta aagaaatcgg atcttcctga aatttttaca gtagattatc tacaggccta   1200

taaacaacat acaaaaattt caacttgatc cgataaacag gtaatgagaa atatcataaa   1260

tacttaactg tccagggtct gaattctgca cattgcagcc acaaattact caatcttcga   1320

actagtaaac atgacctgat tctcctgaga tttttatggt acctctaccg tgtaattagt   1380

tattagatac taaaatttca ttaaaatcca accaccggat cttaaattat cagtataata   1440

aaacatgcat actagggtga attcgtcgac ttaattaatg acaagaac                1488
```

<210> SEQ ID NO 33
<211> LENGTH: 610
<212> TYPE: DNA
<213> ORGANISM: Poppy

<400> SEQUENCE: 33

```
acgacataag cgattacttt gtgtgggatg aagtggtgga ctacaatccc atggtttgtt     60

caatttgctg ctggtggtgt tgctactcct gctgatgctg ctctgatgat ccaattgggt    120

tgtgatggtg ttttcgttgg ttccggtgtt tttaagagtg gtgatcctgc taaacgtgct    180

agggcgattg tgcaagctgt gactcattat agcgatcctg acattcttgc tgatgttagc    240

tctggtttgg gtgaagctat ggttggaatt aaccttaatg cccgtaaggt tgaaaggttt    300
```

-continued

```
gctgctcggt ctgaatgaat aatcaaaggc tttgattcga ctgaattgca ttggaggtga    360

gaattagacc tcatttcctt gcacactttg gttattcata ggaaaaaaaa agaaaatttc    420

atatatgagt gtttcgtttt ttatttgttc ccatgtgtct ggtagatata gatagtcgtg    480

gggatctttt aaaatgttag gtgctctagt ttcgtttctc ttctgtgtaa ctgaagaaga    540

agggttgttg tttttaagaa tcttatggaa tgatgttggt tcagatatat tctattgaat    600

atttcctaat                                                           610
```

<210> SEQ ID NO 34
<211> LENGTH: 618
<212> TYPE: DNA
<213> ORGANISM: Poppy

<400> SEQUENCE: 34

```
ttaattaagt cgacgaattc aaaaggattc ataaaatctt tccctcattt atgtctcaca     60

aaccctagaa attaacgata ccccaaaccc taccagagaa aaatcaatct ctttatttaa    120

gaggacaaca caaagttgaa attgttgcaa agaaagaaga aaaaaaaagt tcgattgaat    180

tggaggtaaa gatgtttgtg gaaaaggaag atttaggatt aagtttgagt ttatgttcat    240

caacatcaac aacaacagca gagaatagat atccattaca actaaatcta atgcctcctt    300

ctgctggttc agtctctaat aatccttcac catttttgat tcatcatcag aagactaaca    360

gtattaccaa ttggaatgaa gctttcggat catctgatcg gattacagca gagatgtaca    420

gaggagaaac mmgatcattt ttaagaggaa ttgatgtgaa cagaatgcca tcaacaacag    480

caacagtaga ttgtgaagaa gaagtaggag tttcatcacc aaatagtaca gtttcgagta    540

taagtgggaa taaaagaaga agtatcgaaa gagataccat aaattgttct ggtggtgatg    600

gggaagataa tgaaatcg                                                  618
```

<210> SEQ ID NO 35
<211> LENGTH: 394
<212> TYPE: DNA
<213> ORGANISM: Poppy
<220> FEATURE:
<221> NAME/KEY: misc_feature
<222> LOCATION: (19)..(19)
<223> OTHER INFORMATION: The residue at this position can be any nucleotide.
<220> FEATURE:
<221> NAME/KEY: misc_feature
<222> LOCATION: (151)..(151)
<223> OTHER INFORMATION: The residue at this position can be any nucleotide.
<220> FEATURE:
<221> NAME/KEY: misc_feature
<222> LOCATION: (161)..(161)
<223> OTHER INFORMATION: The residue at this position can be any nucleotide.
<220> FEATURE:
<221> NAME/KEY: misc_feature
<222> LOCATION: (166)..(166)
<223> OTHER INFORMATION: The residue at this position can be any nucleotide.
<220> FEATURE:
<221> NAME/KEY: misc_feature
<222> LOCATION: (187)..(187)
<223> OTHER INFORMATION: The residue at this position can be any nucleotide.

<400> SEQUENCE: 35

```
gacaccacca gcaacaaana gccttgccca ccaatccttg ggcccaaact cctgttgtct     60

ttagaaaatg aatagtttag ttagttgttg ttaggatcta ggagattagt cttagtttta    120
```

```
cttttatctc ctttttggtt ttattgggtt ntttatttaa ncttgngact cctttcggtt    180

ttccatntac tttttggagg aattccaaag ttagcttgtg aaaggcaata gatgaaaaaa    240

aacctcaact cttttttgt catatggaaa ataggtttgg gatgtaaagt tttatcaaac    300

tgaaattctg aagtttgaat taatttctaa ttcaatgaaa agaaaaaaag aagtatgtta    360

atagtaagaa aaaaaaaaaa aaaaaaaaaa aaaa                                394
```

<210> SEQ ID NO 36
<211> LENGTH: 897
<212> TYPE: DNA
<213> ORGANISM: Poppy

<400> SEQUENCE: 36

```
gtgttcttgt cattaattaa gtcgacgaat tcacacaatc acacaattac tggattagca     60

gttgcactga aacaggcaac taccccagaa tacaaggctt atcaagaaca agtgctcaaa    120

aattgctcac agtttgccaa aaccttgaac gcattgggat atgaccttgt ttccggtggt    180

actgaaaacc atttagtctt ggtcaatttg aaaaacaagg gtattgatgg ctcaagagtt    240

gagaaagtaa tggaattggt tcatatcgct gctaacaaga acactgttcc cggggatgtc    300

tctgccatgg ttcctggtgg cattcgaatg ggaacacctg ctctcacttc aaggggattc    360

cttgaggaag atttcgctaa agtagcagag ttctttgatg ctgctgtgaa tttggccttg    420

aaagccaaag ctgaatgcaa aaaaggtgca aaattgaagg actttatggc cgcggttgaa    480

aacagtgcta gcattcagtc tgaaattaaa cagctccgtc atgacgttga ggaatatgca    540

aagcaattcc ctacaatcgg gttctgcaaa acaacaatga aatacaagca ataaactcca    600

ctattataag tgggcatata tgcttcggta gtgcagtgga gtstctacaa aggcgaatga    660

gatggacacg ggaagggagc aaactgcctt ttaatgtagg gaatatatga atgctttcaa    720

tcagtgaatg ggatatattg ttgacactac agggttctaa gcatgaagag agtaccattt    780

ggttcaaatt tcattcttca ttcaagaatt gaattatatg tatattatta aacttgatca    840

attataatgc aacaatataa agcttgtccc aaaaaaaaaa aaaaaaaaaa aaaaaaa       897
```

<210> SEQ ID NO 37
<211> LENGTH: 700
<212> TYPE: DNA
<213> ORGANISM: Poppy

<400> SEQUENCE: 37

```
ttaattaagt cgacgaattc acaacaacaa caacaagaga agtagattaa gcagttaagg     60

tagagaaaca aagttgagga gaacggccat ggcaacctct tctatggcat ctgcagcatc    120

tggttttgtg ttaacatcta gtctttcctc caccaccacc acaacctcat ccaggagcag    180

catatacttc caaataagaa ctaacaataa ctcaaggctc gttgttcgtg cagcagatga    240

agccgccacc cctgccccag ctgctgctgc cgctactaaa gaagctgaag ctccagccgc    300

agtcaagaaa cctcctccaa ttggccccaa gagaggcact aaggtgaaga ttctcaggaa    360

ggaatcctat tggtacaacg gcattggatc agtcgtagct gttgatcagg acccaaagac    420

tcgctaccca gtcgtcgtcc ggttcaccaa ggtcaactat gctaatgtct ctacaaacaa    480

ctacgccttg gatgagatta cggaagtgaa gtgatgagta atcagcaatc caaaaatgtt    540

gaatttgtag ctagctagct tatcctatca agtctttgta ttataccttg ttccgtgtga    600

tctatttttc tgtattctta tttatatttt caacaaattc cagtgaagtc gaactgaaat    660
```

-continued

```
gcataatcac tcaaaaaaaa aaaaaaaaaa aaaaaaaaaa                          700


<210> SEQ ID NO 38
<211> LENGTH: 462
<212> TYPE: DNA
<213> ORGANISM: Poppy

<400> SEQUENCE: 38

gaattcagga ctctataagt cttcaggaaa tggcgttaca cattgcgaag ctgagggttt     60

caggaagata acatattacc aggatcgccc tgacgtgatg gctaagtaca cttgcagggt    120

tgaaggcgac aaggcgctat atccagtatt gctgtcgaat ggaaatctca tagaacaagg    180

agatctcgag ggtggtaagc attatgcagt ttgggaggat ccacacaaga aaccatgcta    240

cttgtttgca ttggttgctg gacagttgca gagcagggat gactctttcg tcactcggtc    300

ggggaggaat gtgtcgctta agatttggac caccgcacag gatttaccaa aaactgctca    360

tgccatgaat tcactcaagg aagctatgaa gtgggatgag gatgtttttg gtcttgagta    420

tgacttggac cttttcaaca tcgtaatggt tgcagatctt aa                       462


<210> SEQ ID NO 39
<211> LENGTH: 989
<212> TYPE: DNA
<213> ORGANISM: Poppy

<400> SEQUENCE: 39

ttaattaagt cgacgaattc atgtaagagg tctttctgtt taatatattc tattatcttt     60

gtttaaaaaa ataaaaaaag agttcgtacg tctttttgtc ccaaactaac ggcaggaaaa    120

aggtggataa ccaccgttag gcattttggt caaaactggc ctacttttgt tatgcgaaag    180

caaacaggcc tagaattgta accctcaaaa aaaacaggcc tatatctgtt ttttacccaa    240

ctttttatac aaagatttaa gaaaagaagc agccaggatt ggtttagaaa tgaacagcgt    300

ccttacttac atctttgaaa agaattttgc caatatcaaa gttcacttct ggattgacag    360

tggcaagctt cattgatagg aactacaaaa agaaaagaga taatgaataa atcaatttgg    420

tctaactcat cttacttctt acttgaatca agttctaaat caatttacaa aatctgggga    480

agaacaagac gaaccctagt tctcaattcc accaccgraa aaacaagaag tgaagatgaa    540

tagttctcaa tttcatcaag tgatggatgc tcaatattta tggtattaaa aacccgtctt    600

gtaatactat ctaactcatc ttacttctta cttgaatcaa gttctaaatc aatttacaaa    660

atctggggaa gaacaagacg aaccctagta agaagtaaga agtaagaact tgcttcacag    720

atttaattga accacaaccc aatcgttatt aatcatctaa caataaccca aataatctct    780

caatcctgca caaaccctaa ccaaaatccc taacttctga ttctctaatc tccaatctca    840

catcatgttg attctgatta tgaaacataa taatctttac cacctgatac acctcatgaa    900

tcaaaccctt attaattctt ctttcaaacc ctcagtttga ttcctcaaac tctcaacaga    960

catagaacat gaaarraaaa aaaaaaaaa                                      989


<210> SEQ ID NO 40
<211> LENGTH: 591
<212> TYPE: DNA
<213> ORGANISM: Artificial
<220> FEATURE:
<223> OTHER INFORMATION: Synthetic

<400> SEQUENCE: 40

gagaaaagca gcgactcttc gtcttcgtct ccaaccacca caatgtctgg ctacaccgtc     60
```

```
cgcaaggttg ctgcccagaa cactctggag caccgcgtct acatcgagaa ggatggcgtc    120

cccgtgtcgc ccttccacga cattcctctc tttgccaacc aggagcagac catcctgaac    180

atggttgtcg agattcctcg atggaccaat ggcaagctcg agatctccaa ggaggagctc    240

cttaacccca tcaagcagga cgtcaagaag ggcaagcttc gcttcgtccg caactgcttc    300

ccccacaagg gctacctctg gaactacggt gccttccccc agacctggga agaccccaac    360

accgtccacc ccgagaccaa ggccaagggt gacaacgacc ctctcgatgt ctgcgagatc    420

ggtgagcttg ttggctaccc cggccagatc aagcaggtca aggtcctcgg tgtcatggcc    480

cttctcgacg aagaggagac tgactggaag gtcattgtca ttgacgtcaa cgaacccctt    540

gatcctaagt tgaacgacgt tgaggacgtc gagcgccacc tgactggcct g             591
```

```
<210> SEQ ID NO 41
<211> LENGTH: 610
<212> TYPE: DNA
<213> ORGANISM: Artificial
<220> FEATURE:
<223> OTHER INFORMATION: Synthetic

<400> SEQUENCE: 41

aatgtctacc tacactaccc ggtccattgg tgcccccaac actctcgact acaaggtcta     60

cattgagaag gacggcaagc ccgtttccgc cttccacgac attcctctgt acgccaatgc    120

tgagaagacc attctcaaca tgattgtcga ggttcctcga tggaccaacg ccaagatgga    180

gatctccaag gaccttgctc tgaaccccat catccaggac accaagaagg gcaagctccg    240

attcgtccga aactggttcc cccaccacgg atacattcac aactacggtg ctttccccca    300

gacctgggag gaacccaacc acgtccaccc cgagaccaag gccaagggtg acaacgaccc    360

gctcgacgtc tgcgagatcg gtgagactgt tggctacact gggcaggtca agcaggtcaa    420

ggtcctcggt gtcatggctc tcctcgacga gggtgagact gactggaaga tcatcgccat    480

cgatgtcaag gaccctcttg cctccaaggt caatgacatt gaggatgttg agcgacacct    540

gcccggtctt ctgcgagcca ccaacgaatg gttccgaatc tacaagatcc ctgacggaaa    600

gcccgagaac                                                           610
```

```
<210> SEQ ID NO 42
<211> LENGTH: 590
<212> TYPE: DNA
<213> ORGANISM: Artificial
<220> FEATURE:
<223> OTHER INFORMATION: Synthetic

<400> SEQUENCE: 42

aaatcattta ttgatttaat ctcctttttc ctttatcata atgcaaagaa tccattaaga     60

gaagcacttc aaacgagcga gagatccccc gccggggcag accttgtcac aagcttcacc    120

cacgcttgat gcgtctcctg gatcaccttg agcgcgtact ccttgccagc agccttgttc    180

cccagcccaa acttattctg cggcttccca tccggcacct tgtagtcgcg gaaccagtcc    240

cggatctcca tcagcgtccc gggaaagtac ttctccacat cactctcatc gttgaaaagc    300

ccagccctgg gatcatccac ggagatggcc accaccttcc agtccagctc cccctcatcg    360

atcatcgcca gcaccgccac cggcttcact cgaagaactt ccccacgccc cgcctttcgc    420

tcgccgatct cgacaacgtc gaccggatca ttgtcaccaa gcgctccctc cacatccggg    480

ttggcgtggt ttggatcttc ccaagtttgc ggaagaagcc cgtagttcca gcgtatgtcg    540
```

-continued

```
tatggataga accgtagctt gcctttcttc acgtcctgct tgatcggcgt          590


<210> SEQ ID NO 43
<211> LENGTH: 635
<212> TYPE: DNA
<213> ORGANISM: Artificial
<220> FEATURE:
<223> OTHER INFORMATION: Synthetic

<400> SEQUENCE: 43

gtcgctccgc cgccgccgcc gctgttcact ccgcaccaac tccgacgatc ccccggcgag     60

ctctcgacga tggcgacggc ggcgacggcg tcggctacgg cggccacccg cttcacgcgg    120

ctggcggggg tcgggctccg gcgcacggcc cgcctcccca cggccgtgcg gttccagcgc    180

cgggtgctcg ccaccaccgc gctcctcagg accgccgagc tccggcccaa ggagcagggc    240

ctgcccgaga cgctcgacta ccgcgtgttc ctcgtcgacg gcgggggccg caaggttgtc    300

gccgtggcac gacgtgcccc tgcgcgcagg cgacggggtt gttccacttc gtcgtggaga    360

atcccaagga gagcagcgcc aagatgggag gtcgccaccg acgagtcatt cacccccatc    420

aagcaggaca ccaagaaggg caacctccga tactacccgt acaacattaa ttggaattat    480

ggattatttc cccaaacatg ggaggaccca actcttgcaa acaccgatgt cgaaggagca    540

tttggggata atgatcctgt tgatgttgtt gagattggtg aaagacgtgc taacattgga    600

gatgttctta aggtaaaacc gttggcagct ttagc                               635


<210> SEQ ID NO 44
<211> LENGTH: 671
<212> TYPE: DNA
<213> ORGANISM: Artificial
<220> FEATURE:
<223> OTHER INFORMATION: Synthetic

<400> SEQUENCE: 44

cccccccccg tttcactcat ccgccgctga gctctatcta tctactagtt agtttagtcg     60

tctcgagggt aaattgagct ttgtgtgcgg ttttgagggg agtacatcgg catgaggatc    120

cagtgcgacg cgtgcgaggc cgcggcggcc acggtggtgt gctgcgcgga cgaggcggcg    180

ctgtgcgcgc gctgcgacgt cgagatccac gccgccaaca agctcgccag caagcaccag    240

cgcctcccgc tcgacgccgc gctccccgcc gccctcccgc gctgcgacgt ctgccaggag    300

aaggcggcgt tcatcttctg cgtggaggac agggcgctct tctgccggga ctgcgacgag    360

cccatccacg tcccggggac gctctccggc aaccaccagc gctacctcac caccggcatc    420

cgcgtcgggt tcagctccgt ctgtagcgcc aacgccgacc acctcccgcc gccagcgccc    480

aaggggaact ccaagccgcc ggcaagcggc atcgctgctg ctgctgctcc caagccggcc    540

gtgtccgcgg cggcgcagga ggtgccgtcg tcaccgttct tgccgccgtc gggctgggcc    600

gtcgaggatc tcctgcagct ctccgactac gagtccagcg acaagaaggg ctctcctatt    660

gggttcaagg a                                                         671


<210> SEQ ID NO 45
<211> LENGTH: 625
<212> TYPE: DNA
<213> ORGANISM: Artificial
<220> FEATURE:
<223> OTHER INFORMATION: Synthetic

<400> SEQUENCE: 45

ttcgcgagag agctgggcga tcaatccaga ttttggaggc gctccacggc cggcgccagc     60
```

-continued

```
gaaatccagg tactcttggt gatttccggg gagagatctc gatcgattcc gtggcgtgat    120
tttggggcgg agagatgagg gtccaatgcg acgtgtgtga gaaggccgag gcggcgctgg    180
tttgctgcgc cgacgaagcc gcgctgtgtg ccgtgtgtga tgccgaggtc catgccgcca    240
acaagcttgc cgggaagcac cagcgattgc ctttgagcgc ctctggaaat tctcctagct    300
gcgacgtctg ccaggagaaa actggatggt ttttttgtgt ggaggaccgt gctttgctct    360
gccgggcttg cgatgtctcc atacactcgt ccaacgcacg ggcttccggc cacaacaggt    420
ttctggtcac cggtgtgaga gtggcgctca atgcgctgtc tgcccaagac tttctcgaag    480
caccaatgac cccacgatgt cggcaacccg ggaacgcgaa ctcctcggct tctggagcca    540
gctcgtcggg aaattcgctt tcggccaatc gcacgcagga ggagaggttt gacagaggag    600
agcccgagac tgtcatggaa aagag                                          625
```

<210> SEQ ID NO 46
<211> LENGTH: 614
<212> TYPE: DNA
<213> ORGANISM: Artificial
<220> FEATURE:
<223> OTHER INFORMATION: Synthetic

<400> SEQUENCE: 46

```
cttggtggct ggggtgcttc tcttgtcaac cacttcaacc gcacggtgga tgtggtgtta     60
agagggtata gcgggtataa cacaaggtgg gcattaaagg tgatagagaa agtttttgat    120
gagggaacgg cgccattggc agtgacagtg ttctttggag caaatgatgc ttgtctccct    180
gatagatgct cttcctttca acatgttcct attgatgagt acaagctgaa tcttcattcc    240
atcgtctcct ttctcaaggg gcgatggcca acaactcaaa ttgtcctcat ctcacctcct    300
ccaattgatg aacctacgcg gctcctatat ccttttatgg agaacaaatt gggcctgtca    360
gagaggacca atgaaactgc tggaaactat gctaaagcaa gtctagctgt agcagctgaa    420
tgtggggttt tggctgtgga tttatggacc agaatgcagc aaattcctgg ctggcaaaca    480
gcttgtttaa gtgatggttt gcacctgagt aaaactggga acgagattgt gtttgaggag    540
gtggtggcgg ctcttaagaa gaaagggttg agtgtggaag ctctaccagt tgatctgcca    600
gtgattaatg aaat                                                      614
```

<210> SEQ ID NO 47
<211> LENGTH: 552
<212> TYPE: DNA
<213> ORGANISM: Artificial
<220> FEATURE:
<223> OTHER INFORMATION: Synthetic

<400> SEQUENCE: 47

```
gaattcacca tacgaatttt attgccggtg actgatacat catgaaaagt ctaccttctc     60
tccttaaatc ctgttaccgg cgtagaatgt tgtgctcatg catgtgatcg atctaatgtc    120
aaacagtcta tacagctata tcaataatac tacaaaactg aaaataaaaa taaatgtgtc    180
tatataatgt aagctatcca actataattg tgataaaaat atcgtcgcct aaccataagg    240
atggacgcag gttatatcct catgtaggtt atccatcagg tctgccggaa aggacgaatg    300
aggctgccgg tgcttatgct aaggcatgtg tggaggttgc tgatgaatgt ggagtgattg    360
gagtggattt atggactaaa atgcaacaat accctaattg ggaaaaatgt tgtctcagtg    420
atggcttaca cctaacacca actgggaaca gaattgtata tgaggaagtg atcaaaaagc    480
```

-continued

```
ttacaaaaga aggggtaaat gttgaaactt tatcagcaga tctccctctc ctatctcaga    540

tcgatccttg tg                                                        552


<210> SEQ ID NO 48
<211> LENGTH: 161
<212> TYPE: DNA
<213> ORGANISM: Artificial
<220> FEATURE:
<223> OTHER INFORMATION: Synthetic

<400> SEQUENCE: 48

aaaggcatca tttcaatgat caaaacaaca aagatgggga gagcagcaaa ctttgtatta     60

attaccacca catatatgtg ttgcttctta aatgataatt tgtgtaacta actaactaaa    120

agagtcccct ggtatatgta atgcggataa ttcaggaatc t                        161


<210> SEQ ID NO 49
<211> LENGTH: 1259
<212> TYPE: DNA
<213> ORGANISM: Artificial
<220> FEATURE:
<223> OTHER INFORMATION: Synthetic

<400> SEQUENCE: 49

gcgcgcctta attaggatcg aaggaaggtc atcaagtaac ttggttcaca agagggaaag     60

caccaatcag ccaaccatta cccggggagt cagaacaaga ttacctagat ttctcttcca    120

agatctcgca cttgaaagga gacagaaagg actacgattt tgttaagact agcctagcag    180

ctgaaggctt tgacgttgtc tatgatatca atggaagaga ggcagataga gagagagaca    240

atggcaatgg caacaagtag gttggtggtg gtgcaacaaa aacaaccatc ctcatgtcta    300

ttaccaccat catctctttc tgatttcaat ggtattagac tgaaacaccc aattcagtac    360

aaaagaaagg aatggcagac aagaggagca ttgcaggtga aagcatcagc tgcaaagaaa    420

atcctgataa tgggaggaac cagatttatt ggaatctttt tgtctaggct ccttgtgaag    480

gaaggtcatc aagtaacttt gttcacaaga gggaaagcac caatcagcca accattaccc    540

ggggagtcag aacaagatta cctagatttc tcttccaaga tctcgcactt gaaaggagac    600

agaaaggact acgattttgt taagactagc ctagcagctg aaggctttga cgttgtctat    660

gatatcaatg gtattggaag agaggcagaa gaagtagaac ccatattgga cgcgcttcca    720

aagcttgagc agtacatata ctgttcatcc gctggtgtgt atctgaagtc tgatttactg    780

cctcattttg agtctgatgc agtggatccc aagagcaggc acaagggaaa acttgaaaca    840

gagagtttac ttgtatcaaa gggcgtgaac tggacttcgc tgagaccagt ttatatctac    900

ggtcctttga attacaaccc tgttgaagaa tggtttttcc acagattgaa ggccggtaga    960

ccaatcccca taccaaattc tggcaaccag atgacacaat tgggtcatgc taaggatttg   1020

gcgaccgcat ttattaacgt tcttggtaac gataaagcga gccagcaagt gtttaacata   1080

tctggagata aatatgtgac attcgacgga ttggcaaggg cttgtgctaa ggctggtgga   1140

tttcctgagc cagaactagt tcactacaat cctaaagaat tcgattttgg caaaaagaag   1200

gcattcccct tcagagacca gcatttcttt gcatcaattg agaaagcaaa gagtgaatt    1259


<210> SEQ ID NO 50
<211> LENGTH: 699
<212> TYPE: DNA
<213> ORGANISM: Artificial
<220> FEATURE:
<223> OTHER INFORMATION: Synthetic
```

<400> SEQUENCE: 50

```
ttttatatca tcagccaaat ttgctgaaga aggcaccacc aaatggctag tttggttgca     60
gttcaacaca aacagccttc ttttgctgtc ctcccttctt cccattctga cttcaatggt    120
gccaaattga tctcctctct tcagtttaag aggaaaccat gccagccaaa aggagcattg    180
catgttactg catcaagtgc caagaaaatc cttataatgg gaggcactcg atttattggt    240
gtctttctat ccagacttct tgtaaaagaa ggccatcagg ttactctgtt cacaagagga    300
aaagctccca tctctcaaca attaccaggt gaatcagacc aggattatgc tgatttttcc    360
tccaagttac tgcacttgaa gggtgacaga atggattttg attttgtgaa gactagtctt    420
tctgcagagg gctttgatgt tgtgtacgac ataaatggac gagaagcagt agaagtggaa    480
ccaatattgg atgcattacc taatttagaa cagtacacat actgctcttc agctggtgta    540
tacctcaaaa ctgattattt accacatttt gaggctgatg cagttgaccc aaagagcagg    600
cataaaggaa agcttgagac agagagcttg ttagaatcac gagatgttaa ttggacttct    660
gtaaggcctg tttatattta tgggccactt aactacaat                           699
```

<210> SEQ ID NO 51
<211> LENGTH: 603
<212> TYPE: DNA
<213> ORGANISM: Artificial
<220> FEATURE:
<223> OTHER INFORMATION: Synthetic

<400> SEQUENCE: 51

```
gtcgacgcac gcgtccgaaa caagaaaaaa aagagagaga gatggcagca acagcctccc     60
tgaagagcag cctcctgcta ccatctccta tctctgactt cagtagtgca gcactctcca    120
tctcaaccca ggctaggagg aggtcatggc agccaagggg ggcaaggatg caggtagcag    180
cagctgcaga ctccaagaac attcttgtga tgggggggaac caggttcatt ggtgtcttct    240
tgtccaggat ccttgtcaag gaggggcacc aggtcacatt gttcactaga ggaaaggccc    300
ccattaccca gcagttgcca ggagagtcag atgcagagta tgcagagttc tcttcaaagg    360
tgttgcactt gaaaggtgac aggcaagact ttgatttcgt taagacaagc cttgcggcaa    420
agggcttcga tgttgtttac gacataaacg ggagagaagc tgttgaggta gccccaatcc    480
tagacgcatt gccaaacctt gaacagtaca tctactgctc atcagcagga gtgtacctga    540
aatcagacct gctcccgcac ttcgagaccg acgccgtcga cccgaaaagc cggcacaagg    600
gga                                                                   603
```

<210> SEQ ID NO 52
<211> LENGTH: 649
<212> TYPE: DNA
<213> ORGANISM: Artificial
<220> FEATURE:
<223> OTHER INFORMATION: Synthetic

<400> SEQUENCE: 52

```
cccacgcgtc cgggcgaaga tgatgatgtt gcaacagcat cagccttctt tctctctcct     60
tacttcttct ctgtctgact tcaatggcgc taagctccat ttacaagtcc agtacaagag    120
gaaggttcat cagccaaaag gagcactcta tgtttcagcg tcgagcgaaa agaagattct    180
gataatgggt ggtactcgat tcattggtct gttcttgtcc aggatccttg tcaaagaggg    240
acatcaggtt acattgttca caaggggtaa atctcctatt gccaaacaat tgcccggtga    300
```

-continued

```
atctgaccaa gactttgctg atttctcttc taagattctt cacttgaaag gagacagaaa    360

ggactatgac tttgtgaagt caagtctttc agcagaaggc ttcgatgttg tttatgatat    420

caacgggagg gaggccgaag aagttgagcc catactagaa gcactaccca aactagagca    480

gtacatctac tgttcttcag ctggtgttta tctgaaatct gatatcttgc cacattgtga    540

ggaggatgca gttgatccga agagcaggca caaggggaag ctggagactg agagcttact    600

gcaatcaaaa ggtgtaaact ggacttctat acgtcctgtc tacatctac                649
```

```
<210> SEQ ID NO 53
<211> LENGTH: 613
<212> TYPE: DNA
<213> ORGANISM: Artificial
<220> FEATURE:
<223> OTHER INFORMATION: Synthetic

<400> SEQUENCE: 53

gaagagtgag ttgatcgaat agatttgatt cctttctctt ggtagggaga gctggcgacg     60

aaagggttgg atcacgcaga gtttccacca cggctttgaa ttccaggcgt cgcgattccc    120

tggtcggtgt ggacgctgcc aggagcttgt gcgtggtagc gcgccttgcc agcttccacg    180

gtggtcgcgg cgcagctccg gctgccggag gtcgcccctc ggatctcttg aacttggccg    240

gcggcggtgt tgccctcccc tcttgctctt ggtcgctgcc acctttccgg ggcatcgatc    300

agtgagcttg tagagaagtg aagtttagtc ctttccagcc aaaagttgga tttttttttt    360

tccctttcc tccgccatgg acaaggtttt gaagattcga aggattccaa ccattgtgtc    420

caattaccag gagagcctcg acttccagtc cggatgtggc aagaattgtc tcgggtcgtg    480

ttgcattcct ggagcaaaat tgccattgta tctctttggc aaaccggatg tggatgagag    540

tggagaagtc cctaccaagg agctgggaca aaactctttc ctggattcag ctattctcgg    600

tcagtgggct gat                                                       613
```

```
<210> SEQ ID NO 54
<211> LENGTH: 453
<212> TYPE: DNA
<213> ORGANISM: Artificial
<220> FEATURE:
<223> OTHER INFORMATION: Synthetic

<400> SEQUENCE: 54

ctcgtggtgc tggctgtggc cgcaactgcc tccgaaactg ctgccttcca gggtcaaagc     60

tgccactgta tgcttgcaag agtttgagaa atggcacgtc tgttgccgat gaaaccaagg    120

aacctcccgt tgacttcttg gaatccctcc ttctcgggga atgggaggat cgtcagcaga    180

aaggtctctt tcgctatgat gtcactgctt gcgaaaccaa ggttattcct ggagaatatg    240

gtttcattgc tcaactgaat gagggaaggc acctcaagaa gagaccaact gagtttcgcg    300

ttgataaggt gctgcagcct tttgatggaa gcaagttcaa cttcactaag gttggtcagg    360

aggagttgct ctttcagttt gaagcaagtg aggataatca agtccaattc tttccaaatg    420

cgcccattga tgccgaaaaa tctccaagtg tcg                                 453
```

```
<210> SEQ ID NO 55
<211> LENGTH: 638
<212> TYPE: DNA
<213> ORGANISM: Artificial
<220> FEATURE:
<223> OTHER INFORMATION: Synthetic

<400> SEQUENCE: 55
```

-continued

```
aagcaagttc aacttcacta aggttggtca ggaagagttg ctcttccagt ttgaagcaag      60

tgaggacaac gaagttcaat tctttccaaa tgcacccatt gatgccgaga aatctcgaag     120

tgttgttgcc atcaatgtca gtcccattga gtatggacat gtgcttttga tccctaaggt     180

ccttgaatgc cttccccaga ggattgacag ggacagccta ttgcttgcac tgcacatggc     240

tgccgaagca gctaacccat acttccgatt gggttataac agcttgggtg catttgctac     300

catcaaccat cttcactttc aggcctatta cttggctgtg ccattcccca ttgagaaggc     360

ccccactcgg aagattacct ttgctgatcc tggagtgaag atatctgaga tgctgaatta     420

tccagttcga ggacttgtct ttgagggtgg aaatactttg gaggatttcg ccaatgttgt     480

ctctggttct tgcatttgcc tgcaagagaa taacattccc tacaatgttc taatctctga     540

ttcggcaaaa agggtattcc ttctcccaca gtgctacgca gagaaacagg ctctagggga     600

ggtcagctct gaactgcttg atactcaagt caatcctg                            638
```

<210> SEQ ID NO 56
<211> LENGTH: 79
<212> TYPE: DNA
<213> ORGANISM: Artificial
<220> FEATURE:
<223> OTHER INFORMATION: Synthetic

<400> SEQUENCE: 56

```
accatacaac cttgggggta atatgtggca aaagtgcgag atgagccccc gaaaaaaaaa      60

tcttcatcct catccttga                                                  79
```

<210> SEQ ID NO 57
<211> LENGTH: 645
<212> TYPE: DNA
<213> ORGANISM: Artificial
<220> FEATURE:
<223> OTHER INFORMATION: Synthetic

<400> SEQUENCE: 57

```
gaattcaaga agaccatcgg agattgttca tccggccgtt tctctacatt ttcggtcatt      60

tcaaggagca agcagtattt taaggaggca aaatgagtca gaaaaaaggg ggtggcaagc     120

tatctgttcc tggtagtagt ggttcacctg caaaagggaa agatgcaggt ggacaaatcc     180

ctggagtttt aggctctggt aaccaaaaga ctggagttgt tcagctgggt tctaatatcg     240

caaacctaag ccttgattcc agtaaagatt ctgagtggga ggtagtgtct cgcaagaatc     300

gaggcgcggc aagtgcacca aaaccatggg gtccccagaa ttcctcttct ccatccttgg     360

tttcaggaag ttcccaaaat tcctcttctg catcctgggt tgcaggaaag gctacaggag     420

gtgcccaaaa ttcctcttct ccatccttgg tttcaggaag ttcccaaaat tcctcttctg     480

catcctgggt tgcaggaaag gctacaggag gtgcctggca ggataataag tcaggtggag     540

gaggaactac gaaaagccaa tctcccaatg catgggagaa aaattacatg gcaccaccaa     600

gtaagattgc tcctccttta caacatggtt ggcagtgggg tgcaa                    645
```

<210> SEQ ID NO 58
<211> LENGTH: 820
<212> TYPE: DNA
<213> ORGANISM: Artificial
<220> FEATURE:
<223> OTHER INFORMATION: Synthetic

<400> SEQUENCE: 58

-continued

```
gaattcacaa agaaatccac tttcattgca gataagcttt tcttcactcc atcaaaggaa    60

caaagtcgag agagagagag cacaacaagt aaattagaac tctctggtca caatttctgc   120

ctctgcaagt cctctctctt cattcgcttc cctttctatc tcaacatcta gaaaatttct   180

cccaaaccac acttctttct ccttctcaaa catcaaaacc cataaactca tcaccccaat   240

ttcttcccta aaattccccc attcaaaacc cccaaaacct aaacccataa aagctacacc   300

ctctgatgca gaaaccattt tcatggaaaa tgaaataagc ccagatgaag atttcacatt   360

tgagccacca ccaagaccag aaggttacat tgaaccacct tcatttgatg atcttccacc   420

agaatctgaa gatgaaattg cagcagccta tgaagaattg tatggtcctg cttatagtgg   480

tatgagtgtg ctaggtaacg atgtatatgt tatggattct aagatgaaga aagcaactgg   540

gtttggtaca aagactaaga aagagaaaat tagagatggt tttgaagaaa gagttgttca   600

agttagaagg gttaccaaag ttgttaaagg tgggaaacaa ttgcatttta aagctgttgt   660

tgttgttggt gataaacaag gtcaagttgg agttggtgtt ggtaaagcta aagaagttgt   720

ttctgcagtt caaaagtctg ctggtaatgc tagaaggaat attattactg tgcccttaac   780

taagtattca actttccctc acagagctga cggagattac                         820
```

```
<210> SEQ ID NO 59
<211> LENGTH: 687
<212> TYPE: DNA
<213> ORGANISM: Artificial
<220> FEATURE:
<223> OTHER INFORMATION: Synthetic

<400> SEQUENCE: 59

agcgacaatc agaaaccacc cgctgtaacc ctaggttttt tcacaaacaa caaatatgac    60

tgagtcatcg cgggaagaaa atgtgtacat ggccaagctt gctgagcagg ccgagcgata   120

tgaggaaatg attgagttta tggagaaggt tgcaaagaca ggtgatgtcg aggagctgac   180

tgttgaggaa aggaatctcc tttctgtggc atacaaaaat gtgattggtg caagaagggc   240

ctcgtggaga ataatctctt caattgagca gaaagaggag agccgtggaa atgaagatca   300

tgtcaaaact attaaagaat acagagccaa aattgaggct gaactcagca agatctgtga   360

tgggattttg ggtctccttg agtcccattt aataccatca gcctccacag ctgagtccaa   420

agtttttac ttgaagatga aaggtgatta ccacaggtac ttggctgagt ttaagacagg    480

ggcagaaagg aaagaagccg cagagaacac tttattaccc tacaagtctg ctcaggatat   540

tgctttggat gaactggctc ctactcaccc aatcaggctg ggacttgccc tcaacttttc   600

agtgttctac tatgaaattc tcaactcgtc ggatcgtgct tgtaatcttg caaagcaagc   660

ctttgatgat gccattgccg agctgga                                       687
```

```
<210> SEQ ID NO 60
<211> LENGTH: 614
<212> TYPE: DNA
<213> ORGANISM: Artificial
<220> FEATURE:
<223> OTHER INFORMATION: Synthetic

<400> SEQUENCE: 60

tggttgttat tgttgttgct gtgtttatct tcttcgcctt cgtgttcgtc ggtggtgttg    60

gtagtgggaa gatgggtgtg gagaaggagc gtgagagtga tgtgtacatg gctaagctcg   120

ctgagcaggc ggaacgttat gatgagatgg tggaattcat gaaaaaggtg gcaaacttgg   180

atgtggagct atctgtagag gagaggaatc tgatgtcagt tgggtacaag aatgtgattg   240
```

-continued

```
gggcacggag ggcctcttgg cgcatcctct cctccatcga gcagaaggag cgagggaaaa    300

ggcaatgaag tgaatgccaa gcgcatcaaa gaatacaagc acaaggtcga ggaagagctt    360

tcaaacatct gcaacgatgt cctctccgtt attgaggatc atctcatccc tgcgtctagc    420

acgggggaat cttctgtctt ctattacaaa atgaaagggg attacttccg atattcggca    480

gagtttaaat ctggaaatga gaagaaggaa gccggagagc agtctttgaa agcataccag    540

gctgctatgg acatagcgac atctagcctt ccgacgactc atccgatcag gcttggtctt    600

gctctcaact tctc                                                      614
```

<210> SEQ ID NO 61
<211> LENGTH: 808
<212> TYPE: DNA
<213> ORGANISM: Artificial
<220> FEATURE:
<223> OTHER INFORMATION: Synthetic

<400> SEQUENCE: 61

```
tcgacccacg cgtccgggcg gcagcgcacg gcgaggaaca ggtgagtgcc cgtggatgtg     60

atctagatct accctccaag ccccaaaatc tcagtagaaa tcctccaaat cgcgccgccg    120

gaagagagat ccaatccacc actgtcccca tttctcggct tgttccaggg atgtcgaatc    180

ttcgcgagga gaatgtctac atggccaagc tcgcggagca ggccgagcgc tacgacgaga    240

tggtggaatt catggagaag gtggtcaagg ccgtggacgt ggaggagctg acggtcgagg    300

agcggaatct cctgtcggtg gcctacaaga acgtgatcgg cgcccgccgg gcatcgtgga    360

ggataatctc ctccatcgag caaaaggagg aatccaaggg caacgacgac cacgtctcga    420

tgatcaagga gtaccgtgcc aaggtggagt cggagctgag caccatctgc gacagcatcc    480

tcaagctgct ggacagccat ctcatcccct catcgtccag tggcgagtcc aaggtctttt    540

acttgaagat gaagggtgac taccaccgat acttggccga gtttaagacc ggggccgaga    600

ggaaagaggc cgcggagaac actctcctcg cctacaagtc ggcccaggac atcgctctca    660

cacagctgcc gccgacgcat cccatccggc tgggtctcgc tctcaatttt tcggtcttct    720

actacgagat tttgaattcg cccgatcgag cttgtacgct tgccaagcag gcatttgacg    780

aggccatagc cgagctggac actttggg                                       808
```

<210> SEQ ID NO 62
<211> LENGTH: 666
<212> TYPE: DNA
<213> ORGANISM: Artificial
<220> FEATURE:
<223> OTHER INFORMATION: Synthetic

<400> SEQUENCE: 62

```
gaatttgaac tccacctgag cacaggagaa gccgcagcca gtgagatttg accttctgtt     60

tctaccagaa aaacacaaac agtgaagatg tcgcagcctg ctgagctttc ccgtgaggag    120

aatgtgtaca tggctaagct tgcagagcag gccgagaggt atgaggagat ggttgagttc    180

atggagaagg ttgctaagac agttgactct gaggagctca ctgttgagga gcgcaacctt    240

ctatcagttg cttacaagaa tgttattggt gctcgccgtg cgtcatggcg catcatatca    300

tccattgaac agaaggaaga gagccgtggt aatgaggatc gttgcacgct catcaaggaa    360

tacaggggaa agattgaaac tgagctctcc aagatctgtg atggcatcct caagcttctt    420

gactcccacc ttgtgccttc atccactgct ccagagtcca aggtcttcta cctcaagatg    480
```

-continued

```
aaaggcgact actacaggta cctcgcagag tttaagactg gagctgagag gaaggatgct    540

gctgagaata ccatggtggc atacaaggct gctcaggaca ttgctttggc tgagctgcct    600

cctactcatc caattaggct tgggcttagc tcttaacttc tcagtgttct actatgagat    660

cctcaa                                                               666
```

<210> SEQ ID NO 63
<211> LENGTH: 946
<212> TYPE: DNA
<213> ORGANISM: Artificial
<220> FEATURE:
<223> OTHER INFORMATION: Synthetic

<400> SEQUENCE: 63

```
ccccgccccc cgggcgaaca aaaagcattc gcatccacga gagcactcga acccgacccg     60

cctcgccgcc gccgccaccg aagtaatccc ttaattggtc aaaatgtctc gggaggagaa    120

tgtctacatg gccaagctgg ccgagcaggc tgaaaggtat gaggacatgg ttgagtacat    180

ggagaaggtt gcaaagactg tagatgtgga agagctcact gttgaggagc gcaacctctt    240

gtctgttgct tacaagaatg tgattggtgc ccgccgtgcc tcctggcgta ttgtctcatc    300

cattgaacag aaggaggagg gtcgtggcaa tgaggaacat gttactctga tcaaggagta    360

ccgtggcaag attgaagctg agctgagcaa gatttgcgat ggtatcctga agttgcttga    420

ctcacacctt gtgccctcat ctactgctgc agaatctaag gtgtttttacc tcaagatgaa    480

gggtgattac cacaggtacc ttgcggaatt taagactggt gccgagagaa aggaagctgc    540

tgagagcaca atggtggctt acaaggctgc tcaggatatt gctctggcgg atcttgctcc    600

cacccatccc ataaggcttg gactggcact taacttctct gtgttctact acgagattct    660

aaactctcca gacaaggctt gcaaccttgc taagcaggcg tttgacgaag ccatctccga    720

gttggatacc ctcggggagg agtcttacaa ggacagcact ttgatcatgc agctcctgag    780

ggacaacttg accctctgga cctctgacct cacggaggac ggtggtgatg aggtgaaaga    840

agcctccaag ggcgacgcct gcgagggcca gtaaaatggg aagatcgatc gatcgatggc    900

tccgcatgtt attggagacc atcgatttag atgcctcatg ctgctg                   946
```

<210> SEQ ID NO 64
<211> LENGTH: 550
<212> TYPE: DNA
<213> ORGANISM: Artificial
<220> FEATURE:
<223> OTHER INFORMATION: Synthetic

<400> SEQUENCE: 64

```
cccccctggag gatcatctct tctatggagc agaaggagga gagccgtggg aatgaggcat     60

atgttgcatc aattaaggag taccgtagca ggattgaaac tgagctcagc aagatctgtg    120

atggtatcct taagcttctg gattcccacc ttgtcccatc tgccactgct gcagagtcca    180

aggtgttcta cctgaaaatg aagggtgact accacaggta ccttgctgag tttaagtcag    240

gagctgagag gaaggaagca gctgagaaca ctcttgtggc atacaagtct gcccaggata    300

ttgcactcgc tgacctgcct acaactcacc cgataaggct tggacttgca ctgaacttct    360

cagtgttcta ctatgagata ctgaactcac cagaccgtgc ttgcaacctt gcaaagcagg    420

cgttcgacga tgctattgct gaactggaca ctcttggcga ggagtcttac aaggacagca    480

ccttgatcat gcaacttctt cgtgacaatc tgactctctg gacctctgac aatgcggagg    540

atggtggtga                                                           550
```

<210> SEQ ID NO 65
<211> LENGTH: 703
<212> TYPE: DNA
<213> ORGANISM: Artificial
<220> FEATURE:
<223> OTHER INFORMATION: Synthetic

<400> SEQUENCE: 65
ttgcaagttc cattccctgt tcttctctct caacgaagca tcaacccccc ttttctccca 60
gaaccgcgtc tcatcgcacc tgccataaaa ctccaaaaaa tctcaaaaac caaccgtcaa 120
aatgggtcac gaagatgctg tttatctggc caagctcgcc gagcaggccg agcgatatga 180
ggagatggtc gagaacatga agatcgtcgc ctccgaggac cgcgacctga ccgtcgagga 240
gcgcaacctc ctctccgtcg cctacaagaa cgtcattggt gcccgccgtg cctcttggag 300
aatagtcact tccatcgagc agaaggagga gtctaagggc aactcttccc aggttaccct 360
tatcaaggag taccgccaga agattgaggc cgagcttgcc aagatctgcg atgacattct 420
cgatgttctt gacaagcacc tgattccttc tgccaagtct ggagagtcca aggtcttcta 480
ccacaagatg aagggtgact accaccgtta ccttgccgag ttcgccattg gcgaccgccg 540
caaggactcc gccgacaagt ctctcgaggc ttacaaggct gctaccgagg ttgcccagac 600
cgagctgcct cctacccacc ctatccgcct gggtcttgcg ctcaacttct ccgtcttcta 660
ctacgagatc ctcaacgccc ctgaccaggc ttgccacctc gct 703

<210> SEQ ID NO 66
<211> LENGTH: 656
<212> TYPE: DNA
<213> ORGANISM: Artificial
<220> FEATURE:
<223> OTHER INFORMATION: Synthetic

<400> SEQUENCE: 66
acgcactctg tcgagaatcc attctatttc gcctaaactt tctctctcta caacaacaac 60
aatggcggct ctgctcacag acaatctcaa ccgcgaacaa tacctctact tagccaaact 120
cgccgaacaa gccgaacgct atgaagaaat ggtccagtac atggacaaac tagtactcag 180
ttccactccc gccgccgaac tcaccgtcga ggaacgaaac ctcctttccg tcgcttacaa 240
aaacgtgatc ggctctcttc gtgccgcgtg gcgtatcgta tcctccattg agcagaaaga 300
ggaatcgcgt aagaacgaag aacacgtttc gctcgttaag gagtacagag gtaaagttga 360
gaatgagtta acggaggttt gtgctggtat cctcaagttg cttgagtcaa atctcgagcc 420
gtctgcttct acgggtgaat cgagggtgtt ttacctcaaa atgaaaggtg attattaccg 480
gtatctagcg gagtttaagg ttggagatga gcggaagcag gctgctgaag acactatgaa 540
ttcttataag gctgctcagg aaattgcact agcagatctg cctccaacac atcctataag 600
gctgggtctt gcacttaatt tctcagtctt ctactttgag attctgaact catctg 656

<210> SEQ ID NO 67
<211> LENGTH: 369
<212> TYPE: DNA
<213> ORGANISM: Artificial
<220> FEATURE:
<223> OTHER INFORMATION: Synthetic

<400> SEQUENCE: 67
gttataaatc cttatctttt tcaacacaca gattaaaatc ttcagaaaga gagagagaga 60
tcccaaaatg ggtgaacgtg agaacttcgt atacatagct aagcttgccg agcaagctga 120
acgctatgat gagatggctg atgcgatgaa gaatcttgca aatatggatg ttgaattgac 180
agcggaagag aggaatttgt tttctgttgg ttataagaat gtggttggag ctaggagagc 240
atcgtggagg atcttgtctt ccatcgagca gaacgaagag tctagaggaa atgagcagaa 300
cgtgaagcgg attaaggagt accagccaaa agtggagtca gagctcaccg acatttgcaa 360
taatatcat 369

<210> SEQ ID NO 68
<211> LENGTH: 390
<212> TYPE: DNA
<213> ORGANISM: Artificial
<220> FEATURE:
<223> OTHER INFORMATION: Synthetic

<400> SEQUENCE: 68
cccacgcgtc cgtagaggaa agaagagagc aaagggaacg aagatcatgt tgctattatc 60
aaggattaca gaggaaagat tgaatccgag cttagcaaaa tctgtgatgg gattttgaat 120
gttcttgaag ctcatcttat tccttctgct tcaccagctg aatctaaagt gttttatctt 180
aagatgaagg gtgattatca taggtatctt gctgagttta aggctggtgc tgaaaggaaa 240
gaagctgctg aaagcacttt ggttgcttac aagtctgctt ccgacattgc cactgctgag 300
ttagctccta ctcacccgat aaggcttggt cttgcactca acttctctgt gttttactat 360
gaaatcctca actcgcctga tcgtgcttgc 390

<210> SEQ ID NO 69
<211> LENGTH: 403
<212> TYPE: DNA
<213> ORGANISM: Artificial
<220> FEATURE:
<223> OTHER INFORMATION: Synthetic

<400> SEQUENCE: 69
cggacgcgtg ggaaaaaaat caaatctctc tctttctctc tctaatggcg gcgacattag 60
gcagagacca gtatgtgtac atggcgaagc tcgccgagca ggcggagcgt tacgaagaga 120
tggttcaatt catggaacag ctcgttacag gcgctactcc agcggaagag ctcaccgttg 180
aagagaggaa tctcctctct gttgcttaca aaaacgtgat cggatctcta cgcgccgcct 240
ggaggatcgt gtcttcgatt gagcagaagg aagagagtag gaagaacgac gagcacgtgt 300
cgcttgtcaa ggattacaga tctaaagttg agtctgagct ttcttctgtt tgctctggaa 360
tccttaagct ccttgactcg catctgatcc catctgctgg agc 403

<210> SEQ ID NO 70
<211> LENGTH: 940
<212> TYPE: DNA
<213> ORGANISM: Artificial
<220> FEATURE:
<223> OTHER INFORMATION: Synthetic

<400> SEQUENCE: 70
aaaagggaga ggaaaagcgc aaaatctccc ttcgattatc agtacaaaac ctctgatttg 60
agagatcgga aatggcttcc tccaaagaac gcgagaactt cgtctacgtc gctaagcttg 120
ctgagcaggc cgaacgctac aatgaaatgg ttgatgcgat gaagagtgta gcaaatatgg 180
atgttgaatt gactgttgag gaaaggaatc tgctttctgt tggttataaa aatgtggtag 240
gttctaggag agcatcttgg aggatcttat cctctattga gcagaaggaa gaatctagag 300
gaaatgagca aaatgtcaag cgaattaagg agtaccgaca aaaggtggag acagagctca 360
ccagcatttg caacgatatc atggtggtca ttgatcagca tctaattcct tcatgcactg 420
caggcgaatc aactgtgttt taccacaaga tgaagggaga ctattatcgt tatcttgcag 480
aatttaaatc tggcaatgac aagaaagagg ttgcagagct ttcattgaaa gcatatcagt 540
cagctacaac tgctgcagag gcggaattac cacccactca tcccattcgg ttgggattgg 600
ctttgaattt ctctgttttc tattatgaga tcatgaattc acctgaaagg gcatgccatc 660
tggcaaagca ggcctttgat gaagcaatat ctgagttgga tagcctgaac gaggattcct 720
acaaagacag caccttgatt atgcagcttc taagggacaa tctcaccttg tggacttctg 780
atcttccaga ggatgcagaa gatgcccaaa agggagatgc cacaaacaaa gcaagtggag 840
gtgaagatgc agagtaaatg ggcctaatgg ttagaactac cttgtgcatt tggagctgtg 900
aggacggtga tacaccaaag ggatgtgtgt gtgttaagtc 940

<210> SEQ ID NO 71
<211> LENGTH: 718
<212> TYPE: DNA
<213> ORGANISM: Artificial
<220> FEATURE:
<223> OTHER INFORMATION: Synthetic

<400> SEQUENCE: 71
tttttctagc acacagacca tcaatggcat cgccgcgcga ggagaacgtg tacctggcga 60
agctggctga gcaagccgag cgctacgagg agatggtaga gttcatggag aaagttgtcg 120
gcgacggcga cgacgaactc accgtcgagg aacgcaacct cctctccgtc gcgtacaaaa 180
acgtgatcgg agcgaggaga gcgtcgtggc gcataatctc atcgatcgag cagaaagaag 240
agagtcgcgg taatgaagat catgttgcct ccattaaaac ctacagatct aagatcgaat 300
ctgaattgac ttcgatctgt aacggtatcc ttaagttgct cgattcaaaa ctcatcggca 360
ccgctgctac cggtgactct aaggtttttt atttgaaaat gaagggagat tattacaggt 420
acttggctga gttcaaaacc ggagctgaga gaaaagaagc cgccgagaat actctttcgg 480
cttacaagtc ggctcaggat attgctaatg tcgaattagc cctacacat ccaatccgat 540 tggggctagc tctcaatttc tcagtgtttt actatgagat attgaattct cctgaccgtg 600
cttgtaatct tgccaaacag gcatttgatg aggcaattgc ggagcttgac acccttggag 660
aggagtctta caaggatagc accttgatta tgcagcttct tcgtgataac cttacgtt 718

<210> SEQ ID NO 72
<211> LENGTH: 716
<212> TYPE: DNA
<213> ORGANISM: Artificial
<220> FEATURE:
<223> OTHER INFORMATION: Synthetic

<400> SEQUENCE: 72
aggagcttag atcgatcgac gacgccatcg ccgccggagc tgccatggga atggagaagg 60
agagggaatg cttcgtctac atggccaagc tcgcggagca agccgagcgt tacgatgaaa 120
tggttgaatc gatgaagaaa gtcgcgaagc tggacgtgga gctgaccgtg gaggagagga 180
atctcctgtc cgtgggctac aagatcgtga ttggggcgcg gcgggcgtcg tggcggatct 240
tgtcctcgat cgagcaaaag gaggagagca aaggcaacga gcagaacgtc aagaggattg 300
gagagtacca gcaaaaggtc gaggacgagc tctccaagat ttgcaatgac attctcacga 360

```
tcattgacga gcatctagtg ccggcttcca gcactggcga atccacggtc ttttactaca    420

agatgaaagg tgactacttt cgataccttg cagagtttaa gaccgggaac gaaagaaaag    480

aagctgccga tcaatcgttc aaggcttacc aggctgcgag cgatactgct tcaagcgatc    540

ttcccccaac acatcctatc cggctgggac tggcattgaa tttctctgtt ttctactacg    600

agattctaaa ctcgccagac cgcgcttgcc agctagcgaa gcaagctttt gacgatgcga    660

ttgcggagct ggacacgctc agcgaagaat cctacaaaga cagcaccttg atcatg        716
```

<210> SEQ ID NO 73
<211> LENGTH: 636
<212> TYPE: DNA
<213> ORGANISM: Artificial
<220> FEATURE:
<223> OTHER INFORMATION: Synthetic

<400> SEQUENCE: 73

```
ttcgcatctc tccatcgccg ccgccgccgt ttctgccgcc gcataggcat ccgtcgccag     60

gtagcgcagc cgcagccgca gccgccgccg caaagctagg ttgtttctcg ccgaaatgcc    120

ggaatccaag gaggagaatg tctacatggc caagctcgcg gagcaggccg agcgctacga    180

cgagatggtg gagtacatgg agaaggtggc caaggccgtg gaggcggagg agctgagcgt    240

ggaggagagg aatctcctgt cggtggcgta caagaatgtg attggggcgc ggcgggcttc    300

gtggcggatc atctcgtcga tcgagcagaa ggaggagtcc aagggcaacg aggagcatgt    360

aggcttgatc aagaactaca ggtccaaggt ggagacggag ctgagcaaca tctgccacgg    420

gatcttgggg ctgctggatt cgcacctcat cggatcctgc tccacgggcg aatccaaggt    480

cttctacctc aagatgaagg gcgactacaa tcgctacctt gccgagttta agacggggca    540

ggagaggcag gaggcagccg aggccacctt gatggcctac aagtcggcac aggacattgc    600

gctggcggag cttgctccaa ctcaccccat tcgact                              636
```

<210> SEQ ID NO 74
<211> LENGTH: 642
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (525)..(525)
<223> OTHER INFORMATION: The residue at this position can be any nucleotide.

<400> SEQUENCE: 74

```
tttctctctc tctctctctc tctctctctc cctccgtcga catgggcatc gagatggagc     60

gagagagcct tgtctaccta tccaagctct ccgagcaggc agaacgctat gagaaatggt    120

ggagtcgatg aagaaagtat ttaagttgga tgtagagctt acgattgagg agaggaattt    180

gctctcagtg ggtataagt attttatcgg agcgcgaagg gcctcgtggc gaattctctc    240

ctccattgag cagaaagaag agagcaaggg caatgagacc aatgtaaaac gcatcaagga    300

gtaccgcaac aaagtggagg aagagctttc caagatttgc agtgacatcc taactatcat    360

cgatgagcat cttatcccct catctggcac agcagaatct accgttttct attacaaaat    420

gaaaggggat tattatcgct accttgctga gttcaagaca ggacatgaga gaaaggaagc    480

tgcagatcaa tctctgaaag cttatcagac tgcaagtgac acggncaaca cggctctgcc    540

atctacccat ccgatcaggc ttggacttgc actcaacttt tcagtctttt actatgagat    600
```

tttgagttcg ccggagcgtg cgtgccatct tgccaagcaa gc 642

<210> SEQ ID NO 75
<211> LENGTH: 696
<212> TYPE: DNA
<213> ORGANISM: Artificial
<220> FEATURE:
<223> OTHER INFORMATION: Synthetic

<400> SEQUENCE: 75
cacgcgtcgc gacagtcgaa acggggtccc gggaggagag tgtgtacatg gccaagctcg 60
cggagcaggc cgagcgctac gaggagatgg ccgagttcat ggacgctgtc tccaagggcg 120
ccggtgctga ggagatgtcc gttgaggagc gtaacctcct ctctgtcgcc tacaagaatg 180
tcattggtgc ccgtagagcc tcctggcgca ttgtctcctc catcgagcag aaggaggaga 240
gcaagggcaa tgaagaccac gtcgccgcca tccgcggcta ccgcgtcaaa gttgaggctg 300
agctcaccaa gatctgccag cgcattctcg acctccttga cagccacctt gtcccctctg 360
cgctcaaccc cgagtgcaag gtcttctacc tgaagatgaa aggggattac caccgttacc 420
ttgccgagtt caagaccggt gctgaccgca aggaagcggc tgagagtacg ctcgtcgctt 480
acaaatctgc cgaggaaatt gccctggctg agctgccttc gacacacccc attcgtttag 540
gccttgctct gaatttttca gttttttact atgaaatttt gaactcccca gacagagctt 600
gcaatctagc taagcaggct tttgatgagg ccattgctga actggacact ctgggggaag 660
attcctataa ggacagtact ttgataatgc aacttc 696

<210> SEQ ID NO 76
<211> LENGTH: 338
<212> TYPE: DNA
<213> ORGANISM: Artificial
<220> FEATURE:
<223> OTHER INFORMATION: Synthetic

<400> SEQUENCE: 76
cccacgcgtc cgcttcagac aaagcttgta acatggccaa acaggctttt gaggaggcca 60
tagctgagct tgacactctg ggagaggaat cctacaaaga cagcactctc ataatgcagt 120
tgctgaggga caatttaacc ctttggacct ccgatatgca ggagcagatg gacgaggcct 180
gaggatctag atgaaggggg ggagggttgt tacgcgatgt ttctgccacc aaatcgatct 240
caaaatcccc ataacctttg ctcaaaaact gtgaaaaaag attgaagtgt ttatgatgat 300
tatgattgtg cacagcttga tgatttatct actctact 338

<210> SEQ ID NO 77
<211> LENGTH: 623
<212> TYPE: DNA
<213> ORGANISM: Artificial
<220> FEATURE:
<223> OTHER INFORMATION: Synthetic

<400> SEQUENCE: 77
cagctctctc tctctccctt caaacatcga tggcgtcgtc gcgcgatgag ttcgtgtaca 60
tggcgaagct tgcggagcaa gctgagcggt acgaggagat ggtagagttt atggagaagg 120
tcgtaaccgc ctcggacggc ggcgaggaac tcaccatcga agaacgtaat cttctatccg 180
tagcatacaa aaacgtgatc ggagcacgac gagcctcgtg gcgaatcatt tcctcaatcg 240
agcaaaaaga agagagccga ggcaatgagg agcacgtgac ctctattaaa acttacagat 300
ctaagatcga gtcggagttg acctcgatct gtgacggtat cctcaagctg ctcgattcga 360

-continued

```
atctcattgg cgctgcgtca atcggagatt ctaaggtgtt ttatttgaaa atgaaaggag    420

attatcaccg gtatttggct gagtttaaga ccggagctga gagaaaggaa gctgctgaga    480

atactctttc gtcttataag tccgctcagg atattgcaaa tgcggaactg gcacctacac    540

atcctattcg attggggcta gttctcaatt tctctgtatt ttactatgag atattgaatt    600

cacctgatcg tgcttgtaat ctg                                             623
```

<210> SEQ ID NO 78
<211> LENGTH: 1057
<212> TYPE: DNA
<213> ORGANISM: Artificial
<220> FEATURE:
<223> OTHER INFORMATION: Synthetic

<400> SEQUENCE: 78

```
agaaaatcga aaaactccca catccagatc tccccccccc ccccccaaaa aaaaatacag     60

agaacaaatc ttaacatggc ggtggcaccg acggcgcgtg aggagaacgt gtacatggca    120

aagcttgcag agcaagctga gaggtacgaa gaaatggttg aattcatgga aaaggtctcc    180

aactctctcg gctcagaaga actcaccgtg gaggaacgaa acctcctttc cgtggcgtac    240

aagaacgtga tcggagcgcg tagggcatcg tggcgtatta tctcatcgat tgagcaaaag    300

gaagagtcca gagggaacga ggaacacgtg aactctatcc gcgagtacag atctaagatt    360

gagaatgagc tctctaagat ctgtgatggt attctgaaat tgctcgatgc aaagcttatc    420

ccttctgcag catctggtga ttctaaggtg ttttacctga aatgaaagg agattaccac    480

cgctatttgg ctgagttcaa gaccggtgct gaacgtaagg aggctgctga gagtacactc    540

actgcctaca aagctgctca ggacattgca actactgaac ttgccccaac acatcccatc    600

cgacttggac tggctcttaa cttctctgtg ttttactatg agatcttgaa ctctcctgac    660

cgtgcttgca atcttgctaa acaggccttt gatgaagcaa ttgctgagct ggatacattg    720

ggcgaggagt cttacaagga tagcactttg atcatgcaac ttcttcgtga caatctcact    780

ctctggactt ctgatatgca ggatgatggg gctgatgaaa tcaaggaaga tcccaaacct    840

gatgaagcca aaaattgaag gaaatgaaac tctctaattt gcttttcact tcttcctggt    900

tgtttttatt ggaagaagct gattatcgta atttccttac tattatggtt ctccactagg    960

gggttgtcat cttattggaa atgaacaact tttaatattg atgtttcaga gttccatctt   1020

tgatttaatg tggttttctg gtgattagtt ttcttct                             1057
```

<210> SEQ ID NO 79
<211> LENGTH: 875
<212> TYPE: DNA
<213> ORGANISM: Artificial
<220> FEATURE:
<223> OTHER INFORMATION: Synthetic

<400> SEQUENCE: 79

```
tacaaaactc cctctctcat ttcctctctc atagcaacat caatggcgtc gccacgcgag     60

gagaacgtgt acatggcaaa gcttgccgag caagccgagc gttacgagga gatggttgag    120

ttcatggaga aagtcatcgc cgccgccgac ggcgccgagg aacttaccgt cgaagaacgg    180

aacctcctct ccgtcgcata caaaaatgtt atcggagcac ggcgagcctc gtggcgtatc    240

atctcctcca ttgagcaaaa agaggagagc cgcggcaacg aagatcacgt tgcctccatc    300

aaggagtaca gatctaagat cgagatcgaa cttacctcga tctgtaacgg cattctcaag    360
```

-continued

```
ctcctcgatt ctaagctcat tggcgccgct gctaccggtg actctaaggt gttttacttg    420

aaaatgaaag gagattatca tcgctatttg gctgagttta aaaccggcgc ggagcgaaag    480

gaagccgccg aaaatactct ctcggcttac aaatccgctc aggatattgc aaataccgag    540

cttgctccta cacatccaat ccgattggga cttgctctca atttctctgt attttactac    600

gaaattttga attctcctga tcgtgcttgt aatctcgcca aacaggcttt tgacgaggca    660

attgccgagc tggacacatt gggcgaagag tcatacaagg atagcactct gatcatgcag    720

cttcttcgcg ataacctcac tttatggact tcagatatgc aggatgatgg aactgatgag    780

atcaaagaag cagcaaaacc agataatgag cagcagtaaa ccggtgacat ttctttagga    840

ttgaaattca tgttgtaact ttttattttt caatt                                875
```

```
<210> SEQ ID NO 80
<211> LENGTH: 485
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (141)..(141)
<223> OTHER INFORMATION: The residue at this position can be any
      nucleotide.

<400> SEQUENCE: 80

aagctgagag atatgatgaa atggtggaag caatgaagac ggttgctaag atggatgtcg     60

aactgactgt tgaggagaga aattggtgtc agtcgggtat aagaatgtaa ttggagcaag    120

aagggcttca tggcggatat ngtcttcgat tgaacaaaag gaggagagta agggtcatga    180

gcagaatgtt aagagaataa agacttacag acagagggtt gaagacgagc ttacaaaaat    240

atgcgttgac attttgtcgg tgatcgatga gcaccttgtt ccttcatcta ctgctggtga    300

atctactgtc ttctactata agatgaaggg agactactat cgctatttag cagagttcaa    360

atcaggggat gatcgtaaag aggcagctga tcagtcactt aatgcttatg aggctgctac    420

tgccacagct agcgcagatc ttgctcctac tcatccaatt agacttggac ttgcattgaa    480

cttct                                                                485
```

```
<210> SEQ ID NO 81
<211> LENGTH: 330
<212> TYPE: DNA
<213> ORGANISM: Artificial
<220> FEATURE:
<223> OTHER INFORMATION: Synthetic

<400> SEQUENCE: 81

cccacgcgtc cgagaagaag aagaagaaga agaaaaaact atggagaatg agagggaaaa     60

gcaggtttac ttggctaagc tctccgagca aaccgaaaga tacgatgaaa tggtggaggc    120

gatgaagaaa gttgctcagc ttgatgtgga gctaactgtg gaagagagga atcttgtatc    180

tgtagggtac aagaatgtga ttggtgcaag gagagcatca tggagaatac tatcttccat    240

tgagcagaag gaagagtcca agggaaatga tgaaaatgtc aagaggctta agaattatcg    300

taagagagtt gaagatgagc ttgctaaagt                                      330
```

```
<210> SEQ ID NO 82
<211> LENGTH: 1002
<212> TYPE: DNA
<213> ORGANISM: Artificial
<220> FEATURE:
```

<223> OTHER INFORMATION: Synthetic

<400> SEQUENCE: 82

```
ccccccgaga tctcaaaaat tcaacattgg cacaaccaaa aagaaaagag atccctaaat     60

tggaattcat tatggcgcgt gaggagaacg tgtacatggc gaagcttgcc gagcaagccg    120

agagatacga ggaaatggtg tcgttcatgg agaaagtctc tacttcctta gggacgtcag    180

aggaactcac ggtagaggag agaaatctcc tctcggtggc gtacaaaaat gttatcgggg    240

ctcgtagagc ctcgtggcgt ataatctcct ccatcgaaca gaaggaggag tcgaggggaa    300

acgaggacca tgtgaaatgc attcaggagt acagatctaa gattgaatct gaactctcta    360

gtatctgtga tggcattctc aagctccttg attcttgtct tattccttct gcttcagctg    420

gtgattctaa ggtgttttac cttaaaatga agggtgatta tcatcgttat ttggctgagt    480

ttaagactgg tgctgaacgt aaggaagccg ctgagagtac tctctccgcc tacaaagccg    540

ctcaggatat tgcaaatgct gaacttgccc caactcaccc aatccgactt ggactggctc    600

tcaacttctc tgtgttttat tatgagattt tgaactctcc tgatcgtgcc tgcaatcttg    660

ctaaacaggc ctttgacgaa gcaattgctg aattggacac actgggagag gagtcttaca    720

aggatagcac tttgatcatg caactgcttc gtgacaatct tactctctgg acctctgata    780

tgcaggatga tggcgctgat gaaatcaagg aaaccaaagc tgacaatgaa caacagtgag    840

gaaactgccc ctcatattgt cttttgactt cttcctgttg gtttttattg ggagaagctg    900

tttcctttta tttccttttt aatgtggttt cccttcagcg ttctcttatc cgtcgcaata    960

acaactttga caattgatgt tcaatgattt tatctttatt tt                      1002
```

<210> SEQ ID NO 83
<211> LENGTH: 629
<212> TYPE: DNA
<213> ORGANISM: Artificial
<220> FEATURE:
<223> OTHER INFORMATION: Synthetic

<400> SEQUENCE: 83

```
cccacgcgtc cggttgaaat gcccaccaat ttcaacaaca ggggttgaat ccaagaagct     60

taaggtgaat cccattaatc atcagaataa gaaggctaac aaagcaagag tagtagcaca    120

agctgcagca gtggtcacaa atgcacaaac aagagaaaga caaaagctta aggagatgtt    180

cgaggatgcc tatgagcgat gccgtactgc acctctcgaa ggtgttgcct ttaccgttga    240

tgattttcac tctgcccttg aaaaatatga ttttgactcc gaagttggta ccaaggtcaa    300

aggaacagtt ttctctctgg atgcaaatgg agctctagtt gacatcactg ctaaatcatc    360

tgcatacttg cctttacggg aggcttcact tcacaccatc aagcacgtag aggaagccgg    420

aatatttcct ggtttgcgtg aggagtttgt ggtggttggc gaaaatgaag ctgatgatag    480

tttgattttg agcttgcaat cgattcaata tgaccttgca tgggaacgat gtaggcagct    540

acaagcggaa gatgttgttg tcaaaggcaa ggtcgttggt gcaaataaag gtggagtggt    600

ggctctggtg gaggggcttc gtggttttg                                      629
```

<210> SEQ ID NO 84
<211> LENGTH: 332
<212> TYPE: DNA
<213> ORGANISM: Artificial
<220> FEATURE:
<223> OTHER INFORMATION: Synthetic

<400> SEQUENCE: 84

```
aaaactctct gtgtgagtga gtgagactca accatggcgt ctttggctca gcaattctcg     60
ggattgagat gttccccact ctcttcttct tctaggttat cgaggagagc ttcgaagaac    120
tttccccaga acaaatctgc ctctgtttct ccgactattg tcgccgcggt tgcaatgtct    180
agcggtcaaa caaaggagcg tcttgagctg aagaagatgt tcgaagatgc ttatgaacga    240
tgtagaactt ctcctatgga aggtgttgct ttcaccgtcg acgatttcgc tgctgctatt    300
gaacaatacg acttcaattc cgaaatcggc ac                                  332
```

<210> SEQ ID NO 85
<211> LENGTH: 629
<212> TYPE: DNA
<213> ORGANISM: Artificial
<220> FEATURE:
<223> OTHER INFORMATION: Synthetic

<400> SEQUENCE: 85

```
gaattcaggg aaaacagagt cgtttctggt acaaattagg tctaaagatg gcgtctttag     60
ctcaacaatt ctcaggatta agatgcccac cactttcttc ttctcatcta acaaaaccct    120
tttcttcaaa accccagaaa accacctttt cacctatagt ttcagcagct gtcatttcta    180
atgcacaaac taaagaaaga agtagactta aagaaatctt cgaagatgct tatgaaagat    240
gtagaactac tccaatgcaa ggtgttggtt ttactgttga tgattttcat gctgctcttg    300
aaaagtatga ttacaattct gagattggta ccagggttaa aggaactgtg ttctgtacag    360
acaacaacgg agcattagtt gacatcacgg cgaaatcttc agcctattta ccaatccaag    420
aggcatgtat tcacaaaata aagcatgtag aagaagcagg aatagttgca ggcctacgtg    480
aagagtttgt gattattgga gagaaccaag ctgatgatag cttgatcttg agtttgcgtt    540
caatccaatt tgacctcgca tgggaacggt gtagacaact tcaggcagag gatgtcgtcc    600
tcaagggtaa ggttgttggt ggaaacaaa                                      629
```

<210> SEQ ID NO 86
<211> LENGTH: 1305
<212> TYPE: DNA
<213> ORGANISM: Artificial
<220> FEATURE:
<223> OTHER INFORMATION: Synthetic

<400> SEQUENCE: 86

```
cggacgcgtg gggccagggc tctgaccgcg tgcctgttga agaatgagcc ggcgactcat     60
aggcagtggc ttggttaagg gaacccaccg gagccgtagc gaaagcgagt cttcataggg    120
caattgtcac tgcttatgga cccgaacctg ggtgatctat ccatgaccag gatgaagctt    180
gggtgaaact aagtggaggt ccgaaccgac tgatgttgaa gaatcagcgg atgagttgtg    240
gttaggggtg aaatgccact cgaacccaga gctagctggt tctccccgaa atgcgttgag    300
gcgcagcagt tgactggaca tctaggggta aagcactgtt tcggtgcggg ccgcgagagc    360
ggtaccaaat cgaggcaaac tctgaatact agatatgacc ccaaaataac aggggtcaag    420
gtcggccagt gagacgatgg gggataagct tcatcgtcga gagggaaaca gcccggatca    480
ccagctaagg cccctaaatg accgctcagt gataaaggag gtaggggtgc agagacagcc    540
aggaggtttg cctagaagca gccacccttg aaagagtgcg taatagctca ctgatcgagc    600
gctcttgcgc cgaagatgaa cggggctaag cgatctgccg aagctgtggg atgtaaaaat    660
gcatcggtag gggagcgttc cgccttagag ggaagcaccc gcgcgagcag gtgtggacga    720
```

-continued

```
agcggaagcg agaatgtcgg cttgagtaac gcaaacattg gtgagaatcc aatgccccga    780

aaacctaagg gttcctccgc aaggttcgtc cacggagggt gagtcagggc ctaagatcag    840

gccgaaaggc gtagtcgatg gacaacaggt gaatattcct gtactacccc ttgttggtcc    900

cgagggacgg aggaggctag gttagccgaa agatggttat cggttcaagg acgcaaggtg    960

accttagggt aagaaggggt agagaaaatg cctcgagcca atgtccgagt accaggcgct   1020

acggcgctga agtaactcat gccatactcc caggaaaagc tcgaacgacc ttcaacaaaa   1080

gggtacctgt acccgaaacc gacacaggtg ggtaggtaga gaatacctag ggcgcgaga    1140

caactctctc taaggaactc ggcaaaatag ccccgtaact tcgggagaag ggtgcctcc    1200

tcacaaaggg ggtcgcagtg accaggcccg ggcgactgtt taccaaaaac acaggtctcc   1260

gcaaagtcgt aagaccatgt atgggggctg acgcctgccc agtgc                   1305
```

```
<210> SEQ ID NO 87
<211> LENGTH: 638
<212> TYPE: DNA
<213> ORGANISM: Artificial
<220> FEATURE:
<223> OTHER INFORMATION: Synthetic

<400> SEQUENCE: 87

catttctggt cccttctctt catagtcttt ttctctttct ccatctcctc catttccgga     60

tctgatgatg attgcgtgta cacagcttac gtccgaacga gttcaataat aaagggtgga    120

acagattcga ttatcagttt gactctctac gatgcaaacg ggtatggtct tagaatcaag    180

aaccttgagg cctggggtgg gcttatgggc tctggttaca actatttcga gaggggaaat    240

ttggacattt tcagcggacg aggcccatgt ttgactgggc ctgtctgcaa gatgaacctc    300

acttccgacg gaactggcca aggccatgga tggtactgta actacgtgga ggtcaccgtc    360

accggagtcc ataaagcatg caaccaacag aatttcgaag tggagcagtg gctcgctact    420

gatgcgccgc cttatcagct tacggctgtt agagacaact gtaagaagac caagtccgat    480

gagaaactgt ccatttccga tgtctacgga actcattcca ctccacctgt ttctgtgatt    540

taaatttcta gttattgggt tttaatgggc ctggacccac atttcccttt tacccttatt    600

actgtgatgt gaaatttatc aggggtaaga atgacatt                           638
```

```
<210> SEQ ID NO 88
<211> LENGTH: 717
<212> TYPE: DNA
<213> ORGANISM: Artificial
<220> FEATURE:
<223> OTHER INFORMATION: Synthetic

<400> SEQUENCE: 88

tcattttcta gagaaagaaa caacaagacg tacagaacga gagttcaaga atctgcaatg     60

ggagtggctc gagttaacca attctggttg catcttgtca tcctcttctc catctccgtt    120

gcttccattt ctagcactga actgaattgt gtatacacag cttatgttcg gactgggaca    180

tactgggggt ctggaactga ctcaaaaatt tccttgtctc tttacgatgc caatggccat    240

ggtcttagaa tcaataacct acaagcctgg ggtgggctta tgggcccggg ttatgactac    300

tttgaaatgg accaattgga tatgtttacg ggccgtggtc catgtttgac tggaccaatc    360

tgtaaaatga acttgacttc tgatggatca ggtgagcacc acggatggta ctgtaactac    420

gtggaagtca cgtctacagc agaacacaaa cgatgcagcc aacaggtgtt caccgtggag    480

acgtggctca gtgccggtca gtacccagat gggttgaccg ccattaggaa caactgtaag    540
```

-continued

```
cgtatttcca acgaacaaca accaattcat gattctgatc aatcttatca tgttgtggat    600

gtaatttaat tcgagtttat tggacgttgt atgatttacg aaggccattt aggccaaggc    660

ctgatatgta ctctcacgag tgctacatag ttggaatgga aaagttttct ttaccca       717
```

<210> SEQ ID NO 89
<211> LENGTH: 579
<212> TYPE: DNA
<213> ORGANISM: Artificial
<220> FEATURE:
<223> OTHER INFORMATION: Synthetic

<400> SEQUENCE: 89

```
gatgtcgacg gggaaaggct tagctctaat cctggcattt gctgccatcg ccacctgcat     60

cacctctgct acgaaccaat gcgtatacac tatttatgtg aggacgggaa aggtgataaa    120

agggggggaca gattcaaaca tttcggcacg attctatgat gccaacggat actatatcaa    180

tttggaaaat ttggcagaat ggggtggttt gggaggtcct ggctacaact actttgagag    240

aggcaatttg gatgtgttca caggccttgg gcagtgcctc acggccccca tttgcgcgct    300

caacctgacc tcagacggca ctggagacca acacgggtgg tactgcaact atgtcgaggt    360

cacctccacc gggccccaca tcccttgcag ccaacaccaa ttcaccatcg agcaatggct    420

tgccactgac acctaccctt tcgagctcaa tgccacccgt gacgattgcc tggtcgaggg    480

caaaaccagc gcctccaagg caatttcatc agagtcgagc tagagttcca gctgggcctt    540

ttttggcttc cgtttttgat gaataagcaa gctccttct                           579
```

<210> SEQ ID NO 90
<211> LENGTH: 374
<212> TYPE: DNA
<213> ORGANISM: Artificial
<220> FEATURE:
<223> OTHER INFORMATION: Synthetic

<400> SEQUENCE: 90

```
aaaaaaacaa aatggctcgt cgcgatgttc tcctcccttt cctcctcctt ctcgccaccg     60

tctccgccgt agctttcgcc gaagatgatc cagactgtgt atacacattc tacctcagaa    120

ccggatcgat ctggaaagcc ggaaccgatt cgatcatcag cgcaagaatc tacgataagg    180

acggtgacta catcggaatc aaaaaccttc aagcttgggc tggattaatg ggacctgatt    240

acaattactt cgagaggggt aatctcgaca ttttcagtgg aagagcaccg tgtttaccta    300

gtccgatctg tgccttaaac ctaacctccg atggctccgg cgatcaccat ggttggtacg    360

ttaattacgt tgag                                                      374
```

<210> SEQ ID NO 91
<211> LENGTH: 752
<212> TYPE: DNA
<213> ORGANISM: Artificial
<220> FEATURE:
<223> OTHER INFORMATION: Synthetic

<400> SEQUENCE: 91

```
acggaaaatc ttaaaagaaa gaaagaaatg atgacgaatc gccacttcct cttcgctctt     60

cttttcactt tctttctttc agctgttgct gcagattctt ctgaagagtg tgtatacaca    120

ttgtatgtta aaactggatc aatcataaag ggtggaacag actccaaaat cagcgttaca    180

cttggcgatg ctaaaggaaa atcagtatat attccagatc tagagaaatg gggtttaatg    240
```

-continued

```
ggcccaaatt atgattacta cgaaaggggt aatgtggata tcttcactgg tagaggccaa    300

tgtttaagcc caccaatttg caggcttaat gttacttccg atggatcagg tgaccaccac    360

ggttggtttc ttgattttgt tgagactact tttactgggc cacacaaaac ttgtagccaa    420

tccatattct atgtcgaaca atggttggct tctgatgctc ctccttatga gttatcagtt    480

tctcttgatg gttgtaaaaa gaagactggg cttcgacatg ctcggcgttt tgtcgtgggc    540

cagcccaatg ggtctgcttc agaatagttt ggcccgttga agttcttttt gtaattttgt    600

cgttgagatg attttgatgt gtagattgcc ctgtgttttc ccttctcttt ggttgaaata    660

aatttcttgt ttggggcttc ctttcttgct tgtttagtcg tcatatcttt gacttattgg    720

ctcttttggc atttgcatct tttatgtact ca                                  752
```

<210> SEQ ID NO 92
<211> LENGTH: 398
<212> TYPE: DNA
<213> ORGANISM: Artificial
<220> FEATURE:
<223> OTHER INFORMATION: Synthetic

<400> SEQUENCE: 92

```
ccccgatctc caccaccact ttcccgggga ccgcggcggg aaagggcctt cgagacttgg     60

gaggttggag cgagcaagct cggccatggc gaagctctcc tgccttctca tcgtctcctt    120

cgccgtcgtc gcggcgttgg cggccacgga cgacgacgcg gcggcggcgg ctgaggggat    180

cacggtggcg gaggcgtcgt cggacccgga gaacaagtgc gtgtacacga tatacgtgcg    240

gacggggacg atctggaagg gcgggacgga ctcggtgatc ggcgtgacgc tgctgggcgc    300

cgacggctcc ggggtgcgga tccgcgacct ggagcggtgg ggcggcctca tgggcgacgg    360

ccacgactac tacgagcgcg gcaacctcga catcttca                            398
```

<210> SEQ ID NO 93
<211> LENGTH: 497
<212> TYPE: DNA
<213> ORGANISM: Artificial
<220> FEATURE:
<223> OTHER INFORMATION: Synthetic

<400> SEQUENCE: 93

```
atttttctag agaaagagag ttcaagaaac catgggagta gctcaagtta accaaatatg     60

gttccatttc atgataatcc tcttcttcat ctccatatct tctagttctg catcagaaga    120

tgattgtgtg tacacagctt acgttcgaac tggatcaatc ataaaggctg gaactgactc    180

aaacattatt ttgactctct acgatgccgc tggctatggg ataagaatca agaacttaga    240

ggcatggggt gggcttatgg gcccaggtta caactatttc gaaagaggaa acttggatat    300

attcagtgga cgtggtccat gtttgactgg gccgatctgc aaaatgaatc tgacttctga    360

tggatcaggc ccacatgccg gatggtactg taactacgtc gaagttaccg ttactggagc    420

ccaccaacaa tgcaaccagc agcttttcac cgtggagcag tggctcggca ctgacgtttc    480

gccgtatgag ctgacgg                                                   497
```

<210> SEQ ID NO 94
<211> LENGTH: 648
<212> TYPE: DNA
<213> ORGANISM: Artificial
<220> FEATURE:
<223> OTHER INFORMATION: Synthetic

<400> SEQUENCE: 94

```
gaattcacat ctaaagtcaa caacaagagc ttctcgcttc tcctcgtctc tgttctcctc     60

tcttttgcaa tcctctctca atctgctgat gattgtgtat acacagtata cacaagaaca    120

ggatcaatca tcaaaggagg aacggattca aaaatctcac taagattata cagcaaatac    180

ggtaagtaca tcgagatccc aaatcttgaa tcatggggtg gattaatggg tcctggttac    240

gattatttcg aaagaggtaa tcttgatatc ttcagcggaa gaggttattg tctgggttca    300

ccggtttgtg ccatgaatct gacttccgat ggtactggtt ccggtcacgg atggtatgtg    360

aattatgttg aagttactac taccggtgca catattaatt gtggtcaaca gaattttgaa    420

gtggaagatt ggcttgctct tgatagatct ccttatagtc ttaccgctat caagaataat    480

tgtaatcaga aattatctga tcatgattct cattctgctg atcagtctat gtaaaatttg    540

atctcttgtt tgattcggtg gtggtctagt atgagtgatc ggacggtcgt cattgtgtgt    600

tgtaatgttg aaattatttt cttgaataaa atgattgagt gagtagtg                 648
```

<210> SEQ ID NO 95
<211> LENGTH: 609
<212> TYPE: DNA
<213> ORGANISM: Artificial
<220> FEATURE:
<223> OTHER INFORMATION: Synthetic

<400> SEQUENCE: 95

```
gaattcatgt tctttattgt ttgtttttct taaggcttcc aactctctac atctcttgct     60

ctctcaatga tcaaaaaaat ttggggagaa gagattaaaa gaaaaaaaga aaagaaaaag    120

aaggttggac aagtttccgt tttggttatg agaattggtt ttgaaaatgc ctgctaagag    180

tccaacttcc tgctggcttt ttatgatttt gcgaggtatc aaaaaccaat gtccaagtgt    240

taatcaatga aatcaacaat cacaatattg gatctctaat tgattaaact taacaacgca    300

caaccagtat tgtttcaatt atataaaata taattcggaa aataaataac acagacacca    360

gaattttgtt aacgaggaaa ccgcaaatgc agaaaaacct cgggacctag tccagattac    420

atacacactg tattaagccg ctatagacac tagccttttc caaactaact tcgggctgac    480

ctatagttga accagtacca gtctcccacg gatacaaggt acaattgcac ctctacgcct    540

ctgatcccag caggatgtta tgtacttgat tccctttgca gatctgacca gcgtagtact    600

cacatggaa                                                            609
```

<210> SEQ ID NO 96
<211> LENGTH: 938
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (209)..(209)
<223> OTHER INFORMATION: The residue at this position can be any nucleotide.

<400> SEQUENCE: 96

```
gaattcggag aggtgatcat caatctaggc taccattggg cacataagac cggattgatt     60

gattaggttc cttaggtacc ttggtattta atatcaaaaa cggaacaaag agtttagggt    120

ttttctgtgg gagacagatt gatccttttg atagacttat ctgtgtgata cagatttgtt    180

tattgttaag cctgcgtttg tgtgcgtanc aactcgttgc agtgggtgag atctgcatcg    240

ggattcaagt acgtggtgtc cagccgtttg ggggatccgg aggcgtagag gtataactgt    300
```

```
accttgtatc agtgggagat tgataggggt tcttctatag atcagtccga agttagttgg    360

agtaggctag tatctgtagc ggcttaatac agtgtatgtc taatctggac taggtcccgg    420

gctttttctg catctgcggt ttcctcgtta acaaaatctc tggtgtctgt gttatttctt    480

ttccgcatct ttttagattg aaataataca ggttgtgcgt tggtaacttt aatcagttta    540

tagatccaat cttgttattg ttgatcttgc tgattaacac ttggatattg gtttttgata    600

ccgtccaagt ctatatctct ttggtttgac tagactcgca aacttgtttg tttgagtagt    660

tctcaaatca agagatagag atatcaactc cttgagtcac tatattctag attgatcctg    720

actgtctagt cgtttctcta gtagcgtgat tcggaggttg tcctaatcag attgctaatc    780

gaaaagtttg gtggtgttgt tagagccccg ctttttcaat ccttagaaga agaaagacat    840

tacgcatgcg cagaagcagc gagaagttct aaaggattag caggttgttg cgaaatctcc    900

tttagttgaa tcggaacttc ttggggaact tccacaaa                            938
```

<210> SEQ ID NO 97
<211> LENGTH: 304
<212> TYPE: DNA
<213> ORGANISM: Artificial
<220> FEATURE:
<223> OTHER INFORMATION: Synthetic

<400> SEQUENCE: 97

```
cccacgcgtc cgcaagccgt cgtctccaaa gttccccctc agagacgaaa aaatgaagac     60

cattttgtcc tcggagacta tggacatccc cgacggcgtc gccattaagg taaacgccaa    120

ggtgattgag gtcgaaggtc cacgaggtaa actcactcgt gacttcaagc atctgaatct    180

cgatttccag ttgattaaag accaagtcac tggaaaacgt cagcttaaga ttgattcttg    240

gtttggttct cgtaagacaa gtgcttcgat tagaactgct ttaagccatg ttgataatct    300

catt                                                                 304
```

<210> SEQ ID NO 98
<211> LENGTH: 588
<212> TYPE: DNA
<213> ORGANISM: Artificial
<220> FEATURE:
<223> OTHER INFORMATION: Synthetic

<400> SEQUENCE: 98

```
cccacgcgtc cggccccgac aacccccaag tcacagcagc catgaggtac attcactctc     60

aggagatcct ggaaattcca gagggcgtca aggtcaacat caagacccgt atcgtcaccg    120

ttgagggtcc ccgaggcaag ctcaccaaga acctcggtca cttggctgtc aacttcggtc    180

accccaagaa gaacaccatc tccatcgaga tccaccacgg caaccgtaag aatgtcgcca    240

ctctccgtac cgtccgctcc atcatcgaga acttgatcac cggtgtcacc aagggcttca    300

agtacaagat gcgatacgtc tacgcccatt ttcccatcaa cgtcaacctg gacaagaaca    360

aggagaccgg tctgttcgag gtggagatcc gaaacttcat cggcgagaag atcgtccgac    420

gggttaccat gcacgagggt gtcgatgttg agatctccaa ggcccagaag gatgagctca    480

tcctgaccgg caactcactc gagaacgttt cccagagcgc cgcagatatc cagcagatct    540

gccgggtgcg caacaaggat atccgaaagt tcttggacgg tctgtacg                 588
```

<210> SEQ ID NO 99
<211> LENGTH: 625
<212> TYPE: DNA

<213> ORGANISM: Artificial
<220> FEATURE:
<223> OTHER INFORMATION: Synthetic

<400> SEQUENCE: 99
gggtgcgagg aggaggaggc gggcgcgatg aagacgatct tgtcggccca gacgatggac 60
atccccgagg gggtgaaggt agagatccgg gcgaagcaga tccgggtgac ggggccgcgg 120
ggggtgctgc acaggaattt caagcacctc aacctcgact tccagctgct ggagaatggg 180
cgcaagctca aggtggaggc gtggtttggg tcgcgcaaga ccatcgccgc catccgcacc 240
gccgtgagcc acgtgaagaa cctcatcacc ggcgtcacca agggcttcca gtacaagatg 300
aggtttgtct acgctcactt ccccatcaac gccaacatct ctgccaccaa gcaaaacatc 360
gagatccgga acttcctcgg cgagaagagg gtgagaactg tcgacatgct tccgggtgtg 420
actgtgacca ggacggagaa ggtcaaggac gagcttgttc tcgaggggaa tgacatcgag 480
cttgtgtcga gatcggccgc tctcatcaac cagaaatgcc atgtcaagaa caaggatatc 540
aggaagttct tggatggtat ctacgtgagc gagaagggaa cgatcgctgt ggaggagtag 600
acctgttgcc tgttctgagt ataat 625

<210> SEQ ID NO 100
<211> LENGTH: 515
<212> TYPE: DNA
<213> ORGANISM: Artificial
<220> FEATURE:
<223> OTHER INFORMATION: Synthetic

<400> SEQUENCE: 100
cccccccccg cttccttctt cttccacgcc gggcatcgcc gccgccgccg ccgccgccgg 60
agagggagag agagagagag agatcgagag caagagatga aaacgatctt ggcttcggag 120
acgatggaga tcccgtcggg ggtgacggtg cacgtggcgg cgaaggtggt gacggtggag 180
ggtccccgtg ggaagctgac gcgcaacttc aagcacctga acctggactt ccagctgctg 240
gaggtggagg gggtgaggaa gctgcaggtg gacgcgtggt tcggcacccg ccgcaccatg 300
gccgccatcc gcaccgccat ctcccacgtc cagaacctca tcaccggcgt caccaagggc 360
taccgctaca agatgcgctt cgtctatgcc catttcccca tcaacgcctc catcaccaac 420
tccaacaccg ccatcgagat caggaacttc ctcggcgaga agaaggtgag gaaagtggac 480
atgcttgagg gtgtgacaat tttgcgttct gagaa 515

<210> SEQ ID NO 101
<211> LENGTH: 548
<212> TYPE: DNA
<213> ORGANISM: Artificial
<220> FEATURE:
<223> OTHER INFORMATION: Synthetic

<400> SEQUENCE: 101
gcaatgaagt catccagtcc gacgttctgc tcgatatccc cgagggtgtc accgttgaca 60
tcaaggcccg acgaatcacc gtcaccggcc cccgaggtac cctcaagaag aacctgtctc 120
acatcaacgt tgccttcgag aaggtctccg atgaccagat caagatcacc atcttcgatg 180
gtgaccgaaa gcacgtcgct gctctgcgaa ccgtcaagac cctcatcaac aacatgatca 240
ccggtgtcac ccgaggttac aagtacaaga tgcgatacgt ctacgcccat ttccccatca 300
acgtcaacct cattaaggac ggttccgtcg ttgagatccg aaacttcctc ggtgagaagc 360
gagtccgaga agtccccatc cacgagggct gcagcgctga gatctctacc aaccagaagg 420

```
atgagatctg catcatcggt aactccatcg agaacgtctc tcagacctgt gctgacatcc    480

agcagatctg gcgagtccga cacaaggata tccgaaagtt ccttgatggt atctacgttt    540

ccgagaat                                                             548
```

<210> SEQ ID NO 102
<211> LENGTH: 720
<212> TYPE: DNA
<213> ORGANISM: Artificial
<220> FEATURE:
<223> OTHER INFORMATION: Synthetic

<400> SEQUENCE: 102

```
gctgctaggg ttttagcgat cgccattttc acacacacag agggagagcg atagagagaa     60

actaagacaa gatgaagacc attctgtcat cagaaaccat ggatatcccc gacggcgtga    120

gcatcaaggt gaaggcaaag caaatcgaag tagagggacc aaggggcaaa cttgtccgaa    180

acttcaagca tctcaacctc gattttcagc tgatcaagga tgaggaaact ggcaagaaga    240

aactgaagat cgacgcttgg tttggttctc gtaagactac cgctgctatc cgtactgctc    300

ttagccatgt tgagaatctc atcactggtg ttacgaaagg ttaccgctac aagatgcgtt    360

tcgtgtatgc tcactttccc atcaatgcct ccatcaccgg tggtaacaag tccattgaga    420

tccgtaactt ccttggcgag aagagagtta ggaaagtgga catgcttgat ggggttacag    480

ttgttcgatc tgagaaggtg aaggatgagc ttgtattgga tggaaatgac attgagctcg    540

tttctcgctc tgctgccctc atcaatcaaa aatgccatgt gaagaacaag gatatccgaa    600

agtttcttga tggtatctat gtcagtgaga agggcagaat tgcagaagaa gaatgagcag    660

ctgttttaga agtaggcata tcactgatga ttcatatcca gaatgccctt tttacttttc    720
```

<210> SEQ ID NO 103
<211> LENGTH: 968
<212> TYPE: DNA
<213> ORGANISM: Artificial
<220> FEATURE:
<223> OTHER INFORMATION: Synthetic

<400> SEQUENCE: 103

```
gccggtaggc agtagtgagc gcagaagcag ggagagacac aaaaaatgaa gactatactc     60

tcatcagaaa cgatggatat ccccgatggg gtgaaaatca aggtaaaagc aaagcaaata    120

gaagtggagg gaccaagagg aaagctaacc cgcaacttca agcacttgaa tcttgatttt    180

cagctcataa aagatgaaga aactggaaag aaaaagctca agattgatgc ttggtttgga    240

tctcgtaaaa ccacagctgc tattcgcact gctcttagtc acgttgataa tctcataact    300

ggtgtcacaa aagggtaccg ttacaagatg cgttttgttt atgcccattt tcctatcaat    360

gcttctatca ctggtgggaa caaggctatt gagatcagga actttctggg cgagaaaagg    420

gtgaggaaag tcgatatgct tgatggggtt actgttgtga ggtctgagaa agttaaggat    480

gaattggtat tggatggaaa tgacattgag cttgtttctc ggtctgctgc cctcatcaat    540

cagaaatgcc atgtgaagaa caaagatatc cgtaagttcc tggatggtat ctatgtgagt    600

gagaagggaa gaatagttga agaagagtga gttttagcag acttgttgtg gggttgtttg    660

ggatcatgtg ctgatttcgt acgaactcat ttgaagttaa ttcaacaatt ttggttccat    720

ggttttctgg atgaattatc tgttaaagtg taatattatg ttttatgtct tgctcattga    780

gtagagatgg atgttttcgt ttgatggttt gcttattaaa agatcaattt ttatgtcagc    840
```

```
ttttcacctt ataaaaaatg tcagtttttt ccttttaact gctgttgcct tatgcatttt    900

gagatgtatt taacttcctt tttctggggt taggtggatt tgacttatat acagaatcga    960

tgtgtctt                                                              968
```

<210> SEQ ID NO 104
<211> LENGTH: 777
<212> TYPE: DNA
<213> ORGANISM: Artificial
<220> FEATURE:
<223> OTHER INFORMATION: Synthetic

<400> SEQUENCE: 104

```
tggtatcaac gcagagtggc cattacggcc ggggatcaca actaactttg acatctcaaa     60

ctagcaacct ctcactttcc tcttgataaa ccatggctgc ttctacaatg gctctttctt    120

ccccttcttt tgctggacag gcagtgaaac tctccccatc tgcctcagaa atcactggaa    180

atggaagggt ctccatgaga aagactgtca ccaaacccgt cgcatctagc agcccatggt    240

acggcccaga ccgtgttaag tacttgggcc cattctccgg tgaggcccca agctacttga    300

ccggtgaatt cccaggtgat tacgggtggg atactgctgg actttcagca gatccagaaa    360

catttgccaa gaaccgtgaa ctcgaagtga tccactgcag atgggctatg cttggagctc    420

ttggatgtgt cttccctgag ctcttggctc gtaacggtgt caagtttggt gaagctgtct    480

ggttcaaggc tggatcccaa atctttagtg agggtggact tgactacttg ggcaacccaa    540

gcttggtcca tgcacaaagc atcttggcca tctgggcttg ccaagttatc ttgatgggag    600

ccgttgaggg ttaccgcgtt gctggtgggc ctcttggtga agttgtcgac ccactctacc    660

ctggtggcag ctttgaccca ttaggccttg ctgatgaccc agaggcattt gctgagctca    720

aagtaaagga gatcaagaat ggtagacttg ccatgttctc tatgttcgga ttctttg       777
```

<210> SEQ ID NO 105
<211> LENGTH: 842
<212> TYPE: DNA
<213> ORGANISM: Artificial
<220> FEATURE:
<223> OTHER INFORMATION: Synthetic

<400> SEQUENCE: 105

```
tttctttatc acttcagcca tcagaaaact cttcattctc cttattaagc catggctgct     60

tctacaatgg ctctttcctc ttcttttgcc gggaaggcac taaaactctc gccatcttcc    120

tctgaaatca ccggaaatgg gaaagttacc atgaggaaga ctgctagcaa gcccaagcct    180

gtatcttctg gcagcccatg gtacggtcct gaccgtgtca agtacttggg tccattctct    240

ggtgagtccc caagctactt gactggtgag ttccctggtg actacgggtg ggacactgct    300

ggactttcag ctgatccaga aacttttgcc aagaaccgtg agttggaggt gatccactgc    360

agatgggcaa tgcttggagc tcttggttgt gtcttccccg agctcttggc ccgtaacggt    420

gtcaagtttg gtgaggctgt atggttcaag gctggatccc aaatttttag cgagggtgga    480

cttgactact tgggcaaccc aagtttggtc catgctcaaa gcatcttggc catttgggct    540

tgtcaagttg tgttgatggg agccgttgag ggttaccgtg ttgctggtgg gcctcttggg    600

gaggttgttg atccactcta ccccggtggc agcttcgacc cattgggcct cgctgaagac    660

ccagaagctt ttgctgagct caaggtaaaa gagatcaaaa atggtagact tgccatgttc    720

tccatgtttg gattctttgt tcaggctatc gtaactggaa agggcccatt ggagaacctt    780

gccgatcacc ttgcagaccc agttaataac aacgcttggg cctacgcaac aaactttgtc    840
```

cc 842

<210> SEQ ID NO 106
<211> LENGTH: 583
<212> TYPE: DNA
<213> ORGANISM: Artificial
<220> FEATURE:
<223> OTHER INFORMATION: Synthetic

<400> SEQUENCE: 106

```
ctgcattcaa gagtttttca tcttctttct ataatggcag cttctacaat ggctctctct     60
tcctcttcat ttgccggaaa ggcggtaaaa ctctcatcat cttcctctga aatcattgga    120
aatgggaaag ttatcatgag gaaggcggtt accaaggcta agccagtctc ttcaggcagc    180
ccatggtacg gtcctgaccg tgtcaagtac ttaggaccat tctccggtga gtctccgagc    240
tacttgactg gtgaatttcc tggtgactat ggatgggaca ctgctggact ttcagctgat    300
ccagaaactt ttgccaagaa ccgagagttg gaggtgattc actgtagatg ggctatgctt    360
ggagctcttg gttgcgtctt ccctgagctc ttggcacgta atggtgtcaa gttcggtgaa    420
gctgtatggt tcaaggctgg atcccaaatt ttcagcgagg gtggacttga ctacttgggt    480
aacccaagtt tggtccacgc acaaagcatc ttagccatct gggcttgcca agttgtgttg    540
atgggagccg ttgagggtta ccgtgttgct ggtggacctc ttg                      583
```

<210> SEQ ID NO 107
<211> LENGTH: 758
<212> TYPE: DNA
<213> ORGANISM: Artificial
<220> FEATURE:
<223> OTHER INFORMATION: Synthetic

<400> SEQUENCE: 107

```
ccccccgaca gctaacttct ctattacttc agccatcaaa aaacacttat ttttccttat     60
taaaccatgg ctgcttctac aatggctctc tcttccactt cttttgccgg aaaggcagta    120
aaactctcac catcttcctc tgaaatcacc ggaaatggga aagttatcat gaggaagact    180
gctagcaagc ccaagcctgt ctcttctggc agcccatggt acggtcctga ccgtgtcaaa    240
tatttgggtc cattctccgg tgaatctcca agttacttaa ctggtgagtt tcctggtgac    300
tatggatggg ataccgctgg actttcagct gatccagaaa cttttgccaa gaatcgtgag    360
ttggaggtaa tccactgcag atgggctatg cttggagctc ttggttgtgt cttccctgag    420
ctcttggctc gtaacggtgt caagttcggt gaagctgtat ggttcaaggc tggatcccag    480
attttcagcg agggtggtct tgactacttg ggcaacccaa gtttggtcca tgctcaaagc    540
atcttggcta tttgggcttg ccaagttatt ttgatgggag ctgttgaagg ttaccgtgtt    600
gccggtggac ctcttggcga ggttgttgat ccactttacc ctggtggcag tttcgacccg    660
ttaggccttg ctgaagaccc agaagctttt gctgagctaa aggtaaagga gatcaagaac    720
ggcagacttg ccatgttttc catgtttgga ttctttgt                            758
```

<210> SEQ ID NO 108
<211> LENGTH: 854
<212> TYPE: DNA
<213> ORGANISM: Artificial
<220> FEATURE:
<223> OTHER INFORMATION: Synthetic

<400> SEQUENCE: 108

```
ctgtgacagt gtgtgtagtg tgcttaattt tgtaaatagt gttagtgctt cttgatcttg      60

cggatgtcga ctccattcag ccgcctcaag aggggtaaca aagaagataa aagaaaattg     120

ttcaaatggc tacttctgca attcaacaat ctgcaattgc tggacagaca gctcttaagt     180

cacagaacga gctcattagg aagattggta gctttaatgg tggacgtgcc actatgcgac     240

gtacggttag aagtgcccca cagagcattt ggtatggaga agacagacca aagtacttgg     300

gaccattctc cgagcaaact ccttcttact tgactggtga gtttccaggt gattatgggt     360

gggacaccgc tggactttca gctgaccctg aaacattcgc caggaaccgt gagcttgagg     420

tgatccattg ccgttgggcc atgcttggtg ctttgggttg tgtcttccct gaaatccttt     480

ccaagaatgg tgttaaattt ggtgaggcag tttggttcaa ggctggatct caaatcttct     540

cagaaggcgg tcttgactac cttggtaacc caaaccttat tcatgcacag agcattcttg     600

ctatttgggc atcccaagtt gtgctcatgg gtttaattga aggatacaga gttggtggag     660

gcccacttgg tgaaggtctt gacaagatct atccgggagg agcttttgac ccactagggc     720

tcgctgatga tcccgaggca tttgctgaat tgaaggtgaa ggaaataaag aacggccgat     780

tggctatgtt ctcaatgttt ggatttttcg ttcaagccat tgtcacagga aagggaccaa     840

ttgaaaacct tttc                                                       854
```

```
<210> SEQ ID NO 109
<211> LENGTH: 779
<212> TYPE: DNA
<213> ORGANISM: Artificial
<220> FEATURE:
<223> OTHER INFORMATION: Synthetic

<400> SEQUENCE: 109

gaattcgcag tctttagttt tctcatccat ccatatatca gttagccatg gcagcttcta      60

caatggctct atcttcaccc gcattggctg gtaaggcact tgttccttcc agctctgaag     120

ttttcggtga aggcagaatc tccatgagaa aaaccgttgc aaagccaaaa accgtttcat     180

ctagcccatg gtacggacct gaccgtgtta agtacttggg accattctct ggtgaatctc     240

catcgtactt aaccggtgag tttgccggtg attacggttg ggacactgcc gggctttctg     300

ctgacccaga aaccttcgcc aagaaccgtg agctggaggt cattcactgc agatgggcta     360

tgttgggagc tcttggatgt gtcttccccg aattgttgtc tcgcaatggt gttaaatttg     420

gtgaagccgt ttggttcaag gctggttcac aaattttcag tgaaggtgga ttggactact     480

tgggtaactc aagcttggtt catgctcaga gcatccttgc catttgggca acacaagtta     540

tcttgatggg tgctgttgaa ggttacagag ttggaggagg accattaggt gaggtggagg     600

acccacttta ccctggtgga agcttcgacc cattaggctt agctgatgat ccagaagctt     660

ttgctgaatt gaaggtgaag gaaattaaga acggcagatt ggctatgttc tccatgtttg     720

gattctttgt tcaagcaatc gtgaccggga aaggtccttt ggaaaatttg gctgaccac      779
```

```
<210> SEQ ID NO 110
<211> LENGTH: 610
<212> TYPE: DNA
<213> ORGANISM: Artificial
<220> FEATURE:
<223> OTHER INFORMATION: Synthetic

<400> SEQUENCE: 110

gaattcaata gtctttcatt tctaacaaca gaaacagtta ctaatggcaa ccatggctct      60

ttcttctcca tcatttgcag ggaaagccgt aactctgaac tcacaaacag aatttccagt     120
```

-continued

```
caatgttaga ttcagcagca atggcaagat ctcgatgagg aagacatccg caaagaagcc    180

agctgcatct tcaggaagtc catggtacgg tccagaccgt gtcaagtacc tcggtccatt    240

ttctggtgag tctccatcct acttaactgg tgaattcgcc ggtgactatg gctgggatac    300

tgctggacta tcagctgatc cggagacctt tgcaaagaac cgcgaacttg aggtgatcca    360

ttcaaggtgg gctatgcttg gcgctttggg atgtgtcttc cctgaactcc tctctagaaa    420

tggagtcaaa ttcggcgaag cagtttggtt caaagctgga tctcagatct tcagtgaagg    480

aggactagac tatttgggta actctagctt ggttcatgca caaagcatct tagctatttg    540

ggccacacag gtcatcctta tgggcgctgt tgagggttac agagttgccg gtggtccact    600

tggtgaggtc                                                           610
```

<210> SEQ ID NO 111
<211> LENGTH: 1092
<212> TYPE: DNA
<213> ORGANISM: Artificial
<220> FEATURE:
<223> OTHER INFORMATION: Synthetic

<400> SEQUENCE: 111

```
gaattcaact accatcttca gttatctttc attttcaata caaaagatac ataagaatgg     60

caaccatggc tctctcttct ccatcatttg caggcaaagc tgtgactcta aaccctcaaa    120

cagaattccc aaccaatgta agatctggca gcaacagcaa gatctcgatg aggaagacat    180

ccgcaaagaa gcctgcagct tcttctggaa gtccatggta tggtccagac cgagtcaagt    240

acctcggtcc cttctctggt gagtctcctt cttacctaac tggtgaattc gctggtgact    300

atggctggga cactgctgga ctatcagctg atccagagac ctttgccaag aaccgtgaac    360

ttgaggtgat ccattcaagg tgggcgatgc tcggcgcttt gggctgtgtc ttccccgaac    420

tcctctctag aaatggagtc aaattcggcg aagcagtttg gttcaaagct ggatctcaga    480

ttttcagtga aggaggacta gactatttgg gaaattccag cttggttcat gcacagagca    540

tcttagctat ttgggccaca caggtcatcc ttatgggagc tgttgagggc tacagagttg    600

ccggtggtcc actaggtgag atcgtcgatc cactttaccc aggaggcagc ttcgatccat    660

taggccttgc agaggaccca gaggcattta ttgaggtaaa ggtaaaggta gttcaaaatg    720

gtcgactcgc tatgttctct agggttgggt tctttgttca ggctagtgtg acaggaaaag    780

gtcctttaga gaacctcggt gaccaccttg cggacccagt gaacaacaat gcttggtcat    840

atgataccaa cttcgctccc gggaagtgag aatagacgta ccaaaggaaa aatgctcttg    900

ggttttttac tttttccagt gatatcctct gtacatccat ttagattgca aaattgtgta    960

gcatgtctga gttttgtctg aatagcactt ctgtataagg tgtaccttgt aaaatgcatg   1020

gtgacttgga tataatcaat ctaatagaat ccatttttgc gaaaatttac cgacaaagtc   1080

caaaaaaaaa aa                                                       1092
```

<210> SEQ ID NO 112
<211> LENGTH: 818
<212> TYPE: DNA
<213> ORGANISM: Artificial
<220> FEATURE:
<223> OTHER INFORMATION: Synthetic

<400> SEQUENCE: 112

```
gaattcacta gatcttcagc agtcttgtta ttttctcttt aacaaaacat ataaatggca     60
```

```
tccatgtctc tctcatcccc atcatttgca ggcacagctg taactttgaa cgcacaatcg    120

aaattcccaa ccaatgttag atccagcagc aatggaatga ttgtgatgag gaagacatca    180

gcaaagaagc ctgctgcttc ttcaggaagt ccatggtacg gtccggaccg tgtcaagtac    240

cttggaccct tctctggtga gtctccatca tacctaactg gtgaattccc tggtgactat    300

ggctgggata ctgctggact atctgcagac ccagagacct ttgccaagaa cagggaattg    360

gaagtgattc attccaggtg ggctatgctt ggcgctttgg gatgtgtttt ccctgaactt    420

ctctctagaa atggagttaa ttttggagaa gcagtctggt tcaaagctgg ttctcagatt    480

ttcagtgaag gcggacttga ctacttggga aactccagcc tggttcatgc acagagcatc    540

ttagctattt gggccactca agttatcctt atgggagctg ttgagggata cagagttgct    600

ggtggtccac taggtgagat cgtcgaccca ctttacccag gtggtagctt tgatcccttg    660

ggacttgcag aggacccaga ggcatttgct gagctgaagg taaaggaact taagaacggg    720

agacttgcta tgttctccat gttcggattc ttcgttcagg ctattgttac cggcaaaggt    780

cctctagaga atcttgcaga tcacctttct gaccctgt                            818
```

<210> SEQ ID NO 113
<211> LENGTH: 763
<212> TYPE: DNA
<213> ORGANISM: Artificial
<220> FEATURE:
<223> OTHER INFORMATION: Synthetic

<400> SEQUENCE: 113

```
cgtccgaaaa ttctttctgt gtgtagtagc tgcattttaa agtatttctt tttatttcta     60

caatggcagc tgctacaatg gctctctctt cctctacttt tgttggaaag gcagtgaaac    120

tctcaccatt ttcctctgaa atcactggaa atgggaaagt taccatgagg aagacggcta    180

gcaaggccaa gccagtttct tctggtagcc catggtacgg tcctgaccgt gtcaagtact    240

tgggaccatt ttctggtgag tccccaagtt acttgactgg tgaatttccc ggtgattatg    300

ggtgggacac tgccggactt tcagctgatc cagaaacttt tgctaagaac cgtgagttgg    360

aggtgatcca ctgtagatgg gctatgcttg gagctcttgg ttgtgtcttc cctgagctct    420

tggcccgtaa cggtgtcaaa ttcggtgaag ctgtatggtt taaggctgga tcccaaattt    480

ttagtgaggg tggacttgac tacttgggca atccaagttt ggtccatgca caaagcatct    540

tggccatttg ggcttgtcaa gtcatgttga tgggagctgt tgagggttac cgcattgctg    600

gtgggcctct tggtgaagtt gttgacccac tttaccccgg tggcagcttc gacccattag    660

gtcttgctga agacccagag gcttttgctg agctcaaggt aaaagagatc aagaatggca    720

gacttgctat gttctccatg tttggattct tcgttcaagc tat                      763
```

<210> SEQ ID NO 114
<211> LENGTH: 649
<212> TYPE: DNA
<213> ORGANISM: Artificial
<220> FEATURE:
<223> OTHER INFORMATION: Synthetic

<400> SEQUENCE: 114

```
gaattctaga gtgctcaaag caagcccaag ctctggggac attagcatgg gataacatcg     60

taggatttcg gtcctattgc gttggccttc gggatcggag taatgattaa cagggacagt    120

cgggggcatt cgtatttcat agtcagaggt gaaattcttg gatttatgaa agacgaacaa    180

ctgcgaaagc atttgccaag gatgttttca ttaatcaaga acgaaagttg gggctcgaa     240
```

gacgatcaga taccgtccta gtctcaacca taaacgatgc cgaccgtgtt aagtacttag 300
gtccattttc cggcgagtct ccatcatacc tcaccggtga attccctggt gattacggtt 360
gggacaccgc agggctctca gctgaccctg aaaccttctc caaaaaccgt gagctagaag 420
ttattcactg cagatgggca atgcttggag ctcttggttg tgtcttccct gaattacttt 480
cccgcaacgg tgtcaaattc ggcgaagccg tatggttcaa agctggttct cagatcttca 540
gtgagggagg attggactac ttgggtaact caagtttggt tcatgctcag agtattctag 600
caatctgggc tacacaggtt atattgatgg gagcagttga gggttaccg 649

<210> SEQ ID NO 115
<211> LENGTH: 675
<212> TYPE: DNA
<213> ORGANISM: Artificial
<220> FEATURE:
<223> OTHER INFORMATION: Synthetic

<400> SEQUENCE: 115
gaattcaacc ttctcatact tcttcctact gcaacgcaaa acatttcgca atggctgctt 60
caactatggc tctctcttct ccctctcttg ctgggaaggc agtgaagctt tcaccagatg 120
tcattggtga aggaaggatc actatgctct tccaaaagaa gacagcgcca aagacagcaa 180
agccaaccaa atctgtatcc tccggcagcc catggtacgg tgccgaccgt gttaagtact 240
tgggtccatt ctccggtgag tctccatctt acctcactgg tgaattccca ggtgattacg 300
gttgggacac agctgggctt tcagctgacc ctgaagcctt ctccaagaac cgtgagctag 360
aagtcattca ctgcagatgg gcaatgcttg gagctcttgg ttgtgtcttc cctgaattgc 420
tttcccgtaa cggtgttaaa ttcggcgaag ctgtatggtt caaagtcggt tcacagatat 480
tcagcgaagg tggattggac tacttgggta actcaagctt ggttcatgct cagagtattc 540
tagctatctg ggctacacaa gttatcttga tgggtgcagt tgaaggttac cgtgttgctg 600
gtggtccact aggagaggtt gtcgacccac tttacccagg tggtagcttt gaccctcttg 660
gtcttgctga tgatc 675

<210> SEQ ID NO 116
<211> LENGTH: 800
<212> TYPE: DNA
<213> ORGANISM: Artificial
<220> FEATURE:
<223> OTHER INFORMATION: Synthetic

<400> SEQUENCE: 116
gaattcaaag gcagtgaaag tgacaccatg cgtgggggag ggtgatggaa gaatcaccat 60
gctcttccag aaaaagacag tggcaaagcc tactaaatct tcaaaacccg cagtttcatc 120
taacagccca tggtacggtc ccgacagagt taagtacttg ggtcccttca atggctgctt 180
caacaatggc tctctcatct ccttctcttg ctggaaaggc agtgaaagtg acaccatgcg 240
ttcaagaggg tgatggaaga atcaccatgc tcttccagaa aaagacagtg gcaaagccta 300
ctaaatcttc aaaacccgca gtttcatcta acagcccatg gtacggtccc gacagagtta 360
agtacttggg tcccttctca ggcgaggctc catcgtatct taatggtgaa ttcccaggtg 420
attatggccg ggacactgcc gggttttctg cagatccaga aactttcgcc aaaaaccgtg 480
aacttgaagt gattcattgc agatgggcta tgcttggagc tctaggatgc atcttccctg 540
aattgctctc acgcaatgga gttaaattcg gtgaagccgt ttggttcaaa gccggagcac 600

-continued

```
agattttcag cgagggagga ttggactact tgggtaactc aagcttagta catgctcaaa    660

gcattttagc tatttgggcg acacaagtta tcctgatggg tgcagtggaa ggttaccgtg    720

tcgccggtgg acctcttggt gagattgtcg acccactgta ccccggtggc agcttcgacc    780

ctcttggact tgctgatgac                                                800
```

<210> SEQ ID NO 117
<211> LENGTH: 632
<212> TYPE: DNA
<213> ORGANISM: Artificial
<220> FEATURE:
<223> OTHER INFORMATION: Synthetic

<400> SEQUENCE: 117

```
gaattcatct tcaataaact tttatttcta acaaaaaaaa catattaatg gcaaccatgg     60

ctctatcttc tccatcattt gcagggaaag ccgtgactgt gaacccacaa acagaattcc    120

caactaatgt tagatccagc agaaataaca agatctccat gaggaagaca tccgcaaaga    180

agcctgctgc ttcttctgga agtccatggt acggtccaga ccgtgtcaag tacctcggtc    240

cattttctgg tgagtctcct tcttacttaa ccggtgaatt tgctggcgac tatggttggg    300

acacggctgg actatcagct gacccagaga cctttgctaa gaaccgcgaa cttgaggtga    360

tccattcaag gtgggccatg ctcggtgctc taggctgtgt tttccccgaa ctcctctcta    420

gaaacggggt caaattcggt gaagcagttt ggttcaaagc cggatctcag attttcagtg    480

aaggaggact agactatttg ggtaattcca gcttggttca tgcacagagc atcctagcta    540

tttgggccac acaggtcatc cttatgggag ctgttgaggg atacagagtt gctggtggtc    600

cacttggtga gatcgtccat ccactttacc ca                                  632
```

<210> SEQ ID NO 118
<211> LENGTH: 758
<212> TYPE: DNA
<213> ORGANISM: Artificial
<220> FEATURE:
<223> OTHER INFORMATION: Synthetic

<400> SEQUENCE: 118

```
gaattcaacc atttataatt aattttagca ttggtactta ctcataatcc agtacttagc     60

aatggcagct gctgcaatgg ctctctcttc acccacattc gccggtaagg cacttgttcc    120

ttccagctct gaagtttttg gtgaaggaag aatctccatg agaaaaaccg ccgcaaagcc    180

aaaaaccgtt tcagctagtc catggtacgg tcctgaccgt gttaagtact tgggaccatt    240

ctctggtgag tctccatcat acttaaccgg tgaattcgcc ggtgattacg gttgggacac    300

cgccgggctt tctgctgacc cagaaacatt cgcaaagaac cgtgagctcg aggtcattca    360

ctgcagatgg gctatgttgg gagctcttgg atgtgttttc cctgaactgt tatctcgcaa    420

cggcgttcag tttggcgaag ccgtttggtt caaggccggt tcacaaattt tcagtgaagg    480

tggattggac tacttgggta acccaagttt ggttcatgct cagagcatcc ttgccatttg    540

ggcaacacaa gttatcttga tgggagcagt tgaaggttac agagttgcag gaggaccact    600

aggtgagatc gtcgacccac tttaccccgg tggaagcttc gacccattag gcttagctga    660

tgacccagaa gctttcgctg aattgaaggt gaaagagatc aagaacggga gattggctat    720

gttctccatg tttggattct ttgttcaagc aatcgtca                            758
```

<210> SEQ ID NO 119
<211> LENGTH: 798

<212> TYPE: DNA
<213> ORGANISM: Artificial
<220> FEATURE:
<223> OTHER INFORMATION: Synthetic

<400> SEQUENCE: 119
catttatata cagttgatgc gggctcatta aactcaagcc ataaatcaaa tattttttct 60
gtatagtagc tgcattttca agagcatttc actttatttc tacaacaatg gcagctacta 120
caatggttct ttcttcctct tcttttgtgg gaaaggcggt gaaactctca ccatcttcct 180
ctgagatcac cggaaatgga aaagttacca tgaggaagac agttaccaag gcgaagccag 240
tctcttctgg cagcccatgg tatggtcctg atcgtgtcaa gtatttgggc ccattctccg 300
gtgagtcccc aagttacttg actggtgagt tccctggtga ttatgggtgg gacactgctg 360
gactttcagc tgatcccgaa acttttgcaa agaatcgtga gctagaggtg atccactgca 420
gatgggccat gcttggagct cttggttgtg tcttccctga gctcttggcc cgtaatggtg 480
tcaaattcgg tgaggctgta tggttcaagg ctggatctca aatttttagc gagggtggac 540
ttgattactt gggcaaccca agtttggtcc atgcacaaag tatcttggcc atctgggctt 600
gccaagtcgt gttgatggga gctgttgagg gttatcgtgt tgctggtggg cctcttggtg 660
aggttgttga cccactctac cctggtggta gctttgaccc attaggtctt gctgatgatc 720
cagaggcttt tgctgagctc aaggtgaagg agatcaagaa cggtagactt gccatgttct 780
caatgtttgg attcttcg 798

<210> SEQ ID NO 120
<211> LENGTH: 572
<212> TYPE: DNA
<213> ORGANISM: Artificial
<220> FEATURE:
<223> OTHER INFORMATION: Synthetic

<400> SEQUENCE: 120
aagagtttct catctacttt ctataatggc agctgctaca atggctctct cttcctcttc 60
atttgccgga aaggcggtaa aactctcacc atcttcctct aaaatcactg gaaatggaaa 120
agttaccatg aggaagacgg ttaccaaggc caagcctgtt tctgctggta gcccgtggta 180
tggtcctgac cgtgtcaagt acttggtacc attctctggt gagtctccca gctatttgac 240
tggtgagttt cctggtgact atggatggga cactgctgga ctttcagccg atcctgaaac 300
tttcgccaaa aaccgtgagc tagaggttat ccactgcaga tgggcgatgc ttggagctct 360
tggttgcgtc ttccccgagc tcttggcacg tagcggtgtc aaattcggtg aagctgtatg 420
gttcaaggct ggatcccaaa ttttcagcga gggtggactt gactacttgg gcaacccaag 480
tttggttcac gcacaaagca tcttagccat atgggcttgc caagttgtgt tgatgggagc 540
tgttgagggt tatcgtgttg ctggtgggcc tc 572

<210> SEQ ID NO 121
<211> LENGTH: 932
<212> TYPE: DNA
<213> ORGANISM: Artificial
<220> FEATURE:
<223> OTHER INFORMATION: Synthetic

<400> SEQUENCE: 121
tggtatcaac gcagagtggc cattcggccg gggaacagaa aagaaaaaaa gaagcttctt 60
tagctcacca attaaaaaaa tggctacttc tgcaattcaa cagtctgcat ttgttggccg 120

```
gacagtggct aaatcacaaa atgagcttgt taggaaaatt ggcagctttg gcggaggccg    180

tgctaccatg agacgtactg ttaaaagcgc tcctcaaagc atctggtatg gagaagaccg    240

tccaaaatat ttgggcccat tctctgagca aactccatct taccttactg gtgaatttcc    300

cggtgattac gggtgggata ctgctggact ctcagctgac ccagaaacat ttgccaaaaa    360

ccgtgaactt gaggtgatcc attgccgttg ggccatgctt ggtgctttgg gttgtgtctt    420

ccctgaaatt ctatcaaaga acggtgttca attcggtgaa gcagtttggt tcaaggcagg    480

agcccaaatc tttttagaag gtggacttga ctaccttggc aacccaaacc tcgtgcatgc    540

ccagagcatc ctcgccattt gggcttgcca agttgtccta atgggcttga ttgaaggata    600

cagagttggt ggaggcccac ttggtgaagg tcttgacaag atctatccag gaggtgcctt    660

cgacccactt ggcctagctg atgatcccga ggcttttgct gagttgaagg ttaaggaaat    720

caagaatgga cgattggcta tgttttcaat gttcggattc tttgttcagg ctattgttac    780

aggaaaaggc ccaatcgaga acctttacga ccacattaat gacccagtag ccaacaatgc    840

ttgggctttt gctaccaact ttgtacccgg aaagtgaaat gttttgtctg tgttatatgt    900

aaaaatttgg gctaatgaag ttttctgctt gt                                  932
```

<210> SEQ ID NO 122
<211> LENGTH: 690
<212> TYPE: DNA
<213> ORGANISM: Artificial
<220> FEATURE:
<223> OTHER INFORMATION: Synthetic

<400> SEQUENCE: 122

```
tcgcgatcta gaactcttat taactaaaga gccttttact tgcgccacac tctcaccgca     60

atggccgcct cgacaatggc tctctcctct cctgctttga ccggaaaggc cgttaagcta    120

tccccggcgg cctccgaagt atttggaacc ggccgaatca ccatgcgcaa agcctccaag    180

cccaccggtc catccggcag cccatggtac ggatccgacc gagtcaagta cttgggtcca    240

ttctccggtg agcctccgag ctacctcact ggagagttcc ccggtgatta cgggtgggac    300

actgccggtc tatccgccga tcccgagacc ttcgctagga accgtgagct agaagttatc    360

cacagcagat gggccatgct cggagcccta ggctgcgttt tccctgagct attggctagg    420

aacggagtga agttcggaga agcggtttgg ttcaaggctg gttcacagat cttcagcgac    480

ggaggattgg actacttggg caacccgagc ttggtccacg ctcagagcat cttagccatt    540

tgggctactc aagttatcct catgggagct gttgagggct acagagtcgc cggagatggt    600

ccattgggag aagcagagga cttgctttac ccaggtggga gcttcgaccc attgggcctc    660

gctactgacc ccgaggcttt cgcggagttg                                     690
```

<210> SEQ ID NO 123
<211> LENGTH: 666
<212> TYPE: DNA
<213> ORGANISM: Artificial
<220> FEATURE:
<223> OTHER INFORMATION: Synthetic

<400> SEQUENCE: 123

```
gcacacacac cccagcagca gcagcagcag cagctgagct tgaagcagca gagcgaggta     60

gacatggccg ccgccaccat ggccctctcg tccccggcgc tggccggcaa ggccgccgcg    120

aaggtgttcg gcgaggggcg catcaccatg cgcaagtcgg cggcgaagcc caagcccgcc    180

gcgtcgggga gcccgtggta cggcgccgac cgcgtgctct acctcggccc gctctccggc    240
```

-continued

```
gagccgccga gctacctgac cggcgagttc cccggcgact acgggtggga caccgcgggg    300

ctctccgccg acccggagac gttcgccaag aaccgggagc tggaggtgat ccactccagg    360

tgggcgatgc tcggcgcgct gggctgcgtg ttcccggagc tcctcgcccg caacggcgtc    420

aagttcggcg aggcggtgtg gttcaaggcg gggtcgcaga tcttcagcga gggcgggctc    480

gactacctcg gcaacccgag cctgatccac gcgcagagca tcctcgccat ctgggcggtc    540

caggtggtgc tcatgggcgc cgtcgagggg taccgcatcg ccggcgggcc gctcggcgag    600

gtcgtcgacc cgctctaccc cggcggcagc ttcgacccgc tcgggctcgc cgacgacccg    660

gaggcc                                                               666
```

<210> SEQ ID NO 124
<211> LENGTH: 169
<212> TYPE: DNA
<213> ORGANISM: Artificial
<220> FEATURE:
<223> OTHER INFORMATION: Synthetic

<400> SEQUENCE: 124

```
gaattcacca acttcgctcc cgggaagtga gagtatttgt aacagtgaac taagacgttt     60

gctctcccat caatggaaaa atggtgttgg tttcctactt tttcattaag atcctctgta    120

catatttacc gatccgtttc ctcagtaata gaatccattt ttttttttg                169
```

<210> SEQ ID NO 125
<211> LENGTH: 603
<212> TYPE: DNA
<213> ORGANISM: Artificial
<220> FEATURE:
<223> OTHER INFORMATION: Synthetic

<400> SEQUENCE: 125

```
gaattcataa cttgttttac gtaaatcaac cgtgttttta gtttgattaa agaataagta     60

agagatagaa atatattaac acctaaatgg aacagaatgc aagtgtaaat tataaaattg    120

atatttggtt acggatttta ttacgggcgt ctgtgaaaaa tggcgcggcc attagtgaag    180

ttggctttat tacattgttg gaaaaatgac ttttgtctct cttgttgaga atttacatga    240

cagacgaatt atcgttggat ttagaatata tgtaatacat tgaatctctt gccgcaggaa    300

actccacagc atggaaaaca tcatgagcaa ccagaaccgg ttttagattc tgagaagaaa    360

ttggacagtg caaaactgaa tgaggagctc ccaacagcca atccacattc ggggagtcat    420

gcatcctctg aaaagctttc tcagaagact agtaagacgc agaaaaggtt atacgtagca    480

aatgtgcagc aggcattgca actttcagct gcgcaaccga ggaagacaag gtctgtcgcg    540

ttgagaatgt cacaatctga tacattgaat gcagagacac cgccatcaaa aaagttgaag    600

aaa                                                                  603
```

<210> SEQ ID NO 126
<211> LENGTH: 699
<212> TYPE: DNA
<213> ORGANISM: Artificial
<220> FEATURE:
<223> OTHER INFORMATION: Synthetic

<400> SEQUENCE: 126

```
gaattcagca ccaaagcata ctgaatttca gtcgttctag tgcatgtgga ggacattttt     60

caggtaagaa aactgccctg aaagttttac aatgtggttt ttactggcca acacttttca    120
```

-continued

```
aagatgcata cttgttttgc aaagcatgtg aaagatgcca aaaggtagga agaaattctc    180

gacatgacat gatgccattg aatcctattt tgattgtcga aatttttgat gtatggggca    240

tagactttat gggcccattt ccttcttctt ttggttatca atacatattg gttgctgttg    300

actatgtttc taaatggatt gaagctgttg cttgtaggga taatgatagt aaggttgtta    360

ctaaatttct gaaagagaac attttgtctc gctttggcac ccctagagct attattagtg    420

atagaggtac tcatttttgt aacaaatcct ttgaaaagct aatgaaatcg tatggcataa    480

ctcacaaagt agctacagca tatcatcctc aaaccagtgg tcaagtagaa gtgtccaacc    540

gagagataaa aggtatattg cataagactg taaatccaga tcgcaaggat tggtcacttc    600

gactcaatga tgcattgtgg gcttatagga cagctttcaa aactccgtta ggtatgtctc    660

cttataggct tgtatttgga aaaccatgtc atctgcctg                           699


<210> SEQ ID NO 127
<211> LENGTH: 606
<212> TYPE: DNA
<213> ORGANISM: Artificial
<220> FEATURE:
<223> OTHER INFORMATION: Synthetic

<400> SEQUENCE: 127

gaattcaagg ggtagatttt ccatatttta ttctgaatgc accaagcaac atctctatgt     60

tttttccttc aaactgtttc ccgttatctg ataccaattg tgctgggatt ccaaatctgc    120

aaattatatt ttcaaagatg aaagtgaaaa catccttatc gcggatgtgc tgaacagctt    180

tcacttctgc ccatttggtg aaatggtctg tcgcaactat caagtatctc ttttgtcttg    240

tacatgataa gaaaggtcca caatatctag cccccacttt ccaaagggcc aacaacttgc    300

tgatgaggtt aaggacgctc ctggggcatg tattcttttg ccatggcgtt gacaatcttt    360

acatctttgc gacagctttt ttggatcatc atgcatatat ggccaaaaat acccttgcgt    420

cttagctctg tgggataatg atctccctgc actgtgattg ccggcttctc cgctatgcat    480

catctgtaat atattttgtc tttcttcttt tgataaacat ctaatagatg gtccactaaa    540

ggtttttcga tataatattc cttctcttaa ttcttagtta gtagctttac ctcttaactt    600

atgggc                                                                606


<210> SEQ ID NO 128
<211> LENGTH: 1007
<212> TYPE: DNA
<213> ORGANISM: Artificial
<220> FEATURE:
<223> OTHER INFORMATION: Synthetic

<400> SEQUENCE: 128

ggcagatatg gctcatatta gtgggttagt tgcagctgga gtcatcccat caccatttga     60

ttatgcagat gttgtgacta ccacaaccca caaatccctt cgcgggcctc gtggtgccat    120

gattttcttc cggaagggtg tgaaggaggt taacaagcaa ggaaaggagg tgttgtacga    180

ctatgaagat aaaattaacc aggcagtctt tcctggactt caaggtggtc ctcacaatca    240

tacaattact ggcttggcag ttgctttgaa acaggcaatg actccagaat acaaagctta    300

ccaagagcaa tgccttagca actgctcaaa atttgcccag gcgttagcgg gaatgggtta    360

tgaacttgtt tctggtggaa cagagaatca cttggtcttg gtgaacttga aaaacaaggg    420

tattgatggt tctagggttg aaaaagtttt ggaagcggta catattgcag ccaataagaa    480

cactgttcct ggagatgtat ctgccatggt ccctggtggc atcagaatgg ggactcctgc    540
```

```
actcacatca aggggattta ttgaggaaga ttttgtgaaa gttgctgaat tctttgatgc    600

tgctgtgaag atagcagtga aaataaaggg tgaagctcaa ggaacaaagt tgaaagactt    660

tgtgacaaca ctgcagtcta gtgcttccat ccagtcggag attgcaaaac tccgccatgg    720

tgtggaggag tatgcaaagc agttccctac aattgggttt gagaaggaaa ccatgaagta    780

caaaaaatga gagctcgact gagtgtatac acaaggacca atatccaact tcttgaaggt    840

gtatgggata gactttcaac tgcagtttgc tctcaaggat aggattctca tcttataata    900

atatgtaaaa tccagcagta cttggttcca gactttgcac tttgtatatt aacgagtgta    960

aatcaactga ggtccttgaa agcaataaac tcctcttatc tcagtga                1007
```

<210> SEQ ID NO 129
<211> LENGTH: 607
<212> TYPE: DNA
<213> ORGANISM: Artificial
<220> FEATURE:
<223> OTHER INFORMATION: Synthetic

<400> SEQUENCE: 129

```
ttttttttt ttatattgtt gcattataat tgatcaagtt taataatata catataattc     60

aattcttgaa tgaagaatga aatttgaacc aaatggtact ctcttcatgc ttagaaccct    120

gtagtgtcaa caatatatcc cattcactga ttgaaagcat tcatatattc cctacattaa    180

aaggcagttt gctcccttcc cgtgtccatc tcattcgcct ttgtagatac tccactgcac    240

taccgaagca tatatgccca cttataatag tggagtttat tgcttgtatt tcattgttgt    300

tttgcagaac ccgattgtag ggaattgctt tgcatattcc tcaacgtcat gacggagctg    360

tttaatttca gactgaatgc tagcactgtt ttcaaccgcg gccataaagt ccttcaattt    420

tgcacctttt ttgcattcag ctttggcttt caaggccaaa ttcacagcag catcaaagaa    480

ctctgctact ttagcgaaat cttcctcaag gaatcccctt gaagtgagag caggtgttcc    540

cattcgaatg ccaccaggaa ccatggcaga gacatccccg ggaacagtgt tcttgttagc    600

agcgata                                                             607
```

<210> SEQ ID NO 130
<211> LENGTH: 666
<212> TYPE: DNA
<213> ORGANISM: Artificial
<220> FEATURE:
<223> OTHER INFORMATION: Synthetic

<400> SEQUENCE: 130

```
gaattcggag agagagacac acagtgagag aggtatggca cttgaccttc cacatggtgg     60

gcatctttct catgggtatc agactgacac caaaaaaata tctgctgtat ctatattttt    120

tgagacaatg ccataccgat tggatgagag cactggttac attgattacg accagttgga    180

gaagagcgct acactcttca ggccgaaact gattgttgct ggtgcaagtg cttattcacg    240

attctacgat tatgcacgca ttcgccaggt gtgcgacaag caaaaagcta tattgttggc    300

agatatggct cacatcagtg ggcttgttgc tgctggtgtc atcccatctc catttgagta    360

tgccgatgtg gtgaccacta caacacataa atcccttcgt ggaccacgtg ggcgatgat     420

attttacaga aagggattga aggaagtcaa caaacaaggc aaagagatca tgtatgacta    480

cgaggacaaa attaatcaag ccgtgtttcc tgggcttcaa ggaggtccac ataatcacac    540

aattactgga ttagcagttg cactgaaaca ggcaactacc ccagaataca aggcttatca    600
```

```
agaacaagtt ctcaaaaatt gctcacagtt tgccaaaacc ttgaacgcat tgggatatga    660

ccttgt                                                               666


<210> SEQ ID NO 131
<211> LENGTH: 347
<212> TYPE: DNA
<213> ORGANISM: Artificial
<220> FEATURE:
<223> OTHER INFORMATION: Synthetic

<400> SEQUENCE: 131

cccacgcgtc cggtggagcc atgattttct tcagaaaggg tgttaaggaa attaacaagc     60

aagggaaaga ggttttgtat gattttgaag acaagatcaa ccaagctgtc ttccctggtc    120

ttcaaggtgg tccacacaac cacactatca caggactagc tgttgctttg aaacaggcaa    180

ctacttcaga gtacaaagca taccaagaac aagtcctgag taacagtgca aagtttgctc    240

agactctaat ggagagagga tatgaacttg tttctggtgg aactgacaac catctggttc    300

tagtgaatct aaagcccaag ggaattgatg gatctagagt tgagaaa                  347


<210> SEQ ID NO 132
<211> LENGTH: 689
<212> TYPE: DNA
<213> ORGANISM: Artificial
<220> FEATURE:
<223> OTHER INFORMATION: Synthetic

<400> SEQUENCE: 132

agcgggctcg tggctgctgg tcaacttgct aatcctttcg agtactgtga tgtggttaca     60

accactactc acaagtcttt aagaggtcct cgtggaggaa tgatattttt ccggaaagat    120

ccagttctgg gactggactt ggaaacagct ataaacaatg cagtattccc cggtctgcag    180

ggaggacctc acaatcacac aattgctgga ctggccgtgt gcctgaagca cgcagtaacc    240

gaagaattca agcagtatca aaagcaggtg attgcgaact gtcaagcgct tgcagacaag    300

ctggtggagt tgggattcac gctggtgtct ggcggaaccg aaaatcacct ggtccttgtt    360

gatctgcgtc ctttgggaat tgacggtgcc agaactgaaa aggtgctgga tcgtgcttcc    420

atcacgctca acaagaactc agtaccaggt gacaagagtg cgttagttcc gggaggtgta    480

cgcatcggca cacctgcatt gacaacgaga ggactcaagg aagaggactt cgtcaaagta    540

gcagagttca ttcacgaagg cgtccaaatc gccagacagc tcaaggaaac agtccggcaa    600

gggaaaatga aagagtacgt ccaggcactc gaatctccag actctccagt ccagacgagc    660

atcgccgatc tacggaacag agtcgaagc                                      689


<210> SEQ ID NO 133
<211> LENGTH: 621
<212> TYPE: DNA
<213> ORGANISM: Artificial
<220> FEATURE:
<223> OTHER INFORMATION: Synthetic

<400> SEQUENCE: 133

ccccccccc gctgctcctc tgcgacatgg cgcacatcag cggcctcgtc gccgcgcagg     60

aagctgcaaa tccttttgag tactgtgatg tggttaccac caccacgcac aagtccctcc    120

gaggaccaag agctggcatg atcttctaca ggaagggccc taagcctccc aagaagggcc    180

agcctgaggg tgctgtctat gactacgagg acaagatcaa cttcgcagtg ttcccgtcac    240

tgcaaggtgg tcctcacaac caccagattg cagcccttgc tgttgctctg cagcaaacca    300
```

```
tgacacctgg attcaaggcc tacgcaaagc aggtcaaggc caacgctgtc gccattggca    360

agtatcttat gagcaagggc tacaaaatgg tgactgatgg aactgagaac caccttgttc    420

tctgggatct tcgccctctt ggcttgactg gcaacaaggt tgagaagatg tgtgaccttt    480

gcagcattac acttaacaag aatgctgtct ttggtgacag cagtgcattg gctcctggcg    540

gtgtccgcat tggtactcct gcgatgacat ccaggggtct tgtcgagaag gactttgagc    600

agatcggcga gttcctccac c                                              621
```

<210> SEQ ID NO 134
<211> LENGTH: 581
<212> TYPE: DNA
<213> ORGANISM: Artificial
<220> FEATURE:
<223> OTHER INFORMATION: Synthetic

<400> SEQUENCE: 134

```
gatcttctac cgcaagggcc ctaagccacc aaagaaggga cagcctgagg atgcggtcta     60

tgactttgaa gacaagatta actttgctgt tttcccctcg ctccagggtg gtcctcacaa    120

ccaccaaatt ggtgctcttg ctgttgccct aaaacaggcc gcaactcctg gttttaaggc    180

ttatgctaag caagttaagg ccaatgcagt tgctctcggc aactacctca tgagcaaagg    240

atacaaactc gtaactggtg ggactgagaa ccatcttgtc ctttgggatc ttagacctct    300

tggtttgact ggtaacaagg ttgagaagct ttgtgacctt gccaacatta ctgttaacaa    360

gaatgctgtt tttggtgaca gcagtgcttt ggccccagga ggtgttcgta ttggtactcc    420

tgcaatgaca tcaaggggat tggttgagaa ggacttcgag cagattgccg agttcctcca    480

cagggctgtt accatcacct tgaacatcca gaaggagtac ggaaagcttt tgaaggattt    540

caacaagggg tcttgtcaat aacaaggaaa ttgaagaact c                        581
```

<210> SEQ ID NO 135
<211> LENGTH: 655
<212> TYPE: DNA
<213> ORGANISM: Artificial
<220> FEATURE:
<223> OTHER INFORMATION: Synthetic

<400> SEQUENCE: 135

```
cccccccgct ttattgagaa gaaattgcag actggttact ggagggactg acaatcacat     60

gatactgtgg gatctgagaa atcttgggtt aacaggtaag aattttgaaa aggtttgcga    120

gttgtgtcac atcactctca ataaagtaat ggtcttcgat gataatggaa gtattactcc    180

tggaggtgtg aggataggta cccctgctat gacatcaaga ggctgtatag agaatgattt    240

tgagacgata acagatttcc tcctcaaggc agcacagatt acaaattcag tacagagaga    300

acatggaaag ctcgcaaagg cttttctgaa aggccttgaa aacaacaaag atgttattga    360

gttaagaaca cgcgttgaaa gttttgcatc actgtttgca atgcctggat ttgaagtata    420

atctagctgg aaatctcgtt ctggtggatg aattcttttt ttattcgttg accaaccttt    480

tttgtggatt gggagaacaa tggtgcaccc aactcttggt tagtaattga ctaggcttga    540

tatgattttt aagtgtcaat tgagctcaaa gcctggatta acttatgatt gccacgttgg    600

agtattttgt gtccttattg actgtgaagg ttggctggag gtgccaaaat aaatc         655
```

<210> SEQ ID NO 136
<211> LENGTH: 624
<212> TYPE: DNA

<213> ORGANISM: Artificial
<220> FEATURE:
<223> OTHER INFORMATION: Synthetic

<400> SEQUENCE: 136

```
gtcaaagatt gttttttctt gtttttcaac aacctcatat ctagtaaaat tttcagacaa     60

gtaagacaat caagtaaact atggcaagtt gtaacatggc ttctgctgca tcaaactttt    120

tggtagcaac tcctaatgtt gcctctaaca caagtactcc tcgtagtact atgttgtttt    180

tctcctccaa gaacaatggc agcaccgccc cgagactaat tgtaagggcg gcggaagagg    240

cggcgtcacc ggctgctgcc actacagctg aaccggctga agctccggtc aaagctgcca    300

agccacctcc aattggaccc aagagaggaa ccaaagtgag aattctaagg aaggaatctt    360

actggtacaa gggcacaggt tcagttgtag cttgtgacca ggatccaaat actcgttacc    420

cagttgttgt acgatttaac aaagtgaatt atgctaatgt ttcaaccaac aactatgcat    480

tggacgaaat tgaagaagtg aaatgagagt gtgcagttca ttattagtat atttgtagaa    540

cgacaaggcc ttttggtttc catgtttatt ctctagttat atactggctt tgattgtgaa    600

tgaatgtcta ttatagtttg ttcc                                           624
```

<210> SEQ ID NO 137
<211> LENGTH: 560
<212> TYPE: DNA
<213> ORGANISM: Artificial
<220> FEATURE:
<223> OTHER INFORMATION: Synthetic

<400> SEQUENCE: 137

```
gcacgcgctc ggctttctcg ttgcgaaggt ttaaggagga agagagaaga gggatggcgt     60

cggcagcggc atccggatgt gttggattgg tgtccggggc agcggcggca acgacgagcg    120

catcgtcgtg cagattgttt ggtgggcaat gcagggtccc gtcgtggaat cgaggctcga    180

cttgttcttc ttcttcgtcg agattggtgg tgagagcttc tgatgccgct gcggctccag    240

ctccagcagc acccgagaag aagccagagc caatcggtcc caagcgtgga tctatggtga    300

agatcttgcg gcctgagtcg tattggttcc tgaacacagg caaggtcgtc actgtggatc    360

agacccctgg cgtgctctac ccggttgttg ttcggttcga gaaggtgaat tacgctggaa    420

acaccacaaa caactacgcg ttggacgagg tcgaacaagt atgaagaaag agaagagagg    480

gtgtcgttgt aaaccacata tatcctcgcc ttatctgttg gaaaggattt ctacacttgt    540

acttaacgat ttaaaacaga                                                560
```

<210> SEQ ID NO 138
<211> LENGTH: 549
<212> TYPE: DNA
<213> ORGANISM: Artificial
<220> FEATURE:
<223> OTHER INFORMATION: Synthetic

<400> SEQUENCE: 138

```
aaaagaaaac cagagatggc gatgacgaca gcatctacgg tatttgttct accggccaat     60

gtcacctcgg tcgccggcgc ttcgtcgtcc aggagctccg tgtctttctt gccgatgaga    120

aacgccggtt ctaggctcgt agtcagggca gccgaagatc ctgctccggc ttcctcttct    180

tcaaaagatt ctccggcagc tgccgctgct ccggatggag ctactgccac caaacccaag    240

ccaccaccga ttggtcctaa gagagggtct aaggtcaaga ttctaaggag agaatcctat    300

tggttcaaga acgttggatc agttgttgcc gttgatcagg accctaagac tcgataccg    360
```

```
gttgtggtcc ggttcgcaaa agtcaattac gccaacatat cgaccaacaa ctatgcattg    420
gatgaggtcg aagaagttgc agcttaaatg ggagaattca aaaactctgt gtattctata    480
ccggtttatc cgtttgtaac ttgacccaaa ccgtatgtac cgcaaaagtt taccaattat    540
ttctcctca                                                            549
```

<210> SEQ ID NO 139
<211> LENGTH: 552
<212> TYPE: DNA
<213> ORGANISM: Artificial
<220> FEATURE:
<223> OTHER INFORMATION: Synthetic

<400> SEQUENCE: 139

```
agagaggggg tagcagcagt gttagtggta gagtcagcag tttgtgcgaa gatagccatg     60
gcgtgtgctt ccttgaccgc caccaccacc gccctcgtag ccgccatggc cttgccctcg    120
ctcggctcat cctcccctt ggcctcctcc ttggcccttc cccaaacccg gagtgctcgc    180
atggtcgccc tcaccgtcgt ccgtgcctcc gacgccgctt cccctgtccc cacccccctct    240
gaaaatcctg ccgccgcccc cgctgccgag aagcccaagc ctatcggccc caagcgtggt    300
accaaggtaa agattttacg ccccgagtcg tattggttta acggagtcgg aacagtggtc    360
tctgtggatc agagccccga tacgcggtac ccagctgtgg tgaggtttga aaaggtgaac    420
tacgccggca tctccactaa taactatgct ttggatgaga tagtggaggt ttaatagtat    480
cttcattgtt tcttgtacac tccttttcat tatccatccc ttattggtaa atttcccacc    540
tcatgagttg cc                                                        552
```

<210> SEQ ID NO 140
<211> LENGTH: 600
<212> TYPE: DNA
<213> ORGANISM: Artificial
<220> FEATURE:
<223> OTHER INFORMATION: Synthetic

<400> SEQUENCE: 140

```
tttggaaatc gatcttgaga ttgtaaaaga taaaagatga attgttggtt aactttttgg     60
tacatacggt tttgtttaag attacaaaca gacgaaccgg tttagagata aaccatgtct    120
ctcattttac ttcttccacc tcgtccaatg cgtagttgtt ggtcgatata ttcgcgtaat    180
tcaccttggc gaaccggacc acaaccggat atcgggtctt cgggtcctga tcaacggcca    240
caactgatcc aacgttcttg taccagtatg attctttcct tagaatcttg accttggatc    300
ctctctttgg gccaattgga ggaggtttag ccttagcggc cggaactttc gccggagcag    360
cagcagcggt ggtggaagaa ctatccgacg aggcggttgc cggaggtgta tcttccgccg    420
ctctgactac tagccttgaa ccgaagcttc tcatcggcaa gaaagacaca atggtggtgc    480
tctttgaaga accaccgcct attgccgccg ggacgttggc cgtgagaata aatccggtag    540
ctgctgacgt catcgccatt tgtgtgtgat cgttggaagt tgtgtgagcg gacgcgtggg    600
```

<210> SEQ ID NO 141
<211> LENGTH: 677
<212> TYPE: DNA
<213> ORGANISM: Artificial
<220> FEATURE:
<223> OTHER INFORMATION: Synthetic

<400> SEQUENCE: 141

-continued

```
gcgtcggcga gcaccattaa cgtggcgtcg gccacctcga ggttcctgct ggccggcggg      60
aacggcggca gcggcggcgg cggggccagc cgcgtgagct tcgcggcgaa cagggtcggg     120
aggaggatgg tggtggtccg cgccgaggag gaggccgcgg cgccgccgcc gccgccgccg     180
cccgcggcgg aggagaagcc ggcggaggcc gaggcggccg tggcgaccaa ggagcccgcc     240
gccgccaagc cgcctcccat tggccccaag agaggcacca aggtgaagat cctgaggagg     300
gagtcctact ggtacaacgg cactggctcc gtcgtcaccg ttgatcagga tcccaacact     360
cgctacccgg tggtggttcg gttcgccaag gtgaactacg ccggcgtgtc gaccaacaac     420
tacgccctgg acgagatcca ggaggtcaaa tgattttaat tcggatggat cgtcgtcgag     480
ctggagctgc aaagaatcat cttaaattga tcacggagtg aggagaggat gcatgtcgta     540
catgtggaag aaattaatta agctgcttga tcgagctttg tgtgtattag tgtaatggtg     600
gtggtttctt ctttataatc cgtataatac tatgtaattt gcctgcctct gcttcttcct     660
cgtggacttg ataatcc                                                    677
```

<210> SEQ ID NO 142
<211> LENGTH: 689
<212> TYPE: DNA
<213> ORGANISM: Artificial
<220> FEATURE:
<223> OTHER INFORMATION: Synthetic

<400> SEQUENCE: 142

```
gcgcgccggg accatcattt gaaggtgata gggcaggtgt atacgatttg ggattatcag      60
atgcagctgg tgcagatggt gatggagcag gggaatgttt tggcgaagat ggaggtggag     120
cattagtaga cggtggagga gccggaggac tattaggttc actaggttaa ggtagagaaa     180
caaagttgag gagaacggcc atggcaacct cttctatggc atctgcagca tctggttttg     240
tgttaacatc tagtctttcc tccaccacca ccacaacctc atccaggagc agcatatact     300
tccaaataag aactaacaat aactcaaggc tcgttgttcg tgcagcagat gaagccgcca     360
cccctgcccc agctgctgct gccgctacta aagaagctga agctccagcc gcagtcaaga     420
aacctcctcc aattggcccc aagagaggca ctaaggtgaa gattctcagg aaggaatcct     480
attggtacaa cggcattgga tcagtcgtag ctgttgatca ggacccaaag actcgctacc     540
cagtcgtcgt ccggttcacc aaggtcaact atgctaatgt ctctacaaac aactacgcct     600
tggatgagat tacggaagtg aagtgatgag taatcagcaa tccaaaaatg ttgaatttgt     660
agctagctag cttatcctat caagtcttt                                       689
```

<210> SEQ ID NO 143
<211> LENGTH: 633
<212> TYPE: DNA
<213> ORGANISM: Artificial
<220> FEATURE:
<223> OTHER INFORMATION: Synthetic

<400> SEQUENCE: 143

```
tttcatcatt tctttgcagc agagacaaat taagacatgg caagtagcag catggcttct      60
gctgcatctg gttttatggt ggccacaccc aatattgcca cctctaacac tgctcctcgc     120
acctctatgt tattcttctc ctcctccaag aacaacacca ccaccaactt ctctaggctc     180
gttgttaggg ccgcggaaga ggctgcgcca ccagctgcta ctgccaccgc tgaaggtgaa     240
gctcctcctg tcaaagctgc caagccacct ccaattggac ccaagagagg aaccaaagtg     300
agagttttaa ggaaggagtc ttactggtac aagggggttg gttcagttgt agctgttgat     360
```

-continued

```
caggatccca acacacgcta cccagttgta gtaaggttca acaaagtgaa ctatgcaaat    420

gtatctacca acaactacgc attggatgaa gtcgaagaag tgaaatgaaa gaatggaagt    480

aattaattag ttcatgctct tcatatttgt aatatgcccg accctgtgct ttccatgttt    540

aatctctagt tctatactgg ctttgaatgt gaatctgtat cataatttct tgcaaatttc    600

tccttccatt acttattaag tttgttggca ttg                                 633


<210> SEQ ID NO 144
<211> LENGTH: 643
<212> TYPE: DNA
<213> ORGANISM: Artificial
<220> FEATURE:
<223> OTHER INFORMATION: Synthetic

<400> SEQUENCE: 144

gccgtaacgt ctccctgaga atctggaccc ctgcacaata tctgtccaag acagcacatg     60

caatgtattc gctgaaggca gctatggagt gggatgaaga tgttttcggt ctggagtatg    120

acctggatct ttttaatatt gttgctgttc ctgattttaa catgggagcg atggaaaaca    180

agagcttgaa tatattcaat tccaagcttg tcctggcatc cccagtaact gcgactgatg    240

ctgattatgc ggcaatattg ggtgtgattg gacatgagta cttccacaac tggacaggca    300

acagagttac ctgtcgtgac tggttccagc tcagcttaaa ggaaggactt actgttttcc    360

gtgatcagga gttctcatct gatatgggaa gccgtaccgt gaaaaggatt gctgatgttt    420

caaagcttcg aatgtatcag tacccacagg attctggtcc aatggctcat cctgtccggc    480

cgcattctta tataaagatg gataacttct acacagttac ggtttatgag aagggagctg    540

aagtggtcag gatgtacaaa actttgttag ggagccaagg attcagaaaa ggcatggatt    600

tatatttcga gaggcacgat ggtcaagcag taacatgtga tga                      643


<210> SEQ ID NO 145
<211> LENGTH: 516
<212> TYPE: DNA
<213> ORGANISM: Artificial
<220> FEATURE:
<223> OTHER INFORMATION: Synthetic

<400> SEQUENCE: 145

agaaagagag agaccagaga gagagagaga gagagactgg taacaatggc aatggcgttg     60

agagcagcgt tccagtgcac gccaagcgca tcatcccttt cgtcctcctc ctcctcggca    120

tcgcccctcc tccgtcgggg tgctgctgcc gccctgaggt ttgcacgctg ctcgaccccc    180

ggtaacgcgg gaagcccact ctgcagccct cctcccttca gagccgccgc tcggtcctgg    240

cgcgccctct ccctccctgc ctcccagctc accgcctccc ctcccacccc cgcttacacc    300

atcaaggagg agggtaagcc cgagtccctc gacttccgcc tcttctactt cagcgatgat    360

tccggcaaaa agatctcacc atggcacgac ataccttag aagccaagga tggcatgttc     420

aactgtatta tagagattcc aaaggaaacc agtgcgaaaa tggaagtggc caccgacgaa    480

ttctacaccc ctatcaagca agatactaag aagggc                              516


<210> SEQ ID NO 146
<211> LENGTH: 583
<212> TYPE: DNA
<213> ORGANISM: Artificial
<220> FEATURE:
<223> OTHER INFORMATION: Synthetic
```

-continued

<400> SEQUENCE: 146

```
ccccccgagt tccccatttc agcagcaaag gcaacaatgg cggctgcaag agtaatgata     60
tcagccaaca acactctaac aacttctctt ttatccaaaa ttcctctcca aaagcccaat    120
agtttcaacc tttgtttccg caataggtct gctgctgcac acaggagcca acttttcact    180
tgcactgcta tttacaatcc ccagattcaa atcaaagaac aaggccagcc cgaaacttta    240
gattaccgtg tctttttcgt tgatgattcc ggcaaaaagg tgtccccttg gcatgacata    300
ccactgcatt taggtgatgg tgttttcaat tttattgctg aaattcctaa agaatcgagt    360
gcaaagatgg aagttgctac agatgagctg tacacaccaa taaagcaaga cacaaagaag    420
gggaaactta gatactaccc atataatatt cattggaact atggattgct tcctcaaacc    480
tgggaagacc cctcatttgc aaatgctgaa gttgaggggg cattcggaga taatgaccct    540
gttgatgttg tccagattgg ggaaagtcgt gctaaaattg gcc                      583
```

<210> SEQ ID NO 147
<211> LENGTH: 574
<212> TYPE: DNA
<213> ORGANISM: Artificial
<220> FEATURE:
<223> OTHER INFORMATION: Synthetic

<400> SEQUENCE: 147

```
cccccgagtc tcccgccgcc gccgccgggg gtcactccgc accaactccg acgatccccc     60
ggcgagctct cgacgatggc gacggcggcg acggcgtcgg ctacggcggc cacccgcttc    120
acgcggctgg cgggggtcgg gctccggcgc acggcccgcc tccccacggc cgtgcggttc    180
cagcgccgcg tgctcgccac caccgcgctc ctcaggaccg ccgagctccg gcccaaggag    240
cagggcctgc ccgagacgct cgactaccgc gtgttcctcg tcgacggcgg gggccgcaag    300
gtgtcgccgt ggcacgacgt gcccctgcgc gcaggcgacg ggtgttccca cttcgtcgtg    360
gagatcccca aggagagcag cgccaagatg gaggtcgcca ccgacgagtc attcaccccc    420
atcaagcagg acaccaagaa gggcaacctc cgatactacc cgtacaacat taattggaat    480
tatggattat ttccccaaac atgggaggac ccaactcttg caaacaccga tgtcgaagga    540
gcatttgggg ataatgatcc tgttgatgtt gttg                                574
```

<210> SEQ ID NO 148
<211> LENGTH: 615
<212> TYPE: DNA
<213> ORGANISM: Artificial
<220> FEATURE:
<223> OTHER INFORMATION: Synthetic

<400> SEQUENCE: 148

```
agcaacatgt ctacctacac tacccggtcc attggtgccc ccaacactct cgactacaag     60
gtctacattg agaaggacgg caagcccgtt tccgccttcc acgacattcc tctgtacgcc    120
aatgctgaga agaccattct caacatgatt gtcgaggttc ctcgatggac caacgccaag    180
atggagatct ccaaggacct tgctctgaac cccatcatcc aggacaccaa gaagggcaag    240
ctccgattcg tccgaaactg cttcccccac cacggataca tccacaacta cggtgctttc    300
ccccagacct gggaggaccc caaccacgtc caccccgaga ccaaggccaa gggtgacaac    360
gacccgctcg acgtctgcga gatcggtgag actgttggct acactggcca ggtcaagcag    420
gtcaaggtcc tcggtgtcat ggctctcctc gacgagggtg agactgactg gaagatcatc    480
gccatcgatg tcaaggaccc tcttgcctcc aaggtcaatg acattgagga tgttgagcga    540
```

```
cacctgcccg gtcttctgcg agccaccaac gaatggttcc gaatctacaa gatccctgac    600

ggaaagcccg agaac                                                     615
```

<210> SEQ ID NO 149
<211> LENGTH: 648
<212> TYPE: DNA
<213> ORGANISM: Artificial
<220> FEATURE:
<223> OTHER INFORMATION: Synthetic

<400> SEQUENCE: 149

```
gcccgtcacc tggagaaaag cagcgactct tcgtcttcgt ctccaaccac cacaatgtct     60

ggctacaccg tccgcaaggt tgctgcccag aacactctgg agcaccgcgt ctacatcgag    120

aaggatggcg tccccgtgtc gcccttccac gacattcctc tctttgccaa ccaggagcag    180

accatcctga acatggttgt cgagattcct cgatggacca atggcaagct cgagatctcc    240

aaggaggagc tccttaaccc catcaagcag gacgtcaaga agggcaagct tcgcttcgtc    300

cgcaactgct tcccccacaa gggctacctc tggaactacg gtgccttccc ccagacctgg    360

gaagacccca acaccgtcca ccccgagacc aaggccaagg gtgacaacga ccctctcgat    420

gtctgcgaga tcggtgagct tgttggctac cccggccaga tcaagcaggt caaggtcctc    480

ggtgtcatgg cccttctcga cgaagaggag actgactgga aggtcattgt cattgacgtc    540

aacgaccccc ttgctcctaa gttgaacgac gttgaggacg tcgagcgcca cctgcctggc    600

ctgctccgtg ccaccaacga gtggttccgt atctacaaga tccccgac                 648
```

<210> SEQ ID NO 150
<211> LENGTH: 623
<212> TYPE: DNA
<213> ORGANISM: Artificial
<220> FEATURE:
<223> OTHER INFORMATION: Synthetic

<400> SEQUENCE: 150

```
cgaccagcgt cgctgtgtga aggttcttag ctacataatt ctctctctct ctctctctcc     60

atgtctagca gatgcaacat tctaaccagt accgttatgg gttcttagcg aaaggaggat    120

aggcagatac cttgaaggaa gcaatgaagg tgcagtgcga tgcatgtgag aaggctccag    180

catcactctt ctgctgtgca gacgaggcgg ctctctgtga ggaatgtgat gtgcgcatcc    240

atgctgccaa caagcttgct ggaaaacacc aacgtgtccc tctcatcctt caaccccctt    300

ccgatgctcc ccgctgcgat atttgccagg agaggtcagc ttacattttc tgcttggagg    360

accgagcact tctttgcagg gagtgtgatg tgcctatcca ttcctccacc accttggcga    420

cgaaacacca gaggtttcta gttgcgggta ttcaagtggc attaggcact attgagggtg    480

gtgctatgaa atactaatac taatactaat actaatacca ctaatcagca gccagaaata    540

gcgaaaatgc aagccatgcc gctagtttct agctctggaa ctgccaaaaa cacatataag    600

aaggaacgga atgtggcggt ttc                                            623
```

<210> SEQ ID NO 151
<211> LENGTH: 649
<212> TYPE: DNA
<213> ORGANISM: Artificial
<220> FEATURE:
<223> OTHER INFORMATION: Synthetic

<400> SEQUENCE: 151

-continued

```
cccacgcgtc cgtatctatc gactagttag tttagtcgtc tcgagggtaa attgagcttt     60

gtgtgcggtt ttgaggggag tacatcggca tgaggatcca gtgcgacgcg tgcgaggccg    120

cggcggccac ggtggtgtgc tgcgcggacg aggcggcgct gtgcgcgcgc tgcgacgtcg    180

agatccacgc cgccaacaag ctcgccagca agcaccagcg cctcccgctc gacgccgcgc    240

tctccgccgc cctcccgcgc tgcgacgtct gccaggagaa ggcggcgttc atcttctgcg    300

tggaggacag ggcgctcttc tgccgggact gcgacgagcc catccacgtc ccggggacgc    360

tctccggcaa ccaccagcgc tacctcgcca ccggcatccg cgtcgggttc agctccgtct    420

gtagcgccaa cgccgaccac ctcccgccgc cagcgcccaa ggggaactcc aagccgccgg    480

caagcggcat cgctgctgct gctgctccca agccggccgt gtccgcggcg gcgcaggagg    540

tgccgtcgtc accgttcttg ccgccgtcgg gctgggccgt cgaggatctc ctgcagctct    600

ccgactacga gtccagcgac aagaagggct ctcctattgg gttcaagga                649
```

<210> SEQ ID NO 152
<211> LENGTH: 554
<212> TYPE: DNA
<213> ORGANISM: Artificial
<220> FEATURE:
<223> OTHER INFORMATION: Synthetic

<400> SEQUENCE: 152

```
ccccccca aa ttgagctttg tgtgcggttt tgaggggagt acatcggcat gaggatccag     60

tgcgacgcgt gcgaggccgc ggcggccacg gtggtgtgct gcgcggacga ggcggcgctg    120

tgcgcgcgct gcgacgtcga gatccacgcc gccaacaagc tcgccagcaa gcaccagcgc    180

ctcccgctcg acgccgcgct ccccgccgcc ctcccgcgct gcgacgtctg ccaggagaag    240

gcggcgttca tcttctgcgt ggaggacagg gcgctcttct gccgggactg cgacgagccc    300

atccacgtcc cggggacgct ctccggcaac caccagcgct acctcaccac cggcatccgc    360

gtcgggttca gctccgtctg tagcgccaac gccgaccacc tcccgccgcc agcgcccaag    420

gggaactcca agccgccggc aagcggcatc gctgctgctg ctgctcccaa gccggccgtg    480

tccgcggcgg cgcaggaggt gccgtcgtca ccgttcttgc cgccgtcggg ctgggccgtc    540

gaggatctcc tgca                                                      554
```

<210> SEQ ID NO 153
<211> LENGTH: 718
<212> TYPE: DNA
<213> ORGANISM: Artificial
<220> FEATURE:
<223> OTHER INFORMATION: Synthetic

<400> SEQUENCE: 153

```
agacaacctt tgatcattct ttgagaaaca acaaaaggaa gatgagaccc aagatttatc     60

tgtttggaga ttccatcact gagatgtcct ttgaggatgg tggctggggt gcttctcttg    120

tcaaccactt caaccgcgcg gtggatgtgg tgttaagagg gtatagtggg tataacacaa    180

gatgggcatt gaaggtgata gagaaagttt tcgacgagga aactgcagtc acagcgccat    240

tggcagtgac agtgttcttt ggagcaaatg atgcttgtct ccctgataga tgctcttcct    300

ttcaacatgt ccctattgat gagtacaagc tgaatcttca ttccatcgtc tcctttctca    360

aggggcgatg gccaacaact caaattgtcc tcatctcacc tcctccaatt gatgaaccta    420

cgcggctcct atatcctttt atggagaaca aattgggcct gtcagagagg accaatgaaa    480

ctgctggaaa ctatgctaaa gcaagtctaa ctgtagcagc tgaatgtggg gttttggctg    540
```

```
tggatttatg gaccagaatg cagcaaattc ctggctggca aacagcttgt ttaagtgatg    600

gtttgcacct gagtaaaact gggaacgaga ttgtgtttga ggaggtggtg gcggctctta    660

agaagaaagg gttgagtgtg gaagctctac cagttgatct gccagtgatt aatgaaat      718
```

<210> SEQ ID NO 154
<211> LENGTH: 687
<212> TYPE: DNA
<213> ORGANISM: Artificial
<220> FEATURE:
<223> OTHER INFORMATION: Synthetic

<400> SEQUENCE: 154

```
gggcggacgc gtgggcggac gcgtggggga tttcaggaaa tttttgaact tctgataatg     60

aggcctcaaa tagtattatt tggggactcc attactgaac aatcttttag attcggtggt    120

tggggtgctg ctcttgctga tacttatgtt cgcaaggctg atatattgaa tcgtggctac    180

ggtggataca acaccaaatg ggattgttc ttgctccacc acctatttcc actggatgct    240

ccaacacctc ctgttgctgc cactatattc tttggagcca atgatgctgc tcttttggga    300

agaactagtg aaaggcaaca tgtcccactc gaggaatata aggaaaacct aagaagaatt    360

atacaacatt tgaagaaatg ttccccgtca atcctagtag tgctgataac tccaccacca    420

gttgatgaag caggacggtt tgaacaagca aggtctatgt atggagacaa agcaatggaa    480

ttgccagaaa ggacaaatga agtgacagga gagtacgcaa aacagtgcgt tcaattggca    540

agggagctag gcctcccttc catcaatcta tggtctaaaa tgcaggaaac agagggttgg    600

caaaaaaaat tcctcagtga tggcttacat ctcacagctg aaggcaatgc cattgttcac    660

caagaagttg ttaaagcgtt caatgaa                                        687
```

<210> SEQ ID NO 155
<211> LENGTH: 603
<212> TYPE: DNA
<213> ORGANISM: Artificial
<220> FEATURE:
<223> OTHER INFORMATION: Synthetic

<400> SEQUENCE: 155

```
ggtcaagatg gcgatggcga tgcaggccac ctcttcctct tctctccgca atacctcctt     60

ccttgcctct ttccgtgggg aacaaattcc cggtgcacag aaatccgcag tcggcggctt    120

tgcctcctct cgtcaagtgc agagtaatgt ttcgacagtt cttatctctg tgaggaatga    180

gaagaaaaag atgaggggag tgagttgcag agcttctgct gcagattctc caaagcaagt    240

tgaaagcaaa aaggttctga tgatgggagg cactcgcttt atcggccttt acttggcccg    300

gttgcttgta cagtctggcc acgaggtcac cctttttacc cgaggaaagg cgcccattac    360

ccaacaatta gcaggggagt ccgatgagga ataccaagaa tatgcctcca aagtgaagca    420

catgcaaggt gatcgtcagg atttcgaagg cttgaagagc aagctttccg aagcatcttt    480

tgacattgtg tatgatataa atggaagaga ggctttggag gttgaaccca ttattgaggc    540

ccttcctaat atggagcagt atatctactg ctcgtctgcg ggagtgtact taaaatcaga    600

tct                                                                  603
```

<210> SEQ ID NO 156
<211> LENGTH: 1312
<212> TYPE: DNA
<213> ORGANISM: Artificial
<220> FEATURE:

<223> OTHER INFORMATION: Synthetic

<400> SEQUENCE: 156

```
gcgcgcctta attaggatcg aaggaaggtc atcaagtaac ttggttcaca agagggaaag     60
caccaatcag ccaaccatta cccggggagt cagaacaaga ttacctagat ttctcttcca    120
agatctcgca cttgaaagga gacagaaagg actacgattt tgttaagact agcctagcag    180
ctgaaggctt tgacgttgtc tatgatatca atggaagaga ggcagataga gagagagaca    240
atggcaatgg caacaagtag gttggtggtg gtgcaacaaa aacaaccatc ctcatgtcta    300
ttaccaccat catctctttc tgatttcaat ggtattagac tgaaacaccc aattcagtac    360
aaaagaaagg aatggcagac aagaggagca ttgcaggtga aagcatcagc tgcaaagaaa    420
atcctgataa tgggaggaac cagatttatt ggaatctttt tgtctaggct ccttgtgaag    480
gaaggtcatc aagtaacttt gttcacaaga gggaaagcac caatcagcca accattaccc    540
ggggagtcag aacaagatta cctagatttc tcttccaaga tctcgcactt gaaaggagac    600
agaaaggact acgattttgt taagactagc ctagcagctg aaggctttga cgttgtctat    660
gatatcaatg gtattggaag agaggcagaa gaagtagaac ccatattgga cgcgcttcca    720
aagcttgagc agtacatata ctgttcatcc gctggtgtgt atctgaagtc tgatttactg    780
cctcattttg agtctgatgc agtggatccc aagagcaggc acaagggaaa acttgaaaca    840
gagagtttac ttgtatcaaa gggcgtgaac tggacttcgc tgagaccagt ttatatctac    900
ggtcctttga attacaaccc tgttgaagaa tggtttttcc acagattgaa ggccggtaga    960
ccaatcccca taccaaattc tggcaaccag ataacacaat tgggtcatgt taaggatttg   1020
gcgaccgcat ttattaacgt tcttggtaac gataaagcga gccagcaagt gtttaacata   1080
tctggagata aatatgtgac attcgacgga ttggcaaggg cttgtgctaa ggctggtgga   1140
tttcctgagc cagaactagt tcactacaat cctaaagaat tcgattttgg caaaaagaag   1200
gcattcccct tcagagacca gcatttcttt gcatcaattg agaaagcaaa gagtgaattg   1260
gggtggaaac cagaatatga tttggtggaa ggtctaacag actcctacga tc           1312
```

<210> SEQ ID NO 157
<211> LENGTH: 1138
<212> TYPE: DNA
<213> ORGANISM: Artificial
<220> FEATURE:
<223> OTHER INFORMATION: Synthetic

<400> SEQUENCE: 157

```
tgaagcaggc accacctaat tacaacaatg gctagtttgg ttgcagttca acacaaacag     60
ccttcttttg ctgtcctccc ttcttcccat tctgacttca atggtgccaa attgatctcc    120
tctcttcagt ttaagaggaa accatgccag ccaaaaggag cattgcatgt tacagcatca    180
agtgccaaga aaatccttat aatgggaggc actcgattta ttggtgtctt tctatccaga    240
cttcttgtaa aagaaggcca tcaggttact ctgttcacaa gaggaaaagc tccaatctct    300
caacaattac caggtgaatc agaccaggat tatgctgatt tttcctccaa gttattgcac    360
ttgaagggtg acagaatgga ttttgatttt gtgaagagca gtctttctgc agagggcttt    420
gatgttgtgt atgacataaa tggacgtgaa gcagtagaag tggaaccaat attggatgca    480
ttacctaatc tggaacagta catatactgc tcttcagctg gtgtatacct caaaactgat    540
tatttaccac attttgaggc tgacgcagtt gacccaaaga gcaggcataa aggaaagctt    600
gagacagaga gcttgttaga atcacgagat gttaattgga cttctgtaag gcctgtttat    660
```

-continued

```
atttatgggc cacttaacta taatccagtt gaagagtggt tcttccaccg attgaaagct    720

ggtcgcccaa ttccaattcc taactcaggg ctgcaaataa ctcaacttgg acatgtgaag    780

gatcttgcaa cggcttttat tcaggttctt ggaaatgaga aagcaagcaa gcaagtattt    840

aacatatctg gagagaaata tgtcacgttc gatggattgg ctaaggcttg cgccaaggct    900

ggcggcttcc ctgaacccga gattgttcac tacaacccta aggagtttga ctttggcaag    960

aagaaagctt tcccattccg tgaccagcat ttctttgcat cggtcgaaaa ggcaaaggct   1020

gtgctaggtt ggaagccgga attcgaattg gtggaaggtt tgacagactc ttacaaccta   1080

gattttggta gaggaactta caggaaagaa gctgatttct ctacagatga tctcattc     1138
```

<210> SEQ ID NO 158
<211> LENGTH: 643
<212> TYPE: DNA
<213> ORGANISM: Artificial
<220> FEATURE:
<223> OTHER INFORMATION: Synthetic

<400> SEQUENCE: 158

```
atggctgcat cgtctgcaat cagaggctac ggtgcagcaa ctgctgcttc tccttacgat     60

gtttcagtgc aggaacgaag atatggagca tccatgttga agaagaatgt ttactgcggc    120

aaagttgagc tatgtcgagc ttcggacttc acacaaaatg tcttgcgcca ggccgcgaat    180

ctaacgagac ttcaagctca agcagtccga aagacgtccg tcgttgccat ggcctcctca    240

tcgaaaaaca ttttgatgat gggaggaacg cggttcattg gagtttacct ggcaaggtta    300

cttgtgaaag ccggacacga ggtgacgctc ttcactcgtg gaaagtcgcc gataacgcaa    360

aaaattgcca gtgaaactga tgaagagtat gcagagtatt cgtcgaaagt acgtttcaca    420

tctggtggct atttatcttt tcgtgtctgc ctttcgccag ataaaacata ttcaaggcga    480

tcgccaggac ttcgagggga tgaagagcaa aattgccaat gctggtttcg agatcgtgta    540

tgatatcaac gggagggagg ctgtcgaagt tgaacccatc cttgatgcac ttccgggctt    600

gaaacagtat gtatattgtt catcagcagg agtatacttg aag                      643
```

<210> SEQ ID NO 159
<211> LENGTH: 649
<212> TYPE: DNA
<213> ORGANISM: Artificial
<220> FEATURE:
<223> OTHER INFORMATION: Synthetic

<400> SEQUENCE: 159

```
cccacgcgtc cgggcgaagg ggatgatgtt gcaacagcat cagccttctt tctctctcct     60

tacttcttct ctgtctgact tcaatggcgc taagctccat ttacaagtcc agtacaagag    120

gaaggttcat cagccaaaag gagcactcta tgtttcagcg tcgagcgaaa agaagattct    180

gataatgggt ggtactcgat tcattggtct gttcttgtcc aggatccttg tcaaagaggg    240

acatcaggtt acattgttca caaggggtaa atctcctatt gccaaacaat tgcccggtga    300

atctgaccaa gactttgctg atttctcttc taagattctt cacttgaaag gagacagaaa    360

ggactatgac tttgtgaagt caagtctttc agcagaaggc ttcgatgttg tttatgatat    420

caacgggagg gaggccgaag aagttgagcc catactagaa gcactaccca aactagagca    480

gtacatctac tgttcttcag ctggtgttta tctgaaatct gatatcttgc cacattgtga    540

ggaggatgca gttgatccga agagcaggca caaggggaag ctggagactg agagcttact    600
```

-continued

```
gcaatcaaaa ggtgtaaact ggacttctat acgtcctgtc tacatctac              649


<210> SEQ ID NO 160
<211> LENGTH: 639
<212> TYPE: DNA
<213> ORGANISM: Artificial
<220> FEATURE:
<223> OTHER INFORMATION: Synthetic

<400> SEQUENCE: 160

cccccccccgg aggagagtaa acaagaaaaa aaagagagag agatggcagc aacagcctcc   60

ctgaagagca gcctcctgct accatctcct atctctgact tcagtagtgc agcactctcc   120

atctcaaccc aggctaggag gaggtcatgg cagccaaggg gggcaaggat gcaggtagca   180

gcagctgcag actccaagaa cattcttgtg atggggggaa ccaggttcat tggtgtcttc   240

ttgtccagga tccttgtcaa ggaggggcac caggtcacat tgttcactag aggaaaggcc   300

cccattaccc agcagttgcc aggagagtca gatgcagagt atgcagagtt ctcttcaaag   360

gtgttgcact tgaaaggtga caggcaagac tttgatttcg ttaagacaag ccttgcggca   420

aagggcttcg atgttgttta cgacataaac gggagagaag ctgttgaggt agccccaatc   480

ctagacgcat tgccaaacct tgaacagtac atctactgct catcagcagg agtgtacctg   540

aaatcagacc tgctcccgca cttcgagacc gacgccgtcg acccgaaaag ccggcacaag   600

gggaagctgg agacggagag cctgctggag acccgggac                         639


<210> SEQ ID NO 161
<211> LENGTH: 373
<212> TYPE: DNA
<213> ORGANISM: Artificial
<220> FEATURE:
<223> OTHER INFORMATION: Synthetic

<400> SEQUENCE: 161

cccacgcgtc cgggcgaaga tgatgatgtt gcaacagcat cagccttctt tctctctcct   60

tacttcttct ctgtctgact tcaatggcgc taagctccat ttacaagtcc agtacaagag   120

gaaggttcat cagccaaaag gagcactcta tgtttcagcg tcgagcgaaa agaagattct   180

gataatgggt ggtactcgat tcattggtct gttcttgtcc aggatccttg tcaaagaggg   240

acatcaggtt acattgttca caaggggtaa atctcctatt gccaaacaat tgcccggtga   300

atctgaccaa gactttgctg atttctcttc taagattctt cacttgaaag gagacagaaa   360

ggactatgac ttt                                                      373


<210> SEQ ID NO 162
<211> LENGTH: 339
<212> TYPE: DNA
<213> ORGANISM: Artificial
<220> FEATURE:
<223> OTHER INFORMATION: Synthetic

<400> SEQUENCE: 162

cggacgcgtg ggtgaggaga ggaaacatca aacaaaagag agagagatgg caggcgcagc   60

ctccctgaag agcagcctcc tgctaccatc tcctatctct gacttcagta gggcagcact   120

ctccatctca acccaggcta ggaggaggtc atggcagcca aggggggcaa ggatgcaggt   180

agcagcagct gcagactcca agaacattct tgtgatgggg ggaaccaggg tcattggcgt   240

cttcttgtcc aggctccttg gcaaggaggg gcaccaagtc acattgttca ctagaggaaa   300

ggcccccatt acccagcagt tgccaggaga gtcagatgc                         339
```

<210> SEQ ID NO 163
<211> LENGTH: 1201
<212> TYPE: DNA
<213> ORGANISM: Artificial
<220> FEATURE:
<223> OTHER INFORMATION: Synthetic

<400> SEQUENCE: 163

```
aagcaagttc aacttcacta aggttggtca ggaagagttg ctcttccagt ttgaagcaag     60

tgaggacaac gaagttcaat tctttccaaa tgcacccatt gatgccgaga aatctcgaag    120

tgttgttgcc atcaatgtca gtcccattga gtatggacat gtgcttttga tccctaaggt    180

ccttgaatgc cttccccaga ggattgacag ggacagccta ttgcttgcac tgcacatggc    240

tgccgaagca gctaacccat acttccgatt gggttataac agcttgggtg catttgctac    300

catcaaccat cttcactttc aggcctatta cttggctgtg ccattcccca ttgagaaggc    360

ccccactcgg aagattacct ttgctgatgc tggagtgaag atatctgaga tgctgaatta    420

tccagttcga ggacttgtct ttgagggtgg aaatactttg gaggatttcg ccaatgttgt    480

ctctggttct tgcatttgcc tgcaagagaa taacattccc tacaatgttc taatctctga    540

ttcggcaaaa agggtattcc ttctcccaca gtgctacgca gagaaacagg ctctagggga    600

ggtcagctct gaactgcttg atactcaagt caatcctgca gtatgggaga ttagtggaca    660

catggtcttg aagaggaagg aggattacga gggtgcaacc gaggcaaatg cctggaggct    720

tctcgctgag gtctcacttt ctgaagcgag gttccaagaa gtgactgctc tcatctttga    780

agccattgat tgcagtgttg aagagaatga gaatgccaat gaaggttctc ctgagaagcc    840

agatgttgca cctcagccta tggaggaaat tgatgctctc aacacccatg ctaccatggt    900

tcccgtgtag ggttttcatg gtcgagctgt ggtgtttgtc ctgttgttac tatttcaact    960

atatgaacat tgagggagtt tctatctatg gctgcacttg tgaaatatcc ctaaataagg   1020

ctagccatgt tctatgtatt gatgaagttg tttggttcct atgtgaattg aaccttgtct   1080

tttattgctt catattaatg tggagttgct cagtgtcctc tgggaatcga ccttggatac   1140

tatgttcgtt gtctgttatt taagacaata tatttggtaa tggaagttgg agtttccctg   1200

t                                                                   1201
```

<210> SEQ ID NO 164
<211> LENGTH: 615
<212> TYPE: DNA
<213> ORGANISM: Artificial
<220> FEATURE:
<223> OTHER INFORMATION: Synthetic

<400> SEQUENCE: 164

```
ggaaatgctg tttgccggcg tccaggcttc ctctttatgc attcaagaat gatgacaatg     60

agccaattga aaacggtatt gatgccttgc ctggggagga ttgtcagata tctttttttga    120

atgatctgct gttgggccta tgggaagagc ggatgagcca gggactgttt cgatatgatg    180

tcacaacctg tgagactaaa gtcattcctg ggagatatgg ttttattgca cagctgaatg    240

aggggcgcca cctaaaaaag cgcccaacag agtttcgcat cgatcaggtt cttcagcctt    300

ttgacgagaa caaattcaat tttaccaaag tgggccagga cgaagtgctt ttcaggtttg    360

agccaagcac tgactgcaag gcccattact tttcgggtgt gggagtagat gctggtgttt    420

caccgagtat tgttgctatc aatgtgagcc caatcgagta tggccatgtg cttttgatac    480
```

-continued

```
ctcgagttct tgattacttt cctcagagaa ttgatcgtga tagtttcacg gttgctctcc    540

atttcgccag agaactggct gatcccttct ttagggtagg ttataacagt ctgggcgcct    600

tcgccactat aaacc                                                     615


<210> SEQ ID NO 165
<211> LENGTH: 364
<212> TYPE: DNA
<213> ORGANISM: Artificial
<220> FEATURE:
<223> OTHER INFORMATION: Synthetic

<400> SEQUENCE: 165

ttattggtgg tagtgatctt caaggaagaa gctttctcta tcgggaattg cattgccaaa     60

tagtaagcct gaaagtgaag atggttaatg gtagcgaaag cgcctagact gttgtatcca    120

agtcggaaat acgtattatc ggcttcagcc gccatttgaa gagcaagcaa aaggcttttg    180

tgatcaatcc tttgaggtaa gcaatcaaga acattccttt caacattctc atctctgact    240

ctggcaaacg aatcttcctt ctccctcagt gttacgcaga gaaacaggct ttaggagaag    300

ttagctcaac gctattggat acgcaagtga atccagcggt ttgggagatg agtggacaca    360

tggt                                                                 364


<210> SEQ ID NO 166
<211> LENGTH: 689
<212> TYPE: DNA
<213> ORGANISM: Artificial
<220> FEATURE:
<223> OTHER INFORMATION: Synthetic

<400> SEQUENCE: 166

gtccatcttt gtgttgtgaa agaagcttgc aggccatggg gacggagaaa gagcgcgaga     60

aaaatgtgta catggccaag cttgctgagc aggcagagcg ttatcaagag atggttgaat    120

acatggaaac agtggccaag cttgatcttg agctaactgt ggaggagcgc aaccttctgt    180

ctgttggcta caaaaatgtt attggagccc acagagcctc ttggcgtatc ctttcttcca    240

ttgaacagaa agaagagaac aagggcaatg agactaatgt gaagcgtacc agggattata    300

ggcataaagt tgagacagaa cttaccaaga ttagcagtga aattttgact atccttgatg    360

agcatctcat cccctcatcg ggaactggcg aatcatctgt cttctactat aaaatgaagg    420

gcgactacta ccgttacctg gcagagtttc agacaggcga gaagaaaaag gaatctgcgg    480

acgagtcctt caaagcatat caggccgcat caagcactgc aaacacagat ctcccgccca    540

cccatccaat caggctgggg cttgccctga acttttctgt tttctactat gaaattatga    600

attcccctga acgggcatgc gagcttgcta aacaagcatt tgatgaggcg attgctgagc    660

ttgacactct gagtgaagag tcatacaag                                      689


<210> SEQ ID NO 167
<211> LENGTH: 700
<212> TYPE: DNA
<213> ORGANISM: Artificial
<220> FEATURE:
<223> OTHER INFORMATION: Synthetic

<400> SEQUENCE: 167

gaggagctcg tcttcatggc caagcttgct gagcaggccg agcgctacga tgagatggct     60

gagttcatgg agaaggttgc ctccatgtcc agctctggtg acgagctcgc tgtcgaggag    120

cgtaacctcc tctccgtcgc gtacaagaac gttgtcggtg cccgccgcgc ctcctggcgt    180
```

-continued

```
attgtctcct ccatcgagca gaaggaggag aacaagggca accaggatca cgtctccgcc    240

atccgcggat accgcaccaa gatcgagaat gagctcgccg gcatctgtga gggcgtgttg    300

aaggtcctcg cctctgccct catccccgcc tgcgcctcca aggagtccaa ggtcttctac    360

ctcaagatga aaggggatta ctaccgatac cttgctgagt tcaagaccgg ccccgagagg    420

aaagacgcgg ctgagtccac acttctctca tacaagtctg ctcaggacat cgcactcact    480

gagatgcctc ccactcaccc gattcgcctt ggcctcgcac tcaacttctc tgtattctac    540

tacgaaatcc taaactcacc cgaacgggct tgcagccttg ctaagcaggc atgtgatgag    600

gccatttctg agctggacac acttggtgag gagtcctaca aggacagcac cctaatcatg    660

cagcttctcc gggataacct cactttgtgg acatcagatc                          700
```

<210> SEQ ID NO 168
<211> LENGTH: 627
<212> TYPE: DNA
<213> ORGANISM: Artificial
<220> FEATURE:
<223> OTHER INFORMATION: Synthetic

<400> SEQUENCE: 168

```
aaaaatctca taaacgaaac acaaaaaaaa aaccctctct cgaaaattaa aaataaaaaa     60

tacccggcga atctccgacg atggctttgc cggaaaattt aaccagagag cagtgcctat    120

acttagcaaa gctcgccgag caagccgagc gttacgagga gatggtaaaa ttcatggacc    180

gactcgtagc tgtctcggct tcctctgaac taaccgtaga agagcgaaac ctcctctcgg    240

tagcttataa gaacgtcatc ggttcacttc gagccgcgtg gaggatagta tcgtcaattg    300

agcaaaagga agaaggtagg aagaacgagg aacacgtggt tctagtgaag gattatagat    360

ctaaggttga atctgagctt agtgatgtat gtgctggaat tttgaagatt ttggatcagt    420

atttgattcc ttcggcttcg gctggtgaat cgaaggtgtt ttacttgaag atgaagggag    480

attattatcg ttatttggct gaatttaaag ttagtaatga acgtaaggag gctgctgagg    540

ccactatgct tgcctacaaa gctgctcagg acattgcgct tgctgagctt gccccaacac    600

atcctatacg acttgggcta gctctca                                        627
```

<210> SEQ ID NO 169
<211> LENGTH: 546
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (457)..(457)
<223> OTHER INFORMATION: The residue at this position can be any nucleotide.

<400> SEQUENCE: 169

```
gctgtgttta tcttcttcgc cttcgtgttc gtcggtggtg ttggtagtgg gaagatgggt     60

gtggagaagg agcgtgagag tgatgtgtac atggctaagc tcgctgagca ggcggaacgt    120

tatgatgaga tggtggaatt catgaaaaag gtggcaaact tggatgtgga gctatctgta    180

gaggagagga atctgatgtc agttgggtac aagaatgtga ttggggcacg gagggcctct    240

tggcgcatcc tctcctccat cgagcagaag gaggagggaa aaggcaatga agtgaatgcc    300

aagcgcatca aagaatacaa gcacaaggtc gaggaagagc tttcaaacat ctgcaacgat    360

gtcctctccg ttattgagga tcatctcatc cctgcgtcta gcacggggga atcttctgtc    420
```

```
ttctattaca aaatgaaagg ggattacttc cgatatntgg cagagtttaa atctggaaat    480

gagaagaagg aagccggaga gcagtctttg aaagcatacc aggctgctat ggacatagcg    540

acatct                                                                546


<210> SEQ ID NO 170
<211> LENGTH: 475
<212> TYPE: DNA
<213> ORGANISM: Artificial
<220> FEATURE:
<223> OTHER INFORMATION: Synthetic

<400> SEQUENCE: 170

tcttgttttt tgttttggtt gttgacggaa gaagaggagg gagaaggcat gggtgtggag     60

aaggatcgcg atggccatat ctacatggcc aagctcgctg agcaggccga acgatacgat    120

gagatggtcg attttatgaa aaaggtggca aacatggatg tggagctcac tgtggaggag    180

cggaatcttt tatcagtagg ctacaaaaat gtgattgggg cccgcagggc ttcgtggcgt    240

attctctcct caattgagca aaaggaggaa gccaaaggca atgagcagaa tgtggggcgt    300

atcaaagact acaaggaaaa ggttgaggaa gagctctcaa agatctgcat tgacatcttg    360

tcgactatcg atgatcatct tatccctgca tccagcactg acgagtcttc tgtgttttat    420

taccaaatga aaggggatta cttccgctat ttagcagagt tcaaagcctc aagcg         475


<210> SEQ ID NO 171
<211> LENGTH: 498
<212> TYPE: DNA
<213> ORGANISM: Artificial
<220> FEATURE:
<223> OTHER INFORMATION: Synthetic

<400> SEQUENCE: 171

tacaaatcct cgactgtgaa aggagctttc gccatctctc tccatgggaa tcgagatgga     60

ccgcgatggg aatgtctaca tggccaagct cgctgagcaa gccgaacgct atgatgagat    120

ggtggagttc atgaagaatg tggcgaatat ggatacggaa ctgactgtgg aggagcgcaa    180

cctattctcc ataggatata aaaatgtgat cggagctcgt cgggcttcct ggcgcattct    240

ctcctccatt gagcagagag aggagagcaa gggcaacgag gtgaatgcga atcgcatcaa    300

ggagtaccgt aacagagtcg acgaagagct ctccaagatc tgcaaagatg tcctgagcat    360

catcgatgat catctcatcc cctcttccac aaccaaagaa tctgaggtct tctattacaa    420

aatgaagggt gattattacc gctatttggc tgagtttaag gctggtagcg agaggaagga    480

tgcggcagat cactccct                                                  498


<210> SEQ ID NO 172
<211> LENGTH: 390
<212> TYPE: DNA
<213> ORGANISM: Artificial
<220> FEATURE:
<223> OTHER INFORMATION: Synthetic

<400> SEQUENCE: 172

cccacgcgtc cgtaaaggaa agaagagagc aaagggaacg aagatcatgt tgctattatc     60

aaggattaca gaggaaagat tgaatccgag cttagcaaaa tctgtgatgg gatttgaat     120

gttcttgaag ctcatcttat tccttctgct tcaccagctg aatctaaagt gttttatctt    180

aagatgaagg gtgattatca taggtatctt gctgagttta aggctggtgc tgaaaggaaa    240
```

-continued

```
gaagctgctg aaagcacttt ggttgcttac aagtctgctt ccgacattgc cactgctgag    300

ttagctccta ctcacccgat aaggcttggt cttgcactca acttctctgt gttttactat    360

gaaatcctca actcgcctga tcgtgcttgc                                      390
```

<210> SEQ ID NO 173
<211> LENGTH: 1132
<212> TYPE: DNA
<213> ORGANISM: Artificial
<220> FEATURE:
<223> OTHER INFORMATION: Synthetic

<400> SEQUENCE: 173

```
agccaagtga aagcaaaaag ggagaggaaa agcgcaaaat ctcccttcga ttatcagtac     60

aaaacctctg atttgagaga tcggaaatgg cttcctccaa agaacgcgag aacttcgtct    120

acgtcgctaa gcttgctgag caggccgaac gctacaatga aatggttgat gcgatgaaga    180

gtgtagcaaa tatggatgtt gaattgactg ttgaggaaag gaatctgctt tctgttggtt    240

ataaaaatgt ggtaggttct aggagagcat cttggaggat cttatcctct attgagcaga    300

aggaagaatc tagaggaaat gagcaaaatg tcaagcgaat taaggagtac cgacaaaagg    360

tggagacaga gctcaccagc atttgcaacg atatcatggt ggtcattgat cagcatctaa    420

ttccttcatg cactgcaggc gaatcaactg tgttttacca caagatgaag ggagactatt    480

atcgttatct tgcagaattt aaatctggca atgacaagaa agaggttgca gagctttcat    540

tgaaagcata tcagtcagct acaactgctg cagaggcgga attaccaccc actcatccca    600

ttcggttggg attggctttg aatttctctg tgttctatta tgagatcatg aattcacctg    660

aaagggcatg ccatctggca aagcaggcct ttgatgaagc aatatctgag ttggatagcc    720

tgaacgagga ttcctacaaa gacagcacct tgattatgca gcttctaagg gacaatctca    780

ccttgtggac ttctgatctt ccagaggatg cagaagatgc ccaaaaggga gatgccacaa    840

acaaagcaag tggaggtgaa gatgcagagt gaatgggcct aatggttaga actaccttgt    900

gcatttggag ctgtgaggac ggtgatacac caaagggatg tgtgtgtgtt aagtcctagt    960

agattcttat cttatgggca tgtcgtgtca gtttctttac atgttaattg ggtgttgcaa   1020

ttcagcatgt gtgtgatttg tatccctgtg ctatttcctc tccgtaaagt gagttgtttc   1080

agtctttaga tgattggtct ggtccatagg tggttttatt tttcagagga ct           1132
```

<210> SEQ ID NO 174
<211> LENGTH: 907
<212> TYPE: DNA
<213> ORGANISM: Artificial
<220> FEATURE:
<223> OTHER INFORMATION: Synthetic

<400> SEQUENCE: 174

```
tacaaaactc cctctctcat ttcctctctc atagcaacat caatggcgtc gccacgcgag     60

gagaacgtgt acatggcaaa gcttgccgag caagccgagc gttacgagga gatggttgag    120

ttcatggaga aagtcatcgc cgccgccgac ggcgccgagg aacttaccgt cgaagaacgg    180

aacctcctct ccgtcgcata caaaaatgtt atcggagcac ggcgagcctc gtggcgtatc    240

atctcctcca ttgagcaaaa agaggagagc cgcggcaacg aagatcacgt tgcctccatc    300

aaggagtaca gatctaagat cgagatcgaa cttacctcga tctgtaacgg cattctcaag    360

ctcctcgatt ctaagctcat tggcgccgct gctaccggtg actctaaggt gttttacttg    420

aaaatgaaag gagattatca tcgctatttg gctgagttta aaaccggcgc ggagcgaaag    480
```

-continued

```
gaagccgccg aaaatactct ctcggcttac aaatccgctc aggatattgc aaataccgag    540

cttgctccta cacatccaat ccgattggga cttgctctca atttctctgt attttactac    600

gaaattttga attctcctga tcgtgcttgt aatctcgcca aacaggcttt tgacgaggca    660

attgccgagc tggacacatt gggcgaagag tcctacaagg atagcactct gatcatgcag    720

cttcttcgcg ataacctcac tttatggact tcagatatgc aggatgatgg aactgatgag    780

atcaaagaag cagcaaaacc agataatgag cagcagtaaa ccggtgacat ttctttagga    840

ttgaaattca tgttgtaact ttttattttt caattgtctg agttcagctc ttttagttct    900

agatctt                                                              907
```

```
<210> SEQ ID NO 175
<211> LENGTH: 360
<212> TYPE: DNA
<213> ORGANISM: Artificial
<220> FEATURE:
<223> OTHER INFORMATION: Synthetic

<400> SEQUENCE: 175

cccacgcgtc cggtaacgat gaccacgtca cggcgatccg tgaatatagg tctaagatcg     60

agacggaact ctccggaatc tgcgacggaa tccttaagtt gcttgactct agactcatcc    120

ctgccgctgc ttctggtgat tccaaggtct tttaccttaa gatgaaggga gattatcaca    180

ggtacttggc tgagtttaag actggtcaag agaggaaaga cgccgccgaa catacactcg    240

ccgcttacaa atctgctcag gatattgcta atgcagagct tgctccaaca cacccaattc    300

gtcttggtct tgcattgaac ttctctgtgt tctattacga gatcctcaat tctcctgatc    360
```

```
<210> SEQ ID NO 176
<211> LENGTH: 617
<212> TYPE: DNA
<213> ORGANISM: Artificial
<220> FEATURE:
<223> OTHER INFORMATION: Synthetic

<400> SEQUENCE: 176

cggccgaaca aaaagcattc gcatccacga gaccactcga acccgacccg cctcgccgcc     60

gccgccaccg aagtaatccc ttaattggtc aaaatgtctc gggaggagaa tgtctacatg    120

gccaagctgg ccgagcaggc tgaaaggtat gaggagatgg ttgagtacat ggagaaggtt    180

gcaaagactg tagatgtgga agagctcact gttgaggagc gcaacctctt gtctgttgct    240

tacaagaatg tgattggtgc ccgccgtgcc tcctggcgta ttgtctcatc cattgaacag    300

aaggaggagg gtcgtggcaa tgaggaacat gttactctga tcaaggagta ccgtggcaag    360

attgaagctg agctgagcaa gatttgcgat ggtatcctga agttgcttga ctcacacctt    420

gtgccctcat ctactgctgc agaatctaag gtgttttacc tcaagatgaa gggtgattac    480

cacaggtacc ttgcggaatt taagactggt gccgagagaa aggaagctgc tgagagcaca    540

atggtggctt acaaggctgc tcaggatatt gctctggcgg atcttgctcc cacccatccc    600

ataaggcttg gactggc                                                   617
```

```
<210> SEQ ID NO 177
<211> LENGTH: 530
<212> TYPE: DNA
<213> ORGANISM: Artificial
<220> FEATURE:
<223> OTHER INFORMATION: Synthetic
```

-continued

<400> SEQUENCE: 177

```
acgagattct aaactctcca gacaaggctt gcaaccttgc taagcaggcg tttgacgaag     60
ccatctctga gttggatacc ctcggggagg agtcttacaa ggacagcact ttgatcatgc    120
agctcctgag ggacaacttg accctctgga cctctgacct cacggaggac ggtggtgatg    180
aggtgaaaga agcctccaag ggcgacgccg gcgagggcca gtaaaatggg aagatcgatc    240
gatcgatggc tccgcatgtt attggagacc attgatttag atgcctcatg ctgctgtcac    300
catgatggat ggattcttct tctgttctac tagaatgttt ttcttcctgt ccccccttcc    360
tctctcttct ctggttttta ctagggtggt agcggtcgaa ttagttcttc cctttgcttt    420
gcatttggtg ctagtggtcc gtctgggctg attgttttcc tctggatatg actctcgtgt    480
gtgttgtctc cagatagtgt tttattgagc aatatttaaa gttgtcgtcc               530
```

<210> SEQ ID NO 178
<211> LENGTH: 1103
<212> TYPE: DNA
<213> ORGANISM: Artificial
<220> FEATURE:
<223> OTHER INFORMATION: Synthetic

<400> SEQUENCE: 178

```
caaaagtcca aaatttcccc cacaaaagct ctcctctctg aattattaaa tccccattca     60
gaaaatcgaa aaactccctc attcagatct cccaaaaaaa tacagagaaa caaatctaaa    120
catggcggtg gcaccgacgg cgcgtgagga gaacgtgtac atggcaaagc ttgcagagca    180
agctgagagg tacgaagaaa tggttgaatt catggaaaag gtctccaact ccctcggctc    240
agaagaactc accgtggagg aacgaaacct cctttccgtg gcgtacaaga acgtgatcgg    300
agcgcgtagg gcatcgtggc gtattatctc atcgattgag caaaaggaag agtccagagg    360
gaacgaggaa cacgtgaact ctatccgcga gtacagatct aagattgaga atgagctctc    420
taagatctgt gatggtattc tgaaattgct cgatgcaaag cttatccctt ctgcagcatc    480
tggtgattct aaggtgtttt acctgaaaat gaaaggagat taccaccgct atttggctga    540
gttcaagacc ggtgctgaac gtaaggaggc tgctgagagt acactcactg cctacaaagc    600
tgctcaggac attgcaacta ctgaacttgc cccaacacat cccatccgac ttggactggc    660
tcttaacttc tctgtgtttt actatgagat cttgaactct cctgaccgtg cttgcaatct    720
tgctaaacag gcctttgatg aagcaattgc tgagctggat acattgggcg aggagtctta    780
caaggatagc actttgatca tgcaacttct tcgtgacaat ctcactctct ggacttctga    840
tatgcaggat gatggggctg atgaaatcaa ggaagatccc aaacctgatg aagccaaaaa    900
ttgaaggaaa tgaaactctc taatttgctt ttcacttctt cctggttgtt tttattggaa    960
gaagctgatt atcgtaattt ccttactatt atggttctcc actagggggt tgtcatctta   1020
ttggaaatga acaactttta atattgatgt ttcagagttc catctttgat ttaatgtggt   1080
tttctggtga ttagttttct tct                                           1103
```

<210> SEQ ID NO 179
<211> LENGTH: 598
<212> TYPE: DNA
<213> ORGANISM: Artificial
<220> FEATURE:
<223> OTHER INFORMATION: Synthetic

<400> SEQUENCE: 179

```
cggacgcgtg ggcccaaaga gagagagcga gagagagagc ggagaaatgg agaaggaaag     60
```

-continued

```
agagaaacag gtttacttgg caaggctagc tgagcaagct gagagatatg atgaaatggt    120
agaagcaatg aagacggttg ctaagatgga tgttgaactg actgttgagg agaggaattt    180
ggtgtcagtt gggtataaga atgttattgg agcaagaagg gcttcatggc ggatattgtc    240
ttcaattgaa caaaaggagg agagtaaggg tcatgaccag aatgttacga gaataaagac    300
ttaccaacag agggtcgaag atgagcttac aaaaatatgc attgacattt tgtcggtgat    360
cgatgagcac cttgttcctt cttccactac cggagaatct actgtcttct actataagat    420
gaagggagat tactatcgct atttagcaga gttcaaatca ggggatgatc gtaaagaggc    480
agctgatcag tcacttaaag cttatgaggc tgctacttcc acagctagtg cagatcttgc    540
tcctactcat ccaattagac ttggacttgc attgaacttc tcagtcttct actatgag      598
```

<210> SEQ ID NO 180
<211> LENGTH: 988
<212> TYPE: DNA
<213> ORGANISM: Artificial
<220> FEATURE:
<223> OTHER INFORMATION: Synthetic

<400> SEQUENCE: 180

```
gaacaatggg tgccgagaag gagagggagg gtcatgtcta cctggccaag cttgcagagc     60
aggctgagcg ttacgatgag atggtcgagt tcatgaagaa ggtagccaag cttgacattg    120
agctgactgt ggaggagcgc aatcttctct cagtggccta taagaatgtg attggagcac    180
gtagggcctc ttggcgtatt ctctcctcca ttgagcagaa ggaggagagc aaagggaatg    240
aggttaacgt gaagcgtata aaggattaca ggcaaaaggt cgatgaggaa ctctcgaaga    300
tctgccatga cattttgact atcatagatg agcatctcat cccctcttct gggactggcg    360
aatcgtctgt cttctactac aaaatgaagg gagattacta ccgctacctc gcagagttca    420
aagctggtcc gcagaaaaag gaagacgcag atgagtcctt caaagcctac caagctgcgt    480
cgagcaccgc gagtactgat ctgccaccta cccatcccat caggcttgga ctcgccttga    540
atttctccgt tttctactat gaaattttga attcgcccga gcaggcatgc caattagcaa    600
aacaagcatt cgatgaggcg attgcagagc tcgatactct gagcgaggag tcatacaagg    660
acagcaccct tattatgcag cttctaagag acaacctgac cttgtggact tcagatctgc    720
aagaagatgg aggtgatgag cactccaagg gagaggatct gaaagtagga gatgcagagg    780
aatcgtagtg ccagtttgat tgttcgagct gagttttgaa ggagtcgagc cggatatgca    840
tccttggtac aaaatttgac atgtgttaga ttctgtgtgg catttgtttg aaggaatatc    900
ctatgtagat tgttatgttc ttgttctgct ctattgctac aagggctgtt gttacaatta    960
caagttatac attttctatt tgagggaa                                       988
```

<210> SEQ ID NO 181
<211> LENGTH: 1105
<212> TYPE: DNA
<213> ORGANISM: Artificial
<220> FEATURE:
<223> OTHER INFORMATION: Synthetic

<400> SEQUENCE: 181

```
agcgacaatc agaaaccacc cgctgtaacc ctaggttttt tcacaaacaa caaatatgac     60
tgagtcatcg cgggaagaaa atgtgtacat ggccaagctt gctgagcagg ccgagcgata    120
tgaggaaatg attgagttta tggagaaggt tgcaaagaca ggtgatgtcg aggagctgac    180
```

-continued tgttgaggaa aggaatctcc tttctgtggc atacaaaaat gtgattggtg caagaagggc 240
ctcgtggaga ataatctctt caattgagca gaaagaggag agccgtggaa atgaagatca 300
tgtcaaaact attaaagaat acagagccaa aattgaggct gaactcagca agatctgtga 360
tgggattttg ggtctccttg agtcccattt aataccatca gcctccacag ctgagtccaa 420 agtttttac ttgaagatga aaggtgatta ccacaggtac ttggctgagt ttaagacagg 480
ggcagaaagg aaagaagccg cagagaacac tttattaccc tacaagtctg ctcaggatat 540
tgctttggat gaactggctc ctactcaccc aatcaggctg ggacttgccc tcaacttttc 600
agtgttctac tatgaaattc tcaactcgtc agatcgtgct tgtaaccttg caaagcaggc 660
ctttgatgat gccatcgccg agctggatac attgggtgag gaatcttaca aggacagtac 720
attgattatg cagcttctcc gagacaatct tacactttgg acttctgata ccacggatga 780
tgccggggat gagatcaagg aagcttcaaa atgcgaatta ggcgaaggag agcagtaacg 840
gcataacatc atagtctttt actctttatt ttgtttgatt ttaatatagg actactgcgt 900
gaaagctaga ctggatatgg atataattcg atgattcctc gtattactgc tgaagtagtt 960
tgatataaaa acatgtttta gtacgataag aaatatagtc atgccgttga tgtattggct 1020
tgtatttcta gtttcaattg catatgttat tgactgttga gctttgtatt ttcaagtcat 1080
tcaataattc aatagttccc aaaaa 1105

<210> SEQ ID NO 182
<211> LENGTH: 572
<212> TYPE: DNA
<213> ORGANISM: Artificial
<220> FEATURE:
<223> OTHER INFORMATION: Synthetic

<400> SEQUENCE: 182
cccacgcgtc cgatggtggc ggcaaggctg ctcaggacat tgctttggct gagctgcctc 60
ctactcatcc aattaggctt gggctagctc ttaacttctc agtgttctac tatgagatcc 120
tcaactcgcc tgatcgtgct tgcaacctcg caaagcaggc ttttgatgag gccatctcgg 180
agctggacac cctgagcgag gagtcctaca aggacagcac tttgatcatg caactcctcc 240
gtgataacct gaccctgtgg acttcagaca tctcggagga caccgcggaa gagatcaggg 300
aagctccgaa gcgcgactcc agcgaggggc agtaaagccg gctttatgtg ccctagaagc 360
ttgtagctag tgctttgcta ctgtgtaatg acacctatgt ggctgtgatt gttgtcggga 420
aatctggggc tcccccgtat gtgaggttgc tagcgatggt tttgcagtct cgcctttaag 480
ctactcgtag cagagcaggt gggggtctgt ggagccaggc ctggttgggg gtgggggagc 540
ctcttgaact gcttggtggc acttcctgtt tt 572

<210> SEQ ID NO 183
<211> LENGTH: 572
<212> TYPE: DNA
<213> ORGANISM: Artificial
<220> FEATURE:
<223> OTHER INFORMATION: Synthetic

<400> SEQUENCE: 183
aaaaaatcag agaagtgaag agaagagatc aagggatcga tccttgagaa ggcaatggga 60
atcgagaagg aacgtgagac cctcgtctac ctctctaagc tcgctgagca agctgagcgc 120
tatgacgaaa tggtggagtc aatgaagaaa gtggctaagt tggacattga gttgagtgtg 180
gaggaaagaa atctgctctc cgttggatac aagaatgtga tcggagcacg cagggcctcc 240

-continued

```
tggcgcatcc tctcttccat tgagcagaag gaagagagca agggcaatga gacaaatgtg    300

aagcgcatta aggactatcg cttcaaggtg gaggaagagc tctccaagat atgcagcgac    360

atcctaacca tcatcgatga gcacctcatc ccctcatcca acaccggtga atccactgtt    420

ttctattaca aaatgaaagg ggattattat cgataccttg ggagttcaa gtctgggcat     480

taaaagaaag aggctggcga tcaatctctg aaagcttatc aagcgggtaa taacactggg    540

aacacggatc tatcatccac ccacccaatc ag                                  572
```

```
<210> SEQ ID NO 184
<211> LENGTH: 1057
<212> TYPE: DNA
<213> ORGANISM: Artificial
<220> FEATURE:
<223> OTHER INFORMATION: Synthetic

<400> SEQUENCE: 184

tccacattct ctcaactttc tctttctaaa aactcttcct atctctttct ctagcacaca     60

gaccatcaat ggcatcgccg cgcgaggaga acgtgtacct ggcgaagctg gctgagcaag    120

ccgagcgcta cgaggagatg gtagagttca tggagaaagt cgtcggcgcc ggcgacgacg    180

aactcaccgt cgaggaacgc aacctcctct ccgtcgcgta caaaaacgtg atcggagcga    240

ggagagcgtc gtggcgcata atctcatcga tcgagcagaa agaagagagt cgcggtaatg    300

aagatcatgt ggcctccatt aaaacctaca gatctaagat cgaatctgaa ttgacttcga    360

tctgtaacgg tatccttaag ttgctcgatt caaaactcat cggcaccgct gctaccggtg    420

actctaaggt tttttatttg aaaatgaagg gagattatta caggtacttg gctgagttca    480

aaaccggagc tgagagaaaa gaagccgccg agaatactct ttcggcttac aagtcggctc    540

aggatattgc taatgtcgaa ttagccccta cacatccaat ccgattgggg ctagctctca    600

atttctcagt gttttactat gagatattga attctcctga ccgtgcttgt aatcttgcca    660

aacaggcatt tgatgaggca attgcggagc ttgacaccct tggagaggag tcttacaagg    720

atagcacctt gattatgcag cttcttcgtg ataaccttac gttgtggacc tcggatatgc    780

aggatgatgg gactgatgag atcgaagtac catcgaaagc agaggagcag cagtaatgtg    840

agtgaagcct ccttgtttag gattgcaatc ctatggactg tgctcattga tcggaatttg    900

ctgtttgtgt agttgtgaat tccgtgaatt gtaatacgta aaagtgctgt ttcttgccat    960

ttgttgtttt cagcaaagat tacttttttg tgcagtatgg tcccttgtat ttggatgctc   1020

cattggtgga aatgaattct tgttgttagg ggaacag                            1057
```

```
<210> SEQ ID NO 185
<211> LENGTH: 873
<212> TYPE: DNA
<213> ORGANISM: Artificial
<220> FEATURE:
<223> OTHER INFORMATION: Synthetic

<400> SEQUENCE: 185

aaatcctgaa ttgcaccaac tagtacaacg acaacaatgt cttctgagag agaaaccaag     60

accttccttg cccggctctg tgagcaggct gaccgatacg acgagatggt caactacatg    120

aaggacgtcg ctaagtccgg tgaggagctt actgtcgacg agcgaaatct ggtttccgtc    180

gcttacaaga acgttatcgg cgctcgacga gccagctgga gagtcatttt ccccatagag    240

cagaaggagg aggccaaggg tggcacccac catctcgagc ttctcaagac ctacagagcc    300
```

-continued

```
cagattgagg gagagctcga agacatctgg agcgatgttc ttgatattct caacaaacaa    360

ctcctcccca aaggcgagaa cgccgagtct aaggtcttct actacaagat gaagggtgac    420

taccatcgat accttgccga gttcacctcc ggcgagaagc gaaaagaggc tgccactgcc    480

gctcacgagt catacaagag cgccactgat gttgcccaga ctgagctcag ctcaactcac    540

cccatccgac ttggtctcgc tctcaacttc tccgtcttct actacgagat tctcaactcg    600

ccagaccgtg cttgccacct tgccaagcag gctttcgatg atgccatcgc tgagctcgac    660

actctctccg aggagtcttt ccgagactct accgtcatta tgcagcttct gcgagacaac    720

ctgaccctct ggaagaacga cctcgaagag tctctgcaag cccagcagtc tgaggagacc    780

cctgccaccg atgctgccgc tgcttccacc gaggctgctg cccccaagga ggaggccaag    840

cccgctgctg aggagcccaa ggagtagagt agt                                 873
```

<210> SEQ ID NO 186
<211> LENGTH: 1043
<212> TYPE: DNA
<213> ORGANISM: Artificial
<220> FEATURE:
<223> OTHER INFORMATION: Synthetic

<400> SEQUENCE: 186

```
tcgacccacg cgtccgggcg gcagcgcacg gcgaggaaca ggtgagtgcc cgtggatgtg     60

atctagatct accctccaag ccccaaaatc tcagtagaaa tcctccaaat cgcgccgccg    120

gaagagagat ccaatccacc actgtcccca tttctcggct tgttccaggg atgtcgaatc    180

ttcgcgagga gaatgtctac atggccaagc tcgcggagca ggccgagcgc tacgacgaga    240

tggtggaatt catggagaag gtggtcaagg ccgtggacgt ggaggagctg acggtcgagg    300

agcggaatct cctgtcggtg gcctacaaga acgtgatcgg cgcccgccgg gcatcgtgga    360

ggataatctc ctccatcgag caaaaggagg aatccaaggg caacgacgac cacgtctcga    420

tgatcaagga gtaccgtgcc aaggtggagt cggagctgag caccatttgc gacagcatcc    480

tcaagctgct ggacagccat ctcatcccct catcgtccag tggcgagtcc aaggtcttct    540

acttgaagat gaagggtgac taccaccgat acttggccga gtttaagacc ggggccgaga    600

ggaaagaggc cgcggagaac actctcctcg cctacaagtc ggcccaggac atcgctctca    660

cacagctgcc gccgacgcat cccatccggc tgggtctcgc tctcaatttt tcggtcttct    720

actacgagat tttgaattcg cccgatcgag cttgtacgct tgccaagcag gcatttgacg    780

aggccatagc cgagctggac actttgggag aggaatctta caaggatagt actctgatca    840

tgcagctgct gcgcgataat ctaacgctgt ggacctcaga catgcaggag gaaggtgccg    900

gcgaggggaa ggacgacaag ccgtgagtaa aataatacgt tcgaatttcg ttttctatgc    960

tactagctag ctgtttagac gccttctctc tcaacacctt ggtactgttg attctttcgt   1020

tcctgaatac attatttggc ttg                                           1043
```

<210> SEQ ID NO 187
<211> LENGTH: 458
<212> TYPE: DNA
<213> ORGANISM: Artificial
<220> FEATURE:
<223> OTHER INFORMATION: Synthetic

<400> SEQUENCE: 187

```
tgctgtccgt ggcgtacaag aacgtcatcg gcgcgcgcag ggcgtcgtgg cgcatcgtgt     60

cctccatcga gcagaaggag gaaggccgcg gcgccgcggg ccacgccgcc gccgcgcgct    120
```

-continued

```
cctaccgcgc ccgcgtcgag gccgagctct ccaacatctg cgcggggata ctccgcctcc    180

tcgacgagcg cctcgtcccc gccgccgccg ccgtcgacgc caaggtcttc tacctcaaga    240

tgaagggcga ctaccaccgc tacctcgccg agttcaagac cggagccgag cgcaaggacg    300

ccgccgacgc caccctcgcc ggctaccagg ccgcgcagga catagccatg aaggagctgt    360

cgccgacgca ccccatcaga ctgggccttg cgctcaactt ctccgtgttc tactacgaga    420

tcctcaactc gcccgaccgc gcgtgcacgc tcgccaag                            458
```

<210> SEQ ID NO 188
<211> LENGTH: 500
<212> TYPE: DNA
<213> ORGANISM: Artificial
<220> FEATURE:
<223> OTHER INFORMATION: Synthetic

<400> SEQUENCE: 188

```
ccaaaatttc cgacgccaga gcgcgaggag acgcacacag agacttggca tttgtagagt     60

ttttagattt atagatagca aagatgtcgg cacaggcgga gctttcccgt gaggagaatg    120

tgtacatggc caagctcgct gagcaagccg agaggtacga ggagatggtc gaattcatgg    180

agaaggtggc caagacggtt gactctgagg agctcaccgt ggaggagcgc aacctcctgt    240

ctgttgcata caagaatgtg attggagccc gccgtgcgtc atggcgcatt atctcctcca    300

ttgagcagaa ggaggaaagc cgtggtaacg aggaccgtgt cacactcatc aaggactacc    360

gtggcaagat cgagactgag ctcaccaaga tttgcgacgg cattctcaag ctgcttgaat    420

cccaccttgt cccctcttcc actgcccctg agtccaaggt cttctacctc aaaatgaagg    480

gtgactacta caggtacctt                                                500
```

<210> SEQ ID NO 189
<211> LENGTH: 371
<212> TYPE: DNA
<213> ORGANISM: Artificial
<220> FEATURE:
<223> OTHER INFORMATION: Synthetic

<400> SEQUENCE: 189

```
aattcggcac cagaatccat cctctttcgc ttaaactttc tctctctaca acaacaatgt     60

cggctctgct cacagaaaat ctcagccacg aacaatacct ctacttagcc aagctcgccg    120

aacaagccga acgctatgaa gaaatggtcc agtacatgga caaactagtc ctcagttcca    180

ctccggccgc cgaactcacc gtcgaggaac gaaacctcct ttccgtcgct tacaaaaacg    240

tgatcggctc tcttcgtgcc gcgtggcgta tcgtatcctc cattgagcag aaagaggaat    300

cgcgcaagaa cgaagaacac gtgtcgctcg ttaaggagta cagaggtaaa gtcgagaatg    360

agttaacgga g                                                         371
```

<210> SEQ ID NO 190
<211> LENGTH: 1160
<212> TYPE: DNA
<213> ORGANISM: Artificial
<220> FEATURE:
<223> OTHER INFORMATION: Synthetic

<400> SEQUENCE: 190

```
gtacgagacc actcgaaccc gacccgcctc gccgccgccg ccaccgaagt aatcccttaa     60

ttggtcaaaa tgtctcggga ggagaatgtc tacatggcca agctggccga gcaggctgaa    120
```

-continued

```
aggtatgagg agatggttga gtacatggag aaggttgcaa agactgtaga tgtggaagag    180

ctcactgttg aggagcgcaa cctcttgtct gttgcttaca agaatgtgat tggtgcccgc    240

cgtgcctcct ggcgtattgt ctcatccatt gaacagaagg aggagggtcg tggcaatgag    300

gaacatgtta ctctgatcaa ggagtaccgt ggcaagattg aagctgagct gagcaagatt    360

tgcgatggta tcctgaagtt gcttgactca caccttgtgc cctcatctac tgctgcagaa    420

tctaaggtgt tttacctcaa gatgaagggt gattaccaca ggtaccttgc ggaatttaag    480

actggtgccg agagaaagga agctgctgag agcacaatgg tggcttacaa ggctgctcag    540

gatattgctc tggcggatct tgctcccacc catcccataa ggcttggact ggcacttaac    600

ttctctgtgt tctactacga gattctaaac tctccagaca aggcttgcaa ccttgctaag    660

caggcgtttg acgaagccat ctccgagttg gataccctcg gggaggagtc ttacaaggac    720

agcactttga tcatgcagct cctgagggac aacttgaccc tctggacctc tgacctcacg    780

gaggacggtg gtgatgaggt gaaagaagcc tccaagggcg acgcctgcga gggccagtaa    840

aatgggaaga tcgatcgatc gatggctccg catgttattg gagaccatcg atttagatgc    900

ctcatgctgc tgtcaccatg atggatggat tcttctcctg ttctactaga atgtttttct    960

tcctgtcccc ccttcctctc tcttctctgg tttttactag ggtggtagcg gtcgaattag   1020

ttcttcccat tgctttgcat ttggtgctag tggtccgtct gggctgattg ttttcctctg   1080

gatatgactc tcgtgtgtgt tgtctccaga tagtgtttta ttgagcaata tttaaagttg   1140

tcgtccacct cctcgatgtt                                               1160
```

<210> SEQ ID NO 191
<211> LENGTH: 953
<212> TYPE: DNA
<213> ORGANISM: Artificial
<220> FEATURE:
<223> OTHER INFORMATION: Synthetic

<400> SEQUENCE: 191

```
gaatttgaac tccacctgag cacaggagaa gccgcagcca ctgagatttg accttctgtt     60

tctaccagaa aaacacaaac agtgaagatg tcgcagcctg ctgagctttc ccgtgaggag    120

aatgtgtaca tggctaagct tgcagagcag gccgagaggt atgaggagat ggttgagttc    180

atggagaagg ttgctaagac agttgactct gaggagctca ctgttgagga gcgcaacctt    240

ctatcagttg cttacaagaa tgttattggt gctcgccgtg cgtcatggcg catcatatca    300

tccattgaac agaaggaaga gagccgtggt aatgaggatc gttgcacgct catcaaggaa    360

tacaggggaa agattgaaac tgagctctcc aagatctgtg atggcatcct caagcttctt    420

gactcccacc ttgtgccttc atccactgct ccagagtcca aggtcttcta cctcaagatg    480

aaaggcgact actacaggta cctcgcagag tttaagactg gagctgagag gaaggatgct    540

gctgagaaca ccatggtggc atacaaagcc gctcaggata ttgccctggc agagttgccc    600

ccaactcatc ctatcagact tgggctggcc ctcaacttct cggtgtttta ttacgagatc    660

ctcaactctc ctgaccgtgc ttgcaatctt gcaaagcagg ctttcgatga ggctatctca    720

gagctggaca ctctgagtga ggaatcctac aaggacagca ctttgatcat gcagcttctg    780

cgtgataacc tgacgctgtg gacttccgat atctcggagg atgctgctga ggaaatcaag    840

gaggccccca agggcgaatc aggagatgga cagtgaacat gatcgaatgc gtgcgcccac    900

aaactagaat agtgacgctg caaatgtgct gtgggttatc gtttcatttt ata          953
```

<210> SEQ ID NO 192
<211> LENGTH: 554
<212> TYPE: DNA
<213> ORGANISM: Artificial
<220> FEATURE:
<223> OTHER INFORMATION: Synthetic

<400> SEQUENCE: 192
cccacgcgtc cgctccacct gagcacagga gaagccgcag ccactgagaa aaacacaaac 60
agtgaagatg tcgcagcctg ctgagctttc ccgtgaggag aatgtgtaca tggctaagct 120
tgcagagcag gccgagaggt atgaggagat ggttgagttc atggagaagg ttgctaagac 180
agttgactct gaggagctca ctgttgagga gcgcaacctt ctatcggttg cttacaagaa 240
tgttattggt gctcgccgtg cgtcatggcg catcatatca tccattgaac agaaggaaga 300
gagccgtggt aatgaggatc gttgcacgct catcaaggaa tacaggggaa agattgaaac 360
tgagctctcc aagatctgtg atggcatcct caagcttctt gactcccacc ttgtgccttc 420
atccactgct ccagagtcca aggtcttcta cctcaagatg aaaggcgact actacaggta 480
cctcgcagag tttaagactg gagctgaaag gaaggatgct gctgagaaca ccatggtggc 540
atacaaagcc gctc 554

<210> SEQ ID NO 193
<211> LENGTH: 629
<212> TYPE: DNA
<213> ORGANISM: Artificial
<220> FEATURE:
<223> OTHER INFORMATION: Synthetic

<400> SEQUENCE: 193
acgcgtcgcc ctaactaacc ctaaccgcca aatattgggg gatttatcat ttgggtttgg 60
atcgagtcag tgcagtctac ggtctgcaag catgtccggg cacgatgagc acgtgttcat 120
ggctaagctc gccgaacagg ccgagcgcta tgaggagatg gccgagttca tggagaaggt 180
tgctggccat ggggacgacc tcactgccga agagcgcaac ctcctctctg tcgcctacaa 240
gaacgtggtg ggtgctagac gtgcctcctg gcgcatcatc tcctccattg agcagaagga 300
ggagggcaag ggcaaccagg accatgtcag tgccatccgt gactaccggg ccaagatcga 360
ggccgagctt tgcactatat gtgggggtgt cctcaagatc ctggacacgc acctcatccc 420
ggccggagaa gctgctgagt cgaaggtctt ctacctcaag atgaagggtg attaccatcg 480
ttacgtggct gaattcaaga ctggttctga aaggaaggag tctgctgaga acaccatgtc 540
tgcctataag tctgcccagg atattgccct tgcagagctt gcttcaactc atcctattcg 600
cctgggactt gcgctcaatt tctcggtat 629

<210> SEQ ID NO 194
<211> LENGTH: 599
<212> TYPE: DNA
<213> ORGANISM: Artificial
<220> FEATURE:
<223> OTHER INFORMATION: Synthetic

<400> SEQUENCE: 194
gaattcaaga tcatgtttct attattaaag aatatagggg aaagattgaa tctgaacttc 60
ataagatttg tcaagggatt ttagggcttt tggattccca tcttattcct tcatcaactg 120
ctgctgaatc taaggtgttt taccttaaga tgaagggtga ttaccacagg tatttggcta 180
agttagctga acaagctgaa cgatatgaag agatggttga atttatggag aacgttgcaa 240

-continued

```
aaactgttga ttctgatgaa ttatcagttg aggaacgaaa cctgttgtct gttgcttata    300

agaatgtgat tggagctagg agagcttcat ggaggattat ttcaagtatt gaacaaaagg    360

aagaaagccg tgggaatgaa gatcatgttt ctattattaa agaatatagg ggaaagattg    420

aatctgaact tcataagatt tgtcaaggga ttttagggct tttggattcc catcttattc    480

cttcatcaac tgctgctgaa tctaaggtgt tttaccttaa gatgaagggt gattaccaca    540

ggtatttggc tgagtttaaa tctggtagtg acaggaaaga agctgctgag agtacattg     599
```

<210> SEQ ID NO 195
<211> LENGTH: 727
<212> TYPE: DNA
<213> ORGANISM: Artificial
<220> FEATURE:
<223> OTHER INFORMATION: Synthetic

<400> SEQUENCE: 195

```
ttgcaagttc cattccctgt tcttctctct caacgaagca tcaacccccc ttttctccca     60

gaaccgcgtc tcatcgcacc tgccataaaa ctccaaaaaa tctcaaaaac caaccgtcaa    120

aatgggtcac gaagatgctg tttatctggc caagctcgcc gagcaggccg agcgatatga    180

ggagatggtc gagaacatga agatcgtcgc ctccgaggac cgcgacctga ccgtcgagga    240

gcgcaacctc ctctccgtcg cctacaagaa cgtcattggt gcccgccgtg cctcttggag    300

aatagtcact tccatcgagc agaaggagga gtctaagggc aactcttccc aggttaccct    360

tatcaaggag taccgccaga agattgaggc cgagcttgcc aagatctgcg atgacattct    420

cgatgttctt gacaagcacc tgattccttc tgccaagtct ggagagtcca aggtcttcta    480

ccacaagatg aagggtgact accaccgtta ccttgccgag ttcgccattg gcgaccgccg    540

caaggactcc gccgacaagt ctctcgaggc ttacaaggct gctaccgagg ttgcccagac    600

cgagctgcct cctacccacc ctatccgcct gggtcttgcg ctcaacttct ccgtcttcta    660

ctacgagatc ctcaacgccc ctgaccaggc ttgccacctc gctaagcagg catttgacga    720

tgctatt                                                              727
```

<210> SEQ ID NO 196
<211> LENGTH: 664
<212> TYPE: DNA
<213> ORGANISM: Artificial
<220> FEATURE:
<223> OTHER INFORMATION: Synthetic

<400> SEQUENCE: 196

```
gtcaggagct gagaggaagg aagcagctga gaacactctt gtggcataca agtctgccca     60

ggatattgca ctcgctgacc tgcctacaac tcacccaata aggcttggac ttgcactgaa    120

cttctcagtg ttctactatg agatcctgaa ctcaccagac cgtgcttgca accttgcaaa    180

gcaggcgttc gacgatgcta ttgctgaact ggacactctt ggcgaggagt cttacaagga    240

cagcaccttg atcatgcaac ttcttcgtga caatctgact ctctggacct ctgacaatgc    300

ggaggatggt ggtgacgaga tcaaggaagc agcgaagcct gaaggagagg gccactaatc    360

tgtcctgaag tctatttctg agtccattta ctcagctacc tgctgtatta ctggatcata    420

agatgtacta ggatcaattg ctatgtggaa tcataagatt agggctgcgt atgtcaaaat    480

gtgtcgagct gaagtaccca gtggacacag tttatgtgca ctacattgct tccgtgactt    540

atttactagt taattagcaa ctttcaacca cttcctgtat ttgcagcaca ttattagtat    600

cgctgtatta gcgttttcca tgggctggtt atgattgaga atacaggcca ggcattgcat    660
```

gtcc 664

<210> SEQ ID NO 197
<211> LENGTH: 708
<212> TYPE: DNA
<213> ORGANISM: Artificial
<220> FEATURE:
<223> OTHER INFORMATION: Synthetic

<400> SEQUENCE: 197
acgcactctg tcgagaatcc attctatttc gcctaaactt tctctctcta caacaacaac 60
aatggcggct ctgctcacag acaatctcaa ccgcgaacaa tacctctact tagccaaact 120
cgccgaacaa gccgaacgct atgaagaaat ggtccagtac atggacaaac tagtactcag 180
ttccactccc gccgccgaac tcaccgtcga ggaacgaaac ctcctttccg tcgcttacaa 240
aaacgtgatc ggctctcttc gtgccgcgtg gcgtatcgta tcctccattg agcagaaaga 300
ggaatcgcgt aagaacgaag aacacgtttc gctcgttaag gagtacagag gtaaagttga 360
gaatgagtta acggaggttt gtgctggtat cctcaagttg cttgagtcaa atctcgagcc 420
gtctgcttct acgggtgaat cgagggtgtt ttacctcaaa atgaaaggtg attattaccg 480
gtatctagcg gagtttaagg ttggagatga gcggaagcag gctgctgaag acactatgaa 540
ttcttataag gctgctcagg aaattgcact agcagatctg cctccaacac atcctataag 600
gctgggtctt gcacttaatt tctcagtctt ctactttgag attctgaact catctgacaa 660
agcttgtagt atggcaaaac agggcttttg aggaagccat agctgagc 708

<210> SEQ ID NO 198
<211> LENGTH: 378
<212> TYPE: DNA
<213> ORGANISM: Artificial
<220> FEATURE:
<223> OTHER INFORMATION: Synthetic

<400> SEQUENCE: 198
gttataaatc cttatctttt tcaacacaca gattaaaatc ttcagaaaga gagagagaga 60
tcccaaaatg ggtgaacgtg agaacttcgt atacatagct aagcttgccg agcaagctga 120
acgctatgat gagatggctg atgcgatgaa gaatcttgca aatatggatg ttgaattgac 180
agcggaagag aggaatttgt ttctgttggg ttataagaat gtggttggag ctaggagagc 240
atcgtggagg atcttgtctt ccatcgagca gaaggaagag tctagaggaa atgagcagaa 300
cgtgaagcgg attaaggagt accagcaaaa agtggagtca gagctcaccg acatttgcaa 360
taatatcatg accgcgat 378

<210> SEQ ID NO 199
<211> LENGTH: 565
<212> TYPE: DNA
<213> ORGANISM: Artificial
<220> FEATURE:
<223> OTHER INFORMATION: Synthetic

<400> SEQUENCE: 199
gggtttggat cgagtcagtg cagtctacgg tctgcaagca tgtccgggca cgatgagcac 60
gtgttcatgg ctaagctcgc cgaacaggcc gagcgctatg aggagatggc cgagttcatg 120
gagaaggttg ctggccatgg ggacgacctc actgccgaag agcgcaacct cctctctgtc 180
gcctacaaga acgtggtggg tgctagacgt gcctcctggc gcatcatctc ctccattgag 240

-continued

```
cagaaggagg agggcaaggg caaccaggac catgtcagtg ccatccgtga ctaccgggcc    300

aagatcgagg ccgagctttg cactatatgt gggggtgtcc tcaagatcct ggacacgcac    360

ctcatcccgg ccggagaagc tgctgagtcg aaggtcttct acctcaagat gaagggtgat    420

taccatcgtt acgtggctga attcaagact ggttctgaaa ggaaggagtc tgctgagaac    480

accatgtctg cctataagtc tgcccaggat attgcccttg cagagcttgc ttcaactcat    540

cctattcgcc tgggacttgc gctca                                          565
```

<210> SEQ ID NO 200
<211> LENGTH: 634
<212> TYPE: DNA
<213> ORGANISM: Artificial
<220> FEATURE:
<223> OTHER INFORMATION: Synthetic

<400> SEQUENCE: 200

```
ttgcagataa cccgtcttgt tcatctctct ctctcatctt ctctagctct ctctctgtct     60

gtcccctgtt tccctgtctt agaccatgac tccgtcgatg gagggggggca agcgggagga    120

gaatgtgtac atggcgaagc ttgcggagca ggccgagcgg tacgaggaga tggcggagtt    180

catggatgcc gtcgtcaagg acggtgctga cgagatgtcg gtggaggagc ggaacctcct    240

ctccgtcgcg tacaagaacg tgattggcgc gcgtcgcgcc tcctggcgca tcgtctcctc    300

cattgagcag cgcgaggaga gcaagggcaa ccaggagcac gtctctgcca tccgcgacta    360

ccgtgcctcc gtcgaaaccg agctcaccaa gatctgcaaa agcatcctta gcctcctcga    420

gatgcacctt gtcccttccg ccaccacccc cgaatccaaa gtcttctacc tcaaaatgaa    480

gggcgactac caccgctacc ttgcggagtt caaaatcggg gcggaccgca aaaaactggc    540

gataaatact ctcaccgcct acaaatctgc tcaggaaata gccttggctg agctgccttc    600

aacacacccc attcgtttgg ggcttgctct aaat                                634
```

<210> SEQ ID NO 201
<211> LENGTH: 499
<212> TYPE: DNA
<213> ORGANISM: Artificial
<220> FEATURE:
<223> OTHER INFORMATION: Synthetic

<400> SEQUENCE: 201

```
gtatgctcac agctcacctc actcctcttt atttttaggg ttcattggaa ggaagagaga     60

gagagagaga gagagagaga gagtcttgct gcaccaaccc aacccaagga gctcttcttt    120

gtgttctact cccatgggta ttgagaagga gagagagagc catgtctaca tggccaagct    180

tgctgagcag gcagagagat atgatgaaat ggtggattcc atgaaaaaga ttgccaagtt    240

ggacgtcgag ctgaccattg aggagagaaa tctgctttcc gtgggctata aaaatgtgat    300

tggggctcgg agggcctcgt ggcgaatcct ctcctcaatt gagcagaaag aggagagcaa    360

gggcaatgaa acaaatgcca agcgcattga gagttaccga cataaggttg aggaagaact    420

ctctggaatc tgcaaggaca tcctgactac catcgatgag tatctcatcc cctcgtctgg    480

cacggcggaa tccaccgtt                                                 499
```

<210> SEQ ID NO 202
<211> LENGTH: 486
<212> TYPE: DNA
<213> ORGANISM: Artificial
<220> FEATURE:
<223> OTHER INFORMATION: Synthetic -continued

<400> SEQUENCE: 202

```
gacatgggca tcgagaagga gcgagagagc cttgtctacc tatccaagct ctccgagcag     60
gcagaacgct atgacgaaat ggtggagtcg atgaagaaag tagctaagtt ggatgtagag    120
cttacgattg aggagaggaa tttgctctca gtggggtata agaatgtgat cggagcgcga    180
agggcctcgt ggcgaattct ctcctccatt gagcagaaag aagagagcaa gggcaatgag    240
accaatgtaa aacgcatcaa ggagtaccgc aacaaagtgg aggaagagct ttccaagatt    300
tgcagtgaca tcctaactat catcgatgag catcttatcc cctcatctgg cacagcagaa    360
tctaccgttt tctattacaa aatgaaaggg gattattatc gctaccttgc tgagttcaag    420
acaggacatg agagaaagga agctgcagat caatctctga aagcttatca gactgcaagt    480
gacacg                                                               486
```

<210> SEQ ID NO 203
<211> LENGTH: 629
<212> TYPE: DNA
<213> ORGANISM: Artificial
<220> FEATURE:
<223> OTHER INFORMATION: Synthetic

<400> SEQUENCE: 203

```
gaattcagag atgatgataa atcaaacata atagggatgt taactacacc ccacacatcg     60
tcatcagcat cctcttcatc ttcttcgaat cctagtcaac aagaaaaaat ttctgtcgta    120
tccatagtgg gcatgggtgg gttaggaaaa actacacttg ctcaattggt ctacaaagat    180
gactcgataa tgagacattt taagaccaga gcatgggttt gtgtttctga tgtttttgat    240
atcaaaaaaa tcaaaactaa cataatcgag tcggttacaa aaaacaagtg tgttgatttt    300
tcaaatgatg atgtcttaac taataaactt caagaagagt tgggtaacaa gttttttta    360
ctagtactag atgatgtttg gagtgacaat ccagaagatt gggataacct tagaggtttg    420
ctaagtgtgg gtgcttgtgg aagtaaagtc ttagtcacaa cacgtagcca caaagttgct    480
tctgcttccg gaggtgttgt tcctccatac aaactagaag acctacctca tagtgtttgt    540
tggtctatca tcaagaccaa agctttttct ccgggtgggg caatagtcag tacaaaaatg    600
acatgtatag gacaggagat tgcaagaaa                                      629
```

<210> SEQ ID NO 204
<211> LENGTH: 674
<212> TYPE: DNA
<213> ORGANISM: Artificial
<220> FEATURE:
<223> OTHER INFORMATION: Synthetic

<400> SEQUENCE: 204

```
gaattccaga gatgaattgg tacgtaaaca gtttgggcta acaatgtggg tctacgtatc     60
tgagcatttt gacgtgataa agcttttgac aaaaattatg gaatcctcaa ctaatgataa    120
gtttgatact ttgtcgaact atgatgtact agtcagtaaa gttcaggaac agctaaatgg    180
gaaaagatat ttgctagtgc tcgacgattt atggaatgag aatgctgatc aatgggatag    240
actctgcagc gcgttgcttg ttggggctca agggagtaaa atattaatca ctactcgcaa    300
aagtcaagtt gcagatatgg ttagggggag tattcttcct tacaaattgg gaaaggaata    360
gcaaagaaat gtagtggcgt acctcttgca gcaaagttcc tgggaagtct aatgcgctca    420
aaaaataaag aagctgattg gttgtcgatt caacaacttg atgttttgaa tacaagcgaa    480
```

-continued

```
atcatgccga tactaaagtt gagctatgat aacttgtcgt ctgagttgaa acaatgtttc    540

tcctactgct ctatatttcc caaagattgg gagataaata gagtaactct gattcagttg    600

tggatagcag aagggtttct cgacacttgt aacctaggaa acagaagatc aattgaagac    660

atcgcggatg aata                                                      674
```

<210> SEQ ID NO 205
<211> LENGTH: 670
<212> TYPE: DNA
<213> ORGANISM: Artificial
<220> FEATURE:
<223> OTHER INFORMATION: Synthetic

<400> SEQUENCE: 205

```
atcaatttcc tcgcttccgc caaaatggct tctttgacac aacaattcgg agggctgaaa     60

tgcccaccaa tttcaacagc aagggttgaa tctaagaagc ttaaggtgaa tcccattaat    120

catcagaata agaaggctaa caaagcaaga gtagtagcac aagctgcagc agtggtcaca    180

aatgcacaaa caagagaaag acaaaagctt aaggagatgt tcgaggatgc ctatgaacga    240

tgccgtactg cacctttgga aggtgttgcc tttactgttg aagattttca ctctgccctt    300

gaaaaatatg attttgactc cgaagttggt accaaggtca aaggaacagt tttctctgtg    360

gatgcaaatg gagctctagt tgacatcact gctaaatcat ctgcatactt gcctttacgg    420

gaggcttcac ttcacaccat caagcacgta gaggaagctg gaatatttcc tggtttgcgt    480

gaggagtttg tggtggttgg cgaaaatgaa gctgatgata gtttggtttt gagcttgcgt    540

tcgattcaat atgaccttgc atgggaacga tgtaggcagc tacaagctga agatgttgtt    600

gtcaaaggca aggtcgttgg tgcaaataaa ggtggagtgg tggctctggt ggaggggctt    660

cgtggttttg                                                           670
```

<210> SEQ ID NO 206
<211> LENGTH: 1523
<212> TYPE: DNA
<213> ORGANISM: Artificial
<220> FEATURE:
<223> OTHER INFORMATION: Synthetic

<400> SEQUENCE: 206

```
gaattcaagc agtgggagga gcctgggctc tgacggggtg cctgttgaag aatgagccgg     60

cgactcatag gcagtggctt ggttaaggga acccaccgga gccgtagcga aagcgagtct    120

tcatagggca attgtcactg cttatggacc cgaacctggg tgatctatcc atgaccagga    180

tgaagcttgg gtgaaactaa gtggaggtcc gaaccgactg atgttgaaga atcagcggat    240

gagttgtggt taggggtgaa atgccactcg aacccagagc tagctggttc tccccgaaat    300

gcgttgaggc gcagcagtcg actagacatc taggggtaaa gcactgtttc ggtgcgggcc    360

gcgagagcgg taccaaatcg aggcaaactc tgaatactag atatgacccc aaaatatggg    420

gtcaaggtcg gccagtgaga cgatggggga taagcttcat cgtcgagagg gaaacagccc    480

ggatcaccag ctaaggcccc taaatgaccg ctcagtgata aaggaggtag gggtgcagag    540

acagccagga ggtttgccta gaagcagcca cccttgaaag agtgcgtaat agctcactga    600

tcgagcgctc ttgcgccgaa gatgaacggg gctaagcgat ctgccgaagc tgtgggatgt    660

aaaaatgcat cggtagggga gcgttccgcc ttagagggaa gcacccgcgc gagcaggtgt    720

ggacgaagcg gaagcgagaa tgtcggcttg agtaacgcaa acattggtga gaatccaatg    780

ccccgaaaac ctaagggttc ctccgcaagg ttcgtccacg gagggtgagt cagggcctaa    840
```

```
gatcaggccg aaaggcgtag tcgatggaca acaggtgaat attcctgtac taccccttgt    900

tggtcccgag ggacggagga ggctaggtta gccgaaagat ggttatcggt tcaaggacgc    960

aaggtgacct tagggtaaga aggggtagag aaaatgcctc gagccaatgt ccgagtacca   1020

ggcgctacgg cgctgaagta actcatgcca tactcccagg aaaagctcga acgaccttca   1080

acaaaagggt acctgtaccc gaaaccgaca caggtgggta ggtagagaat acctaggggc   1140

gcgagacaac tctctctaag gaactcggca aaatagcccc gtaacttcgg gagaaggggt   1200

gcctcctcac aaaggggggtc gcagtgacca ggcccgggcg actgtttacc aaaaacacag   1260

gtctccgcaa agtcgtaaga ccatgtatgg gggctgacgc ctgcccagtg ccggaaggtc   1320

aaggaagttg gtgacctgat gacagggaag ccggcgaccg aagccccggt gaacggcggc   1380

cgtaactata acggtcctaa ggtagcgaaa ttccttgtcg ggtaagttcc gacccgcacg   1440

aaaggcgtaa cgatctgggc actgtctcgg agagaggctc ggtgaaatag acatgtctgt   1500

gaagatgcgg actacctgca cct                                          1523
```

<210> SEQ ID NO 207
<211> LENGTH: 657
<212> TYPE: DNA
<213> ORGANISM: Artificial
<220> FEATURE:
<223> OTHER INFORMATION: Synthetic

<400> SEQUENCE: 207

```
cgcgtccggg ataattggag atctgaccgc gtgctgttga agaatgagcc ggcgacttat     60

aggcggcggc ctggttaagg aaacccaccg gagccgtagc gaaagcgagt cttcccaggg    120

gcaactgtcg ctgcttatgg acccgaaccc gggtgatcta tccatgacca ggatgaagct    180

tggatgaaac taggtggagg tccgatattg actgatgttg aaaaatcagc ggatgagtcg    240

tggttagggg tgaaatgcca ctcgaacccg gagctagctg gttctccccg aaatgcgttg    300

aggcgcagcg gttgacgagg ctacctgggg gtaaagcact gttacggtgc gggctgcgag    360

atcggtacca aaccgaggca aactctgaat actaggtatg agccccgagt aacacggggg    420

ctgagggtca gccagtgaga cggtggggga taagcttcac cgtcgagagg ggaacagccc    480

ggatcaccag ctaaggcccc taaatgaccg ctcagtggta aaggaggtag gagtgcaaag    540

acagccggga ggtttgccca gaagcagcca cccttgaaag agtgcgtaat agctcactga    600

tcaagcgctc ctgcgccgag gatgaacggg actaagcggt ctgccgaagc tgtggga      657
```

<210> SEQ ID NO 208
<211> LENGTH: 283
<212> TYPE: DNA
<213> ORGANISM: Artificial
<220> FEATURE:
<223> OTHER INFORMATION: Synthetic

<400> SEQUENCE: 208

```
aattcggcac gagacccttg aaagagtgcg taatagctca ctgatcgagc gctcttgcgc     60

cgaagatgaa cggggctaag cgatctgccg aagctgtggg atgtcaaaat gcatcggtag    120

gggagcgttc cgccttaggg ggaagcaacc gcgcgagcgg cggtggacga agcggaagcg    180

agaatgtcgg cttgagtaac gcaaacattg gtgagaatcc aatgccccga aaacccaagg    240

gttcctccgc aaggttcgtc cacggagggt gagtcagggc cta                      283
```

<210> SEQ ID NO 209

-continued

<211> LENGTH: 1250
<212> TYPE: DNA
<213> ORGANISM: Artificial
<220> FEATURE:
<223> OTHER INFORMATION: Synthetic

<400> SEQUENCE: 209

```
cggacgcgtg gggccagggc tctgaccgcg tgcctgttga agaatgagcc ggcgactcat     60

aggcagtggc ttggttaagg gaacccaccg gagccgtagc gaaagcgagt cttcataggg    120

caattgtcac tgcttatgga cccgaacctg ggtgatctat ccatgaccag gatgaagctt    180

gggtgaaact aagtggaggt ccgaaccgac tgatgttgaa gaatcagcgg atgagttgtg    240

gttaggggtg aaatgccact cgaacccaga gctagctggt tctccccgaa atgcgttgag    300

gcgcagcagt tgactggaca tctaggggta aagcactgtt tcggtgcggg ccgcgagagc    360

ggtaccaaat cgaggcaaac tctgaatact agatatgacc tcaaaataac aggggtcaag    420

gtcggctagt gagacgatgg gggataagct tcatcgtcga gagggaaaca gcccggatca    480

ccagctaagg cccctaaatg atcgctcagt gataaaggag gtaggggtgc agagacagcc    540

aggaggtttg cctagaagca gccacccttg aaagagtgcg taatagctca ctgatcgacc    600

gctcttgcgc cgaagatgaa cggggctaag cgatctgccg aagctgtggg atgtaaaaat    660

acatcggtag gggagcgttc cgccttagag agaagcctcc gcgcgagcgg tggtggacga    720

agcggaagcg agaatgtcgg cttgagtaac gcaaacattg gtgagaatcc aatgccccga    780

aaacctaagg gttcctccgc aaggttcgtc cacggagggt gagtcagggc ctaagatcag    840

gccgaaaggc gtagtcgatg gacaacaggt gaatattcct gtactgcccc ttgttggtcc    900

cgagggacgg aggaggctag gttagccgaa agatggttat cggttcaaga acgtgaggtg    960

tccctgcttt gtcagggtaa gaaggggtag agaaaatgcc tcgagccaat gttcgaatac   1020

caggcgctac ggcgctgaag taacccatgc catactccca ggaaaagctc gaacgacttt   1080

gagcaagagg gtacctgtac ccgaaaccga cacaggtggg taggtagaga atacctaggg   1140

gcgcgagaca actctctcta aggaactcgg caaaatagcc ccgtaacttc gggagaaggg   1200

gtgcctcctc acaaaggggg tcgcagtgac caggcccggc cgtaatggcc              1250
```

<210> SEQ ID NO 210
<211> LENGTH: 583
<212> TYPE: DNA
<213> ORGANISM: Artificial
<220> FEATURE:
<223> OTHER INFORMATION: Synthetic

<400> SEQUENCE: 210

```
cccacgcgtc cgcccacggg tccggaggtc cgaaccgact gatgttgaag aatcagcgga     60

tgagttgtgg ttaggggtga aatgccactc gaacccagag ctagctggtt ctccccgaaa    120

tgcgttgagg cgcagcagtt gactggacat ctaggggtaa agcactgttt cggtgcgggc    180

tgcgcgagcg gtaccaaatc gaggcaaact ctgaatacta gatatgaccc aaaaataaca    240

ggggtcaagg tcggccagtg agacgatggg ggataagctt catcgtcgag agggaaacag    300

cccggatcac cagctaaggc ccctaaatga ccgctcagtg ataaaggagg tgggggtgca    360

aagacagcca ggaggtttgc ctagaagcag ccacccttta aagagtgcgt aatagctcac    420

tgatcgagcg cccttgcgct gaagatgaac ggggctaagc gatctgccga agctgtggga    480

tgtcaaaatg catcggtagg ggagcgttcc gccttagagg gaagcaaccg cgaaagcggg    540

ggtcgacgaa gcggaagcga gaatgtcggc ttgagtaacg aaa                      583
```

<210> SEQ ID NO 211
<211> LENGTH: 801
<212> TYPE: DNA
<213> ORGANISM: Artificial
<220> FEATURE:
<223> OTHER INFORMATION: Synthetic

<400> SEQUENCE: 211
tgtatggcgc agagtggcca ttcggccggg ggaagccaag tttgggaaaa tcttaaaaga 60
aagaaagaaa tgatgacgaa tcgccacttc ctcttcgctc ttcttttcac tttctttctt 120
tcagctgttg ctgcagattc ttctgaagag tgtgtataca cattgtatgt taaaactgga 180
tcaatcataa agggtggaac agactccaaa atcagcgtta cacttggcga tgctaaagga 240
aaatcagtat atattccaga tctagagaaa tggggtttaa tgggcccaaa ttatgattac 300
tacgaaaggg gtaatgtgga tatcttcact ggtagaggcc aatgtttaag cccaccaatt 360
tgcaggctta atgttacttc cgatggatca ggtgaccacc acggttggtt tcttgatttt 420
gttgagacta cttttactgg gccacacaaa acttgtagcc aatccatatt ctatgtcgaa 480
caatggttgg cttctgatgc tcctccttat gagttatcag tttctcttga tggttgtaaa 540
aagaagactg ggcttcgaca tgctcggcgt tttgtcgtgg gccagcccaa tgggtctgct 600
tcagaatagt ttggcccgtt gaagttcttt ttgtaatttt gtcgttgaga tgattttgat 660
gtgtagattg ccctgtgttt tcccttctct ttggttgaaa taaatttctt gtttggggct 720
tcctttcttg cttgtttagt cgtcatatct ttgacttatt ggctcttttg gcaatttgca 780
atcttttatg tactcaataa g 801

<210> SEQ ID NO 212
<211> LENGTH: 692
<212> TYPE: DNA
<213> ORGANISM: Artificial
<220> FEATURE:
<223> OTHER INFORMATION: Synthetic

<400> SEQUENCE: 212
gagaggaaga aaaagctcaa gagaagacat gggaatagca gctcactcca accatttctg 60
gtcccttctc ttcatagtct ttttctcttt ctccatctcc tccatttccg gatctgatga 120
tgattgcgtg tacacagctt acgtccgaac gagttcaata ataaagggtg gaacagattc 180
gattatcagt ttgactctct acgatgcaaa cgggtatggt cttagaatca agaaccttga 240
ggcctggggt gggcttatgg gtcctggtta caactatttc gagaggggaa atttggacat 300
tttcagcgga cgaggcccat gtttgactgg gcctgtctgc aagatgaacc tcacttccga 360
cggaacaggc aaaggccatg gatggtactg taactacgtg gaggtcaccg tcaccggagt 420
ccataaagca tgcaaccaac agaatttcga agtggagcag tggctcgcta ctgatgcgcc 480
gccttatgag cttacggctg ttagagacaa ctgtaagaag tccaagtccg atgagaaact 540
gtccatttcc gatgtctacg gaactcatcc cactccacat gtttctgtga tttaagtttc 600
tagttattgg gctttaatgg gcctgggcca acatttccct gttttacaat gacatttggt 660
gtgtgccaat gttgctttca tgtttatagt at 692

<210> SEQ ID NO 213
<211> LENGTH: 629
<212> TYPE: DNA
<213> ORGANISM: Artificial
<220> FEATURE:

<223> OTHER INFORMATION: Synthetic

<400> SEQUENCE: 213

```
ccccgatctc caccaccact ttcccgggga ccgcggcggg aaagggcctt cgagacttgg     60

gaggttggag cgagcaagct cggccatggc gaagctctcc tgccttctca tcgtctcctt    120

cgccgtcgtc gcggcgttgg cggccacgga cgacgacgcg gcggcggcgg ctgaggggat    180

cacggtggcg gaggcgtcgt cggacccgga gaacaagtgc gtgtacacga tatacgtgcg    240

gacggggacg atctggaagg gcgggacgga ctcggtgatc ggcgtgacgc tgctgggcgc    300

cgacggctcc ggggtgcgga tccgcgacct ggagcggtgg ggcggcctca tgggcgacgg    360

ccacgactac tacgagcgcg gcaacctcga catcttcagc ggcctcggcc cctgcatgcg    420

ccaggcgccg tgccggatga acctcacctc cgacggcacc ggcccgcacc acggctggta    480

ctgcaactac ctcgaggcca ccgtcacggg tccccacctc ggctgcgcgc agcagctctt    540

caccgtcgag cagtggctcg ccaccgacgc atcgccctac cgcctctacg ccgtcgtcga    600

caactgcaac aaggccaagg acgccgccg                                      629
```

<210> SEQ ID NO 214
<211> LENGTH: 614
<212> TYPE: DNA
<213> ORGANISM: Artificial
<220> FEATURE:
<223> OTHER INFORMATION: Synthetic

<400> SEQUENCE: 214

```
tttgccttta ttcgttctca tttttctaga gaaagagagt tcaagaaacc atgggagtag     60

ctcaagttaa ccaaatatgg ttccatttca tgataatcct cttcttcatc tccatatctt    120

ctagttctgc atcagaagat gattgtgtgt acacagctta cgttcgaact ggatcaatca    180

taaaggctgg aactgactca aacattagtt tgactctcta cgatgccgct ggctatggga    240

taagaatcaa gaacttagag gcatggggtg ggcttatggg cccaggttac aactatttcg    300

aaagaggaaa cttggatata ttcagtggac gtggtccatg tttgactggg ccgatctgca    360

aaatgaatct gacttctgat ggatcaggcc cacatgccgg atggtactgt aactacgtcg    420

aagttaccgt tactggagcc caccaacaat gcaaccagca gcttttcacc gtggagcagt    480

ggctcggcac tgacgtttcg ccgtatgagc tgacggccgt caggaacaac tgtaagaagc    540

caaagtttga gaaacaacag gccttttatg attctgaatc ttatccagtt gttgatgtaa    600

tttaatgggg gtag                                                      614
```

<210> SEQ ID NO 215
<211> LENGTH: 619
<212> TYPE: DNA
<213> ORGANISM: Artificial
<220> FEATURE:
<223> OTHER INFORMATION: Synthetic

<400> SEQUENCE: 215

```
agagagttca agaaaccatg ggagtagctc aagttaacca aatatggttc catttcatga     60

tcatcctctt tttcatatct tctatttcgg catctgaaga tgattgtgtg tacacagctt    120

acgttcgaac tggatcaatc ataaaggctg gaactgactc aaacattagt ttgactctct    180

acgatgccga tggctatggg ataagaatca agaacttaga ggcatggggt gggcttatgg    240

gcccaggtta caactatttt gaaagaggaa acttggatat attcagtgga cgtggtccat    300

gtttgaatgg gccgatctgc aaaatgaatc tgacatctga tggatcgggc ccacatgccg    360
```

```
gatggtactg taactacgtc gaagttacag ttactggagc ccaccaacaa tgcaaccagc    420

agcttttcac cgtggagcag tggctcggca ctaacgtttc gccatatgag ctgacggccg    480

tcaggaacaa ctgtaagaag tccaagtcca cagtttatga ttctgaatct tatccagttg    540

ttgatgtaat ttaatggggg cagccccaca tattgtctct gtggtttttt ctttagagtg    600

agaagaatta acgtgatgc                                                 619
```

<210> SEQ ID NO 216
<211> LENGTH: 750
<212> TYPE: DNA
<213> ORGANISM: Artificial
<220> FEATURE:
<223> OTHER INFORMATION: Synthetic

<400> SEQUENCE: 216

```
cgaccatctc aaaatcactt gctttttcg tctcattttc tagagaaaga aacaacaaga      60

cgtacagaac gagagttcaa gaatctgcaa tgggagtggc tcgagttaac caattctggt    120

tgcatcttct catcctcttc tccatctccg tttcttccat ttctggcact gaactgaatt    180

gtgtatacac agcttatgtt cggactggga catactgggg atctggaact gactcaaaaa    240

tttccttgtc tctttatgat gccactggcc atggacttag aatcaataac ctacaagcct    300

ggggcgggct tatgggcccg ggttatgact actttgaaat ggaccaattg gatatgttta    360

cgggccgtgg tccatgtttg actgggccaa tctgtaaaat gaacttgact tctgatggat    420

caggtgagca ccacggatgg tactgtaact acggggaaat cacgtctaca gcagaacaca    480

aacgatgcag ccaacaggcg ttcaccgtgg aggcgtggct cagtgccggt cagtacccag    540

atgggttgac cgccattaag gaacaactgt aagcgtattt ccaacgaaca acaaccaatt    600

catgattctg atcaatctta tcatgttgtg gatgtaattt aattcgagtt tattggacgt    660

tgtatgattt acgaaggcca tttaggccaa ggcctgatat gtactctcac gagtgctaca    720

tagttggaat ggaaaagttt tctttaccca                                     750
```

<210> SEQ ID NO 217
<211> LENGTH: 417
<212> TYPE: DNA
<213> ORGANISM: Artificial
<220> FEATURE:
<223> OTHER INFORMATION: Synthetic

<400> SEQUENCE: 217

```
tggtatcaac gcaaagtggc cttacggccg gggaaagata aagagagtaa cagagaaagc     60

tcaagagaag acatgggaat agcagctcac ttcaaccatt tctggttcct tctcttcatc    120

ctcttcttct ctttctccat ctccttcatt tccgcatccg atgatgattg cgtgtacaca    180

gcttatgtcc gaacgagttc aataataaag ggtggaacag attcgattat cagtttgagt    240

ctctacgatg caaacgggta tggtattaga atcaagaacc ttgaggcctg ggtgggctt     300

atgggtcctg gttacaacta tttcgagagg ggaaatttgg acattttcag tggacgaggc    360

ccatgtttga ctgagccagt ctgcaaaatg aatttgactt ccgacggaac aggcaaa       417
```

<210> SEQ ID NO 218
<211> LENGTH: 713
<212> TYPE: DNA
<213> ORGANISM: Artificial
<220> FEATURE:
<223> OTHER INFORMATION: Synthetic -continued

<400> SEQUENCE: 218

```
gtcatcacac aagtgaagaa gcagtagcag tagaaggaga tagaagggaa cctctctctc     60
tctctctctc tctttgctga tgatgaagac gactatggct gttttcgccc ttctctctct    120
cttccttctt ctcctccccc cttttccttc atcagctgat gatccttgtg tatactcaat    180
ctatgtacga acggggtcaa tattcaaggg gggaacggat tcgaagatga gtgtggagct    240
ctacgatgcg aatgggtact acattacgat caacaatttg gaggagtggg gggggttaat    300
gggtccagac cacgactact atgagagggg caatcttgac atctttagtg gtttgggga     360
ctgcctgacc ggacccatct gcgctctcaa cctcacctcg gacggcacgg gggcccacca    420
tgggtggtat tgcaactacc tggaagttac tgccacgggt gcccacatcc cttgctccca    480
acagctcttt accatagagc aatggcttgc cactgatacc tctccttact ccctcactgc    540
ccttcgatat aattgccctg atgctttgtc ctcgcctcgc ttccctcgca tgccttccaa    600
ttcgcaaccg aagaatggtc aactaatgtc ccattagtac tctatcaccc tgcttcgtaa    660
taaaaagata gccccttctt gtgtactatg gagggagggg ggtatctctc tca           713
```

<210> SEQ ID NO 219
<211> LENGTH: 628
<212> TYPE: DNA
<213> ORGANISM: Artificial
<220> FEATURE:
<223> OTHER INFORMATION: Synthetic

<400> SEQUENCE: 219

```
gaattccaag acttcattgg gattgtgaag ccagatcgat actacttttt attgtagttg     60
ggttatctga tcctacatct tctatcgtta ggagtacaat tgtttctgat cggctcgaga    120
acctgattct ccgataggta ggataaacgt gttcacggac atcttcgtct cactgttcgt    180
gaatccttga tattctcttt gtgtattcaa agatcgagta ttgagaggtg attgattaat    240
ctagactgct cttcgggaat ataagaccgg attaatcaat tggtttcttg aatatacctt    300
gatagatttt atcaaaaaac agaaaaaaag ttagggttta tctgtgggag acagattaat    360
cctttgatag acttgtctgt gtgagacaaa tttgtttatt ggcaaagcct gcgattttgg    420
gtcgtagcaa ctctttgttg tgggtcagat cagcaaagag aatcaagtgc gtagtatcct    480
gctgggatca gaggcgtagg ggtgcaattg taccttgtat cagtgggaga ctggtagggg    540
ttcaattata gatcagtccg aagttagttt agagtaggct agtgtctgta gcggcttaat    600
acagtgtgta tctaacatgg actatgtc                                       628
```

<210> SEQ ID NO 220
<211> LENGTH: 619
<212> TYPE: DNA
<213> ORGANISM: Artificial
<220> FEATURE:
<223> OTHER INFORMATION: Synthetic

<400> SEQUENCE: 220

```
gaattcgttc tcaaatagag agatagagat gtgaactcct tgagtcacta tattctagat     60
ttatctagta gagtgattcg gaggttgtcc ttatcatatt gctaatcgaa aagtttggtg    120
gtgttgttag acccccgctt tttcaattgg tatcagagca ggcaaacact taaagaccta    180
atcagtctgt gtttgttgca atctgattgt atggactgtg ctatctccaa gaacgccata    240
ccagttaaag gtcattcgat ggaggggaaa tcatccatgg agaataactc caacacatgt    300
tcttcgcccg tgtcttcaca tgactgggat aaatcacttg atgagcagct tgatgaactc    360
```

```
tcagatgaca gtgattcaga agaaggacca aatgttgatg aggaagtctc agaatatatt    420

ttgatgatta atcgtgacct aaaagaaaca aggtcctcct catgcatacg gaagcatttg    480

ggaccacttt gtcgagaaaa cagaaagttg agaaaactct ttaatgggta tgacagtggt    540

tataaattat tgcaagccac tgttaaagat cacaaagaag atgttcttct aaaaggaacc    600

gagtgtgata atcttcttc                                                 619
```

<210> SEQ ID NO 221
<211> LENGTH: 461
<212> TYPE: DNA
<213> ORGANISM: Artificial
<220> FEATURE:
<223> OTHER INFORMATION: Synthetic

<400> SEQUENCE: 221

```
aagactccta aactacaata ctattaaatg atggcaaaca gacattcaat gataaagtaa     60

ggatcaaaaa tcttaaatca agactacact gaaaaatcct ggttttacta ttctatatgt    120

ccaaaacttt caaagaaaaa tgaacacgtc ccgtggcttc ttcagcctac tgctgctcat    180

cgccctcaat gactcctctc tcactcacgt agatgccatc caaaaacttt ctgatatcct    240

tctttttgac aaggcatttc tggtttataa gagcacatga acgagagacg agttcgatgt    300

cattcccctc caggaccagc tcatccttta ctttctcaga ccgggtaatt gtcacaccag    360

gaagcatttc tactttccgt acccgctttt ctccgagaaa gtttcggatt tcgatgcaat    420

cattgcctcc ggagatgcta gcattgatgg ggaaatgggc a                        461
```

<210> SEQ ID NO 222
<211> LENGTH: 837
<212> TYPE: DNA
<213> ORGANISM: Artificial
<220> FEATURE:
<223> OTHER INFORMATION: Synthetic

<400> SEQUENCE: 222

```
gagagagaga ggggagaggg taggagagag aggtagcagg gttagggggg gccagcagca     60

ggcagaggag gatagagaga gagagaggca agcagcgatg aagacgatct tggcctcgca    120

gacgttcgag gtgccggagg gtgtttccct cgagatcaag gcgaagcaga tccgggtcaa    180

ggggccccgc ggtaccctca cccgtgactt caagcacctt aaccttgact tccagctcca    240

ggagggtggc cgtaaggtca aggtcgacgc ctggttcggc tcgcgtaaga ccatggccgc    300

catccgcacc gctatctccc acattggtaa cctcatcggt ggtgtcacca agggctaccg    360

ttacaagatg cggcttgtct acgctcattt ccccatcaat gccagcatct ccggagtcaa    420

cgattgcatt gaaatccgaa actttctcgg agaaaagcgg gttcggaaag tagagatgct    480

tccaggtgtg acaataaccc ggtctgagaa agtcaaggat gagctagtcc ttgagggaaa    540

cgatattgag cttgtctctc gttcgtgtgc tctcattaac cagaaatgtc atgttaagaa    600

gaaggacatc aggaagtttc tggatggtat ttatgtgagc gagcgaggtg tcattgaggg    660

tgatgaccag cagtagtctt gattcaagtt ttttgatcct tattttctca tttgcaatgt    720

ctgtttgcaa tcatttagta gttagtagtt taggagtatt aaaactaaaa ggggttcctt    780

gccatagttg ttgttactat tcattcaaag gtgtcacaat gaggaagttt taatgat       837
```

<210> SEQ ID NO 223
<211> LENGTH: 720
<212> TYPE: DNA

<213> ORGANISM: Artificial
<220> FEATURE:
<223> OTHER INFORMATION: Synthetic

<400> SEQUENCE: 223
gctgctaggg ttttagcgat cgccattttc acacacacag aaggagagcg gaagagagaa 60
actaagacaa gatgaagacc attctgtcat cagaaaccat ggatatcccc gacggcgtga 120
gcatcaaggt gaaggcaaag caaatcgaag tagagggacc aaggggcaaa cttgtccgaa 180
acttcaagca tctcaacctc gattttcagc tgatcaagga tgaggaaact ggcaagaaga 240
aactgaagat cgacgcttgg tttggttctc gtaagactac cgctgctatc cgtactgctc 300
ttagccatgt tgagaatctc atcactggtg ttacgaaagg ttaccgctac aagatgcgtt 360
tcgtgtatgc tcactttccc atcaatgcct ccatcaccgg tggtaacaag tccattgaga 420
tccgtaactt ccttggcgag aagagagtta ggaaagtgga catgcttgat ggggttacag 480
ttgttcgatc tgagaaggtg aaggatgagc ttgtattgga tggaaatgac attgagctcg 540
tttctcgctc tgctgccctc atcaatcaaa aatgccatgt gaagaacaag gatatccgaa 600
agtttcttga tggtatctat gtcagtgaga agggcagaat tgcagaagaa gaatgagcag 660
ctgttttaga agtaggcata tcactgatga ttcatatcca gaatgccctt tttacttttc 720

<210> SEQ ID NO 224
<211> LENGTH: 383
<212> TYPE: DNA
<213> ORGANISM: Artificial
<220> FEATURE:
<223> OTHER INFORMATION: Synthetic

<400> SEQUENCE: 224
ggagagcaaa acaaagatcg gagaagatga agacgattct ttcttccgaa acgatggaca 60
tccccgacag tgttaccatc aaggttcacg ctaaagtgat cgaagtcgaa ggacctcgcg 120
ggaagcttgt tcgcgatttc aagcatctca acctcgattt ccagctgatc aaggatccag 180
agactggaaa gaagaagctt aagatcgatt cgtggtttgg aacacgcaaa accagcgcct 240
ccatcagaac cgctcttagc cacgtcgata acttgatctc cggtgttacc agaggtttcc 300
gttacaagat gaggttcgtg tacgcccatt ttcccatcaa cgcctccatc ggcggtgacg 360
gaaagtctat cgagatccgt aac 383

<210> SEQ ID NO 225
<211> LENGTH: 741
<212> TYPE: DNA
<213> ORGANISM: Artificial
<220> FEATURE:
<223> OTHER INFORMATION: Synthetic

<400> SEQUENCE: 225
gggtgcgagg aggaggaggc gggcgcgatg aagacgatct tgtcggccca gacgatggac 60
atccccgagg gggtgaaggt agagatccgg gcgaagcaga tccgggtgac ggggccgcgg 120
ggggtgctgc acaggaattt caagcacctc aacctcgact tccagctgct ggagaatggg 180
cgcaagctca aggtggaggc gtggtttggg tcgcgcaaga ccatcgccgc catccgcacc 240
gccgtgagcc acgtgaagaa cctcatcacc ggcgtcacca agggcttcca gtacaagatg 300
aggtttgtct acgctcactt ccccatcaac gccaacatct ctgccaccaa gcaaaacatc 360
gagatccgga acttcctcgg cgagaagagg gtgagaactg tcgacatgct tccgggtgtg 420
actgtgacca ggacggagaa ggtcaaggac gagcttgttc tcgaggggaa tgacatcgag 480
cttgtgtcga gatcggccgc tctgatcaac caggtgagct catcagagtg gaagattcat 540
gtgtctaata tgtgtctgtt tctcttgtgt gtgtagaaat gccatgtcaa gaacaaggat 600
atcaggaagt tcttggatgg tatctacgtg agcgagaagg gaacgatcgc tgtggaggag 660
tagacctttt gcctgttctg agtataattt tgtgctttgc ttgtctgaaa tcaatcaaac 720
accaactctt ttggaaattt t 741

<210> SEQ ID NO 226
<211> LENGTH: 656
<212> TYPE: DNA
<213> ORGANISM: Artificial
<220> FEATURE:
<223> OTHER INFORMATION: Synthetic

<400> SEQUENCE: 226
cccacgcgtc cggccccgac aacccccaag tcacagcagc catgaggtac attcactctc 60
aggagatcct ggaaattcca gagggcgtca aggtcaacat caagacccgt atcgtcaccg 120
ttgagggtcc ccgaggcaag ctcaccaaga acctcggtca cttggctgtc aacttcggtc 180
accccaagaa gaacaccatc tccatcgaga tccaccacgg caaccgtaag aatgtcgcca 240
ctctccgtac cgtccgctcc atcatcgaga acttgatcac cggtgtcacc aagggcttca 300
agtacaagat gcgatacgtc tacgcccatt ttcccatcaa cgtcaacctg gacaagaaca 360
aggagaccgg tctgttcgag gtggagatcc gaaacttcat cggcgagaag atcgtccgac 420
gggttaccat gcacgagggt gtcgatgttg agatctccaa ggcccagaag gatgagctca 480
tcctgaccgg caactcactc gagaacgttt cccagagcgc cgcagatatc cagcagatct 540
gccgggtgcg caacaaggat atccgaaagt tcttggacgg tctgtacgtt tccgagaagg 600
gcaacgttgt tgaggaggct taaatgtacc ggacaaggat ctctgtttct tttgcg 656

<210> SEQ ID NO 227
<211> LENGTH: 887
<212> TYPE: DNA
<213> ORGANISM: Artificial
<220> FEATURE:
<223> OTHER INFORMATION: Synthetic

<400> SEQUENCE: 227
tggtatgaac gcagagtggc cattacggcc ggggacagct attttctcta ttacttcagc 60
catcaaaaaa cacttatttc tccttattaa accatggctg cttctacaat ggctctctct 120
tcctcttctt ttgccggaaa ggcagtaaaa ctattaccgt cttcctctga aatcaccgga 180
aatgggaaag ttaccatgag gaagactgct agcaagccca agcctgtctc ttctggcagt 240
ccatggtatg gccctgaccg tgtcaagtac ttgggcccat tctctggtga gtccccaagc 300
tacttgactg gtgagttccc tggtgactac gggtgggaca ctgctggact ttcagctgat 360
ccagaaactt ttgccaagaa ccgtgagttg gaggtgatcc actgcagatg ggcaatgctt 420
ggagctcttg gttgtgtctt ccccgagctc ttggcccgta acggtgtcaa gtttggtgag 480
gctgtatggt tcaaggctgg atcccaaatt tttagcgagg gtggacttga ctacttgggc 540
aacccaagtt tggtccatgc tcaaagcatc ttggccattt gggcttgtca agttgtgttg 600
atgggagccg ttgagggtta ccgtgttgct ggtgggcctc ttggggaggt tgttgatcca 660
ctctaccccg gtggcagctt cgacccattg ggcctcgctg aagacccaga agcttttgct 720
gagctcaagg taaaagagat caaaaatggt agacttgcca tgttctccat gtttggattc 780

-continued

```
tttgttcagg ctatcgtaac tggaaagggc ccattggaga accttgccga tcaccttgca    840

gacccagtta ataacaacgc ttgggcctac gcaacaaact ttgtccc                  887
```

```
<210> SEQ ID NO 228
<211> LENGTH: 906
<212> TYPE: DNA
<213> ORGANISM: Artificial
<220> FEATURE:
<223> OTHER INFORMATION: Synthetic

<400> SEQUENCE: 228

tggtatcaac gcagagtggc cattacggcc ggggatcaca actaactttg acatctcaaa     60

ctagcaacct ctcactttcc tcttgataaa ccatggctgc ttctacaatg gctctttctt    120

ccccttcttt cgctggacag gcagtgaaac tctccccatc tgcctcagaa atcactggaa    180

atggaagggt ctccatgaga aagactgtcg ccaaacccgt cgcatctagc agcccatggt    240

acggtccaga ccgtgttaag tacttgggcc cattctccgg tgaggcccca agctacttga    300

ccggtgaatt cccaggtgat tacgggtggg atactgctgg actttcagca gatccagaaa    360

catttgccaa gaaccgtgaa ctcgaggtga tccactgcag gtgggctatg cttggagctc    420

ttggatgtgt cttccctgag ctcttggctc gtaacggtgt caagtttggt gaagctgtct    480

ggttcaaagc tggatcacaa atctttagtg agggtggact tgactacttg ggcaacccaa    540

gcttggtcca tgcacaaagc atcttggcaa tctgggcttg ccaagttatc ttgatgggag    600

ctgttgaggg ttaccgtgtt gctggtgggc cccttggtga ggttgtcgac ccactctacc    660

ctggtggcag ctttgaccca ttaggccttg ctgatgaccc agaggcattt gctgagctca    720

aggtaaagga gatcaagaat gggagacttg ccatgttttc tatgttcgga ttctttgttc    780

aggccattgt taccggaaaa ggtccattgg agaaccttgc tgaccatctt gctgacccag    840

ttaacaacaa cgcctggtcc tacgccacaa actttgtccc cggaaaatga atattgtaaa    900

aaaatc                                                               906
```

```
<210> SEQ ID NO 229
<211> LENGTH: 404
<212> TYPE: DNA
<213> ORGANISM: Artificial
<220> FEATURE:
<223> OTHER INFORMATION: Synthetic

<400> SEQUENCE: 229

tggtatcaac gcttagtggc cattacggcc ggggaccatt gtctgagcaa actccatcat     60

acctcactgg tgagtttccg ggtgattacg ggtgggacac tgctggactc tcagctgacc    120

cagaaacatt cgcaagaaac cgtgaacttg aagtgatcca ttgtcgttgg gccatgcttg    180

gtgctttggg ttgtgtcttc cctgaaatcc tttcaaagaa cggtgttcaa ttcggtgaag    240

cagtttggtt caaggcagga gcccaaatct tttcagaagg tggactcgac taccttggca    300

acccaaacct cgtgcatgcc cagagcatcc tcgccatttg ggcttgccaa gttgtcctaa    360

tgggcttgat tgaaggatac agagttggtg gaggcccact tggt                     404
```

```
<210> SEQ ID NO 230
<211> LENGTH: 819
<212> TYPE: DNA
<213> ORGANISM: Artificial
<220> FEATURE:
<223> OTHER INFORMATION: Synthetic

<400> SEQUENCE: 230
```

```
aggactttgg tcctacctag ttatttatat acagttgctg caaggccatt aaactcaagc     60
cataaatcaa atattctttc tgtgtagtag ctgcattttc aagagcattt cactttattt    120
ctgcaacaat ggcagcttct acaatggctc tctcttcctc ttcttttgcc ggaaaggcgc    180
tgaaactctc accatcttcc tctgagatca ccggaaatgg aaaagtcacc atgaggaaga    240
cagttaccaa ggcgaagcca gtctcttctg gcagcccatg gtatggtcct gatcgcgtca    300
agtatttggg cccattctct ggtgagtctc caagctactt gactggtgag ttccctggtg    360
actacggatg ggatactgct ggactttcag ctgatccaga aacttttgct aagaaccgtg    420
agctagaggt gatccactgt agatgggcca tgcttggagc tcttggttgt gtcttccccg    480
agctcttggc ccgtaatggt gtcaaattcg gtgaggctgt atggttcaag gctggatccc    540
agatttttag cgatggtgga cttgactact tgggcaaccc aagtttggtc catgcacaaa    600
gtatcttggc catttgggct tgccaagtcg tgttgatggg agctgttgag ggttaccgtg    660
ttgctggtgg gcctcttggt gaggttgtcg acccactcta tcctggtggt agctttgacc    720
cattaggtct tgctgatgat ccagaggctt ttgctgagct caaggtgaag gagatcaaga    780
acggtagact tgccatgttc tcaatgtttg gattcttcg                           819
```

```
<210> SEQ ID NO 231
<211> LENGTH: 743
<212> TYPE: DNA
<213> ORGANISM: Artificial
<220> FEATURE:
<223> OTHER INFORMATION: Synthetic

<400> SEQUENCE: 231

gaattcaggg gcagtgaaag tgacaccatg cgttcaagag ggtgatggaa gaatcaccat     60
gctcttccag aaaaagacag tggcaaagcc tactaaatct tcaaaacccg cagtttcatc    120
taacagccca tggtacggtc ccgacagagt taagtacttg ggtcccttca atggctgctt    180
caacaatggc tctctcatct ccttctcttg ctggaaaggc agtgaaagtg acaccatgcg    240
ttcaagaggg tgatggaaga atcaccatgc tcttccagaa aaagacagtg gcaaagccta    300
ctaaatcttc aaaacccgca gtttcatcta acagcccatg gtacggtccc gacagagtta    360
agtacttggg tcccttctca ggcgaggctc catcgtatct taatggtgaa ttcccaggtg    420
attatggccg ggacactgcc gggttttctg cagatccaga aactttcgcc aaaaaccgtg    480
aacttgaagt gattcattgc agatgggcta tgcttggagc tctaggatgc atcttccctg    540
aattgctctc acgcaatgga gttaaattcg gtgaagccgt ttggttcaaa gccggagcac    600
agattttcag cgagggtgga ttggactact tgggtaactc aagcttagta catgctcaaa    660
gcattttagc tatttgggcg acacaagtta tcttgatggg tgcagttgaa ggttaccgtg    720
ttgccggtgg acctcttggt gag                                            743
```

```
<210> SEQ ID NO 232
<211> LENGTH: 639
<212> TYPE: DNA
<213> ORGANISM: Artificial
<220> FEATURE:
<223> OTHER INFORMATION: Synthetic

<400> SEQUENCE: 232

gaattcaatg gctgcttcaa caatggctct ctcttctcct tctcttgctg gaaaggcagt     60
gaagctaact ccatccattc cagaaggcga aggaagaatt accatgctct tccagaaaaa    120
```

-continued

```
gacaccggca aaagcagcta aatcatccaa acccgcagtt tcatctaaca gcccatggta    180

tggtcctgac agagttaagt acttgggacc tttctccggt gaggcaccat catatctcaa    240

tggtgaattt cctggtgact atggttggga taccgctggg ttatctgctg atcctgaaac    300

tttcgccaag aaccgtgagc ttgaagtgat ccattgcaga tgggctatgc tcggagctct    360

aggatgcatc ttccctgaat tgctctcgcg caatggagtt aaattcggtg aagccgtttg    420

gttcaaagcc ggagcacaga ttttcagcga gggaggattg gactacttag gtaactcaag    480

cttagtacat gctcaaagca ttttagctat ttgggcgaca caagttatcc tgatgggtgc    540

agtggaaggt taccgtgtcg ccggtggacc tcttggtgag attgtcgacc cactgtaccc    600

cggtggcagc ttcgaccctc ttggacttgc tgatgaccc                            639
```

<210> SEQ ID NO 233
<211> LENGTH: 630
<212> TYPE: DNA
<213> ORGANISM: Artificial
<220> FEATURE:
<223> OTHER INFORMATION: Synthetic

<400> SEQUENCE: 233

```
gaattcactg ccgggctttc tgcagatcca gggactttcg ccaaaaacca tgaacttgaa     60

gtgattcatt gcagatgggc tatgcttgga gctctaggat gcatcttccc ttcaatggct    120

gcttcaacaa tggctctctc atctccttct cttgctggaa aggcagtgaa agtgatggaa    180

gaatcaccat gctcttccag aaaaagacag tggcaaagcc tactaaatct tcaaaacccg    240

cagtttcatc taacagccca tggtacggtc ccgacagagt taagtacttg ggtcccttct    300

caggcgaggc tccatcgtat cttaatggtg aattcccagg tgattatggc cgggacactg    360

ccgggctttc tgcagatcca gaaactttcg ccaaaaaccg tgaacttgaa gtgattcatt    420

gcagatgggc tatgcttgga gctctaggat gcatcttccc tgaattgctc tcacgcaatg    480

gagttaaatt cggtgaagcc gtttggttca aagccggagc acagattttc agcgagggag    540

gattggacta cttgggtaac tcaagcttag tacatgctca aagcatttta gctatttggg    600

cgacacaagt tatcttgatg ggtgcagttg                                     630
```

<210> SEQ ID NO 234
<211> LENGTH: 782
<212> TYPE: DNA
<213> ORGANISM: Artificial
<220> FEATURE:
<223> OTHER INFORMATION: Synthetic

<400> SEQUENCE: 234

```
gaattcaaca cagtctttag ttttctcatc catccatata tcagttagcc atggcagctt     60

ctacaatggc tctatcttca cccgcattgg ctggtaaggc acttgttcct tccagctctg    120

aagttttcgg tgaaggcaga atctccatga gaaaaaccgt tgcaaagcca aaaaccgttt    180

catctagccc atggtacgga cctgaccgtg ttaagtactt gggaccattc tctggtgaat    240

ctccatcgta cttaaccggt gagtttgccg gtgattacgg ttgggacact gccgggcttt    300

ctgctgaccc agaaaccttc gccaagaacc gtgagctgga ggtcattcac tgcagatggg    360

ctatgttggg agctcttgga tgtgtcttcc ccgaattgtt gtctcgcaat ggtgttaaat    420

ttggtgaagc cgtttggttc aaggctggtt cacaaatttt cagtgaaggt ggattggact    480

acttgggtaa ctcaagcttg gttcatgctc agagcatcct tgccatttgg gcaacacaag    540

ttatcttgat gggagcagtt gaaggttaca gagttgctgg aggaccattg ggtgaggtgg    600
```

aggacccact ttaccctggt ggaagcttcg acccattagg cttagctgat gatccagaag 660
cttttgctga attaaaggtg aaggaaatta agaacgggag attggctatg ttctccatgt 720
ttggattctt tgttcaagca atcgtgaccg ggaaaggtcc tttggaaaat ttggctgacc 780
ac 782

<210> SEQ ID NO 235
<211> LENGTH: 377
<212> TYPE: DNA
<213> ORGANISM: Artificial
<220> FEATURE:
<223> OTHER INFORMATION: Synthetic

<400> SEQUENCE: 235
aattcggcac gagcttcaat ctccttatta aacaatggct gcttctacaa tggctctctc 60
ctcttctttt gccggaaagg cagtaaaact ctcaccatct tcccctgaaa tcaccggaaa 120
tggaaaagtt accatgagga agactgctag caaggccaag cctgcctctt ctggtagccc 180
atggtacggt cctgaccgcg tcaagtactt gggccctttc tctggtgagt ctccaagcta 240
cttgactggt gagtttcctg gtgactacgg atgggacact gccggacttt cagctgatcc 300
agaaactttt gccaagaacc gtgagttgga ggtgatccac tgcagatggg ccatgcttgg 360
agctcttgga tgtgtct 377

<210> SEQ ID NO 236
<211> LENGTH: 982
<212> TYPE: DNA
<213> ORGANISM: Artificial
<220> FEATURE:
<223> OTHER INFORMATION: Synthetic

<400> SEQUENCE: 236
gaattcaact accatcttca gttatctttc attttcaata caaaagatac ataagaatgg 60
caaccatggc tctctcttct ccatcatttg caggcaaagc tgtgactcta aaccctcaaa 120
cagaattccc aaccaatgta agatctggca gcaacagcaa gatctcgatg aggaagacat 180
ccgcaaagaa gcctgcagct tcttctggaa gtccatggta tggtccagac cgagtcaagt 240
acctcggtcc cttctctggt gagtctcctt cttacctaac tggtgaattc gctggtgact 300
atggctggga cactgctgga ctatcagctg atccagagac ctttgccaag aaccgcgaac 360
ttgaggtgat ccattcaagg tgggcgatgc ttggcgcttt gggctgtgtc ttccctgaac 420
tcctctcgag aaatggagtc aaattcggcg aagcagtttg gttcaaagcc ggctctcaga 480
tattcagtga aggaggactt gactatttgg gaaattccag cttggttcat gcacagagca 540
tcctggctat atgggccact caagtcatcc ttatgggcgc cgtcgaaggc tacagagttg 600
ctggcggtcc actaggtgag gttgttgatc ccctttaccc aggtggaagc ttcgatccat 660
taggccttgc agaggaccca gaggcatttg ccgagctaaa ggtaaaagaa ctaaagaacg 720
ggcgacttgc tatgttctcc atgtttgggt tcttcgttca ggctattgtg acgggcaaag 780
gtcctctaga gaacctggca gaccaccttg ccgacccagt gaacaacaat gcctggtcat 840
atgctacgaa cttcgctccc gggaagtgag cataagcata gcaaaggcaa aatggagttt 900
gatttcctac ttttttctg taatatcctc tgtacattca tttagcttgt aaaattgtgt 960
agaatgtagc tgcggttggt ct 982

<210> SEQ ID NO 237

<211> LENGTH: 675
<212> TYPE: DNA
<213> ORGANISM: Artificial
<220> FEATURE:
<223> OTHER INFORMATION: Synthetic

<400> SEQUENCE: 237

```
cccgagcacg cacacacacc ccagcagcag cagcagcagc agctgagctt gaagcagcag     60

agcgaggtag acatggccgc cgccaccatg gccctctcgt ccccggcgct ggccggcaag    120

gccgccgcga aggtgttcgg cgaggggcgc atcaccatgc gcaagtcggc ggcgaagccc    180

aagcccgccg cgtcggggag cccgtggtac ggcgccgacc gcgtgctcta cctcggcccg    240

ctctccggcg agccgccgag ctacctgacc ggcgagttcc ccggcgacta cgggtgggac    300

accgcggggc tctccgccga cccggagacg ttcgccaaga accgggagct ggaggtgatc    360

cactccaggt gggcgatgct cggcgcgctg ggctgcgtgt tcccggagct cctcgcccgc    420

aacggcgtca agttcggcga ggcggtgtgg ttcaaggcgg ggtcgcagat cttcagcgag    480

ggcgggctcg actacctcgg caacccgagc ctgatccacg cgcagagcat cctcgccatc    540

tgggcggtcc aggtggtgct catgggcgcc gtcgaggggt accgcatcgc cggcgggccg    600

ctcggcgagg tcgtcgaccc gctctacccc ggcggcagct tcgacccgct cgggctcgcc    660

gacgacccgg aggcc                                                     675
```

<210> SEQ ID NO 238
<211> LENGTH: 620
<212> TYPE: DNA
<213> ORGANISM: Artificial
<220> FEATURE:
<223> OTHER INFORMATION: Synthetic

<400> SEQUENCE: 238

```
cccagcacgc acacacaccc cagcagcagc agctgagctt gaagcagcag agcgaggtag     60

acatggccgc cgccaccatg gccctctcgt ccccggcgct ggccggcaag gccgccgcga    120

aggtgttcgg cgaggggcgc atcaccatgc gcaagtcggc ggcgaagccc aagcccgccg    180

cgtcggggag cccgtggtac ggcgccgacc gcgtgctcta cctcggcccg ctctccggcg    240

agccgccgag ctacctgacc ggcgagttcc ccggcgacta cgggtgggac accgcggggc    300

tctccgccga cccggagacg ttcgccaaga accgggagct ggaggtgatc cactccaggt    360

gggcgatgct cggcgcgctg ggctgcgtgt tcccggagct cctcgcccgc aacggcgtca    420

agttcggcga ggcggtgtgg ttcaaggcgg ggtcgcagat cttcagcgag ggcgggctcg    480

actacctcgg caacccgagc ctgatccacg cgcagagcat cctcgccatc tgggcggtcc    540

aggtggtgct catgggcgcc gtcgaggggt accgcatcgc cggcgggccg ctcggcgagg    600

tcgtcgaccc gctctacccc                                                620
```

<210> SEQ ID NO 239
<211> LENGTH: 1006
<212> TYPE: DNA
<213> ORGANISM: Artificial
<220> FEATURE:
<223> OTHER INFORMATION: Synthetic

<400> SEQUENCE: 239

```
gaattcacta gatcttcagc agtcttgtta ttttctcttt aacaaaacat ataaatggca     60

tccatgtctc tctcatcccc atcatttgca ggcacagctg taactttgaa cgcacaatcg    120

aaattcccaa ccaatgttag atccagcagc aatggaatga ttgtgatgag gaagacatca    180
```

gcaaagaagc ctgctgcttc ttcaggaagt ccatggtacg gtccggaccg tgtcaagtac 240
cttggaccct tctctggtga gtctccatca tacctaactg gtgagttccc tggtgactat 300
ggctgggata ctgctggact atctgcagac ccagagacct ttgccaagaa cagggaattg 360
gaagtgattc attccaggtg ggctatgctt ggcgctttgg gatgtgtttt ccctgaactt 420
ctctctagaa atggagttaa ttttggagaa gcagtctggt tcaaagctgg ttcccagatt 480
ttcagtgaag gtggacttga ctacttggga aactccagcc tggttcatgc acagagcatc 540
ttagctattt gggcaaccca agttatcctt atgggagctg ttgagggata cagagttgcc 600
ggtggtccac taggtgagat cgtcgaccca ctttacccag gtggtagctt tgaccccctta 660 ggacttgcag aggacccaga ggcatttgct gagctgaagg taaaggaact taagaacggg 720
agacttgcta tgttctccat gttcggattc ttcgttcagg ctattgttac cggcaaaggt 780
cctttagaga atctggcaga tcacctgtct gaccctgtga acaacaatgc ttggtcatat 840
gctaccaatt ttgctccagg aaagtgagaa tgtacatgat agtcaactaa gatgatttca 900
tttccttcaa aaggcgaagg agatggcttt tcttatcttt caacttttgt acatacatcc 960
atttagcttg taaaacaatc tggcattcgg attaatttgt acttaa 1006

<210> SEQ ID NO 240
<211> LENGTH: 691
<212> TYPE: DNA
<213> ORGANISM: Artificial
<220> FEATURE:
<223> OTHER INFORMATION: Synthetic

<400> SEQUENCE: 240
tcgcgatcta gaactcttat taactaaaga gccttttact tgcgccacac tctcaccgca 60
atggccgcct cgacaatggc tctctcctct cctgctttga ccggaaaggc cgttaagcta 120
tccccggcgg cctccgaagt atttggaacc ggccgaatca ccatgcgcaa agcctccaag 180
cccaccggtc catccggcag cccatggtac ggatccgacc gagtcaagta cttgggtcca 240
ttctccggtg agcctccgag ctacctcact ggagagttcc ccggtgatta cgggtgggac 300
actgccggtc tatccgccga tcccgagacc ttcgctagga accgtgagct agaagttatc 360
cacagcagat gggccatgct cggagcccta ggctgcgttt tccctgagct attggctagg 420
aacggagtga agttcggaga agcggtttgg ttcaaggctg gttcacagat cttcagcgac 480
ggaggattgg actacttggg caacccgagc ttggtccacg ctcagagcat cttagccatt 540
tgggctactc aagttatcct catgggagct gttgagggct acagagtcgc cggagatggt 600
ccattgggag aagcagagga cttgctttac ccaggtggga gcttcgaccc attgggcctc 660
gctactgacc ccgaggcttt cgcggagttg a 691

<210> SEQ ID NO 241
<211> LENGTH: 675
<212> TYPE: DNA
<213> ORGANISM: Artificial
<220> FEATURE:
<223> OTHER INFORMATION: Synthetic

<400> SEQUENCE: 241
tgcagtcaag aatactttct tatctcttcc ttctacaatg gcaactgcta caatgtctct 60
ctcttcccct tcttttgccg gaaaggcaat aaaactctca ccatcttcct ctgaaattac 120
tggaaatgga aaagtcacca tgaggaagac tgttaccaag gctaagcctg tctcctctgg 180

-continued

```
cagcccatgg tacggtcctg atcgtgtcaa gtatttgggc ccattttctg gtgagtcccc    240
aagttatttg actggtgaat ttcctggtga ttacggttgg gatactgctg gactttcagc    300
tgatccggaa acctttgcca aaaaccgtga gctagaggtt attcactgca gatgggctat    360
gcttggagct cttggttgcg tctttcctga gctcttggcc cgtaacggtg tcaagttcgg    420
cgaagctgta tggttcaaag ctggatcgca gattttcagt gagggtggac ttgactactt    480
gggcaaccca agcttggtcc acgcgcaaag catcttggct atttgggctt gccaagttgt    540
gttgatggga gccgtcgagg gttatcgtat tgctggtgga cctcttggtg aggttgttga    600
cccactttat cctggtggta gttttgaccc attgggtctt gcagatgacc cggaagcttt    660
tgctgagctt aaagt                                                     675
```

<210> SEQ ID NO 242
<211> LENGTH: 752
<212> TYPE: DNA
<213> ORGANISM: Artificial
<220> FEATURE:
<223> OTHER INFORMATION: Synthetic

<400> SEQUENCE: 242

```
catttatata cagttgatgc gggctcatta aactcaagcc ataaatcaaa tatttttttct     60
gtatagtagc tgcattttca agagcatttc actttatttc tacaacaatg gcagctacta    120
caatggttct ttcttcctct tcttttgtgg gaaaggcggt gaaactctca ccatcttcct    180
ctgagatcac cggaaatgga aaagttacca tgaggaagac tgttaccaag gcgaagccag    240
tctcttctgg cagcccatgg tatggtcctg atcgtgtcaa gtacttgggc ccattctccg    300
gtgagtcccc aagttacttg actggtgagt tccctggtga ttatgggtgg gacactgctg    360
gactttcagc tgatcccgaa acttttgcaa agaatcgtga gctagaggtg atccactgca    420
gatgggccat gcttggagct cttggttgtg tcttccctga gctcttggcc cgtaatggtg    480
tcaaattcgg tgaggctgta tggttcaagg ctggatctca aattttcagc gagggtggac    540
ttgattactt gggcaaccca agtttggtcc atgcacaaag tatcttggcc atctgggctt    600
gccaagtcgt gttgatggga gccgttgagg gttatcgtgt tgctggtgga cctcttggtg    660
aggttgttga cccactctac cctggtggta gctttgaccc attaggcctt gctgatgacc    720
ccgaggcttt tgccgagctc aaggtgaagg ag                                  752
```

<210> SEQ ID NO 243
<211> LENGTH: 628
<212> TYPE: DNA
<213> ORGANISM: Artificial
<220> FEATURE:
<223> OTHER INFORMATION: Synthetic

<400> SEQUENCE: 243

```
gaattccgta ggaacatgat gcccttgaac ccgggtttaa ttgttgaggt ctttcatgtg     60
tggggtattg actttatggg tccgtttcct aattcttttg gtaacttata catccttgtc    120
gccgtagact atgtctccaa gtggattgag gcggttgcgt gtaaaaccaa tgaccatagg    180
gttgtgattg agttcttgaa aaataatata cttacacgtt ttggtacacc gcgagctata    240
attagtgatg gagggtcgca tttttgtaat ggtcctttta ggcttttgat gaagaaatat    300
ggtatcacac ataaggtagc caccccgtat catccacaga ctagtggtca ggtagaggtt    360
tccaataagg agataaaacg tatattagag aaaacagtca atcctaatcg gaaagactgg    420
tcgtctaggc tcactgatgc cttatgggat taccgtactg cgtttaaaac cccaattgga    480
```

atgtcgcctt atcgacttgt gtatggcaag gcatgtcatt tacctgttga gttagaacat 540
agagcttatt gggctgtcaa gcagctaaat ttttcactcg acaaggcagc agcccatagg 600
aaactccagc tcaatgagtt ggatgaaa 628

<210> SEQ ID NO 244
<211> LENGTH: 1096
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1031)..(1031)
<223> OTHER INFORMATION: The residue at this position can be any nucleotide.

<400> SEQUENCE: 244
ggcagatatg gctcatatta gtgggttagt tgcagctgga gtcatcccat caccatttga 60
ttatgcagat gttgtgacta ccacaaccca caaatccctt cgcgggcctc gtggtgccat 120
gattttcttc cggaagggtg tgaaggaggt taacaagcaa ggaaaggagg tgttgtacga 180
ctatgaagat aaaattaacc aggcagtctt tcctggactt caaggtggtc ctcacaatca 240
tacaattact ggcttggcag ttgctttgaa acaggcaatg actccagaat acaaagctta 300
ccaagagcaa tgccttagca actgctcaaa atttgcccag gcgttagcgg gaatgggtta 360
tgaacttgtt tctggtggaa cagagaatca cttggtcttg gtgaacttga aaaacaaggg 420
tattgatggt tctagggttg aaaaagtttt ggaagcggta catattgcag ccaataagaa 480
cactgttcct ggagatgtat ctgccatggt ccctggtggc atcagaatgg ggactcctgc 540
actcacatca aggggattta ttgaggaaga ttttgtgaaa gttgctgaat tctttgatgc 600
tgctgtgaag atagcagtga aaataaaggg tgaggctcaa ggaacaaagt tgaaagactt 660
tgtgacaaca ctacagtcta gtgcttccat ccagtcggag attgcaaaac tccgccatgg 720
tgtggaggag tatgcaaagc agttccctac aattgggttt gagaaggaaa ccatgaagta 780
caaaaactga gagctcgact gagtatatac acaaggacca atatccaatt tcttgaaggt 840
gtatgggatg cacattcaaa ctgcagtttg ctctcaagga taggattttc atcttataat 900
attatgtaaa atccagcagt acttggttcc caactttgca ctttgtatat taacgattgt 960
aaatcatctc aggtccttga aagcaataaa ctcctcttat ctcagtaaaa aagaaagaag 1020
aaaaacattg ncctgtattg cttaatattt tccttttatt aatgagagta ccatgtgttg 1080
tgttggaaaa aaaatg 1096

<210> SEQ ID NO 245
<211> LENGTH: 386
<212> TYPE: DNA
<213> ORGANISM: Artificial
<220> FEATURE:
<223> OTHER INFORMATION: Synthetic

<400> SEQUENCE: 245
cccacgcgtc cggtggagcc atgattttct tcagaaaggg tgttaaggaa attaacaagc 60
aagggaaaga ggttttgtat gattttgaag acaagatcaa ccaagctgtc ttccctggtc 120
ttcaaggtgg tccacacaac cacactatca caggactagc tgttgctttg aaacaggcaa 180
ctacttcaga gtacaaagca taccaagaac aagtcctgag taacagtgca aagtttgctc 240
agactctaat ggagagagga tatgaacttg tttctggtgg aactgacaac catctggttc 300
tagtgaatct aaagcccaag ggaattgatg gatctagagt tgagaaagtg ttggaagctg 360
ttcacattgc atccaacaaa aacact 386

<210> SEQ ID NO 246
<211> LENGTH: 372
<212> TYPE: DNA
<213> ORGANISM: Artificial
<220> FEATURE:
<223> OTHER INFORMATION: Synthetic

<400> SEQUENCE: 246
cacccctcga cccacgctcc gaaagggtgt taaggaaatc aacaagcatt ggaaagaggt 60
tttttatgat tttgaagaca agatcaacca agctgtcttc cctggtcttc aaggtggtcc 120
acacaaccac actatcacag gactagctgt tgctttgaaa caggcaacta cttcagagta 180
caaagcatac caagaacaag tcctgagtaa cagtgcaaag ttcgctcaga ctctaatgga 240
gagaggatat gaacttgttt ctggtggaac tgacaaccat ctggttctag tgaatctaaa 300
gcccaaggga attgatggat ctacaattga taaagtgttg gaagctgttt acattgcatc 360
caacaaaaac ac 372

<210> SEQ ID NO 247
<211> LENGTH: 621
<212> TYPE: DNA
<213> ORGANISM: Artificial
<220> FEATURE:
<223> OTHER INFORMATION: Synthetic

<400> SEQUENCE: 247
gccattacgg ccggggcata ttgcagccaa taaaaacact gtgcctggtg atgtatccgc 60
catggtgcct ggtggcattc gcatgggaac cccagctctg acttctaggg gatttattga 120
ggaggatttt gtgaaagtgg ctgaattttt tgatgctgct gtgaagttgg cccttaaggt 180
caaggctgag acccaaggaa caaagttgaa ggactttgtg gaaactttga gttcagactc 240
caaaattcaa tctgagattg ccaggctaag gcaggacgtt gaggactatg caaaacaatt 300
tcctactgtt ggtttcgaga aagaaacaat gaaatacaag gattgagctg ggatctagta 360
ttcagatgga atcggaaggc atttttctcc aatgaagtta gaacttgtct ttagaagtct 420
tctggaagtc acttgcaggc gaggaaaaca gttgcacgga tcacatttgt ataattttct 480
aaatcaaagt catgatcaga tgtaattttc aagctgtaaa acaactgttc caaaattcaa 540
tttgtctcac tcttggttta gagaaggacg agaaagccaa caatggttta cggaaagtcc 600
tttgtggaat actcgcaaag g 621

<210> SEQ ID NO 248
<211> LENGTH: 690
<212> TYPE: DNA
<213> ORGANISM: Artificial
<220> FEATURE:
<223> OTHER INFORMATION: Synthetic

<400> SEQUENCE: 248
gagcgggctc gtggctgctg gtcaacttgc taatcctttc gagtactgtg atgtggttac 60
aaccactact cacaagtctt taagaggtcc tcgtggagga atgatatttt tccggaaaga 120
tccagttctg ggactggact tggaaacagc tataaacaat gcagtattcc ccggtctgca 180
gggaggacct cacaatcaca caattgctgg actggccgtg tgcctgaagc acgcagtaac 240

-continued

```
cgaagaattc aagcagtatc aaaagcaggt gattgcgaac tgtcaagcgc ttgcagacaa    300

gctggtggag ttgggattca cgctggtgtc tggcggaacc gaaaatcacc tggtccttgt    360

tgatctgcgt cctttgggaa ttgacggtgc cagaactgaa aggtgctgg atcgtgcttc    420

catcacgctc aacaagaact cagtaccagg tgacaagagt gcgttagttc cgggaggtgt    480

acgcatcggc acacctgcat tgacaacgag aggactcaag gaagaggact tcgtcaaagt    540

agcagagttc attcacgaag gcgtccaaat cgccagacag ctcaaggaaa cagtccggca    600

agggaaaatg aaagagtacg tccaggcact cgaatctcca gactctccag tccagacgag    660

catcgccgat ctacggaaca gagtcgaagc                                      690
```

<210> SEQ ID NO 249
<211> LENGTH: 398
<212> TYPE: DNA
<213> ORGANISM: Artificial
<220> FEATURE:
<223> OTHER INFORMATION: Synthetic

<400> SEQUENCE: 249

```
tggtatcaac gcagagtggc cttacggccg gggactccag aatacaaagc ttaccaagag     60

caatgcctta gcaactgctc aaaatttgcc caggcgttag cgggaatggg ttatgaactt    120

gtttctggtg gaacagagaa tcacttggtc ttggtgaact tgaaaaacaa gggtattgat    180

ggctctaggg ttgaagaagt tttggaagcg gtacatattg cagccaataa gaacactgtt    240

cctggagatg tatctgccat ggtccctggt ggcatcagaa tggggactcc tgcactcaca    300

tcaaggggat ttattgagga agattttgtg aaagttgctg aattctttga tgctgctgtg    360

aagatagcag tgaaaataaa gggtgaagct caaggaac                            398
```

<210> SEQ ID NO 250
<211> LENGTH: 641
<212> TYPE: DNA
<213> ORGANISM: Artificial
<220> FEATURE:
<223> OTHER INFORMATION: Synthetic

<400> SEQUENCE: 250

```
tgtttctggt ggaacagaga atcacttggt cttggtgaac ttgaaaaaca agggtattga     60

tggctctagg gttgaaaaag ttttggaagc ggtacatatt gcagccaata agaacactgt    120

tcctggagat gtatctgcca tggtccctgg tggcatcaga atggggactc ctgcactcac    180

atcaagggga tttattgagg aagattttgt gaaagttgct gaattctttg atgctgctgt    240

gaagatagca gtgaaaataa agggtgaagc tcaaggaaca aagttgaaag actttgtgac    300

aacactgcag tctagtgctt ccatccagtc ggagattgca aaactccgcc atggtgtgga    360

ggagtatgca aagcagttcc ctacaattgg gtttgagaag gaaaccatga agtacaaaaa    420

atgagagctc gactgagtgt atacacaagg accaatatcc aacttcttga aggtgtatgg    480

gatagacttt caactgcagt ttgctctcaa ggataggatt ctcatcttat aataatatgt    540

aaaatccagc agtacttggt tccagacttt gcactttgta tattaacgag tgtaaatcaa    600

ctgaggtcct tgaaagcaat aaactcctct tatctcagtg a                         641
```

<210> SEQ ID NO 251
<211> LENGTH: 678
<212> TYPE: DNA
<213> ORGANISM: Artificial
<220> FEATURE:
<223> OTHER INFORMATION: Synthetic

<400> SEQUENCE: 251

```
ctcaaatcct acttgtgttt ttgcctcaat ccattaattt ttgtgtttca tcatttcttt     60
gcagcagaga caaattaaga catggcaagt agcagcatgg cttctgctgc atctggtttt    120
atggtggcca cacccaatat tgccacctct aacactgctc ctcgcacctc tatgttattc    180
ttctcctcct ccaagaacaa caccaccacc aacttcccga ggctcgttgt tagggccgcg    240
gaagaggctg cgccgccagc tgctaccgcc accgctgaag gtgaagctcc tcctgccaaa    300
gctaccaagc cacctccaat tggacccaag agaggaacca aagtgagagt tttaaggaag    360
gagtcttact ggtacaaggg ggttggttca gttgtagctg ttgatcagga tccaaacaca    420
cgctacccag ttgtagtaag gttcaacaaa gtgaactatg caaatgtatc taccaacaac    480
tacgcattgg atgaagtcga agaagtgaaa tgaaagaatg gaagtaatta attagttcat    540
gctcttcata tttgtaatat gcccgaccct gtgctttcca tgtttaatct ctagttacat    600
actggctttg aatgtgaatc tgtatcataa tttcttgcaa atttctcctt ccattactta    660
ttaagtttgt tggcattg                                                   678
```

<210> SEQ ID NO 252
<211> LENGTH: 600
<212> TYPE: DNA
<213> ORGANISM: Artificial
<220> FEATURE:
<223> OTHER INFORMATION: Synthetic

<400> SEQUENCE: 252

```
gagaagcaaa gcacagcagg gatggttacc atggcttctt ccagcacatt gggcgccctc     60
gctccttgtt cctcctcctc gatttcgagc accagcagtc aggctcgctt ccttcatttc    120
gccccttccc ctttccgctt gcgcaggaat ggctcgcctg cattgagcgt gcgtgctgcc    180
gatgccgctg cccccgctga gtctgcccct gttgtggaaa agcccaagcc cattggaccc    240
aagaggggta ctaaggtgaa gatcttgagg cctgaatcat actggttcaa cggtgttgga    300
acagtggttt ctgttgatca gtctcctggt acaaggtacc ctgttgtggt cagatttgag    360
aaggtcaact atgccggcat ctccaccaac aattatgctt tggatgaaat atcagaagtg    420
taggcgacat tatctactta tcaaatgcta gaaggtctcc gaagaattga atcagtgtat    480
cttggccttt tggaaggctt gtaaatgtat gttaaaagct tttcctgcaa tgttaagaga    540
ttctgatttt attggcttga atatgagtta gtccatgata aatgcatgca cttgtatagg    600
```

<210> SEQ ID NO 253
<211> LENGTH: 538
<212> TYPE: DNA
<213> ORGANISM: Artificial
<220> FEATURE:
<223> OTHER INFORMATION: Synthetic

<400> SEQUENCE: 253

```
agcagtgtta gtggtagagt cagcagtttg tgcgaagata gccatggcgt gtgcttcctt     60
gaccgccgcc accaccgccc tcgtagccgc catggccttg ccctcgctcg gctcatcctc    120
ccccttggcc tcctccttgg cccttcccca aacccggagt gctcgcatgg tcgccctcac    180
cgtcgtccgt gcctccgacg ccgcttcccc tgtccccacc ccctctgaaa atcctgccgc    240
cgcccccgct gccgagaagc ccaagcctat cggccccaag cgtggtacca aggtaaagat    300
tttacgcccc gagtcgtatt ggtttaacgg agtcggaaca gtggtctctg tggatcagag    360
```

-continued

```
ccccgatacg cggtacccag ctgtggtgag gtttgaaaag gtgaactacg ccggcatctc    420

cactaataac tatgctttgg atgagatagt ggaggtttaa tagtatcttc attgtttctt    480

gtacactcct tttcattatc catcccttat tggtaaattt cccacctcat gagttgcc      538
```

<210> SEQ ID NO 254
<211> LENGTH: 622
<212> TYPE: DNA
<213> ORGANISM: Artificial
<220> FEATURE:
<223> OTHER INFORMATION: Synthetic

<400> SEQUENCE: 254

```
gcacgcgctc ggctttctcg ttgcgaaggt ttaaggagga agagagaaga gggatggcgt     60

cggcggcggc atccggatgt gttggattgg tgtccggggc agcggcggcg gcgacgacga    120

gcgcatcgtc gtgcagattg tttggcgggc aatgcagggt cccgtcgtgg aatcgaggct    180

cgacttgttc ttcttcttcg tcgagattgg tggtgagagc ttctgatgcc gctgcggctc    240

cagctccagc agcacccgag aagaagccag agccaatcgg tcccaagcgt ggatctatgg    300

tgaagatctt gcggcctgag tcgtattggt tcctgaacac aggcaaggtc gtcactgtgg    360

atcagacccc tggcgtgctc tacccggttg ttgttcggtt cgagaaggtg aattacgctg    420

gaaacaccac aaacaactac gcattggacg aggtcgaaga agtatgaaga aagagaagag    480

agggtctcgc tgtaaaccac atatatcctc gccttatctg ttggaaagga tttctacact    540

tgtacttagc gatttaaaac agataaaagc acaacacctg ctcccgtggc ctaatggata    600

aggcatttga cttctaatca aa                                             622
```

<210> SEQ ID NO 255
<211> LENGTH: 666
<212> TYPE: DNA
<213> ORGANISM: Artificial
<220> FEATURE:
<223> OTHER INFORMATION: Synthetic

<400> SEQUENCE: 255

```
gagttggaag agaagcaaag cacagcaggg atggttacca tggcttcttc cagcacattg     60

ggcgccctcg ctccttgttc ctcctcctcg atttcgagca ccagcagtca ggctcgcttc    120

tttcatttcg ccccttcccc tttccgcttg cgcaggaata gctcgcctgc attgagcgtg    180

cgtgctgccg atgccgctgc ccccgctgag tctgcccctg ttgtggaaaa gcccaagccc    240

attggaccca agaggggtac taaggtgaag atcttgaggc ctgaatcata ctggttcaac    300

ggtgttggaa cagtggtttc tgttgatcag tctcctggta caaggtaccc tgttgtggtc    360

agatttgaga aggtcaacta tgccggcatc tccaccaaca attatgcttt ggatgaaata    420

tcagaagtgt aggcgacatt atctacttat caaatgctag aaggtctccg aagaattgaa    480

tcagtgtatc ttggcctttt ggaaggcttg taaatgtatg ttaaaagctt ttcctgcaat    540

gttaagagat tctgatttta ttggcttgaa tatgagttag tccatgataa atgcatgcac    600

ttgtataggc aactaggctt aatgtgctta tttccttgag tttcatggaa tcccttctag    660

ttttgc                                                               666
```

<210> SEQ ID NO 256
<211> LENGTH: 551
<212> TYPE: DNA
<213> ORGANISM: Artificial
<220> FEATURE:
<223> OTHER INFORMATION: Synthetic

<400> SEQUENCE: 256

```
ctgcacctcc acctccacca cgctgctccc acttcacttg gaattcgaaa tccacacgag     60
cgccgccgcc gcccgcggcg gaggagaagc cggcggaggc cgaggcggcc gtggcgacca    120
aggagcccgc cgccgccaag ccgcctccca ttggccccaa gagaggcacc aaggtgaaga    180
tcctgaggag ggagtcctac tggtacaacg gcactggctc cgtcgtcacc gttgatcagg    240
atcccaacac tcgctacccg gtggtggttc ggttcgccaa ggtgaactac gccggcgtgt    300
cgaccaacaa ctacgccctg gacgagatcc aggaggtcaa atgattttaa ttcggatgga    360
tcgtcgtcga gctggagctg caaagaatca tctttaattg atcacggagt gaggagagga    420
tgcatgtcgt acatgtggaa gaaattaatt aagctgcttg atcgagcttt gtgtgtatta    480
gtgtaatggt ggtggtttct tctttataat ccgtataata ctatgtaatt tgcctgcctc    540
tgcttcttcc t                                                         551
```

<210> SEQ ID NO 257
<211> LENGTH: 749
<212> TYPE: DNA
<213> ORGANISM: Artificial
<220> FEATURE:
<223> OTHER INFORMATION: Synthetic

<400> SEQUENCE: 257

```
gcgtcggcga gcaccattaa cgtggcgtcg gccacctcga ggttcctgct ggccggcggg     60
aacggcggca gcggcggcgg cggggccagc cgcgtgagct tcgcggcgaa cagggtcggg    120
aggaggatgg tggtggtccg cgccgaggag gaggccgcgg cgccgccgcc gccgccgccg    180
cccgcggcgg aggagaagcc ggcggaggcc gaggcggccg tggcgaccaa ggagcccgcc    240
gccgccaagc cgcctcccat tggccccaag agaggcacca aggtgaagat cctgaggagg    300
gagtcctact ggtacaacgg cactggctcc gtcgtcaccg ttgatcagga tcccaacact    360
cgctacccgg tggtggttcg gttcgccaag gtgaactacg ccggcgtgtc gaccaacaac    420
tacgccctgg acgagatcca ggaggtcaaa tgattttaat tcggatggat cgtcgtcgag    480
ctggagctgc aaagaatcat cttaaattga tcacggagtg aggagaggat gcatgtcgta    540
catgtggaag aaattaatta agctgcttga tcgagctttg tgtgtattag tgtaatggtg    600
gtggtttctt ctttataatc cgtataatac tatgtaattt gcctgcctct gcttcttcct    660
cgtggacttg ataatccctt gcttataacc attgtattct ttcttctacg gccaaattgt    720
acatgcacat aaatttccat cattctaag                                      749
```

<210> SEQ ID NO 258
<211> LENGTH: 634
<212> TYPE: DNA
<213> ORGANISM: Artificial
<220> FEATURE:
<223> OTHER INFORMATION: Synthetic

<400> SEQUENCE: 258

```
tagaaagaga cttttaactg aattttccaa acacattctg tgaaagaata agaaaaccgg     60
ctcgagattc agatgaggag aaataattgg taaacttttg cggtacatac ggtttgggtc    120
aagttacaaa cggataaacc ggtatagaat acacagagtt tttgaattct cccatttaag    180
ctgcaacttc ttcgacctca tccaatgcat agttgttggt cgatatgttg gcgtaattga    240
cttttgcgaa ccggaccaca accgggtatc gagtcttagg gtcctgatca acggcaacaa    300
```

```
ctgatccaac gttcttgaac caataggatt ctctccttag aatcttgacc ttagaccctc    360

tcttaggacc aatcggtggt ggcttgggtt tggtggcagt agctccatcc ggagcagcgg    420

cagctgccgg agaatctttt gaagaagagg aagccggagc aggatcttcg gctgccctga    480

ctacgagcct agaaccggcg tttctcatcg gcaagaaaga cacggagctc ctggacgacg    540

aagcgccggc gaccgaggtg acattggccg gtagaacaaa taccgtagat gctgtcgtca    600

tcgccatctc tggttttctt ttcggacgcg tggg                                634
```

<210> SEQ ID NO 259
<211> LENGTH: 610
<212> TYPE: DNA
<213> ORGANISM: Artificial
<220> FEATURE:
<223> OTHER INFORMATION: Synthetic

<400> SEQUENCE: 259

```
ggtagcagca gtgttagtgg tagagtcagc agtttgtgcg aagatagcca tggcgtgtgc     60

ttccttgacc gccgccacca ccgccctcgt agccgccatg gccttgccct cgctcggctc    120

atcctccccc ttggcctcct ccttggccct tccccaaacc cggagtgctc gcatggtcgc    180

cctcaccgtc gtccgtgcct ccgacgccgc ttcccctgtc cccacccccct ctgaaaatcc   240

tgccgccgcc cccgctgccg agaagcccaa gcctatcggc cccaagcgtg gtaccaaggt    300

aaagatttta cgcccccgagt cgtattggtt taacggagtc ggaacagtgg tctctgtgga   360

tcaggtgaag tagtagaaca cagtttagtt tgggctgtct ttctaatgat aatagaactc    420

agtaaaaagt gtaggatctt ccaatgtggg ttttaattac cttttttttaa tgcatttttt   480

cagagccccg atacgcggta cccagctgtg gtgaggtttg aaaaggtgaa ctacgccggc    540

atctccacta ataactatgc tttggatgag atagtggagg tttaatagta ttttcattgt    600

ttcttgtaca                                                           610
```

<210> SEQ ID NO 260
<211> LENGTH: 643
<212> TYPE: DNA
<213> ORGANISM: Artificial
<220> FEATURE:
<223> OTHER INFORMATION: Synthetic

<400> SEQUENCE: 260

```
gccgtaacgt ctccctgaga atctggaccc ctgcacaata tctgtccaag acagcacatg     60

caatgtattc gctgaaggca gctatggagt gggatgaaga tgttttcggt ctggagtatg    120

acctggatct ttttaatatt gttgctgttc ctgattttaa catgggagcg atggaaaaca    180

agagcttgaa tatattcaat tccaagcttg tcctggcatc cccagtaact gcgactgatg    240

ctgattatgc ggcaatattg ggtgtgattg gacatgagta cttccacaac tggacaggca    300

acagagttac ctgtcgtgac tggttccagc tcagcttaaa ggaaggactt actgttttcc    360

gtgatcagga gttctcatct gatatgggaa gccgtaccgt gaaaaggatt gctgatgttt    420

caaagcttcg aatgtatcag tacccacagg attctggtcc aatggctcat cctgtccggc    480

cgcattctta tataaagatg gataacttct acacagttac ggtttatgag aagggagctg    540

aagtggtcag gatgtacaaa actttgttag ggagccaagg attcagaaaa ggcatggatt    600

tatatttcga gaggcacgat ggtcaagcag taacatgtga tga                      643
```

<210> SEQ ID NO 261
<211> LENGTH: 2137

<212> TYPE: DNA
<213> ORGANISM: Artificial
<220> FEATURE:
<223> OTHER INFORMATION: Synthetic

<400> SEQUENCE: 261

```
acgcgtccgt gccaattcca ttcctctaca tcttcttctt ttccttacca atccacctcc     60
aatctctttg aaatcaagtt acagaaatct tttgttcgtg taggaaattc gagaaatctt    120
agaaaaaaaa tatattattg ctgtttagaa agggtaaatc ccaggtgaac aagttgtaga    180
catcacggct atacacaaag caaaccgccg accattctta catgttcgtt cagtacgacg    240
taagggttgt gtaactgcca ccaatcctgc gccgcacggc ggacgtggcg ctttgccctc    300
tgaaggcggt agtccttccg acctcctctt ccttgccggc ggtggttctc tcctttcttc    360
tacctgctag atttacttac ttatatacct tacatagtta attccttctc cgtaaattac    420
taattgtttt gcacattagc aattattaag gttgttcttg tacctagtat ttttaccttg    480
aaaaatcaaa ggaaaaaaaa gcaaacatga tgctcaagat taagagggtt cctacacttg    540
tttccaactt ccaaaaggaa gaggctgaag aagctcttgc tcgtggtgct ggctgtggcc    600
gcaattgcct ccgaaactgc tgccttccag ggtcaaagct gccactgtat gcttccaaga    660
acttgagaaa gggcaagtct gttgccgatg aaaccaagga gcctcctgtt gacttcttgg    720
aatccctcct tcttggagaa tgggaggatc gtcagcagaa aggtctcttt cgctatgatg    780
tcactgcttg cgaaaccaag gttattcctg gagaatatgg tttcgttgct cagctgaatg    840
agggaaggca cctcaagaag aggccaactg agtttcgcgt tgataaggtg ctgcagcctt    900
ttgatggaag caagttcaac ttcactaagg ttggtcagga agagttgctc ttccagtttg    960
aagcaagtga ggacaacgaa gttcaattct ttccaaatgc acccattgat gccgagaaat   1020
ctcgaagtgt tgttgccatc aatgtcagtc ccattgagta tggacatgtg cttttgatcc   1080
ctaaggtcct tgaatgcctt ccccagagga ttgacaggga cagcctattg cttgcactgc   1140
acatggctgc cgaagcagct aacccatact tccgattggg ttataacagc ttgggtgcat   1200
ttgctaccat caaccatctt cactttcagg cctattactt ggctgtgcca ttccccattg   1260
agaaggcccc cactcggaag attacctttg ctgatgctgg agtgaagata tctgagatgc   1320
tgaattatcc agttcgagga cttgtctttg agggtggaaa tactttggag gatttcgcca   1380
atgttgtctc tggttcttgc atttgcctgc aagagaataa cattccctac aatgttctaa   1440
tctctgattc ggcaaaaagg gtattccttc tcccacagtg ctacgcagag aaacaggctc   1500
taggggaggt cagctctgaa ctgcttgata ctcaagtcaa tcctgcagta tgggagatta   1560
gtggacacat ggtcttgaag aggaaggagg attacgaggg tgcaaccgag gcaaatgcct   1620
ggaggcttct cgctgaggtc tcactttctg aagcgaggtt ccaagaagtg actgctctca   1680
tctttgaagc cattgattgc agtgttgaag agaatgagaa tgccaatgaa ggttctcctg   1740
agaagccaga tgttgcacct cagcctatgg aggaaattga tgctctcaac acccatgcta   1800
ccatggttcc cgtgtagggt tttcatggtc gagctgtggt gtttgtcctg ttgttactat   1860
ttcaactata tgaacattga gggagtttct atctatggct gcacttgtga aatatcccta   1920
aataaggcta gccatgttct atgtattgat gaagttgttt ggttcctatg tgaattgaac   1980
cttgtctttt attgcttcat attaatgtgg agttgctcag tgtcctctgg gaattgacct   2040
tggatactat gtttgttgtc tgttatttaa gacaatatat ttggtaatgg aagttggagt   2100
ttccctgaaa aaaaaaaaaa aaaaaaaaaa aaaaaaa                            2137
```

<210> SEQ ID NO 262
<211> LENGTH: 516
<212> TYPE: DNA
<213> ORGANISM: Artificial
<220> FEATURE:
<223> OTHER INFORMATION: Synthetic

<400> SEQUENCE: 262
agaaagagag agaccagaga gagagagaga gagagactgg taacaatggc aatggcgttg 60
agagcagcgt tccagtgcac gccaagcgca tcatcccttt cgtcctcctc ctcctcggca 120
tcgcccctcc tccgtcgggg tgctgctgcc gccctgaggt ttgcacgctg ctcgaccccc 180
ggtaacgcgg gaagcccact ctgcagccct cctcccttca gagccgccgc tcggtcctgg 240
cgcgccctct ccctccctgc ctcccagctc accgcctccc ctcccacccc cgcttacacc 300
atcaaggagg agggtaagcc cgagtccctc gacttccgcc tcttctactt cagcgatgat 360
tccggcaaaa agatctcacc atggcacgac atacctttag aagccaagga tggcatgttc 420
aactgtatta tagagattcc aaaggaaacc agtgcgaaaa tggaagtggc caccgacgaa 480
ttctacaccc ctatcaagca agatactaag aagggc 516

<210> SEQ ID NO 263
<211> LENGTH: 635
<212> TYPE: DNA
<213> ORGANISM: Artificial
<220> FEATURE:
<223> OTHER INFORMATION: Synthetic

<400> SEQUENCE: 263
gtcgctccgc cgccgccgcc gctgttcact ccgcaccaac tccgacgatc cccggcgag 60 ctctcgacga tggcgacggc ggcgacggcg tcggctacgg cggccacccg cttcacgcgg 120
ctggcggggg tcgggctccg gcgcacggcc cgcctcccca cggccgtgcg gttccagcgc 180
cgggtgctcg ccaccaccgc gctcctcagg accgccgagc tccggcccaa ggagcagggc 240
ctgcccgaga cgctcgacta ccgcgtgttc ctcgtcgacg gcgggggccg caaggttgtc 300
gccgtggcac gacgtgcccc tgcgcgcagg cgacggggtt gttccacttc gtcgtggaga 360
atcccaagga gagcagcgcc aagatgggag gtcgccaccg acgagtcatt cacccccatc 420
aagcaggaca ccaagaaggg caacctccga tactacccgt acaacattaa ttggaattat 480
ggattatttc cccaaacatg ggaggaccca actcttgcaa acaccgatgt cgaaggagca 540
tttggggata atgatcctgt tgatgttgtt gagattggtg aaagacgtgc taacattgga 600
gatgttctta aggtaaaacc gttggcagct ttagc 635

<210> SEQ ID NO 264
<211> LENGTH: 590
<212> TYPE: DNA
<213> ORGANISM: Artificial
<220> FEATURE:
<223> OTHER INFORMATION: Synthetic

<400> SEQUENCE: 264
aaatcattta ttgatttaat ctcctttttc ctttatcata atgcaaagaa tccattaaga 60
gaagcacttc aaacgagcga gagatccccc gccggggcag accttgtcac aagcttcacc 120
cacgcttgat gcgtctcctg gatcaccttg agcgcgtact ccttgccagc agccttgttc 180
cccagcccaa acttattctg cggcttccca tccggcacct tgtagtcgcg gaaccagtcc 240
cggatctcca tcagcgtccc gggaaagtac ttctccacat cactctcatc gttgaaaagc 300
ccagccctgg gatcatccac ggagatggcc accaccttcc agtccagctc cccctcatcg 360
atcatcgcca gcaccgccac cggcttcact cgaagaactt ccccacgccc cgcctttcgc 420
tcgccgatct cgacaacgtc gaccggatca ttgtcaccaa gcgctccctc cacatccggg 480
ttggcgtggt ttggatcttc ccaagtttgc ggaagaagcc cgtagttcca gcgtatgtcg 540
tatggataga accgtagctt gcctttcttc acgtcctgct tgatcggcgt 590

<210> SEQ ID NO 265
<211> LENGTH: 549
<212> TYPE: DNA
<213> ORGANISM: Artificial
<220> FEATURE:
<223> OTHER INFORMATION: Synthetic

<400> SEQUENCE: 265
gccattacgg ccggggactg gaaaatagtt gctatttcac tagacgatcc aagagcttca 60
cttgttaatg atgttgatga tgtagagaaa cattttccgg gcactctcac cgcaatcagg 120
gactggttta gagactataa gatacctgat ggaaaacctg ccaataggtt tgctcttggc 180
aacaagccag caaacaagga ttacgctctt aaggtgatta cggaaaccaa tgaatcttgg 240
gcaaagcttg tcaaaagatc tatccccgct ggtgagcttt cacttgtata gatgccaatt 300
gatagagctt gagccagcta gttttcatgc tcgtaaccta aactggacgc ggaaaatggc 360
cccaggatta tgctcttcgc ttttgaggtg gaagtccatt catattctta agacagtttt 420
ttgttaaaaa tgttactgtt tttctatttc atcatccata attttgttca tgcagtagtg 480
ttttcaaatt ttatttaggg tgaaaacagg tgtactgact actgataatt gaattgatcg 540
tcattcctc 549

<210> SEQ ID NO 266
<211> LENGTH: 583
<212> TYPE: DNA
<213> ORGANISM: Artificial
<220> FEATURE:
<223> OTHER INFORMATION: Synthetic

<400> SEQUENCE: 266
ccccccgagt tccccatttc agcagcaaag gcaacaatgg cggctgcaag agtaatgata 60
tcagccaaca acactctaac aacttctctt ttatccaaaa ttcctctcca aaagcccaat 120
agtttcaacc tttgtttccg caataggtct gctgctgcac acaggagcca acttttcact 180
tgcactgcta tttacaatcc ccagattcaa atcaaagaac aaggccagcc cgaaacttta 240
gattaccgtg tctttttcgt tgatgattcc ggcaaaaagg tgtccccttg gcatgacata 300
ccactgcatt taggtgatgg tgttttcaat tttattgctg aaattcctaa agaatcgagt 360
gcaaagatgg aagttgctac agatgagctg tacacaccaa taaagcaaga cacaaagaag 420
gggaaactta gatactaccc atataatatt cattggaact atggattgct tcctcaaacc 480
tgggaagacc cctcatttgc aaatgctgaa gttgaggggg cattcggaga taatgaccct 540
gttgatgttg tccagattgg ggaaagtcgt gctaaaattg gcc 583

<210> SEQ ID NO 267
<211> LENGTH: 574
<212> TYPE: DNA
<213> ORGANISM: Artificial
<220> FEATURE:
<223> OTHER INFORMATION: Synthetic

<400> SEQUENCE: 267

```
cccccgagtc tcccgccgcc gccgccgggg gtcactccgc accaactccg acgatccccc     60
ggcgagctct cgacgatggc gacggcggcg acggcgtcgg ctacggcggc cacccgcttc    120
acgcggctgg cgggggtcgg gctccggcgc acggcccgcc tccccacggc cgtgcggttc    180
cagcgccgcg tgctcgccac caccgcgctc ctcaggaccg ccgagctccg gcccaaggag    240
cagggcctgc ccgagacgct cgactaccgc gtgttcctcg tcgacggcgg gggccgcaag    300
gtgtcgccgt ggcacgacgt gcccctgcgc gcaggcgacg gggtgttcca cttcgtcgtg    360
gagatcccca aggagagcag cgccaagatg gaggtcgcca ccgacgagtc attcaccccc    420
atcaagcagg acaccaagaa gggcaacctc cgatactacc cgtacaacat taattggaat    480
tatggattat ttccccaaac atgggaggac ccaactcttg caaacaccga tgtcgaagga    540
gcatttgggg ataatgatcc tgttgatgtt gttg                                574
```

<210> SEQ ID NO 268
<211> LENGTH: 615
<212> TYPE: DNA
<213> ORGANISM: Artificial
<220> FEATURE:
<223> OTHER INFORMATION: Synthetic

<400> SEQUENCE: 268

```
gtctgatttg gtctgtatac ggttgataca tatgacgaag tgattgaagc ttggagtgag     60
tggattttca tcaagcttat cggatttgtt gagctggtga aggtcaagat ggcgatggcg    120
atgcaggcca cctcttcctc ttctctccgc aatacctcct tccttgcctc tttccgtggg    180
gaacaaattc ccggtgcaca gaaatccgca gtcggtggct ttgcctcctc tcgtcaagtg    240
cagagtaacg tttcgacagt tcttatctct gtgaggaatg agaagaaaaa gatgagggga    300
gtgagttgca gagcttctgc tgcagattct ccaaagcaag ttgaaagcaa aaaggttctg    360
atgatgggag gcactcgctt tatcggcctt tacttggccc ggttgcttgt acagtctggc    420
cacgaggtca cccttttac ccgaggaaag gcgcccatta cccaacaatt agcaggggag    480
tccgatgagg aataccaaga atatgcctcc aaagtgaagc acatgcaagg tgatcgtcag    540
gatttcgaag gcttgaagag caagctttcc gaagcatctt ttgacattgt gtatgatata    600
aatggaagag aggct                                                     615
```

<210> SEQ ID NO 269
<211> LENGTH: 700
<212> TYPE: DNA
<213> ORGANISM: Artificial
<220> FEATURE:
<223> OTHER INFORMATION: Synthetic

<400> SEQUENCE: 269

```
cccccccctc aggccggtgt acatctacgg cccgctcaac tacaaccccg tggaggagtg     60
gttcttccac cggctcaagg ctggccgccc catccctgtc cccggtgccg gcaaccaaat    120
cacccagctc ggccatgtca aggacttggc gacggcgttc gtgctggcgc tcggcaaccc    180
gaaggcgagc aagcaggtgt tcaacatctc cggcgccaag tacgtcacct tcgacggtct    240
agcacgggcg tgcgccaagg ctggaggatt ccccgagccg gagatcgtcc actacaaccc    300
caaggacttc gatttcggga agaagaaggc cttccccttc agagaccagc atttcttcgc    360
gtcaatcgag aaggcgacct tggagctcgg gtggaagccg gagtacgacc tggtggaggg    420
cctcaccgac tcgtacaacc tcgacttcgg ccgcggcacg ttcaggaagg cggccgactt    480
```

-continued

```
caccaccgac gacatgatcc tcggcaagaa gctcgtcagc gtctgagctc gccgccgtcc    540

tttccggaca gcggacggat tgcttgctgc gcgacgcgag cggctgaccg gccgggccgc    600

catggccggt gggcaggagc aagcggagac ggtttcagtt ttgttatcaa cgctggtttg    660

gtacaatatg gatagttgga tacacgcgta caggcgtaag                          700
```

```
<210> SEQ ID NO 270
<211> LENGTH: 339
<212> TYPE: DNA
<213> ORGANISM: Artificial
<220> FEATURE:
<223> OTHER INFORMATION: Synthetic

<400> SEQUENCE: 270

cggacgcgtg ggtgaggaga ggaaacatca aacaaaagag agagagatgg caggcgcagc     60

ctccctgaag agcagcctcc tgctaccatc tcctatctct gacttcagta gggcagcact    120

ctccatctca acccaggcta ggaggaggtc atggcagcca agggggcaa ggatgcaggt     180

agcagcagct gcagactcca agaacattct tgtgatgggg ggaaccaggg tcattggcgt    240

cttcttgtcc aggctccttg gcaaggaggg gcaccaagtc acattgttca ctagaggaaa    300

ggcccccatt acccagcagt tgccaggaga gtcagatgc                           339
```

```
<210> SEQ ID NO 271
<211> LENGTH: 435
<212> TYPE: DNA
<213> ORGANISM: Artificial
<220> FEATURE:
<223> OTHER INFORMATION: Synthetic

<400> SEQUENCE: 271

cggacgcgtg ggcggcccgc tcaactacaa gcccgtggag gagtggttct tccaccggct     60

caaggctggc cgccccatcc ctgtccccgg tgccggcaac caaatcaccc agctcggcca    120

tgtcaaggac ttggcgacgg cgttcgtgct ggcgctcggc aacccgaagg cgagcaagca    180

ggtgttcaac atctccggcg ccaagtacgt caccttcgac ggtctagcac gggcgtgcgc    240

caaggctgga ggattccccg agccggagat cgtccactac aaccccaagg acttcgattt    300

cgggaagaag aaggccttcc ccttcagaga ccagcatttc ttcgcgtcaa tcgagaaggc    360

gaccttggag ctcgggtgga agccggagta cgacctggtg gagggcctca ccgactcgta    420

caacctcgac ttcgg                                                     435
```

```
<210> SEQ ID NO 272
<211> LENGTH: 649
<212> TYPE: DNA
<213> ORGANISM: Artificial
<220> FEATURE:
<223> OTHER INFORMATION: Synthetic

<400> SEQUENCE: 272

cccacgcgtc cgggcgaagg ggatgatgtt gcaacagcat cagccttctt tctctctcct     60

tacttcttct ctgtctgact tcaatggcgc taagctccat ttacaagtcc agtacaagag    120

gaaggttcat cagccaaaag gagcactcta tgtttcagcg tcgagcgaaa agaagattct    180

gataatgggt ggtactcgat tcattggtct gttcttgtcc aggatccttg tcaaagaggg    240

acatcaggtt acattgttca caaggggtaa atctcctatt gccaaacaat tgcccggtga    300

atctgaccaa gactttgctg atttctcttc taagattctt cacttgaaag gagacagaaa    360
```

```
ggactatgac tttgtgaagt caagtctttc agcagaaggc ttcgatgttg tttatgatat    420

caacgggagg gaggccgaag aagttgagcc catactagaa gcactaccca aactagagca    480

gtacatctac tgttcttcag ctggtgttta tctgaaatct gatatcttgc cacattgtga    540

ggaggatgca gttgatccga agagcaggca caaggggaag ctggagactg agagcttact    600

gcaatcaaaa ggtgtaaact ggacttctat acgtcctgtc tacatctac               649
```

<210> SEQ ID NO 273
<211> LENGTH: 1271
<212> TYPE: DNA
<213> ORGANISM: Artificial
<220> FEATURE:
<223> OTHER INFORMATION: Synthetic

<400> SEQUENCE: 273

```
tgaagcaggc accacctaat tacaacaatg gctagtttgg ttgcagttca acacaaacag     60

ccttcttttg ctgtcctccc ttcttcccat tctgacttca atggtgccaa attgatctcc    120

tctcttcagt ttaagaggaa accatgccag ccaaaaggag cattgcatgt tacagcatca    180

agtgccaaga aaatccttat aatgggaggc actcgattta ttggtgtctt tctatccaga    240

cttcttgtaa aagaaggcca tcaggttact ctgttcacaa gaggaaaagc tccaatctct    300

caacaattac caggtgaatc agaccaggat tatgctgatt tttcctccaa gttattgcac    360

ttgaagggtg acagaatgga ttttgatttt gtgaagagca gtctttctgc agagggcttt    420

gatgttgtgt atgacataaa tggacgtgaa gcagtagaag tggaaccaat attggatgca    480

ttacctaatc tggaacagta catatactgc tcttcagctg gtgtatacct caaaactgat    540

tatttaccac attttgaggc tgacgcagtt gacccaaaga gcaggcataa aggaaagctt    600

gagacagaga gcttgttaga atcacgagat gttaattgga cttctgtaag gcctgtttat    660

atttatgggc cacttaacta taatccagtt gaagagtggt tcttccaccg attgaaagct    720

ggtcgcccaa ttccaattcc taactcaggg ctgcaaataa ctcaacttgg acatgtgaag    780

gatcttgcaa cggcttttat tcaggttctt ggaaatgaga aagcaagcaa gcaagtattt    840

aacatatctg gagagaaata tgtcacgttc gatggattgg ctaaggcttg cgccaaggct    900

ggcggcttcc ctgaacccga gattgttcac tacaacccta aggagtttga ctttggcaag    960

aagaaagctt tcccattccg tgaccagcat ttctttgcat cggtcgaaaa ggcaaaggct   1020

gtgctaggtt ggaagccgga attcgaattg gtggaaggtt tgacagactc ttacaaccta   1080

gattttggta ggggaactta caggaaagaa gctgatttct ctacagatga tcttattcta   1140

ggaaagaatt agttctccac acctacgctt tctgctttca attttttcaa attttggctt   1200

cttgcttttg tgaaattggg aatataacat tcatacacat ctgcgtatga tatatttttc   1260

attgttttga g                                                        1271
```

<210> SEQ ID NO 274
<211> LENGTH: 643
<212> TYPE: DNA
<213> ORGANISM: Artificial
<220> FEATURE:
<223> OTHER INFORMATION: Synthetic

<400> SEQUENCE: 274

```
atggctgcat cgtctgcaat cagaggctac ggtgcagcaa ctgctgcttc tccttacgat     60

gtttcagtgc aggaacgaag atatggagca tccatgttga agaagaatgt ttactgcggc    120

aaagttgagc tatgtcgagc ttcggacttc acacaaaatg tcttgcgcca ggccgcgaat    180
```

```
ctaacgagac ttcaagctca agcagtccga aagacgtccg tcgttgccat ggcctcctca    240

tcgaaaaaca ttttgatgat gggaggaacg cggttcattg gagtttacct ggcaaggtta    300

cttgtgaaag ccggacacga ggtgacgctc ttcactcgtg gaaagtcgcc gataacgcaa    360

aaaattgcca gtgaaactga tgaagagtat gcagagtatt cgtcgaaagt acgtttcaca    420

tctggtggct atttatcttt tcgtgtctgc ctttcgccag ataaaacata ttcaaggcga    480

tcgccaggac ttcgagggga tgaagagcaa aattgccaat gctggtttcg agatcgtgta    540

tgatatcaac gggagggagg ctgtcgaagt tgaacccatc cttgatgcac ttccgggctt    600

gaaacagtat gtatattgtt catcagcagg agtatacttg aag                      643
```

<210> SEQ ID NO 275
<211> LENGTH: 546
<212> TYPE: DNA
<213> ORGANISM: Artificial
<220> FEATURE:
<223> OTHER INFORMATION: Synthetic

<400> SEQUENCE: 275

```
gtttttgcag ggattgtgag ggggaggccg gtgccgatcc cggggtcggg gatgcaggtg     60

acgaacatat cgcacgtgcg cgacctggcg agcatggtgg cgctcgccgt ggagagcccc    120

ggcgcggcgg cggggaggat cttcaactgc gtctccgacc gcgccgtcac cttcaacggc    180

ctcgtcaaga tgtgcgccgc cgccgccggc gcccagccgg agatcctcca ctacgacccc    240

gccgccgtcg gcgtcgacgc caagaaggcc ttccccttcc gcaacatgca cttctacgcg    300

gagccgaggg cggcgaagga ggtgcttgga tggaggagct cgacgaacct gccggaggac    360

ctcaaggaga ggttcgcgga gtacgccagc agcggcagag ggcacaagga gatgagcttc    420

gacctcgacg acaagatcat cgccgccgcc taacaacacc catctcatct cacctcgtca    480

tggtcaaata caaatacaaa gtggtcgggg atctcttctt ctcgtgattg atttcttct     540

ccctct                                                               546
```

<210> SEQ ID NO 276
<211> LENGTH: 639
<212> TYPE: DNA
<213> ORGANISM: Artificial
<220> FEATURE:
<223> OTHER INFORMATION: Synthetic

<400> SEQUENCE: 276

```
ccccccccgg aggagagtaa acaagaaaaa aaagagagag agatggcagc aacagcctcc     60

ctgaagagca gcctcctgct accatctcct atctctgact tcagtagtgc agcactctcc    120

atctcaaccc aggctaggag gaggtcatgg cagccaaggg gggcaaggat gcaggtagca    180

gcagctgcag actccaagaa cattcttgtg atggggggaa ccaggttcat tggtgtcttc    240

ttgtccagga tccttgtcaa ggagggcac caggtcacat tgttcactag aggaaaggcc     300

cccattaccc agcagttgcc aggagagtca gatgcagagt atgcagagtt ctcttcaaag    360

gtgttgcact tgaaaggtga caggcaagac tttgatttcg ttaagacaag ccttgcggca    420

aagggcttcg atgttgttta cgacataaac gggagagaag ctgttgaggt agccccaatc    480

ctagacgcat tgccaaacct tgaacagtac atctactgct catcagcagg agtgtacctg    540

aaatcagacc tgctcccgca cttcgagacc gacgccgtcg acccgaaaag ccggcacaag    600

gggaagctgg agacggagag cctgctggag acccgggac                           639
```

-continued

<210> SEQ ID NO 277
<211> LENGTH: 1312
<212> TYPE: DNA
<213> ORGANISM: Artificial
<220> FEATURE:
<223> OTHER INFORMATION: Synthetic

<400> SEQUENCE: 277

```
gcgcgcctta attaggatcg aaggaaggtc atcaagtaac ttggttcaca agagggaaag     60
caccaatcag ccaaccatta cccggggagt cagaacaaga ttacctagat ttctcttcca    120
agatctcgca cttgaaagga gacagaaagg actacgattt tgttaagact agcctagcag    180
ctgaaggctt tgacgttgtc tatgatatca atggaagaga ggcagataga gagagagaca    240
atggcaatgg caacaagtag gttggtggtg gtgcaacaaa aacaaccatc ctcatgtcta    300
ttaccaccat catctctttc tgatttcaat ggtattagac tgaaacaccc aattcagtac    360
aaaagaaagg aatggcagac aagaggagca ttgcaggtga aagcatcagc tgcaaagaaa    420
atcctgataa tgggaggaac cagatttatt ggaatctttt tgtctaggct ccttgtgaag    480
gaaggtcatc aagtaacttt gttcacaaga gggaaagcac caatcagcca accattaccc    540
ggggagtcag aacaagatta cctagatttc tcttccaaga tctcgcactt gaaaggagac    600
agaaaggact acgattttgt taagactagc ctagcagctg aaggctttga cgttgtctat    660
gatatcaatg gtattggaag agaggcagaa gaagtagaac ccatattgga cgcgcttcca    720
aagcttgagc agtacatata ctgttcatcc gctggtgtgt atctgaagtc tgatttactg    780
cctcattttg agtctgatgc agtggatccc aagagcaggc acaagggaaa acttgaaaca    840
gagagtttac ttgtatcaaa gggcgtgaac tggacttcgc tgagaccagt ttatatctac    900
ggtcctttga attacaaccc tgttgaagaa tggtttttcc acagattgaa ggccggtaga    960
ccaatcccca taccaaattc tggcaaccag ataacacaat tgggtcatgt taaggatttg   1020
gcgaccgcat ttattaacgt tcttggtaac gataaagcga gccagcaagt gtttaacata   1080
tctggagata aatatgtgac attcgacgga ttggcaaggg cttgtgctaa ggctggtgga   1140
tttcctgagc cagaactagt tcactacaat cctaaagaat tcgattttgg caaaaagaag   1200
gcattcccct tcagagacca gcatttcttt gcatcaattg agaaagcaaa gagtgaattg   1260
ggtggaaac cagaatatga tttggtggaa ggtctaacag actcctacga tc          1312
```

<210> SEQ ID NO 278
<211> LENGTH: 707
<212> TYPE: DNA
<213> ORGANISM: Artificial
<220> FEATURE:
<223> OTHER INFORMATION: Synthetic

<400> SEQUENCE: 278

```
gatttcctta tgcttattat tattattcct tgaagccact cgctctcatt tctacttccc     60
gtcaggtgca agcgtttacc ttcaggggct gtaccctagc tatggccgct tccatgaccc    120
tagggcacca agtcacagtg ggaggaggtg taggtggggg tgcgaatgcg cctccccccgc    180
ctttcttgcg caacggattt gccaaagggc tgggactggg tataggggga ggagtagggg    240
ctttgaccaa aggtcggcga gaagggggcg ctcggtgctc ggtggccact ctggccatcc    300
ctaagcccaa ccgtgatctc ctctcggagt tcgagaagcg atggcaaagg gctgtggaca    360
accccttgga aggcgtcccc ttcacctacg aagacttccg aggtgccctc tccaagtacg    420
acttcaactt cgagattggt gataccgtga aaggtaccgt gttcatgacg gaatccaatg    480
```

```
gtgctcttgt tgatattggt gccaaggcac cagcctttct acctactgtt gaagcttcat    540
tgcacaaggt caaacatgtt ctggaagtag ggatatcttc aggtattgtt gaagaatttc    600
agattatccg agaggacgat aacaatggaa gaatgatttt aagccttagg aaagcacaat    660
atgacatggc ttgggaacga tgcaaacagt tgatggagga ggatgtt                  707
```

<210> SEQ ID NO 279
<211> LENGTH: 359
<212> TYPE: DNA
<213> ORGANISM: Artificial
<220> FEATURE:
<223> OTHER INFORMATION: Synthetic

<400> SEQUENCE: 279

```
caaagcttgt cctcagcaac cgtaaagctg tagcagatag ccaagctcag cttggaattg     60
gatctgtggt cctcggagtt gttcagagct tgaaacctta tggtgccttc attgacattg    120
gtggaatcaa tgggcttctt catgtcagtc agataagtca tgaccgtgtc tcagatatcg    180
caactgttct tcagcctggt gacactttga aggttatgat attgagtcac gaccgtgaca    240
gaggaagagt aagtctctcc acaaagaagc tggagccaac acctggtgat atgattcgta    300
acccaaaact tgtgttcgag aaggctgagg agatggctca gacattcaga cagagaatt     359
```

<210> SEQ ID NO 280
<211> LENGTH: 332
<212> TYPE: DNA
<213> ORGANISM: Artificial
<220> FEATURE:
<223> OTHER INFORMATION: Synthetic

<400> SEQUENCE: 280

```
aaaactctct gtgtgagtga gtgagactca accatggcgt ctttggctca gcaattctcg     60
ggattgagat gttccccact ctcttcttct tctaggttat cgaggagagc ttcgaagaac    120
tttccccaga acaaatctgc ctctgtttct ccgactattg tcgccgcggt tgcaatgtct    180
agcggtcaaa caaaggagcg tcttgagctg aagaagatgt tcgaagatgc ttatgaacga    240
tgtagaactt ctcctatgga aggtgttgct ttcaccgtcg acgatttcgc tgctgctatt    300
gaacaatacg acttcaattc cgaaatcggc ac                                  332
```

<210> SEQ ID NO 281
<211> LENGTH: 603
<212> TYPE: DNA
<213> ORGANISM: Artificial
<220> FEATURE:
<223> OTHER INFORMATION: Synthetic

<400> SEQUENCE: 281

```
ggcgatccat cgatcgagcg gcgatggcgg cggcagtggc ggcggcgacg gcagcacagg     60
taaacctagt aggattcagc agcagcagcg gcttcggcgg caggccaggg ttcctcggca    120
gcaatcggcg gaccggcatc gtcgccagga atcccgcccg gatccactgc gtggtcgcat    180
tcgccgaccc gcggtcccgg aacctggacg tcaaggaaga gatcgagcgg cggtgggaag    240
ctctccagga gaatccacta gagggcgttc cattcacggt ggaagaattc gaggaagctc    300
taaccaagta tgatttcgat cacagcgttg gagacgttgt caaggggacc gtcttcgtca    360
ccgacaagct tggagctctc gtcgacatcg gtggcaagtc catggccttt cttccaatgg    420
acctggcgtc ggtcttcaag ctcaaggatc tccgggtgat gggactcttc tccggcgtcc    480
```

-continued

```
gggaagagtt cgaggtggtg agagaagacg aggagaacag ccggttcata ctctctctcc    540

gggagatgca cgtaaagatg tcgtgggaga ggctgcggca gatccaggcc gaggacgctg    600

ttt                                                                  603
```

<210> SEQ ID NO 282
<211> LENGTH: 1464
<212> TYPE: DNA
<213> ORGANISM: Artificial
<220> FEATURE:
<223> OTHER INFORMATION: Synthetic

<400> SEQUENCE: 282

```
atcaatttcc tcgcttccgc caaaatggct tctttgacac aacaattcgg agggttgaaa     60

tgcccaccaa tttcaacagc aagggttgaa tctaagaagc ttaaggtgaa tcccattaat    120

catcagaata agaaggctaa caaagcaaga gtagtagcac aagctgcagc agtggtcaca    180

aatgcacaaa caagagaaag acaaaagctt aaggagatgt tcgaggatgc ctatgaacga    240

tgccgtactg cacctttgga aggtgttgcc tttactgttg aagattttca ctctgccctt    300

gaaaaatatg attttgactc cgaagttggt accaaggtca aaggaacagt tttctctgtg    360

gatgcaaatg gagctctagt tgacatcact gcaaaatcat ctgcatactt gcctttacgg    420

gaggcttcac ttcacaccat caagcacgta gaggaagctg gaatatttcc tggtttgcgt    480

gaggagtttg tggtggttgg cgaaaatgaa gctgatgata gtttggtttt gagcttgcgt    540

tcgattcaat atgaccttgc atgggaacga tgtaggcagc tacaagctga agatgttgtt    600

gtcaaaggca aggtcgttgg tgcaaacaaa ggtggagtgg tggctctggt ggaggggctt    660

cgtggttttg ttccgttctc gcagatatca acgaaatcaa ctgcagagga acttttggaa    720

aaggagcttc ctctgaagtt tgttgaggtt gatgaagagc aatccagact tgtgctcagc    780

aatcgtaagg ccatggctga tagtcaggca caattgggaa taggctcagt cgttcttgga    840

acagttcaga gcttgaaacc atatggtgcc ttcattgaca ttggtgggat caatggcctt    900

cttcatgtga gtcagattag tcatgatcgt gtctctgata ttgcaacagt cctccagcct    960

ggtgacactc tcaaggtcat gatattgagc catgatcgtg agagaggtcg agtgagcctt   1020

tcaacaaaga agctagagcc tacacccgga gacatgattc gcaatccaaa gcttgtcttt   1080

gagaaagccg aggagatggc ccaaacattc aggcagagaa ttgcccaagc ggaagccatg   1140

gcccgtgcag atatgctgag gttccaacct gagagtggat tgaccctgaa ctctgacggg   1200

atattatgcc cgctgacctc tgaactacct gaagatggac tggatttgag tgagattccg   1260

tcagctgaag attaatgatt ctaaatggag atcccgcttc tttttgacct tttgttgca    1320

gaaattggat aaatgctctt tgtaggctta ggaaccattc atgataaacg tattccgtcc   1380

gcaatcattc tattgcatta ttaccatgat tctaaacaat ttggcttgca ctacttgcta   1440

acaatgaatc attgttaaat agca                                          1464
```

<210> SEQ ID NO 283
<211> LENGTH: 629
<212> TYPE: DNA
<213> ORGANISM: Artificial
<220> FEATURE:
<223> OTHER INFORMATION: Synthetic

<400> SEQUENCE: 283

```
gaattcaggg aaaacagagt cgtttctggt acaaattagg tctaaagatg gcgtctttag     60

ctcaacaatt ctcaggatta agatgcccac cactttcttc ttctcatcta acaaaaccct    120
```

-continued

```
tttcttcaaa accccagaaa accacctttt cacctatagt ttcagcagct gtcatttcta    180

atgcacaaac taaagaaaga agtagactta aagaaatctt cgaagatgct tatgaaagat    240

gtagaactac tccaatgcaa ggtgttggtt ttactgttga tgattttcat gctgctcttg    300

aaaagtatga ttacaattct gagattggta ccagggttaa aggaactgtg ttctgtacag    360

acaacaacgg agcattagtt gacatcacgg cgaaatcttc agcctattta ccaatccaag    420

aggcatgtat tcacaaaata aagcatgtag aagaagcagg aatagttgca ggcctacgtg    480

aagagtttgt gattattgga gagaaccaag ctgatgatag cttgatcttg agtttgcgtt    540

caatccaatt tgacctcgca tgggaacggt gtagacaact tcaggcagag gatgtcgtcc    600

tcaagggtaa ggttgttggt ggaaacaaa                                      629
```

<210> SEQ ID NO 284
<211> LENGTH: 801
<212> TYPE: DNA
<213> ORGANISM: Artificial
<220> FEATURE:
<223> OTHER INFORMATION: Synthetic

<400> SEQUENCE: 284

```
tgtatggcgc agagtggcca ttcggccggg ggaagccaag tttgggaaaa tcttaaaaga     60

aagaaagaaa tgatgacgaa tcgccacttc ctcttcgctc ttcttttcac tttctttctt    120

tcagctgttg ctgcagattc ttctgaagag tgtgtataca cattgtatgt taaaactgga    180

tcaatcataa agggtggaac agactccaaa atcagcgtta cacttggcga tgctaaagga    240

aaatcagtat atattccaga tctagagaaa tggggtttaa tgggcccaaa ttatgattac    300

tacgaaaggg gtaatgtgga tatcttcact ggtagaggcc aatgtttaag cccaccaatt    360

tgcaggctta atgttacttc cgatggatca ggtgaccacc acggttggtt tcttgatttt    420

gttgagacta cttttactgg gccacacaaa acttgtagcc aatccatatt ctatgtcgaa    480

caatggttgg cttctgatgc tcctccttat gagttatcag tttctcttga tggttgtaaa    540

aagaagactg ggcttcgaca tgctcggcgt tttgtcgtgg gccagcccaa tgggtctgct    600

tcagaatagt ttggcccgtt gaagttcttt ttgtaatttt gtcgttgaga tgattttgat    660

gtgtagattg ccctgtgttt tcccttctct ttggttgaaa taaatttctt gtttggggct    720

tcctttcttg cttgtttagt cgtcatatct ttgacttatt ggctcttttg gcaatttgca    780

atcttttatg tactcaataa g                                              801
```

<210> SEQ ID NO 285
<211> LENGTH: 579
<212> TYPE: DNA
<213> ORGANISM: Artificial
<220> FEATURE:
<223> OTHER INFORMATION: Synthetic

<400> SEQUENCE: 285

```
gatgtcgacg gggaaaggct tagctctaat cctggcattt gctgccatcg ccacctgcat     60

cacctctgct acgaaccaat gcgtatacac tatttatgtg aggacgggaa aggtgataaa    120

aggggggaca gattcaaaca tttcggcacg attctatgat gccaacggat actatatcaa    180

tttggaaaat ttggcagaat ggggtggttt gggaggtcct ggctacaact actttgagag    240

aggcaatttg gatgtgttca caggccttgg gcagtgcctc acggccccca tttgcgcgct    300

caacctgacc tcagacggca ctggagacca acacgggtgg tactgcaact atgtcgaggt    360
```

-continued

```
cacctccacc gggccccaca tcccttgcag ccaacaccaa ttcaccatcg agcaatggct    420

tgccactgac acctaccctt tcgagctcaa tgccacccgt gacgattgcc tggtcgaggg    480

caaaaccagc gcctccaagg caatttcatc agagtcgagc tagagttcca gctgggcctt    540

ttttggcttc cgtttttgat gaataagcaa gctccttct                           579
```

<210> SEQ ID NO 286
<211> LENGTH: 741
<212> TYPE: DNA
<213> ORGANISM: Artificial
<220> FEATURE:
<223> OTHER INFORMATION: Synthetic

<400> SEQUENCE: 286

```
gagaggaaga aaaagctcaa gagaagacat gggaatagca gctcactcca accatttctg     60

gtcccttctc ttcatagtct ttttctcttt ctccatctcc tccatttccg gatctgatga    120

tgattgcgtg tacacagctt atgtccgaac gagttcaata ataaagggtg gaacagattc    180

gattatcagt ttgagtctct acgatgcaaa cgggtatggt cttagaatca agaaccttga    240

ggcctggggt gggcttatgg gctctggtta caactatttc gagaggggaa atttggacat    300

tttcagcgga cgaggcccat gtttgactgg gcctgtctgc aaaatgaatt tgacttccga    360

cggaacaggc aaaggccatg gatggtactg taactacgtg gaggtcaccg tcaccggagt    420

ccataaagca tgcaaccaac agaatttcga agtggagcag tggctagcta ctgatgcttc    480

gccgtatgag cttacggctg ttagagacaa ctgtaagaag tccaagtccg atgagaaact    540

gtccatttcc gatgtctacg gaactcattc cactccacct gtttctgtga tttaaatttc    600

tagttattgg gttttaatgg gcctggaccc acatttccct tttaccctta ttactgtgat    660

gtgaaattta tcaggggtaa gaatgacatt tcatgtgtgt caatgttgct ttcatgttat    720

agtatgagat agaggagtag t                                              741
```

<210> SEQ ID NO 287
<211> LENGTH: 374
<212> TYPE: DNA
<213> ORGANISM: Artificial
<220> FEATURE:
<223> OTHER INFORMATION: Synthetic

<400> SEQUENCE: 287

```
aaaaaaacaa aatggctcgt cgcgatgttc tcctcccttt cctcctcctt ctcgccaccg     60

tctccgccgt agctttcgcc gaagatgatc cagactgtgt atacacattc tacctcagaa    120

ccggatcgat ctggaaagcc ggaaccgatt cgatcatcag cgcaagaatc tacgataagg    180

acggtgacta catcggaatc aaaaaccttc aagcttgggc tggattaatg ggacctgatt    240

acaattactt cgagaggggt aatctcgaca ttttcagtgg aagagcaccg tgtttaccta    300

gtccgatctg tgccttaaac ctaacctccg atggctccgg cgatcaccat ggttggtacg    360

ttaattacgt tgag                                                      374
```

<210> SEQ ID NO 288
<211> LENGTH: 1020
<212> TYPE: DNA
<213> ORGANISM: Artificial
<220> FEATURE:
<223> OTHER INFORMATION: Synthetic

<400> SEQUENCE: 288

```
ttttcctctc atttctaga gaaagaaaca acaagacgta cagaacgaga gttcaagaat     60
```

```
ctgcaatggg agtggctcga gttaaccaat tctggttgca tcttgtcatc ctcttctcca    120

tctccgttgc ttccatttct agcactgtaa gtcacccttc tctacttcta ctacgttgac    180

agatttagag tagatgcact ggattacgtc gaactcaccg cgttaaaaag ctgcccggtg    240

caataagctc ccgtagtgga cgggtccgga gaagggtcga actcactgct ttacttctta    300

attaccttat atgtaagaaa agaaacaaat atatatgagt aagaatacaa cacattgatt    360

ctaaattata aatttgtcac tgtgtaccat aatatttttc attttgcaat tgctgaattg    420

atgggaaaat gcaggaactg aattgtgtat acacagctta tgttcggact gggacatact    480

ggggatctgg aactgactca aaaatttcct tgtctcttta tgatgccact ggccatggac    540

ttagaatcaa taacctacaa gcctggggcg ggcttatggg cccgggttat gactactttg    600

aaatggacca attggatatg tttacgggcc gtggtccatg tttgactggg ccaatctgta    660

aaatgaactt gacttctgat ggatcaggtg agcaccacgg atggtactgt aactacgggg    720

aaatcacgtc tacagcagaa cacaaacgat gcagccaaca ggcgttcacc gtggaggcgt    780

ggctcagtgc cggtcagtac ccagatgggt tgaccgccat taaggaacaa ctgtaagcgt    840

atttccaacg aacaacaacc aattcatgat tctgatcaat cttatcatgt tgtggatgta    900

atttaattcg agtttattgg acgttgtatg atttacgaag gccatttagg ccaaggcctg    960

atatgtactc tcacgagtgc tacatagttg gaatgaaaag ttttctttac ccatatcttt   1020
```

<210> SEQ ID NO 289
<211> LENGTH: 666
<212> TYPE: DNA
<213> ORGANISM: Artificial
<220> FEATURE:
<223> OTHER INFORMATION: Synthetic

<400> SEQUENCE: 289

```
gggcggacgc gtgggcggac gcgtgggcgg acgcgtgggg ccttttatcc tctcatttct     60

agagaaagaa aaaatttctc ttgcacaact agctgccatg ggagtagctc atcaagttaa    120

ccaattctgg ttccctctca ttatcatcct cttctccatc accatttctt ctacttctgg    180

aactgaatca aattgtgtgt acacagctta cattcggact gggccattca tggaggatgc    240

aactgactca aaaataagct tgactctcta cgatgcgagt ggctatggaa ttagaatcaa    300

gaacctagtg gcttggggtg ggcttatggg atcagggtac aactactttg aaacggacca    360

ctcggatatg ttcagtggcc atggaccatg tttgactggg ccgatctgca aaatggtctt    420

gacttctgat ggtacaggcc gacactcagc atggtactgt aactacgtgg aagtcacctc    480

aacaggagac cacaaacaat gcagtcaaca gctgttcaaa gtggatcagt ggcttagcac    540

agatcgttcg ccgtatcagt tgactgccac aagaaacaac tgtaggcgta tatccggtga    600

ccaacaaccc attgttgttg atgtaattta attcgagttc atcatattgg gctacttaca    660

aactac                                                               666
```

<210> SEQ ID NO 290
<211> LENGTH: 619
<212> TYPE: DNA
<213> ORGANISM: Artificial
<220> FEATURE:
<223> OTHER INFORMATION: Synthetic

<400> SEQUENCE: 290

```
agagagttca agaaaccatg ggagtagctc aagttaacca aatatggttc catttcatga     60
```

-continued

```
tcatcctctt tttcatatct tctatttcgg catctgaaga tgattgtgtg tacacagctt    120

acgttcgaac tggatcaatc ataaaggctg gaactgactc aaacattagt ttgactctct    180

acgatgccga tggctatggg ataagaatca agaacttaga ggcatggggt gggcttatgg    240

gcccaggtta caactatttt gaaagaggaa acttggatat attcagtgga cgtggtccat    300

gtttgaatgg gccgatctgc aaaatgaatc tgacatctga tggatcgggc ccacatgccg    360

gatggtactg taactacgtc gaagttacag ttactggagc ccaccaacaa tgcaaccagc    420

agcttttcac cgtggagcag tggctcggca ctaacgtttc gccatatgag ctgacggccg    480

tcaggaacaa ctgtaagaag tccaagtcca cagtttatga ttctgaatct tatccagttg    540

ttgatgtaat ttaatggggg cagccccaca tattgtctct gtggtttttt ctttagagtg    600

agaagaatta acgtgatgc                                                 619
```

<210> SEQ ID NO 291
<211> LENGTH: 587
<212> TYPE: DNA
<213> ORGANISM: Artificial
<220> FEATURE:
<223> OTHER INFORMATION: Synthetic

<400> SEQUENCE: 291

```
agggccttcg agacttggga ggttggagcg agcaagctcg gccatggcga agctctcctg     60

ccttctcatc gtctccttcg ccgtcgtcgc ggcgttggcg gccacggacg acgacgcggc    120

ggcggcggct gaggggatca cggtggcgga ggcgtcgtcg gacccggaga acaagtgcgt    180

gtacacgata tacgtgcgga cggggacgat ctggaagggc gggacggact cggtgatcgg    240

cgtgacgctg ctgggcgccg acggctccgg ggtgcggatc cgcgacctgg agcggtgggg    300

cggcctcatg ggcgacggcc acgactacta cgagcgcggc aacctcgaca tcttcagcgg    360

cctcggcccc tgcatgcgcc aggcgccgtg ccggatgaac ctcacctccg acggcaccgg    420

cccgcaccac ggctggtact gcaactacct cgaggccacc gtcacgggtc cccacctcgg    480

ctgcgcgcag cagctcttca ccgtcgagca gtggctcgcc accgacgcat cgccctaccg    540

cctctacgcc gtcgtcgaca actgcaacaa ggccaaggac gccgccg                  587
```

<210> SEQ ID NO 292
<211> LENGTH: 799
<212> TYPE: DNA
<213> ORGANISM: Artificial
<220> FEATURE:
<223> OTHER INFORMATION: Synthetic

<400> SEQUENCE: 292

```
gtcatcacac aagtgaagaa gcagtagcag tagaaggaga tagaagggaa cctctctctc     60

tctctctctc tctttgctga tgatgaagac gactatggct gttttcgccc ttctctctct    120

cttccttctt ctcctccccc cttttccttc atcagctgat gatccttgtg tatactcaat    180

ctatgtacga acggggtcaa tattcaaggg gggaacggat tcgaagatga gtgtggagct    240

ctacgatgcg aatgggtact acattacgat caacaatttg gaggagtggg gggggttaat    300

gggtccagac cacgactact atgagagggg caatcttgac atctttagtg gtttggggga    360

ctgcctgacc ggacccatct gcgctctcaa cctcacctcg gacggcacgg gggcccacca    420

tgggtggtat tgcaactacc tggaagttac tgccacgggt gcccacatcc cttgctccca    480

acagctcttt accatagagc aatggcttgc cactgatacc tctccttact ccctcactgc    540

ccttcgatat aattgccctg atgctttgtc ctcgcctcgc ttccctcgca tgccttccaa    600
```

ttcgcaaccg aagaatggtc aactaatgtc ccattagtac tctatcaccc tgcttcgtaa 660
taaaaagata gccccttctt gtgtactatg gagggagggg ggtatctctc tcaaggtacc 720
ttatttgttg atgtttctcg aggcacctcg cattaatgta tgtgttgttt actatcttgt 780
acgcttgtgt gataaatct 799

<210> SEQ ID NO 293
<211> LENGTH: 614
<212> TYPE: DNA
<213> ORGANISM: Artificial
<220> FEATURE:
<223> OTHER INFORMATION: Synthetic

<400> SEQUENCE: 293
tttgccttta ttcgttctca tttttctaga gaaagagagt tcaagaaacc atgggagtag 60
ctcaagttaa ccaaatatgg ttccatttca tgataatcct cttcttcatc tccatatctt 120
ctagttctgc atcagaagat gattgtgtgt acacagctta cgttcgaact ggatcaatca 180
taaaggctgg aactgactca aacattagtt tgactctcta cgatgccgct ggctatggga 240
taagaatcaa gaacttagag gcatggggtg ggcttatggg cccaggttac aactatttcg 300
aaagaggaaa cttggatata ttcagtggac gtggtccatg tttgactggg ccgatctgca 360
aaatgaatct gacttctgat ggatcaggcc cacatgccgg atggtactgt aactacgtcg 420
aagttaccgt tactggagcc caccaacaat gcaaccagca gcttttcacc gtggagcagt 480
ggctcggcac tgacgtttcg ccgtatgagc tgacggccgt caggaacaac tgtaagaagc 540
caaagtttga gaaacaacag gccttttatg attctgaatc ttatccagtt gttgatgtaa 600
tttaatgggg gtag 614

<210> SEQ ID NO 294
<211> LENGTH: 699
<212> TYPE: DNA
<213> ORGANISM: Artificial
<220> FEATURE:
<223> OTHER INFORMATION: Synthetic

<400> SEQUENCE: 294
aaaaatctca taaacgaaac acaaaaaaaa aaccctctct cgaaaattaa aaataaaaaa 60
tacccggcga atctccgacg atggctttgc cggaaaattt aaccagagag cagtgcctat 120
acttagcaaa gctcgccgag caagccgagc gttacgagga gatggtaaaa ttcatggacc 180
gactcgtagc tgtctcggct tcctctgaac taaccgtaga agagcgaaac ctcctctcgg 240
tagcttataa gaacgtcatc ggttcacttc gagccgcgtg gaggatagta tcgtcaattg 300
agcaaaagga agaaggtagg aagaacgagg aacacgtggt tctagtgaag gattatagat 360
ctaaggttga atctgagctt agtgatgtat gtgctggaat tttgaagatt ttggatcagt 420
atttgattcc ttcggcttcg gctggtgaat cgaaggtgtt ttacttgaag atgaagggag 480
attattatcg ttatttggct gaatttaaag ttagtaatga acgtaaggag gctgctgagg 540
ccactatgct tgcctacaaa gctgctcagg acattgcgct tgctgagctt gccccaacac 600
atcctatacg acttgggcta gctctcaact attcagtatt ctactatgag attctgaatg 660
catcagaaaa agcatgcagc atggccaaac aggcctttg 699

<210> SEQ ID NO 295
<211> LENGTH: 667
<212> TYPE: DNA

-continued

<213> ORGANISM: Artificial
<220> FEATURE:
<223> OTHER INFORMATION: Synthetic

<400> SEQUENCE: 295
gctgtgttta tcttcttcgc cttcgtgttc gtcggtggtg ttggtagtgg gaagatgggt 60
gtggagaagg agcgtgagag tgatgtgtac atggctaagc tcgctgagca ggcggaacgt 120
tatgatgaga tggtggaatt catgaaaaag gtggcaaact tggatgtgga gctatctgta 180
gaggagagga atctgatgtc agttgggtac aagaatgtga ttggggcacg gagggcctct 240
tggcgcatcc tctcctccat cgagcagaag gaggagggaa aaggcaatga agtgaatgcc 300
aagcgcatca aagaatacaa gcacaaggtc gaggaagagc tttcaaacat ctgcaacgat 360
gtcctctccg ttattgagga tcatctcatc cctgcgtcta gcacgggga atcttctgtc 420 ttctattaca aaatgaaagg ggattacttc cgatatttgg cagagtttaa atctggaaat 480
gagaagaagg aagccggaga gcagtctttg aaagcatacc aggctgctat ggacatagcg 540
acatctagcc ttccgacgac tcatccgatc aggcttggtc ttgctctcaa cttctccgtt 600
ttctactatg aaattatcaa ctcccccgag aaggcatgcc agctggcaaa acaagctttt 660
gatgatg 667

<210> SEQ ID NO 296
<211> LENGTH: 659
<212> TYPE: DNA
<213> ORGANISM: Artificial
<220> FEATURE:
<223> OTHER INFORMATION: Synthetic

<400> SEQUENCE: 296
acctctaagc cttgcagata acccgtcttg ttcatctctc tttctctctc tctctctctc 60
atcttctcta gctctctctc tgtgtgtccc ctgtttccct gtcttagacc atgactccgt 120
cgatggaggg gggcaagcgg gaggagaatg tgtacatggc gaagcttgcg gagcaggccg 180
agcggtacga ggagatggcg gagttcatgg atgccgtcgt caaggacggt gctgacgaga 240
tgtcggtgga ggagcggaac ctcctctccg tcgcgtacaa gaacgtgatt ggcgcgcgtc 300
gcgcctcctg gcgcatcgtc tcctccattg agcagcgcga ggagagcaag ggcaaccagg 360
agcacgtctc tgccatccgc gactaccgtg cctccgtcga aaccgagctc accaagatct 420
gcaaaagcat ccttagcctc ctcgagatgc accttgtccc ttccgccacc acccccgaat 480
ccaaagtctt ctacctcaaa atgaagggcg actaccaccg ctaccttgcg gagttcaaaa 540
tcggggcgga ccgcaaaaaa ctggcgataa atactctcac cgcctacaaa tctgctcagg 600
aaatagcctt ggctgagctg ccttcaacac accccattcg tttggggctt gctctaaat 659

<210> SEQ ID NO 297
<211> LENGTH: 498
<212> TYPE: DNA
<213> ORGANISM: Artificial
<220> FEATURE:
<223> OTHER INFORMATION: Synthetic

<400> SEQUENCE: 297
tacaaatcct cgactgtgaa aggagctttc gccatctctc tccatgggaa tcgagatgga 60
ccgcgatggg aatgtctaca tggccaagct cgctgagcaa gccgaacgct atgatgagat 120
ggtggagttc atgaagaatg tggcgaatat ggatacggaa ctgactgtgg aggagcgcaa 180
cctattctcc ataggatata aaaatgtgat cggagctcgt cgggcttcct ggcgcattct 240

```
ctcctccatt gagcagagag aggagagcaa gggcaacgag gtgaatgcga atcgcatcaa    300

ggagtaccgt aacagagtcg acgaagagct ctccaagatc tgcaaagatg tcctgagcat    360

catcgatgat catctcatcc cctcttccac aaccaaagaa tctgaggtct tctattacaa    420

aatgaagggt gattattacc gctatttggc tgagtttaag gctggtagcg agaggaagga    480

tgcggcagat cactccct                                                   498
```

<210> SEQ ID NO 298
<211> LENGTH: 1105
<212> TYPE: DNA
<213> ORGANISM: Artificial
<220> FEATURE:
<223> OTHER INFORMATION: Synthetic

<400> SEQUENCE: 298

```
agcgacaatc agaaaccacc cgctgtaacc ctaggttttt tcacaaacaa caaatatgac     60

tgagtcatcg cgggaagaaa atgtgtacat ggccaagctt gctgagcagg ccgagcgata    120

tgaggaaatg attgagttta tggagaaggt tgcaaagaca ggtgatgtcg aggagctgac    180

tgttgaggaa aggaatctcc tttctgtggc atacaaaaat gtgattggtg caagaagggc    240

ctcgtggaga ataatctctt caattgagca gaaagaggag agccgtggaa atgaagatca    300

tgtcaaaact attaaagaat acagagccaa aattgaggct gaactcagca agatctgtga    360

tgggattttg ggtctccttg agtcccattt aataccatca gcctccacag ctgagtccaa    420

agtttttac ttgaagatga aaggtgatta ccacaggtac ttggctgagt ttaagacagg    480

ggcagaaagg aaagaagccg cagagaacac tttattagcc tacaagtctg ctcaggatat    540

tgctttggat gaactggctc ctactcaccc aatcaggctg ggacttgccc tcaacttttc    600

agtgttctac tatgaaattc tcaactcgtc ggatcgtgct tgtaatcttg caaagcaggc    660

ctttgatgat gccattgccg agctggatac attgggtgag gaatcttaca aggacagtac    720

attgattatg cagcttctcc gagacaatct tacactttgg acttctgata ccacggatga    780

tgccggggat gagatcaagg aagcttcaaa atgcgaatta ggcgaaggag agcagtaacg    840

gcataacatc atagtctttt actctttatt ttgtttgatt ttaatatagg actactgcgt    900

gaaagctaga ctggatatgg atataattcg atgattcctc gtattactgc tgaagtagtt    960

tgatataaaa acatgtttta gtacgataag aaatatagtc atgccgttga tgtattggct   1020

tgtatttcta gtttcaattg catatgttat tgactgttga gctttgtatt ttcaagtcat   1080

tcaataattc aatagttccc aaaaa                                          1105
```

<210> SEQ ID NO 299
<211> LENGTH: 624
<212> TYPE: DNA
<213> ORGANISM: Artificial
<220> FEATURE:
<223> OTHER INFORMATION: Synthetic

<400> SEQUENCE: 299

```
gtggtttgga ttgggcaaag tttgaaagag aagagaagaa gattcccctc actccctcct     60

cccccactat ttgggttttt ctctctctct ttctttctcc tagttagtct tcacttttag    120

atctatatgc tcacagctca cctcactcct ctttattttt agggttcatt ggaaggaaga    180

gagagagaga gagagagaga ggtcttgctg caccaaccca acccaaggag ctcttctttg    240

tgttctactc ccatgggtat tgagaaggag agagagagcc atgtctacat ggccaagctt    300
```

-continued

```
gctgagcagg cagagagata tgatgaaatg gtggattcca tgaaaaagat tgccaagttg    360

gacgtcgagc tgaccattga ggagagaaat ctgctttccg tgggctataa aaatgtgatt    420

ggggctcgga gggcctcgtg gcgaatcctc tcctcaattg agcagaaaga ggagagcaag    480

ggcaatgaaa caaatgccaa gcgcattgag agttaccgac ataaggttga ggaagaactc    540

tctggaatct gcaaggacat cctgactacc atcgatgagt atctcatccc ctcgtctggc    600

acggcggaat ccaccgtttt ctat                                           624
```

<210> SEQ ID NO 300
<211> LENGTH: 598
<212> TYPE: DNA
<213> ORGANISM: Artificial
<220> FEATURE:
<223> OTHER INFORMATION: Synthetic

<400> SEQUENCE: 300

```
cggacgcgtg ggcccaaaga gagagagcga gagagagagc ggagaaatgg agaaggaaag     60

agagaaacag gtttacttgg caaggctagc tgagcaagct gagagatatg atgaaatggt    120

agaagcaatg aagacggttg ctaagatgga tgttgaactg actgttgagg agaggaattt    180

ggtgtcagtt gggtataaga atgttattgg agcaagaagg gcttcatggc ggatattgtc    240

ttcaattgaa caaaaggagg agagtaaggg tcatgaccag aatgttacga gaataaagac    300

ttaccaacag agggtcgaag atgagcttac aaaaatatgc attgacattt tgtcggtgat    360

cgatgagcac cttgttcctt cttccactac cggagaatct actgtcttct actataagat    420

gaagggagat tactatcgct atttagcaga gttcaaatca ggggatgatc gtaaagaggc    480

agctgatcag tcacttaaag cttatgaggc tgctacttcc acagctagtg cagatcttgc    540

tcctactcat ccaattagac ttggacttgc attgaacttc tcagtcttct actatgag      598
```

<210> SEQ ID NO 301
<211> LENGTH: 892
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (695)..(695)
<223> OTHER INFORMATION: The residue at this position can be any nucleotide.

<400> SEQUENCE: 301

```
gggtttggat cgagtcagtg cagtctacgg tctgcaagca tgtccgggca cgatgagcac     60

gtgttcatgg ctaagctcgc cgaacaggcc gagcgctatg aggagatggc cgagttcatg    120

gagaaggttg ctggccatgg ggacgacctc actgccgaag agcgcaacct cctctctgtc    180

gcctacaaga acgtggtggg tgctagacgt gcctcctggc gcatcatctc ctccattgag    240

cagaaggagg agggcaaggg caaccaggac catgtcagtg ccatccgtga ctaccgggcc    300

aagatcgagg ccgagctttg cactatatgt gggggtgtcc tcaagatcct ggacacgcac    360

ctcatcccgg ccggagaagc tgctgagtcg aaggtcttct acctcaagat gaagggtgat    420

taccatcgtt acgtggctga attcaagact ggttctgaaa ggaaggagtc tgctgagaac    480

accatgtctg cctataagtc tgcccaggat attgcccttg cagagcttgc ttcaactcat    540

cctattcgcc tgggacttgc gctcaatttc tcggtatttt actacgagat tttgaattct    600

cccgacagag cctgttctct tgccaagcag gcttttgatg aggctatttc tgaattggac    660
```

-continued

```
acccttggag aggagtccta caaggatagc acatngatca tgcagctttt aagggataac    720

ttaacactgt ggacatcaga tttgcaggaa gatggaggtg atgaaggtat caaactgaag    780

gatgtagatg gtcactagcc tctttgaggc atatattggt aagcgttgta atggtttaat    840

gctttcacag gaccagtcat gatacggcga ttggttatat agaacagtac tg            892
```

<210> SEQ ID NO 302
<211> LENGTH: 507
<212> TYPE: DNA
<213> ORGANISM: Artificial
<220> FEATURE:
<223> OTHER INFORMATION: Synthetic

<400> SEQUENCE: 302

```
aaagacttgg tcttttcatc aactttcgat ttaaccaaat tcaaaactat cttcaaggat     60

gaaagaaaag atcttgtgtt tatggcgcgc accgcagaaa ctgcggaacg ctatgaagat    120

atgtgccgcg tcatgagaga attagtgaag tttaccaacg gtaaaaaagt cgatttgact    180

gtcgaagagc gcaatttgct ctctgttgca tacaagaatg ttattggtgc tcgcagagca    240

tcttggagaa ctctcaatgt tgacgaacat aaagacgatg ctttgatcgt tgaatacaag    300

aagcaagtcg aaaatgaact tcagactatc tgcaaggatg ttcttgattt attagagaaa    360

ttccttattc aacctcatgg agcggaagac gagtctcaag tcttctatct taaaatgacc    420

ggtgattatt accgctatct tgctgagttt gttggcgatc aaggctatgc tccaaaagcc    480

gctgaattct acgacaaagc gagaact                                        507
```

<210> SEQ ID NO 303
<211> LENGTH: 636
<212> TYPE: DNA
<213> ORGANISM: Artificial
<220> FEATURE:
<223> OTHER INFORMATION: Synthetic

<400> SEQUENCE: 303

```
ttcgcatctc tccatcgccg ccgccgccgt ttctgccgcc gcataggcat ccgtcgccag     60

gtagcgcagc cgcagccgca gccgccgccg caaagctagg ttgtttctcg ccgaaatgcc    120

ggaatccaag gaggagaatg tctacatggc caagctcgcg gagcaggccg agcgctacga    180

cgagatggtg gagtacatgg agaaggtggc caaggccgtg gaggcggagg agctgagcgt    240

ggaggagagg aatctcctgt cggtggcgta caagaatgtg attggggcgc ggcgggcttc    300

gtggcggatc atctcgtcga tcgagcagaa ggaggagtcc aagggcaacg aggagcatgt    360

aggcttgatc aagaactaca ggtccaaggt ggagacggag ctgagcaaca tctgccacgg    420

gatcttgggg ctgctggatt cgcacctcat cggatcctgc tccacgggcg aatccaaggt    480

cttctacctc aagatgaagg gcgactacaa tcgctacctt gccgagttta agacggggca    540

ggagaggcag gaggcagccg aggccacctt gatggcctac aagtcggcac aggacattgc    600

gctggcggag cttgctccaa ctcaccccat tcgact                              636
```

<210> SEQ ID NO 304
<211> LENGTH: 1043
<212> TYPE: DNA
<213> ORGANISM: Artificial
<220> FEATURE:
<223> OTHER INFORMATION: Synthetic

<400> SEQUENCE: 304

```
tcgacccacg cgtccgggcg gcagcgcacg gcgaggaaca ggtgagtgcc cgtggatgtg     60
```

-continued

```
atctagatct accctccaag ccccaaaatc tcagtagaaa tcctccaaat cgcgccgccg    120
gaagagagat ccaatccacc actgtcccca tttctcggct tgttccaggg atgtcgaatc    180
ttcgcgagga gaatgtctac atggccaagc tcgcggagca ggccgagcgc tacgacgaga    240
tggtggaatt catggagaag gtggtcaagg ccgtggacgt ggaggagctg acggtcgagg    300
agcggaatct cctgtcggtg gcctacaaga acgtgatcgg cgcccgccgg gcatcgtgga    360
ggataatctc ctccatcgag caaaaggagg aatccaaggg caacgacgac cacgtctcga    420
tgatcaagga gtaccgtgcc aaggtggagt cggagctgag caccatttgc gacagcatcc    480
tcaagctgct ggacagccat ctcatcccct catcgtccag tggcgagtcc aaggtcttct    540
acttgaagat gaagggtgac taccaccgat acttggccga gtttaagacc ggggccgaga    600
ggaaagaggc cgcggagaac actctcctcg cctacaagtc ggcccaggac atcgctctca    660
cacagctgcc gccgacgcat cccatccggc tgggtctcgc tctcaatttt tcggtcttct    720
actacgagat tttgaattcg cccgatcgag cttgtacgct tgccaagcag gcatttgacg    780
aggccatagc cgagctggac actttgggag aggaatctta caaggatagt actctgatca    840
tgcagctgct gcgcgataat ctaacgctgt ggacctcaga catgcaggag gaaggtgccg    900
gcgaggggaa ggacgacaag ccgtgagtaa aataatacgt tcgaatttcg ttttctatgc    960
tactagctag ctgtttagac gccttctctc tcaacacctt ggtactgttg attctttcgt   1020
tcctgaatac attatttggc ttg                                           1043
```

```
<210> SEQ ID NO 305
<211> LENGTH: 104
<212> TYPE: DNA
<213> ORGANISM: Artificial
<220> FEATURE:
<223> OTHER INFORMATION: Synthetic

<400> SEQUENCE: 305

atcgacccac gcgtccggct actagctagc agtttagacg ccttctctct ccacacctgg     60
tactgttgat tctttgttcc tgaatacatt atttggcttg cact                     104
```

```
<210> SEQ ID NO 306
<211> LENGTH: 458
<212> TYPE: DNA
<213> ORGANISM: Artificial
<220> FEATURE:
<223> OTHER INFORMATION: Synthetic

<400> SEQUENCE: 306

tgctgtccgt ggcgtacaag aacgtcatcg gcgcgcgcag ggcgtcgtgg cgcatcgtgt     60
cctccatcga gcagaaggag gaaggccgcg gcgccgcggg ccacgccgcc gccgcgcgct    120
cctaccgcgc ccgcgtcgag gccgagctct ccaacatctg cgcggggata ctccgcctcc    180
tcgacgagcg cctcgtcccc gccgccgccg ccgtcgacgc caaggtcttc tacctcaaga    240
tgaagggcga ctaccaccgc tacctcgccg agttcaagac cggagccgag cgcaaggacg    300
ccgccgacgc caccctcgcc ggctaccagg ccgcgcagga catagccatg aaggagctgt    360
cgccgacgca ccccatcaga ctgggccttg cgctcaactt ctccgtgttc tactacgaga    420
tcctcaactc gcccgaccgc gcgtgcacgc tcgccaag                           458
```

```
<210> SEQ ID NO 307
<211> LENGTH: 550
<212> TYPE: DNA
```

<213> ORGANISM: Artificial
<220> FEATURE:
<223> OTHER INFORMATION: Synthetic

<400> SEQUENCE: 307
ccccctggag gatcatctct tctatggagc agaaggagga gagccgtggg aatgaggcat 60
atgttgcatc aattaaggag taccgtagca ggattgaaac tgagctcagc aagatctgtg 120
atggtatcct taagcttctg gattcccacc ttgtcccatc tgccactgct gcagagtcca 180
aggtgttcta cctgaaaatg aagggtgact accacaggta ccttgctgag tttaagtcag 240
gagctgagag gaaggaagca gctgagaaca ctcttgtggc atacaagtct gcccaggata 300
ttgcactcgc tgacctgcct acaactcacc cgataaggct tggacttgca ctgaacttct 360
cagtgttcta ctatgagata ctgaactcac cagaccgtgc ttgcaacctt gcaaagcagg 420
cgttcgacga tgctattgct gaactggaca ctcttggcga ggagtcttac aaggacagca 480
ccttgatcat gcaacttctt cgtgacaatc tgactctctg gacctctgac aatgcggagg 540
atggtggtga 550

<210> SEQ ID NO 308
<211> LENGTH: 953
<212> TYPE: DNA
<213> ORGANISM: Artificial
<220> FEATURE:
<223> OTHER INFORMATION: Synthetic

<400> SEQUENCE: 308
gaatttgaac tccacctgag cacaggagaa gccgcagcca ctgagatttg accttctgtt 60
tctaccagaa aaacacaaac agtgaagatg tcgcagcctg ctgagctttc ccgtgaggag 120
aatgtgtaca tggctaagct tgcagagcag gccgagaggt atgaggagat ggttgagttc 180
atggagaagg ttgctaagac agttgactct gaggagctca ctgttgagga gcgcaacctt 240
ctatcagttg cttacaagaa tgttattggt gctcgccgtg cgtcatggcg catcatatca 300
tccattgaac agaaggaaga gagccgtggt aatgaggatc gttgcacgct catcaaggaa 360
tacaggggaa agattgaaac tgagctctcc aagatctgtg atggcatcct caagcttctt 420
gactcccacc ttgtgccttc atccactgct ccagagtcca aggtcttcta cctcaagatg 480
aaaggcgact actacaggta cctcgcagag tttaagactg gagctgagag gaaggatgct 540
gctgagaaca ccatggtggc atacaaagcc gctcaggata ttgccctggc agagttgccc 600
ccaactcatc ctatcagact tgggctggcc ctcaacttct cggtgtttta ttacgagatc 660
ctcaactctc ctgaccgtgc ttgcaatctt gcaaagcagg ctttcgatga ggctatctca 720
gagctggaca ctctgagtga ggaatcctac aaggacagca ctttgatcat gcagcttctg 780
cgtgataacc tgacgctgtg gacttccgat atctcggagg atgctgctga ggaaatcaag 840
gaggccccca agggcgaatc aggagatgga cagtgaacat gatcgaatgc gtgcgcccac 900
aaactagaat agtgacgctg caaatgtgct gtgggttatc gtttcatttt ata 953

<210> SEQ ID NO 309
<211> LENGTH: 554
<212> TYPE: DNA
<213> ORGANISM: Artificial
<220> FEATURE:
<223> OTHER INFORMATION: Synthetic

<400> SEQUENCE: 309
cccacgcgtc cgctccacct gagcacagga gaagccgcag ccactgagaa aaacacaaac 60

```
agtgaagatg tcgcagcctg ctgagctttc ccgtgaggag aatgtgtaca tggctaagct    120

tgcagagcag gccgagaggt atgaggagat ggttgagttc atggagaagg ttgctaagac    180

agttgactct gaggagctca ctgttgagga gcgcaacctt ctatcggttg cttacaagaa    240

tgttattggt gctcgccgtg cgtcatggcg catcatatca tccattgaac agaaggaaga    300

gagccgtggt aatgaggatc gttgcacgct catcaaggaa tacaggggaa agattgaaac    360

tgagctctcc aagatctgtg atggcatcct caagcttctt gactcccacc ttgtgccttc    420

atccactgct ccagagtcca aggtcttcta cctcaagatg aaaggcgact actacaggta    480

cctcgcagag tttaagactg gagctgaaag gaaggatgct gctgagaaca ccatggtggc    540

atacaaagcc gctc                                                      554
```

<210> SEQ ID NO 310
<211> LENGTH: 599
<212> TYPE: DNA
<213> ORGANISM: Artificial
<220> FEATURE:
<223> OTHER INFORMATION: Synthetic

<400> SEQUENCE: 310

```
gaattcaaga tcatgtttct attattaaag aatataggggg aaagattgaa tctgaacttc     60

ataagatttg tcaagggatt ttagggcttt tggattccca tcttattcct tcatcaactg    120

ctgctgaatc taaggtgttt taccttaaga tgaagggtga ttaccacagg tatttggcta    180

agttagctga acaagctgaa cgatatgaag agatggttga atttatggag aacgttgcaa    240

aaactgttga ttctgatgaa ttatcagttg aggaacgaaa cctgttgtct gttgcttata    300

agaatgtgat tggagctagg agagcttcat ggaggattat ttcaagtatt gaacaaaagg    360

aagaaagccg tgggaatgaa gatcatgttt ctattattaa agaatatagg ggaaagattg    420

aatctgaact tcataagatt tgtcaaggga ttttagggct tttggattcc catcttattc    480

cttcatcaac tgctgctgaa tctaaggtgt tttaccttaa gatgaagggt gattaccaca    540

ggtatttggc tgagtttaaa tctggtagtg acaggaaaga agctgctgag agtacattg     599
```

<210> SEQ ID NO 311
<211> LENGTH: 727
<212> TYPE: DNA
<213> ORGANISM: Artificial
<220> FEATURE:
<223> OTHER INFORMATION: Synthetic

<400> SEQUENCE: 311

```
ttgcaagttc cattccctgt tcttctctct caacgaagca tcaacccccc ttttctccca     60

gaaccgcgtc tcatcgcacc tgccataaaa ctccaaaaaa tctcaaaaac caaccgtcaa    120

aatgggtcac gaagatgctg tttatctggc caagctcgcc gagcaggccg agcgatatga    180

ggagatggtc gagaacatga agatcgtcgc ctccgaggac cgcgacctga ccgtcgagga    240

gcgcaacctc ctctccgtcg cctacaagaa cgtcattggt gcccgccgtg cctcttggag    300

aatagtcact tccatcgagc agaaggagga gtctaagggc aactcttccc aggttaccct    360

tatcaaggag taccgccaga agattgaggc cgagcttgcc aagatctgcg atgacattct    420

cgatgttctt gacaagcacc tgattccttc tgccaagtct ggagagtcca aggtcttcta    480

ccacaagatg aagggtgact accaccgtta ccttgccgag ttcgccattg gcgaccgccg    540

caaggactcc gccgacaagt ctctcgaggc ttacaaggct gctaccgagg ttgcccagac    600
```

-continued cgagctgcct cctacccacc ctatccgcct gggtcttgcg ctcaacttct ccgtcttcta 660
ctacgagatc ctcaacgccc ctgaccaggc ttgccacctc gctaagcagg catttgacga 720
tgctatt 727

<210> SEQ ID NO 312
<211> LENGTH: 664
<212> TYPE: DNA
<213> ORGANISM: Artificial
<220> FEATURE:
<223> OTHER INFORMATION: Synthetic

<400> SEQUENCE: 312
gtcaggagct gagaggaagg aagcagctga gaacactctt gtggcataca agtctgccca 60
ggatattgca ctcgctgacc tgcctacaac tcacccaata aggcttggac ttgcactgaa 120
cttctcagtg ttctactatg agatcctgaa ctcaccagac cgtgcttgca accttgcaaa 180
gcaggcgttc gacgatgcta ttgctgaact ggacactctt ggcgaggagt cttacaagga 240
cagcaccttg atcatgcaac ttcttcgtga caatctgact ctctggacct ctgacaatgc 300
ggaggatggt ggtgacgaga tcaaggaagc agcgaagcct gaaggagagg gccactaatc 360
tgtcctgaag tctatttctg agtccattta ctcagctacc tgctgtatta ctggatcata 420
agatgtacta ggatcaattg ctatgtggaa tcataagatt agggctgcgt atgtcaaaat 480
gtgtcgagct gaagtaccca gtggacacag tttatgtgca ctacattgct tccgtgactt 540
atttactagt taattagcaa ctttcaacca cttcctgtat ttgcagcaca ttattagtat 600
cgctgtatta gcgttttcca tgggctggtt atgattgaga atacaggcca ggcattgcat 660
gtcc 664

<210> SEQ ID NO 313
<211> LENGTH: 708
<212> TYPE: DNA
<213> ORGANISM: Artificial
<220> FEATURE:
<223> OTHER INFORMATION: Synthetic

<400> SEQUENCE: 313
acgcactctg tcgagaatcc attctatttc gcctaaactt tctctctcta caacaacaac 60
aatggcggct ctgctcacag acaatctcaa ccgcgaacaa tacctctact tagccaaact 120
cgccgaacaa gccgaacgct atgaagaaat ggtccagtac atggacaaac tagtactcag 180
ttccactccc gccgccgaac tcaccgtcga ggaacgaaac ctcctttccg tcgcttacaa 240
aaacgtgatc ggctctcttc gtgccgcgtg gcgtatcgta tcctccattg agcagaaaga 300
ggaatcgcgt aagaacgaag aacacgtttc gctcgttaag gagtacagag gtaaagttga 360
gaatgagtta acggaggttt gtgctggtat cctcaagttg cttgagtcaa atctcgagcc 420
gtctgcttct acgggtgaat cgagggtgtt ttacctcaaa atgaaaggtg attattaccg 480
gtatctagcg gagtttaagg ttggagatga gcggaagcag gctgctgaag acactatgaa 540
ttcttataag gctgctcagg aaattgcact agcagatctg cctccaacac atcctataag 600
gctgggtctt gcacttaatt tctcagtctt ctactttgag attctgaact catctgacaa 660
agcttgtagt atggcaaaac agggcttttg aggaagccat agctgagc 708

<210> SEQ ID NO 314
<211> LENGTH: 378
<212> TYPE: DNA
<213> ORGANISM: Artificial -continued
<220> FEATURE:
<223> OTHER INFORMATION: Synthetic

<400> SEQUENCE: 314
gttataaatc cttatctttt tcaacacaca gattaaaatc ttcagaaaga gagagagaga 60
tcccaaaatg ggtgaacgtg agaacttcgt atacatagct aagcttgccg agcaagctga 120
acgctatgat gagatggctg atgcgatgaa gaatcttgca aatatggatg ttgaattgac 180
agcggaagag aggaatttgt tttctgttgg ttataagaat gtggttggag ctaggagagc 240
atcgtggagg atcttgtctt ccatcgagca gaaggaagag tctagaggaa atgagcagaa 300
cgtgaagcgg attaaggagt accagcaaaa agtggagtca gagctcaccg acatttgcaa 360
taatatcatg accgcgat 378

<210> SEQ ID NO 315
<211> LENGTH: 403
<212> TYPE: DNA
<213> ORGANISM: Artificial
<220> FEATURE:
<223> OTHER INFORMATION: Synthetic

<400> SEQUENCE: 315
cggacgcgtg ggaaaaaaat caaatctctc tctttctctc tctaatggcg gcgacattag 60
gcagagacca gtatgtgtac atggcgaagc tcgccgagca ggcggagcgt tacgaagaga 120
tggttcaatt catggaacag ctcgttacag gcgctactcc agcggaagag ctcaccgttg 180
aagagaggaa tctcctctct gttgcttaca aaaacgtgat cggatctcta cgcgccgcct 240
ggaggatcgt gtcttcgatt gagcagaagg aagagagtag gaagaacgac gagcacgtgt 300
cgcttgtcaa ggattacaga tctaaagttg agtctgagct ttcttctgtt tgctctggaa 360
tccttaagct ccttgactcg catctgatcc catctgctgg agc 403

<210> SEQ ID NO 316
<211> LENGTH: 875
<212> TYPE: DNA
<213> ORGANISM: Artificial
<220> FEATURE:
<223> OTHER INFORMATION: Synthetic

<400> SEQUENCE: 316
tacaaaactc cctctctcat ttcctctctc atagcaacat caatggcgtc gccacgcgag 60
gagaacgtgt acatggcaaa gcttgccgag caagccgagc gttacgagga gatggttgag 120
ttcatggaga aagtcatcgc cgccgccgac ggcgccgagg aacttaccgt cgaagaacgg 180
aacctcctct ccgtcgcata caaaaatgtt atcggagcac ggcgagcctc gtggcgtatc 240
atctcctcca ttgagcaaaa agaggagagc cgcggcaacg aagatcacgt tgcctccatc 300
aaggagtaca gatctaagat cgagatcgaa cttacctcga tctgtaacgg cattctcaag 360
ctcctcgatt ctaagctcat tggcgccgct gctaccggtg actctaaggt gttttacttg 420
aaaatgaaag gagattatca tcgctatttg gctgagttta aaaccggcgc ggagcgaaag 480
gaagccgccg aaaatactct ctcggcttac aaatccgctc aggatattgc aaataccgag 540
cttgctccta cacatccaat ccgattggga cttgctctca atttctctgt attttactac 600
gaaattttga attctcctga tcgtgcttgt aatctcgcca aacaggcttt tgacgaggca 660
attgccgagc tggacacatt gggcgaagag tcatacaagg atagcactct gatcatgcag 720
cttcttcgcg ataacctcac tttatggact tcagatatgc aggatgatgg aactgatgag 780

-continued

```
atcaaagaag cagcaaaacc agataatgag cagcagtaaa ccggtgacat ttctttagga    840

ttgaaattca tgttgtaact ttttattttt caatt                              875


<210> SEQ ID NO 317
<211> LENGTH: 98
<212> TYPE: DNA
<213> ORGANISM: Artificial
<220> FEATURE:
<223> OTHER INFORMATION: Synthetic

<400> SEQUENCE: 317

gggcagagaa ccaaaaagaa aggggaaact gaaaagtgaa gaatctcctt tggctcacag     60

aaatcggaca tggcttcctc caaagaacgc gagaactt                            98


<210> SEQ ID NO 318
<211> LENGTH: 623
<212> TYPE: DNA
<213> ORGANISM: Artificial
<220> FEATURE:
<223> OTHER INFORMATION: Synthetic

<400> SEQUENCE: 318

cagctctctc tctctccctt caaacatcga tggcgtcgtc gcgcgatgag ttcgtgtaca     60

tggcgaagct tgcggagcaa gctgagcggt acgaggagat ggtagagttt atggagaagg    120

tcgtaaccgc ctcggacggc ggcgaggaac tcaccatcga agaacgtaat cttctatccg    180

tagcatacaa aaacgtgatc ggagcacgac gagcctcgtg gcgaatcatt tcctcaatcg    240

agcaaaaaga agagagccga ggcaatgagg agcacgtgac ctctattaaa acttacagat    300

ctaagatcga gtcggagttg acctcgatct gtgacggtat cctcaagctg ctcgattcga    360

atctcattgg cgctgcgtca atcggagatt ctaaggtgtt ttatttgaaa atgaaaggag    420

attatcaccg gtatttggct gagtttaaga ccggagctga gagaaaggaa gctgctgaga    480

atactctttc gtcttataag tccgctcagg atattgcaaa tgcggaactg gcacctacac    540

atcctattcg attggggcta gttctcaatt tctctgtatt ttactatgag atattgaatt    600

cacctgatcg tgcttgtaat ctg                                           623


<210> SEQ ID NO 319
<211> LENGTH: 873
<212> TYPE: DNA
<213> ORGANISM: Artificial
<220> FEATURE:
<223> OTHER INFORMATION: Synthetic

<400> SEQUENCE: 319

aaatcctgaa ttgcaccaac tagtacaacg acaacaatgt cttctgagag agaaaccaag     60

accttccttg cccggctctg tgagcaggct gaccgatacg acgagatggt caactacatg    120

aaggacgtcg ctaagtccgg tgaggagctt actgtcgacg agcgaaatct ggtttccgtc    180

gcttacaaga acgttatcgg cgctcgacga gccagctgga gagtcatttt ccccatagag    240

cagaaggagg aggccaaggg tggcacccac catctcgagc ttctcaagac ctacagagcc    300

cagattgagg gagagctcga agacatctgg agcgatgttc ttgatattct caacaaacaa    360

ctcctcccca aaggcgagaa cgccgagtct aaggtcttct actacaagat gaagggtgac    420

taccatcgat accttgccga gttcacctcc ggcgagaagc gaaaagaggc tgccactgcc    480

gctcacgagt catacaagag cgccactgat gttgcccaga ctgagctcag ctcaactcac    540

cccatccgac ttggtctcgc tctcaacttc tccgtcttct actacgagat tctcaactcg    600
```

```
ccagaccgtg cttgccacct tgccaagcag gctttcgatg atgccatcgc tgagctcgac    660

actctctccg aggagtcttt ccgagactct accgtcatta tgcagcttct gcgagacaac    720

ctgaccctct ggaagaacga cctcgaagag tctctgcaag cccagcagtc tgaggagacc    780

cctgccaccg atgctgccgc tgcttccacc gaggctgctg cccccaagga ggaggccaag    840

cccgctgctg aggagcccaa ggagtagagt agt                                 873
```

<210> SEQ ID NO 320
<211> LENGTH: 385
<212> TYPE: DNA
<213> ORGANISM: Artificial
<220> FEATURE:
<223> OTHER INFORMATION: Synthetic

<400> SEQUENCE: 320

```
aaccatgacg cgacaagaca acatctacct ggctcgtctt tccgagcagg ccgaccgtta     60

cgaatacatg gtggactaca tgaaggagat tgccaccggc gaccaggagc tgtctgtgga    120

ggagcgaaac ctgctctccg tggcatacaa gaacgtgatt ggcgctcacc gagcatggtg    180

gcgactggtc agcagctgcg atcagaagga ggagcaaaag ggcaaggaga ccaagatcat    240

ccacgacttc cgtcagaaga ttgatgccgg tctgcacgac atttgccatg acattctcaa    300

cgtgcttgac aagcacctga tccccaagct cgagaagccc tcggccgagg ccactgacgc    360

tgctgccaag gatggcgccg acccc                                          385
```

<210> SEQ ID NO 321
<211> LENGTH: 716
<212> TYPE: DNA
<213> ORGANISM: Artificial
<220> FEATURE:
<223> OTHER INFORMATION: Synthetic

<400> SEQUENCE: 321

```
aggagcttag atcgatcgac gacgccatcg ccgccggagc tgccatggga atggagaagg     60

agagggaatg cttcgtctac atggccaagc tcgcggagca agccgagcgt tacgatgaaa    120

tggttgaatc gatgaagaaa gtcgcgaagc tggacgtgga gctgaccgtg gaggagagga    180

atctcctgtc cgtgggctac aagatcgtga ttggggcgcg gcgggcgtcg tggcggatct    240

tgtcctcgat cgagcaaaag gaggagagca aaggcaacga gcagaacgtc aagaggattg    300

gagagtacca gcaaaaggtc gaggacgagc tctccaagat ttgcaatgac attctcacga    360

tcattgacga gcatctagtg ccggcttcca gcactggcga atccacggtc ttttactaca    420

agatgaaagg tgactacttt cgataccttg cagagtttaa gaccgggaac gaaagaaaag    480

aagctgccga tcaatcgttc aaggcttacc aggctgcgag cgatactgct tcaagcgatc    540

ttcccccaac acatcctatc cggctgggac tggcattgaa tttctctgtt ttctactacg    600

agattctaaa ctcgccagac cgcgcttgcc agctagcgaa gcaagctttt gacgatgcga    660

ttgcggagct ggacacgctc agcgaagaat cctacaaaga cagcaccttg atcatg        716
```

<210> SEQ ID NO 322
<211> LENGTH: 642
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (525)..(525)

-continued

<223> OTHER INFORMATION: The residue at this position can be any nucleotide.

<400> SEQUENCE: 322
tttctctctc tctctctctc tctctctctc cctccgtcga catgggcatc gagatggagc 60
gagagagcct tgtctaccta tccaagctct ccgagcaggc agaacgctat gagaaatggt 120
ggagtcgatg aagaaagtat ttaagttgga tgtagagctt acgattgagg agaggaattt 180
gctctcagtg gggtataagt attttatcgg agcgcgaagg gcctcgtggc gaattctctc 240
ctccattgag cagaaagaag agagcaaggg caatgagacc aatgtaaaac gcatcaagga 300
gtaccgcaac aaagtggagg aagagctttc caagatttgc agtgacatcc taactatcat 360
cgatgagcat cttatcccct catctggcac agcagaatct accgttttct attacaaaat 420
gaaaggggat tattatcgct accttgctga gttcaagaca ggacatgaga gaaaggaagc 480
tgcagatcaa tctctgaaag cttatcagac tgcaagtgac acggncaaca cggctctgcc 540
atctacccat ccgatcaggc ttggacttgc actcaacttt tcagtctttt actatgagat 600
tttgagttcg ccggagcgtg cgtgccatct tgccaagcaa gc 642

<210> SEQ ID NO 323
<211> LENGTH: 629
<212> TYPE: DNA
<213> ORGANISM: Artificial
<220> FEATURE:
<223> OTHER INFORMATION: Synthetic

<400> SEQUENCE: 323
acgcgtcgcc ctaactaacc ctaaccgcca aatattgggg gatttatcat ttgggtttgg 60
atcgagtcag tgcagtctac ggtctgcaag catgtccggg cacgatgagc acgtgttcat 120
ggctaagctc gccgaacagg ccgagcgcta tgaggagatg gccgagttca tggagaaggt 180
tgctggccat ggggacgacc tcactgccga agagcgcaac ctcctctctg tcgcctacaa 240
gaacgtggtg ggtgctagac gtgcctcctg gcgcatcatc tcctccattg agcagaagga 300
ggagggcaag ggcaaccagg accatgtcag tgccatccgt gactaccggg ccaagatcga 360
ggccgagctt tgcactatat gtgggggtgt cctcaagatc ctggacacgc acctcatccc 420
ggccggagaa gctgctgagt cgaaggtctt ctacctcaag atgaagggtg attaccatcg 480
ttacgtggct gaattcaaga ctggttctga aaggaaggag tctgctgaga acaccatgtc 540
tgcctataag tctgcccagg atattgccct tgcagagctt gcttcaactc atcctattcg 600
cctgggactt gcgctcaatt tctcggtat 629

<210> SEQ ID NO 324
<211> LENGTH: 696
<212> TYPE: DNA
<213> ORGANISM: Artificial
<220> FEATURE:
<223> OTHER INFORMATION: Synthetic

<400> SEQUENCE: 324
cacgcgtcgc gacagtcgaa acggggtccc gggaggagag tgtgtacatg gccaagctcg 60
cggagcaggc cgagcgctac gaggagatgg ccgagttcat ggacgctgtc tccaagggcg 120
ccggtgctga ggagatgtcc gttgaggagc gtaacctcct ctctgtcgcc tacaagaatg 180
tcattggtgc ccgtagagcc tcctggcgca ttgtctcctc catcgagcag aaggaggaga 240
gcaagggcaa tgaagaccac gtcgccgcca tccgcggcta ccgcgtcaaa gttgaggctg 300

-continued

```
agctcaccaa gatctgccag cgcattctcg acctccttga cagccacctt gtcccctctg    360

cgctcaaccc cgagtgcaag gtcttctacc tgaagatgaa aggggattac caccgttacc    420

ttgccgagtt caagaccggt gctgaccgca aggaagcggc tgagagtacg ctcgtcgctt    480

acaaatctgc cgaggaaatt gccctggctg agctgccttc gacacacccc attcgtttag    540

gccttgctct gaatttttca gtttttttact atgaaatttt gaactcccca gacagagctt    600

gcaatctagc taagcaggct tttgatgagg ccattgctga actggacact ctgggggaag    660

attcctataa ggacagtact ttgataatgc aacttc                              696
```

<210> SEQ ID NO 325
<211> LENGTH: 614
<212> TYPE: DNA
<213> ORGANISM: Artificial
<220> FEATURE:
<223> OTHER INFORMATION: Synthetic

<400> SEQUENCE: 325

```
tggttgttat tgttgttgct gtgtttatct tcttcgcctt cgtgttcgtc ggtggtgttg     60

gtagtgggaa gatgggtgtg gagaaggagc gtgagagtga tgtgtacatg gctaagctcg    120

ctgagcaggc ggaacgttat gatgagatgg tggaattcat gaaaaaggtg gcaaacttgg    180

atgtggagct atctgtagag gagaggaatc tgatgtcagt tgggtacaag aatgtgattg    240

gggcacggag ggcctcttgg cgcatcctct cctccatcga gcagaaggag cgagggaaaa    300

ggcaatgaag tgaatgccaa gcgcatcaaa gaatacaagc acaaggtcga ggaagagctt    360

tcaaacatct gcaacgatgt cctctccgtt attgaggatc atctcatccc tgcgtctagc    420

acgggggaat cttctgtctt ctattacaaa atgaaagggg attacttccg atattcggca    480

gagtttaaat ctggaaatga gaagaaggaa gccggagagc agtctttgaa agcataccag    540

gctgctatgg acatagcgac atctagcctt ccgacgactc atccgatcag gcttggtctt    600

gctctcaact tctc                                                      614
```

<210> SEQ ID NO 326
<211> LENGTH: 500
<212> TYPE: DNA
<213> ORGANISM: Artificial
<220> FEATURE:
<223> OTHER INFORMATION: Synthetic

<400> SEQUENCE: 326

```
ccaaaatttc cgacgccaga gcgcgaggag acgcacacag agacttggca tttgtagagt     60

ttttagattt atagatagca aagatgtcgg cacaggcgga gctttcccgt gaggagaatg    120

tgtacatggc caagctcgct gagcaagccg agaggtacga ggagatggtc gaattcatgg    180

agaaggtggc caagacggtt gactctgagg agctcaccgt ggaggagcgc aacctcctgt    240

ctgttgcata caagaatgtg attggagccc gccgtgcgtc atggcgcatt atctcctcca    300

ttgagcagaa ggaggaaagc cgtggtaacg aggaccgtgt cacactcatc aaggactacc    360

gtggcaagat cgagactgag ctcaccaaga tttgcgacgg cattctcaag ctgcttgaat    420

cccaccttgt cccctcttcc actgcccctg agtccaaggt cttctacctc aaaatgaagg    480

gtgactacta caggtacctt                                                500
```

<210> SEQ ID NO 327
<211> LENGTH: 1160
<212> TYPE: DNA
<213> ORGANISM: Artificial
<220> FEATURE:
<223> OTHER INFORMATION: Synthetic

<400> SEQUENCE: 327
gtacgagacc actcgaaccc gacccgcctc gccgccgccg ccaccgaagt aatcccttaa 60
ttggtcaaaa tgtctcggga ggagaatgtc tacatggcca agctggccga gcaggctgaa 120
aggtatgagg agatggttga gtacatggag aaggttgcaa agactgtaga tgtggaagag 180
ctcactgttg aggagcgcaa cctcttgtct gttgcttaca agaatgtgat tggtgcccgc 240
cgtgcctcct ggcgtattgt ctcatccatt gaacagaagg aggagggtcg tggcaatgag 300
gaacatgtta ctctgatcaa ggagtaccgt ggcaagattg aagctgagct gagcaagatt 360
tgcgatggta tcctgaagtt gcttgactca caccttgtgc cctcatctac tgctgcagaa 420
tctaaggtgt tttacctcaa gatgaagggt gattaccaca ggtaccttgc ggaatttaag 480
actggtgccg agagaaagga agctgctgag agcacaatgg tggcttacaa ggctgctcag 540
gatattgctc tggcggatct tgctcccacc catcccataa ggcttggact ggcacttaac 600
ttctctgtgt tctactacga gattctaaac tctccagaca aggcttgcaa ccttgctaag 660
caggcgtttg acgaagccat ctccgagttg gataccctcg gggaggagtc ttacaaggac 720
agcactttga tcatgcagct cctgagggac aacttgaccc tctggacctc tgacctcacg 780
gaggacggtg gtgatgaggt gaaagaagcc tccaagggcg acgcctgcga gggccagtaa 840
aatgggaaga tcgatcgatc gatggctccg catgttattg gagaccatcg atttagatgc 900
ctcatgctgc tgtcaccatg atggatggat tcttctcctg ttctactaga atgtttttct 960
tcctgtcccc ccttcctctc tcttctctgg tttttactag ggtggtagcg gtcgaattag 1020
ttcttcccat tgctttgcat ttggtgctag tggtccgtct gggctgattg ttttcctctg 1080
gatatgactc tcgtgtgtgt tgtctccaga tagtgtttta ttgagcaata tttaaagttg 1140
tcgtccacct cctcgatgtt 1160

<210> SEQ ID NO 328
<211> LENGTH: 1002
<212> TYPE: DNA
<213> ORGANISM: Artificial
<220> FEATURE:
<223> OTHER INFORMATION: Synthetic

<400> SEQUENCE: 328
ccccccgaga tctcaaaaat tcaacattgg cacaaccaaa aagaaaagag atccctaaat 60
tggaattcat tatggcgcgt gaggagaacg tgtacatggc gaagcttgcc gagcaagccg 120
agagatacga ggaaatggtg tcgttcatgg agaaagtctc tacttcctta gggacgtcag 180
aggaactcac ggtagaggag agaaatctcc tctcggtggc gtacaaaaat gttatcgggg 240
ctcgtagagc ctcgtggcgt ataatctcct ccatcgaaca gaaggaggag tcgaggggaa 300
acgaggacca tgtgaaatgc attcaggagt acagatctaa gattgaatct gaactctcta 360
gtatctgtga tggcattctc aagctccttg attcttgtct tattccttct gcttcagctg 420
gtgattctaa ggtgttttac cttaaaatga agggtgatta tcatcgttat ttggctgagt 480
ttaagactgg tgctgaacgt aaggaagccg ctgagagtac tctctccgcc tacaaagccg 540
ctcaggatat tgcaaatgct gaacttgccc caactcaccc aatccgactt ggactggctc 600
tcaacttctc tgtgttttat tatgagattt tgaactctcc tgatcgtgcc tgcaatcttg 660
ctaaacaggc ctttgacgaa gcaattgctg aattggacac actgggagag gagtcttaca 720

-continued

```
aggatagcac tttgatcatg caactgcttc gtgacaatct tactctctgg acctctgata    780

tgcaggatga tggcgctgat gaaatcaagg aaaccaaagc tgacaatgaa caacagtgag    840

gaaactgccc ctcatattgt cttttgactt cttcctgttg gtttttattg ggagaagctg    900

tttcctttta tttcctttt aatgtggttt cccttcagcg ttctcttatc cgtcgcaata    960

acaactttga caattgatgt tcaatgattt tatctttatt tt                      1002
```

<210> SEQ ID NO 329
<211> LENGTH: 1057
<212> TYPE: DNA
<213> ORGANISM: Artificial
<220> FEATURE:
<223> OTHER INFORMATION: Synthetic

<400> SEQUENCE: 329

```
tccacattct ctcaactttc tctttctaaa aactcttcct atctctttct ctagcacaca     60

gaccatcaat ggcatcgccg cgcgaggaga acgtgtacct ggcgaagctg gctgagcaag    120

ccgagcgcta cgaggagatg gtagagttca tggagaaagt cgtcggcgcc ggcgacgacg    180

aactcaccgt cgaggaacgc aacctcctct ccgtcgcgta caaaaacgtg atcggagcga    240

ggagagcgtc gtggcgcata atctcatcga tcgagcagaa agaagagagt cgcggtaatg    300

aagatcatgt tgcctccatt aaaacctaca gatctaagat cgaatctgaa ttgacttcga    360

tctgtaacgg tatccttaag ttgctcgatt caaaactcat cggcaccgct gctaccggtg    420

actctaaggt tttttatttg aaaatgaagg gagattatta caggtacttg gctgagttca    480

aaaccggagc tgagagaaaa gaagccgccg agaatactct ttcggcttac aagtcggctc    540

aggatattgc taatgtcgaa ttagccccta cacatccaat ccgattgggg ctagctctca    600

atttctcagt gttttactat gagatattga attctcctga ccgtgcttgt aatcttgcca    660

aacaggcatt tgatgaggca attgcggagc ttgacaccct tggagaggag tcttacaagg    720

atagcacctt gattatgcag cttcttcgtg ataaccttac gttgtggacc tcggatatgc    780

aggatgatgg gactgatgag atcgaagtac catcgaaagc agaggagcag cagtaatgtg    840

agtgaagcct ccttgtttag gattgcaatc ctatggactg tgctcattga tcggaatttg    900

ctgtttgtgt agttgtgaat tccgtgaatt gtaatacgta aaagtgctgt ttcttgccat    960

ttgttgtttt cagcaaagat tacttttttg tgcagtatgg tcccttgtat ttggatgctc   1020

cattggtgga aatgaattct tgttgttagg ggaacag                            1057
```

<210> SEQ ID NO 330
<211> LENGTH: 1086
<212> TYPE: DNA
<213> ORGANISM: Artificial
<220> FEATURE:
<223> OTHER INFORMATION: Synthetic

<400> SEQUENCE: 330

```
ccacaaaaaa gctctcctct ctcaattatt aaatccccat tcagaaaatc gaaaaactcc     60

ctcattcaga tctcccaaaa aaatacagag aaacaaatct aaacatggcg gtggcaccga    120

cggcgcgtga ggagaacgtg tacatggcaa agcttgcaga gcaagctgag aggtacgaag    180

aaatggttga attcatggaa aaggtctcca actccctcgg ctcagaagaa ctcaccgtgg    240

aggaacgaaa cctcctttcc gtggcgtaca agaacgtgat cggagcgcgt agggcatcgt    300

ggcgtattat ctcatcgatt gagcaaaagg aagagtccag agggaacgag gaacacgtga    360

actctatccg cgagtacaga tctaagattg agaatgagct ctctaagatc tgtgatggta    420
```

```
ttctgaaatt gctcgatgca aagcttatcc cttctgcagc atctggtgat tctaaggtgt    480

tttacctgaa aatgaaagga gattaccacc gctatttggc tgagttcaag accggtgctg    540

aacgtaagga ggctgctgag agtacactca ctgcctacaa agctgctcag gacattgcaa    600

ctactgaact tgccccaaca catcccatcc gacttggact ggctcttaac ttctctgtgt    660

tttactatga gatcttgaac tctcctgacc gtgcttgcaa tcttgctaaa caggcctttg    720

atgaagcaat tgctgagctg gatacattgg gcgaggagtc ttacaaggat agcactttga    780

tcatgcaact tcttcgtgac aatctcactc tctggacttc tgatatgcag gatgatgggg    840

ctgatgaaat caaggaagat cccaaacctg atgaagccaa aaattgaagg aaatgaaact    900

ctctaatttg cttttcactt cttcctggtt gtttttattg gaagaagctg attatcgtaa    960

tttccttact attatggttc tccactaggg ggttgtcatc ttattggaaa tgaacaactt   1020

ttaatattga tgtttcagag ttccatcttt gatttaatgt ggttttctgg tgattagttt   1080

tcttct                                                              1086
```

```
<210> SEQ ID NO 331
<211> LENGTH: 333
<212> TYPE: DNA
<213> ORGANISM: Artificial
<220> FEATURE:
<223> OTHER INFORMATION: Synthetic

<400> SEQUENCE: 331

catcatggct aaacaggcct ttgaggaagc tattgccgaa ctggacactt tgggggagga     60

atcctataag gatagcaccc ttatcatgca gttattgagg gacaatctca ctctctggac    120

ttccgatatg caggagcaga tggacgaggc ttgacattaa actgctcctc cggggggtgg    180

gctcaaattt cacacagcaa ctctgtaatc tacgcatgca actgatagct tttgtaattt    240

tatttctcat ccctcctttg ataattatct tattcaaact ctggtttgaa acttaatgtt    300

tttgatttta tttctcgagc ttccctttttt aag                                 333
```

```
<210> SEQ ID NO 332
<211> LENGTH: 812
<212> TYPE: DNA
<213> ORGANISM: Artificial
<220> FEATURE:
<223> OTHER INFORMATION: Synthetic

<400> SEQUENCE: 332

tcttttctag tgcaaaggtg ggaatctaag gaggaggagg aggaggagga ggaggggagt     60

agtagattct tccattgctg attccgatct gcctctagct atggccccca gagaggagct    120

cgttttcatg gccaagcttg ctgagcaggc cgagcgctac gatgagatgg ctgagttcat    180

ggagaaggtt gcctccatgt ccagctctgg tgacgagctc gctgtcgagg agcgtaacct    240

cctctccgtc gcgtacaaga acgttgtcgg tgcccgccgc gcctcctggc gtattgtctc    300

ctccatcgag cagaaggagg agaacaaggg caaccaggat cacgtctccg ccatccgcgg    360

ataccgcacc aagatcgaga atgagctcgc cggcatctgt gagggcgtgt tgaaggtcct    420

cgcctctgcc ctcatccccg cctgcgcctc caaggagtcc aaggtcttct acctcaagat    480

gaaaggggat tactaccgat accttgctga gttcaagacc ggccccgaga ggaaagacgc    540

ggctgagtcc acacttctct catacaagtc tgctcaggac atcgcactca ctgagatgcc    600

tcccactcac ccgattcgcc ttggcctcgc actcaacttc tctgtattct actacgaaat    660
```

-continued

```
cctacactca cccgaacggg cttgcagcct tgctaagcag gcatgtgatg aggccatttc    720

tgagctggac acacttggtg aggagtccta caaggacagc accctaatca tgcagcttct    780

ccgggataac ctcactttgt ggacatcaga tc                                  812
```

<210> SEQ ID NO 333
<211> LENGTH: 572
<212> TYPE: DNA
<213> ORGANISM: Artificial
<220> FEATURE:
<223> OTHER INFORMATION: Synthetic

<400> SEQUENCE: 333

```
cccacgcgtc cgatggtggc ggcaaggctg ctcaggacat tgctttggct gagctgcctc     60

ctactcatcc aattaggctt gggctagctc ttaacttctc agtgttctac tatgagatcc    120

tcaactcgcc tgatcgtgct tgcaacctcg caaagcaggc ttttgatgag gccatctcgg    180

agctggacac cctgagcgag gagtcctaca aggacagcac tttgatcatg caactcctcc    240

gtgataacct gaccctgtgg acttcagaca tctcggagga caccgcggaa gagatcaggg    300

aagctccgaa gcgcgactcc agcgaggggc agtaaagccg gctttatgtg ccctagaagc    360

ttgtagctag tgctttgcta ctgtgtaatg acacctatgt ggctgtgatt gttgtcggga    420

aatctggggc tcccccgtat gtgaggttgc tagcgatggt tttgcagtct cgcctttaag    480

ctactcgtag cagagcaggt gggggtctgt ggagccaggc ctggttgggg gtgggggagc    540

ctcttgaact gcttggtggc acttcctgtt tt                                  572
```

<210> SEQ ID NO 334
<211> LENGTH: 628
<212> TYPE: DNA
<213> ORGANISM: Artificial
<220> FEATURE:
<223> OTHER INFORMATION: Synthetic

<400> SEQUENCE: 334

```
aaaaaatcag agaagtgaag agaagagatc aagggatcga tccttgagaa ggcaatggga     60

atcgagaagg aacgtgagac cctcgtctac ctctctaagc tcgctgagca agctgagcgc    120

tatgacgaaa tggtggagtc aatgaagaaa gtggctaagt tggacattga gttgagtgtg    180

gaggaaagaa atctgctctc cgttggatac aagaatgtga tcggagcacg cagggcctcc    240

tggcgcatcc tctcttccat tgagcagaag gaagagagca agggcaatga gacaaatgtg    300

aagcgcatta aggactatcg cttcaaggtg gaggaagagc tctccaagat atgcagcgac    360

atcctaacca tcatcgatga gcacctcatc ccctcatcca acaccgctga atccactgtt    420

ttctattaca aaatgaaagg ggattattat cgataccttg cggagttcaa gtctgggcat    480

gagaggaagg aggctgccga tcaatctctg aaagcttatc aggcggctag taacactgcg    540

aacacggatc taccatccac ccacccaatc aggcttgggc tcgcacttaa cttctcagtc    600

ttctactatg agattttgaa ttctcctg                                       628
```

<210> SEQ ID NO 335
<211> LENGTH: 626
<212> TYPE: DNA
<213> ORGANISM: Artificial
<220> FEATURE:
<223> OTHER INFORMATION: Synthetic

<400> SEQUENCE: 335

```
tcttgttttt tgttttggtt gttgacggaa gaagaggagg gagaaggcat gggtgtggag     60
```

```
aaggatcgcg atggccatat ctacatggcc aagctcgctg agcaggccga acgatacgat    120

gagatggtcg attttatgaa aaaggtggca aacatggatg tggagctcac tgtggaggag    180

cggaatcttt tatcagtagg ctacaaaaat gtgattgggg cccgcagggc ttcgtggcgt    240

attctctcct caattgagca aaaggaggaa gccaaaggca atgagcagaa tgtggggcgt    300

atcaaagact acaaggaaaa ggttgaggaa gagctctcaa agatctgcat tgacatcttg    360

tcgactatcg atgatcatct tatccctgca tccagcactg acgagtcttc tgtgttttat    420

tacaaaatga aggggatta cttccgctat ttagcagagt tcaaagcctc aagcgagaaa    480

aaagatgctg cagagcagtc tctgaaagca taccaggttg cagcagataa agcagccaag    540

agtcttccaa caactaatcc gatcaggctt gggcttgctt tgaacttttc agttttctac    600

tatgaaatca tgaactcccc tgaaaa                                         626
```

<210> SEQ ID NO 336
<211> LENGTH: 1132
<212> TYPE: DNA
<213> ORGANISM: Artificial
<220> FEATURE:
<223> OTHER INFORMATION: Synthetic

<400> SEQUENCE: 336

```
agccaagtga aagcaaaaag ggagaggaaa agcgcaaaat ctcccttcga ttatcagtac     60

aaaacctctg atttgagaga tcggaaatgg cttcctccaa agaacgcgag aacttcgtct    120

acgtcgctaa gcttgctgag caggccgaac gctacaatga aatggttgat gcaatgaaga    180

gtgtagcaaa tatggatgtt gaattgactg ttgaggaaag gaatctgctt tctgttggtt    240

ataaaaatgt ggtaggttct aggagagcat cttggaggat cttatcctct attgagcaga    300

aggaagaatc tagaggaaat gagcaaaatg tcaagcgaat taaggagtac cgacaaaagg    360

tggagacaga gctcaccagc atttgcaacg atatcatggt ggtcattgat cagcatctaa    420

ttccttcatg cactgcaggc gaatcaactg tgttttacca caagatgaag ggagactatt    480

atcgttatct tgcagaattt aaatctggca atgacaagaa agaggttgca gagctttcat    540

tgaaagcata tcagtcagct acaactgctg cagaggcgga attaccaccc actcatccca    600

ttcggttggg attggctttg aatttctctg tgttctatta tgagatcatg aattcacctg    660

aaagggcatg ccatctggca aagcaggcct ttgatgaagc aatatctgag ttggatagcc    720

tgaacgagga ttcctacaaa gacagcacct tgattatgca gcttctaagg gacaatctca    780

ccttgtggac ttctgatctt ccagaggatg cagaagatgc ccaaaaggga gatgccacaa    840

acaaagcaag tggaggtgaa gatgcagagt gaatgggcct aatggttaga actaccttgt    900

gcatttggag ctgtgaggac ggtgatacac caaagggatg tgtgtgtgtt aagtcctagt    960

agattcttat cttatgggca tgtcgtgtca gtttctttac atgttaattg ggtgttgcaa   1020

ttcagcatgt gtgtgatttg tatccctgtg ctatttcctc tccgtaaagt gagttgtttc   1080

agtctttaga tgattggtct ggtccatagg tggttttatt tttcagagga ct           1132
```

<210> SEQ ID NO 337
<211> LENGTH: 617
<212> TYPE: DNA
<213> ORGANISM: Artificial
<220> FEATURE:
<223> OTHER INFORMATION: Synthetic

<400> SEQUENCE: 337

-continued

```
cggccgaaca aaaagcattc gcatccacga gaccactcga acccgacccg cctcgccgcc     60

gccgccaccg aagtaatccc ttaattggtc aaaatgtctc gggaggagaa tgtctacatg    120

gccaagctgg ccgagcaggc tgaaaggtat gaggagatgg ttgagtacat ggagaaggtt    180

gcaaagactg tagatgtgga agagctcact gttgaggagc gcaacctctt gtctgttgct    240

tacaagaatg tgattggtgc ccgccgtgcc tcctggcgta ttgtctcatc cattgaacag    300

aaggaggagg gtcgtggcaa tgaggaacat gttactctga tcaaggagta ccgtggcaag    360

attgaagctg agctgagcaa gatttgcgat ggtatcctga agttgcttga ctcacacctt    420

gtgccctcat ctactgctgc agaatctaag gtgttttacc tcaagatgaa gggtgattac    480

cacaggtacc ttgcggaatt taagactggt gccgagagaa aggaagctgc tgagagcaca    540

atggtggctt acaaggctgc tcaggatatt gctctggcgg atcttgctcc cacccatccc    600

ataaggcttg gactggc                                                   617
```

```
<210> SEQ ID NO 338
<211> LENGTH: 530
<212> TYPE: DNA
<213> ORGANISM: Artificial
<220> FEATURE:
<223> OTHER INFORMATION: Synthetic

<400> SEQUENCE: 338

acgagattct aaactctcca gacaaggctt gcaaccttgc taagcaggcg tttgacgaag     60

ccatctctga gttggatacc ctcggggagg agtcttacaa ggacagcact ttgatcatgc    120

agctcctgag ggacaacttg accctctgga cctctgacct cacggaggac ggtggtgatg    180

aggtgaaaga agcctccaag ggcgacgccg gcgagggcca gtaaaatggg aagatcgatc    240

gatcgatggc tccgcatgtt attggagacc attgatttag atgcctcatg ctgctgtcac    300

catgatggat ggattcttct tctgttctac tagaatgttt ttcttcctgt ccccccttcc    360

tctctcttct ctggttttta ctagggtggt agcggtcgaa ttagttcttc cctttgcttt    420

gcatttggtg ctagtggtcc gtctgggctg attgttttcc tctggatatg actctcgtgt    480

gtgttgtctc cagatagtgt tttattgagc aatatttaaa gttgtcgtcc               530
```

```
<210> SEQ ID NO 339
<211> LENGTH: 694
<212> TYPE: DNA
<213> ORGANISM: Artificial
<220> FEATURE:
<223> OTHER INFORMATION: Synthetic

<400> SEQUENCE: 339

gaattcatat gaagaaatgg ttgaatttat ggggggagta acaacaaatg ttgaatcaga     60

ggaactttca gttgaagaga gaaatttatt gtcagttgct tacaaaaatg tgattggtgc    120

acgcagagca tcatggagaa ttatttcatc aattgaacag aaagaagaaa gccgtggtaa    180

cgaagagaat gtattgacca ttcgtgatta tagatctaag attgaaactg aactttcagg    240

catctgtgat gggattttga agttgcttga tactagattg attccatctg catcttctgg    300

tgattctaaa gtgttttatt tgaaaatgaa aggtgattat catcgttatt tggctgagtt    360

taaaactggt accgaaagga aagaagctgc tgaaagtacc ctttctgctt ataaatctgc    420

tcaggatatc gcaactgctg aacttgcacc cactcaccca atcaggctgg gacttgctct    480

taacttctcc gtcttttact acgagatctt gaattctcct gaccgtgctt gtaatctcgc    540

caaacaggca tttgatgagg ctatcgcgga gctggatacc cttggtgaag aatcatacaa    600
```

agacagcact ctaatcatgc agctccttcg tgacaatctt actctgtgga cctccgacat 660
gcaggatgat ggtgcagatg aaattaaaga agca 694

<210> SEQ ID NO 340
<211> LENGTH: 723
<212> TYPE: DNA
<213> ORGANISM: Artificial
<220> FEATURE:
<223> OTHER INFORMATION: Synthetic

<400> SEQUENCE: 340
gtccatcttt gtgttgtgaa agaagcttgc aggccatggg gacggagaaa gagcgcgaga 60
aaaatgtgta catggccaag cttgctgagc aggcagagcg ttatcaagag atggttgaat 120
acatggaaac agtggccaag cttgatcttg agctaactgt ggaggagcgc aaccttctgt 180
ctgttggcta caaaaatgtt attggagccc acagagcctc ttggcgtatc ctttcttcca 240
ttgaacagaa agaagagaac aagggcaatg agactaatgt gaagcgtacc agggattata 300
ggcataaagt tgagacagaa cttaccaaga ttagcagtga aattttgact atccttgatg 360
agcatctcat cccctcatcg ggaactggcg aatcatctgt cttctactat aaaatgaagg 420
gcgactacta ccgttacctg gcagagtttc agacaggcga gaagaaaaag gaatctgcgg 480
acgagtcctt caaagcatat caggccgcat caagcactgc aaacacagat ctcccgccca 540
cccatccaat caggctgggg cttgccctga acttttctgt tttctactat gaaattatga 600
attcccctga acgggcatgc gagcttgcta aacaagcatt tgatgaggcg attgctgagc 660
ttgacactct gagtgaagag tcatacaagg acagcactct cattatgcag ctactgagag 720
aca 723

<210> SEQ ID NO 341
<211> LENGTH: 1046
<212> TYPE: DNA
<213> ORGANISM: Artificial
<220> FEATURE:
<223> OTHER INFORMATION: Synthetic

<400> SEQUENCE: 341
ttttcttcct tcatcaagct gtctctctct ctctctctct ctctctcttc ctctttgtga 60
acaatgggtg ccgagaagga gagggagggt catgtctacc tggccaagct tgcagagcag 120
gctgagcgtt acgatgagat ggtcgagttc atgaagaagg tagccaagct tgacattgag 180
ctgactgtgg aggagcgcaa tcttctctca gtggcctata agaatgtgat tggagcacgt 240
agggcctctt ggcgtattct ctcctccatt gagcagaagg aggagagcaa agggaatgag 300
gttaacgtga agcgtataaa ggattacagg caaaaggtcg atgaggaact ctcgaagatc 360
tgccatgaca ttttgactat catagatgag catctcatcc cctcttctgg gactggcgaa 420
tcgtctgtct tctactacaa aatgaaggga gattactacc gctacctcgc agagttcaaa 480
gctggtccgc agaaaaagga agacgcagat gagtccttca aagcctacca agctgcgtcg 540
agcaccgcga gtactgatct gccacctacc catcccatca ggcttggact cgccttgaat 600
ttctctgttt tctactatga aattttgaat tcgcccgagc aggcatgcca attagcaaaa 660
caagcattcg atgaggcgat tgcagagctc gatactctga gcgaggagtc atacaaggac 720
agcaccctta ttatgcagct tctaagagac aacctgacct tgtggacttc agatctgcaa 780
gaagatggag gtgatgagca ctccaaggga gaggatctga aagtaggaga tgcagaggaa 840

-continued

```
tcgtagtgcc agtttgattg ttcgagctga gttttgaagg agtcgagccg gatatgcatc     900

cttggtacaa aatttgacat gtgttagatt ctgtgtggca tttgtttgaa ggaatatcct     960

atgtagattg ttatgttctt gttctgctct attgctacaa gggctgttgt tacaattaca    1020

agttatacat tttctatttg agggaa                                          1046
```

```
<210> SEQ ID NO 342
<211> LENGTH: 654
<212> TYPE: DNA
<213> ORGANISM: Artificial
<220> FEATURE:
<223> OTHER INFORMATION: Synthetic

<400> SEQUENCE: 342

gaattcgaga gaaacagaaa aaggagattc agaattgggt aatcacggct atatttggag      60

acggagggtg gaatttccac cacaaccaaa gattgattca ttcatcatca tcttgtaacc     120

aaatcgaaaa aagaaaccct tcaccacacg gtggtagagg agctttgccg tcagaaggtg     180

gttctcctcc tgatcttctt ttccttgccg gtggtggtga atttctcatc aaatacccaa     240

tcaactgacc cccttattct tttgattttt tcctagattt accaattcat tttcttaact     300

tgaaaaccaa atcatattct agtacataat acattacaat atacaatatg ttgaccatca     360

aaagagttcc tactgttgtt tctaattacc aagaagatgg ttctgccgct gctgctgaaa     420

ctgttggctg tggccgtaat tgccttggaa agtgctgttt acctgtgtcc aagcttcctt     480

tgtatgcatt caagggagat gggattgatt caatcaaagg aggagaggaa cctgaggtgt     540

ctttctttga taccttaatt cttgggcaat gggaggatcg aatgagccgt ggcctttttcc    600

gatatgatgt aacacagtgt gagactaagg ttattcccgg agagtatgga tttg           654
```

```
<210> SEQ ID NO 343
<211> LENGTH: 712
<212> TYPE: DNA
<213> ORGANISM: Artificial
<220> FEATURE:
<223> OTHER INFORMATION: Synthetic

<400> SEQUENCE: 343

acgcgtcgga ctccagtccg gatgcggcaa gaatgtctcg ggtcgtgtgc attcctggag      60

caaagttgcc attgtatctc tttggcaaac cggatgtgga tgagagtgga gaagtcccta     120

ccaaggagct gggacaaaac tctttcctgg attcagctat tctcggtcag tgggctgata     180

ggcaagccaa gggactattt cgctacgacg ttaccgcgtg cgacacaaag gtgctgcctg     240

ggaagtatgg ttttattgcg caattgaatg aaggccgaca cctgaagaaa cgtcccactg     300

aattccgcgt tgatcaagtc ctccagcctt tcgatgcaaa gaagtttaac ttcacaaagg     360

tcggtcagga ggggatgatc ttttgcttcg agcagagcca cgaggacaag agcttccacc     420

acgaacaagc tcaagtgaaa ggaagtccaa acgttgtggt gatcaacgtg agcccgatcg     480

agtatggaca tgttttgctg gttcctcgag ttctcgattg tatcccgcag catctggaaa     540

cggatacttt ccttttggct cttcatatgg ctgcagaggc atccagtcca tatttccgct     600

tgggatataa tagtcttgga gctttcgcga cgatcaatca tctccatttc caggcatatt     660

atttgggaaa catattcccc gtggagaagg ctccacagaa attaatatac ag             712
```

```
<210> SEQ ID NO 344
<211> LENGTH: 379
<212> TYPE: DNA
<213> ORGANISM: Artificial
```

<220> FEATURE:
<223> OTHER INFORMATION: Synthetic

<400> SEQUENCE: 344
catcaatgtt agtccgatag agtatggcca tgtgctgctg attcctcgtg ttcttgactg 60
cttgcctcaa aggatcgatc acaaaagcct tttgcttgca gttcacatgg ctgctgaggc 120
tgctaatcca tacttcagac tcggttacaa cagcttgggt gcttttgcca ctatcaatca 180
tctccacttt caggcttatt acttggccat gcctttccca ctggagaaag ctcctaccaa 240
gaagataact accactgtta gtggtgtcaa aatctcagag cttctaagtt accctgtgag 300
aagtcttctc tttgaaggtg gaagctctat gcaagaacta tctgatactg tttcagactg 360
ctgtgtttgc cttcaaaac 379

<210> SEQ ID NO 345
<211> LENGTH: 364
<212> TYPE: DNA
<213> ORGANISM: Artificial
<220> FEATURE:
<223> OTHER INFORMATION: Synthetic

<400> SEQUENCE: 345
ttattggtgg tagtgatctt caaggaagaa gctttctcta tcgggaattg cattgccaaa 60
tagtaagcct gaaagtgaag atggttaatg gtagcgaaag cgcctagact gttgtatcca 120
agtcggaaat acgtattatc ggcttcagcc gccatttgaa gagcaagcaa aaggcttttg 180
tgatcaatcc tttgaggtaa gcaatcaaga acattccttt caacattctc atctctgact 240
ctggcaaacg aatcttcctt ctccctcagt gttacgcaga gaaacaggct ttaggagaag 300
ttagctcaac gctattggat acgcaagtga atccagcggt ttgggagatg agtggacaca 360
tggt 364

<210> SEQ ID NO 346
<211> LENGTH: 935
<212> TYPE: DNA
<213> ORGANISM: Artificial
<220> FEATURE:
<223> OTHER INFORMATION: Synthetic

<400> SEQUENCE: 346
accggatccc ttcccctcac ggcggtaggg gtgcctctcc ttctgaaggc ggttgcccct 60
ccgatctcct cttcctcgcc ggcggcggtc cccttttttcc tctctcctaa tttttcttat 120
ttgtaaagcg cacatacgga tttggatact ggtgtatatt acgtatagca tacgcagaaa 180
atatttatat ttttgatcat ccatccaaga ataataggaa gggatgctga ctattaaaag 240
ggtgccgacc ctagtttcca actaccaaga ggatgtgcct gaaagcaaca acgtagttgg 300
ttgtggccgc aattgccttg gaaaatgctg tttgccggcg tccaggcttc ctctttatgc 360
attcaagaat gatgacaatg agccaattga aaacggtatt gatgccttgc ctggggagga 420
ttgtcagata tctttttga atgatctgct gttgggccta tgggaagagc ggatgagcca 480
gggactgttt cgatatgatg tcacaacctg tgagactaaa gtcattcctg ggagatatgg 540
ttttattgca cagctgaatg aggggcgcca cctaaaaaag cgcccaacag agtttcgcat 600
cgatcaggtt cttcagcctt ttgacgagaa caaattcaat tttaccaaag tgggccagga 660
cgaagtgctt ttcaggtttg agccaagcac tgactgcaag gcccattact tttcgggtgt 720
gggagtagat gctggtgttt caccgagtat tgttgctatc aatgtgagcc caatcgagta 780

-continued

```
tggccatgtg cttttgatac ctcgagttct tgattacttt cctcagagaa ttgatcgtga    840

tagtttcacg gttgctctcc atttcgccag agaactggct gatcccttct ttagggtagg    900

ttataacagt ctgggcgcct tcgccactat aaacc                               935
```

<210> SEQ ID NO 347
<211> LENGTH: 676
<212> TYPE: DNA
<213> ORGANISM: Artificial
<220> FEATURE:
<223> OTHER INFORMATION: Synthetic

<400> SEQUENCE: 347

```
ttttttttta acaaatttc atttttcata taaggtagag agagagatgt acacaaccac     60

ttcactgagc aaagtacaca tgcattaaga tcattattga atgatcaaaa tcaaactaca    120

cgcaataact actaaaacta tcctactttg ttacgcaggt aacagaaaag ttgaaagaac    180

aagagacaac actgcaaccc tcttgaaacc ctaatagtac ttcttcactg ctgaaccaga    240

caaccttggg ggtaatatgt ggcagaggtg cgagatgagc cccgaaaaa agaatcttca    300

tcctcatcct tgacatctcc ttcctctttt tctgcaacac aaaccatttc ctgaacacct    360

gcagcttcaa atatataggt tttcacttct tgaaaccttt cctcggagag agacacctct    420

gcaaggagcc tccaagcata attttcagat gcgtcctcgt agtcattctt cctcttcaac    480

actatatgtc cacttatctc ccacacagct ggatttactt gggtatcaag aagctcctga    540

ctcacttctc caagtgcttg cttttcagcg taacactgag ggaagaggaa gattcgtttt    600

ccacaatcag agatgagaac attgtatgga atgttggtct cttgaagaaa aatgcaagca    660

ttagagacaa cgtcag                                                    676
```

<210> SEQ ID NO 348
<211> LENGTH: 669
<212> TYPE: DNA
<213> ORGANISM: Artificial
<220> FEATURE:
<223> OTHER INFORMATION: Synthetic

<400> SEQUENCE: 348

```
gcattcgtgc atgcagaagt gtttgcactg accggcctag actggggctg gtccgtgccg     60

catgttccgc aaccacggct ctgattaatc tccccgggcg ccccagcctc gcctatgcgc    120

gcactggttt ccccacttgc aacactctgc tgagctcgcc atctttccac ggcggtcgag    180

gggccagccc ctcggaagga gggcatccct ccgacctcac cttcctcgcc ggtggtggtg    240

gtgccgccgc cgccgccgct tcttgcagcc aggggaaagt tcgcgttttt ttatacaact    300

taacttccga agatgctgac tattaagcga gttccaacgc tcctgtccgt gaaccaggac    360

gagtgcttgg caagctgctg cattacagag atggaccttc ctttgtttaa gtatacaaag    420

aagagtgtta ggcgtccttc cgatgaggag ttgccaccag ccattgaaac atccttcctc    480

gggacgttgc tgctgtctca gtgggaagaa cgcgcatgcc aaggattgtt tcgatacgat    540

gtcactgctt gtgaatcgca ggtgcttccg gggaaacatg gatttattgc acagctcaac    600

gaaggacggc acctgaagaa gcggccgact gagtttcgag ttgatcaagt ccttcaagag    660

tttgatccc                                                            669
```

<210> SEQ ID NO 349
<211> LENGTH: 2100
<212> TYPE: DNA
<213> ORGANISM: Artificial -continued
<220> FEATURE:
<223> OTHER INFORMATION: Synthetic

<400> SEQUENCE: 349

```
aattaccaat tccattcctc cacagcttct tcttttcctt agtaacccgc cactaatctc      60
tttgaaatcc aagttacaaa atcttttgtt cgtgtaggaa attcgagaaa tcttaggaaa     120
agagtattat tgttgtttag agagggtaaa tcccaggtaa acaagttgta gacatcacgg     180
ctatacacaa agcaaaccgt cgatcattct tacatgttcg ttcagtacga cgtaagggtt     240
gtgtaactgc caccaatcct gcgccgcacg gcggacgtgg cgctttgccc tctgaaggcg     300
gtagtccttc cgacctcctc ttccttgccg gcggtggttc tctcctttct tctacctgct     360
agatttagtt acttatcctt acatagttac ttccttctcc gtaaattatt tttaattgtt     420
ttgcacatta gcaattatta aggttgttct tgtacctagt atttttccct tgaaaaatca     480
aagcaaaaaa aaccaaacat gatgctcaag attaagaggg ttcctacgct tgtttccaac     540
ttccaaaagg aagaggctga agaaactctt gctcgtggtg ctggctgtgg ccgcaactgc     600
ctccgaaact gctgccttcc agggtcaaag ctgccactgt atgcttgcaa gagtttgaga     660
aatggcacgt ctgttgccga tgaaaccaag gaacctcccg ttgacttctt ggaatccctc     720
cttctcgggg aatgggagga tcgtcagcag aaaggtctct ttcgctatga tgtcactgct     780
tgcgaaacca aggttattcc tggagaatat ggtttcgttg ctcaactgaa tgagggaagg     840
cacctcaaga agaggccaac tgagtttcgc gttgataagg tgctgcagcc ttttgatgga     900
agcaagttca acttcactaa ggttggtcag gaggagttgc tcttccagtt tgaagcaagt     960
gaggataatg aagtccaatt ctttccaaat gcgcccattg atgccgaaaa atctccaagt    1020
gtcgttgcca tcaatgtcag tcccattgag tacggacacg tgcttttgat acctaaggtt    1080
cttgaatgcc ttccccagag gatcgacagg gacagcttat tgcttgcact gcaaatggct    1140
gccgaagcag caaacccata cttccgtttg ggttataaca gcttgggtgc atttgcgact    1200
atcaaccatc ttcactttca ggcttattac ttggctgtgc cattccccat ggagaaggcc    1260
cccacgcgga agataatctt tgctgatgct ggcgtgatga tatctgagat gctgaattat    1320
ccagttcgag gacttgtctt tgagggtgga aatactttgg aggatttcgc caatgttgtc    1380
tctggttctt gcatttgcct gcaagagaat aacattccct acaatgttct aatctctgat    1440
tcggcaaaaa gggtattcct tctcccacag tgctacgcag agaaacaggc tctaggggag    1500
gtcagctctg aactgcttga tactcaagtc aatcctgcag tatgggagat tagtggacac    1560
atggtcttga agaggaagga ggattacgag ggtgcaaccg aggcaaatgc ctggaggctt    1620
ctcgctgagg tctcactttc tgaagcgagg ttccaagaag tgactgctct catctttgaa    1680
gccattgatt gcagtgttga agagaatgag aatgccaatg aaggttctcc tgagaagcca    1740
gatgttgcac ctcagcctat ggaggaaatt gatgctctca acacccatgc taccatggtt    1800
cccgtgtagg gttttcatgg tcgagctgtg gtgtttgtcc tgttgttact atttcaacta    1860
tatgaacatt gagggagttt ctatctatgg ctgcacttgt gaaatatccc taaataaggc    1920
tagccatgtt ctatgtattg atgaagttgt ttggttccta tgtgaattga accttgtctt    1980
ttattgcttc atattaatgt ggagttgctc agtgtcctct gggaattgac cttggatact    2040
atgtttgttg tctgttattt aagacaatat atttggtaat ggaagttgga gtttccctgt    2100
```

<210> SEQ ID NO 350
<211> LENGTH: 712
<212> TYPE: DNA

<213> ORGANISM: Artificial
<220> FEATURE:
<223> OTHER INFORMATION: Synthetic

<400> SEQUENCE: 350

```
acgcgtcgga ctccagtccg gatgcggcaa gaatgtctcg ggtcgtgtgc attcctggag     60
caaagttgcc attgtatctc tttggcaaac cggatgtgga tgagagtgga gaagtcccta    120
ccaaggagct gggacaaaac tctttcctgg attcagctat tctcggtcag tgggctgata    180
ggcaagccaa gggactattt cgctacgacg ttaccgcgtg cgacacaaag gtgctgcctg    240
ggaagtatgg ttttattgcg caattgaatg aaggccgaca cctgaagaaa cgtcccactg    300
aattccgcgt tgatcaagtc ctccagcctt tcgatgcaaa gaagtttaac ttcacaaagg    360
tcggtcagga ggggatgatc ttttgcttcg agcagagcca cgaggacaag agcttccacc    420
acgaacaagc tcaagtgaaa ggaagtccaa acgttgtggt gatcaacgtg agcccgatcg    480
agtatggaca tgttttgctg gttcctcgag ttctcgattg tatcccgcag catctggaaa    540
cggatacttt ccttttggct cttcatatgg ctgcagaggc atccagtcca tatttccgct    600
tgggatataa tagtcttgga gctttcgcga cgatcaatca tctccatttc caggcatatt    660
atttgggaaa catattcccc gtggagaagg ctccacagaa attaatatac ag            712
```

<210> SEQ ID NO 351
<211> LENGTH: 716
<212> TYPE: DNA
<213> ORGANISM: Artificial
<220> FEATURE:
<223> OTHER INFORMATION: Synthetic

<400> SEQUENCE: 351

```
tgcaattgcc aattccattc ctctacatct tcttctttc cttaccaatc cacctccaat     60
ctctttgaaa tcaagttaca gaaatctttt gttcgtgtag gaaattcgag aaatcttaga    120
aaaaaaatat attattgctg tttagaaagg gtaaatccca ggtgaacaag ttgtagacat    180
cacggctata cacaaagcaa accgccgacc attcttacat gttcgttcag tacgacgtaa    240
gggttgtgta actgccacca atcctgcgcc gcacggcgga cgtggcgctt tgccctctga    300
aggcggtagt ccttccgacc tcctcttcct tgccggcggt ggttctctcc tttcttctac    360
ctgctagatt tacttactta tataccttac atagttaatt ccttctccgt aaattactaa    420
ttgttttgca cattagcaat tattaaggtt gttcttgtac ctagtatttt taccttgaaa    480
aatcaaagga aaaaaaagca aacatgatgc tcaagattaa gagggttcct acacttgttt    540
ccaacttcca aaaggaagag gctgaagaag ctcttgctcg tggtgctggc tgtggccgca    600
attgcctccg aaactgctgc cttccagggt caaagctgcc actgtatgct tccaagaact    660
tgagaaaggg caagtctgtt gccgatgaaa ccaaggagcc tcctgttgac ttcttg        716
```

<210> SEQ ID NO 352
<211> LENGTH: 379
<212> TYPE: DNA
<213> ORGANISM: Artificial
<220> FEATURE:
<223> OTHER INFORMATION: Synthetic

<400> SEQUENCE: 352

```
catcaatgtt agtccgatag agtatggcca tgtgctgctg attcctcgtg ttcttgactg     60
cttgcctcaa aggatcgatc acaaaagcct tttgcttgca gttcacatgg ctgctgaggc    120
tgctaatcca tacttcagac tcggttacaa cagcttgggt gcttttgcca ctatcaatca    180
```

-continued

```
tctccacttt caggcttatt acttggccat gcctttccca ctggagaaag ctcctaccaa    240

gaagataact accactgtta gtggtgtcaa aatctcagag cttctaagtt accctgtgag    300

aagtcttctc tttgaaggtg gaagctctat gcaagaacta tctgatactg tttcagactg    360

ctgtgtttgc cttcaaaac                                                 379
```

<210> SEQ ID NO 353
<211> LENGTH: 364
<212> TYPE: DNA
<213> ORGANISM: Artificial
<220> FEATURE:
<223> OTHER INFORMATION: Synthetic

<400> SEQUENCE: 353

```
ttattggtgg tagtgatctt caaggaagaa gctttctcta tcgggaattg cattgccaaa     60

tagtaagcct gaaagtgaag atggttaatg gtagcgaaag cgcctagact gttgtatcca    120

agtcggaaat acgtattatc ggcttcagcc gccatttgaa gagcaagcaa aaggcttttg    180

tgatcaatcc tttgaggtaa gcaatcaaga acattccttt caacattctc atctctgact    240

ctggcaaacg aatcttcctt ctccctcagt gttacgcaga gaaacaggct ttaggagaag    300

ttagctcaac gctattggat acgcaagtga atccagcggt ttgggagatg agtggacaca    360

tggt                                                                 364
```

<210> SEQ ID NO 354
<211> LENGTH: 935
<212> TYPE: DNA
<213> ORGANISM: Artificial
<220> FEATURE:
<223> OTHER INFORMATION: Synthetic

<400> SEQUENCE: 354

```
accggatccc ttcccctcac ggcggtaggg gtgcctctcc ttctgaaggc ggttgcccct     60

ccgatctcct cttcctcgcc ggcggcggtc ccctttttcc tctctcctaa tttttcttat    120

ttgtaaagcg cacatacgga tttggatact ggtgtatatt acgtatagca tacgcagaaa    180

atatttatat ttttgatcat ccatccaaga ataataggaa gggatgctga ctattaaaag    240

ggtgccgacc ctagtttcca actaccaaga ggatgtgcct gaaagcaaca acgtagttgg    300

ttgtggccgc aattgccttg gaaaatgctg tttgccggcg tccaggcttc ctctttatgc    360

attcaagaat gatgacaatg agccaattga aaacggtatt gatgccttgc ctggggagga    420

ttgtcagata tctttttttga atgatctgct gttgggccta tgggaagagc ggatgagcca    480

gggactgttt cgatatgatg tcacaacctg tgagactaaa gtcattcctg ggagatatgg    540

ttttattgca cagctgaatg aggggcgcca cctaaaaaag cgcccaacag agtttcgcat    600

cgatcaggtt cttcagcctt ttgacgagaa caaattcaat tttaccaaag tgggccagga    660

cgaagtgctt ttcaggtttg agccaagcac tgactgcaag gcccattact tttcgggtgt    720

gggagtagat gctggtgttt caccgagtat tgttgctatc aatgtgagcc caatcgagta    780

tggccatgtg cttttgatac ctcgagttct tgattacttt cctcagagaa ttgatcgtga    840

tagtttcacg gttgctctcc atttcgccag agaactggct gatcccttct ttagggtagg    900

ttataacagt ctgggcgcct tcgccactat aaacc                               935
```

<210> SEQ ID NO 355
<211> LENGTH: 669
<212> TYPE: DNA

<213> ORGANISM: Artificial
<220> FEATURE:
<223> OTHER INFORMATION: Synthetic

<400> SEQUENCE: 355

```
gcattcgtgc atgcagaagt gtttgcactg accggcctag actggggctg gtccgtgccg     60

catgttccgc aaccacggct ctgattaatc tccccgggcg ccccagcctc gcctatgcgc    120

gcactggttt ccccacttgc aacactctgc tgagctcgcc atctttccac ggcggtcgag    180

gggccagccc ctcggaagga gggcatccct ccgacctcac cttcctcgcc ggtggtggtg    240

gtgccgccgc cgccgccgct tcttgcagcc aggggaaagt tcgcgttttt ttatacaact    300

taacttccga agatgctgac tattaagcga gttccaacgc tcctgtccgt gaaccaggac    360

gagtgcttgg caagctgctg cattacagag atggaccttc ctttgtttaa gtatacaaag    420

aagagtgtta ggcgtccttc cgatgaggag ttgccaccag ccattgaaac atccttcctc    480

gggacgttgc tgctgtctca gtgggaagaa cgcgcatgcc aaggattgtt tcgatacgat    540

gtcactgctt gtgaatcgca ggtgcttccg gggaaacatg gatttattgc acagctcaac    600

gaaggacggc acctgaagaa gcggccgact gagtttcgag ttgatcaagt ccttcaagag    660

tttgatccc                                                            669
```

<210> SEQ ID NO 356
<211> LENGTH: 654
<212> TYPE: DNA
<213> ORGANISM: Artificial
<220> FEATURE:
<223> OTHER INFORMATION: Synthetic

<400> SEQUENCE: 356

```
gaattcgaga gaaacagaaa aaggagattc agaattgggt aatcacggct atatttggag     60

acggagggtg gaatttccac cacaaccaaa gattgattca ttcatcatca tcttgtaacc    120

aaatcgaaaa aagaaaccct tcaccacacg gtggtagagg agctttgccg tcagaaggtg    180

gttctcctcc tgatcttctt ttccttgccg gtggtggtga atttctcatc aaatacccaa    240

tcaactgacc cccttattct tttgattttt tcctagattt accaattcat tttcttaact    300

tgaaaaccaa atcatattct agtacataat acattacaat atacaatatg ttgaccatca    360

aaagagttcc tactgttgtt tctaattacc aagaagatgg ttctgccgct gctgctgaaa    420

ctgttggctg tggccgtaat tgccttggaa agtgctgttt acctgtgtcc aagcttcctt    480

tgtatgcatt caagggagat gggattgatt caatcaaagg aggagaggaa cctgaggtgt    540

ctttctttga taccttaatt cttgggcaat gggaggatcg aatgagccgt ggccttttcc    600

gatatgatgt aacacagtgt gagactaagg ttattcccgg agagtatgga tttg          654
```

<210> SEQ ID NO 357
<211> LENGTH: 676
<212> TYPE: DNA
<213> ORGANISM: Artificial
<220> FEATURE:
<223> OTHER INFORMATION: Synthetic

<400> SEQUENCE: 357

```
ttttttttta acaaattttc atttttcata taaggtagag agagagatgt acacaaccac     60

ttcactgagc aaagtacaca tgcattaaga tcattattga atgatcaaaa tcaaactaca    120

cgcaataact actaaaacta tcctactttg ttacgcaggt aacagaaaag ttgaaagaac    180

aagagacaac actgcaaccc tcttgaaacc ctaatagtac ttcttcactg ctgaaccaga    240
```

```
caaccttggg ggtaatatgt ggcagaggtg cgagatgagc ccccgaaaaa agaatcttca    300
tcctcatcct tgacatctcc ttcctctttt tctgcaacac aaaccatttc ctgaacacct    360
gcagcttcaa atatataggt tttcacttct tgaaaccttt cctcggagag agacacctct    420
gcaaggagcc tccaagcata attttcagat gcgtcctcgt agtcattctt cctcttcaac    480
actatatgtc cacttatctc ccacacagct ggatttactt gggtatcaag aagctcctga    540
ctcacttctc caagtgcttg cttttcagcg taacactgag ggaagaggaa gattcgtttt    600
ccacaatcag agatgagaac attgtatgga atgttggtct cttgaagaaa aatgcaagca    660
ttagagacaa cgtcag                                                    676
```

<210> SEQ ID NO 358
<211> LENGTH: 1374
<212> TYPE: DNA
<213> ORGANISM: Poppy

<400> SEQUENCE: 358

```
ttaattaagt cgacgaattc agaggcagat agagagagag acaatggcaa tggcaacaag     60
taggttgatg gtggtgcaac aaaaacaacc atcctcatgt ctattaccac catcatctct    120
ttctgacttc aatggtatta gactgaaaca cccaattcag tacaaaagaa aggaatggca    180
gacaagagga gcattgcagg tgaaagcatc agctgcaaag aaaatcctga ttatgggagg    240
aaccagattt attggtatct ttttgtctag gctccttgtg aaggaaggtc atcaagtaac    300
tttgttcaca agagggaaag caccaatcag ccaaccatta cccggggagt cggaacaaga    360
ttacctagat tttcttccaa agatttccca cttgaaagga gacagaaagg actatgattt    420
tgttaagact agcctagcag ctgaaggctt tgacgttgtc tatgatatca atggaagaga    480
ggcagaagaa gtagaaccca tattggacgc gcttccaaag cttgagcagt acatatactg    540
ttcatccgct ggtgtgtatc tgaagtctga tttactgcct cattttgagt ctgatgcagt    600
ggatcccaag agcaggcaca agggaaaact tgaaacagag agtttacttg tatcaaaggg    660
cgtgaactgg acttcgctga gaccagttta tatctacggt cctttgaatt acaaccctgt    720
tgaagaatgg tttttccaca gattgaaggc cggtagacca atccccatac caaattctgg    780
caaccagata acacaattgg gtcatgttaa ggatttggcg accgcattta ttaacgttct    840
tggtaacgat aaagcgagcc agcaagtgtt taacatatct ggagataaat atgtgacatt    900
cgacggattg gcaagggctt gtgctaaggc tggtggattt cctgagccag aactagttca    960
ctacaatcct aaagaattcg attttggcaa aaagaaggca ttccccttca gagaccagca   1020
tttctttgca tcaattgaga aagcaaagag tgaattgggg tggaaaccag aatatgattt   1080
ggtggaaggt ctaacagact cctacgatct tgatttcggt aggggaactt tcaggaaagc   1140
ggctgacttc tcaactgatg acatgattct tgaaaaatgt cttgttccac aataatttaa   1200
gctttccatt gtatgaaatt caagtaggca tttatgattg tttgtgagtc taccgaaggt   1260
tatagctatc attcaacttt tgaacatggg aaaggacaat cttgtttcca gcgtatgttt   1320
cttggcagat aataaaacac agctttttaa ataaaaaaaa aaaaaaaaaa aaaa         1374
```

<210> SEQ ID NO 359
<211> LENGTH: 1477
<212> TYPE: DNA
<213> ORGANISM: Poppy

<400> SEQUENCE: 359

-continued

```
ttaattaagt cgacgaattc aaattaggtc taaagatggc gtctttagct caacaattct     60
caggattaag atgcccacca ctttcttctt ctcatctaac aaaacccttt tcttcaaaac    120
cccagaaaac caccttttca cctatagttt cagcagctgt catttctaat gcacaaacta    180
aagaaagaag tagacttaaa gaaatcttcg aagatgctta tgaaagatgt agaactactc    240
caatgcaagg tgttggtttt actgttgatg attttcatgc tgctcttgaa aagtatgatt    300
acaattctga gattggtacc agggttaaag gaactgtgtt ctgtacagac aacaacggag    360
cattagttga catcacggcg aaatcttcag cctatttacc aatccaagag gcatgtattc    420
acaaaataaa gcatgtagaa gaagcaggaa tagttgcagg cctacgtgaa gagtttgtga    480
ttattggaga gaaccaagct gatgatagct tgatcttgag tttgcgttca atccaatttg    540
acctcgcatg ggaacggtgt agacaacttc aggcagagga tgtcgtcctc aagggtaagg    600
ttgttggtgg aaacaaaggc ggtgtggtgg caattgtcga aggccttcgt ggttttattc    660
cattctcaca aatatcttca aaatcaaccg cggaagatct cattgataag gagcttcctc    720
tgaaatttgt ggaagttgat gaggagcagt ctagacttgt cctcagtaat cgcaaggcca    780
tggcagacag ccaggcacag cttggtattg gatcagttgt cactggaaca gtacagagtc    840
ttaagccata tggcgctttc atcgacattg gtggaatcaa tggtcttctt catgttagtc    900
aaattagtca tgatcgtgtc tcggatattg caacagttct tcaacccggc gacactctaa    960
aggtgatgat attgagccac gaccgtgaga gaggccgagt cagtctatcc accaaaaagc   1020
tagagcctac tccaggagat atgatccgta accccaagct tgttttcgag aaggctgaag   1080
aaatggctca gacattcagg cagagaatag ctcaagcaga agctatggcc cgtgcggaca   1140
tgctgagatt ccaacccgag agtggattga ctctaagctc agacggcatc ttaggtcccc   1200
tgacgccaga cttgcctgct gaaggtctag atttgagcga cattcctgca gctgatgatg   1260
catagaaacc aataaatatg aattaaatct gtcttgacgt ttcttctcat caccattttt   1320
aggctatgta agatgggtct ataggttgtt caaagtgttg acttgtgtat ttatcttgat   1380
agttcaaagt gtacttcttt aagcgataat cattgaaaag aaaaaatgga gaaggtaaaa   1440
gataaaaata tccaaaaaaa aaaaaaaaaa aaaaaaa                            1477
```

```
<210> SEQ ID NO 360
<211> LENGTH: 805
<212> TYPE: DNA
<213> ORGANISM: Poppy

<400> SEQUENCE: 360

ttaattaagt cgacgaattc acatctaaag tcaacaacaa gagcttctct cttctcctcg     60
tctctgttct cctctctttt gcaatcctct ctcaatctgc tgatgattgt gtatacacag    120
tatacacaag aacaggatca atcatcaaag gaggaacgga ttcaaaaatc tcactaagat    180
tatacagcaa atacggtaag tacatcgaga tcccaaatct tgaatcatgg ggtggattaa    240
tgggtcctgg ttacgattat ttcgaaagag gtaatcttga tatcttcagc ggaagaggtt    300
attgtctggg ttcaccggtt tgtgccatga atctgacttc cgatggtact ggttccggtc    360
acggatggta tgtgaattat gttgaagtta ctactaccgg tgcacatatt aattgtggtc    420
aacagaattt tgaagtggaa gattggcttg ctcttgatag atctccttat agtcttaccg    480
ctatcaagaa taattgtaat cagaaattat ctgatcatga ttctcattct gctgatcagt    540
ctatgtaaaa tttgatctct tgtttgattc ggtggtggtc tagtatgagt gatcggacgg    600
tcgtcattgt gtgttgtaat gttgaaatta ttttcttgaa taaaatgatt gagtgagtag    660
```

```
tgtttgattt tgcttggcca tcttagacat gatggtgaga ctgtttctcg attcgatgca    720

atttttggt tttcttggtt gcaatcaatt cacgtttggt gaaaaaaaaa aaaaaaaaaa    780

aaaaaaaaaa aaaaaaaaaa aaaaa                                         805
```

<210> SEQ ID NO 361
<211> LENGTH: 1072
<212> TYPE: DNA
<213> ORGANISM: Poppy

<400> SEQUENCE: 361

```
gaattcaatc aaatggctac tgctagagtt ttagctgcta gtatgttgca tgaatgcaac     60

aacactcaca gtgcttcatt tcttttgaga caatcttctt tcatcttacc tattaaacat    120

caaagtatta atttcagtag aagagcatct tctaggagag cttttacttg caaatctctt    180

tacaaacctg aaattcaaat caaacaagaa ggtgaacctc aaaccctaga ttacagagtc    240

ttctttcatg ataaatctgg caaaaagctt tcaccttggc atgatgtacc attgcaattg    300

ggtgatggag tgttcaattt tatcgtggaa ataccaaaag agacaagtgc aaagatggaa    360

gttgcaactg atgagccata tactcccatt aaacaggaca ccaagaaggg aaaacttaga    420

ttctacccct acaacatcaa ttggaactat ggattgctcc cacagacatg ggaagaccca    480

acagtagcta attctgaagt tgaaggggca ttcggagata atgatccagt tgatgttgtt    540

gaaattgggg agaggcaagg aaaaattggc gagattctta aagtcaagcc tttaggtgct    600

ttggctatga ttgacgaagg agaactcgac tggaaaattg ttgcgatttc gttggatgac    660

ccaaaagctt cactcgtcaa tgatgttggt gatgttgaga aacatttccc gggcactctc    720

actgctataa gagattggtt cagagactac aagatcccag atggaaagcc tgccaataag    780

tttggacttg ggaacaaagc agccaacaag gattatgctc tgaaggtaat aactgaaacc    840

aacgaagctt gggctaaact tgtcaagaga actgttcctg ctggggagct ctcccttctg    900

taaattttga atttttaaaa gttgaagata agaggcactt tggcccgctc ctatcccccct    960

cctctctcta ttgttttctt tcatgctgga ttccaaacaa acttcctcca attttttgga   1020

cgaagtattg ataatttcta atcattgagc tccatttttc aaaaaaaaaa aa           1072
```

<210> SEQ ID NO 362
<211> LENGTH: 1012
<212> TYPE: DNA
<213> ORGANISM: Saleginella lepidophylla

<400> SEQUENCE: 362

```
ttaattaact cgacccacgc gtccgcacca cgagaaaaag ctctcccttt gggctctccc     60

aaaccctagg aaagcaaggg cggcagcgca cggcgaggaa cagggatgtc gaatcttcgc    120

gaggagaatg tctacatggc caagctcgcg gagcaggccg agcgctacga cgagatggtg    180

gaattcatgg agaaggtggt caaggccgtg gacgtggagg agctgacggt cgaggagcgg    240

aatctcctgt cggtggccta caagaacgtg atcggcgccc gccgggcatc gtggaggata    300

atctcctcca tcgagcaaaa ggaggaatcc aagggcaacg acgagcacgt ctcgatgatc    360

aaggagtacc gtgccaaggt ggagtcggag ctgagcacca tttgcgacag catcctcaag    420

ctgctggaca gccatctcat cccctcatcg tccagtggcg agtccaaggt cttctacttg    480

aagatgaagg gtgactacca ccgatacttg gccgagttta agaccggggc cgagaggaaa    540

gaggccgcgg agaacactct cctcgcctac aagtcggccc aggacatcgc tctcacacag    600
```

-continued

```
ctgccgccga cgcaccccat ccggctgggt ctcgctctca atttttcggt cttctactac    660

gagattttga attcgcccga tcgagcttgt acgcttgcca agcaggcatt tgacgaggcc    720

atagccgagc tggacacttt gggagaggaa tcttacaagg atagtactct gatcatgcag    780

ctgctgcgcg ataatctaac gctgtggacc tcagacatgc aggaggaagg tgccggcgag    840

gggaaggacg agaagccgtg agtaaaataa tacgttcgaa tttcgttttc tatgctacta    900

gctagctgtt tagacgcctt ctctctcaac accttggtac tgttgattct tttgttcctg    960

aatacattat ttggcttgca ctaaaaaaaa aaaaaaaaaa aaaaaaaaaa aa           1012
```

<210> SEQ ID NO 363
<211> LENGTH: 1752
<212> TYPE: DNA
<213> ORGANISM: Saleginella lepidophylla

<400> SEQUENCE: 363

```
ctcgacccac gcgtccgcga agagtgagtt gatcgaatag atttgattcc tttctcttgg     60

tagggagagc tggcgacgaa agggttggat cacgcagagt ttccaccacg gctttgaatt    120

ccaggcgtcg cgattccctg gtcggtgtgg acgctgccag gagcttgtgc gtggtagcgc    180

gccttgccag cttccacggt ggtcgcggcg cagctccggc tgccggaggt cgcccctcgg    240

atctcttgaa cttggccggc ggcggtgttg ccctcccctc ttgctcttgg tcgctgccac    300

ctttccgggg catcgatcag tgagcttgta gagaagtgaa gtttagtcct ttccagccaa    360

aagttggatt tttttttttc ccttttcctc cgccatggac aaggttttga agattcgaag    420

gattccaacc attgtgtcca attaccagga gagcctcgac ttccagtccg gatgtggcaa    480

gaattgtctc gggtcgtgtt gcattcctgg agcaaaattg ccattgtatc tctttggcaa    540

accggatgtg gatgagagtg gagaagtccc taccaaggag ctgggacaaa actctttcct    600

ggattcagct attctcggtc agtgggctga taggcaagcc aagggactat ttcgctacga    660

cgttaccgcg tgcgacacaa aggtgctgcc tggaaagtat ggttttattg cgcaattgaa    720

tgaaggccga cacctgaaga aacgtcccac tgaattccgc gttgatcaag tcctccagcc    780

tttcgatgca aagaagttta acttcacaaa ggtcggtcag gaggagatga tcttttgctt    840

cgagcagagc cacgaggaca agagcttcca ccacgaacaa gctcaagtga aaggaagtcc    900

aaacgttgtg gtgatcaacg tgagcccgat cgagtatgga catgttttgc tggttcctcg    960

agttctcgat tgtatcccgc agcatctgga gacggatact ttccttttgg ctcttcatat   1020

ggctgcagag gcatccagtc catatttccg cttgggatat aatagtcttg gagctttcgc   1080

gacgatcaat catctccatt tccaggcata ttatttggga aacatcttcc ccgtggagaa   1140

ggctccacag aaattaatat acagtcacag caaaggtttc aggatttacg aactggagga   1200

ttatccagtc aagggccttg tttacgagct tggaacaagc agctttgaag agcttgcgtt   1260

ttacgtggct aaagtctgca aagctctcca aggtcgaaac atcccatata acgttctcat   1320

tgcgaacaaa ggttcacgag tattcttatt tcctcagtgc tttgcggaga aacaagcact   1380

cggccaggtt gacgtcgaga tactggaaac tcaagtcaat cccgcggtgt gggagattag   1440

cggccacatc gtgttgaagc gcaaggaaga ttacgagcga gctacagagg aatacgcatg   1500

gaagctgctg gccgaagttt ctttgactga gaaggcattt ggcgatatat cgaagctttg   1560

catcaactca gccgaggaca agtttgacga caggactcac gaaaagaacg aaaagagctc   1620

gtgttccacg gagatcacgt attatacaac tggagaaaac catattattg tggtataaga   1680

taaaagcaag aaaaaaaata aatatattag ttaggaaaat gctcaaaaaa aaaaaaaaaa   1740
```

aaaaaaaaaa aa 1752

<210> SEQ ID NO 364
<211> LENGTH: 2137
<212> TYPE: DNA
<213> ORGANISM: Nicotiana benthamiana

<400> SEQUENCE: 364
acgcgtccgt gccaattcca ttcctctaca tcttcttctt ttccttacca atccacctcc 60
aatctctttg aaatcaagtt acagaaatct tttgttcgtg taggaaattc gagaaatctt 120
agaaaaaaaa tatattattg ctgtttagaa agggtaaatc ccaggtgaac aagttgtaga 180
catcacggct atacacaaag caaaccgccg accattctta catgttcgtt cagtacgacg 240
taagggttgt gtaactgcca ccaatcctgc gccgcacggc ggacgtggcg ctttgccctc 300
tgaaggcggt agtccttccg acctcctctt ccttgccggc ggtggttctc tcctttcttc 360
tacctgctag atttacttac ttatatacct tacatagtta attccttctc cgtaaattac 420
taattgtttt gcacattagc aattattaag gttgttcttg tacctagtat ttttaccttg 480
aaaaatcaaa ggaaaaaaaa gcaaacatga tgctcaagat taagagggtt cctacacttg 540
tttccaactt ccaaaaggaa gaggctgaag aagctcttgc tcgtggtgct ggctgtggcc 600
gcaattgcct ccgaaactgc tgccttccag ggtcaaagct gccactgtat gcttccaaga 660
acttgagaaa gggcaagtct gttgccgatg aaaccaagga gcctcctgtt gacttcttgg 720
aatccctcct tcttggagaa tgggaggatc gtcagcagaa aggtctcttt cgctatgatg 780
tcactgcttg cgaaaccaag gttattcctg gagaatatgg tttcgttgct cagctgaatg 840
agggaaggca cctcaagaag aggccaactg agtttcgcgt tgataaggtg ctgcagcctt 900
ttgatggaag caagttcaac ttcactaagg ttggtcagga agagttgctc ttccagtttg 960
aagcaagtga ggacaacgaa gttcaattct ttccaaatgc acccattgat gccgagaaat 1020
ctcgaagtgt tgttgccatc aatgtcagtc ccattgagta tggacatgtg cttttgatcc 1080
ctaaggtcct tgaatgcctt ccccagagga ttgacaggga cagcctattg cttgcactgc 1140
acatggctgc cgaagcagct aacccatact tccgattggg ttataacagc ttgggtgcat 1200
ttgctaccat caaccatctt cactttcagg cctattactt ggctgtgcca ttccccattg 1260
agaaggcccc cactcggaag attacctttg ctgatgctgg agtgaagata tctgagatgc 1320
tgaattatcc agttcgagga cttgtctttg agggtggaaa tactttggag gatttcgcca 1380
atgttgtctc tggttcttgc atttgcctgc aagagaataa cattccctac aatgttctaa 1440
tctctgattc ggcaaaaagg gtattccttc tcccacagtg ctacgcagag aaacaggctc 1500
taggggaggt cagctctgaa ctgcttgata ctcaagtcaa tcctgcagta tgggagatta 1560
gtggacacat ggtcttgaag aggaaggagg attacgaggg tgcaaccgag gcaaatgcct 1620
ggaggcttct cgctgaggtc tcactttctg aagcgaggtt ccaagaagtg actgctctca 1680
tctttgaagc cattgattgc agtgttgaag agaatgagaa tgccaatgaa ggttctcctg 1740
agaagccaga tgttgcacct cagcctatgg aggaaattga tgctctcaac acccatgcta 1800
ccatggttcc cgtgtagggt tttcatggtc gagctgtggt gtttgtcctg ttgttactat 1860
ttcaactata tgaacattga gggagtttct atctatggct gcacttgtga aatatcccta 1920
aataaggcta gccatgttct atgtattgat gaagttgttt ggttcctatg tgaattgaac 1980
cttgtctttt attgcttcat attaatgtgg agttgctcag tgtcctctgg gaattgacct 2040

-continued tggatactat gtttgttgtc tgttatttaa gacaatatat ttggtaatgg aagttggagt 2100
ttccctgaaa aaaaaaaaaa aaaaaaaaaa aaaaaaa 2137

<210> SEQ ID NO 365
<211> LENGTH: 51
<212> TYPE: DNA
<213> ORGANISM: Artificial
<220> FEATURE:
<223> OTHER INFORMATION: Synthetic

<400> SEQUENCE: 365
gaggatgtta attaagcggc cgctgcagtt tttttttttt tttttttttt t 51

<210> SEQ ID NO 366
<211> LENGTH: 24
<212> TYPE: DNA
<213> ORGANISM: Artificial
<220> FEATURE:
<223> OTHER INFORMATION: Synthetic

<400> SEQUENCE: 366
gatcttaatt aagtcgacga attc 24

<210> SEQ ID NO 367
<211> LENGTH: 20
<212> TYPE: DNA
<213> ORGANISM: Artificial
<220> FEATURE:
<223> OTHER INFORMATION: Synthetic

<400> SEQUENCE: 367
gaattcgtcg acttaattaa 20

<210> SEQ ID NO 368
<211> LENGTH: 20
<212> TYPE: DNA
<213> ORGANISM: Artificial
<220> FEATURE:
<223> OTHER INFORMATION: Synthetic

<400> SEQUENCE: 368
ttaattaagt cgacgaattc 20

<210> SEQ ID NO 369
<211> LENGTH: 23
<212> TYPE: DNA
<213> ORGANISM: Artificial
<220> FEATURE:
<223> OTHER INFORMATION: Synthetic

<400> SEQUENCE: 369
attcagaatt gggtaatcac ggc 23

<210> SEQ ID NO 370
<211> LENGTH: 24
<212> TYPE: DNA
<213> ORGANISM: Artificial
<220> FEATURE:
<223> OTHER INFORMATION: Synthetic

<400> SEQUENCE: 370
caacagtagg aactcttttg atgg 24

<210> SEQ ID NO 371
<211> LENGTH: 23

<212> TYPE: DNA
<213> ORGANISM: Artificial
<220> FEATURE:
<223> OTHER INFORMATION: Synthetic

<400> SEQUENCE: 371
gaggaagaat gactacgagg acg 23

<210> SEQ ID NO 372
<211> LENGTH: 23
<212> TYPE: DNA
<213> ORGANISM: Artificial
<220> FEATURE:
<223> OTHER INFORMATION: Synthetic

<400> SEQUENCE: 372
ttcactgagc aaagtacaca tgc 23

<210> SEQ ID NO 373
<211> LENGTH: 31
<212> TYPE: DNA
<213> ORGANISM: Artificial
<220> FEATURE:
<223> OTHER INFORMATION: Synthetic

<400> SEQUENCE: 373
tagcattaat taaggttgtt cttgtaccta g 31

<210> SEQ ID NO 374
<211> LENGTH: 21
<212> TYPE: DNA
<213> ORGANISM: Artificial
<220> FEATURE:
<223> OTHER INFORMATION: Synthetic

<400> SEQUENCE: 374
aggctactgt cgccgaatcg g 21

<210> SEQ ID NO 375
<211> LENGTH: 25
<212> TYPE: DNA
<213> ORGANISM: Artificial
<220> FEATURE:
<223> OTHER INFORMATION: Synthetic

<400> SEQUENCE: 375
caccatctca gttcgtgttc ttgtc 25

<210> SEQ ID NO 376
<211> LENGTH: 23
<212> TYPE: DNA
<213> ORGANISM: Artificial
<220> FEATURE:
<223> OTHER INFORMATION: Synthetic

<400> SEQUENCE: 376
gcaccacgtg tgattacgga cac 23

<210> SEQ ID NO 377
<211> LENGTH: 30
<212> TYPE: DNA
<213> ORGANISM: Artificial
<220> FEATURE:
<223> OTHER INFORMATION: Synthetic

<400> SEQUENCE: 377

-continued

```
taaggaacca agttcggcat ttgtgaaaac                                        30


<210> SEQ ID NO 378
<211> LENGTH: 30
<212> TYPE: DNA
<213> ORGANISM: Artificial
<220> FEATURE:
<223> OTHER INFORMATION: Synthetic

<400> SEQUENCE: 378

ccccatatgc aggagcggat cattcattgt                                        30
```

NUCLEIC ACID COMPOSITIONS CONFERRING HERBICIDE RESISTANCE

FIELD OF THE INVENTION

This invention relates to nucleic acid and amino acid sequences that confer herbicide resistance in plants, as well as herbicide resistant plants, plant seeds, plant tissues and plant cells comprising such sequences.

BACKGROUND OF THE INVENTION

Weeds are the most prevalent and universally present pests encountered by modern crop producers. Approximately 10 to 30% of crop yields are lost annually to weed infestation. Therefore, weed control is one of the first concerns a grower must consider in a farming operation. Farmers have come to increasingly rely on herbicides as their primary means of weed management.

The growth regulator herbicides are the oldest class of synthetic organic herbicides. Originally discovered in the 1930's, most of the synthetic auxins are primarily useful for annual and perennial broadleaf weed control, with little effect on grasses. Essentially, there are four categories of synthetic auxin herbicides, benzoic acids, phenoxy carboxylic acids, pyridine carboxylic acids, and quinoline carboxylic acids. General symptoms of injury include epinastic growth (leaf and stem twisting, cupping, and curling), abnormal root growth, and eventually chlorosis and necrosis. By mimicking native auxins, the synthetic auxin compounds disrupt natural auxin-regulated growth processes, thereby enabling herbicidal activity. The exact mechanisms are still unknown. With inherent tolerance to many auxinic herbicides in agronomically valuable monocot species, these compounds have been and continue to be used for weed management in small grain, rice, corn, and sorghum farming. Such selective herbicides, however, may be limited in their efficacy against weeds closely related to the naturally resistant crop (e.g., red rice and drill-seeded or water-seeded rice).

In contrast, broad-spectrum ("nonselective") herbicides offer control over a wide range of weed species, but are deleterious to crop species as well. An ideal herbicidal compound can be described as having a broad spectrum of grass and broadleaf weed control, selectivity (non-harmful) to many crops, soil and foliar activity, low use rate requirements, low toxicity to mammals and other non-target organisms, novel mode of action, and low probability of natural resistance developing. Although many good quality herbicides exist, none meet all of these criteria. Thus, the development of herbicide tolerant crops (HTC) has been the focus of conventional breeding and selection efforts for over two decades. A more recent solution to this dilemma has been to develop chemicals meeting most of the criteria above, then engineer crop selectivity through introduction of a herbicide tolerance trait. Crops expressing transgenes that provide resistance to nonselective, post-emergent herbicides offer the farmer effective and simplistic weed control programs.

Crops resistant to the nonselective herbicide glyphosate have been widely adopted in agricultural production, accounting for 68% of all 75.4 million US soybean acres (51.3 million acres) and 7% of all 76.1 million US corn acres (5.3 million acres). Other herbicide tolerance traits include resistance to glufosinate, imazethapyr/imazapyr, and sethoxydim. Additionally, reports exist of resistance being developed for novel inhibitors of protoporphyrinogen oxidase (PPO). None of these herbicide resistance input traits meet all of the criteria listed above. Glyphosate and glufosinate are non-residual herbicides that must be applied multiple times within a growing season to provide adequate control. Resistant weeds represent a significant threat to the efficacy of the imidazolinone and sulfonylurea (and other ALS-inhibiting) herbicide families. Sethoxydim does not control broadleaf weeds and grassy weeds have developed resistance to this and other ACCase inhibiting herbicides. PPO-inhibiting herbicides affect heme synthesis in addition to chlorophyll synthesis, raising questions regarding toxicity to mammals.

A novel group of auxinic herbicides, 4-aminopicolinates, picloram derivatives within the pyridine carboxylic acid chemistry, has been disclosed as nonselective compounds with an excellent opportunity for developing HTC traits. These compounds are highly active (low use-rate) herbicides with soil and foliar activity. They are related to other pyridine molecules having low mammalian toxicity, so it is likely that the 4-aminopicolinates will also have low toxicity. These compounds have typical auxin symptomology; however, they also control many grasses indicating a novelty to this class of chemicals. Although resistance to some auxin analogs has been reported since their initial use in the 1940's, none represent an agronomically important pest.

Accordingly, what is needed in the art are gene sequences and polypeptide sequences whose expression in plants provides tolerance to novel, broad-spectrum herbicidal pyridine analogs, as well as traditional auxin chemistries.

SUMMARY OF THE INVENTION

This invention relates to nucleic acid and amino acid sequences that confer herbicide resistance phenotypes in plants, as well as herbicide resistant plants, plant seeds, plant tissues and plant cells comprising such sequences. In some embodiments, the present invention provides polynucleotides and polypeptides that confer herbicide resistance phenotypes when expressed in plants (for example, resistance to: auxinic herbicides, ALS-inhibitors, EPSPS-inhibitors, GS-inhibitors, PPO-inhibitors, ACCase-inhibitors, etc.). The present invention is not limited to any particular polypeptide or polynucleotide sequences that confer herbicide resistance phenotypes. Indeed, a variety of such sequences are contemplated. Accordingly, in some embodiments the present invention provides an isolated nucleic acid selected from the group consisting of SEQ ID NOs: 1-365 and nucleic acid sequences that hybridize to any thereof under conditions of low stringency, wherein expression of the isolated nucleic acid in a plant results in a herbicide resistance phenotype. The present invention is not limited to sequences that provide tolerance to any particular herbicide. Indeed, the present invention contemplates the introduction into plants of tolerance to a wide variety of herbicides, including, but not limited to, growth regulator herbicides (for example, synthetic auxin herbicides, benzoic acids, phenoxy carboxylic acids, and pyridine carboxylic acids) and broad spectrum herbicides (for example, glyphosphate, glufosinate, imazethapyr/imazapyr, and sethoxydim). In further preferred embodiments, the present invention provides vectors comprising the foregoing polynucleotide sequences. In still further embodiments, the foregoing sequences are operably linked to an exogenous promoter, most preferably a plant promoter. However, the present invention is not limited to the use of any particular promoter. Indeed, the use of a variety of promoters is contemplated, including, but not limited to, 35S and 19S of Cauliflower Mosaic virus, rice actin, ubiquitin, Cassava Vein Mosaic virus, heat shock and rubisco promoters. In some embodiments, the nucleic acid sequences of the present invention are arranged in sense orientation, while in other embodiments, the nucleic acid sequences are arranged in the vector in antisense orientation. In still further embodiments, the present invention provides a plant comprising one of the foregoing nucleic acid sequences or vectors, as well as seeds, leaves, and fruit from the plant. In some particularly preferred embodiments, the present invention provides at least one of the foregoing sequences for use in conferring herbicide tolerance or resistance in a plant.

In still other embodiments, the present invention provides processes for making a transgenic plant comprising providing a vector as described above and a plant, and transfecting the plant with the vector. In other preferred embodiments, the present invention provides processes for providing a herbicide tolerance or resistance phenotype in a plant or population of plants comprising providing a vector as described above and a plant, and transfecting the plant with the vector such that a herbicide resistant phenotype is conferred by expression of the isolated nucleic acid from the vector. In still further embodiments, the present invention provides an isolated nucleic acid selected from the group consisting of SEQ ID NOs: 1-365 and nucleic acid sequences that hybridize to any thereof under conditions of low stringency for use in producing a herbicide resistant plant. In other embodiments, the present invention provides an isolated nucleic acid, composition or vector substantially as described herein in any of the examples, figures or claims.

DESCRIPTION OF THE DRAWINGS

FIG. 1 presents the hit contig sequences corresponding to SEQ ID NOs:1-40 and 359-365.

FIG. 2 presents homologous sequences 41-358.

FIG. 3 is a table describing BLAST search results of hit sequences.

FIG. 4 is a table of BLAST search results from the Derwent amino acid database.

FIG. 5 is a table of BLAST search results from the Derwent nucleotide database.

FIG. 6 is a table summarizing herbicide resistance screen results from seedling and greenhouse evaluations of hit sequences.

FIG. 7 summarizes data from an auxin tolerance study examining cross-resistance testing of 5 hit sequences SEQ ID NOs:10, 14, 359, 360 and 361 against 5 classes of auxin compounds.

FIG. 8 summarizes results from the testing of homologs to sequences 129965 (SEQ ID NO:10) and 130213 (SEQ ID NO:14) using the greenhouse evaluation method as described in Example 9.

DEFINITIONS

Before the present proteins, nucleotide sequences, and methods are described, it should be noted that this invention is not limited to the particular methodology, protocols, cell lines, vectors, and reagents described herein as these may vary. It should also be understood that the terminology used herein is for the purpose of describing particular aspects of the invention, and is not intended to limit its scope, which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies that are reported in the publications that might be used in connection with the invention. Nothing herein is to be construed as an admission that the invention is not entitled to antedate such disclosure by virtue of prior invention.

"Acylate", as used herein, refers to the introduction of an acyl group into a molecule, (for example, acylation).

"Adjacent", as used herein, refers to a position in a nucleotide sequence immediately 5' or 3' to a defined sequence.

"Agonist", as used herein, refers to a molecule which, when bound to a polypeptide (for example, a polypeptide encoded by a nucleic acid of the present invention), increases the biological or immunological activity of the polypeptide. Agonists may include proteins, nucleic acids, carbohydrates, or any other molecules that bind to the protein.

"Alterations" in a polynucleotide (for example, a polypeptide encoded by a nucleic acid of the present invention), as used herein, comprise any deletions, insertions, and point mutations in the polynucleotide sequence. Included within this definition are alterations to the genomic DNA sequence that encodes the polypeptide.

"Amino acid sequence", as used herein, refers to an oligopeptide, peptide, polypeptide, or protein sequence, and fragments or portions thereof, and to naturally occurring or synthetic molecules. "Amino acid sequence" and like terms, such as "polypeptide" or "protein" as recited herein are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

"Antibody" refers to intact molecules as well as fragments thereof that are capable of specific binding to a epitopic determinant. Antibodies that bind a polypeptide (for example, a polypeptide encoded by a nucleic acid of the present invention) can be prepared using intact polypeptides or fragments as the immunizing antigen. These antigens may be conjugated to a carrier protein, if desired.

"Antigenic determinant", "determinant group", or "epitope of an antigenic macromolecule", as used herein, refer to any region of the macromolecule with the ability or potential to elicit, and combine with, one or more specific antibodies. Determinants exposed on the surface of the macromolecule are likely to be immunodominant, that is, more immunogenic than other (immunorecessive) determinants that are less exposed, while some (for example, those within the molecule) are non-immunogenic (immunosilent). As used herein, "antigenic determinant" refers to that portion of a molecule that makes contact with a particular antibody (for example, an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (the immunogen used to elicit the immune response) for binding to an antibody.

"Antisense", as used herein, refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, for example, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases.

"Anti-sense inhibition", as used herein, refers to a type of gene regulation based on cytoplasmic, nuclear, or organelle inhibition of gene expression due to the presence in a cell of an RNA molecule complementary to at least a portion of the mRNA being translated. It is specifically contemplated that DNA molecules may be from either an RNA virus or mRNA from the host cell genome or from a DNA virus.

"Antagonist" or "inhibitor", as used herein, refer to a molecule that, when bound to a polypeptide (for example, a polypeptide encoded by a nucleic acid of the present invention), decreases the biological or immunological activity of the polypeptide. Antagonists and inhibitors may include proteins, nucleic acids, carbohydrates, or any other molecules that bind to the polypeptide.

"Biologically active", as used herein, refers to a molecule having the structural, regulatory, or biochemical functions of a naturally occurring molecule.

"Cell culture", as used herein, refers to a proliferating mass of cells that may be in either an undifferentiated or differentiated state.

"Chimeric plasmid", as used herein, refers to any recombinant plasmid formed (by cloning techniques) from nucleic acids derived from organisms that do not normally exchange genetic information (for example, *Escherichia coli* and *Saccharomyces cerevisiae*).

"Chimeric sequence" or "chimeric gene", as used herein, refer to a nucleotide sequence derived from at least two heterologous parts. The sequence may comprise DNA or RNA.

"Coding sequence", as used herein, refers to a deoxyribonucleotide sequence that, when transcribed and translated, results in the formation of a cellular polypeptide or a ribonucleotide sequence that, when translated, results in the formation of a cellular polypeptide.

"Compatible", as used herein, refers to the capability of operating with other components of a system. A vector or plant viral nucleic acid that is compatible with a host is one that is capable of replicating in that host. A coat protein that is compatible with a viral nucleotide sequence is one capable of encapsidating that viral sequence.

"Coding region", as used herein, refers to that portion of a gene that codes for a protein. The term "non-coding region" refers to that portion of a gene that is not a coding region.

"Complementary" or "complementarity", as used herein, refer to the Watson-Crick base-pairing of two nucleic acid sequences. For example, for the sequence 5'-AGT-3' binds to the complementary sequence 3'-TCA-5'. Complementarity between two nucleic acid sequences may be "partial", in which only some of the bases bind to their complement, or it may be complete as when every base in the sequence binds to it's complementary base. The degree of complementarity between nucleic acid strands has significant effects on the efficiency and strength of hybridization between nucleic acid strands.

"Contig" refers to a nucleic acid sequence that is derived from the contiguous assembly of two or more nucleic acid sequences.

"Correlates with expression of a polynucleotide", as used herein, indicates that the detection of the presence of ribonucleic acid that is similar to a nucleic acid (for example, SEQ ID NOs:1-365) and is indicative of the presence of mRNA encoding a polypeptide (for example, a polypeptide encoded by a nucleic acid of the present invention) in a sample and thereby correlates with expression of the transcript from the polynucleotide encoding the protein.

"Deletion", as used herein, refers to a change made in either an amino acid or nucleotide sequence resulting in the absence of one or more amino acids or nucleotides, respectively.

"Encapsidation", as used herein, refers to the process during virion assembly in which nucleic acid becomes incorporated in the viral capsid or in a head/capsid precursor (for example, in certain bacteriophages).

"Exon", as used herein, refers to a polynucleotide sequence in a nucleic acid that encodes information for protein synthesis and that is copied and spliced together with other such sequences to form messenger RNA.

"Expression", as used herein, is meant to incorporate transcription, reverse transcription, and translation.

"Expressed sequence tag (EST)" as used herein, refers to relatively short single-pass DNA sequences obtained from one or more ends of cDNA clones and RNA derived therefrom. They may be present in either the 5' or the 3' orientation. ESTs have been shown to be useful for identifying particular genes.

"Industrial crop", as used herein, refers to crops grown primarily for consumption by humans or animals or use in industrial processes (for example, as a source of fatty acids for manufacturing or sugars for producing alcohol). It will be understood that either the plant or a product produced from the plant (for example, sweeteners, oil, flour, or meal) can be consumed. Examples of food crops include, but are not limited to, corn, soybean, rice, wheat, oilseed rape, cotton, oats, barley, and potato plants.

"Foreign gene", as used herein, refers to any sequence that is not native to the organism.

"Fusion protein", as used herein, refers to a protein containing amino acid sequences from each of two distinct proteins; it is formed by the expression of a recombinant gene in which two coding sequences have been joined together such that their reading frames are in phase. Hybrid genes of this type may be constructed in vitro in order to label the product of a particular gene with a protein that can be more readily assayed (for example, a gene fused with lacZ in *E. coli* to obtain a fusion protein with β-galactosidase activity). As a non-limiting second example, a fusion protein may comprise a protein linked to a signal peptide to allow its secretion by the cell. The products of certain viral oncogenes are fusion proteins.

"Gene", as used herein, refers to a discrete nucleic acid sequence responsible for a discrete cellular product. The term "gene", as used herein, refers not only to the nucleotide sequence encoding a specific protein, but also to any adjacent 5' and 3' non-coding nucleotide sequence involved in the regulation of expression of the protein encoded by the gene of interest. These non-coding sequences include terminator sequences, promoter sequences, upstream activator sequences, regulatory protein binding sequences, and the like. These non-coding sequence gene regions may be readily identified by comparison with previously identified eukaryotic non-coding sequence gene regions. Furthermore, the person of average skill in the art of molecular biology is able to identify the nucleotide sequences forming the non-coding regions of a gene using well-known techniques such as a site-directed mutagenesis, sequential deletion, promoter probe vectors, and the like.

"Growth cycle", as used herein, is meant to include the replication of a nucleus, an organelle, a cell, or an organism.

The term "heterologous gene", as used herein, means a gene encoding a protein, polypeptide, RNA, or a portion of any thereof, whose exact amino acid sequence is not normally found in the host cell, but is introduced by standard gene transfer techniques.

"Host", as used herein, refers to a cell, tissue or organism capable of replicating a vector or plant viral nucleic acid and that is capable of being infected by a virus containing the viral vector or plant viral nucleic acid. This term is intended to include prokaryotic and eukaryotic cells, organs, tissues or organisms, where appropriate.

The term "homolog" as in a "homolog" of a given nucleic acid sequence, refers to a nucleic acid sequence (for example, a nucleic acid sequence from another organism), that shares a given degree of "homology" with the nucleic acid sequence.

"Homology" refers to a degree of complementarity. There may be partial homology or complete homology (identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (the hybridization) of a completely homologous sequence to a target under conditions of low stringency. This is not to say that conditions of low stringency are such that non-specific binding is permitted; low stringency conditions require that the binding of two sequences to one another be a specific (selective) interaction. The absence of non-specific binding may be tested by the use of a second target that lacks even a partial degree of complementarity (for example, less than about 30% identity); in the absence of non-specific binding the probe will not hybridize to the second non-complementary target.

Numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, conditions that promote hybridization under conditions of high stringency (for example, increasing the temperature of the hybridization and/or wash steps, the use of formamide in the hybridization solution, etc.) are readily apparent to one skilled in the art.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity, they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (it is the complement of) the single-stranded nucleic acid sequence under conditions of low stringency as described above.

The term "hybridization" is used in reference to the pairing of complementary nucleic acids. Hybridization and the strength of hybridization (for example, the strength of the association between the nucleic acids) is impacted by such factors as the degree of complementary between the nucleic acids, stringency of the conditions involved, the melting temperature ($T_m$) of the formed hybrid, and the G:C ratio within the nucleic acids.

"Hybridization complex", as used herein, refers to a complex formed between nucleic acid strands by virtue of hydrogen bonding, stacking or other non-covalent interactions between bases. A hybridization complex may be formed in solution or between nucleic acid sequences present in solution and nucleic acid sequences immobilized on a solid support (for example, membranes, filters, chips, pins or glass slides to which cells have been fixed for in situ hybridization).

"Immunologically active" refers to the capability of a natural, recombinant, or synthetic polypeptide, or any oligopeptide thereof, to bind with specific antibodies and induce a specific immune response in appropriate animals or cells.

"Induction" and the terms "induce", "induction" and "inducible", as used herein, refer generally to a gene and a promoter operably linked thereto which is in some manner dependent upon an external stimulus, such as a molecule, in order to actively transcribed and/or translate the gene.

"Infection", as used herein, refers to the ability of a virus to transfer its nucleic acid to a host or introduce viral nucleic acid into a host, wherein the viral nucleic acid is replicated, viral proteins are synthesized, and new viral particles assembled. In this context, the terms "transmissible" and "infective" are used interchangeably herein.

"Insertion" or "addition", as used herein, refers to the replacement or addition of one or more nucleotides or amino acids, to a nucleotide or amino acid sequence, respectively.

"In cis", as used herein, indicates that two sequences are positioned on the same strand of RNA or DNA.

"In trans", as used herein, indicates that two sequences are positioned on different strands of RNA or DNA.

"Intron", as used herein, refers to a polynucleotide sequence in a nucleic acid that does not encode information for protein synthesis and is removed before translation of messenger RNA.

"Isolated", as used herein, refers to a polypeptide or polynucleotide molecule separated not only from other peptides, DNAs, or RNAs, respectively, that are present in the natural source of the macromolecule. "Isolated" and "purified" do not encompass either natural materials in their native state or natural materials that have been separated into components (for example, in an acrylamide gel) but not obtained either as pure substances or as solutions.

"Kinase", as used herein, refers to an enzyme (for example, hexokinase and pyruvate kinase) that catalyzes the transfer of a phosphate group from one substrate (commonly ATP) to another.

"Marker" or "genetic marker", as used herein, refer to a genetic locus that is associated with a particular, usually readily detectable, genotype or phenotypic characteristic (for example, an antibiotic resistance gene).

"Metabolome", as used herein, indicates the complement of relatively low molecular weight molecules that is present in a plant, plant part, or plant sample, or in a suspension or extract thereof. Examples of such molecules include, but are not limited to: acids and related compounds; mono-, di-,and tri-carboxylic acids (saturated, unsaturated, aliphatic and cyclic, aryl, alkaryl); aldo-acids, keto-acids; lactone forms; gibberellins; abscisic acid; alcohols, polyols, derivatives, and related compounds; ethyl alcohol, benzyl alcohol, methanol; propylene glycol, glycerol, phytol; inositol, furfuryl alcohol, menthol; aldehydes, ketones, quinones, derivatives, and related compounds; acetaldehyde, butyraldehyde, benzaldehyde, acrolein, furfural, glyoxal; acetone, butanone; anthraquinone; carbohydrates; mono-, di-, tri-saccharides; alkaloids, amines, and other bases; pyridines (including nicotinic acid, nicotinamide); pyrimidines (including cytidine, thymine); purines (including guanine, adenine, xanthines/hypoxanthines, kinetin); pyrroles; quinolines (including isoquinolines); morphinans, tropanes, cinchonans; nucleotides, oligonucleotides, derivatives, and related compounds; guano sine, cytosine, adeno sine, thymidine, inosine; amino acids, oligopeptides, derivatives, and related compounds; esters; phenols and related compounds; heterocyclic compounds and derivatives; pyrroles, tetrapyrroles (corrinoids and porphines/porphyrins, w/w/o metal-ion); flavonoids; indoles; lipids (including fatty acids and triglycerides), derivatives, and related compounds; carotenoids, phytoene; and sterols, isoprenoids including terpenes.

"Modulate", as used herein, refers to a change or an alteration in the biological activity of a polypeptide (for example, a polypeptide encoded by a nucleic acid of the present invention). Modulation may be an increase or a decrease in protein activity, a change in binding characteristics, or any other change in the biological, functional or immunological properties of the polypeptide.

"Movement protein", as used herein, refers to a noncapsid protein required for cell to cell movement of replicons or viruses in plants.

"Multigene family", as used herein, refers to a set of genes descended by duplication and variation from some ancestral gene. Such genes may be clustered together on the same chromosome or dispersed on different chromosomes. Examples of multigene families include those which encode the histones, hemoglobins, immunoglobulins, histocompatibility antigens, actins, tubulins, keratins, collagens, heat shock proteins, salivary glue proteins, chorion proteins, cuticle proteins, yolk proteins, and phaseolins.

"Nucleic acid sequence", as used herein, refers to a polymer of nucleotides in which the 3' position of one nucleotide sugar is linked to the 5' position of the next by a phosphodiester bridge. In a linear nucleic acid strand, one end typically has a free 5' phosphate group, the other a free 3' hydroxyl group. Nucleic acid sequences may be used herein to refer to oligonucleotides, or polynucleotides, and fragments or portions thereof, and to DNA or RNA of genomic or synthetic origin that may be single- or double-stranded, and represent the sense or antisense strand.

"Polypeptide", as used herein, refers to an amino acid sequence obtained from any species and from any source whether natural, synthetic, semi-synthetic, or recombinant.

"Oil-producing species," as used herein, refers to plant species that produce and store triacylglycerol in specific organs, primarily in seeds. Such species include soybean (*Glycine nizax*), rapeseed and canola (including *Brassica napus, Brassica rapa* and *Brassica campestris*), sunflower (*Helianthus annus*), cotton (*Gossypium hirsutum*), corn (*Zea mays*), cocoa (*Theobroina cacao*), safflower (*Carthamus tinctorius*), oil palm (*Elaeis guineensis*), coconut palm (*Cocos nucifera*), flax (*Linum usitatissimuin*), castor (*Ricinus commiunis*) and peanut (*Arachis hypogaea*). The group also includes non-agronomic species that are useful in developing appropriate expression vectors such as tobacco, rapid cycling *Brassica* species, and *Arabidopsis thaliana*, and wild species that may be a source of unique fatty acids.

"Operably linked" refers to a juxtaposition of components, particularly nucleotide sequences, such that the normal function of the components can be performed. Thus, a coding sequence that is operably linked to regulatory sequences refers to a configuration of nucleotide sequences wherein the coding sequences can be expressed under the regulatory control, that is, transcriptional and/or translational control, of the regulatory sequences.

"Origin of assembly", as used herein, refers to a sequence where self-assembly of the viral RNA and the viral capsid protein initiates to form virions.

"Ortholog" refers to genes that have evolved from an ancestral locus.

"Overexpression" refers to the production of a gene product in transgenic organisms that exceeds levels of production in normal or non-transformed organisms.

"Cosuppression" refers to the expression of a foreign gene that has substantial homology to an endogenous gene resulting in the suppression of expression of both the foreign and the endogenous gene. As used herein, the term "altered levels" refers to the production of gene product(s) in transgenic organisms in amounts or portions that differ from that of normal or non-transformed organisms.

"Phenotype" or "phenotypic trait(s)", as used herein, refers to an observable property or set of properties resulting from the expression of a gene. "Visual phenotype", as used herein, refers to a plant displaying a symptom or group of symptoms that meet defined criteria. "Herbicide resistance phenotype" and "herbicide tolerance phenotype", as used herein, refers to a phenotype where substantial resistance or tolerance to any herbicide is displayed (for example, by an inherently sensitive species) upon challenge with a herbicide.

"Plant", as used herein, refers to any plant and progeny thereof. The term also includes parts of plants, including seed, cuttings, tubers, fruit, flowers, etc. In a preferred embodiment, "plant" refers to cultivated plant species, such as corn, cotton, canola, sunflower, soybeans, sorghum, alfalfa, wheat, rice, plants producing fruits and vegetables, and turf and ornamental plant species.

"Plant cell", as used herein, refers to the structural and physiological unit of plants, consisting of a protoplast and the cell wall.

"Plant organ", as used herein, refers to a distinct and visibly differentiated part of a plant, such as root, stem, leaf or embryo.

"Plant tissue", as used herein, refers to any tissue of a plant in planta or in culture. This term is intended to include a whole plant, plant cell, plant organ, protoplast, cell culture, or any group of plant cells organized into a structural and functional unit.

"Portion", as used herein, with regard to a protein ("a portion of a given protein") refers to fragments of that protein. The fragments may range in size from four amino acid residues to the entire amino acid sequence minus one amino acid (10 nucleotides, 20, 30, 40, 50, 100, 200, etc.). A "portion" is preferably at least 25 nucleotides, more preferably at least 50 nucleotides, and even more preferably at least 100 nucleotides.

"Positive-sense inhibition", as used herein, refers to a type of gene regulation based on cytoplasmic inhibition of gene expression due to the presence in a cell of an RNA molecule substantially homologous to at least a portion of the "mRNA being translated.

"Production cell", as used herein, refers to a cell, tissue or organism capable of replicating a vector or a viral vector, but which is not necessarily a host to the virus. This term is intended to include prokaryotic and eukaryotic cells, organs, tissues or organisms, such as bacteria, yeast, fungus, and plant tissue.

"Progeny" of a particular plant, as used herein, refers to any descendents of the plant containing all or part of the plant's DNA.

"Promoter", as used herein, refers to the 5'-flanking, non-coding sequence adjacent a coding sequence that is involved in the initiation of transcription of the coding sequence.

"Protoplast", as used herein, refers to an isolated plant cell without cell walls, having the potency for regeneration into cell culture or a whole plant.

"Purified", as used herein, when referring to a peptide or nucleotide sequence, indicates that the molecule is present in the substantial absence of other biological macromolecular, for example, polypeptides, polynucleic acids, and the like of the same type. The term "purified" as used herein preferably means at least 95% by weight, more preferably at least 99.8% by weight, of biological macromolecules of the same type present (but water, buffers, and other small molecules, especially molecules having a molecular weight of less than 1000 can be present).

"Pure", as used herein, preferably has the same numerical limits as "purified" immediately above. "Substantially purified", as used herein, refers to nucleic or amino acid sequences that are removed from their natural environment, isolated or separated, and are at least 60% free, preferably 75% free, and most preferably 90% free from other components with which they are naturally associated.

"Recombinant plant viral nucleic acid", as used herein, refers to a plant viral nucleic acid that has been modified to contain non-native nucleic acid sequences. These non-native nucleic acid sequences may be from any organism or purely synthetic, however, they may also include nucleic acid sequences naturally occurring in the organism into which the recombinant plant viral nucleic acid is to be introduced.

"Recombinant plant virus", as used herein, refers to a plant virus containing a recombinant plant viral nucleic acid.

"Regulatory region" or "regulatory sequence", as used herein, in reference to a specific gene refers to the non-coding nucleotide sequences within that gene that are necessary or sufficient to provide for the regulated expression of the coding region of a gene. Thus the term regulatory region includes promoter sequences, regulatory protein binding sites, upstream activator sequences, and the like. Specific nucleotides within a regulatory region may serve multiple functions. For example, a specific nucleotide may be part of a promoter and participate in the binding of a transcriptional activator protein.

"Replication origin", as used herein, refers to the minimal terminal sequences in linear viruses that are necessary for viral replication.

"Replicon", as used herein, refers to an arrangement of RNA sequences generated by transcription of a transgene that is integrated into the host DNA that is capable of replication in the presence of a helper virus. A replicon may require sequences in addition to the replication origins for efficient replication and stability.

"Sample", as used herein, is used in its broadest sense. A biological sample suspected of containing nucleic acid encoding a polypeptide (for example, a polypeptide encoded by a nucleic acid of the present invention) or fragments thereof may comprise a tissue, a cell, an extract from cells, chromosomes isolated from a cell (for example, a spread of metaphase chromosomes), genomic DNA (in solution or bound to a solid support such as for Southern analysis), RNA (in solution or bound to a solid support such as for northern analysis), cDNA (in solution or bound to a solid support), and the like.

"Silent mutation", as used herein, refers to a mutation that has no apparent effect on the phenotype of the organism.

"Site-directed mutagenesis", as used herein, refers to the in vitro induction of mutagenesis at a specific site in a given target nucleic acid molecule.

"Subgenomic promoter", as used herein, refers to a promoter of a subgenomic mRNA of a viral nucleic acid.

"Specific binding" or "specifically binding", as used herein, in reference to the interaction of an antibody and a protein or peptide, mean that the interaction is dependent upon the presence of a particular structure (the antigenic determinant or epitope) on the protein; in other words, the antibody is recognizing and binding to a specific protein structure rather than to proteins in general.

"$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See for example, Anderson and Young, Quantitative Filter Hybridization, in *Nucleic Acid Hybridization* [1985]). Other references include more sophisticated computations that take structural as well as sequence characteristics into account for the calculation of $T_m$.

"Stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (for example, hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (for example, hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/1 NaCl, 6.9 g/l $NaH_2PO_4$ $H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 μg/ml denatured salmon sperm DNA followed by washing in a solution comprising 5×SSPE, 0.1 % SDS at 42° C. when a probe of about 500 nucleotides in length is employed.

"Substitution", as used herein, refers to a change made in an amino acid of nucleotide sequence that results in the replacement of one or more amino acids or nucleotides by different amino acids or nucleotides, respectively.

"Symptom", as used herein refers to a visual condition resulting from the action of the GENEWARE® vector or the clone insert.

"Systemic infection", as used herein, denotes infection throughout a substantial part of an organism including mechanisms of spread other than mere direct cell inoculation but rather including transport from one infected cell to additional cells either nearby or distant.

"Transcription", as used herein, refers to the production of an RNA molecule by RNA polymerase as a complementary copy of a DNA sequence.

"Transcription termination region", as used herein, refers to the sequence that controls formation of the 3' end of the transcript. Self-cleaving ribozymes and polyadenylation sequences are examples of transcription termination sequences.

"Transformation", as used herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

"Transfection", as used herein, refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transfection may, for example, result in cells in which the inserted nucleic acid is capable of replication either as an autonomously replicating molecule or as part of the host chromosome, or cells that transiently express the inserted nucleic acid for limited periods of time.

"Transposon", as used herein, refers to a nucleotide sequence such as a DNA or RNA sequence that is capable of transferring location or moving within a gene, a chromosome or a genome.

"Transgenic plant", as used herein, refers to a plant that contains a foreign nucleotide sequence inserted into either its nuclear genome or organellar genome.

"Transgene", as used herein, refers to a nucleic acid sequence that is inserted into a host cell or host cells by a transformation technique.

"Variants" of a polypeptide (for example, a polypeptide encoded by a nucleic acid of the present invention), as used herein, refers to a sequence resulting when a polypeptide is altered by one or more amino acids. The variant may have "conservative" changes, wherein a substituted amino acid has similar structural or chemical properties, for example, replacement of leucine with isoleucine. More rarely, a variant may have "nonconservative" changes, for example, replacement of a glycine with a tryptophan. Variants may also include sequences with amino acid deletions or insertions, or both. Guidance in determining which amino acid residues may be substituted, inserted, or deleted without abolishing biological or immunological activity may be found using computer programs well known in the art.

"Vector", as used herein, refers to a DNA and/or RNA molecule, typically a plasmid containing an origin of replication, that transfers a nucleic acid segment between cells.

"Virion", as used herein, refers to a particle composed of viral RNA and viral capsid protein.

"Virus", as used herein, refers to an infectious agent composed of a nucleic acid encapsidated in a protein. A virus may be a mono-, di-, tri- or multi-partite virus.

DESCRIPTION OF THE INVENTION

I. Identification of Nucleotide and Amino Acid Sequences

The invention is based on the discovery of deoxyribonucleic acid (DNA) and amino acid sequences that confer herbicide resistance and/or tolerance when expressed in plants. In particular, the present invention encompasses the nucleic acid sequences encoded by SEQ ID NOs:1-365 and variants and portions thereof. Some of these sequences are contiguous sequences prepared from a database of 5' single pass sequences and are thus referred to as contig sequences, while others are full-length sequences determined by standard sequencing protocols.

Nucleic acids of the present invention were identified in clones generated from a variety of cDNA libraries. The cDNA libraries were constructed in the GENEWARE® vector. The GENEWARE® vector is described in U.S. application Ser. No. 09/008,186 (incorporated herein by reference). Each of the complete set of clones from the GENEWARE® library were used to prepare an infectious viral unit. An infectious unit corresponding to each clone was used to inoculate *Nicotiana benthamiana* (a dicotyledonous plant). The plants were grown under identical conditions, challenged by herbicide application, and a phenotypic analysis of each plant was carried out. The herbicide resistance phenotype was observed in the plants that had been infected by an infectious unit created from the nucleic acids of the present invention.

Following the identification of the herbicide resistance or tolerance phenotype in plant samples, further analyses of the sequences were carried out. In particular, the nucleotide sequences of the present invention were analyzed using bioinformatics methods as described below.

II. Bioinformatics Methods

A. Phred, Phrap and Consed

Phred, Phrap and Consed are a set of programs that read DNA sequencer traces, make base calls, assemble the shotgun DNA sequence data and analyze the sequence regions that are likely to contribute to errors. Phred is the initial program used to read the sequencer trace data, call the bases and assign quality values to the bases. Phred uses a Fourier-based method to examine the base traces generated by the sequencer. The output files from Phred are written in FASTA, phd or scf format. Phrap is used to assemble contiguous sequences from only the highest quality portion of the sequence data output by Phred. Phrap is amenable to high-throughput data collection. Finally, Consed is used as a finishing tool to assign error probabilities to the sequence data. Detailed description of the Phred, Phrap and Consed software and its use can be found in the following references: Ewing et al., Genome Res., 8:175 [1998]; Ewing and Green, Genome Res. 8:186 [1998]; Gordon et al., Genome Res. 8: 195 [1998].

B. BLAST

The BLAST (Basic Local Alignment Search Tool) set of programs may be used to compare the large numbers of sequences and obtain homologies to known protein families. These homologies provide information regarding the function of newly sequenced genes. Detailed descriptions of the BLAST software and its uses can be found in the following references Altschul et al., J. Mol. Biol., 215:403 [1990]; Altschul, J. Mol. Biol. 219:555 [1991].

Generally, BLAST performs sequence similarity searching and is divided into 5 basic subroutines: (1) BLASTP compares an amino acid sequence to a protein sequence database; (2) BLASTN compares a nucleotide sequence to a nucleic acid sequence database; (3) BLASTX compares translated protein sequences done in 6 frames to a protein sequence database; (4) TBLASTN compares a protein sequence to a nucleotide sequence database that is translated into all 6 reading frames; (5) TBLASTX compares the 6 frame translated protein sequence to the 6-frame translation of a nucleotide sequence database. Subroutines (3)-(5) may be used to identify weak similarities in nucleic acid sequence.

The BLAST program is based on the High Segment Pair (HSP), two sequence fragments of arbitrary but equal length whose alignment is locally maximized and whose alignment meets or exceeds a cutoff threshold. BLAST determines multiple HSP sets statistically using sum statistics. The score of the HSP is then related to its expected chance of frequency of occurrence, E. The value, E, is dependent on several factors such as the scoring system, residue composition of sequences, length of query sequence and total length of database. In the output file will be listed these E values, typically in a histogram format, which are useful in determining levels of statistical significance at the user's predefined expectation threshold. Finally, the Smallest Sum Probability, P(N), is the probability of observing the shown matched sequences by chance alone and is typically in the range of 0-1.

BLAST measures sequence similarity using a matrix of similarity scores for all possible pairs of residues and these specify scores for aligning pairs of amino acids. The matrix of choice for a specific use depends on several factors: the length of the query sequence and whether or not a close or distant relationship between sequences is suspected. Several matrices are available including PAM40, PAM120, PAM250, BLOSUM 62 and BLOSUM 50. Altschul et al. (1990) found PAM120 to be the most broadly sensitive matrix (for example point accepted mutation matrix per 100 residues). However, in some cases the PAM120 matrix may not find short but strong or long but weak similarities between sequences. In these cases, pairs of PAM matrices may be used, such as PAM40 and PAM 250, and the results compared. Typically, PAM 40 is used for database searching with a query of 9-21 residues long, while PAM 250 is used for lengths of 47-123.

The BLOSUM (Blocks Substitution Matrix) series of matrices are constructed based on percent identity between two sequence segments of interest. Thus, the BLOSUM62 matrix is based on a matrix of sequence segments in which the members are less than 62% identical. BLOSUTM62 shows very good performance for BLAST searching. However, other BLOSUM matrices, like the PAM matrices, may be useful in other applications. For example, BLOSUM45 is particularly strong in profile searching.

C. FASTA

The FASTA suite of programs permits the evaluation of DNA and protein similarity based on local sequence alignment. The FASTA search algorithm utilizes Smith/Waterma- and Needleman/Wunsch-based optimization methods. These algorithms consider all of the alignment possibilities between the query sequence and the library in the highest scoring sequence regions. The search algorithm proceeds in four basic steps:

1. The identities or pairs of identities between the two DNA or protein sequences are determined. The ktup parameter, as set by the user, is operative and determines how many consecutive sequence identities are required to indicate a match.
2. The regions identified in step 1 are re-scored using a PAM or BLOSUM matrix. This allows conservative replacements and runs of identities shorter than that specified by ktup to contribute to the similarity score.
3. The region with the single best scoring initial region is used to characterize pairwise similarity and these scores are used to rank the library sequences.
4. The highest scoring library sequences are aligned using the Smith-Waterman algorithm. This final comparison takes into account the possible alignments of the query and library sequence in the highest scoring region.

Further detailed description of the FASTA software and its use can be found in the following reference: Pearson and Lipman, Proc. Natl. Acad. Sci., 85: 2444 [1988].

D. Pfam

Despite the large number of different protein sequences determined through genomics-based approaches, relatively few structural and functional domains are known. Pfam is a computational method that utilizes a collection of multiple alignments and profile hidden Markov models of protein domain families to classify existing and newly found protein sequences into structural families. Detailed descriptions of the Pfam software and its uses can be found in the following references: Sonhammer et al., Proteins: Structure, Function and Genetics, 28:405 [1997]; Sonhammer et al., Nucleic Acids Res., 26:320 [1998]; Bateman et al., Nucleic Acids Res., 27: 260 [1999].

Pfam 3.1, the latest version, includes 54% of proteins in SWISS_PROT and SP-TrEMBL-5 as a match to the database and includes expectation values for matches. Pfam consists of parts A and B. Pfam-A contains a hidden Markov model and includes curated families. Pfam-B uses the Domainer program to cluster sequence segments not included in Pfam-A. Domainer uses pairwise homology data from Blastp to construct aligned families.

Alternative protein family databases that may be used include PRINTS and BLOCKS, which both are based on a set of ungapped blocks of aligned residues. However, these programs typically contain short conserved regions whereas Pfam represents a library of complete domains that facilitates automated annotation. Comparisons of Pfam profiles may also be performed using genomic and EST data with the programs, Genewise and ESTwise, respectively. Both of these programs allow for introns and frame shifting errors.

E. BLOCKS

The determination of sequence relationships between unknown sequences and those that have been categorized can be problematic because background noise increases with the number of sequences, especially at a low level of similarity detection. One recent approach to this problem has been tested that efficiently detects and confirms weak or distant relationships among protein sequences based on a database of blocks. The BLOCKS database provides multiple alignments of sequences and contains blocks or protein motifs found in known families of proteins.

Other programs such as PRINTS and Prodom also provide alignments, however, the BLOCKS database differs in the manner in which the database was constructed. Construction of the BLOCKS database proceeds as follows: one starts with a group of sequences that presumably have one or motifs in common, such as those from the PROSITE database. The PROTOMAT program then uses a motif finding program to scan sequences for similarity looking for spaced triplets of amino acids. The located blocks are then entered into the MOTOMAT program for block assembly. Weights are computed for all sequences. Following construction of a BLOCKS database one can use BLIMPS to performs searches of the BLOCKS database. Detailed description of the construction and use of a BLOCKS database can be found in the following references: Henikoff, S. and Henikoff, J. G., Genomics, 19:97 [1994]; Henikoff, J. G. and Henikoff, S., Meth. Enz., 266:88 [1996].

F. PRINTS

The PRINTS database of protein family fingerprints can be used in addition to BLOCKS and PROSITE. These databases are considered to be secondary databases because they diagnose the relationship between sequences that yield function information. Presently, however, it is not recommended that these databases be used alone. Rather, it is strongly suggested that these pattern databases be used in conjunction with each other so that a direct comparison of results can be made to analyze their robustness.

Generally, these programs utilize pattern recognition to discover motifs within protein sequences. However, PRINTS goes one step further, it takes into account not simply single motifs but several motifs simultaneously that might characterize a family signature. Other programs, such as PROSITE, rely on pattern recognition but are limited by the fact that query sequences must match them exactly. Thus, sequences that vary slightly will be missed. In contrast, the PRINTS database fingerprinting approach is capable of identifying distant relatives due to its reliance on the fact that sequences do not have match the query exactly. Instead they are scored according to how well they fit each motif in the signature. Another advantage of PRINTS is that it allows the user to search both PRINTS and PROSITE simultaneously. A detailed description of the use of PRINTS can be found in the following reference: Attwood et al., Nucleic Acids Res. 25: 212 [1997].

III. Nucleic Acid Sequences, Including Related, Variant, Altered and Extended Sequences This invention encompasses nucleic acids, polypeptides encoded by the nucleic acid sequences, and variants that retain at least one biological or other functional activity of the polynucleotide or polypeptide of interest. A preferred polynucleotide variant is one having at least 80%, and more preferably 90%, sequence identity to the sequence of interest. A most preferred polynucleotide variant is one having at least 95% sequence identity to the polynucleotide of interest.

In particularly preferred embodiments, the invention encompasses the polynucleotides comprising a polynucleotide encoded by SEQ ID NOs:1-40 and 359-365. In particularly preferred embodiments, the nucleic acids are operably linked to an exogenous promoter (and in most preferred embodiments to a plant promoter) or present in a vector.

It will be appreciated by those skilled in the art that as a result of the degeneracy of the genetic code, a multitude of nucleotide sequences encoding a given polypeptide (for example, a polypeptide encoded by a nucleic acid of the present invention), some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of the naturally occurring polypeptide, and all such variations are to be considered as being specifically disclosed.

Although nucleotide sequences that encode a given polypeptide (for example, a polypeptide encoded by a nucleic acid of the present invention) and its variants are preferably capable of hybridizing to the nucleotide sequence of the naturally occurring polypeptide under appropriately selected conditions of stringency, it may be advantageous to produce nucleotide sequences encoding the polypeptide or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding a polypeptide and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, that encode a polynucleotide and its variants, entirely by synthetic chemistry. After production, the synthetic sequence may be inserted into any of the many available expression vectors and cell systems using reagents that are well known in the art. Moreover, synthetic chemistry may be used to introduce mutations into a sequence encoding a polynucleotide of the present invention or any portion thereof.

Also encompassed by the invention are polynucleotide sequences that are capable of hybridizing to SEQ ID NOs:1-40 and 359-365 under various conditions of stringency (for example, conditions ranging from low to high stringency). Hybridization conditions are based on the melting temperature $T_m$ of the nucleic acid binding complex or probe, as taught in Wahl and Berger, Methods Enzymol., 152:399 [1987] and Kimmel, Methods Enzymol., 152:507 [1987], and may be used at a defined stringency.

Altered nucleic acid sequences encoding a polynucleotide of the present invention include deletions, insertions, or substitutions of different nucleotides resulting in a polynucleotide that encodes the same polypeptide or a functionally equivalent polynucleotide or polypeptide. The encoded protein may also contain deletions, insertions, or substitutions of amino acid residues that produce a silent change and result in a functionally equivalent polypeptide. Deliberate amino acid substitutions may be made on the basis of similarity in polarity, charge, solubility, hydrophobicity, hydrophilicity, and/or the amphipathic nature of the residues as long as the biological activity of the polypeptide is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding polypeptides. As used herein, an "allele" or "allelic sequence" is an alternative form of the gene that may result from at least one mutation in the nucleic acid sequence. Alleles may result in altered mRNAs or polypeptides whose structure or function may or may not be altered. Any given gene may have none, one, or many allelic forms. Common mutational changes that give rise to alleles are generally ascribed to natural deletions, additions, or substitutions of nucleotides. Each of these types of changes may occur alone, or in combination with the others, one or more times in a given sequence.

Methods for DNA sequencing that are well known and generally available in the art may be used to practice any embodiments of the invention. The methods may employ such enzymes as the Kienow fragment of DNA polymerase I, SEQUENASE (US Biochemical Corporation, Cleveland, Ohio), TAQ polymerase (U.S. Biochemical Corporation, Cleveland, Ohio), thermostable T7 polymerase (Amersham Pharmacia Biotech, Chicago, Ill.), or combinations of recombinant polymerases and proofreading exonucleases such as the ELONGASE amplification system (Life Technologies, Rockville, Md.). Preferably, the process is automated with machines such as the MICROLAB 2200 (Hamilton Company, Reno, Nev.), PTC200 DNA Engine thermal cycler (MJ Research, Watertown, Mass.) and the ABI 377 DNA sequencer (Perkin Elmer).

The nucleic acid sequences encoding a polynucleotide of the present invention may be extended utilizing a partial nucleotide sequence and employing various methods known in the art to detect upstream sequences such as promoters and regulatory elements. For example, one method that may be employed, "restriction-site" PCR, uses universal primers to retrieve an unknown sequence adjacent to a known locus (Sarkar, PCR Methods Applic. 2:318 [1993]). In particular, genomic DNA is first amplified in the presence of primer to linker sequence and a primer specific to the known region. The amplified sequences are then subjected to a second round of PCR with the same linker primer and another specific primer internal to the-first one. Products of each round of PCR are transcribed with an appropriate RNA polymerase and sequenced using reverse transcriptase.

Inverse PCR may also be used to amplify or extend sequences using divergent primers based on a known region (Triglia et al., Nucleic Acids Res. 16:8186 [1988]). The primers may be designed using OLIGO 4.06 primer analysis software (National Biosciences Inc., Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method that may be used is capture PCR that involves PCR amplification of DNA fragments adjacent to a known sequence in human and yeast artificial chromosome DNA (Lagerstrom et al., PCR Methods Applic. 1:111 [1991]). In this method, multiple restriction enzyme digestions and ligations may also be used to place an engineered double-stranded sequence into an unknown portion of the DNA molecule before performing PCR.

Another method that may be used to retrieve unknown sequences is that of Parker et al., Nucleic Acids Res., 19:3055 [1991]. Additionally, one may use PCR, nested primers, and PROMOTERFINDER DNA Walking Kits libraries (Clontech, Palo Alto, Calif.) to walk in genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems that are commercially available (for example, from PE Biosystems, Inc., Foster City, Calif.) may be used to analyze the size or confirm the nucleotide sequence of sequencing or PCR products. In particular, capillary sequencing may employ flowable polymers for electrophoretic separation, four different fluorescent dyes (one for each nucleotide) that are laser activated, and detection of the emitted wavelengths by a charge coupled device camera. Output/light intensity may be converted to electrical signal using appropriate software (for example, GENOTYPER and SEQUENCE NAVIGATOR from PE Biosystems, Foster City, Calif.) and the entire process from loading of samples to computer analysis and electronic data display may be computer controlled. Capillary electrophoresis is especially preferable for the sequencing of small pieces of DNA that might be present in limited amounts in a particular sample.

It is contemplated that the nucleic acids disclosed herein can be utilized as starting nucleic acids for directed evolution. In some embodiments, artificial evolution is performed by random mutagenesis (for example, by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 [1996]; Leung et al., Technique, 1:11-15 [1989]; Eckert and Kunkel, PCR Methods Appl., 1:17-24 [1991]; Caldwell and Joyce, PCR Methods Appl., 2:28-33 (1992); and Zhao and Arnold, Nuc. Acids. Res., 25:1307-08 [1997]). After mutagenesis, the resulting clones are selected for desirable activity. Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (for example, Smith, Nature, 370: 324-25 [1994]; U.S. Pat. Nos. 5,837,458; 5,830,721; 5,811,238; and 5,733,731, each of which is herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398-91 [1994]; Stemmer, Proc. Natl. Acad. Sci. USA, 91, 10747-51 [1994]; Crameri et al., Nat. Biotech., 14:315-19 [1996]; Zhang et al., Proc. Natl. Acad. Sci. USA, 94:4504-09 [1997]; and Crameri et al., Nat. Biotech., 15:436-38 [1997]).

IV. Vectors, Engineering, and Expression of Sequences

In another embodiment of the invention, the polynucleotide sequences of the present invention, and fragments and portions thereof, may be used in recombinant DNA molecules to direct expression of an mRNA or polypeptide in appropriate host cells. Due to the inherent degeneracy of the genetic code, other DNA sequences that encode substantially the same or a functionally equivalent amino acid or mRNA sequence may be produced and these sequences may be used to clone and express polypeptides (for example, a polypeptide encoded by a nucleic acid of the present invention).

As will be understood by those of skill in the art, it may be advantageous to produce nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life that is longer than that of a transcript generated from the naturally occurring sequence.

The nucleotide sequences of the present invention can be engineered using methods generally known in the art in order to alter the polypeptide sequences for a variety of reasons, including but not limited to, alterations that modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding a polypeptide may be ligated to a heterologous sequence to encode a fusion protein. For example, to screen peptide libraries for inhibitors of the polypeptides activity (for example, enzymatic activity), it may be useful to encode a chimeric protein that can be recognized by a commercially available antibody. A fusion protein may also be engineered to contain a cleavage site located between the polypeptide encoding sequence and the heterologous protein sequence, so that the polypeptide of interest may be cleaved and purified away from the heterologous moiety.

In another embodiment, sequences encoding a polypeptide (for example, a polypeptide encoded by a nucleic acid of the present invention) may be synthesized, in whole or in part, using chemical methods well known in the art (See for example, Caruthers et al., Nucl. Acids Res. Symp. Ser. 215 [1980]; Hom et al., Nucl. Acids Res. Symp. Ser. 225 [1980]). Alternatively, the protein itself may be produced using chemical methods to synthesize the amino acid sequence of the polypeptide of interest (for example, a polypeptide encoded by a nucleic acid of the present invention), or a portion thereof. For example, peptide synthesis can be performed using various solid phase techniques (Roberge et al., Science 269:202 [1995]) and automated synthesis may be achieved, for example, using the ABI 431A peptide synthesizer (PE Corporation, Norwalk, Conn.).

The newly synthesized peptide may be substantially purified by preparative high performance liquid chromatography (See for example, Creighton, T. (1983) Proteins, Structures and Molecular Principles, W H Freeman and Co., New York, N.Y.). The composition of the synthetic peptides may be confirmed by amino acid analysis or sequencing (for example, the Edman degradation procedure; or Creighton, supra). Additionally, the amino acid sequence of the polypeptide of interest or any part thereof, may be altered during direct synthesis and/or combined using chemical methods with sequences from other proteins, or any part thereof, to produce a variant polypeptide.

In order to express a biologically active polypeptide (for example, a polypeptide encoded by a nucleic acid of the present invention) or RNA, the nucleotide sequences encoding the polypeptide or functional equivalents, may be inserted into appropriate expression vector, that is, a vector that contains the necessary elements for the transcription and translation of the inserted coding sequence.

Methods that are well known to those skilled in the art may be used to construct expression vectors containing sequences encoding polypeptides (for example, a polypeptide encoded by a nucleic acid of the present invention) and appropriate transcriptional and translational control elements. These methods include in vitro recombinant DNA techniques, synthetic techniques, and in vivo genetic recombination. Such techniques are described in Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding a polypeptide of interest. These include, but are not limited to, microorganisms such as bacteria transformed with recombinant bacteriophage, plasmid, or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV; brome mosaic virus) or with bacterial expression vectors (for example, Ti or pBR322 plasmids); or animal cell systems.

The "control elements" or "regulatory sequences" are those non-translated regions of the vector (for example, enhancers, promoters, 5' and 3' untranslated regions) that interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Life Technologies, Inc., Rockville, Md.) and the like may be used. The baculovin's polyhedrin promoter may be used in insect cells. Promoters or enhancers derived from the genomes of plant cells (for example, heat shock, RUBISCO; and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence encoding a polypeptide, vectors based on SV40 or EBV may be used with an appropriate selectable marker.

In bacterial systems, a number of expression vectors may be selected depending upon the use intended for the polypeptide of interest. For example, when large quantities of the polypeptide are needed for the induction of antibodies, vectors that direct high level expression of fusion proteins that are readily purified may be used. Such vectors include, but are not limited to, the multifunctional *E. coli* cloning and expression vectors such as BLUESCRIPT phagemid (Stratagene, La Jolla, Calif.), in which the sequence encoding the polypeptide of interest may be ligated into the vector in frame with sequences for the amino-terminal Met and the subsequent 7 residues of beta-galactosidase so that a hybrid protein is produced; pIN vectors (Van Heeke and Schuster, J. Biol. Chem. 264:5503 [1989]; and the like. pGEMX vectors (Promega Corporation, Madison, Wis.) may also be used to express foreign polypeptides as fusion proteins with glutathione S-transferase (GST). In general, such fusion proteins are soluble and can easily be purified from lysed cells by adsorption to glutathione agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharontyces cerevisiae*, a number of vectors containing constitutive or inducible promoters such as alpha factor, alcohol oxidase, and PGH may be used. For reviews, See for example, Ausubel et al. (supra) and Grant et al., Methods Enzymol. 153:516 [1987].

In cases where plant expression vectors are used, the expression of sequences encoding polypeptides may be driven by any of a number of promoters. In a preferred embodiment, plant vectors are created using a recombinant plant virus containing a recombinant plant viral nucleic acid, as described in PCT publication WO 96/40867. Subsequently, the recombinant plant viral nucleic acid that contains one or more non-native nucleic acid sequences may be transcribed or expressed in the infected tissues of the plant host and the product of the coding sequences may be recovered from the plant, as described in WO 99/36516.

An important feature of this embodiment is the use of recombinant plant viral nucleic acids that contain one or more non-native subgenomic promoters capable of transcribing or expressing adjacent nucleic acid sequences in the plant host and that result in replication and local and/or systemic spread in a compatible plant host. The recombinant plant viral nucleic acids have substantial sequence homology to plant viral nucleotide sequences and may be derived from an RNA, DNA, cDNA or a chemically synthesized RNA or DNA. A partial listing of suitable viruses is described below.

The first step in producing recombinant plant viral nucleic acids according to this particular embodiment is to modify the nucleotide sequences of the plant viral nucleotide sequence by known conventional techniques such that one or more non-native subgenomic promoters are inserted into the plant viral nucleic acid without destroying the biological function of the plant viral nucleic acid. The native coat protein coding sequence may be deleted in some embodiments, placed under the control of a non-native subgenomic promoter in other embodiments, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, that may be native or a nonnative coat protein coding sequence, under control of one of the native or non-native subgenomic promoters. The coat protein is involved in the systemic infection of the plant host.

Some of the viruses that meet this requirement include viruses from the tobamovirus group such as Tobacco Mosaic virus (TMV), Ribgrass Mosaic Virus (RGM), Cowpea Mosaic virus (CMV), Alfalfa Mosaic virus (AMV), Cucumber Green Mottle Mosaic virus watermelon strain (CGMMV-W) and Oat Mosaic virus (OMV) and viruses from the brome mosaic virus group such as Brome Mosaic virus (BMV), broad bean mottle virus and cowpea chlorotic mottle virus. Additional suitable viruses include Rice Necrosis virus (RNV), and geminiviruses such as tomato golden mosaic virus (TGMV), Cassava latent virus (CLV) and maize streak virus (MSV). However, the invention should not be construed as limited to using these particular viruses, but rather the method of the present invention is contemplated to include all plant viruses at a minimum.

Other embodiments of plant vectors used for the expression of sequences encoding polypeptides include, for example, viral promoters such as the 35S and 19S promoters of CaMV used alone or in combination with the omega leader sequence from TMV (Takamatsu, EMBO J. 6:307 [1987]). Alternatively, plant promoters such as ubiquitin, wheat peroxidase, the small subunit of RUBISCO or heat shock promoters may be used (Coruzzi et al., EMBO J. 3:1671 [1984]; Broglie et al., Science 224:838 [1984]; and Winter et al., Results Probl. Cell Differ. 17:85 [1991]). These constructs can be introduced into plant cells by direct DNA transformation or pathogen-mediated transfection. Such techniques are described in a number of generally available reviews (See for example, Hobbs, S. or Murry, L. E. in McGraw Hill Yearbook of Science and Technology (1992) McGraw Hill, New York, N.Y.; pp. 191-196.

The present invention further provides transgenic plants comprising the polynucleotides of the present invention. In some embodiments, the plants comprise more than one of the sequences. The sequences may be contained in the same vector or in different vectors. In some preferred embodiments, *Agrobacterium* mediated transfection is utilized to create transgenic plants. Since most dicotyledonous plant are natural hosts for *Agrobacterium*, almost every dicotyledonous plant may be transformed by *Agrobacterium* in vitro. Although monocotyledonous plants, and in particular, cereals and grasses, are not natural hosts to *Agrobacteriuin*, work to successfully transform them using *Agrobacterium* has also been carried out (Hooykas-Van Slogteren et al. (1984) Nature 311:763-764). Plant genera that may be transformed by *Agrobacterium* include *Arabidopsis, Chrysanthemum, Dianthus, Gerbera, Euphorbia, Pelaronium, Ipomoea, Passiflora, Cyclamen, Malus, Prunus, Rosa, Rubus, Populus, Santalum, Allium, Lilium, Narcissus, Ananas, Arachis, Phaseolus* and *Pisum*.

For transformation with *Agrobacterium*, disarmed *Agrobacterium* cells are transformed with recombinant Ti plasmids of *Agrobacteriuin tumefaciens* or Ri plasmids of *Agrobacterium rhizogenes* (such as those described in U.S. Pat. No. 4,940,838, the entire contents of which are herein incorporated by reference). The nucleic acid sequence of interest is then stably integrated into the plant genome by infection with the transformed *Agrobacterium* strain. For example, heterologous nucleic acid sequences have been introduced into plant tissues using the natural DNA transfer system of *Agrobacterium tumefaciens* and *Agrobacterium rhizogenes* bacteria (for review, see Klee et al. (1987) Ann. Rev. Plant Phys. 38:467-486).

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be transformed by *Agrobacterium* and (b) that the transformed cells or tissues can be induced to regenerate into whole plants. The third method is transformation of seeds, apices or meristems with *Agrobacterium*. This method requires micropropagation.

The efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al., (1987) Plant Molec. Biol. 8:291-298). Alternatively, transformation efficiency may be enhanced by wounding the target tissue to be transformed. Wounding of plant tissue may be achieved, for example, by punching, maceration, bombardment with microprojectiles, etc. (See e.g., Bidney et al., (1992) Plant Molec. Biol. 18:301-313).

In still further embodiments, the plant cells are transfected with vectors via particle bombardment (i.e., with a gene gun). Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing the nucleic acid sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles that maximizes the number of cells receiving particles under uniform conditions, resulting in the introduction of the nucleic acid sample into the target tissue.

An insect system may also be used to express polypeptides (for example, a polypeptide encoded by a nucleic acid of the present invention). For example, in one such system, *Autographa californica* nuclear polyhedrosis virus (AcNPV) is used as a vector to express foreign genes in *Spodoptera fugiperda* cells or in *Trichoplusia larvae*. The sequences encoding a polypeptide of interest may be cloned into a non-essential region of the virus, such as the polyhedrin gene, and placed under control of the polyhedrin promoter. Successful insertion of the nucleic acid sequence encoding the polypeptide of interest will render the polyhedrin gene inactive and produce recombinant virus lacking coat protein. The recombinant viruses may then be used to infect, for example, *S. frugiperda* cells or *Tuichoplusia* larvae in which the polypeptide may be expressed (Engelhard et al., Proc. Nat. Acad. Sci. 91:3224 [1994]).

In mammalian host cells, a number of viral-based expression systems may be utilized. In cases where an adenovirus is used as an expression vector, sequences encoding polypeptides may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells Logan and Shenk, Proc. Natl. Acad. Sci., 81:3655 [1984]). In addition, transcription enhancers, such as the Rous sarcoma virus (RSV) enhancer, may be used to increase expression in mammalian host cells.

Specific initiation signals may also be used to achieve more efficient translation of sequences encoding the polypeptide of interest. Such signals include the ATG initiation codon and adjacent sequences. In cases where sequences encoding the polypeptide of interest, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers that are appropriate for the particular cell system that is used, such as those described in the literature (Scharf et al., Results Probl. Cell Differ., 20:125 [1994]).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing that cleaves a “prepro” form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines that stably express the polypeptide of interest (for example, a polypeptide encoded by a nucleic acid of the present invention) may be transformed using expression vectors that may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 11:223 [1977]) and adenine phosphoribosyltransferase (Lowy et al., Cell 22:817 [1980]) genes that can be employed in $tk^-$ or $aprt^-$ cells, respectively. Also, antimetabolite, antibiotic, or herbicide resistance can be used as the basis for selection; for example, dhfr, which confers resistance to methotrexate (Wigler et al., Proc. Natl. Acad. Sci., 77:3567 [1980]); npt, which confers resistance to the aminoglycosides neomycin and G-418 (Colbere-Garapin et al., J. Mol. Biol., 150:1 [1981]); and als or pat, which confer resistance to chlorsulfuron and phosphinotricin, respectively (Murry, supra). Additional selectable genes have been described, for example, trpB, which allows cells to utilize indole in place of tryptophan, or hisD, which allows cells to utilize histinol in place of histidine (Hartman and Mulligan, Proc. Natl. Acad. Sci., 85:8047 [1988]). Recently, the use of visible markers has gained popularity with such markers as anthocyanins, α-glucuronidase and its substrate GUS, and luciferase and its substrate luciferin, being widely used not only to identify transformants, but also to quantify the amount of transient or stable protein expression attributable to a specific vector system (Rhodes et al., Methods Mol. Biol., 55:121 [1995]).

Although the presence/absence of marker gene expression suggests that the gene of interest is also present, its presence and expression may need to be confirmed. For example, if the sequence encoding a polypeptide is inserted within a marker gene sequence, recombinant cells containing sequences encoding the polypeptide can be identified by the absence of marker gene function. Alternatively, a marker gene can be placed in tandem with a sequence encoding the polypeptide under the control of a single promoter. Expression of the marker gene in response to induction or selection usually indicates expression of the tandem gene as well.

Alternatively, host cells that contain the nucleic acid sequence encoding the polypeptide of interest (for example, a polypeptide encoded by a nucleic acid of the present invention) and express the polypeptide may be identified by a variety of procedures known to those of skill in the art. These procedures include, but are not limited to, DNA-DNA or DNA-RNA hybridizations and protein bioassay or immunoassay techniques that include membrane, solution, or chip based technologies for the detection and/or quantification of nucleic acid or protein.

The presence of polynucleotide sequences encoding a polypeptide of interest (for example, a polypeptide encoded by a nucleic acid of the present invention) can be detected by DNA-DNA or DNA-RNA hybridization or amplification using probes or portions or fragments of polynucleotides encoding the polypeptide. Nucleic acid amplification based assays involve the use of oligonucleotides or oligomers based on the sequences encoding the polypeptide to detect transformants containing DNA or RNA encoding the polypeptide. As used herein "oligonucleotides" or "oligomers" refer to a nucleic acid sequence of at least about 10 nucleotides and as many as about 60 nucleotides, preferably about 15 to 30 nucleotides, and more preferably about 20-25 nucleotides, that can be used as a probe or amplimer.

A variety of protocols for detecting and measuring the expression of a polypeptide (for example, a polypeptide encoded by a nucleic acid of the present invention), using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on the polypeptide is preferred, but a competitive binding assay may be employed. These and other assays are described, among other places, in Hampton et al., 1990; Serological Methods, a Laboratory Manual, APS Press, St Paul, Minn. and Maddox et al., J. Exp. Med., 158:1211 [1983]).

A wide variety of labels and conjugation techniques are known by those skilled in the art and may be used in various nucleic acid and amino acid assays. Means for producing labeled hybridization or PCR probes for detecting sequences related to polynucleotides encoding a polypeptide of interest include oligonucleotide labeling, nick translation, end-labeling or PCR amplification using a labeled nucleotide. Alternatively, the sequences encoding the polypeptide, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.), Promega Corporation (Madison, Wis.) and U.S. Biochemical Corp. (Cleveland, Ohio). Suitable reporter molecules or labels, that may be used, include radionuclides, enzymes, fluorescent, chemiluminescent, or chromogenic agents as well as substrates, cofactors, inhibitors, magnetic particles, and the like.

Host cells transformed with nucleotide sequences encoding a polypeptide of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides that encode the polypeptide of interest (for example, a polypeptide encoded by a nucleic acid of the present invention) may be designed to contain signal sequences that direct secretion of the polypeptide through a prokaryotic or eukaryotic cell membrane. Other recombinant constructions may be used to join sequences encoding the polypeptide to nucleotide sequence encoding a polypeptide domain that will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (available from Invitrogen, San Diego, Calif.) between the purification domain and the polypeptide of interest may be used to facilitate purification. One such expression vector provides for expression of a fusion protein containing the polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al., Prot. Exp. Purif., 3:263 [1992] while the enterokinase cleavage site provides a means for purifying the polypeptide from the fusion protein. A discussion of vectors that contain fusion proteins is provided in Kroll et al., DNA Cell Biol., 12:441 [1993]).

In addition to recombinant production, fragments of the polypeptide of interest may be produced by direct peptide synthesis using solid-phase techniques (Merrifield, J. Am. Chem. Soc., 85:2149 [1963]). Protein synthesis may be performed using manual techniques or by automation. Automated synthesis may be achieved, for example, using the Applied Biosystems 431A peptide synthesizer (Perkin Elmer). Various fragments of the polypeptide may be chemically synthesized separately and combined using chemical methods to produce the fall length molecule.

V. Alteration of Gene Expression

It is contemplated that the polynucleotides of the present invention (for example, SEQ ID NOs:1-40 and 359-365) may be utilized to either increase or decrease the level of corresponding mRNA and/or protein in transfected cells as compared to the levels in wild-type cells. Accordingly, in some embodiments, expression in plants by the methods described above leads to the overexpression of the polypeptide of interest in transgenic plants, plant tissues, or plant cells. The present invention is not limited to any particular mechanism. Indeed, an understanding of a mechanism is not required to practice the present invention. However, it is contemplated that overexpression of the polynucleotides of the present invention will alter the expression of the gene comprising the nucleic acid sequence of the present invention.

In other embodiments of the present invention, the polynucleotides are utilized to decrease the level of the protein or mRNA of interest in transgenic plants, plant tissues, or plant cells as compared to wild-type plants, plant tissues, or plant cells. One method of reducing protein expression utilizes expression of antisense transcripts (for example, U.S. Pat. Nos. 6,031,154; 5,453,566; 5,451,514; 5,859,342; and 4,801,340, each of which is incorporated herein by reference). Antisense RNA has been used to inhibit plant target genes in a tissue-specific manner (for example, Van der Krol et al., Biotechniques 6:958-976 [1988]). Antisense inhibition has been shown using the entire cDNA sequence as well as a partial cDNA sequence (for example, Sheehy et al., Proc. Natl. Acad. Sci. USA 85:8805-8809 [1988]; Cannon et al., Plant Mol. Biol. 15:39-47 [1990]). There is also evidence that 3' non-coding sequence fragment and 5' coding sequence fragments, containing as few as 41 base-pairs of a 1.87 kb cDNA, can play important roles in antisense inhibition (Ch'ng et al., Proc. Nati. Acad. Sci. USA 86:10006-10010 [1989]).

Accordingly, in some embodiments, the nucleic acids of the present invention (for example, SEQ ID NOs: 1-40 and 359-365, and fragments and variants thereof) are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be fall length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and up to about the full length of the coding region should be used, although a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, Solanum nodiflorum mottle virus and subterranean clover mottle virus. The design and use of target RNA-specific ribozymes is described in Haseloff, et al., Nature 334:585-591 (1988).

Another method of reducing protein expression utilizes the phenomenon of cosuppression or gene silencing (for example, U.S. Pat. Nos. 6,063,947; 5,686,649; and 5,283,184; each of which is incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (for example, Napoli et al., Plant Cell 2:279-289 [1990]; van der Krol et al., Plant Cell 2:291-299 [1990]; Smith et al., Mol. Gen. Genetics 224:477-481 [1990]). Accordingly, in some embodiments the nucleic acids (for example, SEQ ID NOs: 1-40 and 359-365, and fragments and variants thereof) from one species of plant are expressed in another species of plant to effect cosuppression of a homologous gene. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

VI. Expression of Sequences Producing Herbicide Resistance Phenotypes

The present invention provides nucleic sequences involved in providing herbicide tolerance or resistance to plants. Plants transformed with viral vectors comprising the nucleic acid sequences of the present invention were screened for a herbicide resistance phenotype. The results are presented in FIG. 6. Accordingly, in some embodiments, the present invention provides nucleic acid sequences that produce a herbicide resistance phenotype when expressed in plant (SEQ ID NOs: 1-40 and 359-365, FIG. 1). The present invention is not limited to the particular nucleic acid sequences listed. Indeed, the present invention encompasses nucleic acid sequences (including sequences of the same, shorter, and longer lengths) that hybridize to the listed nucleic sequences under conditions ranging from low to high stringency and that also cause the herbicide resistance phenotype. These sequences are conveniently identified by insertion into GENEWARE® vectors and expression in plants as detailed in the Examples.

In some embodiments, the sequences are operably linked to a plant promoter or provided in a vector as described in more detail above. The present invention also contemplates plants transformed or transfected with these sequences as well as seeds from such transformed plants. Furthermore, the sequences can be expressed in either sense or antisense orientation. In particularly preferred embodiments, the sequences are at least 30 nucleotides in length up to the length of the full-length of the corresponding gene. It is contemplated that sequences of less than fall length (for example, greater than about 30 nucleotides) are useful for down regulation of gene expression via antisense or cosuppression. Suitable sequences are selected by chemically synthesizing the sequences, cloning into GENEWARE® expression vectors, expressing in plants, and selecting plants with a herbicide tolerant phenotype.

VII. Identification of Homologs to Sequences

The present invention also provides homologs and variants of the sequences described above, but which may not hybridize to the sequences described above under conditions ranging from low to high stringency. In some preferred embodiments, the homologous and variant sequences are operably linked to an exogenous promoter. FIG. 3 provides BLAST search results from publicly available databases. The relevant sequences are identified by Accession number in these databases. FIG. 5 shows the top blastn hits (identified by accession number) versus all the nucleotide sequences in the Derwent biweekly database. FIG. 4 shows the top blastp hits (identified by accession number) versus all the amino acid sequences in the Derwent biweekly database.

In some embodiments, the present invention comprises homologous nucleic acid sequences (SEQ ID NOs:41-358) identified by screening an internal database with SEQ ID NOs.:140 and 359-365 at a confidence level of Pz<1.00E-20. These sequences are provided in FIG. 2. The headers list the sequence identifier for the sequence that produced the actual phenotypic hit first and the sequence identifier for the homologous contig second.

As will be understood by those skilled in the art, the present invention is not limited to the particular sequences of the homologs described above. Indeed, the present invention encompasses portions, fragments, and variants of the homologs as described above. Such variants, portions, and fragments can be produced and identified as described in Section III above. In particularly preferred embodiments, the present invention provides sequences that hybridize to SEQ ID NOs:41-358 under conditions ranging from low to high stringency. In other preferred embodiments, the present invention provides nucleic acid sequences that inhibit the binding of SEQ ID NOs:41-358 to their complements under conditions ranging from low to high stringency. Furthermore, as described above in Section IV, the homologs can be incorporated into vectors for expression in a variety of hosts, including transgenic plants.

EXAMPLES

Example 1

Poppy cDNA Library Construction in GENEWARE® Vectors

A. Plant Growth. A wild population of *Papaver rhoeas* resistant to auxin (2,4-dichlorophenoxy)acetic acid (2,4-D) was identified from a location in Spain and seed was collected. The seed was germinated and yielded a morphologically heterogeneous population. Leaf shape varied from deeply to shallowly indented. Latex color in some individuals was pure white when freshly cut, slowly changing to light orange then brown. Latex in other individuals was bright yellow or orange and rapidly changed to dark brown upon exposure to air. A single plant (PR4) with the white latex phenotype was used to generate the library.

B. RNA extraction. Approximately 1.5 g of leaves and stems were collected and frozen on liquid nitrogen. The tissue was ground to a fine powder and transferred to a 50 mL conical polypropylene screw cap centrifuge tube. Ten mL of TRIZOL reagent (Life Technologies, Rockville, Md.) was added and vortexed at high speed for several minutes of short intervals until an aqueous mixture was attained. Two mL of chloroform was added and the suspension was again vortexed at high speed for several minutes. The tube was centrifuged 15 minutes at 3100 rpm in a tabletop centrifuge (GP Centrifuge, Beckman Coulter, Inc, Fullerton, Calif.) for resolution of the phases. The aqueous supernatant was then carefully transferred to diethylpyrocarbonate (DEPC)-treated 1.5 mL microtubes and total RNA was precipitated with 0.6 volumes of isopropanol. To facilitate precipitation, the solution was allowed to stand 10 minutes at room temperature after thorough mixing. Following centrifugation for 10 minutes at 8000 rpm in a microcentrifuge (model 5415C, Eppendorf AG, Hamburg), the pellet of total RNA was washed with 70% ethanol, briefly dried and resuspended in 200 μL DEPC-treated deionized water. A 10 μL aliquot was examined by non-denaturing agarose gel electrophoresis.

C. cDNA synthesis. To generate cDNA, approximately 50 μg of total RNA was primed with 250 pmole of first strand oligo (TAIL: 5'-GAG-GAT-GTT-AAT-TAA-GCG-GCC-GCT-GCA-G$(T)_{23}$-3')(SEQ ID NO:366) in a volume of 250 μL using 1000 units of Superscript reverse transcriptase (Life Technologies, Rockville, Md.) for 90 minutes at 42° C. Phenol extraction was performed by adding an equal volume of phenol:chloroform:isoamyl alcohol (25:24:1 v/v), vortexing thoroughly, and centrifuging 5 minutes at 14,000 rpm in an Eppendorf microfuge. The aqueous supernatant phase was transferred to a fresh microfage tube and the first strand cDNA:mRNA hybrids were precipitated with ethanol by adding 0.1 volume of 3 M sodium acetate and 2 volumes of absolute ethanol. After 5 minutes at room temperature, the tube was centrifuged 15 minutes at 14,000 rpm. The pellet was washed with 80% ethanol, dried briefly and resuspended in 100 μL TE buffer (10 mM TrisCl, 1 mM EDTA, pH 8.0). After adding 10 μL Klenow buffer (RE buffer 2, Life Technologies, Rockville, Md.) and dNTPs (Life Technologies, Rockville, Md.) to a final concentration of 1 mM, second strand cDNA was generated by adding 10 units of Klenow enzyme (Life Technologies, Rockville, Md.), 2 units of RNase H (Life Technologies, Rockville, Md.) and incubating at 37° C. for 2 hrs. The buffer was adjusted with β-nicotinamide adenine dinucleotide (β-NAD) by addition of *E. coli* ligase buffer (Life Technologies, Rockville, Md.) and adenosine triphosphate (ATP, Sigma Chemical Company, St. Louis, Mo.) added to a final concentration of 0.6 mM. Double stranded phosphorylated cDNA was generated by addition of 10 units of *E. coli* DNA ligase (Life Technologies, Rockville, Md.), 10 units of T4 polynucleotide kinase (Life Technologies, Rockville, Md.) and incubating for 20 minutes at ambient temperature.

The double stranded cDNA was isolated through phenol extraction and ethanol precipitation, as described above. The pellet was washed with 80% ethanol, dried briefly and resuspended in a minimal volume of TE. The resuspended pellet was ligated overnight at 16° C. with 50 pmole of kinased AP3-AP4 adapter (AP-3: 5'-GAT-CTT-AAT-TAA-GTC-GAC-GAA-TTC-3'/AP-4: 5'-GAA-TTC-GTCGAC-TTA-ATT-AA-3')(SEQ ID NOs:367 and 368) and 2 units of T4 DNA ligase (Life Technologies, Rockville, Md.). Ligation products were amplified by 20 cycles of PCR using AP-3 primer and examined by agarose gel electrophoresis.

Expanded adapter-ligated cDNA was digested overnight at 37° C. with PacI and NotI restriction endonucleases. The GENEWARE® vector pBSG1056 (Large Scale Biology Corporation, Vacaville, Calif.) was similarly treated. Digested cDNA and vector were electrophoresed a short distance through low-melting temperature agarose. After visualizing with ethidium bromide and excising the appropriate fraction(s), the fragments were then isolated by melting the agarose and quickly diluting 5:1 with TE buffer to keep from solidifying. The diluted fractions were mixed in the appropriate ratio (approximately 10:1 vector:insert ratio) and ligated overnight at 16° C. using T4 DNA ligase.

Characterization of the ligation revealed an average insert size of 1.27 kb. The ligation was transferred to Large Scale Biology Corporation (LSBC) (Vacaville, Calif.), where large scale arraying was carried out. Random sequencing of nearly 100 clones indicated that about 40% of the inserts had full length open reading frames.

Example 2

Colony Array

A. Colony Array—Picking. Ligations were transformed into E. coli DH5α cells and plated onto 22×22cm Genetix "Q Trays" prepared with 200 ml agar, Amp[100]. A Qbot device (Genetix, Inc., Christchurch, Dorset UK) fitted with a 96 pin picking head was used to pick and transfer desired colonies into 384-well plates according to the manufacturers specifications and picking program SB384.SC1, with the following parameters:

Source

Container: Genetix bioassay tray
Color: White
Agar Volume: 200 ml

Destination

Container: Hotel (9 High)
Plate: Genetix 384 well plate
Time In Wells (sec): 2
Max Plates to use: # of 384 well plates
1st Plate: 1
Dips to Inoculate: 10
Well Offset: 1

Head

Head: 96 Pin Picking Head
First Picking Pin: 1
Pin Order: A1-H1, H2-A2. . . (snaking)
Sterilizing
Qbot Bath #1
Bath Cycles: 4
Seconds in Dryer: 10
Wait After Drying: 10
(approximate picking time: 8 hrs /20,000 colonies)

Following picking, 384 well plates containing bacterial inoculum were grown in a HiGro chamber fitted with $O_2$ at 30° C., speed 6.5 for 12-14 hours. Following growth, plates were replicated using the Qbot with the following parameters, 2 replication runs per plate:

Source
Container: Hotel (9 High)
Plate: Genetix Plate 384 Well
Plates to replicate: 24
Start plate No.: 1
No. of copies: 1
Destination
Container: Universal Dest Plate Holder
Plate: Genetix Plate 384 Well
No. of Dips: 5
Head
Head: 384 Pin Gravity Gridding Head
Sterilizing
Qbot Bath #1
Bath cycles: 4
Seconds in Dryer: 10
Wait After Drying: 10

Airpore tape was placed over the replicated 384 well plates and the replicated plates were grown in the HiGro as above for 18-20 hours, sealed with foil tapes and stored at −80° C.

B. Colony Array—Gridding. Membrane filters were soaked in LB/Ampicillin for 10 minutes. Filters were aligned onto fresh 22×22 cm agar plates and allowed to dry on the plates 30 min. in a Laminar flowhood. Plates and filters were placed in the Qbot and UV sterilized for 20 minutes. Following sterilization, plates/filters were gridded from 384 well plates using the Qbot according to the manufacturers specifications with the following parameters:

Gridding Routine
Name: 3×3

Source
Container: Hotel (9 High)
Plate: Genetix Plate 384 Well
Max Plates: 8
Inking time (ms): 1000
Destination
Filter holder: Qtray
Gridding Pattern: 3×3, non-duplicate, 8
Field Order: front 6 fields
No. Filters: up to 15
Max stamps per ink: 1
Max stamps per spot: 1
Stamp time (ms): 1000
No. Fields in Filter: 2
No. Identical Fields: 2
Stamps between sterilize: 1
Head: 384 pin gravity gridding head
Pin Height Adjustment: No change
Qbot Bath #1
Bath cycles: 4
Dry time: 10 (Seconds)
Wait After Drying: 10 (Seconds)

C. Plate Rearray. 384 well plates were rearrayed into deep 96 well block format using the Qbot according to the manufacturers instructions and the following rearray parameters ×2 per plate:

Source
Container: Hotel (9 High)
Plate: Genetix Plate 384 Well
$1^{st}$ Plate: 1
Destination
Container: Universal Dest Plate Holder
Plate: Beckman 96 Deep Well Plate
$1^{st}$ plate: 1
Dips to Inoculate: 5
Well offset: 1
Max plates to use: 12 (or less)
Time in wells (sec): 2
Qbot Bath #1
Head: 96 pin picking head
First Picking Pin: 1
Pin Order: A1-H1, A2-H2, A3-H3 . . .
Bath cycles: 4
Sec. In dryer: 10
Wait after drying: 10

Following rearray, the 96-well blocks were covered with air-pore tape and placed in incubator shakers at 37° C., 500 rpm for a total of 24 hours. Plates were removed and used for DNA preparation.

Example 3

DNA Preparation

Plasmid DNA was prepared in a 96-well block format using a Qiagen Biorobot 9600 instrument according to the manufacturer's specifications. In this 96-well block format, 900 μL of cell lysates was transferred to the Qiaprep filter and vacuumed 5 min at 600 mbar. Following this vacuum, the filter was discarded and the Qiaprep Prep-Block was vacuumed for 2 min at 600 mbar. After adding buffer, samples were centrifuged for 5 min at 600 rpm (Eppendorf benchtop centrifuge fitted with 96-wp rotor) and subsequently washed ×2 with PE buffer. Elution was carried out for 1 minute, followed by a 5 min centrifugation at 6000 rpm. Final volume of DNA product was approximately 75 μL.

Example 4

Generation of Raw Sequence Data

High-throughput sequencing was carried out using the PCT200 and TETRAD PCR machines (MJ Research, Watertown, Mass.) in 96-well plate format in combination with two ABI 377™ automated DNA sequencers (PE Corporation, Norwalk, Conn.). The quality of sequence data was improved by filtering the raw sequence output from the sequencers. High quality sequences were defined as those having less than 10% unreadable bases and no more than ten consecutive Ns in the middle of the sequence (40-450). The second step for improving the quality of a sequence was to remove the vectors from the sequence. There are two advantages of this process. First, when locating the vector sequence, its position can be used to align to the input sequence. The quality of the sequence can be evaluated by the alignment between the vector sequence and the target sequence. Second, the removal of the vector sequence greatly improves the signal-to-noise ratio and makes the analysis of the resulting database easier to search.

Example 5

Unigene Selection

Sequence data was utilized to generate a unigene set of clones, for the purpose of eliminating redundancy in the cDNA library. Following 5' sequence analysis, adapter sequence was trimmed at the EcoRI site (viz. 5'-TTAATTAAGTCGACGAATTC*)(SEQ ID NO:369). Insert sequence was further trimmed to a Phred score of 20 or higher. Each member of the data set was then aligned by BLAST against all other members to form contigs with a minimum overlap of 50. For clusters of size greater than one, the 5' most sequence was chosen as the unigene. A final unigene set was then arrayed from glycerol stocks using the Qbot.

Example 6

Automated Transcriptions

Plasmid DNA preparations were subjected to automated transcription reactions in a 96-well plate format using a Tecan Genesis Assay Workstation 200 robotic liquid handling system (Tecan, Inc., Research Triangle Park, N.C.) according to the manufacturers specifications, operating on the Gemini Software (Tecan, Inc.) program "Automated_Txns.gem." For these reactions, reagents from Ambion, Inc. (Austin, Tex.) were used according to the manufacturer's specifications at 0.8× reaction volumes (11.2 μL/well).

Example 7

Encapsidated Transcriptions

Transcript was prepared manually using the T7 mMessage mMachine Capped RNA Transcription Kit (Ambion, Austin, Tex.) according to the manufacturer's instructions, with addition of 2 μL per reaction of RNA Cap Structure Analog (New England BioLabs, Beverly, Mass.), and 1 μL per reaction of RNAsin (Promega, Madison, Wis.), plasmid DNA, and autoclaved water, then incubated at 37° C. for 90-120 minutes. Encapsidation (NCAP) of the RNA transcript (txn) was done by mixing 2 μL txn, 10 μL coat protein (Large Scale Biology Corporation, Inc., Vacaville, Calif.), 10 μL 1M $NaPO_4$ buffer, and 78 μL autoclaved water, and incubating at room temperature overnight. Prior to inoculation, transcript was sampled and subjected to agarose gel analysis for quality control.

Example 8

Evaluation of Auxin Tolerance in Seedlings

Sterilization of seed. Working in a horizontal laminar flow clean bench (Baker Company, Sanford, Me.), 1-1.5 g of Nicotiana benthamiana (Nb) seed was placed in a 100 μM cell strainer (Falcon, Franklin Lakes, N.J.), along with a magnetic stir bar. The seed was imbibed for 10 minutes by placing the strainer into a sterile 60×20 mm petri dish (Fisher Scientific, Pittsburgh, Pa.) containing a 0.02% TritonX 100 (Sigma, St.Louis, Mo.) solution. Using sterilized forceps, the strainer was then transferred to another 60×20 mm petri dish containing 70% ethanol where the seed was immersed for two minutes. After the ethanol soak, the strainer was moved to a third petri dish containing 0.02% TritonX 100 prepared with a 50% bleach solution. The dish and strainer were placed on a magnetic stir plate and the seeds agitated for seven minutes. The strainer was then transferred to a petri dish containing sterile water and swirled gently for rinsing. A total of three rinses were done, each with fresh sterile water. The seed was then dried in the strainer under the laminar flow hood. When completely dry, the seed was stored in sterile glass vials at 4° C.

Germination of seed. Using aseptic technique, Nb seed was divided into 6-9 mg aliquots by weighing and collection in sterile 1.2 mL microtubes (Fisher Scientific, Pittsburgh, Pa.). For each microtube, 10 mL of liquid TOB medium [10×MS salts 524 (PhytoTechnology Labs, Shawnee Mission, Kans.) 100 mL/L; B5 vitamins {Myo-Inositol 10 g/L, Nicotinic Acid 100 mg/L, Pyroxidine 10 mg/L, Thiamine-HCl 1 g/L (all Sigma, St. Louis, Mo.)} 10 mL/L; Sucrose (Fisher Scientific, Pittsburgh, Pa.) 30 g/L; autoclave 20 minutes] was delivered to a sterile conical 50 mL centrifuge tube (Falcon, Franklin Lakes, N.J.). Seed from one microtube was added to 10 mL of medium. The conical tubes were then capped tightly and placed on a roller drun (drive model #7736-10164, wheel model #7736-20020; Bellco Glass Co., Vineland, N.J.) inside a 27° C. culture chamber under continuous light, intensity averaging 230 lumens/ft2. The roller drum operated continuously at 30 RPM for 7 days.

A. Primary Screen

Whisker-mediated inoculation of *Nicotiana benthamiana* (Nb) seedlings. After one week on the roller drum, the conical tubes were removed and the liquid medium drained from each, under the laminar flow hood. Seedlings were emptied onto sterile filter paper and gently blotted to remove excess media. Using aseptic technique, 1.2 mL sterile tubes arrayed in 96-well racks (Costar, Coming, N.Y.) were prepared by adding the following per tube: (1) 5 seedlings; (2) 10 μL of sterile 5% (w/v) silicon carbide whisker (Advanced Composite Materials Corp, Greer, S.C.) solution in deionized water, and (3) 10 μL of viral transcript (txn) from a single cDNA sequence. Standard format for each set of 96 tubes included green fluorescent protein (GFP; Chalfie et al., Science 263: 802 [1994]) transcript in 4 control wells and 91 different test genes. The last tube remained empty. Once all the components were added, the tubes were individually capped and lids were placed on the racks. The racks were then secured in a Kleco 4-96 Pulverizer (custom model, Kinetic Laboratory Equipment Company, Visalia, Calif.) and agitated at full speed for 3 minutes. The seedlings from each tube were rinsed together in approximately 2 mL of sterile water. Immediately after rinsing, they were transferred to sterile Phytatrays (Sigma, St. Louis, Mo.) containing solid TOB medium [liquid TOB with 8 g/L TC agar (PhytoTechnology Labs, Shawnee Mission, Kans.) added before autoclaving] and cultured in a 27° C. growth chamber with a 16-hour photoperiod (600 lumens/$ft^2$). The 5 seedlings inoculated per transcript were maintained together in the same box and a single sequence identification number was used to track the group. Twenty-five seedlings (5 groups) were cultured per Phytatray.

Infection Assessment. At 7 days post-inoculation, seedlings from the 4 GFP control tubes were examined under ultraviolet light for GFP expression, as in indication of general inoculation efficacy. If less than 80% of GFP-inoculated plants were systemically fluorescent, inoculation with the 91 test genes was repeated.

Selection on auxinic herbicide. Also at 7 days post-inoculation, using aseptic technique, each seedling was transferred to Phytatrays of TOB+40 ppb 4-amino-3,6-dichloropyridine-2-carboxylic acid medium [solid TOB medium with 40 μg/L 4-amino-3,6-dichloropyridine-2-carboxylic acid (Dow AgroSciences, Indianapolis, Ind.) added after autoclaving]. Again, 25 seedlings were cultured per box and tracking was maintained for each group of 5 seedlings.

Hit identification. After 14 days on herbicide selection, each seedling was visually assessed in comparison to GFP-inoculated negative controls for the presence of an auxin tolerant phenotype. Tolerance was defined as a seedling having a minimum of 2 expanded upper leaves that maintained a healthy green color and resisted curling. If any of the 5 seedlings from the same inoculation tube demonstrated tolerance, the corresponding sequence was identified as a primary hit.

Clones identified as primary hits in the auxin tolerance screen were rearrayed from master 384well plates of frozen *E. coli* glycerol stocks using a Tecan Genesis RSP200 device fitted with a ROMA arm, according to the manufacturer's specifications and operating on Gemini software (Tecan) program "worklist.gem" according to instructions downloaded from a proprietary LIMS program (LSBC, Vacaville, Calif.).

B. Secondary Screen

Seedling inoculation was performed as described above, using transcript from rearrayed primary hit sequences. However, to better assess the frequency of the tolerant phenotype, 5 inoculation tubes (containing 5 seedlings each) were used for each test sequence, totaling 25 plants evaluated per clone in the secondary screen. Infection assessment, selection, and hit identification criteria were identical to the methods used in the primary screen. A sequence was determined to be a secondary hit when at least one of the 25 seedlings displayed the tolerant phenotype. FIG. 6 lists 29 sequences identified as primary hits. Of those 29 sequences, 12 were also secondary hits in the seedling screens.

Example 9

Evaluation of Auxin Tolerance in Greenhouse Plants

All primary hit sequences were evaluated for tolerance in larger plants, maintained under greenhouse conditions as described below.

Plant Growth and Maintenance. Nb seeds were sown in 6.5 cm pots filled with Redi-earth medium (The Scotts Company, Marysville, Ohio) pre-wetted by injection of Hoagland's fertilizer solution [all from the Scotts Company: 147 kg Peters Excel 15-15-15 Cal-Mag, 68 kg Peters Excel 15-0-0 Cal-Lite (15% Ca), and 45 kg Peters Excel 10-0-0 MagNitrate (10% Mg) in hot tap water to 596 L total volume] into irrigation water at a ratio of 200:1, using an injection system (H. E. Anderson, Muskogee Okla,). Seededpots were placed in the greenhouse for 1 day, transferred to a 27° C. germination chamber (Carolina Greenhouses, Kinston, N.C.) for 2 days, and then returned to the greenhouse. Shade curtains (33% transmittance) were used in the greenhouse to reduce solar intensity. To ensure 16 hour day length and supplement solar radiation on overcast days, artificial lighting consisting of a 1:1 mixture of metal halide and high pressure Sylvania sodium lamps was used, delivering approximately 220 μmol/$m^2$/s. Evaporative cooling and steam heat were used to maintain a daytime set point of 27° C. and a nighttime temperature of 22° C. At approximately 7 days post sowing (dps), seedlings were thinned to one seedling per pot and at 17 to 21 dps, the pots were spaced farther apart to accommodate plant growth. Plants were watered with Hoagland's solution as required. Following inoculation, waste irrigation water was collected and treated with 0.5% sodium hypochlorite for 10 minutes to neutralize any viral contamination before discharging into the municipal sewer.

Plant Inoculation. For each clone, 50 test plants as well as 10 GFP and bar (Thompson et al., EMBO J. 6:2519 [19870]) negative control plants were inoculated as follows: 2.0 mL of inoculum per clone were prepared by combining equal volumes of NCAP transcript and FES buffer [0.1 M glycine, 0.06 M $K_2HPO_4$, 1% sodium pyrophosphate, 1% diatomaceous earth (Sigma Chemical Company, St. Louis, Mo.), and either 1% silicon carbide (Aldrich Chemical Company, Milwaukee, Wis.), or 1% Bentonite (Sigma Chemical Company, St. Louis, Mo.)]. The inoculum was applied to each plant at 17 days post sowing by pipetting onto the upper surface of leaves 3 and 4 (~20 μL per leaf). The inoculum was then spread across each leaf surface using a 3" cotton tipped applicator (Calapro Swab, Fisher Scientific, Pittsburgh, Pa.) and a gloved finger to support the leaf. Following inoculation the plants were misted with deionized water.

Infection Scoring. At 8 days post inoculation (dpi), the plants were visually examined and a numerical score was assigned to each plant to indicate the extent of viral infection symptoms: 0=no infection, 1=possible infection, 2=infection symptoms limited to leaves <50-75% fully expanded, 3=typical systemic infection, 4=atypically severe infection, often accompanied by moderate to severe wilting and/or necrosis. Plants receiving an infection rating of 0, 1, or 4 were discarded.

Herbicide spraying. At 9 dpi, the well infected plants (infection score of 3, sometimes 2) were divided into 3 treatment groups. Group 1, to be sprayed with solvent only, contained 4 plants per test clone (2 plants per negative control) and Groups 2 and 3, to be treated with 13 or 40 g ae/ha, respectively, each consisted of 12 test plants per clone and 2 plants per negative control. The plants were labeled for tracking according to clone, treatment, and repetition number. Plants were placed in flats, with 8 or fewer plants per flat.

A potassium salt formulation of 4-amino-3,6-dichloropyridine-2-carboxylic acid (Dow AgroSciences, Indianapolis, Ind.) herbicide solution was diluted in 0.25% X-77 Spreader (Spraymate, Greeley, Colo.) for a concentration of 40 g ae/ha. That solution was further diluted with solvent (1:3) to acquire the 13 g ae/ha dose. For a spray volume of 187 L/ha, 30 mL herbicide solution was prepared per flat for each dose used.

Individual flats were treated with herbicide or solvent in an automated track sprayer (Nandel Scientific Company Ltd, Guelph, Ontario) at the following specifications: spray volume=187 L/ha; spray nozzle=TeeJet 8002E single nozzle; spray height=18 inches above canopy; nozzle speed=1.8 mph; spray pressure=54 psi at rest. Plants were allowed to dry 20 seconds before returning to the greenhouse.

Injury assessments. Each plant was scored at 2, 7, and 14 days after treatment (dat) for auxin tolerance by estimating percent injury. Degree of epinasty was the primary symptom evaluated. However, other observations affecting injury ratings included stunting, size of the upper leaves, chlorosis, and necrosis. Below are the general guidelines used.

0%—no injury

10%—small upper leaves, upright stem, little stunting

20%—small upper leaves, upright stem, noticeable stunting

30%—stem is curvilinear but relatively upright

40%—bottom half of the stem is upright, top half is approaching horizontal

50%—high epinastic curling in top half of the stem

70%—entire stem is horizontal

80%—chlorosis in upper leaves

90%—chlorosis in upper and middle leaves and/or necrosis in upper leaves

100%—total necrosis

An auxin tolerant phenotype was defined as 25% injury or less after treatment with either 13 or 40 g ae/ha at any of the evaluation days. The percentage of plants per treatment group demonstrating tolerance was calculated at 2, 7, and 14 dat (FIG. 6). Results in FIG. 6 show a range within the greenhouse data from 0% tolerant plants for some sequences at each evaluation date to more than 90% tolerant plants for another sequence 2 weeks post application (Trial #1). Discrepancies between seedling and greenhouse results for a given sequence may be attributed to obvious variables: differences in plant maturity between the two testing systems; differences in herbicide application method; and differences in herbicide exposure time (chronic vs. acute). Only sequences demonstrating reproducible auxin tolerance, that is, sequences considered a "hit" either from primary to secondary screening, from primary to greenhouse testing, or for more than one seedling within the primary screen were included in FIG. 6.

Reproducibility in the greenhouse was also tested for some sequences to exemplify claims. For a second evaluation under greenhouse conditions (Trial #2), procedures from this example were repeated. FIG. 6 includes data demonstrating reproducible auxin tolerance observed from Trial #1 to Trial #2 for clones 129965 (SEQ ID NO:10), 130213 (SEQ ID NO:14), 130294 (SEQ ID NO:360), 130994 (SEQ ID NO:361), and 129870 (SEQ ID NO:359). Taking into account the innate variability of any transient expression system, reproducibility in the greenhouse was judged on a general trend in tolerance over time, noting the 3 evaluation dates, as well as observance of 30% or more of the test population demonstrating tolerance by 14 dat. FIG. 8 summarizes results from the testing of homologs to sequences 129965 (SEQ ID NO:10) and 130213 (SEQ ID NO:14) using the greenhouse evaluation method described in this Example 9.

Example 10

Bioinformatic Analysis of Hits

A. Phred anid Phrap. Phred is a UNIX based program which can read DNA sequencer traces and make nucleotide base calls independent of any software provided by the DNA sequencer manufacturer. Phred also provides a quality score for each base that can be used by the investigator to trim those sequences or preferably by Phrap to help its assembly process.

Phrap is another UNIX based program which takes the output of Phred and tries to assemble the individual sequencing runs into larger contiguous segments on the assumption that they all belong to a single DNA molecule. While this is clearly not the case with collections of Expressed Sequence Tags (ESTs) or with heterogeneous collections of sequencing runs belonging to more than one contiguous segment, the program does a very good job of uniquely assembling these collections with the proper manipulation of its parameters (mainly –penalty and –minscore; settings of 15 and 40 respectively provide contiguous sequences with exact homology approaching 95% over lengths of approximately 50 nucleotide base pairs or more). As with all assemblies it is possible for proper assemblies to be missed and for improper assemblies to be constructed, but the use of the above parameters and judicious use of input sequences will keep these to a minimum.

Detailed descriptions of the Phred and Phrap software and it's use can be found in the following references which are hereby incorporated herein by reference: Ewing et al, Genome Res. 8:175 [1998]; Ewing & Green, Genome Res. 8:186 [1998]; Gordon et al., Genome Res. 8:195 [1998].

Blast

The BLAST set of programs may be used to compare a set of sequences against databases composed of large numbers of nucleotide or protein sequences and obtain homologies to sequences with known function or properties. Detailed description of the BLAST software and its uses can be found in the following references which are hereby incorporated herein by reference: Altschul et al., J. Mol. Biol. 215:403 [1990]; Altschul et al., J. Mol. Biol. 219:555 [1991].

Generally, BLAST performs sequence similarity searching and is divided into 5 basic subroutines of which 3 were used: (1) BLASTN compares a nucleotide sequence to a nucleic acid sequence database; (2) BLASTX compares translated protein sequences from a nucleotide sequence done in six frames to a protein sequence database; (3) TBLASTX compares translated protein sequences from a nucleotide sequence done in six frames to the six frame translation of a nucleotide database. BLASTX and TBLASTX are used to identify homologies at the protein level of the nucleotide sequence.

B. Contig Sequence Assembly for Hits. Phred sequence calls and quality data for the individual sequencing runs associated with SEQ ID NOs: 1-40 (FIG. 1) were stored in a relational database. All the sequence runs stored in the database for the sequences to be assembled were extracted from the database and the files needed by Phrap recreated with the aid of a Perl script. Perl is an interpreted computer language useful for data manipulation. The same script ran Phrap on the assembled files and then stored the assembled contiguous sequences and singletons in a relational database. The script then assembled two files. One file was a FASTA format file of the sequences of the assembled contigs and singletons (FIG. 1). The other file was a record of the assembled sequences and which sequencing runs they contained (data not shown). FASTA format is a standard DNA sequence format recognized by the BLAST suite of programs as well as by Phrap. Both of these files were then inspected manually to detect incorrect assemblies or to add sequence information not present in the relational database. Any incorrect assemblies found were corrected before this file was used in BLAST searches to identity function and well as other homologous sequences in our databases. Correct assemblies that contained more than one SEQ ID were separated. Although these represent parts of the same sequence, since these are ESTs and contain limited gene sequence data, a one-to-one nucleotide match cannot be predicted at this time for the entire length of a contig representing a single SEQ ID with those containing multiple SEQ IDs. Some full length sequences were obtained and are designated with a FL.

C. Identification of Function. The FASTA formatted file obtained as described above was used to run a BLASTX query against the GenBank non-redundant protein database using a Perl script. The data from this analysis was parsed out by the Perl script such that the following information was extracted: the query sequence name, the level of homology to the hit and the description of the hit sequence (the highest scoring hit from the analysis). The script filtered all hits less than 1.00E-04, to eliminate spurious homologies. The data from this file was used to identify putative functions and properties for the query sequences (see FIG. 3).

D. Identification of Similar Sequences in Derwent. The FASTA formatted file obtained as described above was used to run a BLASTN query against the Derwent non-redundant nucleotide database as well as a BLASTX against the Derwent non-redundant protein database using Perl scripts. These Derwent non-redundant databases were created by extracting all the sequence information in the Derwent database. The data from this analysis was parsed out by the Perl script such that the following information was extracted, the query sequence name, the level of homology to the hit and the description of the hit sequence (the highest scoring hit from the analysis). The script filtered all hits less than 1.00E-04, to eliminate spurious homologies (see FIGS. 4 and 5)

E. Identification of Homologous Sequences. eBRAD, an internal relational database, stored sequence data and results from biological and metabolic screens of multiple organisms (*Nicotiana benthamiana, Oryzae sativa* (var. Indica IR7), *Papaver rhoeas, Saccharornyces cerevisiae* and *Trichoderna harzianum* (Rifai 1295-22). In order to identify sequences in the database with high levels of homology to the sequences functionally identified as "hits" and contained in the FASTA formatted file described above, the following analysis was performed.

All the sequences were extracted in FASTA format from the eBRAD relational database with standard SQL commands and converted into a searchable BLAST database using tools provided in the BLAST download from the National Center for Biotechnology Information (NCBI). A Perl script then ran a BLASTN search of our query file against the eBRAD database containing all relevant sequences. The script then extracted from all hits the following information: the query name, the level of homology and the identity of the hit sequences. The script then filtered all homologies less than 1.00E-20 as well as all the redundant hit sequences.

This analysis was repeated again using a TBLASTX query. Both files were then combined and the redundancies eliminated. Since the query sequences are also present in the database, those query sequences were eliminated as redundant.

These results were used to extract the sequence and quality score data from the eBRAD relational database in order to repeat the analysis described in "Contig Sequence Assembly for Hits" (except that contig assemblies from the same organism were permitted to be comprised of independently cloned, but overlapping sequences). FIG. 2 provides the assembled search hits with homologies better than 100E-20 to the sequences shown in FIG. 1. FIG. 8 identifies homologs to sequences 129965 (SEQ ID NO:10) and 130213 (SEQ ID NO:14) which were tested for auxin tolerance using the greenhouse evaluation method of Example 9.

Example 11

Full-Length Sequencing

Five hits (SEQ ID NOs:10, 14, 359, 360 and 361) from the auxin tolerance screening and three homologous clones (SEQ ID NOs:363, 364, and 365) were analyzed from plasmid DNA for generation of nucleotide sequence of the full-length insert. Sequencing reactions were prepared using the ABI Prism BigDye Terminator Cycle Sequencing Kit (Applied Biosystems, Foster City, Calif.). Each reaction was prepared as follows: 8 μL Terminator Ready Reaction Mix, 0.5 jig template DNA, 3.2 μg desired primer, 1 μL dimethyl sulfoxide and sterile water to a final volume of 20 μL. The thermal cycler program was as follows:

Step 1: 95° C. for 20 seconds

Step 2: 50° C. for 20 seconds

Step 3: 60° C. for 4 minutes 30 times to Step 1

Sequencing was performed using a Perlin Elmer ABI Prism 377™ DNA sequencer (Norwalk, Conn.). The data was analyzed with Sequencher™ software (Gene Codes Corp., Ann Arbor, Mich.). Results are shown in FIG. 1 (SEQ ID NO. 10, 14 and 359-365).

Example 12

RT-PCR Analysis

Plants inoculated with sequence 129965 (SEQ ID NO: 10), a primary and secondary hit in seedlings also demonstrating strong and consistent tolerance in the greenhouse (FIG. 6), were evaluated at the molecular level for correlation of 129965 message with the tolerant phenotype. The following gene-specific primers were used in the combinations indicated to amplify specific regions of the 129965 insert:

```
ARG1
5'-ATT-CAG-AAT-TGG-GTA-ATC-ACG-GC-3'   SEQ ID NO:370

ARG2
5'-CAA-CAG-TAG-GAA-CTC-TTT-TGA-TGG-3'  SEQ ID NO:371

ARG3
5'-GAG-GAA-GAA-TGA-CTA-CGA-GGA-CG-3'   SEQ ID NO:372

ARG4
5'-TTC-ACT-GAG-CAA-AGT-ACA-CAT-GC-3'   SEQ ID NO:372
```

5'=ARG1+ARG2, 3=ARG3+ARG4, full-length=ARG1+ARG4.

*N. benthamiatia* plants were grown, inoculated with 129965 encapsidated transcript, sprayed with 4-amino-3,6-dichloropyridine-2-carboxylic acid, and scored for injury as described in Example 9.

Leaf tissues from inoculated plants were harvested at 23 days post inoculation (dpi) to evaluate the presence of RNA message, corresponding to 2 weeks after application of the herbicide. Samples were taken from the base of leaf 11 near the petiole. RNA microsamples were isolated by disruption of leaf samples (two leaf punches of approximately 56 mm2) in 400 μL Trizo™ reagent (Invitrogen, Carlsbad, Calif.) with the remainder of the protocol proportionately scaled according to manufacturer's instructions. The RNA pellet was resuspended in 20 μL RNase-free $H_2O$.

For RT-PCR, first strand synthesis was carried out in the presence of 1×MMLV reverse transcriptase buffer (Invitrogen, Carlsbad, Calif.) according to manufacturer's instructions with the following exceptions: 10 pmoles of first strand primer (ARG4 or ARG2) were used and incubation was done at 42° C. PCR was performed using 1 μL of first strand products in a 25 μL volume reaction mixture according to the manufacturer's protocol (Invitrogen, Carlsbad, Calif.). Cycling was carried out using denaturation at 95° C. for 45 seconds, annealing at 50° C. for 30 sec, extension at 72° C. for 3 minutes for a total of 25 cycles. After completion, 10 μL of the reaction products were examined by 1% agarose gel electrophoresis. Negative and positive controls were water and 129965 plasmid, respectively.

As a negative control, GFP-inoculated plant samples were also harvested at 23 dpi for RT-PCR analysis. Using the 129965 gene-specific primers, no product was detected. However, from two 129965-inoculated plants, both demonstrating a tolerant phenotype with injury ratings of only 25% at two weeks post herbicide application, full-length message was detected. Conversely, from a 129965-inoculated auxin susceptible plant, sampled at the same time point and leaf designation, no product was detected. These data indicate that the presence of 129965 message correlates with observed auxin tolerance.

Example 13

Cross-Resistance Testing

Six compounds, representing five classes of auxin chemistry, were selected for testing the extent of auxinic tolerance of five hit sequences (129965 (SEQ ID NO:10), 130213 (SEQ ID NO: 14), 130294 (SEQ ID NO:360), 130994 (SEQ ID NO:361), and 129870 (SEQ ID NO:359)). The compounds included the following:

1) quinclorac (BASF Corp., Research Triangle, N.C.)
2) (2,4-dichlorophenoxy) acetic acid (Dow AgroSciences, Indianapolis, Ind.)
3) dicamba (Monsanto, St. Louis, Mo.)
4) benazolin (AgrEvo USA Company, Wilmington, Del.)
5) picloram (Dow AgroSciences, Indianapolis, Ind.)
6) 4-amino-3,6-dichloropyridine-2-carboxylic acid (Dow AgroSciences, Indianapolis, Ind.)

Compound #6 served as a positive control, as these five sequences were identified for their herbicide tolerant function using this auxin (see Example 9). Compound #1 represents the quinoline carboxylic acid chemical family, #2 is in the phenoxy carboxylic acid class, #3 is benzoic acid chemistry, #4 is unique to any currently defined class, and #5 is in the same family as the positive control, pyridine carboxylic acids.

Each of the five sequences was evaluated twice for tolerance to each of the six compounds. The protocol was essentially the same as that described in Example 9 for greenhouse evaluations. However, an individual experiment consisted of 200 test plants plus 35 GFP and 35 bar negative control plants inoculated per clone. For a single sequence, this allowed comparison of tolerance to each of the six compounds in parallel. Two doses per auxin were tested, with as many as 12 well-infected test plants and 2 of each of the negative controls per dose.

The six auxin solutions were prepared by dissolving solid compound in General Purpose Solvent (GPS: 97%DMSO: 3% acetone) to achieve the following spray rates (g ae/ha) when using the spray applicator and parameters outlined in Example 9: Compound #1) 200; 2) 42; 3) 64; 4) 200; 5) 10; 6)

10. From each of these solutions, a portion was diluted with an equal volume of GPS, resulting in 1× ("high dose") and ½× ("low dose") concentrations for spraying. Before spray application, each auxin solution was mixed with an equal volume of diluent containing surfactants for effective penetration. The diluent was prepared as follows: 420 mL GPS, 460 mL DI water, 120 mL isopropyl alcohol, 10.167 mL Agri-Dex (Helena Chemical Co., Memphis, Tenn.), and 0.167 mL Triton X-155 (Sigma Chemical Co., St. Louis, Mo.). In addition to the 200 and 100 g ae/ha rates tested for Compound #4 (benazolin), a concentration of 250 g ae/ha was also formulated as described above and tested.

Plants were sprayed and evaluated as described in Example 9. FIG. 7 summarizes the sequences tested and the highest dose of the compounds against which tolerance was observed. Using two different thresholds to define a 'tolerant' plant (25% injury or less and 35% injury or less) the percentages of the test populations demonstrating tolerance were calculated. Results are reported in FIG. 7 for each of the trials with each construct.

The positive control (Compound #6) was formulated differently in this set of evaluations from that described in Example 9, for consistency in the solvent/surfactant background from which to compare the activity of the individual sequences against each auxin. Thus, the spray rate used for evaluation was lower than previous experiments, 5 vs. 13 g ae/ha. The need to lower the dose with this formulation to prevent total chlorosis and/or necrosis was likely due to the addition of DMSO, Agri-Dex, and Triton X-155 which were not used in Example 9.

129965 demonstrated the greatest degree of cross-resistance, showing tolerance to each of the six compounds, representing all 5 groups of auxins. Also, for four of the compounds to which tolerance was conferred, resistance was consistently observed using the most stringent threshold, 25% injury or less. For the other two compounds, benazolin (Compound #4) and (2,4-dichlorophenoxy) acetic acid (Compound #2), tolerance was demonstrated using the 35% injury threshold. As noted in FIG. 7, benazolin was used at a higher rate in Trial #2 than Trial #1 for this clone, so variability was expected.

With the remaining sequences, 130213, 130294, 130994, and 129870, tolerance was observed against four compounds: the positive control (Compound #6), picloram (Compound #5), dicamba (Compound #3) and quinclorac (Compound #1). For each of these sequences, tolerance consistently occurred at the lower threshold (25% injury or less) when testing the positive control. These data further support the reproducibility reported in Example 9 (FIG. 6).

130213 was strongly effective against dicamba, with additional tolerance to picloram and quinclorac when the 35% injury tolerance criterion was used. 130294 was consistently tolerant to quinclorac exposure at the 25% injury threshold and demonstrated clear resistance to dicamba and picloram when the 35% rating was considered. 130994 and 129870 demonstrated tolerance to each of the three compounds using the 35% injury threshold.

In summary, these cross-resistance data demonstrate the utility of the claimed sequences for tolerance to auxins across a wide range of chemistries.

Example 14

Homolog Identification, Engineering, and Auxin Tolerance Evaluation

Two sequences, 129965 (SEQ ID NO:10) and 130213 (SEQ ID NO:14), were selected for identification and testing of homologous sequences to exemplify claims.

A. Identification of functional 130213 Homologs. BLAST analysis of 5' sequences from internal GENEWARE® cDNA libraries identified multiple 130213 homologs. From *Selaginella lepidophylla*, a total of 8 clones representing 4 distinct forms were closely examined. All were potentially full-length and in the sense orientation. The *S. lepidophylla* clone 232732 (SEQ ID NO:363) is 87% homologous to 130213 and a member of the most abundantly represented form. 232732 was selected for auxin tolerance testing.

B. Identification and Construction of Functional 129965 Homologs. BLAST analysis of 5' sequences from internal GENEWARE® cDNA libraries was also used to identify 129965 homologs. However, for the majority of homologs in the sense orientation, examination of 5' sequences revealed the presence of an upstream ORF in the 5' UTR, which would render the 129965 homologous portion of the transcript non-expressible. Of this group, one of the two homologs without the upstream ORF, *S. lepidophylla* clone 238465 (SEQ ID NO:364) (62% homologous to 129965) was selected for auxin tolerance testing. Additionally, an examination of antisense clones with high homology to 129965 revealed three *N. benthamiana* clones with insert that would give PCR amplification products of the expected range for the hit sequence, approximately 2.0-2.2 kb. The largest clone (273716; SEQ ID NO:365) was chosen for engineering of a functional 129965 homolog for herbicide tolerance testing.

Engineering expressible 273716 involved PCR amplification of the insert using primers PAC15685 [TAG-CAT-TAA-TTA-AGG-TTG-TTC-TTG-TAC-CTA-G; SEQ ID NO:375] and VIF [AGG-CTA-CTG-TCG-CCG-AAT-CGG; SEQ ID NO:376] to generate a truncated clone containing only the 129965 homologous ORF with a 5' flanking Pac I site and a 3' flanking Not I site for insert into the GENEWARE® vector in the sense orientation. The PCR reaction was done with 20 ng template in a 50 μL volume using Taq DNA polymerase (nvirogen, Carlsbad, Calif.) according to the manufacturer's protocol. Initial denaturation was performed at 94° C. for 2 min. Cycling conditions were 94° C. for 30 sec, 55° C. for 30 sec and 72° C. for 3 min for a total of 15 cycles. Although Taq DNA polymerase was used to amplify the insert, the number of cycles was kept low to minimize the total errors being propagated. Following examination of 10 μL of PCR products on 1% agarose gel, the remaining 40 μL were extracted with phenol:chloroform:isoamyl alcohol (52:24:1 v/v) (Invitrogen, Carlsbad, Calif.), precipitated with 0.3M sodium acetate and two volumes of absolute ethanol and resuspended in 10 μL TE. Restriction digests were done at 37° C. for 2 hr after addition of 2 μL RE Buffer 1 (ew England Biolabs, Beverly, Mass.), $H_2O$ to 20 μL, 1×BSA, 1 unit Pac I (New England Biolabs, Beverly, Mass.) and 1 unit Not I (New England Biolabs, Beverly, Mass.). One μg pBSG1057 plasmid (Large Scale Biology Corporation, Vacaville, Calif.) was similarly digested. Reactions were terminated by incubation at 68° C. for 15 min. Heat-killed products were quick spun in a microfage for collection. Digested products (2 μL each of vector and insert) were ligated in a 15 μL volume using 1 unit of T4 DNA ligase (Invitrogen, Carlsbad, Calif.) according to manufacturer's instructions. Following transformation into *E. coli* DH5α cells Invitrogen, Carlsbad, Calif.) using standard protocols, clones were screened for the presence of inserts excised by Pac I and Not I digestion. Three such clones (designated RTH-1, -5 and -10) were randomly selected for simultaneous greenhouse evaluation and full-length sequencing to detect any errors that may have been introduced during construction.

For full-length sequencing of RTH clones and the 273716 parent, cycle sequencing was carried out using Big Dye teminator mix (ABI Prism BigDye Terminator Cycle Sequencing Kit, Applied Biosystems, Foster City, Calif.) according to manufacturer's instructions as described in Example 11. Results indicated all three clones had sequence identical to each other and the corresponding fragment of the parent clone. This ORF fragment is 82% homologous to 129965.

C. Evaluation of homologs for auxin tolerance. All homologs were tested in comparison to the original hit sequence for tolerance to 4-amino-3,6-dichloropyridine-2-carboxylic acid as described and defined in Example 9. However, numbers of plants per treatment group varied based on the infection rate of the clone, as indicated in FIG. 8.

The 130213 homolog, 232732, resulted in 42% of plants demonstrating auxin tolerance 14 days after treatment (dat), in comparison to only 17% with the positive control (130213). The fact that the percentage of tolerant plants resulting from the control construct was unusually low in this trial (compare to FIGS. 6 and 7) suggests environmental conditions may not have been optimal. However, under the same circumstances the homolog performed as well as and even better than the original hit.

Clone 238465, a homolog of 129965, was evaluated in two trials, resulting in 25% and 32%, respectively, of the test population demonstrating an auxin tolerant phenotype 14 dat. 129965 in the same trials resulted in 73% and 50% of plants with auxin tolerance. Poor inoculation efficiency occurred in Trial #1 with the homologue and Trial #2 with the control, resulting in low numbers of plants available for herbicide application. These data do, however, indicate the homologous sequence confers a degree of auxin tolerance, possibly correlated to the level of homology.

The three RTH clones were tested simultaneously, representing three repetitions of the same homolog, considering that sequences were found to be identical. RTH-1, -5, and -10 consistently resulted in a high percentage of plants with auxin tolerance (100%, 100%, and 82%, respectively). For the 129965 control, 55% of plants were resistant. These and previous 129965 data (FIG. 6) indicate the homolog confers tolerance as well as and possibly more effectively than the hit sequence. Given that the homologous ORF in 129965 and 273716 is highly conserved and the ORF without a leader sequence was tested with the RTH constructs, these data suggest that deletion of the leader from the poppy clone (129965) may enhance the efficacy of the hit sequence.

In summary, these data exemplify a functional similarity between clones that were identified based on sequence similarity. Thus, the approach of predicting function from sequence homology is strongly demonstrated.

Example 15

Expression and evaluation in *Arabidopsis thaliana*

One of the auxin tolerance sequences, 129965 (SEQ ID NO:10), was selected for stable expression analysis using a model plant system, *Arabidopsis thaliana*. This required cloning of the GENEWARE® vector insert into a binary vector suitable for Agrobacterium transformation. *Agrobacteriuni* encoding the gene of interest as well as a selectable marker was then utilized to transform *Arabidopsis* plants. Transgenic plants derived from the first generation of seed (T1) were selected based on glufosinate resistance and subsequently tested for tolerance to auxin 4-amino-3,6-dichloropyridine-2-carboxylic acid.

Plant growth and maintenance. Freshly harvested *Arabidopsis thaliana* (Columbia ecotype) seed was allowed to dry at least 7 days at room temperature in the presence of desiccant. Dried seed was sterilized with a 0.1% Triton X-100 (Sigma Chemical Co., St. Louis, Mo.) and 70% ethanol solution (3 min) using 95% ethanol as a wash (30 sec). After sterilization, seed was suspended in a 0.1% agarose (Sigma Chemical Co., St. Louis, Mo.) solution. The suspended seed was stored at 4° C. for 2 days to complete dormancy requirements and ensure synchronous seed germination (stratification).

Sunshine Mix LP5 (Sun Gro Horticulture Inc., Bellevue, Wash.) was covered with fine vermiculite and subirrigated with Hoagland's solution (see Example 9) until wet. The soil mix was allowed to drain for 24 hours. Stratified seed was sown onto the vermiculite and covered with humidity domes (KORD Products, Bramalea, Ontario, Canada) for 7 days.

Seeds were germinated and plants were grown in a Conviron (models CMP4030 and CMP3244, Controlled Environments Limited, Winnipeg, Manitoba, Canada) under long day conditions (16 hours light/8 hours dark) at a light intensity of 120-150 μmol/m$^2$/sec under constant temperature (22° C.) and humidity (40-50%). Plants were initially watered with Hoagland's solution and subsequently with DI water to keep the soil moist but not wet. Plants nearing seed harvest were allowed to dry out (1-2 weeks before harvest).

Subcloning. The 129965 insert was cloned out of the GENEWARE® vector backbone (Large Scale Biology, Vacaville, Calif.) into an entry vector, pENTR/D-TOPO® (Invitrogen, Carlsbad, Calif.), and finally into a binary vector, pMYC3446 (Dow AgroSciences, Indianapolis, Ind.), via Gateway™ cloning technology (Invitrogen, Carlsbad, Calif.).

Cloning into entry vector. Cloning from the GENEWARE® vector into the pENTR/D-TOPO® vector first required modification of the entry vector to include restriction endonuclease cloning sites for the PacI and XhoI enzymes between the attL1 and attL2 recognition sites. Primers were designed to PCR amplify a region of DNA that would include the directional cloning sequence for standard pENTR/D-TOPO® cloning (a CACC inserted at the 5' end of the PCR product), and the PacI (5') and XhoI (3') restriction sites. [CAVIF: CAC-CAT-CTC-AGT-TCG-TGT-TCT-TGT-C; SEQ ID NO:377 and VIR: GCA-CCA-CGT-GTG-ATT -ACG-GAC-AC; SEQ ID NO:378]. The PCR reaction used Taq DNA polymerase (Invitrogen, Carlsbad, Calif.) according to the manufacturer's instructions. Denaturation was initially performed at 94° C. for 3 min. Cycling conditions were 94° C. for 45 sec, 55° C. for 30 sec, 72° C. for 90 sec for a total of 30 cycles. The PCR product was electrophoresed and visualized via ethidium bromide staining on a 1% agarose gel to verify a clean band of expected size.

The TOPO® cloning reaction was performed according to manufacturer's instructions, using 2-3 μL of fresh PCR product. The reaction was incubated 30 min at room temperature then placed on ice. Three μL of the reaction were added to 50 μL of *E. coli* MaxEfficiency DH5α cells (Invitrogen, Carlsbad, Calif.). The mixture was placed on ice for 30 min, then heat shocked at 37° C. for 30 sec. 300 μL of SOC media [20 g/L Bacto™ tryptone (Difco Laboratories, Becton, Dickinson, and Company, Sparks, Md.) 5 g/L Bacto™ yeast extract (Difco Laboratories, Becton, Dickinson, and Company, Sparks, Md.), 0.5 g/L NaCl, 20 mM glucose] were added to the cells and incubated at 37° C. for 60 min with constant agitation. Various amounts of the culture were plated onto LB (10 g/L Bacto™ tryptone, 5 g/L Bacto™ yeast extract, 10 g/L NaCl)+agar plates containing 50 mg/L kanamycin (Sigma Chemical Co., St. Louis, Mo.). The plates were incubated overnight at 37° C., after which individual colonies were visible. The colonies were streaked onto fresh LB+agar with kanamycin plates and incubated an additional 6-12 hours. Individual colonies were then used to inoculate 4 mL cultures (liquid LB+kanamycin) which were incubated overnight at 37° C. with agitation. Qiagen Spin Mini Preps (Qiagen, Valencia, Calif.) were performed for each culture per manufacturer's instructions. The recovered DNA was digested with Pacd and XhoI enzymes and the products were electrophoresed on an agarose gel containing ethidium bromide. A sample with the expected band numbers and sizes was identified and selected for excising the desired vector band (approximately 2.3 kb) using the Qiaex II Gel Extraction kit (Qiagen, Valencia, Calif.). Once the vector DNA was isolated, 129965 GENEWARE® plasmid DNA was also digested with PacI and XhoI for compatible sticky ends on the desired insert. These digestion products were electrophoresed on an agarose gel containing ethidium bromide and the smaller band (approximately 1.9 kb) was excised and purified as above.

The 129965 insert and the modified pENTR/D-TOPO vector were ligated using T4 ligase (Invitrogen, Carlsbad, Calif.), according to the manufacturer's protocol with 5 μL of insert and 2 μL vector DNA. The ligation mixture was incubated in a 16° C. water bath overnight then used to transform MaxEfficiency DH5α cells as described above. After minipreps from isolated colonies were completed, recovered DNA was digested with PacI and XhoI. Digestion products were electrophoresed and clones producing the expected band sizes were identified. Large (100 mL) cultures were inoculated from those colonies and incubated overnight at 37° C. with agitation. Qiagen Midi Preps (Qiagen, Valencia, Calif.) were performed per manufacturer's instructions and the recovered DNA was verified by PacI and XhoI digestion and electrophoresis. Midi prep plasmid DNA was sequenced using primers M13 and M13R (Invitrogen, Carlsbad, Calif.) which allow for sequencing across the junctions of the vector and insert. The sequence data verified that the 129965 insert had been cloned into the entry vector and was in the right orientation.

Gateway™ cloning into the binary vector. The binary vector pMYC3446 contained sites for Gateway™ cloning (Invitrogen, Carlsbad, Calif.). The recombination reaction was assembled according to manufacturer's instructions, using 300 ng of the modified pENTR/D-TOPO with 129965 insert as the entry clone and 300 ng of pMYC3446 as the destination vector. The reaction products were transformed into MaxEfficiency DH5α cells as previously described. Colonies were grown under 100 mg/L spectinomycin (Sigma Chemical Co., St. Louis, Mo.) selection and DNA mini preps were completed as above. Recovered DNA was digested with PacI and XhoI enzymes, electrophoresed, and visualized on a gel for selection of one colony with the expected band pattern. A 100 mL culture in LB+spectinomycin was inoculated from that colony, a DNA midi prep was done as previously described, and the recovered DNA was digested with PacI and XhoI for verification. Recovered midi prep plasmid DNA was also sequenced with primers designed specifically for sequencing across the junctions of inserts in pMYC3446 (3446-F: TAAGGAACCAAGTTCGGCATTTGTGAAAAC SEQ ID NO:379 and M3446-R: CCCCAT ATGCAGGAGCGGATCATTCATTGT SEQ ID NO:380). The sequence data verified that 129965 insert was present in the binary vector in the correct orientation. The verified binary expression vector with the 129965 insert was named pDAB9001.

Transformation of *Agrobacterium*. Electro-competent *Agrobacterium tumefaciens* (strain Z707S) cells were prepared according to Weigel and Glazebrook (Arabidopsis: A Laboratory Manual. Cold Spring Harbor Laboratory Press. 2002). Fifty μL of competent cells were thawed on ice and 25 ng of pDAB9001 were added. The cell-plasmid mix was transferred to a pre-chilled electroporation cuvette (2 mm) and electroporated under the following conditions: 25 μF capacitance, 2.4 kV, 200 Ω resistance, 5 msec pulse length (Eppendorf Electroporator 2510, Hamburg, Germany). After electroporation, 1 mL of YEP broth [10 g/L Bacto™ yeast extract, 10 g/L Bacto™ peptone (Difco Laboratories, Becton, Dickinson, and Company, Sparks, Md.), 5 g/L NaCl] was added to the cuvette and the cell-YEP mixture was transferred to a 15 mL culture tube. The tube was incubated in a 28° C. water bath with agitation for 4 hours. The culture was then plated on YEP medium with 100 mg/L spectinomycin and 250 mg/L streptomycin (Sigma Chemical Co., St. Louis, Mo.). The plates were incubated for 2 days at 28° C., after which colonies were selected for PCR analysis. A few cells of the selected colonies were diluted into 10 μL water, lysed at 100° C. for 5 min and used as template for PCR. The primers were specific to the pMYC3446 insert (M3446-F and M3446-R). PCR was performed using Taq polymerase (Invitrogen, Carlsbad, Calif.) per manufacturer's instructions. A positive control was included, using the original plasmid DNA as template. The PCR products were electrophoresed on a 1% agarose gel containing ethidium bromide and visualized using UV light. A colony was selected whose PCR product was identical to the plasmid control.

Transformation of *Arabidopsis*. The floral dip method, as described by Weigel and Glazebrook (Arabidopsis: A Laboratory Manual. Cold Spring Harbor Laboratory Press. 2002), was used for *Arabidopsis* transformation. From the selected *Agrobacterium* colony was grown a 400 mL culture in YEP broth containing spectinomycin (100 mg/L) and streptomycin (250 mg/L) by overnight incubation at 28° C. The cells were pelleted via centrifugation at approximately 8700 g for 15 min then gently resuspended in 400 mL infiltration media [½×MS salts+B5 vitamins (Sigma Chemical Co., St. Louis, Mo.), 5% sucrose, 0.044 μM benzylamino purine (Sigma Chemical Co., St. Louis, Mo.), 50 μM/L Silwet L-77 (Lehle Seeds, Round Rock, Tex.)]. *Arabidopsis* plants approximately 1 month old were dipped into the media for 30 sec, being sure to submerge the newest inflourescences. The plants were then placed horizontally and covered for 24 hours. After that time, they were misted lightly with water and returned upright to normal growth conditions. Approximately four weeks after dipping, the T1 seeds were harvested.

Selection of Transformed Plants. T1 seed was dried, sterilized and stratified as previously described then sown on Sunshine Mix LP5 in10.5"×21" germination trays (T.O. Plastics Inc., Clearwater, Minn.). After 5-6 days, humidity domes were removed and plants were sprayed with a 1000× solution of Finale (5.78% glufosinate ammonium, Farnam Companies Inc., Phoenix, Ariz.). Two subsequent sprays were performed at 5-7 day intervals. Survivors (actively growing plants) were identified 7-10 days after the final spraying and transplanted into individual pots. Transplanted plants were covered with a humidity dome for 2 days and maintained under growth conditions previously described.

Auxin Tolerance Testing. Eight glufosinate resistant plants were tested for auxin tolerance, two days after transfer to individual pots. A potassium salt formulation of 4-amino-3,6-dichloropyridine-2-carboxylic acid (Dow AgroSciences, Indianapolis, Ind.) herbicide solution was diluted in 0.25% X-77 Spreader (Spraymate, Greeley, Colo.) for a concentration of 3.75 g ae/ha. Fifty μL of the solution was pipetted onto one lower leaf of each of the transformed plants, as well as several wild type plants of the same age for use as negative controls. Other wild type plants were treated with 50 μL of solvent only (X-77 spreader). Five days after application, solvent treated plants were unaffected, with the exception of the treated leaf, which was necrotic in every plant to which any solution was applied. Within those five days, each auxin-treated wild type plant developed systemic symptoms of epinasty and leaf cupping, as well as meristem swelling and significant chlorosis. However, two of the transformed plants demonstrated approximately 70-80% less auxin symptomology than the auxin-treated wild type controls. In both plants, leaf cupping was observed to a limited degree on a few leaves (nonsystemic), an active meristem resulted in emergence of a shoot with new leaves, and no chlorosis was evident. These results indicate the 129965 sequence, when stably expressed in a whole plant system, confers auxin tolerance.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with particular preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

What is claimed is:

1. An isolated nucleic acid comprising SEQ ID NO: 30, wherein expression of said isolated nucleic acid in a plant results in a herbicide resistance phenotype of said plant.

2. A vector comprising the isolated nucleic acid of claim 1.

3. The vector of claim 2, wherein said isolated nucleic acid is operably linked to a plant promoter.

4. The vector according to claim 2, wherein said isolated nucleic acid is operably linked and in sense orientation with respect to a plant promoter or a bacterial promoter.

5. The vector according to claim 2, wherein expression of said isolated nucleic acid of said vector in a plant confers a herbicide resistance phenotype to said plant.

6. A process for making a transgenic plant comprising:

a. providing the vector according to claim 2 and a plant, b. and transfecting said plant with said vector.

7. A process for providing herbicide resistance in a plant or population of plants comprising:

a. providing the vector according to claims 2 and a plant, b. and transfecting said plant with said vector under conditions such that a herbicide resistant phenotype is conferred by expression of said isolated nucleic acid from said vector.

8. A plant transfected with the isolated nucleic acid according to claim 1.

9. A seed produced by the plant of claim 8 and comprising the isolated nucleic acid.

10. At least one progeny plant produced by the plant of claim 8 and comprising the isolated nucleic acid.

* * * * *